(12) United States Patent
Wiltzius

(10) Patent No.: US 10,603,380 B2
(45) Date of Patent: Mar. 31, 2020

(54) CHIMERIC ANTIGEN AND T CELL RECEPTORS AND METHODS OF USE

(71) Applicant: Kite Pharma, Inc., Santa Monica, CA (US)

(72) Inventor: Jed Wiltzius, Woodland Hills, CA (US)

(73) Assignee: KITE PHARMA, INC., Santa Monica, CA (US)

( * ) Notice: Subject to any disclaimer, the term of this patent is extended or adjusted under 35 U.S.C. 154(b) by 0 days.

(21) Appl. No.: 15/475,681

(22) Filed: Mar. 31, 2017

(65) Prior Publication Data

US 2017/0281766 A1    Oct. 5, 2017

Related U.S. Application Data

(60) Provisional application No. 62/317,258, filed on Apr. 1, 2016.

(51) Int. Cl.
| | | |
|---|---|---|
| C07K 14/705 | (2006.01) | |
| C07K 16/30 | (2006.01) | |
| A61K 39/395 | (2006.01) | |
| C07K 14/73 | (2006.01) | |
| C07K 16/24 | (2006.01) | |
| C07K 14/47 | (2006.01) | |
| C07K 14/735 | (2006.01) | |
| C07K 14/725 | (2006.01) | |
| A61K 39/00 | (2006.01) | |

(52) U.S. Cl.
CPC .... *A61K 39/39558* (2013.01); *C07K 14/4748* (2013.01); *C07K 14/7051* (2013.01); *C07K 14/7056* (2013.01); *C07K 14/70514* (2013.01); *C07K 14/70517* (2013.01); *C07K 14/70535* (2013.01); *C07K 14/70575* (2013.01); *C07K 14/70589* (2013.01); *C07K 16/245* (2013.01); *C07K 16/30* (2013.01); *A61K 2039/505* (2013.01); *A61K 2039/5156* (2013.01); *A61K 2039/57* (2013.01); *C07K 2317/53* (2013.01); *C07K 2317/56* (2013.01); *C07K 2317/565* (2013.01); *C07K 2317/94* (2013.01); *C07K 2319/02* (2013.01); *C07K 2319/03* (2013.01); *C07K 2319/33* (2013.01); *C07K 2319/70* (2013.01)

(58) Field of Classification Search
CPC ....................... C07K 14/7051; A61K 39/39558
See application file for complete search history.

(56) References Cited

U.S. PATENT DOCUMENTS

| | | | |
|---|---|---|---|
| 4,946,778 A | 8/1990 | Ladner et al. | |
| 5,260,203 A | 11/1993 | Ladner et al. | |
| 5,728,388 A | 3/1998 | Terman | |
| 5,827,642 A | 10/1998 | Riddell et al. | |
| 5,830,462 A | 11/1998 | Crabtree et al. | |
| 5,834,266 A | 11/1998 | Crabtree et al. | |
| 5,869,337 A | 2/1999 | Crabtree et al. | |
| 6,040,177 A | 3/2000 | Riddell et al. | |
| 6,165,787 A | 12/2000 | Crabtree et al. | |
| 6,319,494 B1 | 11/2001 | Capon et al. | |
| 6,797,514 B2 | 9/2004 | Berenson et al. | |
| 6,867,041 B2 | 3/2005 | Berenson et al. | |
| 6,905,874 B2 | 6/2005 | Berenson et al. | |
| 7,709,226 B2 | 5/2010 | Foote | |
| 7,741,465 B1 | 6/2010 | Eshhar et al. | |
| 8,465,743 B2 | 6/2013 | Rosenberg et al. | |
| 8,486,693 B2 | 7/2013 | Park et al. | |
| 8,536,310 B2 | 9/2013 | Abo et al. | |
| 9,034,324 B2 | 5/2015 | Kalled et al. | |
| 9,163,090 B2 | 10/2015 | Jiang et al. | |
| 9,845,362 B2 * | 12/2017 | Mukherjee | ......... A61K 47/6851 |
| 2002/0006409 A1 | 1/2002 | Wood | |
| 2002/0164588 A1 | 11/2002 | Eisenberg et al. | |
| 2004/0014194 A1 | 1/2004 | Beyer et al. | |
| 2004/0197328 A1 | 10/2004 | Young et al. | |
| 2010/0285037 A1 | 11/2010 | Abo | |
| 2011/0280889 A1 | 11/2011 | Schendel et al. | |
| 2011/0286980 A1 | 11/2011 | Brenner | |
| 2012/0130076 A1 | 5/2012 | Holt et al. | |
| 2012/0213783 A1 * | 8/2012 | Rosenberg | ......... C07K 14/7051 |
| | | | 424/134.1 |
| 2012/0227134 A1 | 9/2012 | Schon et al. | |
| 2013/0079246 A1 | 3/2013 | De Smedt et al. | |
| 2013/0287748 A1 | 10/2013 | June et al. | |

(Continued)

FOREIGN PATENT DOCUMENTS

| | | | |
|---|---|---|---|
| JP | 6262724 B2 | 1/2018 | |
| WO | 88/01649 A1 | 3/1988 | |

(Continued)

OTHER PUBLICATIONS

Dotti et al., Immunol Rev. 257(1): doi:10.1111/imr/12131 (Year: 2014).*

(Continued)

*Primary Examiner* — Jessica H Roark

(74) *Attorney, Agent, or Firm* — Arrigo LeeGuttman Mouta-Bellum

(57) ABSTRACT

The invention provides a chimeric antigen receptor (CAR) or a T cell receptor (TCR) comprising extracellular domain disclosed herein. Some aspects of the invention relate to a polynucleotide encoding a chimeric antigen receptor (CAR) or a T cell receptor (TCR) comprising the extracellular domain disclosed herein. Other aspects of the invention relate to cells comprising the CAR or the TCR and their use in a T cell therapy.

27 Claims, 49 Drawing Sheets

Specification includes a Sequence Listing.

(56) References Cited

U.S. PATENT DOCUMENTS

| | | |
|---|---|---|
| 2013/0295118 A1 | 11/2013 | Jiang |
| 2014/0010861 A1 | 1/2014 | Bancel et al. |
| 2014/0050708 A1 | 2/2014 | Powell et al. |
| 2014/0099309 A1 | 4/2014 | Powell, Jr. et al. |
| 2014/0154228 A1 | 6/2014 | Volk et al. |
| 2014/0171649 A1 | 6/2014 | Li et al. |
| 2014/0227237 A1 | 8/2014 | June et al. |
| 2014/0286987 A1 | 9/2014 | Spencer et al. |
| 2014/0328812 A1* | 11/2014 | Campana ........... C07K 16/2866 424/93.21 |
| 2015/0051266 A1 | 2/2015 | Kochenderfer |
| 2015/0225480 A1 | 8/2015 | Powell, Jr. |
| 2015/0266973 A1 | 9/2015 | Jarjour et al. |
| 2015/0368360 A1 | 12/2015 | Liang et al. |
| 2016/0046700 A1 | 2/2016 | Foster et al. |
| 2016/0046724 A1 | 2/2016 | Brogdon et al. |
| 2016/0051651 A1 | 2/2016 | Brogdon et al. |
| 2016/0297884 A1 | 10/2016 | Kuo et al. |
| 2016/0297885 A1 | 10/2016 | Kuo et al. |
| 2016/0311907 A1 | 10/2016 | Brogdon et al. |
| 2016/0340649 A1 | 11/2016 | Brown et al. |
| 2017/0183418 A1 | 7/2017 | Cellectis |
| 2017/0281766 A1 | 10/2017 | Wiltzius et al. |
| 2017/0283500 A1* | 10/2017 | Wiltzius ............. C07K 14/7051 |
| 2017/0283504 A1* | 10/2017 | Wiltzius ............. C07K 16/2878 |

FOREIGN PATENT DOCUMENTS

| | | |
|---|---|---|
| WO | 2005000894 | 1/2005 |
| WO | 2012031744 | 3/2012 |
| WO | 2012033885 | 3/2012 |
| WO | WO2012033885 A1 | 3/2012 |
| WO | 2012/163805 A1 | 5/2012 |
| WO | 2008081035 | 6/2012 |
| WO | WO2012079000 A1 | 6/2012 |
| WO | 2012129514 | 9/2012 |
| WO | 2013/154760 A1 | 3/2013 |
| WO | 2013/142034 A1 | 9/2013 |
| WO | 2013169625 A1 | 11/2013 |
| WO | 2014/122143 A1 | 8/2014 |
| WO | 2014127261 | 8/2014 |
| WO | WO2014127261 A1 | 8/2014 |
| WO | 2014186469 | 11/2014 |
| WO | WO2014186469 A1 | 11/2014 |
| WO | 2015077789 | 5/2015 |
| WO | 2015077789 A2 | 5/2015 |
| WO | 2015080981 | 6/2015 |
| WO | 2015090229 | 6/2015 |
| WO | WO2015080981 A1 | 6/2015 |
| WO | 2015120096 | 8/2015 |
| WO | 2015142675 | 9/2015 |
| WO | WO2015142675 A2 | 9/2015 |
| WO | 2015158671 | 10/2015 |
| WO | 2016/014789 A2 | 1/2016 |
| WO | 2016014535 | 1/2016 |
| WO | 2016014565 | 1/2016 |
| WO | 2016044745 | 3/2016 |
| WO | WO2016044745 A1 | 3/2016 |
| WO | 2016090369 | 6/2016 |
| WO | 2016094304 | 6/2016 |
| WO | WO2016090369 A1 | 6/2016 |
| WO | 2017173256 | 10/2017 |
| WO | 2017173349 | 10/2017 |
| WO | 2017173384 | 10/2017 |
| WO | 2017173410 | 10/2017 |
| WO | WO-2017173410 A1 * | 10/2017 ........... C07K 14/705 |

OTHER PUBLICATIONS

Geldres et al., Sem Immunol 28:3-9 (Year: 2016).*
Fesnak et al., Nature Reviews Cancer 16:566-581 (Year: 2016).*
De Oliveira et al., Human Gene Ther. 24:824-39 (Year: 2013).*
Kariv et al., J. Immunol. 157:29-38 (Year: 1996).*

Kowolik, Claudia M., "CD28 Costimulation Provided through a CD19-Specific Chimeric Antigen Receptor EnhancesInvivoPersistence and AntitumorEfficacy of Adoptively Transferred T Cells", Cancer Res 2006; 66: (22). Nov. 15, 2006.

Sadelain, M., et al., "The Basic Principles of Chimeric Antigen Receptor Design", Cancer Discovery, Apr. 2, 2013, pp. 388-398.

Evans, E., et al., "Crystal Structure of a Soluble CD28-Fab Complex", Nature Immunology, vol. 6, No. 3 Mar. 2005, pp. 271-279.

Al-Lazikani B et al., Standard conformations for the canonical structures of immunoglobulins, J Mol Biol, 273:927-948 (1997).

Bricogne G., "Bayesian statistical viewpoint on structure determination: Basic concepts and examples," Meth Enzymol 276A:361-423 (1997).

Bricogne G., "Direct phase determination by entropy maximization and likelihood ranking: status report and perspectives," Acta Crystallogr D Biol Crystallogr, 49(Pt 1):37-60 (1993).

Champe M et al., "Monoclonal antibodies that block the activity of leukocyte function-associated antigen 1 recognize three discrete epitopes in the inserted domain of CD11a," J Biol Chem, 270:1388-1394 (1995).

Cheung, et al., "Epitope-specific antibody response to the surface antigen of duck hepatitis B virus in infected ducks," Virology, 176:546-552 (1990).

Chayen NE, "The role of oil in macromolecular crystallization," Structure, 5:1269-1274 (1997).

Chothia C & Lesk AM, "Canonical structures for the hypervariable regions of immunoglobulins," J Mol Biol 196:901-917 (1987).

Chothia C et al., "Structural repertoire of the human VH segments," J Mol Biol, 227:799-817 (1992).

Cunningham BC & Wells JA, "High-resolution epitope mapping of hGH-receptor interactions by alanine-scanning mutagenesis," Science, 244:1081-1085 (1989).

Dayhoff et al., 1978, Atlas of Protein Sequence and Structure 5:345-352.

Devereux et al., "A comprehensive set of sequence analysis programs for the VAX," Nucl. Acid Res., 12:387-395 (1984).

Fegan et al., "Chemically controlled protein assembly: techniques and applications," Chem. Rev., 110:3315-3336 (2010).

Finney et al., "Chimeric receptors providing both primary and costimulatory signaling in T cells from a single gene product," Journal of Immunology,161:2791-2797 (1998).

Giegé R. et al., "Crystallogenesis of biological macromolecules: facts and perspectives," Acta Crystallogr D Biol Crystallogr, 50(Pt 4):339-350 (1994).

Gross et al., "Therapeutic Potential of T Cell Chimeric Antigen Receptors (CARs) in Cancer Treatment: Counteracting Off-Tumor Toxicities for Safe CAR T Cell Therapy," Annu. Rev. Pharmacol. Toxicol., 56:59-83 (2016).

Henikoff et al., "Amino acid substitution matrices from protein blocks," Proc. Natl. Acad. Sci. U.S.A., 89:10915-10919 (1992).

Kabat EA & Wu TT, "Attempts to locate complementarity-determining residues in the variable positions of light and heavy chains," Ann NY Acad Sci, 190:382-391 (1971).

Kalos et al., "T cells with chimeric antigen receptors have potent antitumor effects and can establish memory in patients with advanced leukemia," Sci Transl. Med., 3:95 (2011).

Kirkland et al., "Analysis of the tine specificity and cross-reactivity of monoclonal anti-lipid a antibodies," J. Immunol. 137:3614-3619 (1986).

Krause et al., "Antigen-dependent CD28 signaling selectively enhances survival and proliferation in genetically modified activated human primary T lymphocytes," J. Exp. Med.,188(4):619-626 (1998).

McPherson A., "Crystallization of proteins from polyethylene glycol.," J Biol Chem, 251:6300-6303 (1976).

McPherson A., "Current approaches to macromolecular crystallization," Eur J Biochem, 189:1-23 (1990).

Moldenhauer et al., "Identity of HML-1 antigen on intestinal intraepithelial T cells and of B-ly7 antigen on hairy cell leukaemia," Scand. J. Immunol., 32:77-82 (1990).

Morel et al., "Monoclonal antibodies to bovine serum albumin: affinity and specificity determinations," Molec. Immunol., 25:7-15 (1988).

(56) References Cited

OTHER PUBLICATIONS

Porter et al., "Chimeric antigen receptor-modified T cells in chronic lymphoid leukemia," N. Engl. J. Med., 365:725-33 (2011).
Roversi P et al., "Modelling prior distributions of atoms for macromolecular refinement and completion," Acta Crystallogr D Biol Crystallogr, 56(Pt 10):1316-1323 (2000).
Song et al., "CD27 costimulation augments the survival and anti-tumor activity of redirected human T cells in vivo," Blood, 119:696-706 (2012).
Stahli et al., "Distinction of epitopes by monoclonal antibodies," Methods in Enzymology, 9:242-253 (1983).
Tramontano A et al., "Framework residue 71 is a major determinant of the position and conformation of the second hypervariable region in the VH domains of immunoglobulins," J Mol Biol, 215(1)175-182 (1990).
Wu et al., "Remote control of therapeutic T Cells through a small molecule-gated chimeric receptor," Science, 350 (6258):293 (2015).
Office Action for Cuban application No. 2018-0121 dated Jan. 8, 2019 (2 pages).
International Search Report for PCT/US20171025351 dated Aug. 22, 2017 (6 pages).
Ashwood-Smith, "Preservation of mouse bone marrow at −79 degreed C. with dimethyl sulphoxide," Nature, 190:1204-1205 (1961).
Bakker et al., "C-type lectin-like molecule-1: a novel myeloid cell surface marker associated with acute myeloid leukemia," Cancer Res., 64:8443-8450 (2004).
Chothia et al., "Conformations of immunoglobulin hypervariable regions," Nature, 342:877-883 (1989).
Chu et al., "SV40 DNA transfection of cells in suspension: analysis of efficiency of transcription and translation of T-antigen," Gene, 13:197-202 (1981).
C-type lectin domain family 12 member A isoform 1 [*Homo sapiens*], NCBI Reference Sequence: NP_612210.4, https://www.ncbi.nlm.nih.gov/protein/NP_61221.4, retrieved on Oct. 2, 2017.
Davis et al., "Basic Methods in Molecular Biology," 1986, Elsevier, Table of Contents only.
Eshhar et al., "Tumor-specific T-bodies: towards clinical application," Cancer Immunol Immunotherapy, 45:131-136 (1997).
Evans et al., "Design of nonpeptidal ligands for a peptide receptor: cholecystokinin antagonists," J. Med. Chem., 30:1229-1239 (1987).
Fauchere, J., Adv. Drug Res., 15:29 (1986).
Gautier et al., "Site-Specific Protein Labeling, Methods and Protocols," Springer 2015, pp. 1-267.
Golub et al., "Immunology—A Synthesis (2nd Edition)," Sinauer Association., Sunderland, Mass. (1991), table of contents only, 13 pages.
Graham et al., "A new technique for the assay of infectivity of human adenovirus 5 DNA," Virology, 52:456-467 (1973).
Guedan et al., "ICOS-based chimeric antigen receptors program bipolar TH17/TH1 cells," Blood,124(7):1070-1080 (2014).
Harlow et al., "Antibodies: A Laboratory Manual," Cold Spring Harbor Laboratory, eds., 1988.
Hartl et al., "Genetics: Principles and Analysis," 1997, Jones and Bartlett Publishers.
Hombach et al., "OX40 costimulation by a chimeric antigen receptor abrogates CD28 and IL-2 induced IL-10 secretion by redirected CD4(+) T cells," Oncoimmunology, 1(4): 458-466 (2012).
Hombach et al., "Tumor-specific T cell activation by recombinant immunoreceptors: CD3 zeta signaling and CD28 costimulation are simultaneously required for efficient IL-2 secretion and can be integrated into one combined CD28/CD3 zeta signaling receptor molecule," Journal of Immun., 167:6123-6131 (2001).
Kabat et al., "Sequences of Proteins of Immunological Interest," 1991, 5th Ed., NIH Publication 91-3242, Bethesda, MD title page, publication page, and table of contents only, 10 pages.
Restriction Requirement for U.S. Appl. No. 15/476,699 dated Jan. 18, 2019 (11 pages).
Non-Final Office Action for U.S. Appl. No. 15/476,309 dated Mar. 1, 2019 (35 pages).
Restriction Requirement for U.S. Appl. No. 15/476,309 dated Sep. 4, 2018 (12 pages).
Written Opinion for PCT/US2017/025573 dated Aug. 11, 2017 (8 pages).
Written Opinion for PCT/US2017/025351 dated Aug. 22, 2017 (6 pages).
Written Opinion for PCT/US20171025516 dated Aug. 25, 2017 (8 pages).
Rudikoff et al., "Single amino acid substitution altering antigen-binding specificity," Proc. Natl. Acad. Sci. USA, 79:1979-1983 (1982).
Solman, "Effects of amino acid sequence changes on antibody-antigen interactions," A Structural View of Immune Recognition by Antibodies, pp. 33-36 (1994).
Ibragimova et al., "Stability of the β-Sheet of the WW Domain: A Molecular Dynamics Simulation Study," Biophysical Journal 77:2191-2198 (1999).
Prazma et al., "Dendritic cell CD83: A therapeutic target or innocent bystander?" Immunology Letters, 115:1-8 (2008).
Lovelock & Bishop, "Prevention of freezing damage to living cells by dimethyl sulphoxide.," Nature, 183:1394-1395 (1959).
Lu et al., "Targeting Human C-Type Lectin-like Molecule-1 (CLL1) with a Bispecific Antibody for Immunotherapy of Acute Myeloid Leukemia," Angew Chem Int. Ed. Engl., 53(37):9841-9845 (2014).
Marshall et al., "Identification and characterization of a novel human myeloid inhibitory C-type lectin-like receptor (MICL) that is predominantly expressed on granulocytes and monocytes," J. Biol. Chem. 279:14792-14802 (2004).
Martin and Thornton, "Structural families in loops of homologous proteins: automatic classification, modelling and application to antibodies," J. Mol. Biol, 263:800-815 (1996).
Rinfret, Ann. N.Y., "Factors affecting the erythrocyte during rapid freezing and thawing," Acad. Sci., 85:576-594 (1960).
Sambrook et al., "Molecular Cloning A Laboratory Manual," 2001, Third Edition, Cold Spring Harbor Laboratory Press, Table of Contents Only.
Shen et al., "Chimeric antigen receptor containing ICOS signaling domain mediates specific and efficient antitumor affect of T cells against EGFRvIII expressing glioma,"Journal of Hematology & Oncology, 6:33 (2013).
Sloviter & Ravdin, "Recovery and transfusion of human erythrocytes after freezing in polyglycol solutions," Nature, 196:899-900 (1962).
Song et al., "Pro-survival signaling via CD27 costimulation drives effective CAR T-cell therapy," Oncoimmunology,1;1 (4): 547-549 (2012).
Tashiro et al., "Treatment of Acute Myeloid Leukemia with T Cells Expressing Chimeric Antigen Receptors Directed to C-type Lectin-like Molecule 1," Molecular Therapy, Jul. 1, 2017 (entire document).
UniProtKB—Q5QGZ9 (CL12A_HUMAN), (2008), http://www.uniprot.org/Q5QGZ9, retrieved on Oct. 2, 2017.
Van Rhenen et al., "The novel AML stem cell associated antigen CLL-1 aids in discrimination between normal and leukemic stem cells" Blood, 110(7):2659-2666 (2007).
Veber & Freidinger, TINS, p. 392 (1985).
Wyckoff et al., eds., Methods in Enzymology vol. 114—Diffraction Methods for Biological Macromolecules, Academic Press, Orlando, FL; title page, publication page, and table of contents only, 5 pages (1985).
Wyckoff et al., eds., Methods for Enzymology vol. 115—Diffraction Methods for Biological Macromolecules, Academic Press, Orlando, FL; title page, publication page, and table of contents only, 4 pages (1985).
Zhao et al., "Targeting C-type lectin-like molecule-1 for antibody-mediated immunotherapy in acute myeloid leukemia," Haematologica, 95(1):71-78 (2010).
Hipp et al., "A Novel BCMA/CD3 Bispecific T-cell Engager for the Treatment of Multiple Myeloma Induces Selective Lysis in Vitro and In Vivo," Leukemia (2017), p. 1743-1751, 31, www.nature.com/leu, doi:10.1038/eu.2016.388.

(56) References Cited

OTHER PUBLICATIONS

Hymowitz et al., "Structures of April-Receptor Complexes," J. Biol. Chem. (2005), 280, pp. 7218-7227, doi: 10.1074/bc.M411714200 originally published online Nov. 12, 2004.
Kochendeifer et al., "Construction and preclinical evaluation of an anti-CD19 chimeric antigen receptor," Journal of Immunotherapy, 32(7):689-702 (2009).
Kochenderfer et al., "A Phase 1 Clinical Trial of Treatment of B-Cell Malignancies with Autologous Anti-CD19-CAR-Transduced T Cells," Blood, 116(1):1179-1180 (2010).
Yu et al., "APRIL and TALL-1 and receptors BCMA and TACI: system for regulating humoral immunity," Nature Immunology, 1(3)252-256 (2000).
International Search Report for PCT/US2017/025516 dated Jul. 21, 2017 (6 pages).
International Search Report for PCT/US2017/025573 dated Jul. 25, 2017 (6 pages).
Office Action for Cuban application No. 2018-0120 dated Jan. 8, 2019 (2 pages).
International Search Report for PCT/US2017/025613 dated Jun. 27, 2017 (13 pages).
Kariv I et al., "Analysis of the site of interaction of CD28 with its counter-receptors CD80 and CD86 and correlation with function", The Journal of Immunology, Jul. 1, 1996; vol. 57, No. 1, pp. 29-38.
Dotti G. et al., "Design and Development of Therapies using Chimeric Antigen Receptor-Expressing T cells", Immunological Reviews Jan. 2014; vol. 257, No. 1, pp. 1-35.
First Office Action in Primary Examination for Taiwanese Patent Application No. 106111228; 883738, which is related to this subject application.
Search Report in Primary Examination for Taiwanese Patent Application No. 106111228; 883738, which is related to this subject application.
English Translation of First Office Action and Search Report in Primary Examination for Taiwanese Patent Application No. 106111228; 883738, which is related to this subject application.
Hua Lu, et al., "Targetting Human C-Type Lectin-Like Molecule-1 (CLL-1) with a Bispecific Antibody for Immunotherapy of Acute Myeloid Leukemia", Angew Chen Int. Engl. Sep. 8, 2014, 53 (37); pp. 9841-9845.
Guest Ryan D el al: The Role of Extracellular Spacer Regions in the Optimal Design of Chimeric Immune Receptors—Evaluation of Four Different SCFVS and ANTIGENS11, Journal of Immunotherapy, Lippincott Williams & Wilkings, US, vol. 28, No. 3, pp. 203-211, Jan. 1, 2005 (Jan. 1, 2005).
Notice of Allowance (U.S. Appl. No. 15/476,699) dated Jul. 22, 2019, related to this subject application.
Notice of Allowance (U.S. Appl. No. 15/476,699) dated Oct. 7, 2019, related to this subject application.
Third Notice of Allowance (U.S. Appl. No. 15/476,699) dated Oct. 23, 2019, related to this subject application.
First Official Action—dated Oct. 7, 2019 (EA Appl. No. 201891992), related to this subject application.
Communication 70(2) and 70a(2)(EP Application No. 17776859.5)(dated Oct. 24, 2019), related to this subject application.
OA—English and Spanish (PE Patent Application No. 001934-2018/DIN)(issued Oct. 18, 2019), related to this subject application.
English translation of Office Action in PE Patent Application No. 001934-2018/DIN)(dated Oct. 19, 2019), related to this subject application.
First Office Action for Ukrainian Patent Application No. a 2018 09953, dated Oct. 31, 2019 and is related to this subject application.
English Translation of First Office Action for Ukrainian Patent Application No. a 2018 09953, dated Oct. 31, 2019 and is related to this subject application.
Communication Pursuant to Rule 164(1) EPC, Application No. EP17776833.0—1116/3436036 PCT/US2017025516 related to this subject application, Oct. 2, 2019.
Communication 70a and 70a(2)(EP Application No. 17776766.2)(issued Nov. 22, 2019), related to this subject application.

International Search Report for PCT/US2017/025613 dated Jul. 12, 2017.
Official Office Action in Colombia Patent Application No.-NC2019/008646, dated Dec. 6, 2019.
Supplementary European Search Report for EP Application No. EP 17776859.5, dated Oct. 7, 2019, and is related to this subject matter.
European search Report for Application No. 17776766.2, PCT/US2017025351 dated Nov. 5, 2019.
First Official Action, English Translation—dated Nov. 7, 2019 (EA Application No. 201831992), related to this subject application.
Notice To Comply with Requirements for Sequence Disclosure (U.S. Appl. No. 15/476,699) dated Aug. 14, 2018.
Examiner Initiated Interview Summary (U.S. Appl. No. 15/476,699) dated Jun. 14, 2019.
Notice of Acceptance of request to add inventor in U.S. Appl. No. 15/476,309, dated Jun. 18, 2019.
Addition of Inventor (Jonathan Bellk added as an inventor to the application)(SG Patent Application No. 11201808403S)—dated Nov. 6, 2019.
Amendment Notification—Request for Correction of Error Accepted Accepted (Jonathan Bellk added as an inventor to the application)(NZ Patent Application No. 746700)—dated Oct. 4, 2019.
Notice to file Corrected Application Papers (U.S. Appl. No. 16/658,480) dated Oct. 29, 2019.
Notice to file Corrected Application Papers (U.S. Appl. No. 16/569,341) dated Sep. 25, 2019.
Notice To File Missing Parts (U.S. Appl. No. 16/570,645) dated Sep. 24, 2019.
First Office Action in Primary Examination for Taiwanese Patent Application No. 106111228; 883738, dated Sep. 23, 2019, and is related to this subject application.
Search Report in Primary Examination for Taiwanese Patent Application No. 106111228; 883738, dated Sep. 23, 2019, and is related to this subject application.
First Office Action and search report, English Translation, in Primary Examination for Taiwanese Patent Application No. 106111228; 883738, dated Sep. 13, 2019, and is related to this subject application.
Notification Prior to Examination of Patent Application No. 261941 According to Section 18 of the Law and Regulation 36 of the Regulations dated Nov. 17, 2019.
English Translation notification Prior to the Examination of Patent Application No. 261941 According to Section 18 of the Law and Regulation 36 of the Regulations dated Nov. 17, 2019.
Notification Prior to Examination of Patent Application No. 262041 According to Section 18 of the Law and Regulation 36 of the Regulations dated Nov. 17, 2019.
English Translation Notification Prior to Examination of Patent Application No. 232041 According to Section 18 of the Law and Regulation 36 of the Regulations dated Nov. 17, 2019.
Notification Prior to Examination of Patent Application No. 261942 According to Section 18 of the Law and Regulation 36 of the Regulation dated Nov. 17, 2019.
English Translation Notification Prior to Examination of Patent Application No. 261942 According to Section 18 of the Law and Regulation 36 of the Regulations dated Nov. 17, 2019.
English Translation Official Office Action in Colombia Patent Application No.-NC2019/0008646, dated Dec. 6, 2019.
Notification of Grant of Patent received in Colombia Patent Application No. NC2018/0010547, dated Nov. 25, 2019, 3 pages.
English Translation of Notification of Grant of Patent received in Colombia Patent Application No. NC2018/0010547, dated Nov. 25, 2019, 3 pages.
Fee receipt for TH application No. 1801006120, dated Oct. 18, 2019, 1 page.
First Examination Report for Canadian Application No. 3019650, dated Sep. 19, 2019, which is related to this subject application.
Supplementary European Search Report for EP Application No. EP 17 77 6859, dated Oct. 7, 2019, and is related to this subject application.
Leong S.R. et al.: "An anti-CD3/anti-CLL-1 bispecific antibody for the treatment of acute myeloid leukemia", Blood, Feb. 2, 2017, vol. 129, No. 5, pp. 609-618.

(56) References Cited

OTHER PUBLICATIONS

First Examination Report of New Zealand Patent Application No. 747172, dated Aug. 29, 2019 and is related to this subject application.
English translation of Office Action and Search Report for Taiwanese Patent Application No. 106111224, dated Sep. 20, 2019 and is related to this application.
Original version of Office Action for Taiwanese Patent Application No. 106111224, dated Sep. 10, 2019 and is related to this subject application.
Original version of Search Report for Taiwanese Patent Application No. 106111224, dated Sep. 10, 2019 and is related to the subject application.
Office Action dated Oct. 2, 2019 for Taiwan Patent Application No. 106111226, which is related to this subject application.
Search Report dated Oct. 2, 2019 for Taiwan Patent Application No. 106111226, which is related to this subject application.
English Translation of Office Action dated Oct. 2, 2019 for Taiwan Patent Application No. 106111226, which is related to this subject application.
Supplementary Partial European Search Report, dated Sep. 19, 2019 for European Patent Application No. 17776833, which is related to this subject application.
Final Office Action for U.S. Appl. No. 15/476,309, dated Sep. 10, 2019, which is related to this subject application.
Jena et al., "Redirecting T-cell specificity by introducing a tumor-specific chimeric antigen receptor", Blood Aug. 19, 2010, vol. 116, No. 7, pp. 1035-1044.
Bonini et al., "Adoptive T-cell therapy for cancer: The era of engineered T cells", European Journal of Immunology; 2015, vol. 45: pp. 2457-2469.
Chames et al., "Therapeutic antibodies: successes, limitations and hoped for the furture", British Journal of Pharmacology; 2009, vol. 157, pp. 220-233.
Gura et al., "Systems for Identifying New Drugs Are Often Faulty", Science, Nov. 7, 1997, vol. 278, pp. 1041-1042.
Kaiser et al., "First Pass at Cancer Genome Reveals Complex Landscape", Science; 2006, vol. 313, pp. 1370.
Austrailian examination report for application No. 2017240788 dated May 24, 2019 (3 pages).
Moroccan examination report for application No. 43603 dated Mar. 14, 2018 (8 pages).
Englsh translation of Moroccan examination report for application No. 43603 dated Mar. 14, 2018.
Original version of Office Action for Japanese Patent Application No. 2018-551953, dated Oct. 29, 2019, which is related to this subject application.
English translation of Office Action for Japanese Patent Application No. 2018-551953, dated Oct. 29, 2019, which is related to this subject application.
Original version of Official Action for Panamanian Patent Application No. PI/2018/92399-01, dated Mar. 14, 2019, which is related to this subject application.
English translation of Official Action for Panamanian Patent Application No. PI/2018/92399-01, dated Mar. 14, 2019, which is related to this subject application.
Original and English Translation of Office Action dated Jan. 6, 2020 in Korean Patent Application No. 10-2018-7031572.

* cited by examiner

FIG. 1A – (SEQ ID NO: 1)

MLRLLLALNLFPSIQVTGNKILVKQSPMLVAYDNAVNLSCKYSYNLFSREFRASLH

KGLDSAVEVCVVYGNYSQQLQVYSKTGFNCDGKLGNESVTFYLQNLYVNQTDIYFC

KIEVMYPPPYLDNEKSNGTIIHVKGKHLCPSPLFPGPSKPFWVLVVVGGVLACYSL
          *Hinge Domain*                    *Transmembrane*

LVTVAFIIFWVRSKRSRLLHSDYMNMTPRPPGPTRKHYQPYAPPRDFAAYRS
*Domain*                  *Signaling Domain*

FIG. 2A – Anti-CLL-1 Binding Molecules

```
              FR1                              CDR1         FR2              CDR2
24C1_VH    QVQLQESGPGLVKPSETLSLTCTVSGGSISS--YYWSWIRQFPGKGLEWIGYIYYSGS-T
24C8_VH    QVQLQESGPGLVKPSQTLSLTCTVSGGSISSGGEYWSWIRQHPGKGLEWIGYIHHSGS-T
20C5.1_VH  QVQLVQSGAEVKKPGASVKVSCKVSGYTLT--ELSMHWVRQAPGKGLEWMGSEDPEDGET
20C5.2_VH  QVQLVESGGGVVQPGRSLRLSCAASGFTFSS--YEMHWVRQAPGKGLEWVAVISYDGSLK
              ****  :**    :  *:  ::  ::*  .*  :::        *;**  *******;.  :    ...:

FR3                                       CDR3             FR4
24C1_VH    NYNPSLKSRVTISVDTSKNQFSLKLSSVTAADTAVYYCVSLVYCGGDCYSGFDYWGQGTL
24C8_VH    HYNPSLKSRVTISIDTSKNLFSLRLSSVTAADTAVYYCASLVYCGGICYSGFDYWGQGTL
20C5.1_VH  IYAQKFQGRVTVTEDTSTDTAYMELSSLRSEDTAVYYCATESRGIG--WPYFDYWGQGTL
20C5.2_VH  YYVDSVKGRFTISRDNSKNRLYLQMNSLKAEDTAVYYCARERYSG------RDYWGQGTL
                 *  ..;.*.*;; *.*.;   {..,.*{ { *******.             *******

FR4
24C1_VH    VTVSS
24C8_VH    VTVSS
20C5.1_VH  VTVSS
20C5.2_VH  VTVSS
              *****
```

| FIG. 2B | SEQ ID NO: | | | |
|---|---|---|---|---|
| | VH | CDR1 | CDR2 | CDR3 |
| 24C1_VH | 125 | 93 | 97 | 101 |
| 24C8_VH | 126 | 94 | 98 | 102 |
| 20C5.1_VH | 127 | 95 | 99 | 103 |
| 20C5.2_VH | 128 | 96 | 100 | 104 |

FIG. 2C – Anti-CLL-1 Binding Molecules

```
              FR1                       CDR1              FR2            CDR2    FR3
24C1_VL    DIQLTQSPSSLSASVGDRVSFTCQASQDINHFLNWYQQKPGKAPKLLIYDASNLETGVPS
24C8_VL    DIQLTQSPSSLSASVGDRVSFTCQASQDINNFLNWYQQKPGKAPKLLIYDASNLETGVPS
20C5.1_VL  DIQMTQSPSSLSASVGDRVTITCRASQSISSYLNWYQQKPGKAPKLLISGASSLKSGVPS
20C5.2_VL  EIVMTQSPATLSVSPGERATLSCRASQSVSSLLTWYQQKPGQAPRLLIFGASTRATGIPA
             *  ****.:**.*  *:*.::::*:***.:..  ********;**;***  .**.  *:*:

FR3                        CDR3            FR4
24C1_VL    RFSGSGSGTDFTFTISSLQPEDIATYYCQQYGILPFTFGGGTKVEIKR
24C8_VL    RFSGSGSGTDFTFTISSLQPEDIATYYCQQYGNLPFTFGGGTKVEIKR
20C5.1_VL  RFSGSGSGTDFTLTISSLPPEDFATYYCQQSYSTPITFGQGTKLEIKR
20C5.2_VL  RFSGSGSGTGFTLTISSLQSEDFAVYYCQQYDTWFFTFGPGTKVDFKR
           *********.**;****** .**;*.*****   *;:****  **;;::**
```

| FIG. 2D | SEQ ID NO: | | | |
|---|---|---|---|---|
| | VL | CDR1 | CDR2 | CDR3 |
| 24C1 VL | 129 | 105 | 109 | 113 |
| 24C8 VL | 130 | 106 | 110 | 114 |
| 20C5.1 VL | 131 | 107 | 111 | 115 |
| 20C5.2 VL | 132 | 108 | 112 | 116 |

FIG. 2E – Anti-BCMA Binding Molecules

```
                  FR1                          CDR1         FR2                CDR2
FS-21495_VH  EVQLLESGGGLVQPGGSLRLSCAASG--FTFSSYAMSWVRQAPGKGLEWVSAISGSGGST
PC-21497_VH  QVQLVESGGGVVQPGRSLRLSCAASG--FTFSSYGMHWVRQAPGKGLEWVAVISYDGSNK
AJ-21508_VH  QVQLVQSGAEVKKPGASVKVSCKASG--YTFTSYYMHWVRQAPGQGLEWMGIINPGGGST
NM-21517_VH  QLQLQESGPGLVKPSETLSLTCTVSGGSISSSYYWGWIRQPPGKGLEWIGSISYSG-ST
TS-21522_VH  EVQLVESGGGLVQPGGSLRLSCAASG--FTFSSYSMNWVRQAPGKGLEWVSTISSSSTI
RY-21527_VH  QVQLVESGGGVVQPGRSLRLSCAASG--FTFSSYEMHWVRQAPGKGLEWVAVISYDGSNK
PP-21528_VH  QVQLVQSGAEVKKPGSSVKVSCKASG--GTFSSYAISWVRQAPGQGLEWMGGIIPIFGTA
RD-21530_VH  QVQLVESGGGVVQPGRSLRLSCAASG--FTFSSYGMHWVRQAPGKGLEWVAVISYDGSNK

CDR2                FR3                         CDR3
FS-21495_VH  YYADSVKGRFTISRDNSKNTLYLQMNSLRAEDTAVYYCAR-AEM------GAVFDIWGQ
PC-21497_VH  YYADSVKGRFTISRDNSKNTLYLQMNSLRAEDTAVYYCARDGYLGGL---WY-FDLWGR
AJ-21508_VH  SYAQKFQGRVTMTRDTSTSTVYMELSSLRSEDTAVYYCAR----------ESWPMDVWGQ
NM-21517_VH  YYNPSLKSRVTISVDTSKNQFSLKLSSVTAADTAVYYCARGRGYATS-----LAFDIWGQ
TS-21522_VH  YYADSVKGRFTISRDNAKNSLYLQMNSLRAEDTAVYYCARGSQE------HLIFDYWGQ
RY-21527_VH  YYADSVKGRFTISRDNSKNTLYLQMNSLRAEDTAVYYCARTDEWGSP---PG-LDYWGQ
PP-21528_VH  NYAQKFQGRVTITADESTSTAYMELSSLRSEDTAVYYCARTPEYSSSIWHYYYGMDVWGQ
RD-21530_VH  YYADSVKGRFTISRDNSKNTLYLQMNSLRAEDTAVYYCVKGPLQEPFY---DYGMDVWGQ

FR4
FS-21495_VH  GTMVTVSS
PC-21497_VH  GTLVTVSS
AJ-21508_VH  GTTVTVSS
NM-21517_VH  GTMVTVSS
TS-21522_VH  GTLVTVSS
RY-21527_VH  GTLVTVSS
PP-21528_VH  GTTVTVSS
RD-21530_VH  GPTVTVSS
```

| FIG. 2F | SEQ ID NO: | | | |
|---|---|---|---|---|
| | VH | CDR1 | CDR2 | CDR3 |
| FS-21495 VH | 77 | 13 | 21 | 29 |
| PC-21497 VH | 78 | 14 | 22 | 30 |
| AJ-21508 VH | 79 | 15 | 23 | 31 |
| NM-21517 VH | 80 | 16 | 24 | 32 |
| TS-21522 VH | 81 | 17 | 25 | 33 |
| RY-21527 VH | 82 | 18 | 26 | 34 |
| PP-21528 VH | 83 | 19 | 27 | 35 |
| RD-21530 VH | 84 | 20 | 28 | 36 |

FIG. 2G – Anti-BCMA Binding Molecules

```
                    FR1                    CDR1              FR2            CDR2
FS-21495_VL  EIVLTQSPATLSLSPGERATLSC RASQSVSR------YLA WYQQKPGQAPRLLIY DASNR
PC-21497_VL  DIVMTQSPLSLPVTPGEPASISC RSSQSLLHSNG-YNYLD WYLQKPGQSPQLLIY LGSNR
AJ-21508_VL  EIVMTQSPATLSVSPGERATLSC RASQSVSS------NLA WYQQKPGQAPRLLIY GASTR
NM-21517_VL  EIVLTQSPATLSLSPGERATLSC RASQSVSS------YLA WYQQKPGQAPRLLIY DASNR
TS-21522_VL  EIVLTQSPATLSLSPGERATLSC RASQSVSR------YLA WYQQKPGQAPRLLIY DASNR
RY-21527_VL  DIQLTQSPSSVSASVGDPVTITC RASQGISS------WLA WYQQKPGKAPKLLIY GASSL
PP-21528_VL  DIVMTQSPDSLAVSLGERATINC KSSQSVLYSSNNKNYLA WYQQKPGQPPKLLIY WASTR
RD-21530_VL  EIVMTQSPATLSVSPGERATLSC RASQSVSS------NLA WYQQKPGQAPRLLIY GASTR

CDR2                 FR3                  CDR3       FR4
FS-21495_VL  ATGIPARFSGSGSGTDFTLTISSLEPEDFAVYYC QQRISWPFT FGGGTKVEIK
PC-21497_VL  ASGVPDRFSGSGSGTDFTLKISRVEAEDVGVYYC MQSLQLPLT FGGGTKVEIK
AJ-21508_VL  ATGIPARFSGSGSGTEFTLTISSLQSEDFAVYYC QQYAAYP-T FGGGTKVEIK
NM-21517_VL  ATGIPARFSGSGSGTDFTLTISSLEPEDFAVYYC QQRHVWPPT FGGGTKVEIK
TS-21522_VL  ATGIPARFSGSGSGTDFTLTISSLEPEDFAVYYC QQRFYYPWT FGGGTKVEIK
RY-21527_VL  QSGVPSRFSGSGSGTDFTLTISSLQPEDFATYYC QQIYTFPFT FGGGTKVEIK
PP-21528_VL  ESGVPDRFSGSGSGTDFTLTISSLQAEDVAVYYC QQEAHTPFT FGGGTKVEIK
RD-21530_VL  ATGIPARFSGSGSGTEFTLTISSLQSEDFAVYYC QQHHVWPLT FGGGTKVEIK
```

| FIG. 2H | SEQ ID NO: | | | |
|---|---|---|---|---|
| | VL | CDR1 | CDR2 | CDR3 |
| FS-21495 VL | 85 | 37 | 45 | 53 |
| PC-21497 VL | 86 | 38 | 46 | 54 |
| AJ-21508 VL | 87 | 39 | 47 | 55 |
| NM-21517 VL | 88 | 40 | 48 | 56 |
| TS-21522 VL | 89 | 41 | 49 | 57 |
| RY-21527 VL | 90 | 42 | 50 | 58 |
| PP-21528 VL | 91 | 43 | 51 | 59 |
| RD-21530 VL | 92 | 44 | 52 | 60 |

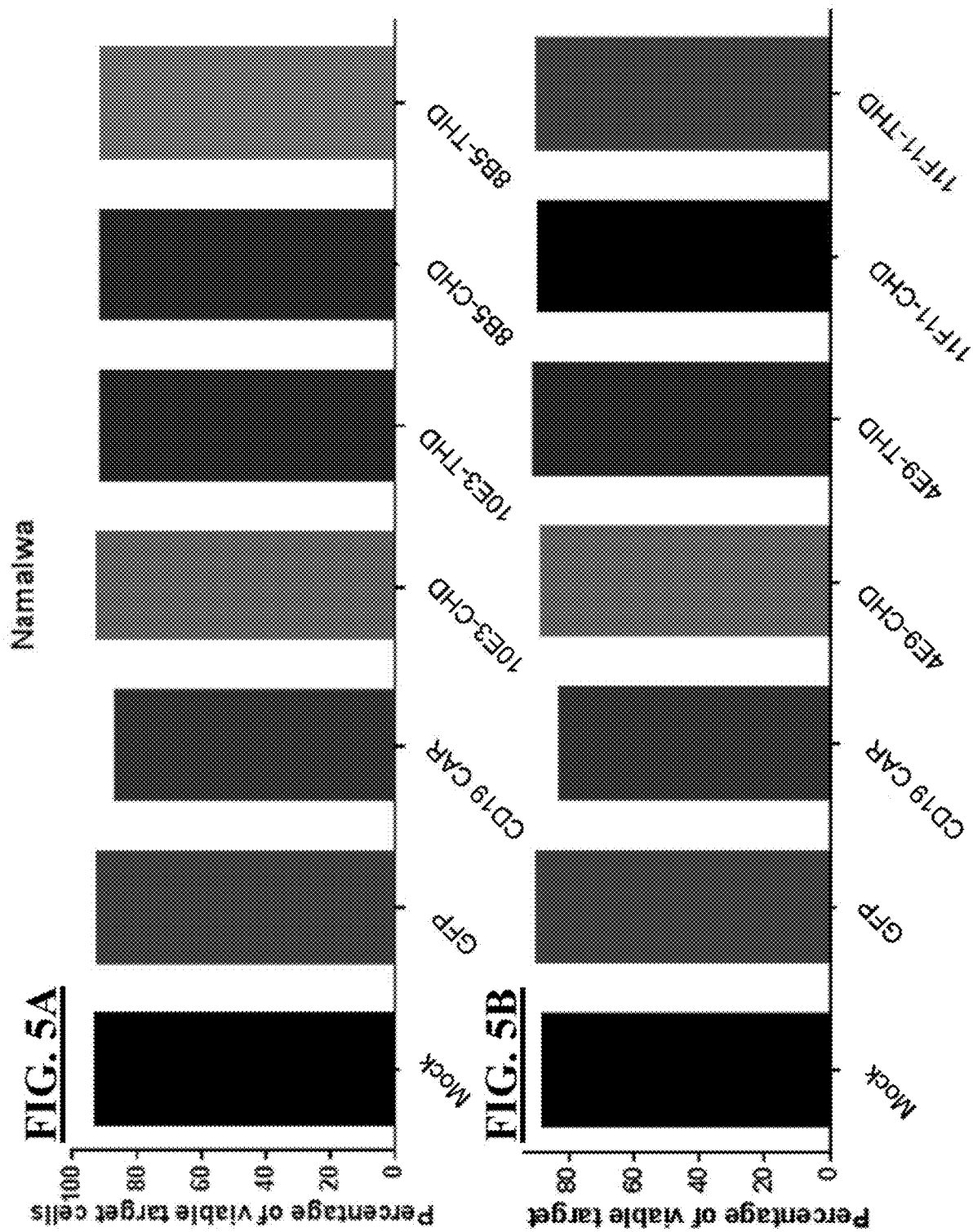

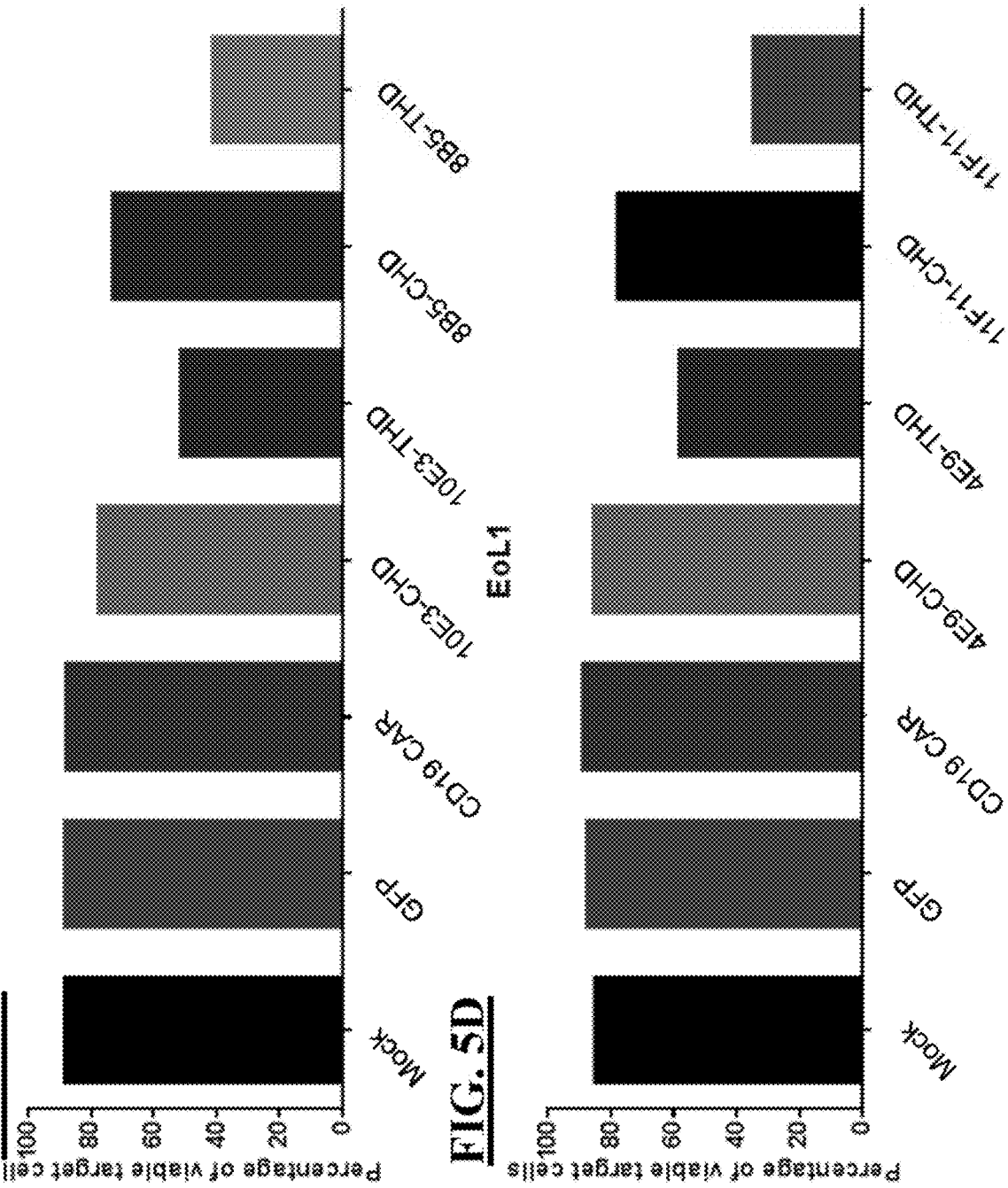

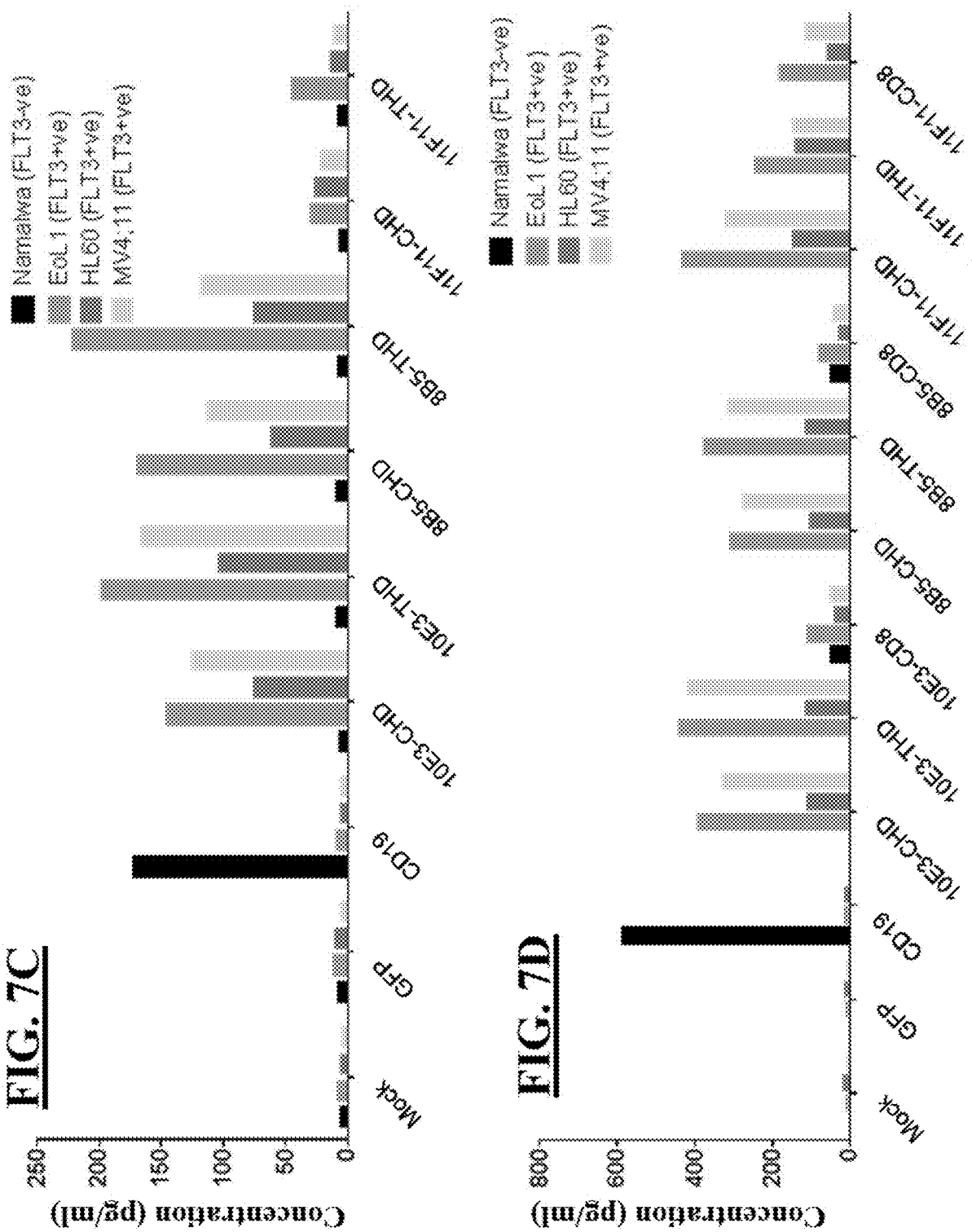

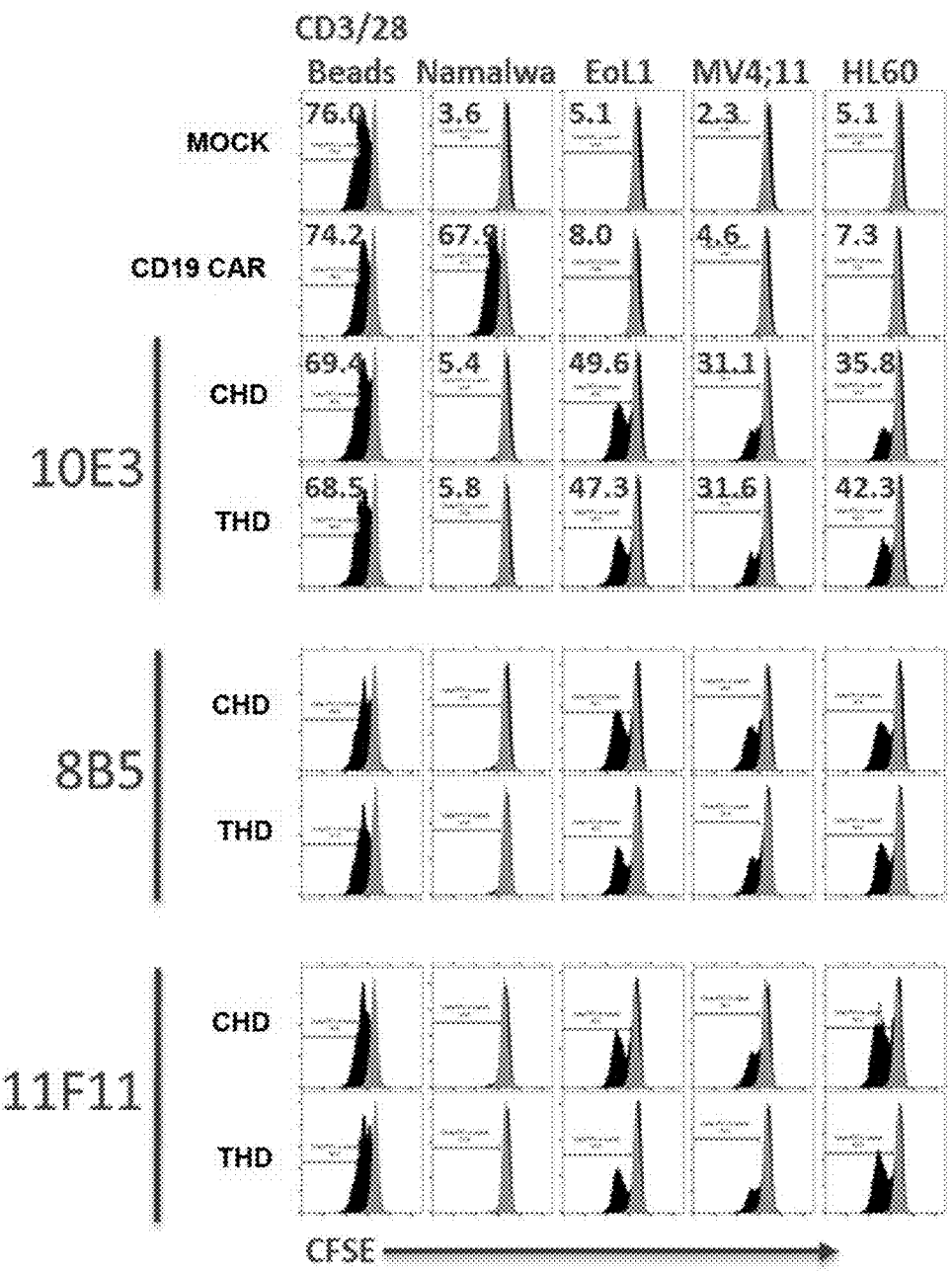

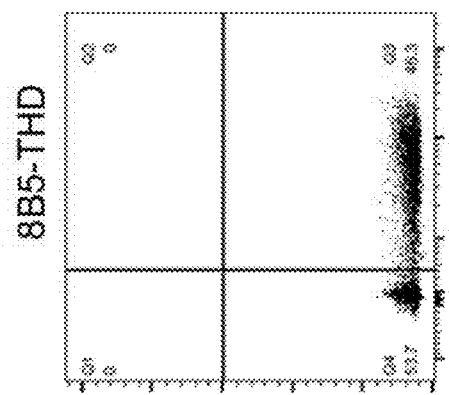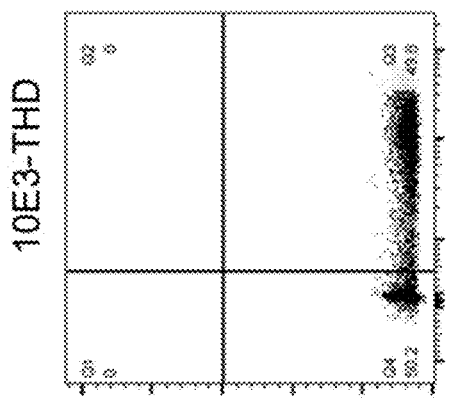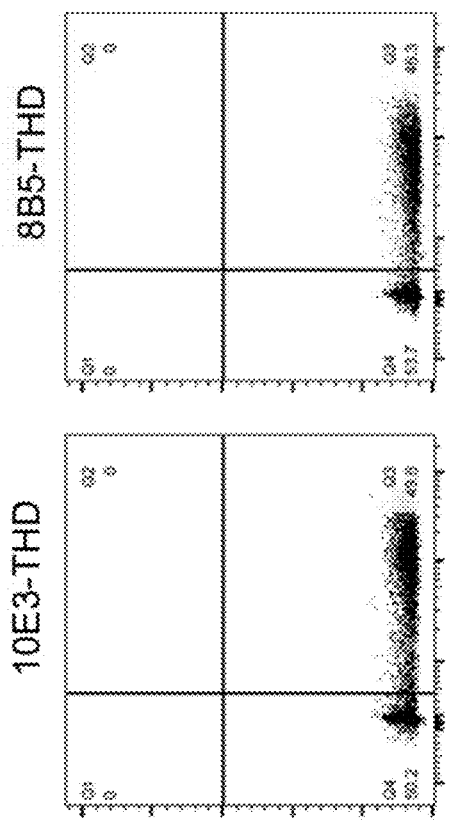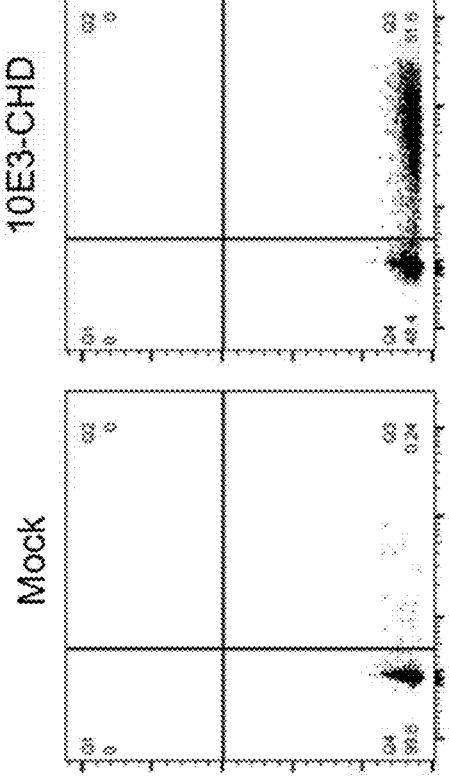

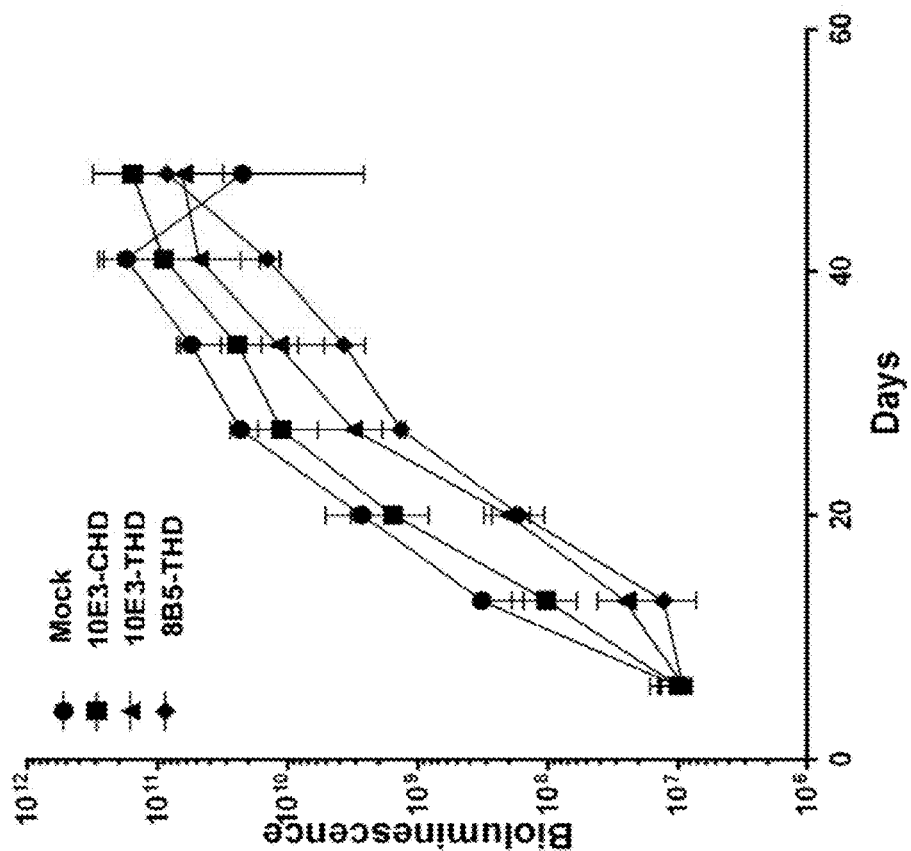
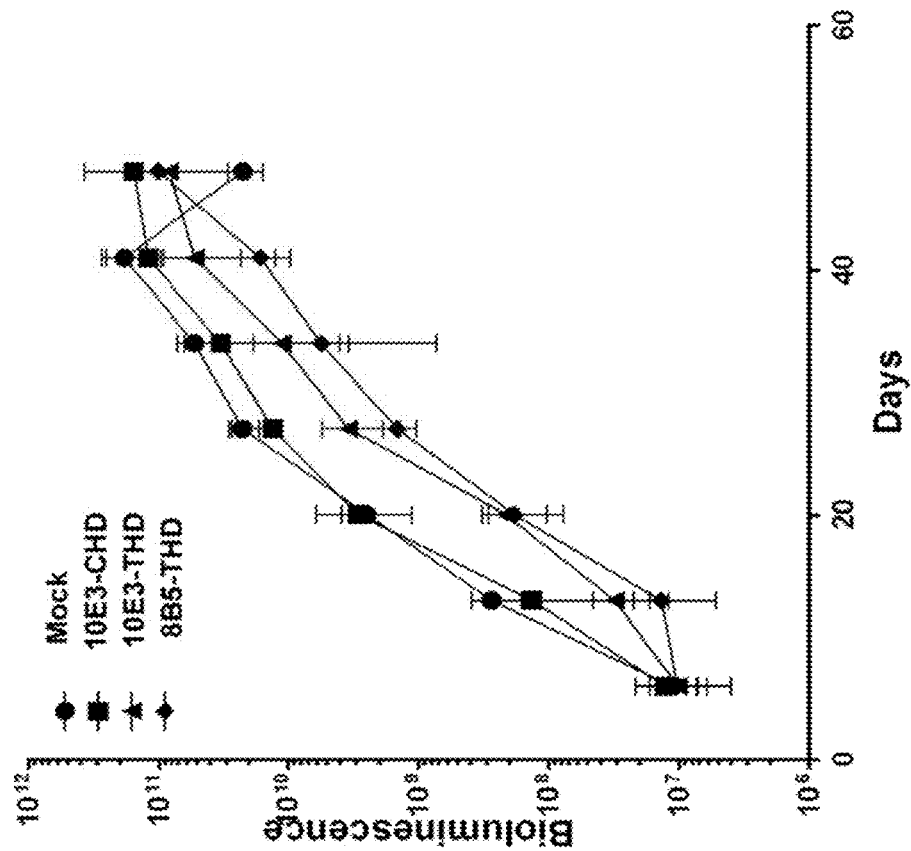

FIG. 10G

| Day | Mock vs 10E3-CHD | Mock vs 10E3-THD | Mock vs 8B5-THD | 10E3-THD vs 8B5-THD |
|---|---|---|---|---|
| 6 | 0.756 | 0.657 | 0.690 | 0.959 |
| 13 | 0.067 | 0.0004 | 0.0002 | 0.028 |
| 20 | 0.777 | 0.0022 | 0.0020 | 0.639 |
| 27 | 0.158 | <0.0001 | <0.0001 | 0.042 |
| 34 | 0.200 | 0.0004 | 0.0001 | 0.142 |
| 41 | 0.376 | 0.0072 | 0.0009 | 0.054 |

24C8 HL THD

24C8 HL CHD

Protein L

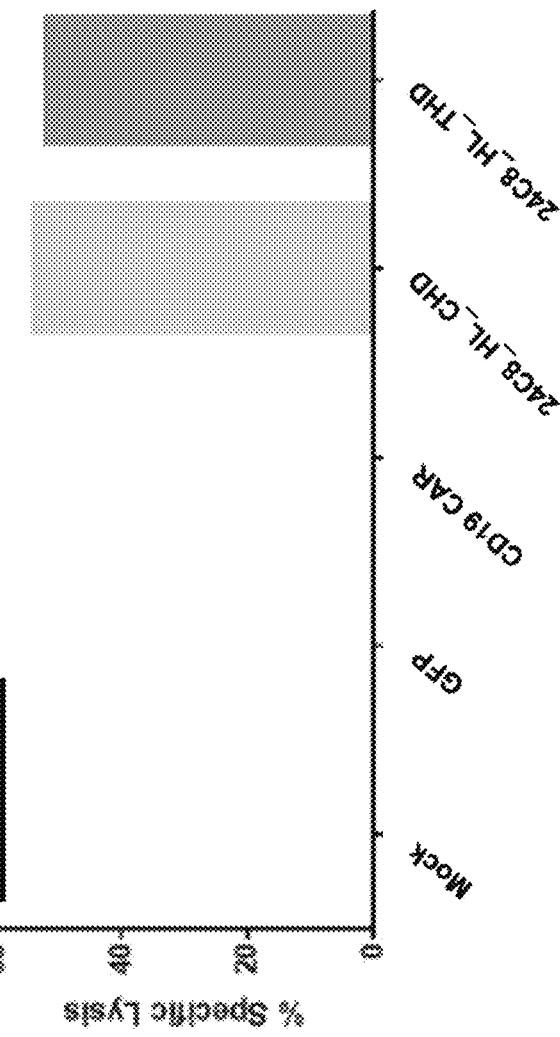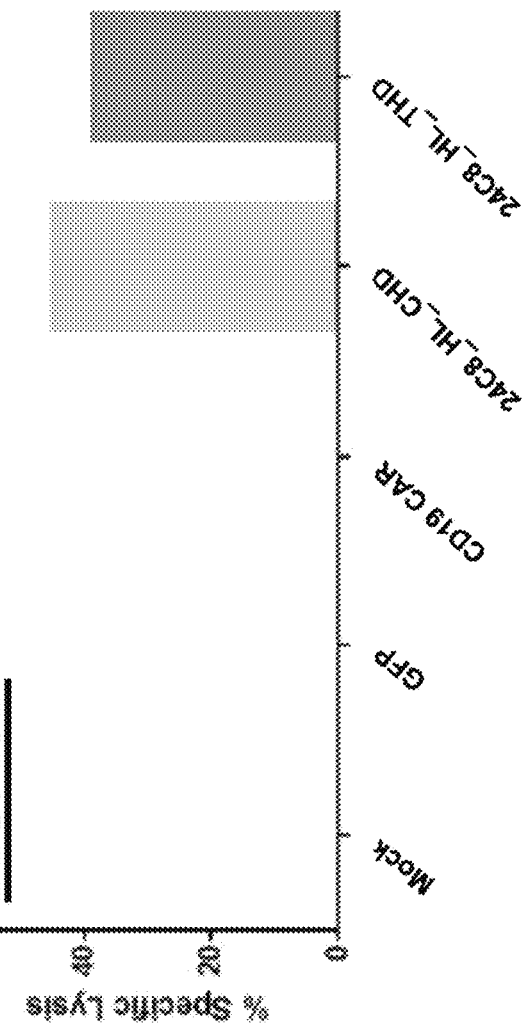

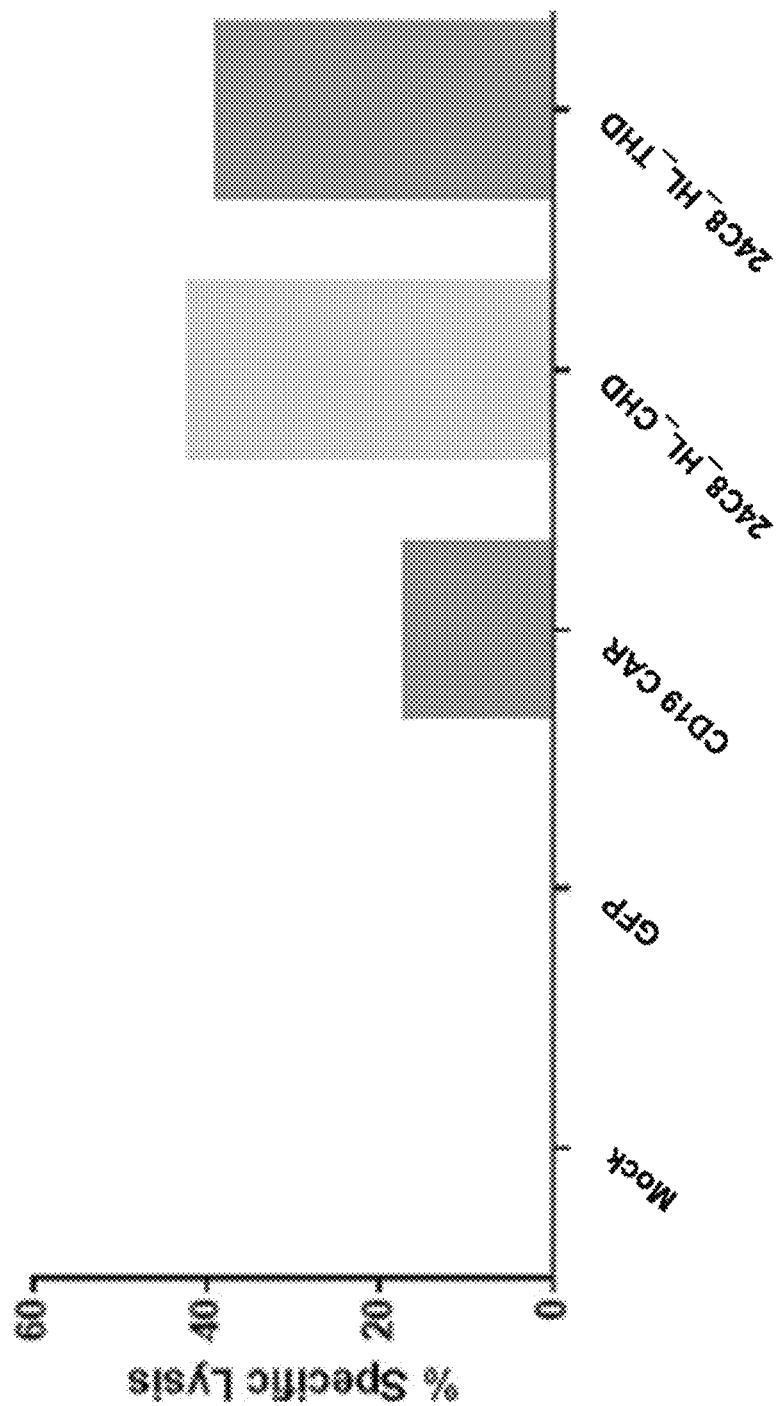

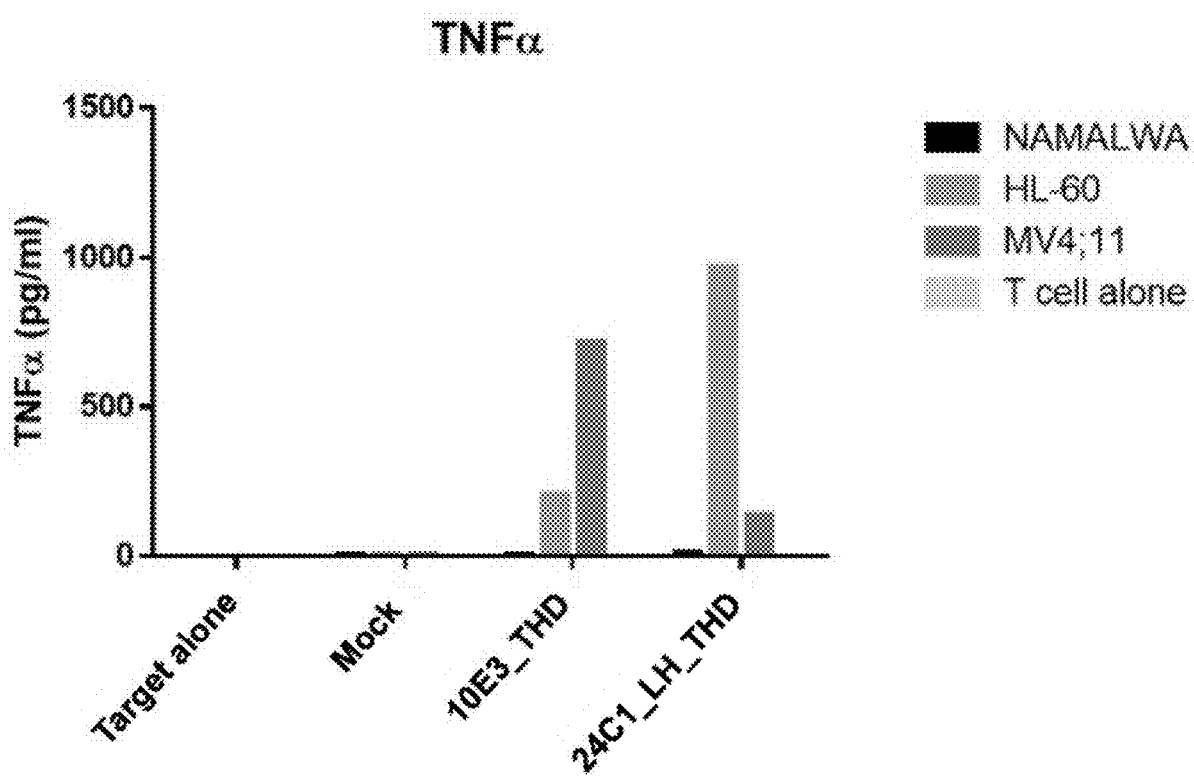

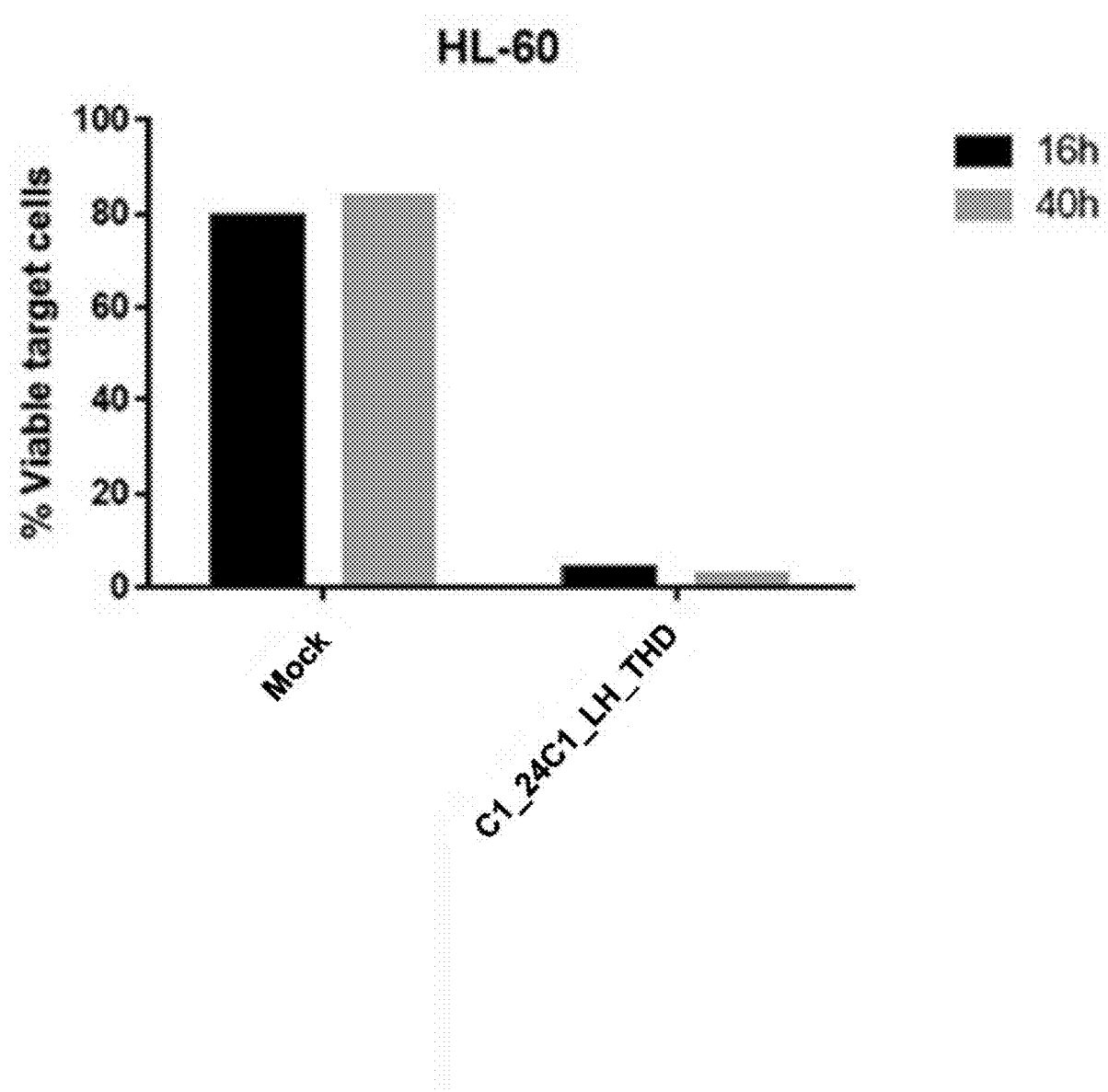

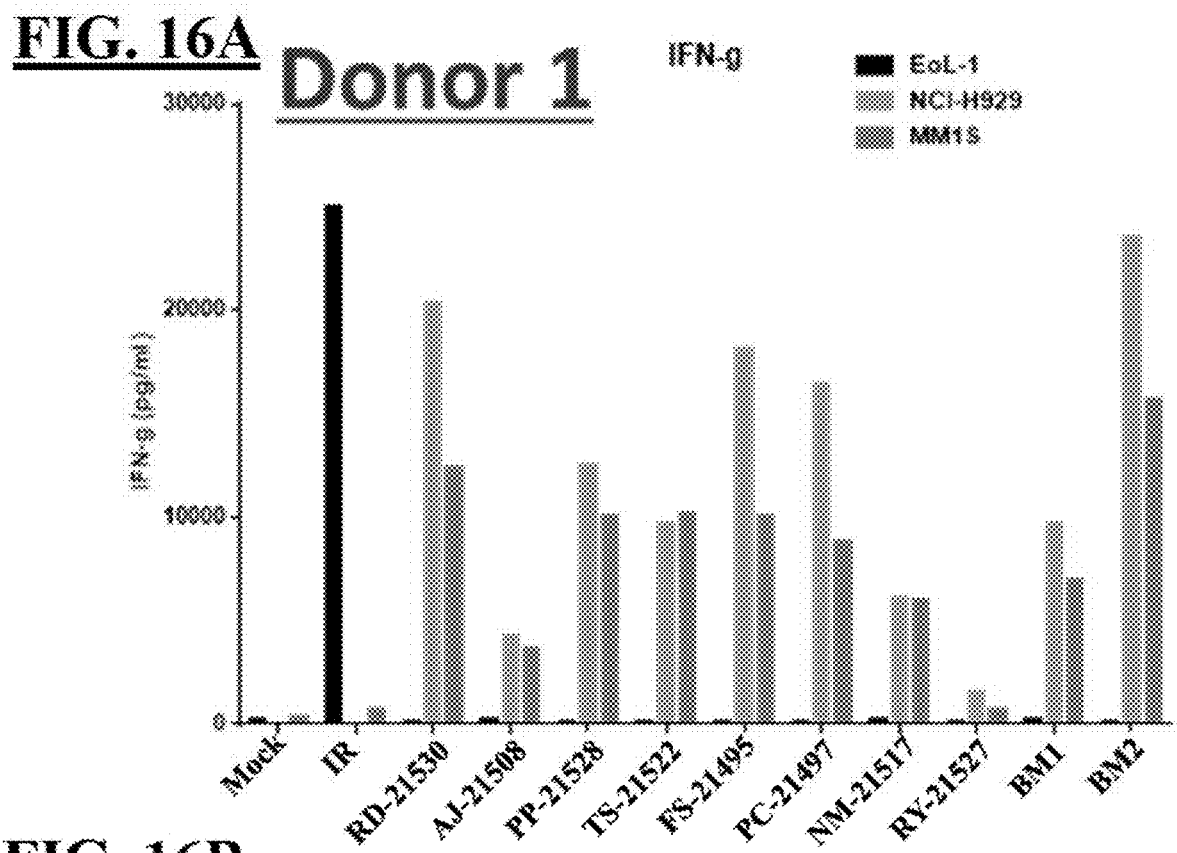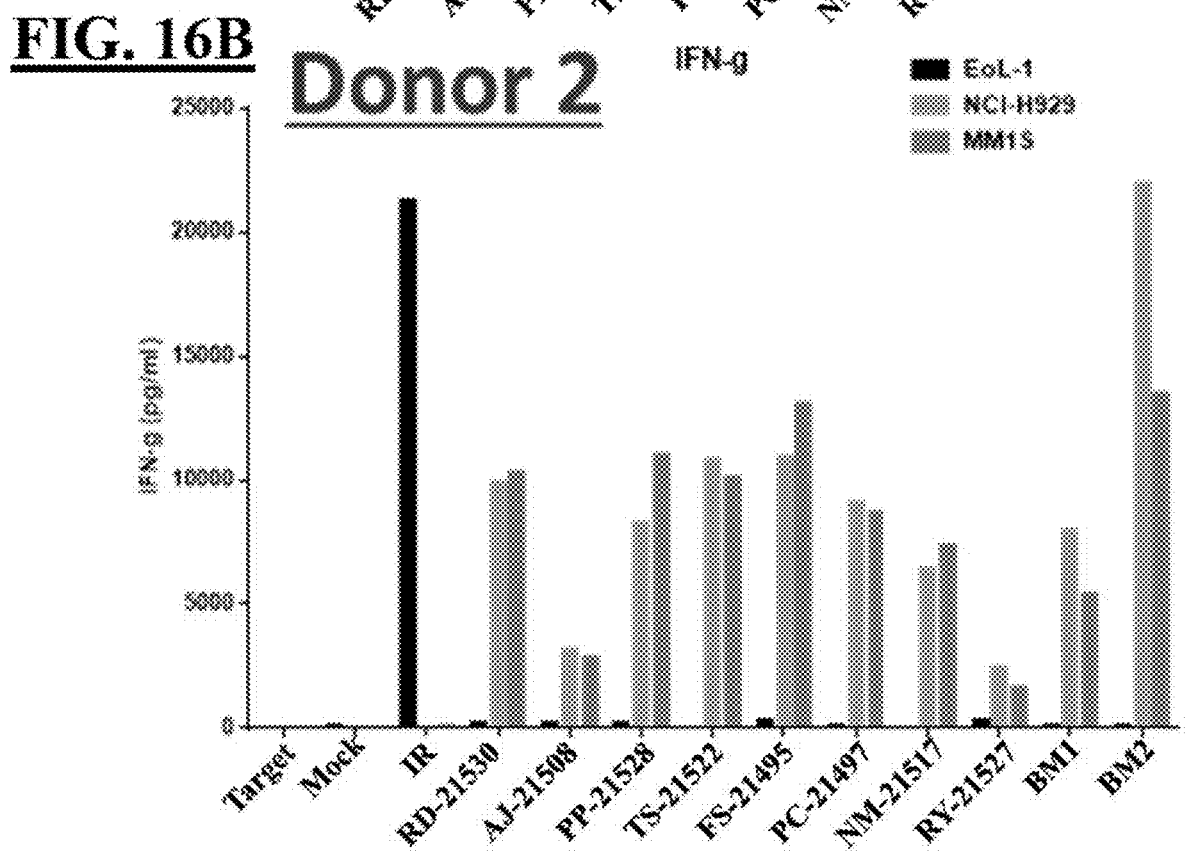

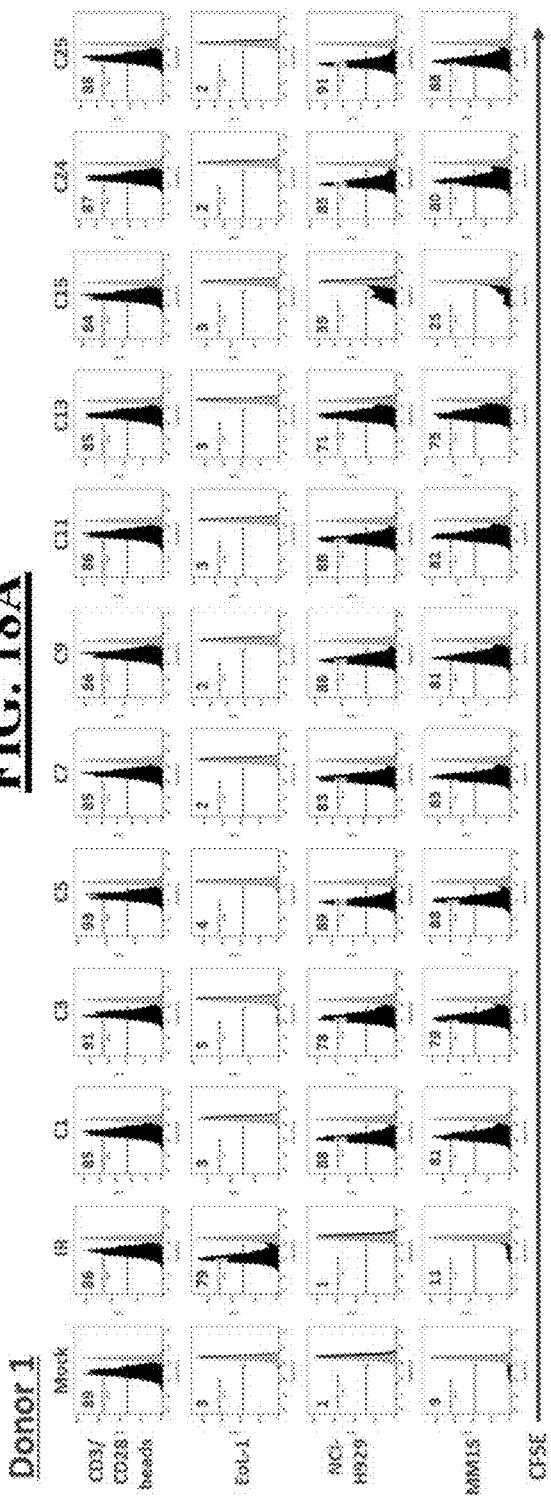
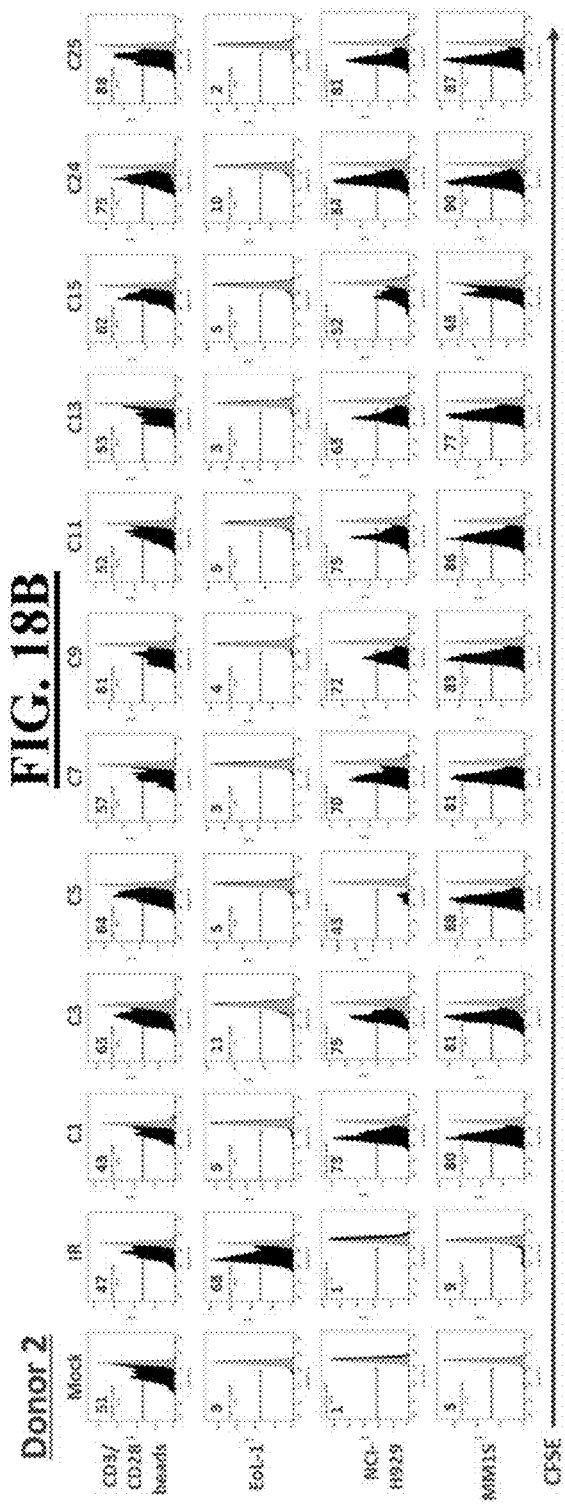
FIG. 18A
FIG. 18B

US 10,603,380 B2

CHIMERIC ANTIGEN AND T CELL RECEPTORS AND METHODS OF USE

CROSS REFERENCE TO RELATED APPLICATIONS

This application claims the benefit of U.S. Provisional Patent Application No. 62/317,258, filed Apr. 1, 2016, which is hereby incorporated by reference in its entirety.

REFERENCE TO SEQUENCE LISTING

The instant application contains a Sequence Listing which has been submitted electronically in ASCII format and is hereby incorporated by reference in its entirety. Said ASCII copy, created on Feb. 28, 2019, is named K-1031_02US SL.txt and is 450,469 bytes in size.

BACKGROUND OF THE INVENTION

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Current therapies T cell therapies rely on enriched or modified human T cells to target and kill cancer cells in a patient. To increase the ability of T cells to target and kill a particular cancer cell, methods have been developed to engineer T cells to express constructs which direct T cells to a particular target cancer cell. Chimeric antigen receptors (CARs) and engineered T cell receptors (TCRs), which comprise binding domains capable of interacting with a particular tumor antigen, allow T cells to target and kill cancer cells that express the particular tumor antigen.

A need exists for improved CARs and TCRs for targeting and killing cancer cells.

SUMMARY OF THE INVENTION

The present invention addresses this need by providing compositions and methods comprising genetically engineered immune cells that express antigen receptors (CARs) or T cell receptors (TCRs) which specifically target and kill cancer cells.

A CAR may comprise, for example, (i) an antigen-specific component ("antigen binding molecule"), (ii) one or more costimulatory domains (which includes a hinge domain), and (iii) one or more activating domains. Each domain may be heterogeneous, that is, comprised of sequences derived from different protein chains. CAR-expressing immune cells (such as T cells) may be used in various therapies, including cancer therapies.

As described in more detail below, including the Examples section, CARs comprising a costimulatory domain which includes a truncated hinge domain ("THD") provides unexpectedly superior properties when compared to a CAR comprising a costimulatory domain which includes a complete hinge domain ("CHD"). Polynucleotides encoding such CARs can be transduced into T cells and the CARs are expressed in T cells, e.g., a patient's own T cells. When the transduced T cells are transplanted back to a patient, the CARS direct the T cells to recognize and bind an epitope present on the surface of cancer cells, thus, allowing binding of cancer cells rather than non-cancerous cells. This binding leads to activation of cytolytic mechanisms in the T cell that specifically kill the bound cancer cells. Prior to the present invention, it was unknown that a CARs comprising a THD is superior to a CAR comprising a CHD. Thus, the present invention satisfies an unmet need that exists for novel and improved therapies for treating cancer.

An aspect of the present invention is an isolated polynucleotide encoding a chimeric antigen receptor (CAR) or a T cell receptor (TCR), which comprises (i) an antigen binding molecule, (ii) a costimulatory domain, and (iii) an activating domain. The costimulatory domain may comprise an extracellular domain, a transmembrane domain, and an intracellular domain, wherein the extracellular domain comprises a truncated hinge domain consisting essentially of or consisting of (i) an amino acid sequence at least about 80%, at least about 85%, at least about 90%, at least about 95%, at least about 96%, at least about 97%, at least about 98%, at least about 99%, or about 100% identical to amino acids 123 to 152 of SEQ ID NO: 1 and, optionally, (ii) one to six amino acids.

In some embodiments, the one to six amino acids are heterologous amino acids.

In some embodiments, the truncated hinge domain consists essentially of or consists of an amino acid sequence at least about 80%, at least about 85%, at least about 90%, at least about 95%, at least about 96%, at least about 97%, at least about 98%, at least about 99%, or about 100% identical to amino acids 123 to 152 of SEQ ID NO: 1.

In some embodiments, the amino acid sequence is encoded by a nucleotide sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 2.

In some embodiments, the transmembrane domain is a transmembrane domain of 4-1BB/CD137, an alpha chain of a T cell receptor, a beta chain of a T cell receptor, CD3 epsilon, CD4, CD5, CD8 alpha, CD9, CD16, CD19, CD22, CD33, CD37, CD45, CD64, CD80, CD86, CD134, CD137, CD154, or a zeta chain of a T cell receptor, or any combination thereof.

In some embodiments, the transmembrane domain comprises an amino acid sequence at least about 80%, at least about 85%, at least about 90%, at least about 95%, at least about 96%, at least about 97%, at least about 98%, at least about 99%, or about 100% identical to SEQ ID NO: 5.

In some embodiments, the transmembrane domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 4.

In some embodiments, the intracellular domain comprises a signaling region of 4-1BB/CD137, activating NK cell receptors, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptors, DAP-10, DNAM1 (CD226), Fc gamma receptor, GADS, GITR, HVEM (LIGHTR), IA4, ICAM-1, ICAM-1, Ig alpha (CD79a), IL2R beta, IL2R gamma, IL7R alpha, Immunoglobulin-like proteins, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX-40, PAG/Cbp, programmed death-1 (PD-1), PSGL1, SELPLG (CD162), signaling lymphocytic activation molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, a Toll ligand receptor, TRANCE/RANKL, VLA1, or VLA-6, or a combination thereof.

In some embodiments, the intracellular domain comprises a 4-1BB/CD137 signaling region.

In some embodiments, the intracellular domain comprises an amino acid sequence at least about 80%, at least about 85%, at least about 90%, at least about 95%, at least about 96%, at least about 97%, at least about 98%, at least about 99%, or about 100% identical to SEQ ID NO: 7.

In some embodiments, the intracellular domain comprises an amino acid sequence encoded by a nucleotide sequence at least about 80%, at least about 85%, at least about 90%, at least about 95%, at least about 96%, at least about 97%, at least about 98%, at least about 99%, or about 100% identical to SEQ ID NO: 6.

In some embodiments, the antigen binding molecule comprises a heavy chain variable region (VH) and a light chain variable region (VL), wherein the VH comprises 3 complementarity determining regions (CDRs) and the VL comprises 3 CDRs.

In some embodiments, the antigen binding molecule specifically binds an antigen selected from the group consisting of 5T4, alphafetoprotein, B cell maturation antigen (BCMA), CA-125, carcinoembryonic antigen, CD19, CD20, CD22, CD23, CD30, CD33, CD56, CD123, CD138, c-Met, CSPG4, C-type lectin-like molecule 1 (CLL-1), EGFRvIII, epithelial tumor antigen, ERBB2, FLT3, folate binding protein, GD2, GD3, HER1-HER2 in combination, HER2-HER3 in combination, HER2/Neu, HERV-K, HIV-1 envelope glycoprotein gp41, HIV-1 envelope glycoprotein gp120, IL-11Ralpha, kappa chain, lambda chain, melanoma-associated antigen, mesothelin, MUC-1, mutated p53, mutated ras, prostate-specific antigen, ROR1, or VEGFR2, or a combination thereof.

In some embodiments, the antigen binding molecule specifically binds BCMA, CLL-1, or FLT3.

In some embodiments, the activation domain comprises an amino acid sequence at least about 80%, at least about 85%, at least about 90%, at least about 95%, at least about 96%, at least about 97%, at least about 98%, at least about 99%, or about 100% identical to SEQ ID NO: 9 or SEQ ID NO: 251.

In some embodiments, the activation domain is encoded by a nucleotide sequence at least about 80%, at least about 85%, at least about 90%, at least about 95%, at least about 96%, at least about 97%, at least about 98%, at least about 99%, or about 100% identical to SEQ ID NO: 8.

In some embodiments, the CAR or TCR further comprises a leader peptide.

In some embodiments, the leader peptide comprises an amino acid sequence at least about 80%, at least about 85%, at least about 90%, at least about 95%, at least about 96%, at least about 97%, at least about 98%, at least about 99%, or about 100% identical to SEQ ID NO: 11.

In some embodiments, the leader peptide is encoded by a nucleotide sequence at least about 80%, at least about 85%, at least about 90%, at least about 95%, at least about 96%, at least about 97%, at least about 98%, at least about 99%, or about 100% identical to SEQ ID NO: 10.

Another aspect of the present invention is a vector comprising the polynucleotide of an above aspect or embodiment.

In some embodiments, the vector is an adenoviral vector, an adenovirus-associated vector, a DNA vector, a lentiviral vector, a plasmid, a retroviral vector, or an RNA vector, or any combination thereof.

Yet another aspect of the present invention is a polypeptide encoded by the polynucleotide of an above aspect or embodiment or the vector of an above aspect or embodiment.

In another aspect, the present invention is a cell comprising the polynucleotide of an above aspect or embodiment, the vector of an above aspect or embodiment, or the polypeptide of an above aspect or embodiment, or any combination thereof.

In some embodiments, the cell is a T cell.

In some embodiments, the T cell is an allogeneic T cell, an autologous T cell, an engineered autologous T cell (eACT™), or a tumor-infiltrating lymphocyte (TIL).

In some embodiments, the T cell is a CD4+ T cell.

In some embodiments, the T cell is a CD8+ T cell.

In some embodiments, the T cell is an in vitro cell.

In some embodiments, the T cell is an autologous T cell.

An aspect of the present invention is a composition comprising the polynucleotide of an above aspect or embodiment, comprising the vector of an above aspect or embodiment, comprising the polypeptide of an above aspect or embodiment, or comprising the cell of an above aspect or embodiment.

In some embodiments, the composition is formulated to be delivered to a subject, optionally, comprising at least one pharmaceutically-acceptable excipient.

Another aspect of the present invention is a method of making a cell expressing a CAR or TCR comprising transducing a cell with the polynucleotide of an above aspect or embodiment under suitable conditions.

In some embodiments, the method further comprises isolating the cell.

Yet another aspect of the present invention is a method of inducing an immunity against a tumor comprising administering to a subject an effective amount of a cell comprising the polynucleotide of an above aspect or embodiment, comprising the vector of an above aspect or embodiment, or the polypeptide of an above aspect or embodiment, or any combination thereof.

In another aspect, the present invention is a method of treating a cancer in a subject in need thereof comprising administering to the subject the polynucleotide of an above aspect or embodiment, the vector of an above aspect or embodiment, the polypeptide of an above aspect or embodiment, the cell of an above aspect or embodiment, or the composition of an above aspect or embodiment.

In some embodiments, the cancer is a hematologic cancer.

In some embodiments, the cancer is of the white blood cells.

In some embodiments, the cancer is of the plasma cells.

In some embodiments, the cancer is leukemia, lymphoma, or myeloma.

In some embodiments, the cancer is acute lymphoblastic leukemia (ALL) (including non T cell ALL), acute myeloid leukemia, B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia, chronic or acute leukemia, diffuse large B cell lymphoma (DLBCL), follicular lymphoma (FL), hairy cell leukemia, Hodgkin's Disease, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome, non-Hodgkin's lymphoma (NHL), plasma cell proliferative disorder (including asymptomatic myeloma (smoldering multiple myeloma or indolent myeloma), plasmablastic lymphoma, plasmacytoid dendritic cell neoplasm, plasmacytomas (including plasma cell dyscrasia; solitary myeloma; solitary plasmacytoma; extramedullary plasmacytoma; and multiple plasmacytoma), POEMS syndrome (also known as Crow-Fukase syndrome; Takatsuki disease; and PEP syndrome), primary mediastinal large B cell lymphoma (PMBC), small cell- or a large cell-follicular lymphoma, splenic marginal zone lymphoma (SMZL), systemic amyloid light chain amyloidosis, T-cell acute lymphoid leukemia ("TALL"), T-cell lymphoma, transformed follicular lymphoma, or Waldenstrom macroglobulinemia, or a combination thereof.

Generally, the present invention relates to Engineered Autologous Cell Therapy, abbreviated as "eACT™," also known as adoptive cell transfer. eACT™, is a process by which a patient's own T cells are collected and subsequently genetically engineered to recognize and target one or more antigens expressed on the cell surface of one or more specific cancer cells. T cells may be engineered to express, for example, a CAR or TCR. CAR positive (CAR+) T cells are engineered to express a CAR. CARs may comprise, e.g., an extracellular single chain variable fragment (scFv) with specificity for a particular tumor antigen, which is directly or indirectly linked to an intracellular signaling part comprising at least one costimulatory domain, which is directly or indirectly linked to at least one activating domain; the components may be arranged in any order. The costimulatory domain may be derived from a costimulatory protein known in the art, e.g., SEQ ID NO: 1, and the activating domain may be derived from, e.g., any form of CD3-zeta. In some embodiments, the CAR is designed to have two, three, four, or more costimulatory domains. In some embodiments, a CAR is engineered such that the costimulatory domain is expressed as a separate polypeptide chain. Examples of CAR T cell therapies and constructs are described in U.S. Patent Publication Nos. 2013/0287748, 2014/0227237, 2014/0099309, and 2014/0050708; International Patent Publications Nos. WO2012033885, WO2012079000, WO2014127261, WO2014186469, WO2015080981, WO2015142675, WO2016044745, and WO2016090369; and Sadelain et al, *Cancer Discovery*, 3: 388-398 (2013), each of which is incorporated by reference in its entirety.

Any aspect or embodiment described herein may be combined with any other aspect or embodiment as disclosed herein. While the present invention has been described in conjunction with the detailed description thereof, the foregoing description is intended to illustrate and not limit the scope of the present invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, dictionaries, documents, manuscripts and scientific literature cited herein are hereby incorporated by reference.

Other features and advantages of the invention will be apparent from the Drawings and the following Detailed Description, including the Examples, and the claims.

BRIEF DESCRIPTION OF THE FIGURES

The above and further features will be more clearly appreciated from the following detailed description when taken in conjunction with the accompanying drawings. The drawings however are for illustration purposes only; not for limitation.

FIG. 1A shows a costimulatory protein having the amino acid sequence of SEQ ID NO: 1. The costimulatory protein's hinge domain (solid underline), transmembrane domain (dotted underline), and signaling domain (dashed underline) are labeled. A novel truncated hinge domain ("THD") is bolded. FIG. 1B shows an example of a region within the amino acid sequence of SEQ ID NO: 1 used to derive one embodiment of a hinge region in the context of CAR, i.e., a region containing amino acids 114 to 152 of SEQ ID NO: 1 (herein referred to as a complete hinge domain or "CHD"; it is marked in black and dark grey). FIG. 1C shows the THD which contain amino acids 123 to 152 of SEQ ID NO: 1 (marked in black). In FIG. 1B, the portion of the hinge region that is excluded from FIG. 1C is marked dark grey and circled.

FIGS. 2A-2H show CLUTSTAL W (2.83) multiple sequence alignments of eight example binding molecules disclosed herein. FIG. 2A shows a sequence alignment of example anti-CLL-1 binding molecules comprising a VH domain. CDRs and framework regions FRs are shown, as determined by Chothia numbering (FIG. 2A). FIG. 2B is a table providing the SEQ ID NO for each VH and CDR illustrated in FIG. 2A. FIG. 2C shows a sequence alignment of example anti-CLL-1 binding molecules comprising a VL domain. CDRs and FRs are shown, as determined by Chothia numbering (FIG. 2C). FIG. 2D is a table providing the SEQ ID NO for each VH and CDR sequence illustrated in FIG. 2C. FIG. 2E shows a sequence alignment of example anti-BCMA binding molecules comprising a VH domain. Complementarity determining regions (CDRs) and framework regions (FRs) are shown, as determined by Chothia numbering (FIG. 2E). SEQ ID NOS 253-260, CDR1 in order from top to bottom; SEQ ID NOS 261-268, CDR2 from top to bottom, SEQ ID NOS 269-276, CDR3 from top to bottom. FIG. 2F is a table providing the SEQ ID NO for each VH and CDR numbered by an alternative method. FIG. 2G shows a sequence alignment of example anti-BCMA binding molecules comprising a VL domain. CDRs and FRs are shown, as determined by Chothia numbering (FIG. 2G). SEQ ID NOS 37-44, CDR1 in order from top to bottom; SEQ ID NOS 45-52, CDR2 from top to bottom, SEQ ID NOS 277-284, CDR3 from top to bottom. FIG. 2H is a table providing the SEQ ID NO for each VH and CDR sequence numbered by an alternative method.

FIGS. 4A-4B, 4G-4H, 4M-4N, and 4S-4T show IFNγ production following co-culture with Namalwa, EoL-1, HL60, and MV4;11 target cells, respectively. FIGS. 4E-4F, 4K-4L, 4Q-4R, and 4W-4X show TNFα production following co-culture with Namalwa, EoL-1, HL60, and MV4;11 target cells, respectively.

FIGS. 5A-5H show cytolytic activity of electroporated anti-FLT3 CAR T cells against Namalwa (FIGS. 5A-5B), EoL1 (FIGS. 5C-5D), HL60 (FIGS. 5E-5F), and MV4;11 (FIGS. 5G-5H) target cell lines following 16 hours of co-culture.

FIGS. 7A-7F show IFNγ (FIGS. 7A-7B), TNFα (FIGS. 7C-7D), and IL-2 (FIGS. 7E-7F) production by lentivirus transduced CAR T cells from two healthy donors following 16 hours of co-culture with the indicated target cell lines.

FIGS. 9A-9B depict proliferation of CFSE-labeled lentivirus transduced CAR T cells from two healthy donors following 5 days of co-culture with CD3-CD28 beads or the indicated target cell lines.

FIGS. 10A-10D depict CAR expression in lentivirus transduced primary human T cells used for in vivo studies. FIGS. 10E-10F show graphical representations of measured bioluminescence imaging of labeled acute myeloid leukemia (AML) cells following intravenous injection of either control (mock) or anti-FLT3 CAR T cells (10E3-CHD, 10E3-THD, or 8B5-THD) in a xenogeneic model, performed in duplicate. FIG. 10G provides the p-values for the respective data points in FIG. 10E.

FIGS. 13A-13E show cytolytic activity of different CLL-1 CAR-T cell constructs 24 hours after mRNA electroporation. T cells electroporated with control constructs (mock, GFP, and CD19 CAR) or anti-CLL-1 CAR constructs (24C8_HL-CHD and 24C8_HL_THD) were co-cultured with Namalwa (FIG. 13A), MV;411 (FIG. 13B), EoL-1 (FIG. 13C), HL-60 (FIG. 13D), and U937 target cells, and the percent of specific lysis of each target cell line was determined.

FIGS. 14A-14C show the results from a cytokine release assay from different transduced anti-CLL-1 CAR T cells 16 hours after co-culture with different cell lines. IFNγ (FIG. 14A), IL-2 (FIG. 14B), and TNFα (FIG. 14C) production levels are shown for controls (target alone and mock) and transduced anti-CLL-1 CAR T cells (10E3 THD and 24C1_LH_THD) co-cultured with Namalwa, HL-60, or MV4;11 target cells, as indicated.

FIGS. 15A-15C show cytolytic activity from anti-CLL-1 CAR T cells (C1_24C1_LH_THD) 16 hours and 40 hours after co-culture with Namalwa (FIG. 15A), MV4;11 (FIG. 15B), or HL-60 (FIG. 15C) target cells.

FIGS. 16A-16F shows IFNγ, TNFα, and IL-2 production by lentivirus transduced CART cells from two healthy donors following 16 hours of co-cultured with EoL-1 (Black), NCI-H929 (light grey), or MM1S (grey) target cell lines. FIGS. 16A and 16B show the IFNγ (pg/ml; y-axis) production in lentivirus transduced CAR T cells from a first donor (FIG. 6A) and a second donor (FIG. 16B). FIGS. 16C and 16D show the TNFα (pg/ml; y-axis) production in lentivirus transduced CAR T cells from a first donor (FIG. 16C) and a second donor (FIG. 16D). FIGS. 16E and 16F show the IL-2 production (pg/ml; y-axis) in lentivirus transduced CAR T cells from a first donor (FIG. 16E) and a second donor (FIG. 16F).

FIGS. 17A and 17B show the average cytolytic activity of transduced CAR T cells from a first donor (FIG. 17A) and a second donor (FIG. 17B) co-cultured with EoL1 target cells for 16 hours, 40 hours, 64 hours, 88 hours, or 112 hours. FIGS. 17C and 17D show the average cytolytic activity of transduced CAR T cells from a first donor (FIG. 17C) and a second donor (FIG. 17D) co-cultured with NCI-H929 target cells for 16 hours, 40 hours, 64 hours, 88 hours, or 112 hours. FIGS. 17E and 17F show the average cytolytic activity of transduced CAR T cells from a first donor (FIG. 17E) and a second donor (FIG. 17F) co-cultured with MM1S target cells for 16 hours, 40 hours, 64 hours, 88 hours, or 112 hours.

FIGS. 18A and 18B show proliferation of CFSE-labeled lentivirus transduced CAR T cells from a first healthy donor (FIG. 18A) and a second healthy donor (FIG. 18B) following 6 days of co-culture with CD3-CD28 beads (top row), EoL-1 (second row), NCI-H929 (third row), or MM1S (bottom row) target cell lines.

FIG. 19A: In a phosphate-buffered saline (PBS) solution, a CAR comprising an extracellular domain with a truncated hinge domain ("THD") has a higher melting temperature relative to a CAR comprising an extracellular domain with a complete hinge domain ("CHD"). FIG. 19B: In the presence of 50 mM NaCl, a CAR comprising an extracellular domain with a THD has a higher melting temperature relative to a CAR comprising an extracellular domain with a CHD.

DETAILED DESCRIPTION OF THE INVENTION

Figure 1B:
FIGS. 1B and 1C provide ribbon diagrams of the extracellular domain of the costimulatory protein having the amino acid sequence of SEQ ID NO: 1.
Figure 1C:

The present invention relates to novel polypeptides comprising a novel truncated hinge domain ("THD") and polynucleotides encoding the same. Some aspects of the invention relate to a polynucleotide encoding a chimeric antigen receptor (CAR) or a T cell receptor (TCR) comprising the THD disclosed herein. The present invention also provides vectors (e.g., viral vectors) comprising such polynucleotides and compositions comprising such vectors. The present invention further provides polynucleotides encoding such CARs or TCRs and compositions comprising such polynucleotides. The present invention additionally provides engineered cells (e.g., T cells) comprising such polynucleotides and/or transduced with such viral vectors and compositions comprising such engineered cells. The present invention provides compositions (e.g., pharmaceutical compositions) including a plurality of engineered T cells. The present invention provides methods for manufacturing such engineered T cells and compositions and uses (e.g., in treating a melanoma) of such engineered T cells and compositions. And, the present invention provides a method of inducing an immunity against a tumor comprising administering to a subject an effective amount of a cell comprising a polynucleotide, a vector, or a polypeptide of the present invention. Other aspects of the invention relate to cells comprising the CAR or the TCR and their use in a T cell therapy, e.g., an autologous cell therapy (eACT™), for the treatment of a patient suffering from a cancer.

Definitions

In order for the present invention to be more readily understood, certain terms are first defined below. Additional definitions for the following terms and other terms are set forth throughout the Specification.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

The term "and/or" where used herein is to be taken as specific disclosure of each of the two specified features or components with or without the other. Thus, the term "and/or" as used in a phrase such as "A and/or B" herein is intended to include A and B; A or B; A (alone); and B (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The terms "e.g.," and "i.e." as used herein, are used merely by way of example, without limitation intended, and should not be construed as referring only those items explicitly enumerated in the specification.

The terms "or more", "at least", "more than", and the like, e.g., "at least one" are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more than the stated value. Also included is any greater number or fraction in between.

Conversely, the term "no more than" includes each value less than the stated value. For example, "no more than 100 nucleotides" includes 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, and 0 nucleotides. Also included is any lesser number or fraction in between.

The terms "plurality", "at least two", "two or more", "at least second", and the like, are understood to include but not limited to at least 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more. Also included is any greater number or fraction in between.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. It is understood that wherever aspects are described herein with the language "comprising," otherwise analogous aspects described in terms of "consisting of" and/or "consisting essentially of" are also provided.

Unless specifically stated or evident from context, as used herein, the term "about" refers to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within one or more than one standard deviation per the practice in the art. "About" or "comprising essentially of" can mean a range of up to 10% (i.e., ±10%). Thus, "about" can be understood to be within 10%, 9%, 8%, 7%, 6%, 5%, 4%, 3%, 2%, 1%, 0.5%, 0.1%, 0.05%, 0.01%, or 0.001% greater or less than the stated value. For example, about 5 mg can include any amount between 4.5 mg and 5.5 mg. Furthermore, particularly with respect to biological systems or processes, the terms can mean up to an order of magnitude or up to 5-fold of a value. When particular values or compositions are provided in the instant disclosure, unless otherwise stated, the meaning of "about" or "comprising essentially of" should be assumed to be within an acceptable error range for that particular value or composition.

As described herein, any concentration range, percentage range, ratio range or integer range is to be understood to be inclusive of the value of any integer within the recited range and, when appropriate, fractions thereof (such as one-tenth and one-hundredth of an integer), unless otherwise indicated.

Units, prefixes, and symbols used herein are provided using their Système International de Unites (SI) accepted form. Numeric ranges are inclusive of the numbers defining the range.

Unless defined otherwise, all technical and scientific terms used herein have the same meaning as commonly understood by one of ordinary skill in the art to which this disclosure is related. For example, Juo, "The Concise Dictionary of Biomedicine and Molecular Biology", $2^{nd}$ ed., (2001), CRC Press; "The Dictionary of Cell & Molecular Biology", $5^{th}$ ed., (2013), Academic Press; and "The Oxford Dictionary Of Biochemistry And Molecular Biology", Cammack et al. eds., $2^{nd}$ ed, (2006), Oxford University Press, provide those of skill in the art with a general dictionary for many of the terms used in this disclosure.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding molecule thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

Antibodies can include, for example, monoclonal antibodies, recombinantly produced antibodies, monospecific antibodies, multispecific antibodies (including bispecific antibodies), human antibodies, engineered antibodies, humanized antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, antibody fusions (sometimes referred to herein as "antibody conjugates"), heteroconjugate antibodies, single domain antibodies, monovalent antibodies, single chain antibodies or single-chain Fvs (scFv), camelized antibodies, affybodies, Fab fragments, F(ab')$_2$ fragments, disulfide-linked Fvs (sdFv), anti-idiotypic (anti-Id) antibodies (including, e.g., anti-anti-Id antibodies), minibodies, domain antibodies, synthetic antibodies (sometimes referred to herein as "antibody mimetics"), and antigen-binding fragments of any of the above. In certain embodiments, antibodies described herein refer to polyclonal antibody populations.

An immunoglobulin may derive from any of the commonly known isotypes, including but not limited to IgA, secretory IgA, IgG, IgE and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or non-human Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "antigen binding molecule," "antigen binding portion," or "antibody fragment" refers to any molecule that comprises the antigen binding parts (e.g., CDRs) of the antibody from which the molecule is derived. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules. Peptibodies (i.e., Fc fusion molecules comprising peptide binding domains) are another example of suitable antigen binding molecules. In some embodiments, the antigen binding molecule binds to an antigen on a tumor cell. In some embodiments, the antigen binding molecule binds to an antigen on a cell involved in a hyperproliferative disease or to a viral or bacterial antigen. In certain embodiments, the antigen binding molecule binds to BCMA, CLL-1, or FLT3. In further embodiments, the antigen binding molecule is an antibody fragment that specifically binds to the antigen, including one or more of the complementarity determining regions (CDRs) thereof. In further embodiments, the antigen binding molecule is a single chain variable fragment (scFv). In some embodiments, the antigen binding molecule comprises or consists of avimers.

As used herein, the term "variable region" or "variable domain" is used interchangeably and are common in the art. The variable region typically refers to a portion of an antibody, generally, a portion of a light or heavy chain, typically about the amino-terminal 110 to 120 amino acids in the mature heavy chain and about 90 to 115 amino acids in the mature light chain, which differ extensively in sequence among antibodies and are used in the binding and specificity of a particular antibody for its particular antigen. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen. In certain embodiments, the variable region is a human variable region. In certain embodiments, the variable region comprises rodent or murine CDRs and human framework regions (FRs). In particular embodiments, the variable region is a primate (e.g., non-human primate) variable region. In certain embodiments, the variable region comprises rodent or murine CDRs and primate (e.g., non-human primate) framework regions (FRs).

The terms "VL" and "VL domain" are used interchangeably to refer to the light chain variable region of an antibody or an antigen-binding molecule thereof.

The terms "VH" and "VH domain" are used interchangeably to refer to the heavy chain variable region of an antibody or an antigen-binding molecule thereof.

A number of definitions of the CDRs are commonly in use: Kabat numbering, Chothia numbering, AbM numbering, or contact numbering. The AbM definition is a compromise between the two used by Oxford Molecular's AbM antibody modelling software. The contact definition is based on an analysis of the available complex crystal structures.

TABLE 1

CDR Numbering

| Loop | Kabat | AbM | Chothia | Contact |
|---|---|---|---|---|
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 | H31-H35B (Kabat Numbering) | H26-H35B | H26-H32..34 | H30-H35B |
| H1 | H31-H35 (Chothia Numbering) | H26-H35 | H26-H32 | H30-H35 |
| H2 | H50-H65 | H50-H58 | H52-H56 | H47-H58 |
| H3 | H95-H102 | H95-H102 | H95-H102 | H93-H101 |

The term "Kabat numbering" and like terms are recognized in the art and refer to a system of numbering amino acid residues in the heavy and light chain variable regions of an antibody, or an antigen-binding molecule thereof. In certain aspects, the CDRs of an antibody can be determined according to the Kabat numbering system (see, e.g., Kabat E A & Wu T T (1971) Ann NY Acad Sci 190: 382-391 and Kabat E A et al., (1991) Sequences of Proteins of Immunological Interest, Fifth Edition, U.S. Department of Health and Human Services, NIH Publication No. 91-3242). Using the Kabat numbering system, CDRs within an antibody heavy chain molecule are typically present at amino acid positions 31 to 35, which optionally can include one or two additional amino acids, following 35 (referred to in the Kabat numbering scheme as 35A and 35B) (CDR1), amino acid positions 50 to 65 (CDR2), and amino acid positions 95 to 102 (CDR3). Using the Kabat numbering system, CDRs within an antibody light chain molecule are typically present at amino acid positions 24 to 34 (CDR1), amino acid positions 50 to 56 (CDR2), and amino acid positions 89 to 97 (CDR3). In a specific embodiment, the CDRs of the antibodies described herein have been determined according to the Kabat numbering scheme.

In certain aspects, the CDRs of an antibody can be determined according to the Chothia numbering scheme, which refers to the location of immunoglobulin structural loops (see, e.g., Chothia C & Lesk A M, (1987), J Mol Biol 196: 901-917; Al-Lazikani B et al., (1997) J Mol Biol 273: 927-948; Chothia C et al., (1992) J Mol Biol 227: 799-817; Tramontano A et al., (1990) J Mol Biol 215(1): 175-82; and U.S. Pat. No. 7,709,226). Typically, when using the Kabat numbering convention, the Chothia CDR-H1 loop is present at heavy chain amino acids 26 to 32, 33, or 34, the Chothia CDR-H2 loop is present at heavy chain amino acids 52 to 56, and the Chothia CDR-H3 loop is present at heavy chain amino acids 95 to 102, while the Chothia CDR-L1 loop is present at light chain amino acids 24 to 34, the Chothia CDR-L2 loop is present at light chain amino acids 50 to 56, and the Chothia CDR-L3 loop is present at light chain amino acids 89 to 97. The end of the Chothia CDR-HI loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). In a specific embodiment, the CDRs of the antibodies described herein have been determined according to the Chothia numbering scheme.

As used herein, the terms "constant region" and "constant domain" are interchangeable and have a meaning common in the art. The constant region is an antibody portion, e.g., a carboxyl terminal portion of a light and/or heavy chain which is not directly involved in binding of an antibody to antigen but which can exhibit various effector functions, such as interaction with the Fc receptor. The constant region of an immunoglobulin molecule generally has a more conserved amino acid sequence relative to an immunoglobulin variable domain.

As used herein, the term "heavy chain" when used in reference to an antibody can refer to any distinct type, e.g., alpha ($\alpha$), delta ($\delta$), epsilon ($\varepsilon$), gamma ($\gamma$) and mu ($\mu$), based on the amino acid sequence of the constant domain, which give rise to IgA, IgD, IgE, IgG and IgM classes of antibodies, respectively, including subclasses of IgG, e.g., $IgG_1$, $IgG_2$, $IgG_3$ and $IgG_4$.

As used herein, the term "light chain" when used in reference to an antibody can refer to any distinct type, e.g., kappa ($\kappa$) or lambda ($\lambda$) based on the amino acid sequence of the constant domains. Light chain amino acid sequences are well known in the art. In specific embodiments, the light chain is a human light chain.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured and/or expressed in a number of ways known in the art, including, but not limited to, equilibrium dissociation constant ($K_D$), and equilibrium association constant ($K_A$). The $K_D$ is calculated from the quotient of $k_{off}/k_{on}$, whereas $K_A$ is calculated from the quotient of $k_{on}/k_{off}$. $k_{on}$ refers to the association rate constant of, e.g., an antibody to an antigen, and $k_{off}$ refers to the dissociation of, e.g., an antibody to an antigen. The $k_{on}$ and $k_{off}$ can be determined by techniques known to one of ordinary skill in the art, such as BIACORE® or KinExA.

As used herein, a "conservative amino acid substitution" is one in which the amino acid residue is replaced with an amino acid residue having a similar side chain. Families of amino acid residues having side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). In certain embodiments, one or more amino acid residues within a CDR(s) or within a framework region(s) of an antibody or antigen-binding molecule thereof can be replaced with an amino acid residue with a similar side chain.

As, used herein, the term "heterologous" means from any source other than naturally occurring sequences. For example, a heterologous sequence included as a part of a costimulatory protein having the amino acid sequence of SEQ ID NO: 1, e.g., the corresponding human costimulatory protein, is amino acids that do not naturally occur as, i.e., do not align with, the wild type human costimulatory protein. For example, a heterologous nucleotide sequence refers to a nucleotide sequence other than that of the wild type human costimulatory protein-encoding sequence.

As used herein, an "epitope" is a term in the art and refers to a localized region of an antigen to which an antibody can specifically bind. An epitope can be, for example, contiguous amino acids of a polypeptide (linear or contiguous epitope) or an epitope can, for example, come together from two or more non-contiguous regions of a polypeptide or polypeptides (conformational, non-linear, discontinuous, or non-contiguous epitope). In certain embodiments, the epitope to which an antibody binds can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligopeptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50(Pt 4): 339-350; McPherson A (1990) Eur J Biochem 189: 1-23; Chayen N E (1997) Structure 5: 1269-1274; McPherson A (1976) J Biol Chem 251: 6300-6303). Antibody:antigen crystals may be studied using well known X-ray diffraction techniques and may be refined using computer software such as X-PLOR (Yale University, 1992, distributed by Molecular Simulations, Inc.; see e.g. Meth Enzymol (1985) volumes 114 & 115, eds Wyckoff H W et al.; U.S. 2004/0014194), and BUSTER (Bricogne G (1993) Acta Crystallogr D Biol Crystallogr 49(Pt 1): 37-60; Bricogne G (1997) Meth Enzymol 276A: 361-423, ed Carter C W; Roversi P et al., (2000) Acta Crystallogr D Biol Crystallogr 56(Pt 10): 1316-1323). Mutagenesis mapping studies may be accomplished using any method known to one of skill in the art. See, e.g., Champe M et al., (1995) J Biol Chem 270: 1388-1394 and Cunningham B C & Wells J A (1989) Science 244: 1081-1085 for a description of mutagenesis techniques, including alanine scanning mutagenesis techniques.

As used herein, an antigen binding molecule, an antibody, or an antigen binding molecule thereof "cross-competes" with a reference antibody or an antigen binding molecule thereof if the interaction between an antigen and the first binding molecule, an antibody, or an antigen binding molecule thereof blocks, limits, inhibits, or otherwise reduces the ability of the reference binding molecule, reference antibody, or an antigen binding molecule thereof to interact with the antigen. Cross competition can be complete, e.g., binding of the binding molecule to the antigen completely blocks the ability of the reference binding molecule to bind the antigen, or it can be partial, e.g., binding of the binding molecule to the antigen reduces the ability of the reference binding molecule to bind the antigen. In certain embodiments, an antigen binding molecule that cross-competes with a reference antigen binding molecule binds the same or an overlapping epitope as the reference antigen binding molecule. In other embodiments, the antigen binding molecule that cross-competes with a reference antigen binding molecule binds a different epitope as the reference antigen binding molecule. Numerous types of competitive binding assays can be used to determine if one antigen binding molecule competes with another, for example: solid phase direct or indirect radioimmunoassay (MA); solid phase direct or indirect enzyme immunoassay (EIA); sandwich competition assay (Stahli et al., 1983, Methods in Enzymology 9:242-253); solid phase direct biotin-avidin EIA (Kirkland et al., 1986, J. Immunol. 137:3614-3619); solid phase direct labeled assay, solid phase direct labeled sandwich assay (Harlow and Lane, 1988, Antibodies, A Laboratory Manual, Cold Spring Harbor Press); solid phase direct label RIA using 1-125 label (Morel et al., 1988, Molec. Immunol. 25:7-15); solid phase direct biotin-avidin EIA (Cheung, et al., 1990, Virology 176:546-552); and direct labeled RIA (Moldenhauer et al., 1990, Scand. J. Immunol. 32:77-82).

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen may bind to other peptides or polypeptides, generally with lower affinity as determined by, e.g., immunoassays, BIACORE®, KinExA 3000 instrument (Sapidyne Instruments, Boise, Id.), or other assays known in the art. In a specific embodiment, molecules that specifically bind to an antigen bind to the antigen with a $K_A$ that is at least 2 logs, 2.5 logs, 3 logs, 4 logs or greater than the $K_A$ when the molecules bind to another antigen.

In another embodiment, molecules that specifically bind to an antigen bind with a dissociation constant ($K_d$) of about $1 \times 10^{-7}$ M. In some embodiments, the antigen binding molecule specifically binds an antigen with "high affinity" when the $K_d$ is about $1 \times 10^{-9}$ M to about $5 \times 10^{-9}$ M. In some embodiments, the antigen binding molecule specifically binds an antigen with "very high affinity" when the $K_d$ is $1 \times 10^{-10}$ M to about $5 \times 10^{-10}$ M. In one embodiment, the antigen binding molecule has a $K_d$ of $10^{-9}$ M. In one embodiment, the off-rate is less than about $1 \times 10^{-5}$. In other embodiments, the antigen binding molecule binds human BCMA with a $K_d$ of between about $1 \times 10^{-7}$ M and about $1 \times 10^{-13}$ M. In yet another embodiment, the antigen binding molecule binds human BCMA with a $K_d$ of about $1 \times 10^{-10}$ M to about $5 \times 10^{-10}$ M.

In a specific embodiment, provided herein is an antibody or an antigen binding molecule thereof that binds to a target human antigen, e.g., human BCMA or human CLL-1, with higher affinity than to another species of the target antigen, e.g., a non-human BCMA or a non-human CLL-1. In certain embodiments, provided herein is an antibody or an antigen binding molecule t thereof that binds to the target human antigen, e.g., human BCMA or human CLL-1, with a 5%, 10%, 15%, 20%, 25%, 30%, 35%, 40%, 45%, 50%, 55%, 60%, 65%, 70% or higher affinity than to another species of the target antigen as measured by, e.g., a radioimmunoassay, surface plasmon resonance, or kinetic exclusion assay. In a specific embodiment, an antibody or an antigen binding molecule thereof described herein, which binds to a target human antigen, will bind to another species of the target antigen with less than 10%, 15%, or 20% of the binding of the antibody or an antigen binding molecule thereof to the human antigen as measured by, e.g., a radioimmunoassay, surface plasmon resonance, or kinetic exclusion assay.

An "antigen" refers to any molecule that provokes an immune response or is capable of being bound by an antibody or an antigen binding molecule. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens. In one particular embodiment, the antigen is all or a fragment of BCMA, FLT3, or CLL-1.

The term "neutralizing" refers to an antigen binding molecule, scFv, antibody, or a fragment thereof, that binds to a ligand and prevents or reduces the biological effect of that ligand. In some embodiments, the antigen binding molecule, scFv, antibody, or a fragment thereof, directly blocking a binding site on the ligand or otherwise alters the ligand's ability to bind through indirect means (such as structural or energetic alterations in the ligand). In some embodiments, the antigen binding molecule, scFv, antibody, or a fragment thereof prevents the protein to which it is bound from performing a biological function.

As used herein, the term "BCMA" refers to B cell maturation antigen, which can include, but is not limited to, native BCMA, an isoform of BCMA, or an interspecies BCMA homolog of BCMA. BCMA (also known as TNFRSF17, CD269, and TNFRSF13A) is a member of the tumor necrosis factor (TNF)-receptor superfamily. BCMA is expressed on the surface of multiple myeloma cells, while highly restricted to plasma cells and a subset of mature B cells in healthy tissue. The amino acid sequence of human BCMA (hBCMA) is provided in NCBI Accession Q02223.2 (GI:313104029). As used herein, BCMA includes human BCMA and non-human BCMA homologs, as well as variants, fragments, or post-transnationally modified forms thereof, including, but not limited to, N- and O-linked glycosylated forms of BCMA. BCMA proteins may further include fragments comprising all or a portion of the extracellular domain of BCMA (e.g., all or a portion of amino acids 1-54 of hBCMA).

As used herein, the term "CLL-1" refers to C-type lectin-like molecule-1, which can include, but is not limited to native CLL-1, an isoform of CLL-1, or an interspecies CLL-1 homolog of CLL-1. CLL-1 (also known as C-type lectin domain family 12 member A, CLEC12A, dendritic cell-associated lectin 2, DCAL-2, myeloid inhibitory C-type lectin-like receptor, and MICL) is a cell surface receptor that modulates signaling cascades and mediates tyrosine phosphorylation of target MAP kinases. CLL-1 expression is observed, e.g., in acute myeloid leukemia (AML) cells. The amino acid sequence of human CLL-1 (hCLL-1) is provided in UniProtKB/Swiss-Prot Accession No. Q5QGZ9.3 (GI: 308153619). As used herein, CLL-1 includes human CLL-1 and non-human CLL-1 homologs, as well as variants, fragments, or post-transnationally modified forms thereof, including, but not limited to, N- and O-linked glycosylated forms of CLL-1.

As used herein the term "FLT3" refers to Fms-like tyrosine kinase 3 (FLT-3), which can include, but is not limited to native FLT3, an isoform of FLT3, or an interspecies FLT3 homolog of FLT3. FLT3 (also known as Cluster of differentiation antigen 135 (CD135), receptor-type tyrosine-protein kinase FLT3, FMS-related tyrosine kinase 3, stem cell tyrosine kinase 1, FL cytokine receptor, growth factor receptor tyrosine kinase type III, STK1, or fetal liver kinase-2 (Flk2)) is a cytokine receptor which belongs to the receptor tyrosine kinase class III. CD135 is the receptor for the cytokine Flt3 ligand (FLT3L). FLT3 is expressed on the surface of various hematopoietic progenitor cells and on the surface of acute myeloid leukemia (AML) cells. The amino acid sequence of human FLT3 (hFLT3) is provided in UniProtKB/Swiss-Prot Accession No. P36888 (GI: 156630887). As used herein, FLT3 includes human FLT3 and non-human FLT3 homologs, as well as variants, fragments, or post-transnationally modified forms thereof, including, but not limited to, N- and O-linked glycosylated forms of FLT3.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

The terms "transduction" and "transduced" refer to the process whereby foreign DNA is introduced into a cell via viral vector (see Jones et al., "Genetics: principles and analysis," Boston: Jones & Bartlett Publ. (1998)). In some embodiments, the vector is a retroviral vector, a DNA vector, a RNA vector, an adenoviral vector, a baculoviral vector, an Epstein Barr viral vector, a papovaviral vector, a vaccinia viral vector, a herpes simplex viral vector, an adenovirus associated vector, a lentiviral vector, or any combination thereof.

As used herein, the term "truncated" refers to anything less than the whole. For example, a truncated hinge domain (alternatively referred to herein as "THD") amino acid sequence can include any amino acid sequence shorter than the full length or complete hinge domain ("CHD"). In some embodiments, a THD consists essentially of or consists of amino acids 118-152, 119-152, 120-152, 121-152, 122-152, 123-152, 124-152, 125-152, 126-152, 127-152, 128-152, 129-152, or 130-152, of SEQ ID NO: 1. In one embodiment, the THD consists essentially of or consists of the amino acid sequence of SEQ ID NO: 3, which consists of amino acids 123 to 152 of SEQ ID NO: 1.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, myeloma, and other leukocyte malignancies. In some embodiments, the methods of the present invention can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, multiple myeloma, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. In one particular embodiment, the cancer is multiple myeloma. The particular cancer can be responsive to chemo- or radiation therapy or the cancer can be refractory. A refractory cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

A "therapeutically effective amount," "effective dose," "effective amount," or "therapeutically effective dosage" of a therapeutic agent, e.g., engineered CAR T cells, is any amount that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory TEM cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells (PBMCs), bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising at least one costimulatory domain and at least one activating domain. The costimulatory domain can be derived from a naturally-occurring costimulatory domain, e.g., having the amino acid sequence of SEQ ID NO: 1, or a variant thereof, e.g., a variant having a truncated hinge domain ("THD"), and the activating domain can be derived from, e.g., CD3-zeta. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. In some embodiments, the CAR is engineered such that the costimulatory domain is expressed as a separate polypeptide chain. Example CART cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

As used herein, the term "in vitro cell" refers to any cell which is cultured ex vivo. In particular, an in vitro cell can include a T cell.

The terms "peptide," "polypeptide," and "protein" are used interchangeably, and refer to a compound comprised of amino acid residues covalently linked by peptide bonds. A protein or peptide contains at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an APC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an anti-CD3 antibody (such as OKT3), an MHC Class I molecule loaded with a peptide, a superagonist anti-CD2 antibody, and a superagonist anti-CD28 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, 3/TR6, 4-1BB ligand, agonist or antibody that binds Toll ligand receptor, B7-1 (CD80), B7-2 (CD86), CD30 ligand, CD40, CD7, CD70, CD83, herpes virus entry mediator (HVEM), human leukocyte antigen G (HLA-G), ILT4, immunoglobulin-like transcript (ILT) 3, inducible costimulatory ligand (ICOS-L), intercellular adhesion molecule (ICAM), ligand that specifically binds with B7-H3, lymphotoxin beta receptor, MHC class I chain-related protein A (MICA), MHC class I chain-related protein B (MICB), OX40 ligand, PD-L2, or programmed death (PD) L1. A co-stimulatory ligand includes, without limitation, an antibody that specifically binds with a co-stimulatory molecule present on a T cell, such as, but not limited to, 4-1BB, B7-H3, CD2, CD27, CD28, CD30, CD40, CD7, ICOS, ligand that specifically binds with CD83, lymphocyte function-associated antigen-1 (LFA-1), natural killer cell receptor C (NKG2C), OX40, PD-1, or tumor necrosis factor superfamily member 14 (TNFSF14 or LIGHT).

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, 4-1BB/CD137, B7-H3, BAFFR, BLAME (SLAMF8), BTLA, CD 33, CD 45, CD100 (SEMA4D), CD103, CD134, CD137, CD154, CD16, CD160 (BY55), CD18, CD19, CD19a, CD2, CD22, CD247, CD27, CD276 (B7-H3), CD28, CD29, CD3 (alpha; beta; delta; epsilon; gamma; zeta), CD30, CD37, CD4, CD4, CD40, CD49a, CD49D, CD49f, CD5, CD64, CD69, CD7, CD80, CD83 ligand, CD84, CD86, CD8alpha, CD8beta, CD9, CD96 (Tactile), CD1-1a, CD1-1b, CD1-1c, CD1-1d, CDS, CEACAM1, CRT AM, DAP-10, DNAM1 (CD226), Fc gamma receptor, GADS, GITR, HVEM (LIGHTR), IA4, ICAM-1, ICAM-1, ICOS, Ig alpha (CD79a), IL2R beta, IL2R gamma, IL7R alpha, integrin, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, LIGHT, LIGHT (tumor necrosis factor superfamily member 14; TNFSF14), LTBR, Ly9 (CD229), lymphocyte function-associated antigen-1 (LFA-1 (CD11a/CD18), MHC class I molecule, NKG2C, NKG2D, NKp30, NKp44, NKp46, NKp80 (KLRF1), OX40, PAG/Cbp, PD-1, PSGL1, SELPLG (CD162), signaling lymphocytic activation molecule, SLAM (SLAMF1; CD150; IPO-3), SLAMF4 (CD244; 2B4), SLAMF6 (NTB-A; Ly108), SLAMF7, SLP-76, TNF, TNFr, TNFR2, Toll ligand receptor, TRANCE/RANKL, VLA1, or VLA-6, or fragments, truncations, or combinations thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

To calculate percent identity, the sequences being compared are typically aligned in a way that gives the largest match between the sequences. One example of a computer program that can be used to determine percent identity is the GCG program package, which includes GAP (Devereux et al., 1984, Nucl. Acid Res. 12:387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span," as determined by the algorithm). In certain embodiments, a standard comparison matrix (see, Dayhoff et al., 1978, Atlas of Protein Sequence and Structure 5:345-352 for the PAM 250 comparison matrix; Henikoff et al., 1992, Proc. Natl. Acad. Sci. U.S.A. 89:10915-10919 for the BLOSUM 62 comparison matrix) is also used by the algorithm.

Various aspects of the invention are described in further detail in the following subsections.

I. Chimeric Antigen Receptors and T Cell Receptors

Chimeric antigen receptors (CARs or CAR-Ts) and T cell receptors (TCRs) are genetically engineered receptors. These engineered receptors can be readily inserted into and expressed by immune cells, including T cells in accordance with techniques known in the art. With a CAR, a single receptor can be programmed to both recognize a specific antigen and, when bound to that antigen, activate the immune cell to attack and destroy the cell bearing that antigen. When these antigens exist on tumor cells, an immune cell that expresses the CAR can target and kill the tumor cell.

One aspect of the present invention is directed to polynucleotides encoding chimeric antigen receptors (CARs) or T cell receptors (TCRs) comprising a costimulatory domain comprising a novel extracellular domain comprising a truncated hinge domain ("THD"), and engineered T cells comprising a costimulatory domain comprising the novel THD. The costimulatory domain can further comprise a transmembrane domain and/or an intracellular domain. In some embodiments, a CAR or TCR encoded by the polynucleotide of the present invention further comprises an antigen binding molecule that specifically binds to a target antigen. In some embodiments, the CAR or TCR encoded by the polynucleotide further comprises an activating domain. In one particular embodiment, the CAR or TCR encoded by the polynucleotide comprises (i) an antigen binding molecule that specifically binds to a target antigen, (ii) a costimulatory domain comprising an extracellular domain, a transmembrane domain, and an intracellular domain, and (iii) an activating domain, wherein the extracellular domain comprises, consists essentially of, or consists of a THD described herein, e.g., SEQ ID NO: 3.

In some embodiments, an orientation of the CARs in accordance with the invention comprises an antigen binding domain (such as scFv) in tandem with a costimulatory domain and an activating domain. The costimulatory domain can comprise one or more of an extracellular portion, a transmembrane portion, and an intracellular portion. In other embodiments, multiple costimulatory domains can be utilized in tandem.

I.A. Costimulatory Domain.

Chimeric antigen receptors incorporates costimulatory (signaling) domains to increase their potency. See U.S. Pat. Nos. 7,741,465, and 6,319,494, as well as Krause et al. and Finney et al. (supra), Song et al., Blood 119:696-706 (2012); Kalos et al., Sci Transl. Med. 3:95 (2011); Porter et al., N. Engl. J. Med. 365:725-33 (2011), and Gross et al., Annu. Rev. Pharmacol. Toxicol. 56:59-83 (2016). The costimulatory protein having the amino acid sequence of SEQ ID NO: 1 is a costimulatory protein found naturally on T-cells. The complete native amino acid sequence of this costimulatory protein is described in NCBI Reference Sequence: NP_006130.1. See FIG. 1A. The complete native nucleic acid sequence of this costimulatory protein is described in NCBI Reference Sequence: NM_006139.1.

Novel Extracellular Domain:

The present disclosure shows that a novel extracellular domain of a costimulatory protein and comprising a truncated hinge domain ("THD") can improve one or more properties of a CAR or a TCR. In some embodiments, the THD domain is a truncated version of a complete hinge domain ("CHD"). In certain embodiments, the isolated polynucleotide encoding a THD comprises (i) an amino acid sequence at least about 80%, at least about 85%, at least about 90%, at least about 95%, at least about 96%, at least about 97%, at least about 98%, at least about 99%, or about 100% identical to amino acids 123 to 152 of SEQ ID NO: 1, wherein the THD domain does not contain amino acids 1 to 122 of SEQ ID NO: 1.

In other embodiments, the THD consists essentially of or consists of an amino acid sequence at least about 80%, at least about 85%, at least about 90%, at least about 95%, at least about 96%, at least about 97%, at least about 98%, at least about 99%, or about 100% identical to amino acids 123 to 152 of SEQ ID NO: 1. In other embodiments, the THD consists essentially of or consists of an amino acid sequence encoded by a nucleotide sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 3.

In some embodiments, the isolated polynucleotide encoding a THD consists essentially of or consists of (i) an amino acid sequence at least about 80%, at least about 85%, at least about 90%, at least about 95%, at least about 96%, at least about 97%, at least about 98%, at least about 99%, or about 100% identical to amino acids 123 to 152 of SEQ ID NO: 1 and (ii) optionally ±one amino acid, ±two amino acids, ±three amino acids, ±four amino acids, ±five amino acids, or ±six amino acids. In some embodiments, the isolated polynucleotide encoding a THD consists essentially of or consists of (i) an amino acid sequence at least about 80%, at least about 85%, at least about 90%, at least about 95%, at least about 96%, at least about 97%, at least about 98%, at least about 99%, or about 100% identical to amino acids 123 to 152 of SEQ ID NO: 1 and (ii) optionally one or two amino acids, one to three amino acids, one to four amino acids, one to five amino acids, or one to six amino acids. The one to six amino acids that can be added or deleted from the amino acid sequence in the THD can be at either the N-terminus, at the C-terminus, or both the N-terminus and the C-terminus.

In some embodiments, the isolated polynucleotide encoding a THD consists essentially of or consists of (i) an amino acid sequence at least about 80%, at least about 85%, at least about 90%, at least about 95%, at least about 96%, at least about 97%, at least about 98%, at least about 99%, or about 100% identical to amino acids 123 to 152 of SEQ ID NO: 1 and (ii) one additional N-terminal amino acid, two additional N-terminal amino acids, three additional N-terminal amino acids, four additional N-terminal amino acids, five additional N-terminal amino acids, or six additional N-terminal amino acids.

In some embodiments, the additional amino acids can be N-terminal amino acids. In some embodiments, the additional amino acids can be heterologous. In other embodiments, the additional amino acids are part of the naturally occurring costimulatory protein sequence.

In some embodiments, the THD consists essentially of or consists of an amino acid sequence at least about 80%, at least about 85%, at least about 90%, at least about 95%, at least about 96%, at least about 97%, at least about 98%, at least about 99%, or about 100% identical to amino acids 123 to 152 of SEQ ID NO: 1, amino acids 122 to 152 of SEQ ID NO: 1, amino acids 121 to 152 of SEQ ID NO: 1, amino acids 120 to 152 of SEQ ID NO: 1, amino acids 119 to 152 of SEQ ID NO: 1, amino acids 118 to 152 of SEQ ID NO: 1, or amino acids 117 to 152 of SEQ ID NO: 1.

In other embodiments, the THD consists essentially of or consists of an amino acid sequence at least about 80%, at least about 85%, at least about 90%, at least about 95%, at least about 96%, at least about 97%, at least about 98%, at least about 99%, or about 100% identical to amino acids 124 to 152 of SEQ ID NO: 1, amino acids 125 to 152 of SEQ ID NO: 1, amino acids 126 to 152 of SEQ ID NO: 1, amino acids 127 to 152 of SEQ ID NO: 1, amino acids 128 to 152 of SEQ ID NO: 1, amino acids 129 to 152 of SEQ ID NO: 1, or amino acids 130 to 152 of SEQ ID NO: 1.

In some embodiments, the THD does not comprise amino acids 1-116 of SEQ ID NO: 1. In some embodiments, the THD does not comprise amino acids 1-117 of SEQ ID NO: 1. In some embodiments, the THD does not comprise amino acids 1-118 of SEQ ID NO: 1. In some embodiments, the THD does not comprise amino acids 1-119 of SEQ ID NO: 1. In some embodiments, the THD does not comprise amino acids 1-120 of SEQ ID NO: 1. In some embodiments, the THD does not comprise amino acids 1-121 of SEQ ID NO: 1. In some embodiments, the THD does not comprise amino acids 1-122 of SEQ ID NO: 1. In some embodiments, the THD does not comprise amino acids 1-123 of SEQ ID NO: 1. In some embodiments, the THD does not comprise amino acids 1-124 of SEQ ID NO: 1. In some embodiments, the THD does not comprise amino acids 1-125 of SEQ ID NO: 1. In some embodiments, the THD does not comprise amino acids 1-126 of SEQ ID NO: 1. In some embodiments, the THD does not comprise amino acids 1-127 of SEQ ID NO: 1. In some embodiments, the THD does not comprise amino acids 1-128 of SEQ ID NO: 1. In some embodiments, the THD does not comprise amino acids 1-129 of SEQ ID NO: 1.

The corresponding amino acid sequence of the THD is set forth in SEQ ID NO. 3 LDNEKSNGTI IHVKGKHLCP SPLFPGPSKP. A nucleotide sequence encoding the extracellular portion of THD is set forth in SEQ ID NO. 2 CTTGATAATGAAAAGTCAAACGGAACAATCATTCACGTGAAGGGCAAGCACCTC TGTCCGTCACCCTTGTTCCCTGGTCCATCCAAGCCA.

In certain embodiments, the polynucleotide encoding a costimulatory domain in a CAR or TCR comprises a nucleotide sequence at least about 60%, at least about 70%, at least about 80%, at least about 85%, at least about 90%, at least about 95%, at least about 96%, at least about 97%, at least about 98%, at least about 99%, or about 100% identical to SEQ ID NO: 3, wherein the nucleotide sequence encodes a THD and wherein the CAR or TCR does not comprise amino acids 1 to 122 of SEQ ID NO: 1.

In one particular embodiment, the THD consists essentially of or consists of an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of SEQ ID NO: 3. In a specific embodiment, the polynucleotide encoding THD consists essentially of or consists of a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 2.

In some embodiments, the THD further comprises some or all of a member of the immunoglobulin family such as IgG1, IgG2, IgG3, IgG4, IgA, IgD, IgE, IgM, or fragment thereof.

In some embodiments, the THD is derived from a human complete hinge domain ("CHD"), e.g., from the costimulatory protein having the amino acid sequence of SEQ ID NO: 1. In other embodiments, the THD is derived from a rodent, murine, or primate (e.g., non-human primate) CHD of a costimulatory protein. In some embodiments, the THD is derived from a chimeric CHD of a costimulatory protein.

Transmembrane Domain:

The costimulatory domain for the CAR or TCR of the invention can further comprise a transmembrane domain and/or an intracellular signaling domain. The transmembrane domain can be designed to be fused to the extracellular domain of the CAR. It can similarly be fused to the intracellular domain of the CAR. In one embodiment, the transmembrane domain that naturally is associated with one of the domains in a CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain can be derived either from a natural or from a synthetic source. Where the source is natural, the domain can be derived from any membrane-bound or transmembrane protein. Transmembrane regions of particular use in this invention can be derived from (i.e., comprise) 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, a ligand that specifically binds with CD83, LIGHT, LIGHT, LTBR, Ly9 (CD229), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A; Ly108), SLAMF7, SLP-76, TNF receptor proteins, TNFR2, TNFSF14, a Toll ligand receptor, TRANCE/RANKL, VLA1, or VLA-6, or a fragment, truncation, or a combination thereof.

Optionally, short linkers can form linkages between any or some of the extracellular, transmembrane, and intracellular domains of the CAR.

In one specific embodiment, the nucleotide sequence of the costimulatory protein's transmembrane domain is set forth in SEQ ID NO. 4: TTCTGGGTGTTGGTCG-TAGTGGGTGGAGTCCTCGCTTGTTACTCTCT-GCTCGTCAC CGTGGCTTTTATAATCTTCTGGGTT In one embodiment, the polynucleotide encoding a transmembrane domain within a costimulatory domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 4.

The amino acid sequence of the costimulatory protein's transmembrane domain is set forth in SEQ ID NO. 5: FWVLVVVGGV LACYSLLVTV AFIIFWV.

In one particular embodiment, the transmembrane domain within a costimulatory domain comprises an amino acid sequence at least about 80%, at least about 85%, at least about 90%, at least about 95%, at least about 96%, at least about 97%, at least about 98%, at least about 99%, or about 100% identical to the amino acid sequence of SEQ ID NO: 5.

In another embodiment, the transmembrane domain is derived from (i.e., comprises) CD8. In one embodiment, the nucleotide sequence of the CD8 extracellular domain and transmembrane domain is set forth in SEQ ID NO: 238 GCTGCAGCATTGAGCAACTCAATAATGTATTTTAGT-CACTTTGTACCAGTGTTCTT GCCGGCTAAGCCTAC-TACCACACCCGCTCCACGGCCACCTACCCCAGCTC-CTACC ATCGCTTCACAGCCTCTGTCCCTGCGCCCAGAG-GCTTGCCGACCGGCCGCAGGGG GCGCTGTTCAT-ACCAGAGGACTGGATTTCGCCTGCGATATC-TATATCTGGGCACC CCTGGCCGGAACCTGCGGCGTACTCCTGCTGTC-CCTGGTCATCACGCTCTATTGT AATCACAGGAAC.

In some embodiments, the polynucleotide encoding a transmembrane domain within a costimulatory domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of the CD8 transmembrane domain.

The amino acid sequence of the CD8 extracellular domain and transmembrane domain is set forth in SEQ ID NO. 239 AAALSNSIMYFSHFVPVFLPAKPTTTPAPRPPTPAP-TIASQPLSLRPEACRPAAGGAVH TRGLDFACDIYIWA-PLAGTCGVLLLSLVITLYCNHRN.

In one particular embodiment, the transmembrane domain within a costimulatory domain comprises an amino acid sequence at least about 80%, at least about 85%, at least about 90%, at least about 95%, at least about 96%, at least about 97%, at least about 98%, at least about 99%, or about 100% identical to the amino acid sequence of the CD8 transmembrane domain.

Intracellular (Signaling) Domain:

The intracellular (signaling) domain of the engineered T cells of the invention can provide signaling to an activating domain, which then activates at least one of the normal effector functions of the immune cell. Effector function of a T cell, for example, can be cytolytic activity or helper activity including the secretion of cytokines.

In certain embodiments, suitable intracellular signaling domain include (i.e., comprise), but are not limited to 4-1BB/CD137, activating NK cell receptors, an Immunoglobulin protein, B7-H3, BAFFR, BLAME (SLAMF8), BTLA, CD100 (SEMA4D), CD103, CD160 (BY55), CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that specifically binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

An example of a nucleotide sequence encoding the intracellular signaling domain is set forth in SEQ ID NO. 6: AGATCCAAAAGAAGCCGCCTGCTCCATAGCGATTA-CATGAATATGACTCCACGC CGCCCTGGCCCCA-CAAGGAAACACTACCAGCCTTACGCACCACCTA-GAGATTTCG CTGCCTATCGGAGC In one embodiment, the polynucleotide encoding an intracellular signaling domain within a costimulatory domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 6.

An example of an intracellular signaling domain is set forth in SEQ ID NO. 7: RSKRSRLLHSDYMNMT-PRRPGPTRKHYQPYAPPRDFAAYRS.

In one particular embodiment, the intracellular signaling domain within a costimulatory domain comprises an amino acid sequence at least about 80%, at least about 85%, at least about 90%, at least about 95%, at least about 96%, at least about 97%, at least about 98%, at least about 99%, or about 100% identical to the amino acid sequence of SEQ ID NO: 7.

In some embodiments, the costimulatory domain comprises, consists essentially of, or consists of the extracellular THD, and the costimulatory proteins's transmembrane and intracellular domains. For example, a nucleotide sequence encoding a costimulatory domain is set forth in SEQ ID NO. 240: CTTGATAATGAAAAGTCAAACGGAACAATCAT-TCACGTGAAGGGCAAGCACCTC TGTCCGTCAC-CCTTGTTCCCTGGTCCATCCAAGCCATTCTGGGT-GTTGGTCGTAGT GGGTGGAGTCCTCGCTTGTTACTCTCTGCTCGT-CACCGTGGCTTTTATAATCTTCT GGGTTAGATC-CAAAAGAAGCCGCCTGCTCCATAGCGATTACAT-GAATATGACTCC ACGCCGCCCTGGCCCCACAAGGAAACACTACCA-GCCTTACGCACCACCTAGAGA TTTCGCTGC-CTATCGGAGC In some embodiments, the polynucleotide encoding a costimulatory domain comprises, consists essentially of, or consists of a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 240, wherein the costimulatory domain does not comprises amino acids 1 to 122 of SEQ ID NO: 1, amino acids 1 to 121 of SEQ ID NO: 1, amino acids 1 to 120 of SEQ ID NO: 1, amino acids 1 to 119 of SEQ ID NO: 1, amino acids 1 to 118 of SEQ ID NO: 1, or amino acids 1 to 118 of SEQ ID NO: 1.

The corresponding amino acid sequence of the costimulatory domain is set forth in SEQ ID NO. 241: LDNEK-SNGTIIHVKGKHLCPSPLFPGPSKPFWVLVVVGGV-LACYSLLVTVAFIIFWVR SKRSRLLHSDYMNMTPRRPGPTRKHYQPYAPPRD-FAAYRS In some embodiments, the costimulatory domain comprises, consists essentially of, or consists of a nucleotide sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of SEQ ID NO: 241, wherein the costimulatory domain does not comprises amino acids 1 to 122 of SEQ ID NO: 1, amino acids 1 to 121 of SEQ ID NO: 1, amino acids 1 to 120 of SEQ ID NO: 1, amino acids 1 to 119 of SEQ ID NO: 1, amino acids 1 to 118 of SEQ ID NO: 1, or amino acids 1 to 118 of SEQ ID NO: 1.

I.B. Activating Domain.

CD3 is an element of the T cell receptor on native T cells, and has been shown to be an important intracellular activating element in CARs. In one embodiment, the CD3 is CD3 zeta, the nucleotide sequence of which is set forth in SEQ ID NO. 8: AGGGTGAAGTTTTCCAGATCTGCA-GATGCACCAGCGTATCAGCAGGGCCAGAAC CAACTGTATAACGAGCTCAACCTGGGACGCA-GGGAAGAGTATGACGTTTTGGAC AAGCGCAGAG-GACGGGACCCTGAGATGGGTGGCAAACCAAGAC-GAAAAAACCC CCAGGAGGGTCTCTATAATGAGCTGCAGAAGGA-TAAGATGGCTGAAGCCTATTC TGAAATAGGCAT-GAAAGGAGAGCGGAGAAGGGGAAAAGGGCAC-GACGGTTTGT ACCAGGGACTCAGCACTGCTACGAAGGATACTTAT-GACGCTCTCCACATGCAAG CCCTGCCACCTAGG In some embodiments, the polynucleotide encoding an activating domain comprises a nucleotide sequence at least about 60%, at least about 65%, at least about 70%, at least about 75%, at least about 80%, at least about 85%, at least about 90%, at least about 95%, at least about 96%, at least about 97%, at least about 98%, at least about 99%, or about 100% identical to the nucleotide sequence of SEQ ID NO: 8.

The corresponding amino acid of intracellular CD3 zeta is set forth in SEQ ID NO. 9: RVKFSRSADAPAYQQGQN-QLYNELNLGRREEYDVLDKRRGRDPEMGGK-

PRRKNPQ EGLYNELQKDKMAEAYSEIGMKGERRRGKGHDGLYQGLSTATKDTYDALHMQALP PR

In some embodiments, the activating domain comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of SEQ ID NO: 9.

In some embodiments, the activating domain comprises an amino acid sequence at least about 70%, at least about 75%, at least about 80%, at least about 85%, at least about 90%, at least about 95%, at least about 96%, at least about 97%, at least about 98%, at least about 99%, or about 100% identical to the amino acid sequence of:

(SEQ ID NO: 251)
RVKFSRSADAPAYKQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR.

I.C. Antigen Binding Molecules

CARs can be engineered to bind to an antigen (such as a cell-surface antigen) by incorporating an antigen binding molecule that interacts with that targeted antigen. In some embodiments, the antigen binding molecule is an antibody fragment thereof, e.g., one or more single chain antibody fragment ("scFv"). An scFv is a single chain antibody fragment having the variable regions of the heavy and light chains of an antibody linked together. See U.S. Pat. Nos. 7,741,465, and 6,319,494 as well as Eshhar et al., Cancer Immunol Immunotherapy (1997) 45: 131-136. An scFv retains the parent antibody's ability to specifically interact with target antigen. scFvs are useful in chimeric antigen receptors because they can be engineered to be expressed as part of a single chain along with the other CAR components. Id. See also Krause et al., J. Exp. Med., Volume 188, No. 4, 1998 (619-626); Finney et al., *Journal of Immunology*, 1998, 161: 2791-2797. It will be appreciated that the antigen binding molecule is typically contained within the extracellular portion of the CAR such that it is capable of recognizing and binding to the antigen of interest. Bispecific and multispecific CARs are contemplated within the scope of the invention, with specificity to more than one target of interest.

In some embodiments, the polynucleotide encodes a CAR or a TCR comprising a THD of the present invention and an antigen binding molecule that specifically binds to a target antigen. In some embodiments, the target antigen is a tumor antigen. In some embodiments, the antigen is selected from a tumor-associated surface antigen, such as 5T4, alphafetoprotein (AFP), B7-1 (CD80), B7-2 (CD86), BCMA, B-human chorionic gonadotropin, CA-125, carcinoembryonic antigen (CEA), carcinoembryonic antigen (CEA), CD123, CD133, CD138, CD19, CD20, CD22, CD23, CD24, CD25, CD30, CD33, CD34, CD4, CD40, CD44, CD56, CD8, CLL-1, c-Met, CMV-specific antigen, CSPG4, CTLA-4, disialoganglioside GD2, ductal-epithelial mucine, EBV-specific antigen, EGFR variant III (EGFRvIII), ELF2M, endoglin, ephrin B2, epidermal growth factor receptor (EGFR), epithelial cell adhesion molecule (EpCAM), epithelial tumor antigen, ErbB2 (HER2/neu), fibroblast associated protein (fap), FLT3, folate binding protein, GD2, GD3, glioma-associated antigen, glycosphingolipids, gp36, HBV-specific antigen, HCV-specific antigen, HER1-HER2, HER2-HER3 in combination, HERV-K, high molecular weight-melanoma associated antigen (HMW-MAA), HIV-1 envelope glycoprotein gp41, HPV-specific antigen, human telomerase reverse transcriptase, IGFI receptor, IGF-II, IL-11Ralpha, IL-13R-a2, Influenza Virus-specific antigen; CD38, insulin growth factor (IGF1)-1, intestinal carboxyl esterase, kappa chain, LAGA-1a, lambda chain, Lassa Virus-specific antigen, lectin-reactive AFP, lineage-specific or tissue specific antigen such as CD3, MAGE, MAGE-A1, major histocompatibility complex (MHC) molecule, major histocompatibility complex (MHC) molecule presenting a tumor-specific peptide epitope, M-CSF, melanoma-associated antigen, mesothelin, mesothelin, MN-CA IX, MUC-1, mut hsp70-2, mutated p53, mutated p53, mutated ras, neutrophil elastase, NKG2D, Nkp30, NY-ESO-1, p53, PAP, prostase, prostase specific antigen (PSA), prostate-carcinoma tumor antigen-1 (PCTA-1), prostate-specific antigen, prostein, PSMA, RAGE-1, ROR1, RU1, RU2 (AS), surface adhesion molecule, surviving and telomerase, TAG-72, the extra domain A (EDA) and extra domain B (EDB) of fibronectin and the A1 domain of tenascin-C (TnC A1), thyroglobulin, tumor stromal antigens, vascular endothelial growth factor receptor-2 (VEGFR2), virus-specific surface antigen such as an HIV-specific antigen (such as HIV gp120), as well as any derivate or variant of these surface markers. In certain embodiments, the antigen binding molecule specifically binds to BCMA. In other embodiments, the antigen binding molecule specifically binds to CLL-1. In other embodiments, the antigen binding molecule specifically binds to FLT3.

In some embodiments, the antigen binding molecule specifically binds BCMA. In certain embodiments, the antigen binding molecule comprises (a) a VH CDR1 comprising an amino acid sequence selected from SEQ ID NOs: 13-20; (b) a VH CDR2 comprising an amino acid sequence selected from SEQ ID NOs: 21-28; (c) a VH CDR3 comprising an amino acid sequence selected from SEQ ID NOs: 29-36; (d) a VL CDR1 comprising an amino acid sequence selected from SEQ ID NOs: 37-44; (e) a VL CDR2 comprising an amino acid sequence selected from SEQ ID NOs: 45-52; and/or (f) a VL CDR3 comprising an amino acid sequence selected from SEQ ID NOs: 53-60.

In one embodiment, the antigen binding molecule comprises (a) a VH CDR1 comprising an amino acid of SEQ ID NO: 13; (b) a VH CDR2 comprising an amino acid sequence of SEQ ID NO: 21; (c) a VH CDR3 comprising an amino acid sequence of SEQ ID NO: 29; (d) a VL CDR1 comprising an amino acid sequence of SEQ ID NO: 37; (e) a VL CDR2 comprising an amino acid sequence of SEQ ID NO: 45; and/or (f) a VL CDR3 comprising an amino acid sequence of SEQ ID NO: 53.

In another embodiment, the antigen binding molecule comprises (a) a VH CDR1 comprising an amino acid of SEQ ID NO: 14; (b) a VH CDR2 comprising an amino acid sequence of SEQ ID NO: 22; (c) a VH CDR3 comprising an amino acid sequence of SEQ ID NO: 30; (d) a VL CDR1 comprising an amino acid sequence of SEQ ID NO: 38; (e) a VL CDR2 comprising an amino acid sequence of SEQ ID NO: 46; and/or (f) a VL CDR3 comprising an amino acid sequence of SEQ ID NO: 54.

In another embodiment, the antigen binding molecule comprises (a) a VH CDR1 comprising an amino acid of SEQ ID NO: 15; (b) a VH CDR2 comprising an amino acid sequence of SEQ ID NO: 23; (c) a VH CDR3 comprising an amino acid sequence of SEQ ID NO: 31; (d) a VL CDR1 comprising an amino acid sequence of SEQ ID NO: 39; (e) a VL CDR2 comprising an amino acid sequence of SEQ ID NO: 47; and/or (f) a VL CDR3 comprising an amino acid sequence of SEQ ID NO: 55.

In another embodiment, the antigen binding molecule comprises (a) a VH CDR1 comprising an amino acid of SEQ ID NO: 16; (b) a VH CDR2 comprising an amino acid sequence of SEQ ID NO: 24; (c) a VH CDR3 comprising an amino acid sequence of SEQ ID NO: 32; (d) a VL CDR1 comprising an amino acid sequence of SEQ ID NO: 40; (e) a VL CDR2 comprising an amino acid sequence of SEQ ID NO: 48; and/or (f) a VL CDR3 comprising an amino acid sequence of SEQ ID NO: 56.

In another embodiment, the antigen binding molecule comprises (a) a VH CDR1 comprising an amino acid of SEQ ID NO: 17; (b) a VH CDR2 comprising an amino acid sequence of SEQ ID NO: 25; (c) a VH CDR3 comprising an amino acid sequence of SEQ ID NO: 33; (d) a VL CDR1 comprising an amino acid sequence of SEQ ID NO: 41; (e) a VL CDR2 comprising an amino acid sequence of SEQ ID NO: 49; and/or (f) a VL CDR3 comprising an amino acid sequence of SEQ ID NO: 57.

In another embodiment, the antigen binding molecule comprises (a) a VH CDR1 comprising an amino acid of SEQ ID NO: 18; (b) a VH CDR2 comprising an amino acid sequence of SEQ ID NO: 26; (c) a VH CDR3 comprising an amino acid sequence of SEQ ID NO: 34; (d) a VL CDR1 comprising an amino acid sequence of SEQ ID NO: 42; (e) a VL CDR2 comprising an amino acid sequence of SEQ ID NO: 50; and/or (f) a VL CDR3 comprising an amino acid sequence of SEQ ID NO: 58.

In another embodiment, the antigen binding molecule comprises (a) a VH CDR1 comprising an amino acid of SEQ ID NO: 19; (b) a VH CDR2 comprising an amino acid sequence of SEQ ID NO: 27; (c) a VH CDR3 comprising an amino acid sequence of SEQ ID NO: 35; (d) a VL CDR1 comprising an amino acid sequence of SEQ ID NO: 43; (e) a VL CDR2 comprising an amino acid sequence of SEQ ID NO: 51; and/or (f) a VL CDR3 comprising an amino acid sequence of SEQ ID NO: 59.

In another embodiment, the antigen binding molecule comprises (a) a VH CDR1 comprising an amino acid of SEQ ID NO: 20; (b) a VH CDR2 comprising an amino acid sequence of SEQ ID NO: 28; (c) a VH CDR3 comprising an amino acid sequence of SEQ ID NO: 36; (d) a VL CDR1 comprising an amino acid sequence of SEQ ID NO: 44; (e) a VL CDR2 comprising an amino acid sequence of SEQ ID NO: 52; and/or (f) a VL CDR3 comprising an amino acid sequence of SEQ ID NO: 60.

In certain embodiments, the antigen binding molecule comprises a VH comprising an amino acid sequence selected from the group consisting of SEQ ID NOs: 77-84 and a VL comprising an amino acid sequence selected from the group consisting of SEQ ID NOs: 85-92. In one embodiment, the antigen binding molecule comprises a VH comprising an amino acid sequence of SEQ ID NO: 77 and a VL comprising an amino acid sequence of SEQ ID NO: 85. In another embodiment, the antigen binding molecule comprises a VH comprising an amino acid sequence of SEQ ID NO: 78 and a VL comprising an amino acid sequence of SEQ ID NO: 86. In another embodiment, the antigen binding molecule comprises a VH comprising an amino acid sequence of SEQ ID NO: 79 and a VL comprising an amino acid sequence of SEQ ID NO: 87. In another embodiment, the antigen binding molecule comprises a VH comprising an amino acid sequence of SEQ ID NO: 80 and a VL comprising an amino acid sequence of SEQ ID NO: 88. In another embodiment, the antigen binding molecule comprises a VH comprising an amino acid sequence of SEQ ID NO: 81 and a VL comprising an amino acid sequence of SEQ ID NO: 89. In another embodiment, the antigen binding molecule comprises a VH comprising an amino acid sequence of SEQ ID NO: 82 and a VL comprising an amino acid sequence of SEQ ID NO: 90. In another embodiment, the antigen binding molecule comprises a VH comprising an amino acid sequence of SEQ ID NO: 83 and a VL comprising an amino acid sequence of SEQ ID NO: 91. In another embodiment, the antigen binding molecule comprises a VH comprising an amino acid sequence of SEQ ID NO: 84 and a VL comprising an amino acid sequence of SEQ ID NO: 92.

In one particular embodiment, the polynucleotide of the present invention comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 61-68. In another embodiment, the polynucleotide of the present invention comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 69-76.

Other known anti-BCMA antibodies or antigen binding molecules thereof can be used as antigen binding molecules of a CAR or TCR comprising a THD of the present invention. Non-limiting examples of such BCMA antibodies or antigen binding molecule thereof include antibodies or antigen binding molecules described in WO2015158671A1, published Oct. 22, 2015 and WO2016014565A2, published Jan. 28, 2016.

In some embodiments, the antigen binding molecule specifically binds CLL-1. In certain embodiments, the antigen binding molecule comprises (a) a VH CDR1 comprising an amino acid sequence selected from SEQ ID NOs: 93-96; (b) a VH CDR2 comprising an amino acid sequence selected from SEQ ID NOs: 97-100; (c) a VH CDR3 comprising an amino acid sequence selected from SEQ ID NOs: 101-104; (d) a VL CDR1 comprising an amino acid sequence selected from SEQ ID NOs: 105-108; (e) a VL CDR2 comprising an amino acid sequence selected from SEQ ID NOs: 109-112; and/or (f) a VL CDR3 comprising an amino acid sequence selected from SEQ ID NOs: 113-116.

In one embodiment, the antigen binding molecule comprises (a) a VH CDR1 comprising an amino acid of SEQ ID NO: 93; (b) a VH CDR2 comprising an amino acid sequence of SEQ ID NO: 97; (c) a VH CDR3 comprising an amino acid sequence of SEQ ID NO: 101; (d) a VL CDR1 comprising an amino acid sequence of SEQ ID NO: 105; (e) a VL CDR2 comprising an amino acid sequence of SEQ ID NO: 109; and/or (f) a VL CDR3 comprising an amino acid sequence of SEQ ID NO: 113.

In one embodiment, the antigen binding molecule comprises (a) a VH CDR1 comprising an amino acid of SEQ ID NO: 94; (b) a VH CDR2 comprising an amino acid sequence of SEQ ID NO: 98; (c) a VH CDR3 comprising an amino acid sequence of SEQ ID NO: 102; (d) a VL CDR1 comprising an amino acid sequence of SEQ ID NO: 106; (e) a VL CDR2 comprising an amino acid sequence of SEQ ID NO: 110; and/or (f) a VL CDR3 comprising an amino acid sequence of SEQ ID NO: 114.

In one embodiment, the antigen binding molecule comprises (a) a VH CDR1 comprising an amino acid of SEQ ID NO: 95; (b) a VH CDR2 comprising an amino acid sequence of SEQ ID NO: 99; (c) a VH CDR3 comprising an amino acid sequence of SEQ ID NO: 103; (d) a VL CDR1 comprising an amino acid sequence of SEQ ID NO: 107; (e)

a VL CDR2 comprising an amino acid sequence of SEQ ID NO: 111; and/or (f) a VL CDR3 comprising an amino acid sequence of SEQ ID NO: 115.

In one embodiment, the antigen binding molecule comprises (a) a VH CDR1 comprising an amino acid of SEQ ID NO: 96; (b) a VH CDR2 comprising an amino acid sequence of SEQ ID NO: 100; (c) a VH CDR3 comprising an amino acid sequence of SEQ ID NO: 104; (d) a VL CDR1 comprising an amino acid sequence of SEQ ID NO: 108; (e) a VL CDR2 comprising an amino acid sequence of SEQ ID NO: 112; and/or (f) a VL CDR3 comprising an amino acid sequence of SEQ ID NO: 116.

In certain embodiments, the antigen binding molecule comprises a VH comprising an amino acid sequence selected from the group consisting of SEQ ID NOs: 125-128 and a VL comprising an amino acid sequence selected from the group consisting of SEQ ID NOs: 129-132. In one embodiment, the antigen binding molecule comprises a VH comprising an amino acid sequence of SEQ ID NO: 125 and a VL comprising an amino acid sequence of SEQ ID NO: 129. In another embodiment, the antigen binding molecule comprises a VH comprising an amino acid sequence of SEQ ID NO: 126 and a VL comprising an amino acid sequence of SEQ ID NO: 130. In another embodiment, the antigen binding molecule comprises a VH comprising an amino acid sequence of SEQ ID NO: 127 and a VL comprising an amino acid sequence of SEQ ID NO: 131. In another embodiment, the antigen binding molecule comprises a VH comprising an amino acid sequence of SEQ ID NO: 128 and a VL comprising an amino acid sequence of SEQ ID NO: 132.

In one particular embodiment, the polynucleotide of the present invention comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 117-120. In another embodiment, the polynucleotide of the present invention comprises a nucleotide sequence at least about 70%, at least about 75%, at least about 80%, at least about 85%, at least about 90%, at least about 95%, at least about 96%, at least about 97%, at least about 98%, at least about 99%, or about 100% identical to a nucleotide sequence selected form the group consisting of SEQ ID NOs: 121-124.

Other examples of anti-CLL-1 antibodies or antigen binding molecules thereof include antibodies or antigen binding molecules described in WO2016014535, published Jan. 28, 2016, and US 2016/0051651 A1, published Feb. 25, 2016.

The antigen binding molecule encoded by the polynucleotide of the present invention can be single chained or double chained. In some embodiments, the antigen binding molecule is single chained. In certain embodiments, the antigen binding molecule is selected from the group consisting of an scFv, an Fab, an Fab', an Fv, an F(ab')2, a dAb, and any combination thereof. In one particular embodiment, the antigen binding molecule comprises an scFv.

In certain embodiments, the antigen binding molecule comprises a single chain, wherein the heavy chain variable region and the light chain variable region are connected by a linker. In some embodiments, the VH is located at the N terminus of the linker and the VL is located at the C terminus of the linker. In other embodiments, the VL is located at the N terminus of the linker and the VH is located at the C terminus of the linker. In some embodiments, the linker comprises at least about 5, at least about 8, at least about 10, at least about 13, at least about 15, at least about 18, at least about 20, at least about 25, at least about 30, at least about 35, at least about 40, at least about 45, at least about 50, at least about 60, at least about 70, at least about 80, at least about 90, or at least about 100 amino acids. In some embodiments, the linker comprises at least about 18 amino acids. In certain embodiments, the linker comprises an amino acid sequence that is at least about 75%, at least about 85%, at least about 85%, at least about 90%, at least about 95%, at least about 96%, at least about 97%, at least about 98%, at least about 99%, or 100% identical to the amino acid sequence GSTSGSGKPGSGEGSTKG (SEQ ID NO: 12) or the amino acid sequence GGGGSGGGGSGGGGS (SEQ ID NO: 237). In one embodiment, the linker is a Whitlow linker. In certain embodiments, the binding molecule comprises a single chain, wherein the heavy chain variable region and the light chain variable region are connected by a linker, wherein the linker comprises the amino acid sequence of SEQ ID NO: 12.

In some embodiments, the antigen binding molecule binds a target antigen (e.g., human BCMA, human FLT3, or human CLL-1) with a $K_D$ of less than $1\times10^{-7}$ M, less than $1\times10^{-8}$ M, less than $1\times10^{-7}$ M, or less than $1\times10^{-9}$ M. In one particular embodiment, the antigen binding molecule binds a target antigen (e.g., human BCMA, human FLT3, or human CLL-1) with a $K_D$ of less than $1\times10^{-7}$ M. In another embodiment, the antigen binding molecule binds a target antigen (e.g., human BCMA, human FLT3, or human CLL-1) with a $K_D$ of less than $1\times10^{-8}$ M. In some embodiments, the antigen binding molecule binds a target antigen (e.g., human BCMA, human FLT3, or human CLL-1) with a $K_D$ of about $1\times10^{-7}$ M, about $2\times10^{-7}$ M, about $3\times10^{-7}$ M, about $4\times10^{-7}$ M, about $5\times10^{-7}$ M, about $6\times10^{-7}$ M, about $7\times10^{-7}$ M, about $8\times10^{-7}$ M, about $9\times10^{-7}$ M, about $1\times10^{-7}$ M, about $2\times10^{-7}$ M, about $3\times10^{-7}$ M, about $4\times10^{-8}$ M, about $5\times10^{-8}$ M, about $6\times10^{-8}$M, about $7\times10^{-8}$ M, about $8\times10^{-8}$ M, about $9\times10^{-8}$ M, about $1\times10^{-9}$M, about $2\times10^{-9}$ M, about $3\times10^{-9}$ M, about $4\times10^{-9}$ M, about $5\times10^{-9}$ M, about $6\times10^{-9}$ M, about $7\times10^{-9}$ M, about $8\times10^{-9}$M, about $9\times10^{-9}$ M, about $1\times10^{-10}$ M, or about $5\times10^{-10}$ M. In certain embodiments, the $K_D$ is calculated as the quotient of $k_{off}/k_{on}$, and the $k_{on}$ and $k_{off}$ are determined using a monovalent antibody, such as a Fab fragment, as measured by, e.g., BIAcore® surface plasmon resonance technology. In other embodiments, the $K_D$ is calculated as the quotient of $k_{off}/k_{on}$, and the $k_{on}$ and $k_{off}$ are determined using a bivalent antibody, such as a Fab fragment, as measured by, e.g., BIAcore® surface plasmon resonance technology.

In some embodiments, the antigen binding molecule binds a target antigen (e.g., human BCMA, human FLT3, or human CLL-1) with an association rate ($k_{on}$) of less than $1\times10^{-4}$ $M^{-1}$ $s^{-1}$, less than $2\times10^{-4}$ $M^{-1}$ $s^{-1}$ less than $3\times10^{-4}$ $M^{-1}$ $s^{-1}$ less than $4\times10^{-4}$ $M^{-1}$ $s^{-1}$ less than $5\times10^{-4}$ $M^{-1}$ $s^{-1}$, less than $6\times10^{-4}$ $M^{-1}$ $s^{-1}$, less than $7\times10^{-4}$ $M^{-1}$ $s^{-1}$, less than $8\times10^{-4}$ $M^{-1}$ $s^{-1}$, less than $9\times10^{-4}$ $M^{-1}$ $s^{-1}$, less than $1\times10^{-5}$ $M^{-1}$ $s^{-1}$, less than $2\times10^{-5}$ $M^{-1}$ $s^{-1}$, less than $3\times10^{-5}$ $M^{-1}$ $s^{-1}$, less than $4\times10^{-5}$ $M^{-1}$ $s^{-1}$ less than $5\times10^{-5}$ $M^{-1}$ $s^{-1}$ less than $6\times10^{-5}$ $M^{-1}$ $s^{-1}$ less than $7\times10^{-5}$ $M^{-1}$ $s^{-1}$, less than $8\times10^{-5}$ $M^{-1}$ $s^{-1}$, less than $9\times10^{-5}$ $M^{-1}$ $s^{-1}$, less than $1\times10^{-6}$ $M^{-1}$ $s^{-1}$, less than $2\times10^{-6}$ $M^{-1}$ $s^{-1}$, less than $3\times10^{-6}$ $M^{-1}$ $s^{-1}$, less than $4\times10^{-6}$ $M^{-1}$ $s^{-1}$, less than $5\times10^{-6}$ $M^{-1}$ $s^{-1}$, less than $6\times10^{-6}$ $M^{-1}$ $s^{-1}$, less than $7\times10^{-6}$ $M^{-1}$ $s^{-1}$, less than $8\times10^{-6}$ $M^{-1}$ $s^{-1}$, less than $9\times10^{-6}$ $M^{-1}$ $s^{-1}$, or less than $1\times10^{-7}M^{-1}$ $s^{-1}$. In certain embodiments, the $k_{on}$ is determined using a monovalent antibody, such as a Fab fragment, as measured by, e.g., BIAcore® surface plasmon resonance technology. In other embodiments, the $k_{on}$ is determined using a bivalent antibody as measured by, e.g., BIAcore® surface plasmon resonance technology.

In some embodiments, the antigen binding molecule binds a target antigen (e.g., human BCMA, human FLT3, or human CLL-1) with an dissociation rate ($k_{off}$) of less than $1 \times 10^{-2}$ s$^{-1}$, less than $2 \times 10^{-2}$ s$^{-1}$, less than $3 \times 10^{-2}$ s$^{-1}$, less than $4 \times 10^{-2}$ s$^{-1}$, less than $5 \times 10^{-2}$ s$^{-1}$, less than $6 \times 10^{-2}$ s$^{-1}$, less than $7 \times 10^{-2}$ s$^{-1}$, less than $8 \times 10^{-2}$ s$^{-1}$, less than $9 \times 10^{-2}$ s$^{-1}$, less than $1 \times 10^{-3}$ s$^{-1}$, less than $2 \times 10^{-3}$ s$^{-1}$, less than $3 \times 10^{-3}$ s$^{-1}$, less than $4 \times 10^{-3}$ s$^{-1}$, less than $5 \times 10^{-3}$ s$^{-1}$, less than $6 \times 10^{-3}$ s$^{-1}$, less than $7 \times 10^{-3}$ s$^{-1}$, less than $8 \times 10^{-3}$ s$^{-1}$, less than $9 \times 10^{-3}$ s$^{-1}$, less than $1 \times 10^{-4}$ s$^{-1}$, less than $2 \times 10^{-4}$ s$^{-1}$, less than $3 \times 10^{-4}$ s$^{-1}$, less than $4 \times 10^{-4}$ s$^{-1}$, less than $5 \times 10^{-4}$ s$^{-1}$, less than $6 \times 10^{-4}$ s$^{-1}$, less than $7 \times 10^{-4}$ s$^{-1}$, less than $8 \times 10^{-4}$ s$^{-1}$, less than $9 \times 10^{-4}$ s$^{-1}$, less than $1 \times 10^{-4}$ s$^{-1}$, or less than $5 \times 10^{-4}$ s$^{-1}$ In certain embodiments, the $k_{off}$ is determined using a monovalent antibody, such as a Fab fragment, as measured by, e.g., BIAcore® surface plasmon resonance technology. In other embodiments, the $k_{off}$ is determined using a bivalent antibody as measured by, e.g., BIAcore® surface plasmon resonance technology.

In some embodiments, the polynucleotide encodes a TCR, wherein the TCR further comprises a fourth complementarity determining region (CDR4). In certain embodiments, the polynucleotide encodes a TCR, wherein the TCR further comprises a constant region. In some embodiments, the constant region is selected from a constant region of IgG1, IgG2, IgG3, IgG4, IgA, IgD, IgE, and IgM.

I.D. Switch Domain

It will be appreciated that adverse events may be minimized by transducing the immune cells (containing one or more CARs or TCRs) with a suicide gene. It may also be desired to incorporate an inducible "on" or "accelerator" switch into the immune cells. Suitable techniques include use of inducible caspase-9 (U.S. Appl. 2011/0286980) or a thymidine kinase, before, after or at the same time, as the cells are transduced with the CAR construct of the present invention. Additional methods for introducing suicide genes and/or "on" switches include TALENS, zinc fingers, RNAi, siRNA, shRNA, antisense technology, and other techniques known in the art.

In accordance with the invention, additional on-off or other types of control switch techniques may be incorporated herein. These techniques may employ the use of dimerization domains and optional activators of such domain dimerization. These techniques include, e.g., those described by Wu et al., Science 2014 350 (6258) utilizing FKBP/Rapalog dimerization systems in certain cells, the contents of which are incorporated by reference herein in their entirety. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787, the contents of which are also incorporated by reference herein in their entirety. Additional dimerization pairs may include cyclosporine-A/cyclophilin, receptor, estrogen/estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/127261, WO 2015/090229, US 2014/0286987, US 2015/0266973, US 2016/0046700, U.S. Pat. No. 8,486,693, US 2014/0171649, and US 2012/0130076, the contents of which are further incorporated by reference herein in their entirety.

I.E. Leader Peptide

In some embodiments, the polynucleotide of the present invention encodes a CAR or a TCR can further comprises a leader peptide (also referred to herein as a "signal peptide"). In certain embodiments, the leader peptide comprises an amino acid sequence that is at least about 75%, at least about 80%, at least about 85%, at least about 90%, at least about 95%, at least about 96%, at least about 97%, at least about 98%, at least about 99%, or 100% identical to the amino acid sequence MALPVTALLLPLALLLHAARP (SEQ ID NO: 11). In some embodiments, the leader peptide comprises the amino acid sequence of SEQ ID NO: 11.

In some embodiments, the polynucleotide of the present invention encodes a CAR or a TCR, wherein the CAR or the TCR comprises a leader peptide (P), an antigen binding molecule (B), a costimulatory protein's extracellular domain (E), a transmembrane domain (T), a costimulatory region (C), and an activation domain (A), wherein the CAR is configured according to the following: P-B-E-T-C-A. In some embodiments, the antigen binding molecule comprises a VH and a VL, wherein the CAR is configured according to the following: P-VH-VL-E-T-C-A or P-VL-VH-E-T-C-A. In some embodiments, the VH and the VL are connected by a linker (L), wherein the CAR is configured according to the following, from N-terminus to C-terminus: P-VH-L-VL-E-T-C-A or P-VH-L-VL-E-T-C-A.

In some embodiments, the polynucleotide of the present invention encodes a CAR, wherein the CAR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence selected from Table 2. In certain embodiments, the polynucleotide of the present invention encodes a CAR, wherein the CAR comprises an amino acid sequence selected from Table 2.

TABLE 2

Example CAR Sequences

| CAR Construct | Nucleotide Sequence | SEQ ID NO: | Amino Acid Sequence | SEQ ID NO: |
|---|---|---|---|---|
| 10E3_CHD | ATGGCACTCCCCGTAACTGCTCTGCTGCT GCCGTTGGCATTGCTCCTGCACGCCGCAC GCCCGCAGGTGACCCTCAAAGAGTCTGGA CCCGTGCTCGTAAACCTACGGAGACCCT GACACTCACCTGCACAGTCTCCGGCTTCA GCCTCATCAATGCCAGGATGGGAGTTTCC TGGATCAGGCAACCGCCCGGAAAGGCCCT GGAATGGCTCGCACATATTTTCAGTAACG CTGAAAAAGCTATCGGACTTCTCTGAAA AGTCGGCTCACGATTAGTAAGGACACATC | 242 | MALPVTALLLPLALLL HAARPQVTLKESGPVL VKPTETLTLTCTVSGF SLINARMGVSWIRQPP GKALEWLAHIFSNAEK SYRTSLKSRLTISKDT SKSQVVLTMTNMDPVD TATYYCARIPGYGGNG DYHYYGMDVWGQGTTV TVSSGGGGSGGGGSGG | 243 |

TABLE 2-continued

Example CAR Sequences

| CAR Construct | Nucleotide Sequence | SEQ ID NO: | Amino Acid Sequence | SEQ ID NO: |
|---|---|---|---|---|
| | CAAGAGCCAAGTGGTGCTTACGATGACTA ACATGGACCCTGTGGATACTGCAACCTAT TACTGTGCTCGAATCCCTGGTTATGGCGG AAATGGGGACTACCACTACTACGGTATGG ATGTCTGGGGCCAAGGGACCACGGTTACT GTTTCAAGCGGAGGGGGAGGGAGTGGGGG TGGCGGATCTGGCGGAGGAGGCAGCGATA TCCAGATGACGCAGTCCCCTAGTTCACTT TCCGCATCCCTGGGGGATCGGGTTACCAT TACATGCCGCGTCACAGGGTATCCGGA ATGATCTGGGATGGTACCAGCAGAAGCCG GGAAAGGCTCCTAAGCGCCTCATCTACGC CAGCTCCACCCTGCAGAGTGGAGTGCCCT CCCGGTTTTCAGGCAGTGGCTCCGGTACG GAGTTTACTCTTACAATTAGCAGCCTGCA GCCAGAAGATTTTGCAACTTACTACTGTT TGCAGCATAATAATTTCCCCTGGACCTTT GGTCAGGGCACCAAGGTGGAGATCAAAAG AGCAGCCGCCATCGAAGTAATGTATCCCC CCCCGTACCTTGACAATGAGAAGTCAAAT GGAACCATTATCCATGTTAAGGGCAAACA CCTCTGCCCTTCTCCACTGTTCCCTGGCC CTAGTAAGCCGTTTTGGGTGCTGGTGGTA GTCGGTGGGGTGCTGGCTTGTTACTCTCT TCTCGTGACCGTCGCCTTTATAATCTTTT GGGTCAGATCCAAAAGAAGCCGCCTGCTC CATAGCGATTACATGAATATGACTCCACG CCGCCCTGGCCCCACAAGGAAACACTACC AGCCTTACGCACCACCTAGAGATTTCGCT GCCTATCGGAGCCGAGTGAAATTTTCTAG ATCAGCTGATGCTCCCGCCTATCAGCAGG GACAGAATCAACTTTACAATGAGCTGAAC CTGGGTCGCAGAGAAGAGTACGACGTTTT GGACAAACGCCGGGGCCGAGATCCTGAGA TGGGGGGGAAGCCGAGAAGGAAGAATCCT CAAGAAGGCCTGTACAACGAGCTTCAAAA AGACAAAATGGCTGAGGCGTACTCTGAGA TCGGCATGAAGGGCGAGCGGAGACGAGGC AAGGGTCACGATGGCTTGTATCAGGGCCT GAGTACAGCCACAAAGGACACCTATGACG CCCTCCACATGCAGGCACTGCCCCACGC TAG | | GGSDIQMTQSPSSLSA SLGDRVTITCRASQGI RNDLGWYQQKPGKAPK RLIYASSTLQSGVPSR FSGSGSGTEFTLTISS LQPEDFATYYCLQHNN FPWTFGQGTKVEIKRA AAIEVMYPPPYLDNEK SNGTIIHVKGKHLCPS PLFPGPSKPFWVLVVV GGVLACYSLLVTVAFI IFWVRSKRSLLHSDY MNMTPRRPGPTRKHYQ PYAPPRDFAAYRSVK FSRSADAPAYQQGQNQ LYNELNLGRREEYDVL DKRRGRDPEMGGKPRR KNPQEGLYNELQKDKM AEAYSEIGMKGERRRG KGHDGLYQGLSTATKD TYDALHMQALPPR | |
| 10E3_THD | ATGGCACTCCCCGTAACTGCTCTGCTGCT GCCGTTGGCATTGCTCCTGCACGCCGCAC GCCCGCAAGTTACTTTGAAGGAGTCTGGA CCTGTACTGGTGAAGCCAACCGAGACACT GACACTCACGTGTACAGTGAGTGGTTTTT CCTTGATCAACGCAAGGATGGGCGTCAGC TGGATCAGGCAACCCCCTGGCAAGGCTCT GGAATGGCTCGCTCACATATTCAGCAATG CCGAAAAAAGCTACCGGACAAGCCTGAAA TCCCGCCTGACTATTTCCAAGGACACTTC TAAGTCTCAGGTGGTGCTGACCATGACCA ACATGGACCCGGTGGACACCGCCACCTAT TACTGCGCAAGAATCCCTGGGTATGGTGG GAATGGTGACTACCATTATTATGGGATGG ATGTGTGGGGCAAGGCACAACCGTAACG GTCTCAAGCGGTGGGGAGGCTCAGGGGG CGGAGGCTCCGGAGGTGGCGGCTCCGACA TTCAGATGACCCAAAGCCCGTCCAGCCTG TCCGCCAGCCTGGGAGATAGAGTGACAAT CACGTGTAGAGCTTCCCAAGGGATAAGAA ATGATCTCGGTGGTATCAGCAGAAGCCC GGCAAAGCCCCCAAAAGGCTTATATATGC TAGTAGTACACTGCAGTCGGAGTTCCTT CCCGATTTCAGGTAGCGGCTCCGGTACA GAGTTCACCCTCACGATAAGCTCACTCCA GCCTGAGGATTTCGCAACGTACTACTGCC TCCAGCACAACAATTTTCCCTGGACTTTC GGCCAGGGCACCAAGGTGGAGATCAAGAG GGCCGCTGCCCTTGATAATGAAAAGTCAA ACGGAACAATCATTCACGTGAAGGGCAAG CACCTCTGTCCGTCACCCTTGTTCCCTGG | 244 | MALPVTALLLPLALLL HAARPQVTLKESGPVL VKPTETLTLTCTVSGF SLINARMGVSWIRQPP GKALEWLAHIFSNAEK SYRTSLKSRLTISKDT SKSQVVLTMTNMDPVD TATYYCARIPGYGGNG DYHYYGMDVWGQGTTV TVSSGGGGSGGGGSGG GGSDIQMTQSPSSLSA SLGDRVTITCRASQGI RNDLGWYQQKPGKAPK RLIYASSTLQSGVPSR FSGSGSGTEFTLTISS LQPEDFATYYCLQHNN FPWTFGQGTKVEIKRA AALDNEKSNGTIIHVK GKHLCPSPLFPGPSKP FWVLVVVGGVLACYSL LVTVAFIIFWVRSKRS RLLHSDYMNMTPRRPG PTRKHYQPYAPPRDFA AYRSVKFSRSADAPA YQQGQNQLYNELNLGR REEYDVLDKRRGRDPE MGGKPRRKNPQEGLYN ELQKDKMAEAYSEIGM KGERRRGKGHDGLYQG LSTATKDTYDALHMQA LPPR | 245 |

TABLE 2-continued

Example CAR Sequences

| CAR Construct | Nucleotide Sequence | SEQ ID NO: | Amino Acid Sequence | SEQ ID NO: |
|---|---|---|---|---|
| | TCCATCCAAGCCATTCTGGGTGTTGGTCG TAGTGGGTGGAGTCCTCGCTTGTTACTCT CTGCTCGTCACCGTGGCTTTTATAATCTT CTGGGTTAGATCCAAAAGAAGCCGCCTGC TCCATAGCGATTACATGAATATGACTCCA CGCCGCCCTGGCCCCACAAGGAAACACTA CCAGCCTTACGCACCACCTAGAGATTTCG CTGCCTATCGGAGCCGAGTGAAATTTTCT AGATCAGCTGATGCTCCCGCCTATCAGCA GGGACAGAATCAACTTTACAATGAGCTGA ACCTGGGTCGCAGAGAAGAGTACGACGTT TTGGACAAACGCCGGGGCCGAGATCCTGA GATGGGGGGAAGCCGAGAAGGAAGAATC CTCAAGAAGGCCTGTACAACGAGCTTCAA AAAGACAAAATGGCTGAGGCGTACTCTGA GATCGGCATGAAGGGCGAGCGGAGACGAG GCAAGGGTCACGATGGCTTGTATCAGGGC CTGAGTACAGCCACAAAGGACACCTATGA CGCCCTCCACATGCAGGCACTGCCCCCAC GCTAG | | | |
| 8B5_CHD | ATGGCACTCCCCGTAACTGCTCTGCTGCT GCCGTTGGCATTGCTCCTGCACGCCGCAC GCCCGCAGATCCAGTTGGTGGAATCAGGG GGCGGTGTGGTGCAGCCGGGTAGGAGCCT GAGACTGTCATGCGTGGCGTCTGGCTTCA CATTCAAGAACTACGGCATGCACTGGGTG CGACAGGCCCCCGGAAAGGGTTTGGAGTG GGTCGCCGTGATCTGGTACGACGGATCTA ATGAGTATTACGGAGATCCTGTGAAGGGA AGGTTCACCATCTCCCGCGACAATAGCAA AAATATGCTCTACCTGCAAATGAACTCAC TCAGGGCGGATGATACGGCGGTCTACTAT TGCGCTCGCTCAGGGATTGCTGTGGCCGG CGCATTCGATTACTGGGGACAGGGTACCC TGGTGACAGTATCAAGCGGAGGCGGCGGC TCTGGCGGCGGCGGATCTGGCGGGGGGGG AAGTGAGATTGTGTTGACACAGTCTCCCG ATACCCTGTCACTGTCACCCGGCGAGAAG GCAACGCTGAGTTGCAGAGCAAGCCAGTC AGTCTCCTCTTCTTTTCTGGCCTGGTATC AGCAAAAACCAGGTCAGGCACCATCTCTC CTGATTTACGTTGCCAGCAGACGGGCGGC TGGCATTCCCGACAGGTTCTCTGGAAGCG GATCTGGGACCGATTTTACCCTGACAATT AGCCGCTTGGAGCCCGAAGACTTTGGTAT GTTTTACTGCCAGCACTACGGAAGGACAC CTTTCACATTTGGCCCGGGCACGAAAGTC GATATAAAACGCGCAGCCGCCATTGAAGT AATGTACCCACCACCTTATTTGGACAATG AAAAGTCCAATGGTACCATTATTCACGTC AAGGGAAAGCATCTCTGTCCAAGCCCTCT GTTCCCCGGCCCCTCCAAACCATTCTGGG TGCTGGTGGTCGTCGGCGGAGTTCTGGCC TGCTATTCTCTGCTCGTGACTGTTGCATT CATCATTTTCTGGGTGAGATCCAAAAGAA GCCGCCTGCTCCATAGCGATTACATGAAT ATGACTCCACGCCGCCCTGGCCCCACAAG GAAACACTACCAGCCTTACGCACCACCTA GAGATTTCGCTGCCTATCGGAGCCGAGTG AAATTTTCTAGATCAGCTGATGCTCCCGC CTATCAGCAGGGACAGAATCAACTTTACA ATGAGCTGAACCTGGGTCGCAGAGAAGAG TACGACGTTTTGGACAAACGCCGGGGCCG AGATCCTGAGATGGGGGGAAGCCGAGAA GGAAGAATCCTCAAGAAGGCCTGTACAAC GAGCTTCAAAAAGACAAAATGGCTGAGGC GTACTCTGAGATCGGCATGAAGGGCGAGC GGAGACGAGGCAAGGGTCACGATGGCTTG TATCAGGGCCTGAGTACAGCCACAAAGGA CACCTATGACGCCCTCCACATGCAGGCAC TGCCCCCACGCTAG | 246 | MALPVTALLLPLALLL HAARPQIQLVESGGGV VQPGRSLRLSCVASGF TFKNYGMHWVRQAPGK GLEWVAVIWYDGSNEY YGDPVKGRFTISRDNS KNMLYLQMNSLRADDT AVYYCARSGIAVAGAF DYWGQGTLVTVSSGGG GSGGGGSGGGGSEIVL TQSPDTLSLSPGEKAT LSCRASQSVSSSFLAW YQQKPGQAPSLLIYVA SRRAAGIPDRFSGSGS GTDFTLTISRLEPEDF GMFYCQHYGRTPFTFG PGTKVDIKRAAAIEVM YPPPYLDNEKSNGTII HVKGKHLCPSPLFPGP SKPFWVLVVVGGVLAC YSLLVTVAFIIFWVRS KRSRLLHSDYMNMTPR RPGPTRKHYQPYAPPR DFAAYRSRVKFSRSAD APAYQQGQNQLYNELN LGRREEYDVLDKRRGR DPEMGGKPRRKNPQEG LYNELQKDKMAEAYSE IGMKGERRRGKHDGL YQGLSTATKDTYDALH MQALPPR | 247 |

TABLE 2-continued

Example CAR Sequences

| CAR Construct | Nucleotide Sequence | SEQ ID NO: | Amino Acid Sequence | SEQ ID NO: |
|---|---|---|---|---|
| 8B5_THD | ATGGCACTCCCCGTAACTGCTCTGCTGCT GCCGTTGGCATTGCTCCTGCACGCCGCAC GCCCGCAGATTCAGCTCGTGGAGTCAGGT GGTGGCGTGGTTCAGCCCGGACGGTCCCT GCGACTCTCTTGTGTGGCAAGCGGATTTA CCTTTAAGAACTATGGCATGCACTGGGTG AGGCAGGCCCCTGGAAAAGGACTGGAGTG GGTTGCTGTGATCTGGTACGACGGGTCCA ACGAATATTATGGCGATCCTGTGAAGGGA CGGTTTACAATCTCACGCGATAACTCAAA GAACATGCTGTACCTGCAAATGAACTCTC TGCGCGCTGATGACACTGCCGTGTATTAT TGCGCTCGGAGTGGTATCGCCGTCGCAGG AGCATTTGATTATTGGGGGCAAGGGACCC TCGTGACAGTGAGTTCCGGAGGGGGAGGT TCTGGTGGAGGCGGCTCTGGTGGGGGAGG CAGCGAGATCGTTCTGACCCAGTCTCCTG ACACACTGTCACTGTCCCCTGGTGAAAAG GCCACACTGTCTTGTAGAGCGTCCCAGAG CGTTTCCAGTTCCTTCCTTGCATGGTATC AACAAAAACCCGGGCAGGCTCCAAGCTTG CTGATCTACGTGGCCAGCCGCCGGGCCGC AGGCATCCCTGATAGGTTTAGCGGTTCTG GGAGCGGGACGGACTTCACCTTGACAATA TCACGGCTGGAACCCGAAGACTTCGGAAT GTTTTATTGCCAGCACTACGGAAGAACTC CATTCACCTTTGGCCCGGGAACGAAGGTA GACATCAAGAGAGCAGCAGCCCTCGACAA CGAGAAATCCAATGGAACCATTATCCATG TGAAGGGGAAACATCTCTGCCCTTCACCA TTGTTCCCTGGACCCAGCAAGCCTTTTTG GGTTCTGGTCGTGGTGGGGGGCGTCCTGG CTTGTTACTCCCTCCTCGTTACAGTCGCC TTCATAATCTTTTGGGTTAGATCCAAAAG AAGCCGCCTGCTCCATAGCGATTACATGA ATATGACTCCACGCCGCCCTGGCCCCACA AGGAAAACACTACCAGCCTTACGCACCACC TAGAGATTTCGCTGCCTATCGGAGCCGAG TGAAATTTTCTAGATCAGCTGATGCTCCC GCCTATCAGCAGGGACAGAATCAACTTTA CAATGAGCTGAACCTGGGTCGCAGAGAAG AGTACGACGTTTTGGACAAACGCCGGGGC CGAGATCCTGAGATGGGGGGGAAGCCGAG AAGGAAGAATCCTCAAGAAGGCCTGTACA ACGAGCTTCAAAAAGACAAATGGCTGAG GCGTACTCTGAGATCGGCATGAAGGGCGA GCGGAGACGAGGCAAGGGTCACGATGGCT TGTATCAGGGCCTGAGTACAGCCACAAAG GACACCTATGACGCCCTCCACATGCAGGC ACTGCCCCCACGCTAG | 248 | MALPVTALLLPLALLL HAARPQIQLVESGGGV VQPGRSLRLSCVASGF TFKNYGMHWVRQAPGK GLEWVAVIWYDGSNEY YGDPVKGRFTISRDNS KNMLYLQMNSLRADDT AVYYCARSGIAVAGAF DYWGQGTLVTVSSGGG GSGGGGSGGGGSEIVL TQSPDTLSLSPGEKAT LSCRASQSVSSSFLAW YQQKPGQAPSLLIYVA SRRAAGIPDRFSGSGS GTDFTLTISRLEPEDF GMFYCQHYGRTPFTFG PGTKVDIKRAAALDNE KSNGTIIHVKGKHLCP SPLFPGPSKPFWVLVV VGGVLACYSLLVTVAF IIFWVRSKRSRLLHSD YMNMTPRRPGPTRKHY QPYAPPRDFAAYRSRV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | 249 |
| FS-21495CARHxL | ATGGCACTCCCCGTAACTGCTCTGCTGCT GCCGTTGGCATTGCTCCTGCACGCCGCAC GCCCGGAGGTGCAGCTGTTGGAGTCTGGG GGAGGCTTGGTACAGCCTGGGGGGTCCCT GAGACTCTCCTGTGCAGCCTCTGGATTCA CCTTTAGCAGCTATGCCATGAGCTGGGTC CGCCAGGCTCCAGGGAAGGGGCTGGAGTG GGTCTCAGCTATTAGTGGTAGTGGTGGTA GCACATACTACGCAGACTCCGTGAAGGGC CGGTTCACCATCTCCAGAGACAATTCCAA GAACACGCTGTATCTGCAAATGAACAGCC TGAGAGCCGAGGACACGGCGGTGTACTAC TGCGCAAGAGCCGAGATGGGAGCCGTATT CGACATATGGGGTCAGGGTACAATGGTCA CCGTCTCCTCAGGGTCTACATCCGGCTCC GGGAAGCCCGGAAGTGGCGAAGGTAGTAC AAAGGGGAAATTGTTGACACAGTCTC CAGCCACCCTGTCTTTGTCTCCAGGGGAA AGAGCCACCCTCTCCTGCAGGGCCAGTCA GAGTGTTAGCAGGTACTTAGCCTGGTACC AACAGAAACCTGGCCAGGCTCCCAGGCTC CTCATCTATGATGCATCCAACAGGGCCAC | 133 | MALPVTALLLPLALLL HAARPEVQLLESGGGL VQPGGSLRLSCAASGF TFSSYAMSWVRQAPGK GLEWVSAISGSGGSTY YADSVKGRFTISRDNS KNTLYLQMNSLRAEDT AVYYCARAEMGAVFDI WGQGTMVTVSSGSTSG SGKPGSGEGSTKGEIV LTQSPATLSLSPGERA TLSCRASQSVSRYLAW YQQKPGQAPRLLIYDA SNRATGIPARFSGSGS GTDFTLTISSLEPEDF AVYYCQQRISWPFTFG GGTKVEIKRAAALDNE KSNGTIIHVKGKHLCP SPLFPGPSKPFWVLVV VGGVLACYSLLVTVAF IIFWVRSKRSRLLHSD YMNMTPRRPGPTRKHY | 134 |

TABLE 2-continued

Example CAR Sequences

| CAR Construct | Nucleotide Sequence | SEQ ID NO: | Amino Acid Sequence | SEQ ID NO: |
|---|---|---|---|---|
| | TGGCATCCCAGCCAGGTTCAGTGGCAGTG GGTCTGGGACAGACTTCACTCTCACCATC AGCAGCCTAGAGCCTGAAGATTTTGCAGT TTATTACTGTCAGCAGAGAATCTCCTGGC CTTTCACTTTTGGCGGAGGGACCAAGGTT GAGATCAAACGGGCCGCTGCCCTTGATAA TGAAAAGTCAAACGGAACAATCATTCACG TGAAGGGCAAGCACCTCTGTCCGTCACCC TTGTTCCCTGGTCCATCCAAGCCATTCTG GGTGTTGGTCGTAGTGGGTGGAGTCCTCG CTTGTTACTCTCTGCTCGTCACCGTGGCT TTTATAATCTTCTGGGTTAGATCCAAAAG AAGCCGCCTGCTCCATAGCGATTACATGA ATATGACTCCACGCCGCCCTGGCCCCACA AGGAAACACTACCAGCCTTACGCACCACC TAGAGATTTCGCTGCCTATCGGAGCAGGG TGAAGTTTTCCAGATCTGCAGATGCACCA GCGTATCAGCAGGGCCAGAACCAACTGTA TAACGAGCTCAACCTGGGACGCAGGGAAG AGTATGACGTTTTGGACAAGCGCAGAGGA CGGGACCCTGAGATGGGTGGCAAACCAAG ACGAAAAAACCCCCAGGAGGGTCTCTATA ATGAGCTGCAGAAGGATAAGATGGCTGAA GCCTATTCTGAAATAGGCATGAAAGGAGA GCGGAGAAGGGGAAAAGGGCACGACGGTT TGTACCAGGGACTCAGCACTGCTACGAAG GATACTTATGACGCTCTCCACATGCAAGC CCTGCCACCTAGGTAA | | QPYAPPRDFAAYRSV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | |
| FS-21495CARLxH | ATGGCACTCCCCGTAACTGCTCTGCTGCT GCCGTTGGCATTGCTCCTGCACGCCGCAC GCCCGGAAATTGTGTTGACACAGTCTCCA GCCACCCTGTCTTTGTCTCCAGGGGAAAG AGCCACCCTCTCCTGCAGGGCCAGTCAGA GTGTTAGCAGGTACTTAGCCTGGTACCAA CAGAAACCTGGCCAGGCTCCCAGGCTCCT CATCTATGATGCATCCAACAGGGCCACTG GCATCCCAGCCAGGTTCAGTGGCAGTGGG TCTGGGACAGACTTCACTCTCACCATCAG CAGCCTAGAGCCTGAAGATTTTGCAGTTT ATTACTGTCAGCAGAGAATCTCCTGGCCT TTCACTTTTGGCGGAGGGACCAAGGTTGA GATCAAACGGGGGTCTACATCCGGCTCCG GGAAGCCCGGAAGTGGCGAAGGTAGTACA AAGGGGGAGGTGCAGCTGTTGGAGTCTGG GGGAGGCTTGGTACAGCCTGGGGGGTCCC TGAGACTCTCCTGTGCAGCCTCTGGATTC ACCTTTAGCAGCTATGCCATGAGCTGGGT CCGCCAGGCTCCAGGGAAGGGGCTGGAGT GGGTCTCAGCTATTAGTGGTAGTGGTGGT AGCACATACTACGCAGACTCCGTGAAGGG CCGGTTCACCATCTCCAGAGACAATTCCA AGAACACGCTGTATCTGCAAATGAACAGC CTGAGAGCCGAGGACACGGCGGTGTACTA CTGCGCAAGAGCCGAGATGGGAGCCGTAT TCGACATATGGGGTCAGGGTACAATGGTC ACCGTCTCCTCAGCCGCTGCCCTTGATAA TGAAAAGTCAAACGGAACAATCATTCACG TGAAGGGCAAGCACCTCTGTCCGTCACCC TTGTTCCCTGGTCCATCCAAGCCATTCTG GGTGTTGGTCGTAGTGGGTGGAGTCCTCG CTTGTTACTCTCTGCTCGTCACCGTGGCT TTTATAATCTTCTGGGTTAGATCCAAAAG AAGCCGCCTGCTCCATAGCGATTACATGA ATATGACTCCACGCCGCCCTGGCCCCACA AGGAAACACTACCAGCCTTACGCACCACC TAGAGATTTCGCTGCCTATCGGAGCAGGG TGAAGTTTTCCAGATCTGCAGATGCACCA GCGTATCAGCAGGGCCAGAACCAACTGTA TAACGAGCTCAACCTGGGACGCAGGGAAG AGTATGACGTTTTGGACAAGCGCAGAGGA CGGGACCCTGAGATGGGTGGCAAACCAAG ACGAAAAAACCCCCAGGAGGGTCTCTATA ATGAGCTGCAGAAGGATAAGATGGCTGAA | 135 | MALPVTALLLPLALLL HAARPEIVLTQSPATL SLSPGERATLSCRASQ SVSRYLAWYQQKPGQA PRLLIYDASNRATGIP ARFSGSGSGTDFTLTI SSLEPEDFAVYYCQQR ISWPFTFGGGTKVEIK RGSTSGSGKPGSGEGS TKGEVQLLESGGGLVQ PGGSLRLSCAASGFTF SSYAMSWVRQAPGKGL EWVSAISGSGGSTYYA DSVKGRFTISRDNSKN TLYLQMNSLRAEDTAV YYCARAEMGAVFDIWG QGTMVTVSSAAALDNE KSNGTIIHVKGKHLCP SPLFPGPSKPFWVLVV VGGVLACYSLLVTVAF IIFWVRSKRSRLLHSD YMNMTPRRPGPTRKHY QPYAPPRDFAAYRSV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | 136 |

TABLE 2-continued

Example CAR Sequences

| CAR Construct | Nucleotide Sequence | SEQ ID NO: | Amino Acid Sequence | SEQ ID NO: |
|---|---|---|---|---|
| | GCCTATTCTGAAATAGGCATGAAAGGAGA<br>GCGGAGAAGGGGAAAAGGGCACGACGGTT<br>TGTACCAGGGACTCAGCACTGCTACGAAG<br>GATACTTATGACGCTCTCCACATGCAAGC<br>CCTGCCACCTAGGTAA | | | |
| PC-21497CARHx<br>L | ATGGCACTCCCCGTAACTGCTCTGCTGCT<br>GCCGTTGGCATTGCTCCTGCACGCCGCAC<br>GCCCGCAGGTGCAGCTGGTGGAGTCTGGG<br>GGAGGCGTGGTCCAGCCTGGGAGGTCCCT<br>GAGACTCTCCTGTGCAGCGTCTGGATTCA<br>CCTTCAGTAGCTATGGCATGCACTGGGTC<br>CGCCAGGCTCCAGGCAAGGGGCTGGAGTG<br>GGTGGCAGTTATATCGTATGATGGAAGTA<br>ATAAATACTATGCAGACTCCGTGAAGGGC<br>CGATTCACCATCTCCAGAGACAATTCCAA<br>GAACACGCTGTATCTGCAAATGAACAGCC<br>TGAGAGCCGAGGACACGGCGGTGTACTAC<br>TGCGCCAGAGACGGTACTTATCTAGGTGG<br>TCTCTGGTACTTCGACTTATGGGGGAGAG<br>GTACCTTGGTCACCGTCTCCTCAGGGTCT<br>ACATCCGGCTCCGGGAAGCCCGGAAGTGG<br>CGAAGGTAGTACAAAGGGGATATTGTGA<br>TGACTCAGTCTCCACTCTCCCTGCCCGTC<br>ACCCCTGGAGAGCCGGCCTCCATCTCCTG<br>CAGGTCTAGTCAGAGCCTCCTGCATAGTA<br>ATGGATACAACTATTTGGATTGGTACCTG<br>CAGAAGCCAGGGCAGTCTCCACAGCTCCT<br>GATCTATTTGGGTTCTAATCGGGCCTCCG<br>GGGTCCCTGACAGGTTCAGTGGCAGTGGA<br>TCAGGCACAGATTTTACACTGAAAATCAG<br>CAGAGTGGAGGCTGAGGATGTTGGGGTTT<br>ATTACTGCATGCAGGGACTCGGCCTCCCT<br>CTCACTTTTGGCGGAGGGACCAAGGTTGA<br>GATCAAACGGGCCGCTGCCCTTGATAATG<br>AAAAGTCAAACGGAACAATCATTCACGTG<br>AAGGGCAAGCACCTCTGTCCGTCACCCTT<br>GTTCCCTGGTCCATCCAAGCCATTCTGGG<br>TGTTGGTCGTAGTGGGTGGAGTCCTCGCT<br>TGTTACTCTGCTCGTCACCGTGGCTTT<br>TATAATCTTCTGGGTTAGATCCAAAAGAA<br>GCCGCCTGCTCCATAGCGATTACATGAAT<br>ATGACTCCACGCCGCCCTGGCCCCACAAG<br>GAAACACTACCAGCCTTACGCACCACCTA<br>GAGATTTCGCTGCCTATCGGAGCAGGGTG<br>AAGTTTTCCAGATCTGCAGATGCACCAGC<br>GTATCAGCAGGGCCAGAACCAACTGTATA<br>ACGAGCTCAACCTGGGACGCAGGGAAGAG<br>TATGACGTTTTGGACAAGCGCAGAGGACG<br>GGACCCTGAGATGGGTGGCAAACCAAGAC<br>GAAAAAACCCCCAGGAGGGTCTCTATAAT<br>GAGCTGCAGAAGGATAAGATGGCTGAAGC<br>CTATTCTGAAATAGGCATGAAAGGAGAGC<br>GGAGAAGGGGAAAAGGGCACGACGGTTTG<br>TACCAGGGACTCAGCACTGCTACGAAGGA<br>TACTTATGACGCTCTCCACATGCAAGCCC<br>TGCCACCTAGGTAA | 137 | MALPVTALLLPLALLL<br>HAARPQVQLVESGGGV<br>VQPGRSLRLSCAASGF<br>TFSSYGMHWVRQAPGK<br>GLEWVAVISYDGSNKY<br>YADSVKGRFTISRDNS<br>KNTLYLQMNSLRAEDT<br>AVYYCARDGTYLGGLW<br>YFDLWGRGTLVTVSSG<br>STSGSGKPGSGEGSTK<br>GDIVMTQSPLSLPVTP<br>GEPASISCRSSQSLLH<br>SNGYNYLDWYLQKPGQ<br>SPQLLIYLGSNRASGV<br>PDRFSGSGSGTDFTLK<br>ISRVEAEDVGVYYCMQ<br>GLGLPLTFGGGTKVEI<br>KRAAALDNEKSNGTII<br>HVKGKHLCPSPLFPGP<br>SKPFWVLVVVGGVLAC<br>YSLLVTVAFIIFWVRS<br>KRSRLLHSDYMNMTPR<br>RPGPTRKHYQPYAPPR<br>DFAAYRSRVKFSRSAD<br>APAYQQGQNQLYNELN<br>LGRREEYDVLDKRRGR<br>DPEMGGKPRRKNPQEG<br>LYNELQKDKMAEAYSE<br>IGMKGERRRGKHDGL<br>YQGLSTATKDTYDALH<br>MQALPPR | 138 |
| PC-21497CARHx<br>L | ATGGCACTCCCCGTAACTGCTCTGCTGCT<br>GCCGTTGGCATTGCTCCTGCACGCCGCAC<br>GCCCGGATATTGTGATGACTCAGTCTCCA<br>CTCTCCCTGCCCGTCACCCCTGGAGAGCC<br>GGCCTCCATCTCCTGCAGGTCTAGTCAGA<br>GCCTCCTGCATAGTAATGGATACAACTAT<br>TTGGATTGGTACCTGCAGAAGCCAGGGCA<br>GTCTCCACAGCTCCTGATCTATTTGGGTT<br>CTAATCGGGCCTCCGGGGTCCCTGACAGG<br>TTCAGTGGCAGTGGATCAGGCACAGATTT<br>TACACTGAAAATCAGCAGAGTGGAGGCTG<br>AGGATGTTGGGGTTTATTACTGCATGCAG<br>GGACTCGGCCTCCCTCTCACTTTTGGCGG<br>AGGGACCAAGGTTGAGATCAAACGGGGGT<br>CTACATCCGGCTCCGGGAAGCCCGGAAGT<br>GGCGAAGGTAGTACAAAGGGGCAGGTGCA | 139 | MALPVTALLLPLALLL<br>HAARPDIVMTQSPLSL<br>PVTPGEPASISCRSSQ<br>SLLHSNGYNYLDWYLQ<br>KPGQSPQLLIYLGSNR<br>ASGVPDRFSGSGSGTD<br>FTLKISRVEAEDVGVY<br>YCMQGLGLPLTFGGGT<br>KVEIKRGSTSGSGKPG<br>SGEGSTKGQVQLVESG<br>GGVVQPGRSLRLSCAA<br>SGFTFSSYGMHWVRQA<br>PGKGLEWVAVISYDGS<br>NKYYADSVKGRFTISR<br>DNSKNTLYLQMNSLRA<br>EDTAVYYCARDGTYLG | 140 |

TABLE 2-continued

Example CAR Sequences

| CAR Construct | Nucleotide Sequence | SEQ ID NO: | Amino Acid Sequence | SEQ ID NO: |
|---|---|---|---|---|
| | GCTGGTGGAGTCTGGGGGAGGCGTGGTCC AGCCTGGGAGGTCCCTGAGACTCTCCTGT GCAGCGTCTGGATTCACCTTCAGTAGCTA TGGCATGCACTGGGTCCGCCAGGCTCCAG GCAAGGGGCTGGAGTGGGTGGCAGTTATA TCGTATGATGGAAGTAATAAATACTATGC AGACTCCGTGAAGGGCCGATTCACCATCT CCAGAGACAATTCCAAGAACACGCTGTAT CTGCAAATGAACAGCCTGAGAGCCGAGGA CACGGCGGTGTACTACTGCGCCAGAGACG GTACTTATCTAGGTGGTCTCTGGTACTTC GACTTATGGGGAGAGGTACCTTGGTCAC CGTCTCCTCAGCCGCTGCCCTTGATAATG AAAAGTCAAACGGAACAATCATTCACGTG AAGGGCAAGCACCTCTGTCCGTCACCCTT GTTCCCTGGTCCATCCAAGCCATTCTGGG TGTTGGTCGTAGTGGGTGGAGTCCTCGCT TGTTACTCTCTGCTCGTCACCGTGGCTTT TATAATCTTCTGGGTTAGATCCAAAAGAA GCCGCCTGCTCCATAGCGATTACATGAAT ATGACTCCACGCCGCCCTGGCCCCACAAG GAAACACTACCAGCCTTACGCACCACCTA GAGATTTCGCTGCCTATCGGAGCAGGGTG AAGTTTTCCAGATCTGCAGATGCACCAGC GTATCAGCAGGGCCAGAACCAACTGTATA ACGAGCTCAACCTGGGACGCAGGGAAGAG TATGACGTTTTGGACAAGCGCAGAGGACG GGACCCTGAGATGGGTGGCAAACCAAGAC GAAAAAACCCCCAGGAGGGTCTCTATAAT GAGCTGCAGAAGGATAAGATGGCTGAAGC CTATTCTGAAATAGGCATGAAAGGAGAGC GGAGAAGGGGAAAAGGGCACGACGGTTTG TACCAGGGACTCAGCACTGCTACGAAGGA TACTTATGACGCTCTCCACATGCAAGCCC TGCCACCTAGGTAA | | GLWYFDLWGRGTLVTV SSAAALDNEKSNGTII HVKGKHLCPSPLFPGP SKPFWVLVVVGGVLAC YSLLVTVAFIIFWVRS KRSRLLHSDYMNMTPR RPGPTRKHYQPYAPPR DFAAYRSRVKFSRSAD APAYQQGQNQLYNELN LGRREEYDVLDKRRGR DPEMGGKPRRKNPQEG LYNELQKDKMAEAYSE IGMKGERRRGKGHDGL YQGLSTATKDTYDALH MQALPPR | |
| AJ-21508CARHxL | ATGGCACTCCCCGTAACTGCTCTGCTGCT GCCGTTGGCATTGCTCCTGCACGCCGCAC GCCCGCAGGTGCAGCTGGTGCAGTCTGGG GCTGAGGTGAAGAAGCCTGGGGCCTCAGT GAAGGTTTCCTGCAAGGCATCTGGATACA CCTTCACCAGCTACTATATGCACTGGGTG CGACAGGCCCCTGGACAAGGGCTTGAGTG GATGGGAATAATCAACCCTGGTGGTGGTA GCACAAGCTACGCACAGAAGTTCCAGGGC AGAGTCACCATGACCAGGGACACGTCCAC GAGCACAGTCTACATGGAGCTGAGCAGCC TGAGATCTGAGGACACGGCGGTGTACTAC TGCGCCAGAGAGAGTTGGCCAATGGACGT ATGGGGCCAGGGAACAACTGTCACCGTCT CCTCAGGGTCTACATCCGGCTCCGGGAAG CCCGGAAGTGGCGAAGGTAGTACAAAGGG GGAAATAGTGATGACGCAGTCTCCAGCCA CCCTGTCTGTGTCTCCAGGGGAAAGAGCC ACCCTCTCCTGCAGGGCCAGTCAGAGTGT TAGCAGCAACTTAGCCTGGTACCAGCAGA AACCTGGCCAGGCTCCCAGGCTCCTCATC TATGGTGCATCCACCAGGGCCACTGGTAT CCCAGCCAGGTTCAGTGGCAGTGGGTCTG GGACAGAGTTCACTCTCACCATCAGCAGC CTGCAGTCTGAAGATTTTGCAGTTTATTA CTGTCAGCAGTACGCCGCCTACCCTACTT TTGGCGGAGGGACCAAGGTTGAGATCAAA CGGGCCGCTGCCCTTGATAATGAAAAGTC AAACGGAACAATCATTCACGTGAAGGGCA AGCACCTCTGTCCGTCACCCTTGTTCCCT GGTCCATCCAAGCCATTCTGGGTGTTGGT CGTAGTGGGTGGAGTCCTCGCTTGTTACT CTCTGCTCGTCACCGTGGCTTTTATAATC TTCTGGGTTAGATCCAAAAGAAGCCGCCT GCTCCATAGCGATTACATGAATATGACTC CACGCCGCCCTGGCCCCACAAGGAAACAC TACCAGCCTTACGCACCACCTAGAGATTT CGCTGCCTATCGGAGCAGGGTGAAGTTTT | 141 | MALPVTALLLPLALLL HAARPQVQLVQSGAEV KKPGASVKVSCKASGY TFTSYYMHWVRQAPGQ GLEWMGIINPGGGSTS YAQKFQGRVTMTRDTS TSTVYMELSSLRSEDT AVYYCARESWPMDVWG QGTTVTVSSGSTSGSG KPGSGEGSTKGEIVMT QSPATLSVSPGERATL SCRASQSVSSNLAWYQ QKPGQAPRLLIYGAST RATGIPARESGSGSGT EFTLTISSLQSEDFAV YYCQQYAAYPTFGGGT KVEIKRAAALDNEKSN GTIIHVKGKHLCPSPL FPGPSKPFWVLVVGG VLACYSLLVTVAFIIF WVRSKRSRLLHSDYMN MTPRRPGPTRKHYQPY APPRDFAAYRSVKFS RSADAPAYQQGQNQLY NELNLGRREEYDVLDK RRGRDPEMGGKPRRKN PQEGLYNELQKDKMAE AYSEIGMKGERRRGKG HDGLYQGLSTATKDTY DALHMQALPPR | 142 |

TABLE 2-continued

Example CAR Sequences

| CAR Construct | Nucleotide Sequence | SEQ ID NO: | Amino Acid Sequence | SEQ ID NO: |
|---|---|---|---|---|
| | CCAGATCTGCAGATGCACCAGCGTATCAG CAGGGCCAGAACCAACTGTATAACGAGCT CAACCTGGGACGCAGGGAAGAGTATGACG TTTTGGACAAGCGCAGAGGACGGGACCCT GAGATGGGTGGCAAACCAAGACGAAAAAA CCCCCAGGAGGGTCTCTATAATGAGCTGC AGAAGGATAAGATGGCTGAAGCCTATTCT GAAATAGGCATGAAAGGAGAGCGGAGAAG GGGAAAAGGGCACGACGGTTTGTACCAGG GACTCAGCACTGCTACGAAGGATACTTAT GACGCTCTCCACATGCAAGCCCTGCCACC TAGGTAA | | | |
| AJ-21508CARLxH | ATGGCACTCCCCGTAACTGCTCTGCTGCT GCCGTTGGCATTGCTCCTGCACGCCGCAC GCCCGGAAATAGTGATGACGCAGTCTCCA GCCACCCTGTCTGTGTCTCCAGGGGAAAG AGCCACCCTCTCCTGCAGGGCCAGTCAGA GTGTTAGCAGCAACTTAGCCTGGTACCAG CAGAAACCTGGCCAGGCTCCCAGGCTCCT CATCTATGGTGCATCCACCAGGGCCACTG GTATCCCAGCCAGGTTCAGTGGCAGTGGG TCTGGGACAGAGTTCACTCTCACCATCAG CAGCCTGCAGTCTGAAGATTTTGCAGTTT ATTACTGTCAGCAGTACGCCGCCTACCCT ACTTTTGGCGGAGGGACCAAGGTTGAGAT CAAACGGGGGTCTACATCCGGCTCCGGGA AGCCCGGAAGTGGCGAAGGTAGTACAAAG GGGCAGGTGCAGCTGGTGCAGTCTGGGGC TGAGGTGAAGAAGCCTGGGGCCTCAGTGA AGGTTTCCTGCAAGGCATCTGGATACACC TTCACCAGCTACTATATGCACTGGGTGCG ACAGGCCCCTGGACAAGGGCTTGAGTGGA TGGGAATAATCAACCCTGGTGGTGGTAGC ACAAGCTACGCACAGAAGTTCCAGGGCAG AGTCACCATGACCAGGGACACGTCCACGA GCACAGTCTACATGGAGCTGAGCAGCCTG AGATCTGAGGACACGGCGGTGTACTACTG CGCCAGAGAGAGTTGGCCAATGGACGTAT GGGGCCAGGGAACAACTGTCACCGTCTCC TCAGCCGCTGCCCTTGATAATGAAAAGTC AAACGGAACAATCATTCACGTGAAGGGCA AGCACCTCTGTCCGTCACCCTTGTTCCCT GGTCCATCCAAGCCATTCTGGGTGTTGGT CGTAGTGGGTGGAGTCCTCGCTTGTTACT CTCTGCTCGTCACCGTGGCTTTTATAATC TTCTGGGTTAGATCCAAAAGAAGCCGCCT GCTCCATAGCGATTACATGAATATGACTC CACGCCGCCCTGGCCCCACAAGGAAACAC TACCAGCCTTACGCACCACCTAGAGATTT CGCTGCCTATCGGAGCAGGGTGAAGTTTT CCAGATCTGCAGATGCACCAGCGTATCAG CAGGGCCAGAACCAACTGTATAACGAGCT CAACCTGGGACGCAGGGAAGAGTATGACG TTTTGGACAAGCGCAGAGGACGGGACCCT GAGATGGGTGGCAAACCAAGACGAAAAAA CCCCCAGGAGGGTCTCTATAATGAGCTGC AGAAGGATAAGATGGCTGAAGCCTATTCT GAAATAGGCATGAAAGGAGAGCGGAGAAG GGGAAAAGGGCACGACGGTTTGTACCAGG GACTCAGCACTGCTACGAAGGATACTTAT GACGCTCTCCACATGCAAGCCCTGCCACC TAGGTAA | 143 | MALPVTALLLPLALLL HAARPEIVMTQSPATL SVSPGERATLSCRASQ SVSSNLAWYQQKPGQA PRLLIYGASTRATGIP ARFSGSGSGTEFTLTI SSLQSEDFAVYYCQQY AAYPTFGGGTKVEIKR GSTSGSGKPGSGEGST KGQVQLVQSGAEVKKP GASVKVSCKASGYTFT SYYMHWVRQAPGQGLE WMGIINPGGGSTSYAQ KFQGRVTMTRDTSTST VYMELSSLRSEDTAVY YCARESWPMDVWGQGT TVTVSSAAALDNEKSN GTIIHVKGKHLCPSPL FPGPSKPFWVLVVVGG VLACYSLLVTVAFIIF WVRSKRSRLLHSDYMN MTPRRPGPTRKHYQPY APPRDFAAYRSRVKFS RSADAPAYQQGQNQLY NELNLGRREEYDVLDK RRGRDPEMGGKPRRKN PQEGLYNELQKDKMAE AYSEIGMKGERRRGKG HDGLYQGLSTATKDTY DALHMQALPPR | 144 |
| NM-21517CARHxL | ATGGCACTCCCCGTAACTGCTCTGCTGCT GCCGTTGGCATTGCTCCTGCACGCCGCAC GCCCGCAGCTGCAGCTGCAGGAGTCGGGC CCAGGACTGGTGAAGCTTCGGAGACCCCT GTCCCTCACCTGCACTGTCTCTGGTGGCT CCATCAGCAGTAGTAGTTACTACTGGGGC TGGATCCGCCAGCCCCCAGGGAAGGGGCT GGAGTGGATTGGGAGTATCTCCTATAGTG GGAGCACCTACTACAACCCGTCCCTCAAG AGTCGAGTCACCATATCCGTAGACACGTC | 145 | MALPVTALLLPLALLL HAARPQLQLQESGPGL VKPSETLSLTCTVSGG SISSSSYYWGWIRQPP GKGLEWIGSISYSGST YYNPSLKSRVTISVDT SKNQFSLKLSSVTAAD TAVYYCARGRGYATSL AFDIWGQGTMVTVSSG STSGSGKPGSGEGSTK | 146 |

TABLE 2-continued

Example CAR Sequences

| CAR Construct | Nucleotide Sequence | SEQ ID NO: | Amino Acid Sequence | SEQ ID NO: |
|---|---|---|---|---|
| | CAAGAACCAGTTCTCCCTGAAGCTGAGTT CTGTGACCGCCGCAGACACGGCGGTGTAC TACTGCGCCAGAGGCAGGGGATATGCAAC CAGCTTAGCCTTCGATATCTGGGGTCAGG GTACAATGGTCACCGTCTCCTCAGGGTCT ACATCCGGCTCCGGGAAGCCCGGAAGTGG CGAAGGTAGTACAAAGGGGGAAATTGTGT TGACACAGTCTCCAGCCACCCTGTCTTTG TCTCCAGGGGAAAGAGCCACCCTCTCCTG CAGGGCCAGTCAGAGTGTTAGCAGCTACT TAGCCTGGTACCAACAGAAACCTGGCCAG GCTCCCAGGCTCCTCATCTATGATGCATC CAACAGGGCCACTGGCATCCCAGCCAGGT TCAGTGGCAGTGGGTCTGGGACAGACTTC ACTCTCACCATCAGCAGCCTAGAGCCTGA AGATTTTGCAGTTTATTACTGTCAGCAGA GACACGTCTGGCCTCCTACTTTTGGCGGA GGGACCAAGGTTGAGATCAAACGGGCCGC TGCCCTTGATAATGAAAAGTCAAACGGAA CAATCATTCACGTGAAGGGCAAGCACCTC TGTCCGTCACCCTTGTTCCCTGGTCCATC CAAGCCATTCTGGGTGTTGGTCGTAGTGG GTGGAGTCCTCGCTTGTTACTCTCTGCTC GTCACCGTGGCTTTTATAATCTTCTGGGT TAGATCCAAAAGAAGCCGCCTGCTCCATA GCGATTACATGAATATGACTCCACGCCGC CCTGGCCCCACAAGGAAACACTACCAGCC TTACGCACCACCTAGAGATTTCGCTGCCT ATCGGAGCAGGGTGAAGTTTTCCAGATCT GCAGATGCACCAGCGTATCAGCAGGGCCA GAACCAACTGTATAACGAGCTCAACCTGG GACGCAGGGAAGAGTATGACGTTTTGGAC AAGCGCAGAGGACGGGACCCTGAGATGGG TGGCAAACCAAGACGAAAAAACCCCCAGG AGGGTCTCTATAATGAGCTGCAGAAGGAT AAGATGGCTGAAGCCTATTCTGAAATAGG CATGAAGGAGAGCGGAGAAGGGGAAAAG GGCACGACGGTTTGTACCAGGGACTCAGC ACTGCTACGAAGGATACTTATGACGCTCT CCACATGCAAGCCCTGCCACCTAGGTAA | | GEIVLTQSPATLSLSP GERATLSCRASQSVSS YLAWYQQKPGQAPRLL IYDASNRATGIPARFS GSGSGTDFTLTISSLE PEDFAVYYCQQRHVWP PTFGGGTKVEIKRAAA LDNEKSNGTIIHVKGK HLCPSPLFPGPSKPFW VLVVVGGVLACYSLLV TVAFIIFWVRSKRSRL LHSDYMNMTPRRPGPT RKHYQPYAPPRDFAAY RSRVKFSRSADAPAYQ QGQNQLYNELNLGRRE EYDVLDKRRGRDPEMG GKPRRKNPQEGLYNEL QKDKMAEAYSEIGMKG ERRRGKHDGLYQGLS TATKDTYDALHMQALP PR | |
| NM-21517CARLxH | ATGGCACTCCCCGTAACTGCTCTGCTGCT GCCGTTGGCATTGCTCCTGCACGCCGCAC GCCCGGAAATTGTGTTGACACAGTCTCCA GCCACCCTGTCTTTGTCTCCAGGGGAAAG AGCCACCCTCTCCTGCAGGGCCAGTCAGA GTGTTAGCAGCTACTTAGCCTGGTACCAA CAGAAACCTGGCCAGGCTCCCAGGCTCCT CATCTATGATGCATCCAACAGGGCCACTG GCATCCCAGCCAGGTTCAGTGGCAGTGGG TCTGGGACAGACTTCACTCTCACCATCAG CAGCCTAGAGCCTGAAGATTTTGCAGTTT ATTACTGTCAGCAGAGACACGTCTGGCCT CCTACTTTTGGCGGAGGGACCAAGGTTGA GATCAAACGGGGGTCTACATCCGGCTCCG GGAAGCCCGGAAGTGGCGAAGGTAGTACA AAGGGGCAGCTGCAGCTGCAGGAGTCGGG CCCAGGACTGGTGAAGCCTTCGGAGACCC TGTCCCTCACCTGCACTGTCTCTGGTGGC TCCATCAGCAGTAGTAGTTACTACTGGGG CTGGATCCGCCAGCCCCCAGGGAAGGGC TGGAGTGGATTGGGAGTATCTCCTATAGT GGGAGCACCTACTACAACCCGTCCCTCAA GAGTCGAGTCACCATATCCGTAGACACGT CCAAGAACCAGTTCTCCCTGAAGCTGAGT TCTGTGACCGCCGCAGACACGGCGGTGTA CTACTGCGCCAGAGGCAGGGGATATGCAA CCAGCTTAGCCTTCGATATCTGGGGTCAG GGTACAATGGTCACCGTCTCCTCAGCCGC TGCCCTTGATAATGAAAAGTCAAACGGAA CAATCATTCACGTGAAGGGCAAGCACCTC TGTCCGTCACCCTTGTTCCCTGGTCCATC CAAGCCATTCTGGGTGTTGGTCGTAGTGG GTGGAGTCCTCGCTTGTTACTCTCTGCTC | 147 | MALPVTALLLPLALLL HAARPEIVLTQSPATL SLSPGERATLSCRASQ SVSSYLAWYQQKPGQA PRLLIYDASNRATGIP ARFSGSGSGTDFTLTI SSLEPEDFAVYYCQQR HVWPPTFGGGTKVEIK RGSTSGSGKPGSGEGS TKGQLQLQESGPGLVK PSETLSLTCTVSGGSI SSSSYYWGWIRQPPGK GLEWIGSISYSGSTYY NPSLKSRVTISVDTSK NQFSLKLSSVTAADTA VYYCARGRGYATSLAF DIWGQGTMVTVSSAAA LDNEKSNGTIIHVKGK HLCPSPLFPGPSKPFW VLVVVGGVLACYSLLV TVAFIIFWVRSKRSRL LHSDYMNMTPRRPGPT RKHYQPYAPPRDFAAY RSRVKFSRSADAPAYQ QGQNQLYNELNLGRRE EYDVLDKRRGRDPEMG GKPRRKNPQEGLYNEL QKDKMAEAYSEIGMKG ERRRGKHDGLYQGLS TATKDTYDALHMQALP PR | 148 |

TABLE 2-continued

Example CAR Sequences

| CAR Construct | Nucleotide Sequence | SEQ ID NO: | Amino Acid Sequence | SEQ ID NO: |
|---|---|---|---|---|
| | GTCACCGTGGCTTTTATAATCTTCTGGGT TAGATCCAAAAGAAGCCGCCTGCTCCATA GCGATTACATGAATATGACTCCACGCCGC CCTGGCCCCACAAGGAAACACTACCAGCC TTACGCACCACCTAGAGATTTCGCTGCCT ATCGGAGCAGGGTGAAGTTTTCCAGATCT GCAGATGCACCAGCGTATCAGCAGGGCCA GAACCAACTGTATAACGAGCTCAACCTGG GACGCAGGGAAGAGTATGACGTTTTGGAC AAGCGCAGAGGACGGGACCCTGAGATGGG TGGCAAACCAAGACGAAAAAACCCCCAGG AGGGTCTCTATAATGAGCTGCAGAAGGAT AAGATGGCTGAAGCCTATTCTGAAATAGG CATGAAAGGAGAGCGGAGAAGGGGAAAAG GGCACGACGGTTTGTACCAGGGACTCAGC ACTGCTACGAAGGATACTTATGACGCTCT CCACATGCAAGCCCTGCCACCTAGGTAA | | | |
| TS-21522CARHxL | ATGGCACTCCCCGTAACTGCTCTGCTGCT GCCGTTGGCATTGCTCCTGCACGCCGCAC GCCCGGAGGTGCAGCTGGTGGAGTCTGGG GGAGGCTTGGTACAGCCTGGGGGGTCCCT GAGACTCTCCTGTGCAGCCTCTGGATTCA CCTTCAGTAGCTATAGCATGAACTGGGTC CGCCAGGCTCCAGGGAAGGGGCTGGAGTG GGTTTCAACCATTAGTAGTAGTAGTAGTA CCATATACTACGCAGACTCTGTGAAGGGC CGATTCACCATCTCCAGAGACAATGCCAA GAACTCACTGTATCTGCAAATGAACAGCC TGAGAGCTGAGGACACGGCGGTGTACTAC TGCGCCAGAGGTTCTCAGGAGCACCTGAT TTTCGATTATTGGGGACAGGGTACATTGG TCACCGTCTCCTCAGGGTCTACATCCGGC TCCGGGAAGCCCGGAAGTGGCGAAGGTAG TACAAAGGGGGAAATTGTGTTGACACAGT CTCCAGCCACCCTGTCTTTGTCTCCAGGG GAAAGAGCCACCCTCTCCTGCAGGGCCAG TCAGAGTGTTAGCAGGTACTTAGCCTGGT ACCAACAGAAACCTGGCCAGGCTCCCAGG CTCCTCATCTATGATGCATCCAACAGGGC CACTGGCATCCCAGCCAGGTTCAGTGGCA GTGGGTCTGGGACAGACTTCACTCTCACC ATCAGCAGCCTAGAGCCTGAAGATTTTGC AGTTTATTACTGTCAGCAGAGATTCTACT ACCCTTGGACTTTTGGCGGAGGGACCAAG GTTGAGATCAAACGGGCCGCTGCCCTTGA TAATGAAAAGTCAAACGGAACAATCATTC ACGTGAAGGGCAAGCACCTCTGTCCGTCA CCCTTGTTCCCTGGTCCATCCAAGCCATT CTGGGTGTTGGTCGTAGTGGGTGGAGTCC TCGCTTGTTACTCTCTGCTCGTCACCGTG GCTTTTATAATCTTCTGGGTTAGATCCAA AAGAAGCCGCCTGCTCCATAGCGATTACA TGAATATGACTCCACGCCGCCCTGGCCCC ACAAGGAAACACTACCAGCCTTACGCACC ACCTAGAGATTTCGCTGCCTATCGGAGCA GGGTGAAGTTTTCCAGATCTGCAGATGCA CCAGCGTATCAGCAGGGCCAGAACCAACT GTATAACGAGCTCAACCTGGGACGCAGGG AAGAGTATGACGTTTTGGACAAGCGCAGA GGACGGGACCCTGAGATGGGTGGCAAACC AAGACGAAAAAACCCCCAGGAGGGTCTCT ATAATGAGCTGCAGAAGGATAAGATGGCT GAAGCCTATTCTGAAATAGGCATGAAAGG AGAGCGGAGAAGGGGAAAAGGGCACGACG GTTTGTACCAGGGACTCAGCACTGCTACG AAGGATACTTATGACGCTCTCCACATGCA AGCCCTGCCACCTAGGTAA | 149 | MALPVTALLLPLALLL HAARPEVQLVESGGGL VQPGGSLRLSCAASGF TFSSYSMNWVRQAPGK GLEWVSTISSSSSTIY YADSVKGRFTISRDNA KNSLYLQMNSLRAEDT AVYYCARGSQEHLIFD YWGQGTLVTVSSGSTS GSGKPGSGEGSTKGEI VLTQSPATLSLSPGER ATLSCRASQSVSRYLA WYQQKPGQAPRLLIYD ASNRATGIPARFSGSG SGTDFTLTISSLEPED FAVYYCQQRFYYPWTF GGGTKVEIKRAAALDN EKSNGTIIHVKGKHLC PSPLFPGPSKPFWVLV VVGGVLACYSLLVTVA FIIFWVRSKRSRLLHS DYMNMTPRRPGPTRKH YQPYAPPRDFAAYRSR VKFSRSADAPAYQQGQ NQLYNELNLGRREEYD VLDKRRGRDPEMGGKP RRKNPQEGLYNELQKD KMAEAYSEIGMKGERR RGKGHDGLYQGLSTAT KDTYDALHMQALPPR | 150 |
| TS-21522CARLxH | ATGGCACTCCCCGTAACTGCTCTGCTGCT GCCGTTGGCATTGCTCCTGCACGCCGCAC GCCCGGAAATTGTGTTGACACAGTCTCCA GCCACCCTGTCTTTGTCTCCAGGGGAAAG AGCCACCCTCTCCTGCAGGGCCAGTCAGA | 151 | MALPVTALLLPLALLL HAARPEIVLTQSPATL SLSPGERATLSCRASQ SVSRYLAWYQQKPGQA PRLLIYDASNRATGIP | 152 |

TABLE 2-continued

Example CAR Sequences

| CAR Construct | Nucleotide Sequence | SEQ ID NO: | Amino Acid Sequence | SEQ ID NO: |
|---|---|---|---|---|
| | GTGTTAGCAGGTACTTAGCCTGGTACCAA CAGAAACCTGGCCAGGCTCCCAGGCTCCT CATCTATGATGCATCCAACAGGGCCACTG GCATCCCAGCCAGGTTCAGTGGCAGTGGG TCTGGGACAGACTTCACTCTCACCATCAG CAGCCTAGAGCCTGAAGATTTTGCAGTTT ATTACTGTCAGCAGAGATTCTACTACCCT TGGACTTTTGGCGGAGGGACCAAGGTTGA GATCAAACGGGGGTCTACATCCGGCTCCG GGAAGCCCGGAAGTGGCGAAGGTAGTACA AAGGGGGAGGTGCAGCTGGTGGAGTCTGG GGGAGGCTTGGTACAGCCTGGGGGGTCCC TGAGACTCTCCTGTGCAGCCTCTGGATTC ACCTTCAGTAGCTATAGCATGAACTGGGT CCGCCAGGCTCCAGGGAAGGGGCTGGAGT GGGTTTCAACCATTAGTAGTAGTAGTAGT ACCATATACTACGCAGACTCTGTGAAGGG CCGATTCACCATCTCCAGAGACAATGCCA AGAACTCACTGTATCTGCAAATGAACAGC CTGAGAGCTGAGGACACGGCGGTGTACTA CTGCGCCAGAGGTTCTCAGGAGCACCTGA TTTTTCGATTATTGGGGACAGGGTACATTG GTCACCGTCTCCTCAGCCGCTGCCCTTGA TAATGAAAAGTCAAACGGAACAATCATTC ACGTGAAGGGCAAGCACCTCTGTCCGTCA CCCTTGTTCCCTGGTCCATCCAAGCCATT CTGGGTGTTGGTCGTAGTGGGTGGAGTCC TCGCTTGTTACTCTCTGCTCGTCACCGTG GCTTTTATAATCTTCTGGGTTAGATCCAA AAGAAGCCGCCTGCTCCATAGCGATTACA TGAATATGACTCCACGCCGCCCTGGCCCC ACAAGGAAACACTACCAGCCTTACGCACC ACCTAGAGATTTCGCTGCCTATCGGAGCA GGGTGAAGTTTTCAGATCTGCAGATGCA CCAGCGTATCAGCAGGGCCAGAACCAACT GTATAACGAGCTCAACCTGGGACGCAGGG AAGAGTATGACGTTTTGGACAAGCGCAGA GGACGGGACCCTGAGATGGGTGGCAAACC AAGACGAAAAAACCCCCAGGAGGGTCTCT ATAATGAGCTGCAGAAGGATAAGATGGCT GAAGCTATTCTGAAATAGGCATGAAAGG AGAGCGGAGAAGGGGAAAAGGGCACGACG GTTTGTACCAGGGACTCAGCACTGCTACG AAGGATACTTATGACGCTCTCCACATGCA AGCCCTGCCACCTAGGTAA | | ARFSGSGSGTDFTLTI SSLEPEDFAVYYCQQR FYYPWTFGGGTKVEIK RGSTSGSGKPGSGEGS TKGEVQLVESGGGLVQ PGGSLRLSCAASGFTF SSYSMNWVRQAPGKGL EWVSTISSSSSTIYYA DSVKGRFTISRDNAKN SLYLQMNSLRAEDTAV YYCARGSQEHLIFDYW GQGTLVTVSSAAALDN EKSNGTIIHVKGKHLC PSPLFPGPSKPFWVLV VVGGVLACYSLLVTVA FIIFWVRSKRSRLLHS DYMNMTPRRPGPTRKH YQPYAPPRDFAAYRSR VKFSRSADAPAYQQGQ NQLYNELNLGRREEYD VLDKRRGRDPEMGGKP RRKNPQEGLYNELQKD KMAEAYSEIGMKGERR RGKGHDGLYQGLSTAT KDTYDALHMQALPPR | |
| RY- 21527CARHx L | ATGGCACTCCCCGTAACTGCTCTGCTGCT GCCGTTGGCATTGCTCCTGCACGCCGCAC GCCCGCAGGTGCAGCTGGTGGAGTCTGGG GGAGGCGTGGTCCAGCCTGGGAGGTCCCT GAGACTCTCCTGTGCAGCGTCTGGATTCA CCTTCAGTAGCTATGGCATGCACTGGGTC CGCCAGGCTCCAGGCAAGGGGCTGGAGTG GGTGGCAGTTATATCGTATGATGGAAGTA ATAAATACTATGCAGACTCCGTGAAGGGC CGATTCACCATCTCCAGAGACAATTCCAA GAACACGCTGTATCTGCAAATGAACAGCC TGAGAGCCGAGGACACGGCGGTGTACTAC TGCGCCAGAACTGACTTCTGGAGCGGATC CCCTCCAGGCTTAGATTACTGGGGACAGG GTACATTGGTCACCGTCTCCTCAGGGTCT ACATCCGGCTCCGGGAAGCCCGGAAGTGG CGAAGGTAGTACAAAGGGGGACATCCAGT TGACCCAGTCTCCATCTTCCGTGTCTGCA TCTGTAGGAGACAGAGTCACCATCACTTG TCGGGCGAGTCAGGGTATTAGCAGCTGGT TAGCCTGGTATCAGCAGAAACCAGGGAAA GCCCCTAAGCTCCTGATCTATGGTGCATC CAGTTTGCAAAGTGGGGTCCCATCAAGGT TCAGCGGCAGTGGATCTGGGACAGATTTC ACTCTCACCATCAGCAGCCTGCAGCCTGA AGATTTTGCAACTTATTACTGTCAGCAGA TATACACCTTCCCTTTCACTTTTGGCGGA GGGACCAAGGTTGAGATCAAACGGGCCGC | 153 | MALPVTALLLPLALLL HAARPQVQLVESGGGV VQPGRSLRLSCAASGF TFSSYGMHWVRQAPGK GLEWVAVISYDGSNKY YADSVKGRFTISRDNS KNTLYLQMNSLRAEDT AVYYCARTDFWSGSPP GLDYWGQGTLVTVSSG STSGSGKPGSGEGSTK GDIQLTQSPSSVSASV GDRVTITCRASQGISS WLAWYQQKPGKAPKLL IYGASSLQSGVPSRFS GSGSGTDFTLTISSLQ PEDFATYYCQQIYTFP FTFGGGTKVEIKRAAA LDNEKSNGTIIHVKGK HLCPSPLFPGPSKPFW VLVVVGGVLACYSLLV TVAFIIFWVRSKRSRL LHSDYMNMTPRRPGPT RKHYQPYAPPRDFAAY RSRVKFSRSADAPAYQ QGQNQLYNELNLGRRE EYDVLDKRRGRDPEMG GKPRRKNPQEGLYNEL QKDKMAEAYSEIGMKG | 154 |

TABLE 2-continued

Example CAR Sequences

| CAR Construct | Nucleotide Sequence | SEQ ID NO: | Amino Acid Sequence | SEQ ID NO: |
|---|---|---|---|---|
| | TGCCCTTGATAATGAAAAGTCAAACGGAA CAATCATTCACGTGAAGGGCAAGCACCTC TGTCCGTCACCCTTGTTCCCTGGTCCATC CAAGCCATTCTGGGTGTTGGTCGTAGTGG GTGGAGTCCTCGCTTGTTACTCTCTGCTC GTCACCGTGGCTTTTATAATCTTCTGGGT TAGATCCAAAAGAAGCCGCCTGCTCCATA GCGATTACATGAATATGACTCCACGCCGC CCTGGCCCCACAAGGAAACACTACCAGCC TTACGCACCACCTAGAGATTTCGCTGCCT ATCGGAGCAGGGTGAAGTTTTCCAGATCT GCAGATGCACCAGCGTATCAGCAGGGCCA GAACCAACTGTATAACGAGCTCAACCTGG GACGCAGGGAAGAGTATGACGTTTTGGAC AAGCGCAGAGGACGGGACCCTGAGATGGG TGGCAAACCAAGACGAAAAAACCCCCAGG AGGGTCTCTATAATGAGCTGCAGAAGGAT AAGATGGCTGAAGCCTATTCTGAAATAGG CATGAAGGAGAGCGGAGAAGGGGAAAAG GGCACGACGGTTTGTACCAGGGACTCAGC ACTGCTACGAAGGATACTTATGACGCTCT CCACATGCAAGCCCTGCCACCTAGGTAA | | ERRRGKGHDGLYQGLS TATKDTYDALHMQALP PR | |
| RY-21527CARLxH | ATGGCACTCCCCGTAACTGCTCTGCTGCT GCCGTTGGCATTGCTCCTGCACGCCGCAC GCCCGGACATCCAGTTGACCCAGTCTCCA TCTTCCGTGTCTGCATCTGTAGGAGACAG AGTCACCATCACTTGTCGGGCGAGTCAGG GTATTAGCAGCTGGTTAGCCTGGTATCAG CAGAAACCAGGGAAAGCCCCTAAGCTCCT GATCTATGGTGCATCCAGTTTGCAAAGTG GGGTCCCATCAAGGTTCAGCGGCAGTGGA TCTGGGACAGATTTCACTCTCACCATCAG CAGCCTGCAGCCTGAAGATTTTGCAACTT ATTACTGTCAGCAGATATACACCTTCCCT TTCACTTTTGGCGGAGGGACCAAGGTTGA GATCAAACGGGGGTCTACATCCGGCTCCG GGAAGCCCGGAAGTGGCGAAGGTAGTACA AAGGGGCAGGTGCAGCTGGTGGAGTCTGG GGGAGGCGTGGTCCAGCCTGGGAGGTCCC TGAGACTCTCCTGTGCAGCGTCTGGATTC ACCTTCAGTAGCTATGGCATGCACTGGGT CCGCCAGGCTCCAGGCAAGGGGCTGGAGT GGGTGGCAGTTATATCGTATGATGGAAGT AATAAATACTATGCAGACTCCGTGAAGGG CCGATTCACCATCTCCAGAGACAATTCCA AGAACACGCTGTATCTGCAAATGAACAGC CTGAGAGCCGAGGACACGGCGGTGTACTA CTGCGCCAGAACTGACTTCTGGAGCGGAT CCCCTCCAGGCTTAGATTACTGGGGACAG GGTACATTGGTCACCGTCTCCTCAGCCGC TGCCCTTGATAATGAAAAGTCAAACGGAA CAATCATTCACGTGAAGGGCAAGCACCTC TGTCCGTCACCCTTGTTCCCTGGTCCATC CAAGCCATTCTGGGTGTTGGTCGTAGTGG GTGGAGTCCTCGCTTGTTACTCTCTGCTC GTCACCGTGGCTTTTATAATCTTCTGGGT TAGATCCAAAAGAAGCCGCCTGCTCCATA GCGATTACATGAATATGACTCCACGCCGC CCTGGCCCCACAAGGAAACACTACCAGCC TTACGCACCACCTAGAGATTTCGCTGCCT ATCGGAGCAGGGTGAAGTTTTCCAGATCT GCAGATGCACCAGCGTATCAGCAGGGCCA GAACCAACTGTATAACGAGCTCAACCTGG GACGCAGGGAAGAGTATGACGTTTTGGAC AAGCGCAGAGGACGGGACCCTGAGATGGG TGGCAAACCAAGACGAAAAAACCCCCAGG AGGGTCTCTATAATGAGCTGCAGAAGGAT AAGATGGCTGAAGCCTATTCTGAAATAGG CATGAAGGAGAGCGGAGAAGGGGAAAAG GGCACGACGGTTTGTACCAGGGACTCAGC ACTGCTACGAAGGATACTTATGACGCTCT CCACATGCAAGCCCTGCCACCTAGGTAA | 155 | MALPVTALLLPLALLL HAARPDIQLTQSPSSV SASVGDRVTITCRASQ GISSWLAWYQQKPGKA PKLLIYGASSLQSGVP SRFSGSGSGTDFTLTI SSLQPEDFATYYCQQI YTFPFTGGGTKVEIK RGSTSGSGKPGSGEGS TKGQVQLVESGGGVVQ PGRSLRLSCAASGFTF SSYGMHWVRQAPGKGL EWVAVISYDGSNKYYA DSVKGRFTISRDNSKN TLYLQMNSLRAEDTAV YYCARTDFWSGSPPGL DYWGQGTLVTVSSAAA LDNEKSNGTIIHVKGK HLCPSPLFPGPSKPFW VLVVVGGVLACYSLLV TVAFIIFWVRSKRSRL LHSDYMNMTPRRPGPT RKHYQPYAPPRDFAAY RSRVKFSRSADAPAYQ QGQNQLYNELNLGRRE EYDVLDKRRGRDPEMG GKPRRKNPQEGLYNEL QKDKMAEAYSEIGMKG ERRRGKGHDGLYQGLS TATKDTYDALHMQALP PR | 156 |

TABLE 2-continued

Example CAR Sequences

| CAR Construct | Nucleotide Sequence | SEQ ID NO: | Amino Acid Sequence | SEQ ID NO: |
|---|---|---|---|---|
| PP-21528CARHxL | ATGGCACTCCCCGTAACTGCTCTGCTGCT GCCGTTGGCATTGCTCCTGCACGCCGCAC GCCCGCAGGTGCAGCTGGTGCAGTCTGGG GCTGAGGTGAAGAAGCCTGGGTCCTCGGT GAAGGTCTCCTGCAAGGCTTCTGGAGGCA CCTTCAGCAGCTATGCTATCAGCTGGGTG CGACAGGCCCCTGGACAAGGGCTTGAGTG GATGGGAGGGATCATCCCTATCTTTGGTA CAGCAAACTACGCACAGAAGTTCCAGGGC AGAGTCACGATTACCGCGGACGAATCCAC GAGCACAGCCTACATGGAGCTGAGCAGCC TGAGATCTGAGGACACGGCGGTGTACTAC TGCGCCAGAACTCCTGAATACTCCTCCAG CATATGGCACTATTACTACGGCATGGACG TATGGGGCCAGGGAACAACTGTCACCGTC TCCTCAGGGTCTACATCCGGCTCCGGGAA GCCCGGAAGTGGCGAAGGTAGTACAAAGG GGGACATCGTGATGACCCAGTCTCCAGAC TCCCTGGCTGTGTCTCTGGGCGAGAGGGC CACCATCAACTGCAAGTCCAGCCAGAGTG TTTTATACAGCTCCAACAATAAGAACTAC TTAGCTTGGTACCAGCAGAAACCAGGACA GCCTCCTAAGCTGCTCATTTACTGGGCAT CTACCCGGGAATCCGGGGTCCCTGACCGA TTCAGTGGCAGCGGGTCTGGGACAGATTT CACTCTCACCATCAGCAGCCTGCAGGCTG AAGATGTGGCAGTTTATTACTGTCAGCAG TTCGCCCACACTCCTTTCACTTTTGGCGG AGGGACCAAGGTTGAGATCAAACGGGCCG CTGCCCTTGATAATGAAAAGTCAAACGGA ACAATCATTCACGTGAAGGGCAAGCACCT CTGTCCGTCACCCTTGTTCCTGGTCCAT CCAAGCCATTCTGGGTGTTGGTCGTAGTG GGTGGAGTCCTCGCTTGTTACTCTCTGCT CGTCACCGTGGCTTTTATAATCTTCTGGG TTAGATCCAAAAGAAGCCGCCTGCTCCAT AGCGATTACATGAATATGACTCCACGCCG CCCTGGCCCCACAAGGAAACACTACCAGC CTTACGCACCACCTAGAGATTTCGCTGCC TATCGGAGCAGGGTGAAGTTTTCCAGATC TGCAGATGCACCAGCGTATCAGCAGGGCC AGAACCAACTGTATAACGAGCTCAACCTG GGACGCAGGGAAGAGTATGACGTTTTGGA CAAGCGCAGAGGACGGGACCCTGAGATGG GTGGCAAACCAAGACGAAAAAACCCCCAG GAGGGTCTCTATAATGAGCTGCAGAAGGA TAAGATGGCTGAAGCCTATTCTGAAATAG GCATGAAAGGAGAGCGGAGAAGGGGAAAA GGGCACGACGGTTTGTACCAGGGACTCAG CACTGCTACGAAGGATACTTATGACGCTC TCCACATGCAAGCCCTGCCACCTAGGTAA | 157 | MALPVTALLLPLALLL HAARPQVQLVQSGAEV KKPGSSVKVSCKASGG TFSSYAISWVRQAPGQ GLEWMGGIIPIFGTAN YAQKFQGRVTITADES TSTAYMELSSLRSEDT AVYYCARTPEYSSSIW HYYYGMDVWGQGTTVT VSSGSTSGSGKPGSGE GSTKGDIVMTQSPDSL AVSLGERATINCKSSQ SVLYSSNNKNYLAWYQ QKPGQPPKLLIYWAST RESGVPDRFSGSGSGT DFTLTISSLQAEDVAV YYCQQFAHTPFTFGGG TKVEIKRAAALDNEKS NGTIIHVKGKHLCPSP LFPGPSKPFWVLVVVG GVLACYSLLVTVAFII FWVRSKRSRLLHSDYM NMTPRRPGPTRKHYQP YAPPRDFAAYRSRVKF SRSADAPAYQQGQNQL YNELNLRREEYDVLD KRRGRDPEMGGKPRRK NPQEGLYNELQKDKMA EAYSEIGMKGERRRGK GHDGLYQGLSTATKDT YDALHMQALPPR | 158 |
| PP-21528CARLxH | ATGGCACTCCCCGTAACTGCTCTGCTGCT GCCGTTGGCATTGCTCCTGCACGCCGCAC GCCCGGACATCGTGATGACCCAGTCTCCA GACTCCCTGGCTGTGTCTCTGGGCGAGAG GGCCACCATCAACTGCAAGTCCAGCCAGA GTGTTTTATACAGCTCCAACAATAAGAAC TACTTAGCTTGGTACCAGCAGAAACCAGG ACAGCCTCCTAAGCTGCTCATTTACTGGG CATCTACCCGGGAATCCGGGGTCCCTGAC CGATTCAGTGGCAGCGGGTCTGGGACAGA TTTCACTCTCACCATCAGCAGCCTGCAGG CTGAAGATGTGGCAGTTTATTACTGTCAG CAGTTCGCCCACACTCCTTTCACTTTTGG CGGAGGGACCAAGGTTGAGATCAAACGGG GGTCTACATCCGGCTCCGGGAAGCCCGGA AGTGGCGAAGGTAGTACAAAGGGGCAGGT GCAGCTGGTGCAGTCTGGGGCTGAGGTGA AGAAGCCTGGGTCCTCGGTGAAGGTCTCC TGCAAGGCTTCTGGAGGCACCTTCAGCAG CTATGCTATCAGCTGGGTGCGACAGGCCC CTGGACAAGGGCTTGAGTGGATGGGAGGG ATCATCCCTATCTTTGGTACAGCAAACTA | 159 | MALPVTALLLPLALLL HAARPDIVMTQSPDSL AVSLGERATINCKSSQ SVLYSSNNKNYLAWYQ QKPGQPPKLLIYWAST RESGVPDRFSGSGSGT DFTLTISSLQAEDVAV YYCQQFAHTPFTFGGG TKVEIKRGSTSGSGKP GSGEGSTKGQVQLVQS GAEVKKPGSSVKVSCK ASGGTFSSYAISWVRQ APGQGLEWMGGIIPIF GTANYAQKFQGRVTIT ADESTSTAYMELSSLR SEDTAVYYCARTPEYS SSIWHYYYGMDVWGQG TTVTVSSAAALDNEKS NGTIIHVKGKHLCPSP LFPGPSKPFWVLVVVG GVLACYSLLVTVAFII FWVRSKRSRLLHSDYM | 160 |

TABLE 2-continued

Example CAR Sequences

| CAR Construct | Nucleotide Sequence | SEQ ID NO: | Amino Acid Sequence | SEQ ID NO: |
|---|---|---|---|---|
| | CGCACAGAAGTTCCAGGGCAGAGTCACGA TTACCGCGGACGAATCCACGAGCACAGCC TACATGGAGCTGAGCAGCCTGAGATCTGA GGACACGGCGGTGTACTACTGCGCCAGAA CTCCTGAATACTCCTCCAGCATATGGCAC TATTACTACGGCATGGACGTATGGGGCCA GGGAACAACTGTCACCGTCTCCTCAGCCG CTGCCCTTGATAATGAAAAGTCAAACGGA ACAATCATTCACGTGAAGGGCAAGCACCT CTGTCCGTCACCCTTGTTCCCTGGTCCAT CCAAGCCATTCTGGGTGTTGGTCGTAGTG GGTGGAGTCCTCGCTTGTTACTCTCTGCT CGTCACCGTGGCTTTTATAATCTTCTGGG TTAGATCCAAAAGAAGCCGCCTGCTCCAT AGCGATTACATGAATATGACTCCACGCCG CCCTGGCCCCACAAGGAAACACTACCAGC CTTACGCACCACCTAGAGATTTCGCTGCC TATCGGAGCAGGGTGAAGTTTTCCAGATC TGCAGATGCACCAGCGTATCAGCAGGGCC AGAACCAACTGTATAACGAGCTCAACCTG GGACGCAGGGAAGAGTATGACGTTTTGGA CAAGCGCAGAGGACGGGACCCTGAGATGG GTGGCAAACCAAGACGAAAAAACCCCCAG GAGGGTCTCTATAATGAGCTGCAGAAGGA TAAGATGGCTGAAGCCTATTCTGAAATAG GCATGAAAGGAGAGCGGAGAAGGGGAAAA GGGCACGACGGTTTGTACCAGGGACTCAG CACTGCTACGAAGGATACTTATGACGCTC TCCACATGCAAGCCCTGCCACCTAGGTAA | | NMTPRRPGPTRKHYQP YAPPRDFAAYRSRVKF SRSADAPAYQQGQNQL YNELNLGRREEYDVLD KRRGRDPEMGGKPRRK NPQEGLYNELQKDKMA EAYSEIGMKGERRRGK GHDGLYQGLSTATKDT YDALHMQALPPR | |
| RD-21530CARHxL | ATGGCACTCCCCGTAACTGCTCTGCTGCT GCCGTTGGCATTGCTCCTGCACGCCGCAC GCCCCGCAGGTGCAGCTGGTGGAGTCTGGG GGAGGCGTGGTCCAGCCTGGGAGGTCCCT GAGACTCTCCTGTGCAGCGTCTGGATTCA CCTTCAGTAGCTATGGCATGCACTGGGTC CGCCAGGCTCCAGGCAAGGGGCTGGAGTG GGTGGCAGTTATATCGTATGATGGAAGTA ATAAATACTATGCAGACTCCGTGAAGGGC CGATTCACCATCTCCAGAGACAATTCCAA GAACACGCTGTATCTGCAAATGAACAGCC TGAGAGCCGAGGACACGGCGGTGTACTAC TGCGTCAAGGGGCCGTTGCAGGAGCCGCC ATACGATTATGGAATGGACGTATGGGGCC AGGGAACAACTGTCACCGTCTCCTCAGGG TCTACATCCGGCTCCGGGAAGCCCGGAAG TGGCGAAGGTAGTACAAAGGGGGAAATAG TGATGACGCAGTCTCCAGCCACCCTGTCT GTGTCTCCAGGGGAAAGAGCCACCCTCTC CTGCAGGGCCAGTCAGAGTGTTAGCAGCA ACTTAGCCTGGTACCAGCAGAAACCTGGC CAGGCTCCCAGGCTCCTCATCTATAGCGC ATCCACCAGGGCCACTGGTATCCCAGCCA GGTTCAGTGGCAGTGGGTCTGGGACAGAG TTCACTCTCACCATCAGCAGCCTGCAGTC TGAAGATTTTGCAGTTTATTACTGTCAGC AGCACCACGTCTGGCCTCTCACTTTTGGC GGAGGGACCAAGGTTGAGATCAAACGGGC CGCTGCCCTTGATAATGAAAAGTCAAACG GAACAATCATTCACGTGAAGGGCAAGCAC CTCTGTCCGTCACCCTTGTTCCCTGGTCC ATCCAAGCCATTCTGGGTGTTGGTCGTAG TGGGTGGAGTCCTCGCTTGTTACTCTCTG CTCGTCACCGTGGCTTTTATAATCTTCTG GGTTAGATCCAAAAGAAGCCGCCTGCTCC ATAGCGATTACATGAATATGACTCCACGC CGCCCTGGCCCCACAAGGAAACACTACCA GCCTTACGCACCACCTAGAGATTTCGCTG CCTATCGGAGCAGGGTGAAGTTTTCCAGA TCTGCAGATGCACCAGCGTATCAGCAGGG CCAGAACCAACTGTATAACGAGCTCAACC TGGGACGCAGGGAAGAGTATGACGTTTTG GACAAGCGCAGAGGACGGGACCCTGAGAT GGGTGGCAAACCAAGACGAAAAAACCCCC | 161 | MALPVTALLLPLALLL HAARPQVQLVESGGGV VQPGRSLRLSCAASGF TFSSYGMHWVRQAPGK GLEWVAVISYDGSNKY YADSVKGRFTISRDNS KNTLYLQMNSLRAEDT AVYYCVKGPLQEPPYD YGMDVWGQGTTVTVSS GSTSGSGKPGSGEGST KGEIVMTQSPATLSVS PGERATLSCRASQSVS SNLAWYQQKPGQAPRL LIYSASTRATGIPARF SGSGSGTEFTLTISSL QSEDFAVYYCQQHHVW PLTFGGGTKVEIKRAA ALDNEKSNGTIIHVKG KHLCPSPLFPGPSKPF WVLVVVGGVLACYSLL VTVAFIIFWVRSKRSR LLHSDYMNMTPRRPGP TRKHYQPYAPPRDFAA YRSRVKFSRSADAPAY QQGQNQLYNELNLGRR EEYDVLDKRRGRDPEM GGKPRRKNPQEGLYNE LQKDKMAEAYSEIGMK GERRRGKGHDGLYQGL STATKDTYDALHMQAL PPR | 162 |

TABLE 2-continued

Example CAR Sequences

| CAR Construct | Nucleotide Sequence | SEQ ID NO: | Amino Acid Sequence | SEQ ID NO: |
|---|---|---|---|---|
| | AGGAGGGTCTCTATAATGAGCTGCAGAAG GATAAGATGGCTGAAGCCTATTCTGAAAT AGGCATGAAAGGAGAGCGGAGAAGGGAA AAGGGCACGACGGTTTGTACCAGGGACTC AGCACTGCTACGAAGGATACTTATGACGC TCTCCACATGCAAGCCCTGCCACCTAGGT AA | | | |
| RD-21530CARLxH | ATGGCACTCCCCGTAACTGCTCTGCTGCT GCCGTTGGCATTGCTCCTGCACGCCGCAC GCCCGGAAATAGTGATGACGCAGTCTCCA GCCACCCTGTCTGTGTCTCCAGGGGAAAG AGCCACCCTCTCCTGCAGGGCCAGTCAGA GTGTTAGCAGCAACTTAGCCTGGTACCAG CAGAAACCTGGCCAGGCTCCCAGGCTCCT CATCTATAGCGCATCCACCAGGGCCACTG GTATCCCAGCCAGGTTCAGTGGCAGTGGG TCTGGGACAGAGTTCACTCTCACCATCAG CAGCCTGCAGTCTGAAGATTTTGCAGTTT ATTACTGTCAGCAGCACCACGTCTGGCCT CTCACTTTTGGCGGAGGGACCAAGGTTGA GATCAAACGGGGGTCTACATCCGGCTCCG GGAAGCCCGGAAGTGGCGAAGGTAGTACA AAGGGGCAGGTGCAGCTGGTGGAGTCTGG GGGAGGCGTGGTCCAGCCTGGGAGGTCCC TGAGACTCTCCTGTGCAGCGTCTGGATTC ACCTTCAGTAGCTATGGCATGCACTGGGT CCGCCAGGCTCCAGGCAAGGGGCTGGAGT GGGTGGCAGTTATATCGTATGATGGAAGT AATAAATACTATGCAGACTCCGTGAAGGG CCGATTCACCATCTCCAGAGACAATTCCA AGAACACGCTGTATCTGCAAATGAACAGC CTGAGAGCCGAGGACACGGCGGTGTACTA CTGCGTCAAGGGGCCGTTGCAGGAGCCGC CATACGATTATGGAATGGACGTATGGGGC CAGGGAACAACTGTCACCGTCTCCTCAGC CGCTGCCCTTGATAATGAAAAGTCAAACG GAACAATCATTCACGTGAAGGGCAAGCAC CTCTGTCCGTCACCCTTGTTCCCTGGTCC ATCCAAGCCATTCTGGGTGTTGGTCGTAG TGGGTGGAGTCCTCGCTTGTTACTCTCTG CTCGTCACCGTGGCTTTTATAATCTTCTG GGTTAGATCCAAAAGAAGCCGCCTGCTCC ATAGCGATTACATGAATATGACTCCACGC CGCCCTGGCCCCACAAGGAAACACTACCA GCCTTACGCACCACCTAGAGATTTCGCTG CCTATCGGAGCAGGGTGAAGTTTTCCAGA TCTGCAGATGCACCAGCGTATCAGCAGGG CCAGAACCAACTGTATAACGAGCTCAACC TGGGACGCAGGGAAGAGTATGACGTTTTG GACAAGCGCAGAGGACGGGACCCTGAGAT GGGTGGCAAACCAAGACGAAAAAACCCCC AGGAGGGTCTCTATAATGAGCTGCAGAAG GATAAGATGGCTGAAGCCTATTCTGAAAT AGGCATGAAAGGAGAGCGGAGAAGGGGAA AAGGGCACGACGGTTTGTACCAGGGACTC AGCACTGCTACGAAGGATACTTATGACGC TCTCCACATGCAAGCCCTGCCACCTAGGT AA | 163 | MALPVTALLLPLALLL HAARPEIVMTQSPATL SVSPGERATLSCRASQ SVSSNLAWYQQKPGQA PRLLIYSASTRATGIP ARFSGSGSGTEFTLTI SSLQSEDFAVYYCQQH HVWPLTFGGGTKVEIK RGSTSGSGKPGSGEGS TKGQVQLVESGGGVVQ PGRSLRLSCAASGFTF SSYGMHWVRQAPGKGL EWVAVISYDGSNKYYA DSVKGRFTISRDNSKN TLYLQMNSLRAEDTAV YYCVKGPLQEPPYDYG MDVWGQGTTVTVSSAA ALDNEKSNGTIIHVKG KHLCPSPLFPGPSKPF WVLVVVGGVLACYSLL VTVAFIIFWVRSKRSR LLHSDYMNMTPRRPGP TRKHYQPYAPPRDFAA YRSRVKFSRSADAPAY QQGQNQLYNELNLGRR EEYDVLDKRRGRDPEM GGKPRRKNPQEGLYNE LQKDKMAEAYSEIGMK GERRRGKGHDGLYQGL STATKDTYDALHMQAL PPR | 164 |
| Clone 24C1 THD CAR DNA HxL | ATGGCACTCCCCGTAACTGCTCTGCTGCT GCCGTTGGCATTGCTCCTGCACGCCGCAC GCCCGCAGGTCCAACTGCAAGAAAGCGGA CCCGGACTGGTGAAGCTTCTGAGACACT TAGTCTGACGTGCACGGTCAGTGGCGGT CCATCTCCTCCTATTATTGGTCATGGATA CGACAACCCCAGGTAAGGGCCTGGAATG GATTGGCTATATCTACTATTCAGGAAGCA CGAACTACAATCCCAGCCTGAAGTCCGA GTGACAATTTCAGTAGATACCAGTAAAAA CCAGTTCAGTCTTAAACTGTCAAGCGTGA CAGCTGCCGACACCGCTGTGTATTACTGC GTCTCACTGGTGTATTGTGGAGGGGATTG TTATAGCGGGTTCGATTATTGGGGACAGG | 165 | MALPVTALLLPLALLL HAARPQVQLQESGPGL VKPSETLSLTCTVSGG SISSYYWSWIRQPPGK GLEWIGYIYYSGSTNY NPSLKSRVTISVDTSK NQFSLKLSSVTAADTA VYYCVSLVYCGGDCYS GFDYWGQGTLVTVSSG GGSGGGGSGGGGSDI QLTQSPSSLSASVGDR VSFTCQASQDINNFLN WYQQKPGKAPKLLIYD ASNLETGVPSRFSGSG | 166 |

TABLE 2-continued

Example CAR Sequences

| CAR Construct | Nucleotide Sequence | SEQ ID NO: | Amino Acid Sequence | SEQ ID NO: |
|---|---|---|---|---|
| | GAACCCTGGTGACTGTATCTTCCGGCGGC GGCGGCTCAGGGGGTGGCGGTAGTGGCGG TGGGGGTTCCGATATTCAACTGACACAAT CCCCCAGCTCACTCAGCGCCAGCGTGGGG GACAGGGTTAGCTTTACCTGTCAAGCCTC TCAGGATATAAATAACTTTCTGAACTGGT ATCAACAGAAGCCTGGGAAGGCGCCCAAA CTCCTGATCTATGATGCGTCCAACCTGGA AACTGGCGTGCCTTCACGCTTTAGCGGCT CTGGCAGTGGTACAGACTTCACTTTTACC ATCTCTTCACTTCAGCCGGAGGACATCGC CACATATTACTGTCAACAGTACGGAAACT TGCCCTTTACTTTTGGAGGCGGCACCAAA GTTGAAATCAAAGGGCCGCTGCCCTGGA TAACGAAAAGAGCAATGGGACTATAATAC ATGTTAAAGGAAAACACCTGTGTCCATCT CCCCTGTTCCCTGGACCGTCAAAGCCATT TTGGGTGCTCGTGGTTGTCGGTGGCGTTC TCGCCTGTTATAGCTTGCTGGTGACAGTA GCCTTCATTATCTTTTGGGTGAGATCCAA AAGAAGCCGCTGCTCCATAGCGATTACA TGAATATGACTCCACGCCGCCCTGGCCCC ACAAGGAAACACTACCAGCCTTACGCACC ACCTAGAGATTTCGCTGCCTATCGGAGCA GGGTGAAGTTTTCCAGATCTGCAGATGCA CCAGCGTATCAGCAGGGCCAGAACCAACT GTATAACGAGCTCAACCTGGGACGCAGGG AAGAGTATGACGTTTTGGACAAGCGCAGA GGACGGGACCCTGAGATGGGTGGCAAACC AAGACGAAAAAACCCCCAGGAGGGTCTCT ATAATGAGCTGCAGAAGGATAAGATGGCT GAAGCCTATTCTGAAATAGGCATGAAAGG AGAGCGGAGAAGGGGAAAAGGGCACGACG GTTTGTACCAGGGACTCAGCACTGCTACG AAGGATACTTATGACGCTCTCCACATGCA AGCCCTGCCACCTAGGTAA | | SGTDFTFTISSLQPED IATYYCQQYGNLPFTF GGGTKVEIKRAAALDN EKSNGTIIHVKGKHLC PSPLFPGPSKPFWVLV VVGGVLACYSLLVTVA FIIFWVRSKRSLLHS DYMNMTPRRPGPTRKH YQPYAPPRDFAAYRSR VKFSRSADAPAYQQGQ NQLYNELNLGRREEYD VLDKRRGRDPEMGGKP RRKNPQEGLYNELQKD KMAEAYSEIGMKGERR RGKGHDGLYQGLSTAT KDTYDALHMQALPPR | |
| (CAR1.1) Clone 24C1 THD CAR DNA HxL | CAGGTCCAACTGCAAGAAAGCGGACCCGG ACTGGTGAAGCTTCTGAGACACTTAGTC TGACGTGCACGGTCAGTGGCGGCTCCATC TCCTCCTATTATTGGTCATGGATACGACA ACCCCCAGGTAAGGGCCTGGAATGGATTG GCTATATCTACTATTCAGGAAGCACGAAC TACAATCCCAGCCTGAAGTCCCGAGTGAC AATTTCAGTAGATACCAGTAAAAACCAGT TCAGTCTTAAACTGTCAAGCGTGACAGCT GCCGACACCGCTGTGTATTACTGCGTCTC ACTGGTGTATTGTGGAGGGGATTGTTATA GCGGGTTCGATTATTGGGACAGGGAACC CTGGTGACTGTATCTTCCGGCGGCGGCGG CTCAGGGGGTGGCGGTAGTGGCGGTGGGG GTTCCGATATTCAACTGACACAATCCCCC AGCTCACTCAGCGCCAGCGTGGGGGACAG GGTTAGCTTTACCTGTCAAGCCTCTCAGG ATATAAATAACTTTCTGAACTGGTATCAA CAGAAGCCTGGGAAGGCGCCCAAACTCCT GATCTATGATGCGTCCAACCTGGAAACTG GCGTGCCTTCACGCTTTAGCGGCTCTGGC AGTGGTACAGACTTCACTTTTACCATCTC TTCACTTCAGCCGGAGGACATCGCCACAT ATTACTGTCAACAGTACGGAAACTTGCCC TTTACTTTTGGAGGCGGCACCAAAGTTGA AATCAAAGGGCCGCTGCCCTGGATAACG AAAAGAGCAATGGGACTATAATACATGTT AAAGGAAAACACCTGTGTCCATCTCCCCT GTTCCCTGGACCGTCAAAGCCATTTTGGG TGCTCGTGGTTGTCGGTGGCGTTCTCGCC TGTTATAGCTTGCTGGTGACAGTAGCCTT CATTATCTTTTGGGTGAGATCCAAAAGAA GCCGCCTGCTCCATAGCGATTACATGAAT ATGACTCCACGCCGCCCTGGCCCCACAAG GAAACACTACCAGCCTTACGCACCACCTA GAGATTTCGCTGCCTATCGGAGCAGGGTG AAGTTTTCCAGATCTGCAGATGCACCAGC | 167 | QVQLQESGPGLVKPSE TLSLTCTVSGGSISSY YWSWIRQPPGKGLEWI GYIYYSGSTNYNPSLK SRVTISVDTSKNQFSL KLSSVTAADTAVYYCV SLVYCGGDCYSGFDYW GQGTLVTVSSGGGGSG GGSGGGGSDIQLTQS PSSLSASVGDRVSFTC QASQDINNFLNWYQQK PGKAPKLLIYDASNLE TGVPSRFSGSGSGTDF TFTISSLQPEDIATYY CQQYGNLPFTFGGGTK VEIKRAAALDNEKSNG TIIHVKGKHLCPSPLF PGPSKPFWVLVVVGGV LACYSLLVTVAFIIFW VRSKRSLLHSDYMNM TPRRPGPTRKHYQPYA PPRDFAAYRSRVKFSR SADAPAYQQGQNQLYN ELNLGRREEYDVLDKR RGRDPEMGGKPRRKNP QEGLYNELQKDKMAEA YSEIGMKGERRRGKGH DGLYQGLSTATKDTYD ALHMQALPPR | 168 |

TABLE 2-continued

Example CAR Sequences

| CAR Construct | Nucleotide Sequence | SEQ ID NO: | Amino Acid Sequence | SEQ ID NO: |
|---|---|---|---|---|
| | GTATCAGCAGGGCCAGAACCAACTGTATA ACGAGCTCAACCTGGGACGCAGGGAAGAG TATGACGTTTTGGACAAGCGCAGAGGACG GGACCCTGAGATGGGTGGCAAACCAAGAC GAAAAAACCCCCAGGAGGGTCTCTATAAT GAGCTGCAGAAGGATAAGATGGCTGAAGC CTATTCTGAAATAGGCATGAAGGAGAGC GGAGAAGGGGAAAAGGGCACGACGGTTTG TACCAGGGACTCAGCACTGCTACGAAGGA TACTTATGACGCTCTCCACATGCAAGCCC TGCCACCTAGG | | | |
| (CAR1.2) Clone 24C1 CHD CAR DNA HxL | ATGGCACTCCCCGTAACTGCTCTGCTGCT GCCGTTGGCATTGCTCCTGCACGCCGCAC GCCCGCAGGTGCAGCTGCAGGAATCCGGA CCGGGGCTGGTGAAGCCCAGCGAGACTCT GAGTCTCACGTGTACAGTTTCTGGAGGTA GCATTAGCTCCTACTATTGGTCATGGATA AGGCAGCCCCCCGGGAAGGGATTGGAATG GATCGGCTATATTTACTACAGTGGGAGCA CCAATTACAACCCCTCACTGAAGTCTAGA GTTACAATCAGCGTTGACACCTCAAAGAA TCAGTTCAGTTTGAAATTGTCTAGCGTCA CAGCAGCTGATACAGCCGTCTATTATTGT GTTTCTCTGGTCTATTGCGGTGGGGATTG TTACAGTGGCTTTGACTATTGGGGGCAGG GTACTCTGGTTACAGTTTCTTCCGGGGGG GGAGGCTCTGGGGGCGGAGGCTCAGGTGG TGGAGGCAGCGACATCCAGTTGACACAGA GCCCGAGTTCCTTGTCCGCCTCCGTCGGG GATAGAGTGTCATTTACCTGTCAGGCCTC TCAGGATATTAATAACTTTCTGAATTGGT ATCAGCAAAAGCCCGGAAAGGCACCCAAG CTGTTGATTTACGACGCCAGTAACCTGGA GACAGGCGTGCCCTCCCGGTTTAGTGGTA GCGGAAGCGGTACGGATTTTACCTTTACT ATCAGCTCTCTCCAACCCGAAGACATTGC AACCTACTATTGTCAACAATATGGAAACC TGCCTTTTACATTTGGCGGCGGCACCAAG GTGGAGATTAAGCGGGCGGCCGCAATATTGA GGTGATGTATCCACCGCCTTACCTGGATA ACGAAAAGAGTAACGGTACCATCATTCAC GTGAAAGGTAAACACCTGTGTCCTTCTCC CCTCTTCCCGGGCCATCAAAGCCCTTCT GGGTTCTTGTGGTCGTGGGAGGCGTGCTT GCTTGTTATTCTCTGCTCGTTACCGTGGC GTTTATCATTTTTTGGGTTAGATCCAAAA GAAGCCGCCTGCTCCATAGCGATTACATG AATATGACTCCACGCCGCCCTGGCCCCAC AAGGAAACACTACCAGCCTTACGCACCAC CTAGAGATTTCGCTGCCTATCGGAGCAGG GTGAAGTTTTCCAGATCTGCAGATGCACC AGCGTATCAGCAGGGCCAGAACCAACTGT ATAACGAGCTCAACCTGGGACGCAGGGAA GAGTATGACGTTTGGACAAGCGCAGAGG ACGGGACCCTGAGATGGGTGGCAAACCAA GACGAAAAAACCCCCAGGAGGGTCTCTAT AATGAGCTGCAGAAGGATAAGATGGCTGA AGCCTATTCTGAAATAGGCATGAAGGAG AGCGGAGAAGGGGAAAAGGGCACGACGGT TTGTACCAGGGACTCAGCACTGCTACGAA GGATACTTATGACGCTCTCCACATGCAAG CCCTGCCACCTAGGTAA | 169 | MALPVTALLLPLALLL HAARPQVQLQESGPGL VKPSETLSLTCTVSGG SISSYYWSWIRQPPGK GLEWIGYIYYSGSTNY NPSLKSRVTISVDTSK NQFSLKLSSVTAADTA VYYCVSLVYCGGDCYS GFDYWGQGTLVTVSSG GGGSGGGSGGGGSDI QLTQSPSSLSASVGDR VSFTCQASQDINNFLN WYQQKPGKAPKLLIYD ASNLETGVPSRFSGSG SGTDFTFTISSLQPED IATYYCQQYGNLPFTF GGGTKVEIKRAAAIEV MYPPPYLDNEKSNGTI IHVKGKHLCPSPLFPG PSKPFWVLVVVGGVLA CYSLLVTVAFIIFWVR SKRSRLLHSDYMNMTP RRPGPTRKHYQPYAPP RDFAAYRSRVKFSRSA DAPAYQQGQNQLYNEL NLGRREEYDVLDKRRG RDPEMGGKPRRKNPQE GLYNELQKDKMAEAYS EIGMKGERRRGKGHDG LYQGLSTATKDTYDAL HMQALPPR | 170 |
| (CAR1.2) Clone 24C1 CHD CAR DNA HxL | CAGGTGCAGCTGCAGGAATCCGGACCGGG GCTGGTGAAGCCCAGCGAGACTCTGAGTC TCACGTGTACAGTTTCTGGAGGTAGCATT AGCTCCTACTATTGGTCATGGATAAGGCA GCCCCCCGGGAAGGGATTGGAATGGATCG GCTATATTTACTACAGTGGGAGCACCAAT TACAACCCCTCACTGAAGTCTAGAGTTAC AATCAGCGTTGACACCTCAAAGAATCAGT TCAGTTTGAAATTGTCTAGCGTCACAGCA GCTGATACAGCCGTCTATTATTGTGTTTC | 171 | QVQLQESGPGLVKPSE TLSLTCTVSGGSISSY YWSWIRQPPGKGLEWI GYIYYSGSTNYNPSLK SRVTISVDTSKNQFSL KLSSVTAADTAVYYCV SLVYCGGDCYSGFDYW GQGTLVTVSSGGGGSG GGGSGGGGSDIQLTQS PSSLSASVGDRVSFTC | 172 |

TABLE 2-continued

Example CAR Sequences

| CAR Construct | Nucleotide Sequence | SEQ ID NO: | Amino Acid Sequence | SEQ ID NO: |
|---|---|---|---|---|
| | TCTGGTCTATTGCGGTGGGGATTGTTACA GTGGCTTTGACTATTGGGGGCAGGGTACT CTGGTTACAGTTTCTTCCGGGGGGGAGG CTCTGGGGGCGGAGGCTCAGGTGGTGGAG GCAGCGACATCCAGTTGACACAGAGCCCG AGTTCCTTGTCCGCCTCCGTCGGGGATAG AGTGTCATTTACCTGTCAGGCCTCTCAGG ATATTAATAACTTTCTGAATTGGTATCAG CAAAAGCCCGGAAAGGCACCCAAGCTGTT GATTTACGACGCCAGTAACCTGGAGACAG GCGTGCCCTCCCGGTTTAGTGGTAGCGGA AGCGGTACGGATTTTACCTTTACTATCAG CTCTCTCCAACCCGAAGACATTGCAACCT ACTATTGTCAACAATATGGAAACCTGCCT TTTACATTTGGCGGCGGCACCAAGGTGGA GATTAAGCGGGCGGCAGCTATTGAGGTGA TGTATCCACCGCCTTACCTGGATAACGAA AAGAGTAACGGTACCATCATTCACGTGAA AGGTAAACACCTGTGTCCTTCTCCCCTCT TCCCCGGGCCATCAAAGCCCTTCTGGGTT CTTGTGGTCGTGGGAGGCGTGCTTGCTTG TTATTCTCTGCTCGTTACCGTGGCGTTTA TCATTTTTTGGGTTAGATCCAAAAGAAGC CGCCTGCTCCATAGCGATTACATGAATAT GACTCCACGCCGCCCTGGCCCCACAAGGA AACACTACCAGCCTTACGCACCACCTAGA GATTTCGCTGCCTATCGGAGCAGGGTGAA GTTTTCCAGATCTGCAGATGCACCAGCGT ATCAGCAGGGCCAGAACCAACTGTATAAC GAGCTCAACCTGGGACGCAGGGAAGAGTA TGACGTTTTGGACAAGCGCAGAGGACGGG ACCCTGAGATGGGTGGCAAACCAAGACGA AAAAACCCCCAGGAGGGTCTCTATAATGA GCTGCAGAAGGATAAGATGGCTGAAGCCT ATTCTGAAATAGGCATGAAAGGAGAGCGG AGAAGGGGAAAAGGGCACGACGGTTTGTA CCAGGGACTCAGCACTGCTACGAAGGATA CTTATGACGCTCTCCACATGCAAGCCCTG CCACCTAGG | | QASQDINNFLNWYQQK PGKAPKLLIYDASNLE TGVPSRFSGSGSGTDF TFTISSLQPEDIATYY CQQYGNLPFTFGGGTK VEIKRAAAIEVMYPPP YLDNEKSNGTIIHVKG KHLCPSPLFPGPSKPF WVLVVVGGVLACYSLL VTVAFIIFWVRSKRSR LLHSDYMNMTPRRPGP TRKHYQPYAPPRDFAA YRSRVKFSRSADAPAY QQGQNQLYNELNLGRR EEYDVLDKRRGRDPEM GGKPRRKNPQEGLYNE LQKDKMAEAYSEIGMK GERRRGKGHDGLYQGL STATKDTYDALHMQAL PPR | |
| (CAR1.3) Clone 24C1 CD8 CAR DNA HxL | ATGGCACTCCCCGTAACTGCTCTGCTGCT GCCGTTGGCATTGCTCCTGCACGCCGCAC GCCCGCAGGTGCAATTGCAAGAGTCCGGC CCCGGACTCGTTAAACCCAGTGAGACGCT TAGCCTGACCTGTACCGTCTCAGGGGGCA GCATCCTCTCTTATTACTGGAGCTGGATC AGGCAGCCTCCAGGAAAGGCCTTGAATG GATTGGGTACATCTACTACTCTGGCTCAA CAAATTATAATCCATCCCTGAAGTCCCGC GTGACTATCTCTGTGGACACCAGCAAGAA TCAGTTTTCACTGAAGTTGTCTAGTGTTA CCGCGGCCGACACCGCCGTATACTACTGT GTGTCTCTTGTGTACTGTGGCGGCGACTG CTATTCCGGGTTCGACTACTGGGGCCAAG GGACTCTGGTAACCGTGTCCTCAGGCGGC GGCGGGTCAGGAGGAGGCGGCAGTGGAGG TGGCGGCTCCGACATCCAGCTGACACAAT CACCATCTTCCCTTTCAGCTTCAGTCGGG GACAGAGTGTCCTTCACATGCCAGGCCAG CCAGGATATCAATAACTTCCTGAACTGGT ACCAACAGAAACCCGGAAAGGCTCCAAAG CTCCTGATCTATGATGCTTCCAACCTGGA GACCGGCGTGCCCTCCAGGTTCAGTGGTT CAGGATCAGGCACTGACTTTACGTTCACC ATATCCTTCAGCCCGAAGACATTGC AACCTATTACTGCCAACAATACGGGAACC TTCCCTTTACATTCGGAGGCGGCACCAAG GTGGAAATCAAAGGGCTGCAGCATTGAG CAACTCAATAATGTATTTTAGTCACTTTG TACCAGTGTTCTTGCCGGCTAAGCCTACT ACCACACCCGCTCCACGGCCACCTACCCC AGCTCCTACCATCGCTTCACAGCCTCTGT CCCTGCGCCCAGAGGCTTGCCGACCGGCC GCAGGGGGCGCTGTTCATACCAGAGGACT | 173 | MALPVTALLLPLALLL HAARPQVQLQESGPGL VKPSETLSLTCTVSGG SISSYYWSWIRQPPGK GLEWIGYIYYSGSTNY NPSLKSRVTISVDTSK NQFSLKLSSVTAADTA VYYCVSLVYCGGDCYS GFDYWGQGTLVTVSSG GGSGGGGSGGGGSDI QLTQSPSSLSASVGDR VSFTCQASQDINNFLN WYQQKPGKAPKLLIYD ASNLETGVPSRFSGSG SGTDFTFTISSLQPED IATYYCQQYGNLPFTF GGGTKVEIKRAAALSN SIMYFSHFVPVFLPAK PTTTPAPRPPTPAPTI ASQPLSLRPEACRPAA GGAVHTRGLDFACDIY IWAPLAGTCGVLLLSL VITLYCNHRNRSKRSR LLHSDYMNMTPRRPGP TRKHYQPYAPPRDFAA YRSRVKFSRSADAPAY QQGQNQLYNELNLGRR EEYDVLDKRRGRDPEM GGKPRRKNPQEGLYNE LQKDKMAEAYSEIGMK GERRRGKGHDGLYQGL STATKDTYDALHMQAL PPR | 174 |

TABLE 2-continued

Example CAR Sequences

| CAR Construct | Nucleotide Sequence | SEQ ID NO: | Amino Acid Sequence | SEQ ID NO: |
|---|---|---|---|---|
| | GGATTTCGCCTGCGATATCTATATCTGGG CACCCCTGGCCGGAACCTGCGGCGTACTC CTGCTGTCCCTGGTCATCACGCTCTATTG TAATCACAGGAACAGATCCAAAAGAAGCC GCCTGCTCCATAGCGATTACATGAATATG ACTCCACGCCGCCCTGGCCCCACAAGGAA ACACTACCAGCCTTACGCACCACCTAGAG ATTTCGCTGCCTATCGGAGCAGGGTGAAG TTTTCCAGATCTGCAGATGCACCAGCGTA TCAGCAGGGCCAGAACCAACTGTATAACG AGCTCAACCTGGGACGCAGGGAAGAGTAT GACGTTTTGGACAAGCGCAGAGGACGGGA CCCTGAGATGGGTGGCAAACCAAGACGAA AAAACCCCCAGGAGGGTCTCTATAATGAG CTGCAGAAGGATAAGATGGCTGAAGCCTA TTCTGAAATAGGCATGAAAGGAGAGCGGA GAAGGGGAAAAGGGCACGACGGTTTGTAC CAGGGACTCAGCACTGCTACGAAGGATAC TTATGACGCTCTCCACATGCAAGCCCTGC CACCTAGGTAA | | | |
| (CAR1.3) Clone 24C1 CD8 CAR DNA HxL | CAGGTGCAATTGCAAGAGTCCGGCCCCGG ACTCGTTAAACCCAGTGAGACGCTTAGCC TGACCTGTACCGTCTCAGGGGGCAGCATC TCCTCTTATTACTGGAGCTGGATCAGGCA GCCTCCAGGAAAAGGCCTTGAATGGATTG GGTACATCTACTACTCTGGCTCAACAAAT TATAATCCATCCCTGAAGTCCCGCGTGAC TATCTCTGTGGACACCAGCAAGAATCAGT TTTCACTGAAGTTGTCTAGTGTTACCGCG GCCGACACCGCCGTATACTACTGTGTGTC TCTTGTGTACTGTGGCGGCGACTGCTATT CCGGGTTCGACTACTGGGGCCAAGGGACT CTGGTAACCGTGTCCTCAGGCGGCGGCGG GTCAGGAGGAGGCGGCAGTGGAGGTGGCG GCTCCGACATCCAGCTGACACAATCACCA TCTTCCCTTTCAGCTTCAGTCGGGGACAG AGTGTCCTTCACATGCCAGGCCAGCCAGG ATATCAATAACTTCCTGAACTGGTACCAA CAGAAACCCGGAAAGGCTCCAAAGCTCCT GATCTATGATGCTTCCAACCTGGAGACCG GCGTGCCCTCCAGGTTCAGTGGTTCAGGA TCAGGCACTGACTTTACGTTCACCATATC CAGTCTTCAGCCCGAAGACATTGCAACCT ATTACTGCCAACAATACGGGAACCTTCCC TTTACATTCGGAGGCGGCACCAAGGTGGA AATCAAAGGGCTGCAGCATTGAGCAACT CAATAATGTATTTAGTCACTTTGTACCA GTGTTCTTGCCGGCTAAGCCTACTACCAC ACCCGCTCCACGGCCACCTACCCCAGCTC CTACCATCGCTTCACAGCCTCTGTCCCTG CGCCCAGAGGCTTGCCGACCGGCCGCAGG GGGCGCTGTTCATACCAGAGGACTGGATT TCGCCTGCGATATCTATATCTGGGCACCC CTGGCCGGAACCTGCGGCGTACTCCTGCT GTCCCTGGTCATCACGCTCTATTGTAATC ACAGGAACAGATCCAAAAGAAGCCGCCTG CTCCATAGCGATTACATGAATATGACTCC ACGCCGCCCTGGCCCCACAAGGAAACACT ACCAGCCTTACGCACCACCTAGAGATTTC GCTGCCTATCGGAGCAGGGTGAAGTTTTC CAGATCTGCAGATGCACCAGCGTATCAGC AGGGCCAGAACCAACTGTATAACGAGCTC AACCTGGGACGCAGGGAAGAGTATGACGT TTTGGACAAGCGCAGAGGACGGGACCCTG AGATGGGTGGCAAACCAAGACGAAAAAAC CCCCAGGAGGGTCTCTATAATGAGCTGCA GAAGGATAAGATGGCTGAAGCCTATTCTG AAATAGGCATGAAAGGAGAGCGGAGAAGG GGAAAAGGGCACGACGGTTTGTACCAGGG ACTCAGCACTGCTACGAAGGATACTTATG ACGCTCTCCACATGCAAGCCCTGCCACCT AGG | 175 | QVQLQESGPGLVKPSE TLSLTCTVSGGSISSY YWSWIRQPPGKGLEWI GYIYYSGSTNYNPSLK SRVTISVDTSKNQFSL KLSSVTAADTAVYYCV SLVYCGGDCYSGFDYW GQGTLVTVSSGGGGSG GGGSGGGGSDIQLTQS PSSLSASVGDRVSFTC QASQDINNFLNWYQQK PGKAPKLLIYDASNLE TGVPSRFSGSGSGTDF TFTISSLQPEDIATYY CQQYGNLPFTFGGGTK VEIKRAAALSNSIMYF SHFVPVFLPAKTTTTP APRPPTPAPTIASQPL SLRPEACRPAAGGAVH TRGLDFACDIYIWAPL AGTCGVLLLSLVITLY CNHRNRSKRSRLLHSD YMNMTPRRPGPTRKHY QPYAPPRDFAAYRSRV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | 176 |

TABLE 2-continued

Example CAR Sequences

| CAR Construct | Nucleotide Sequence | SEQ ID NO: | Amino Acid Sequence | SEQ ID NO: |
|---|---|---|---|---|
| (CAR1.4) Clone 24C1 THD CAR DNA LxH | ATGGCACTCCCCGTAACTGCTCTGCTGCT GCCGTTGGCATTGCTCCTGCACGCCGCAC GCCCGGATATCCAGCTCACGCAATCCCCC TCAAGCTTGAGTGCCTCCGTGGGCGACCG GGTGTCCTTCACATGTCAGGCAAGCCAAG ACATAAATAATTTCCTGAATTGGTACCAA CAAAAACCCGGCAAGGCTCCCAAACTCCT GATTTATGATGCCTCCAATCTGGAGACCG GGGTCCCTTCTAGATTCAGCGGAAGTGGC AGCGGCACAGACTTTACATTTACTATCTC TTCTCTGCAACCAGAGGACATCGCCACAT ACTATTGCCAGCAATACGGCAATCTGCCC TTCACCTTCGGAGGCGGAACCAAGGTAGA AATTAAAGGGGCGGTGGAGGCTCCGGAG GGGGGAGGCTCTGGCGGAGGGGGCTCCCA GTACAATTGCAGGAGTCAGGGCCTGGACT CGTGAAGCCTTCAGAAACTTTGTCACTGA CATGTACAGTGTCCGGCGGAAGCATTTCC AGTTACTATTGGTCCTGGATTAGACAGCC ACCCGGCAAAGGACTGGAATGGATTGGAT ATATCTACTACTCTGGATCTACAAACTAT AATCCCAGCCTCAAATCCAGGGTCACTAT TAGTGTGGATACATCAAAGAATCAGTTCT CCTTGAAGCTGAGCTCAGTCACTGCTGCC GACACCGCAGTGTACTATTGTGTGAGCCT GGTCTACTGCGGCGGAGATTGCTACAGCG GTTTCGATTACTGGGGCCAGGGCACCCTG GTTACCGTTAGTTCCGCGGCTGCTCTTGA TAACGAGAAGTCCAACGGTACGATTATCC ACGTTAAGGGTAAGCACCTTTGCCCTAGC CCGCTGTTCCCAGGCCCCAGTAAGCCCTT TTGGGTCCTCGTTGTGGTAGGTGGGGTAC TCGCCTGCTACTCCCTGCTCGTCACTGTC GCATTCATCATCTTCTGGGTCAGATCCAA AAGAAGCCGCCTGCTCCATAGCGATTACA TGAATATGACTCCACGCCGCCCTGGCCCC ACAAGGAAACACTACCAGCCTTACGCACC ACCTAGAGATTTCGCTGCCTATCGGAGCA GGGTGAAGTTTTCCAGATCTGCAGATGCA CCAGCGTATCAGCAGGGCCAGAACCAACT GTATAACGAGCTCAACCTGGGACGCAGGG AAGAGTATGACGTTTTGGACAAGCGCAGA GGACGGGACCCTGAGATGGGTGGCAAACC AAGACGAAAAAACCCCCAGGAGGGTCTCT ATAATGAGCTGCAGAAGGATAAGATGGCT GAAGCCTATTCTGAAATAGGCATGAAAGG AGAGCGGAGAAGGGGAAAAGGGCACGACG GTTTGTACCAGGGACTCAGCACTGCTACG AAGGATACTTATGACGCTCTCCACATGCA AGCCCTGCCACCTAGGTAA | 177 | MALPVTALLLPLALLL HAARPDIQLTQSPSSL SASVGDRVSFTCQASQ DINNFLNWYQQKPGKA PKLLIYDASNLETGVP SRFSGSGSGTDFTFTI SSLQPEDIATYYCQQY GNLPFTFGGGTKVEIK RGGGGSGGGGSGGGGS QVQLQESGPGLVKPSE TLSLTCTVSGGSISSY YWSWIRQPPGKGLEWI GYIYYSGSTNYNPSLK SRVTISVDTSKNQFSL KLSSVTAADTAVYYCV SLVYCGGDCYSGFDYW GQGTLVTVSSAALDN EKSNGTIIHVKGKHLC PSPLFPGPSKPFWVLV VVGGVLACYSLLVTVA FIIFWVRSKRSLLHS DYMNMTPRRPGPTRKH YQPYAPPRDFAAYRSR VKFSRSADAPAYQQGQ NQLYNELNLGRREEYD VLDKRRGRDPEMGGKP RRKNPQEGLYNELQKD KMAEAYSEIGMKGERR RGKGHDGLYQGLSTAT KDTYDALHMQALPPR | 178 |
| (CAR1.4) Clone 24C1 THD CAR DNA LxH | GATATCCAGCTCACGCAATCCCCCTCAAG CTTGAGTGCCTCCGTGGGCGACCGGGTGT CCTTCACATGTCAGGCAAGCCAAGACATA AATAATTTCCTGAATTGGTACCAACAAAA ACCCGGCAAGGCTCCCAAACTCCTGATTT ATGATGCCTCCAATCTGGAGACCGGGGTC CCTTCTAGATTCAGCGGAAGTGGCAGCGG CACAGACTTTACATTTACTATCTCTTCTC TGCAACCAGAGGACATCGCCACATACTAT TGCCAGCAATACGGCAATCTGCCCTTCAC CTTCGGAGGCGGAACCAAGGTAGAAATTA AAGGGGCGGTGGAGGCTCCGGAGGGGGG GGCTCTGGCGGAGGGGGCTCCCAAGTACA ATTGCAGGAGTCAGGGCCTGGACTCGTGA AGCCTTCAGAAACTTTGTCACTGACATGT ACAGTGTCCGGCGGAAGCATTTCCAGTTA CTATTGGTCCTGGATTAGACAGCCACCCG GCAAAGGACTGGAATGGATTGGATATATC TACTACTCTGGATCTACAAACTATAATCC CAGCCTCAAATCCAGGGTCACTATTAGTG TGGATACATCAAAGAATCAGTTCTCCTTG AAGCTGAGCTCAGTCACTGCTGCCGACAC CGCAGTGTACTATTGTGTGAGCCTGGTCT | 179 | DIQLTQSPSSLSASVG DRVSFTCQASQDINNF LNWYQQKPGKAPKLLI YDASNLETGVPSRFSG SGSGTDFTFTISSLQP EDIATYYCQQYGNLPF TFGGGTKVEIKRGGGG SGGGGSGGGGSQVQLQ ESGPGLVKPSETLSLT CTVSGGSISSYYWSWI RQPPGKGLEWIGYIYY SGSTNYNPSLKSRVTI SVDTSKNQFSLKLSSV TAADTAVYYCVSLVYC GGDCYSGFDYWGQGTL VTVSSAALDNEKSNG TIIHVKGKHLCPSPLF PGPSKPFWVLVVGGV LACYSLLVTVAFIIFW VRSKRSLLHSDYMNM TPRRPGPTRKHYQPYA PPRDFAAYRSRVKFSR SADAPAYQQGQNQLYN | 180 |

TABLE 2-continued

Example CAR Sequences

| CAR Construct | Nucleotide Sequence | SEQ ID NO: | Amino Acid Sequence | SEQ ID NO: |
|---|---|---|---|---|
| | ACTGCGGCGGAGATTGCTACAGCGGTTTC GATTACTGGGGCCAGGGCACCCTGGTTAC CGTTAGTTCCGCGGCTGCTCTTGATAACG AGAAGTCCAACGGTACGATTATCCACGTT AAGGGTAAGCACCTTTGCCCTAGCCCGCT GTTCCCAGGCCCCAGTAAGCCCTTTTGGG TCCTCGTTGTGGTAGGTGGGGTACTCGCC TGCTACTCCCTGCTCGTCACTGTCGCATT CATCATCTTCTGGGTCAGATCCAAAAGAA GCCGCCTGCTCCATAGCGATTACATGAAT ATGACTCCACGCCGCCCTGGCCCCACAAG GAAACACTACCAGCCTTACGCACCACCTA GAGATTTCGCTGCCTATCGGAGCAGGGTG AAGTTTTCCAGATCTGCAGATGCACCAGC GTATCAGCAGGGCCAGAACCAACTGTATA ACGAGCTCAACCTGGGACGCAGGGAAGAG TATGACGTTTTGGACAAGCGCAGAGGACG GGACCCTGAGATGGGTGGCAAACCAAGAC GAAAAAACCCCAGGAGGGTCTCTATAAT GAGCTGCAGAAGGATAAGATGGCTGAAGC CTATTCTGAAATAGGCATGAAGGAGAGC GGAGAAGGGGAAAAGGGCACGACGGTTTG TACCAGGGACTCAGCACTGCTACGAAGGA TACTTATGACGCTCTCCACATGCAAGCCC TGCCACCTAGG | | ELNLGRREEYDVLDKR RGRDPEMGGKPRRKNP QEGLYNELQKDKMAEA YSEIGMKGERRRGKGH DGLYQGLSTATKDTYD ALHMQALPPR | |
| (CAR1.5) Clone 24C1 CHD CAR DNA LxH | ATGGCACTCCCCGTAACTGCTCTGCTGCT GCCGTTGGCATTGCTCCTGCACGCCGCAC GCCCCGGATATCCAGCTGACCCAGTCTCCA TCCTCTTTGAGTGCCTCCGTGGGTGACCG CGTCTCTTTCACTTGCCAAGCCAGCCAAG ACATCAACAACTTTCTGAATTGGTACCAG CAGAAACCAGGCAAAGCACCAAAGCTCCT CATCTACGACGCCTCCAACCTGGAAACCG GGGTGCCCAGCAGGTTTAGCGGGAGCGGT TCTGGCACGGATTTTACGTTCACCATCTC CTCTCTGCAGCCCGAGGATATAGCTACTT ATTACTGTCAGCAGTACGGGAATCTGCCA TTTACTTTTGGGGGTGGAACTAAGGTGGA AATCAAAAGGGGCGGCGGGGAAGCGGGG GCGGGGGCTCAGGTGGCGGAGGGGAGCCAG GTGCAACTCCAGGAAAGTGGCCCAGGATT GGTGAAGCCCAGCGAGACCCTTTCCCTTA CTTGTACTGTTAGCGGAGGCAGCATAAGC AGCTACTATTGGTCCTGGATCAGACAGCC ACCAGGGAAAGGGCTTGAATGGATTGGCT ACATTTACTATTCCGGGTCCACCAACTAC AACCCATCCCTCAAGTCCCGCGTGACAAT TTCCGTCGACACAAGCAAGAACCAGTTCT CCCTGAAACTTAGTAGCGTCACTGCTGCA GATACAGCAGTGTACTATTGTGTCAGCCT TGTCTACTGTGGCGGCGACTGCTACAGTG GCTTTGATTACTGGGGACAGGGCACGCTC GTGACAGTGTCCAGCGCTGCGGCTATCGA GGTAATGTATCCGCCACCGTATCTGGACA ACGAGAAGTCTAATGGGACAATCATTCAC GTGAAGGGAAGCACCTGTGTCCATCCCC CCTGTTTCCGGGTCCCAGTAAACCCTTCT GGGTGCTTGTTGTCGTTGGCGGGGTGCTG GCCTGCTATTCCTGCTGGTGACCGTCGC GTTTATTATTTTCTGGGTTAGATCCAAAA GAAGCCGCCTGCTCCATAGCGATTACATG AATATGACTCCACGCCGCCCTGGCCCCAC AAGGAAACACTACCAGCCTTACGCACCAC CTAGAGATTTCGCTGCCTATCGGAGCAGG GTGAAGTTTTCCAGATCTGCAGATGCACC AGCGTATCAGCAGGGCCAGAACCAACTGT ATAACGAGCTCAACCTGGGACGCAGGGAA GAGTATGACGTTTTGGACAAGCGCAGAGG ACGGGACCCTGAGATGGGTGGCAAACCAA GACGAAAAAACCCCAGGAGGGTCTCTAT AATGAGCTGCAGAAGGATAAGATGGCTGA AGCCTATTCTGAAATAGGCATGAAGGAG AGCGGAGAAGGGGAAAAGGGCACGACGGT | 181 | MALPVTALLLPLALLL HAARPDIQLTQSPSSL SASVGDRVSFTCQASQ DINNFLNWYQQKPGKA PKLLIYDASNLETGVP SRFSGSGSGTDFTFTI SSLQPEDIATYYCQQY GNLPFTFGGGTKVEIK RGGGGSGGGGSGGGGS QVQLQESGPGLVKPSE TLSLTCTVSGGSISSY YWSWIRQPPGKGLEWI GYIYYSGSTNYNPSLK SRVTISVDTSKNQFSL KLSSVTAADTAVYYCV SLVYCGGDCYSGFDYW GQGTLVTVSSAAAIEV MYPPPYLDNEKSNGTI IHVKGKHLCPSPLFPG PSKPFWVLVVVGGVLA CYSLLVTVAFIIFWVR SKRSRLLHSDYMNMTP RRPGPTRKHYQPYAPP RDFAAYRSRVKFSRSA DAPAYQQGQNQLYNEL NLGRREEYDVLDKRRG RDPEMGGKPRRKNPQE GLYNELQKDKMAEAYS EIGMKGERRRGKGHDG LYQGLSTATKDTYDAL HMQALPPR | 182 |

TABLE 2-continued

Example CAR Sequences

| CAR Construct | Nucleotide Sequence | SEQ ID NO: | Amino Acid Sequence | SEQ ID NO: |
|---|---|---|---|---|
| | TTGTACCAGGGACTCAGCACTGCTACGAA GGATACTTATGACGCTCTCCACATGCAAG CCCTGCCACCTAGGTAA | | | |
| (CAR1.5) Clone 24C1 CHD CAR DNA LxH | GATATCCAGCTGACCCAGTCTCCATCCTC TTTGAGTGCCTCCGTGGGTGACCGCGTCT CTTTCACTTGCCAAGCCAGCCAAGACATC AACAACTTTCTGAATTGGTACCAGCAGAA ACCAGGCAAAGCACCCAAAGCTCCTCATCT ACGACGCCTCCAACCTGGAAACCGGGGTG CCCAGCAGGTTTAGCGGGAGCGGTTCTGG CACGGATTTTACGTTCACCATCTCCTCTC TGCAGCCCGAGGATATAGCTACTTATTAC TGTCAGCAGTACGGGAATCTGCCATTTAC TTTTGGGGGTGGAACTAAGGTGGAAATCA AAAGGGGCGGCGGGGGAAGCGGGGGCGGG GGCTCAGGTGGCGGAGGGAGCCAGGTGCA ACTCCAGGAAAGTGGCCCAGGATTGGTGA AGCCCAGCGAGACCCTTTCCCTTACTTGT ACTGTTAGCGGAGGCAGCATAAGCAGCTA CTATTGGTCCTGGATCAGACAGCCACCAG GGAAAGGGCTTGAATGGATTGGCTACATT TACTATTCCGGGTCCACCAACTACAACCC ATCCCTCAAGTCCCGCGTGACAATTTCCG TCGACACAAGCAAGAACCAGTTCTCCCTG AAACTTAGTAGCGTCACTGCTGCAGATAC AGCAGTGTACTATTGTGTCAGCCTTGTCT ACTGTGGCGGCGACTGCTACAGTGGCTTT GATTACTGGGGACAGGGCACGCTCGTGAC AGTGTCCAGCGCTGCGGCTATCGAGGTAA TGTATCCGCCACCGTATCTGGACAACGAG AAGTCTAATGGGACAATCATTCACGTGAA GGGGAAGCACCTGTGTCCATCCCCCCTGT TTCCGGGTCCCAGTAAACCCTTCTGGGTG CTTGTTGTCGTTGGCGGGGTGCTGGCCTG CTATTCCCTGCTGGTGACCGTCGCGTTTA TTATTTTCTGGGTTAGATCCAAAAGAAGC CGCCTGCTCCATAGCGATTACATGAATAT GACTCCACGCCGCCCTGGCCCCACAAGGA AACACTACCAGCCTTACGCACCACCTAGA GATTTCGCTGCCTATCGGAGCAGGGTGAA GTTTTCCAGATCTGCAGATGCACCAGCGT ATCAGCAGGGCCAGAACCAACTGTATAAC GAGCTCAACCTGGGACGCAGGGAAGAGTA TGACGTTTTGGACAAGCGCAGAGGACGGG ACCCTGAGATGGGTGGCAAACCAAGACGA AAAAACCCCCAGGAGGGTCTCTATAATGA GCTGCAGAAGGATAAGATGGCTGAAGCCT ATTCTGAAATAGGCATGAAAGGAGAGCGG AGAAGGGGAAAAGGGCACGACGGTTTGTA CCAGGGACTCAGCACTGCTACGAAGGATA CTTATGACGCTCTCCACATGCAAGCCCTG CCACCTAGG | 183 | DIQLTQSPSSLSASVG DRVSFTCQASQDINNF LNWYQQKPGKAPKLLI YDASNLETGVPSRFSG SGSGTDFTFTISSLQP EDIATYYCQQYGNLPF TFGGGTKVEIKRGGGG SGGGGSGGGGSQVQLQ ESGPGLVKPSETLSLT CTVSGGSISSYYWSWI RQPPGKGLEWIGYIYY SGSTNYNPSLKSRVTI SVDTSKNQFSLKLSSV TAADTAVYYCVSLVYC GGDCYSGFDYWGQGTL VTVSSAAAIEVMYPPP YLDNEKSNGTIIHVKG KHLCPSPLFPGPSKPF WVLVVVGGVLACYSLL VTVAFIIFWVRSKRSR LLHSDYMNMTPRRPGP TRKHYQPYAPPRDFAA YRSRVKFSRSADAPAY QQGQNQLYNELNLGRR EEYDVLDKRRGRDPEM GGKPRRKNPQEGLYNE LQKDKMAEAYSEIGMK GERRRGKGHDGLYQGL STATKDTYDALHMQAL PPR | 184 |
| (CAR1.6) Clone 24C1 CD8 CAR DNA LxH | ATGGCACTCCCCGTAACTGCTCTGCTGCT GCCGTTGGCATTGCTCCTGCACGCCGCAC GCCCGGACATTCAATTGACCCAGTCCCCT AGCAGTCTCTCAGCAAGTGTGGGAGATAG GGTGTCATTCACCTGTCAGGCTTCACAGG ACATCAACAACTTCCTCAATTGGTATCAG CAGAAGCCAGGGAAGGCACCAAAGCTCCT CATATATGACGCTTCAAACCTTGAAACCG GAGTACCTAGCCGCTTCAGCGGAAGCGGA TCAGGGACTGACTTCACTTTTACCATCTC TTCACTGCAGCCCGAAGACATCGCCACAT ACTACTGCCAGCAGTACGGAAACTTGCCT TTTACATTTGGGGGCGGCACCAAAGTGGA GATTAAGCGAGGGGAGGCGGCTCAGGAG GCGGTGGCTCCGGAGGCGGGGGTTCCCAG GTCCAGCTCCAGGAATCCGGCCCAGGTCT GGTTAAGCCCAGTGAACTTTGTCCCTCA CGTGTACTGTGAGCGGTGGTTCAATCTCC TCATACTATTGGTCTTGGATACGGCAACC TCCTGGAAAGGGCCTCGAGTGGATCGGCT | 185 | MALPVTALLLPLALLL HAARPDIQLTQSPSSL SASVGDRVSFTCQASQ DINNFLNWYQQKPGKA PKLLIYDASNLETGVP SRFSGSGSGTDFTFTI SSLQPEDIATYYCQQY GNLPFTFGGGTKVEIK RGGGGSGGGGSGGGGS QVQLQESGPGLVKPSE TLSLTCTVSGGSISSY YWSWIRQPPGKGLEWI GYIYYSGSTNYNPSLK SRVTISVDTSKNQFSL KLSSVTAADTAVYYCV SLVYCGGDCYSGFDYW GQGTLVTVSSAALSN SIMYFSHFVPVFLPAK PTTTPAPRPPTPAPTI ASQPLSLRPEACRPAA | 186 |

TABLE 2-continued

Example CAR Sequences

| CAR Construct | Nucleotide Sequence | SEQ ID NO: | Amino Acid Sequence | SEQ ID NO: |
|---|---|---|---|---|
| | ATATCTACTATAGTGGCTCCACTAATTAC AACCCTTCCCTCAAGTCCAGAGTCACCAT TTCCGTGGACACATCTAAGAACCAGTTCA GTCTGAAGTTGTCCAGCGTTACAGCCGCA GACACAGCCGTTTATTACTGTGTGTCTCT TGTTTACTGCGGGGGAGACTGTTATAGCG GCTTCGATTACTGGGGCCAGGGCACCTTG GTCACAGTCTCTTCCGCGGCCGCCCTCTC TAACAGTATTATGTACTTTTCTCATTTTG TACCCGTGTTCCTTCCCGCTAAGCCAACT ACTACCCCGGCCCCACGGCCGCCTACCCC TGCACCCACAATAGCCAGTCAGCCTTTGA GCCTGAGACCTGAGGCTTGTCGGCCGGCT GCTGGGGGTGCAGTGCACACACGAGGTCT TGATTTTGCTTGCACATATACATCTGGG CCCCTCTGGCCGGGACCTGTGGGGTGCTG CTTCTGAGCTTGGTCATCACGCTCTATTG CAACCATCGCAACAGATCCAAAAGAAGCC GCCTGCTCCATAGCGATTACATGAATATG ACTCCACGCCGCCCTGGCCCCACAAGGAA ACACTACCAGCCTTACGCACCACCTAGAG ATTTCGCTGCCTATCGGAGCAGGGTGAAG TTTTCCAGATCTGCAGATGCACCAGCGTA TCAGCAGGGCCAGAACCAACTGTATAACG AGCTCAACCTGGGACGCAGGGAAGAGTAT GACGTTTTGGACAAGCGCAGAGGACGGGA CCCTGAGATGGGTGGCAAACCAAGACGAA AAAACCCCCAGGAGGGTCTCTATAATGAG CTGCAGAAGGATAAGATGGCTGAAGCCTA TTCTGAAATAGGCATGAAAGGAGAGCGGA GAAGGGGAAAAGGGCACGACGGTTTGTAC CAGGGACTCAGCACTGCTACGAAGGATAC TTATGACGCTCTCCACATGCAAGCCCTGC CACCTAGGTAA | | GGAVHTRGLDFACDIY IWAPLAGTCGVLLLSL VITLYCNHRNRSKRSR LLHSDYMNMTPRRPGP TRKHYQPYAPPRDFAA YRSRVKFSRSADAPAY QQGQNQLYNELNLGRR EEYDVLDKRRGRDPEM GGKPRRKNPQEGLYNE LQKDKMAEAYSEIGMK GERRRGKGHDGLYQGL STATKDTYDALHMQAL PPR | |
| (CAR1.6) Clone 24C1 CD8 CAR DNA LxH | GACATTCAATTGACCCAGTCCCCTAGCAG TCTCTCAGCAAGTGTGGGAGATAGGGTGT CATTCACCTGTCAGGCTTCACAGGACATC AACAACTTCCTCAATTGGTATCAGCAGAA GCCAGGGAAGGCACCAAAGCTGCTCATAT ATGACGCTTCAAACCTTGAAACCGGAGTA CCTAGCCGCTTCAGCGGAAGCGGATCAGG GACTGACTTCACTTTTACCATCTCTTCAC TGCAGCCCGAAGACATCGCCACATACTAC TGCCAGCAGTACGGAAACTTGCCTTTTAC ATTTGGGGCGGCACCAAAGTGGAGATTA AGCGAGGGGGAGGCGGCTCAGGAGGCGGT GGCTCCGGAGGCGGGGGTTCCCAGGTCCA GCTCCAGGAATCCGGCCCAGGTCTGGTTA AGCCCAGTGAAACTTTGTCCCTCACGTGT ACTGTGAGCGGTGGTTCAATCTCCTCATA CTATTGGTCTTGGATACGGCAACCTCCTG GAAAGGGCCTCGAGTGGATCGGCTATATC TACTATAGTGGCTCCACTAATTACAACCC TTCCCTCAAGTCCAGAGTCACCATTTCCG TGGACACATCTAAGAACCAGTTCAGTCTG AAGTTGTCCAGCGTTACAGCCGAGACAC AGCCGTTTATTACTGTGTGTCTCTTGTTT ACTGCGGGGAGACTGTTATAGCGGCTTC GATTACTGGGGCCAGGGCACCTTGGTCAC AGTCTCTTCCGCGGCCGCCCTCTCTAACA GTATTATGTACTTTTCTCATTTTGTACCC GTGTTCCTTCCCGCTAAGCCAACTACTAC CCCGGCCCCACGGCCGCCTACCCCTGCAC CCACAATAGCCAGTCAGCCTTTGAGCCTG AGACCTGAGGCTTGTCGGCCGGCTGCTGG GGGTGCAGTGCACACACGAGGTCTTGATT TTGCTTGCACATATACATCTGGGCCCCT CTGGCCGGGACCTGTGGGGTGCTGCTTCT GAGCTTGGTCATCACGCTCTATTGCAACC ATCGCAACAGATCCAAAAGAAGCCGCCTG CTCCATAGCGATTACATGAATATGACTCC ACGCCGCCCTGGCCCCACAAGGAAACACT ACCAGCCTTACGCACCACCTAGAGATTTC | 187 | DIQLTQSPSSLSASVG DRVSFTCQASQDINNF LNWYQQKPGKAPKLLI YDASNLETGVPSRFSG SGSGTDFTFTISSLQP EDIATYYCQQYGNLPF TFGGGTKVEIKRGGGG SGGGGSGGGGSQVQLQ ESGPGLVKPSETLSLT CTVSGGSISSYYWSWI RQPPGKGLEWIGYIYY SGSTNYNPSLKSRVTI SVDTSKNQFSLKLSSV TAADTAVYYCVSLVYC GGDCYSGFDYWGQGTL VTVSSAAALSNSIMYF SHFVPVFLPAKPTTTP APRPPTPAPTIASQPL SLRPEACRPAAGGAVH TRGLDFACDIYIWAPL AGTCGVLLLSVITLY CNHRNRSKRSLLHSD YMNMTPRRPGPTRKHY QPYAPPRDFAAYRSRV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | 188 |

TABLE 2-continued

Example CAR Sequences

| CAR Construct | Nucleotide Sequence | SEQ ID NO: | Amino Acid Sequence | SEQ ID NO: |
|---|---|---|---|---|
| | GCTGCCTATCGGAGCAGGGTGAAGTTTTC CAGATCTGCAGATGCACCAGCGTATCAGC AGGGCCAGAACCAACTGTATAACGAGCTC AACCTGGGACGCAGGGAAGAGTATGACGT TTTGGACAAGCGCAGAGGACGGGACCCTG AGATGGGTGGCAAACCAAGACGAAAAAAC CCCCAGGAGGGTCTCTATAATGAGCTGCA GAAGGATAAGATGGCTGAAGCCTATTCTG AAATAGGCATGAAAGGAGAGCGGAGAAGG GGAAAAGGGCACGACGGTTTGTACCAGGG ACTCAGCACTGCTACGAAGGATACTTATG ACGCTCTCCACATGCAAGCCCTGCCACCT AGG | | | |
| (CAR2.1) Clone 24C8 THD CAR DNA HxL | ATGGCACTCCCCGTAACTGCTCTGCTGCT GCCGTTGGCATTGCTCCTGCACGCCGCAC GCCCGCAGGTACAGCTGCAGGAATCTGGG CCCGGACTTGTCAAGCCAAGTCAGACACT TTCTCTTACATGTACCGTGAGCGGCGGAA GTATAAGCAGTGGAGGCTTTTACTGGTCT TGGATACGGCAGCACCCAGGCAAAGGCTT GGAGTGGATTGGATACATTCATCATTCAG GATCTACACACTATAATCCATCCCTTAAG TCCCGGGTCACCATTAGCATTGATACGTC TAAGAATCTGTTCAGTCTCAGGCTGTCCT CCGTCACTGCTGCCGACACAGCCGTGTAC TACTGCGCCTCCTTGGTTTACTGCGGAGG CGACTGTTATAGCGGCTTTGATTATTGGG GCAGGGGACCCTCGTAACCGTGAGCTCT GGAGGGGGTGGGAGCGGGGAGGAGGTTC AGGGGGGGGCGGCTCCGATATCCAGCTCA CTCAAAGCCCCTCTAGTCTCTCTGCCTCA GTGGGGGATCGGGTCAGTTTTACTTGTCA AGCTTCACAGGATATCAACAACTTCCTTA ATTGGTATCAGCAGAAGCCAGGAAAAGCA CCCAAGCTGCTCATCTATGATGCCTCAAA TTTGGAGACGGGTGTTCCCAGTCGATTCT CTGGGTCAGGGTCCGGGACCGACTTTACG TTTACGATCTCCTCTCTGCAGCCCGAAGA CATCGCCACATACTATTGTCAACAGTACG GCAACTTGCCTTTCACATTTGGGGCGGG ACTAAGGTTGAAATCAAGAGGGCCGCTGC ACTGGACAATGAGAAGTCCAACGGCACCA TCATCCACGTGAAGGGCAAGCACCTGTGC CCTAGTCCTCTGTTCCCAGGCCCATCCAA ACCTTTTTGGGTTCTTGTTGTGGTCGGGG GGGTGCTGGCCTGCTATTCTCTGCTGGTC ACGGTGGCCTTCATAATTTTCTGGGTTAG ATCCAAAAGAAGCCGCCTGCTCCATAGCG ATTACATGAATATGACTCCACGCCGGCCT GGCCCCACAAGGAAACACTACCAGCCTTA CGCACCACCTAGAGATTTCGCTGCCTATC GGAGCAGGGTGAAGTTTTCCAGATCTGCA GATGCACCAGCGTATCAGCAGGGCCAGAA CCAACTGTATAACGAGCTCAACCTGGGAC GCAGGGAAGAGTATGACGTTTTGGACAAG CGCAGAGGACGGGACCCTGAGATGGGTGG CAAACCAAGACGAAAAAACCCCCAGGAGG GTCTCTATAATGAGCTGCAGAAGGATAAG ATGGCTGAAGCCTATTCTGAAATAGGCAT GAAAGGAGAGCGGAGAAGGGGAAAAGGGC ACGACGGTTTGTACCAGGGACTCAGCACT GCTACGAAGGATACTTATGACGCTCTCCA CATGCAAGCCCTGCCACCTAGGTAA | 189 | MALPVTALLLPLALLL HAARPQVQLQESGPGL VKPSQTLSLTCTVSGG SISSGGFYWSWIRQHP GKGLEWIGYIHHSGST HYNPSLKSRVTISIDT SKNLFSLRLSSVTAAD TAVYYCASLVYCGGDC YSGFDYWGQGTLVTVS SGGGGSGGGGSGGGGS DIQLTQSPSSLSASVG DRVSFTCQASQDINNF LNWYQQKPGKAPKLLI YDASNLETGVPSRFSG SGSGTDFTFTISSLQP EDIATYYCQQYGNLPF TFGGGTKVEIKRAAAL DNEKSNGTIIHVKGKH LCPSPLFPGPSKPFWV LVVVGGVLACYSLLVT VAFIIFWVRSKRSRLL HSDYMNMTPRRPGPTR KHYQPYAPPRDFAAYR SRVKFSRSADAPAYQQ GQNQLYNELNLGRREE YDVLDKRRGRDPEMGG KPRRKNPQEGLYNELQ KDKMAEAYSEIGMKGE RRRGKGHDGLYQGLST ATKDTYDALHMQALPP R | 190 |
| (CAR2.1) Clone 24C8 THD CAR DNA HxL | CAGGTACAGCTGCAGGAATCTGGGCCCGG ACTTGTCAAGCCAAGTCAGACACTTTCTC TTACATGTACCGTGAGCGGCGGAAGTATA AGCAGTGGAGGCTTTTACTGGTCTTGGAT ACGGCAGCACCCAGGCAAAGGCTTGGAGT GGATTGGATACATTCATCATTCAGGATCT ACACACTATAATCCATCCCTTAAGTCCCG GGTCACCATTAGCATTGATACGTCTAAGA ATCTGTTCAGTCTCAGGCTGTCCTCCGTC | 191 | QVQLQESGPGLVKPSQ TLSLTCTVSGGSISSG GFYWSWIRQHPGKGLE WIGYIHHSGSTHYNPS LKSRVTISIDTSKNLF SLRLSSVTAADTAVYY CASLVYCGGDCYSGFD YWGQGTLVTVSSGGGG SGGGGSGGGGSDIQLT | 192 |

TABLE 2-continued

Example CAR Sequences

| CAR Construct | Nucleotide Sequence | SEQ ID NO: | Amino Acid Sequence | SEQ ID NO: |
|---|---|---|---|---|
| | ACTGCTGCCGACACAGCCGTGTACTACTG CGCCTCCTTGGTTTACTGCGGAGGCGACT GTTATAGCGGCTTTGATTATTGGGGGCAG GGGACCCTCGTAACCGTGAGCTCTGGAGG GGGTGGGAGCGGGGGAGGAGGTTCAGGGG GGGGCGGCTCCGATATCCAGCTCACTCAA AGCCCCTCTAGTCTCTCTGCCTCAGTGGG GGATCGGGTCAGTTTTACTTGTCAAGCTT CACAGGATATCAACAACTTCCTTAATTGG TATCAGCAGAAGCCAGGAAAAGCACCCAA GCTGCTCATCTATGATGCCTCAAATTTGG AGACGGGTGTTCCCAGTCGATTCTCTGGG TCAGGGTCGGGACCGACTTTACGTTTAC GATCTCCTCTCTGCAGCCCGAAGACATCG CCACATACTATTGTCAACAGTACGGCAAC TTGCCTTTCACATTTGGGGCGGGACTAA GGTTGAAATCAAGAGGGCCGCTGCACTGG ACAATGAGAAGTCCAACGGCACCATCATC CACGTGAAGGGCAAGCACCTGTGCCCTAG TCCTCTGTTCCCAGGCCCATCCAAACCTT TTTGGGTTCTTGTTGTGGTCGGGGGGGTG CTGGCCTGCTATTCTCTGCTGGTCACGGT GGCCTTCATAATTTTCTGGGTTAGATCCA AAAGAAGCCGCCTGCTCCATAGCGATTAC ATGAATATGACTCCACGCCGCCCTGGCCC CACAAGGAAACACTACCAGCCTTACGCAC CACCTAGAGATTTCGCTGCCTATCGGAGC AGGGTGAAGTTTTCCAGATCTGCAGATGC ACCAGCGTATCAGCAGGGCCAGAACCAAC TGTATAACGAGCTCAACCTGGGACGCAGG GAAGAGTATGACGTTTTGGACAAGCGCAG AGGACGGGACCCTGAGATGGGTGGCAAAC CAAGACGAAAAAACCCCCAGGAGGGTCTC TATAATGAGCTGCAGAAGGATAAGATGGC TGAAGCCTATTCTGAAATAGGCATGAAAG GAGAGCGGAGAAGGGGAAAAGGGCACGAC GGTTTGTACCAGGGACTCAGCACTGCTAC GAAGGATACTTATGACGCTCTCCACATGC AAGCCCTGCCACCTAGG | | QSPSSLSASVGDRVSF TCQASQDINNFLNWYQ QKPGKAPKLLIYDASN LETGVPSRFSGSGSGT DFTFTISSLQPEDIAT YYCQQYGNLPFTFGGG TKVEIKRAAALDNEKS NGTIIHVKGKHLCPSP LFPGPSKPFWVLVVVG GVLACYSLLVTVAFII FWVRSKRSRLLHSDYM NMTPRRPGPTRKHYQP YAPPRDFAAYRSRVKF SRSADAPAYQQGQNQL YNELNLGRREEYDVLD KRRGRDPEMGGKPRRK NPQEGLYNELQKDKMA EAYSEIGMKGERRRGK GHDGLYQGLSTATKDT YDALHMQALPPR | |
| (CAR2.2) Clone 24C8 CHD CAR DNA HxL | ATGGCACTCCCCGTAACTGCTCTGCTGCT GCCGTTGGCATTGCTCCTGCACGCCGCAC GCCCGCAGGTGCAGCTGCAGGAAAGCGGT CCGGGACTTGTCAAGCCGTCCCAAACGCT GAGTCTGACGTGTACTGTCTCTGGTGGCT CTATTTCTTCCGGGGCTTTTATTGGTCT TGGATCAGACAACACCCTGGCAAAGGGCT GGAGTGGATAGGGTATATTCACCACTCTG GGTCCACTCACTACAACCCATCATTGAAA TCCAGAGTGACTATCTCAATCGACACATC CAAGAACCTTTTCAGCCTGAGGTTGTCAT CAGTTACCGCCGCTGACACCGCGGTGTAT TATTGCGCCTCTCTCGTGTACTGCGGTGG CGATTGTTATAGTGGCTTTGACTACTGGG GCAGGGGACATTGGTTACCGTTTCAAGT GGAGGCGGTGGGTCTGGCGGGGGCGGTAG CGGAGGTGGGGGGAGCGACATACAGCTTA CGCAGAGCCCCTCCAGCCTTTCAGCCTCC GTGGGGATAGGGTGTCCTTTACCTGCCA GGCTTCCCAGGACATAAACAACTTCCTCA ATTGGTATCAGCAAAAGCCCGGGAAAGCA CCAAAGCTGCTCATCTACGATGCCAGCAA CCTGGAAACCGGAGTGCCGTCTGCTTCT CTGGAAGTGGCAGTGGGACCGATTTCACT TTTACAATCTCAAGTTTGCAGCCAGAAGA CATTGCAACATACTACTGTCAACAGTACG GCAATCTCCCCTTTACATTTGGGGGGGA ACTAAAGTGGAGATTAAGCGCGCTGCAGC CATTGAAGTTATGTATCCGCCCCCCGTATC TGGATAACGAGAAATCTAATGGTACCATA ATACATGTGAAGGGGAAGCACCTCTGTCC ATCACCGCTGTTCCCCGGCCCTTCAAAAC CTTTCTGGGTACTCGTTGTCGTGGGTGGA GTTCTGGCCTGCTATAGTCTGCTGGTGAC | 193 | MALPVTALLLPLALLL HAARPQVQLQESGPGL VKPSQTLSLTCTVSGG SISSGGFYWSWIRQHP GKGLEWIGYIHHSGST HYNPSLKSRVTISIDT SKNLFSLRLSSVTAAD TAVYYCASLVYCGGDC YSGFDYWGQGTLVTVS SGGGGSGGGGSGGGGS DIQLTQSPSSLSASVG DRVSFTCQASQDINNF LNWYQQKPGKAPKLLI YDASNLETGVPSRFSG SGSGTDFTFTISSLQP EDIATYYCQQYGNLPF TFGGGTKVEIKRAAAI EVMYPPPYLDNEKSNG TIIHVKGKHLCPSPLF PGPSKPFWVLVVVGGV LACYSLLVTVAFIIFW VRSKRSRLLHSDYMNM TPRRPGPTRKHYQPYA PPRDFAAYRSRVKFSR SADAPAYQQGQNQLYN ELNLGRREEYDVLDKR RGRDPEMGGKPRRKNP QEGLYNELQKDKMAEA YSEIGMKGERRRGKGH DGLYQGLSTATKDTYD ALHMQALPPR | 194 |

TABLE 2-continued

Example CAR Sequences

| CAR Construct | Nucleotide Sequence | SEQ ID NO: | Amino Acid Sequence | SEQ ID NO: |
|---|---|---|---|---|
| | CGTGGCGTTTATCATCTTCTGGGTAAGAT CCAAAAGAAGCCGCCTGCTCCATAGCGAT TACATGAATATGACTCCACGCCGCCCTGG CCCCACAAGGAAACACTACCAGCCTTACG CACCACCTAGAGATTTCGCTGCCTATCGG AGCAGGGTGAAGTTTTCCAGATCTGCAGA TGCACCAGCGTATCAGCAGGGCCAGAACC AACTGTATAACGAGCTCAACCTGGGACGC AGGGAAGAGTATGACGTTTTGGACAAGCG CAGAGGACGGGACCCTGAGATGGGTGGCA AACCAAGACGAAAAAACCCCCAGGAGGGT CTCTATAATGAGCTGCAGAAGGATAAGAT GGCTGAAGCCTATTCTGAAATAGGCATGA AAGGAGAGCGGAGAAGGGGAAAAGGGCAC GACGGTTTGTACCAGGGACTCAGCACTGC TACGAAGGATACTTATGACGCTCTCCACA TGCAAGCCCTGCCACCTAGGTAA | | | |
| (CAR2.2) Clone 24C8 CHD CAR DNA HxL | CAGGTGCAGCTGCAGGAAAGCGGTCCGGG ACTTGTCAAGCCGTCCCAAACGCTGAGTC TGACGTGTACTGTCTCTGGTGGCTCTATT TCTTCCGGGGGCTTTTATTGGTCTTGGAT CAGACAACACCCTGGCAAAGGGCTGGAGT GGATAGGGTATATTCACCACTCTGGGTCC ACTCACTACAACCCATCATTGAAATCCAG AGTGACTATCTCAATGACACATCCAAGAA ACCTTTTCAGCCTGAGGTTGTCATCAGTT ACCGCCGCTGACACCGCGGTGTATTATTG CGCCTCTCTCGTGTACTGCGGTGGCGATT GTTATAGTGGCTTTGACTACTGGGGCAG GGGACATTGGTTACCGTTTCAAGTGGAGG CGGTGGGTCTGGCGGGGCGGTAGCGGAG GTGGGGGAGCGACATACAGCTTACGCAG AGCCCCTCCAGCCTTTCAGCCTCCGTGGG GGATAGGGTGTCCTTTACCTGCCAGGCTT CCCAGGACATAAACAACTTCCTCAATTGG TATCAGCAAAAGCCCGGGAAAGCACCAAA GCTGCTCATCTACGATGCCAGCAACCTGG AAACCGGAGTGCCGTCTCGCTTCTCTGGA AGTGGCAGTGGGACCGATTTCACTTTTAC AATCTCAAGTTTGCAGCCAGAAGACATTG CAACATACTACTGTCAACAGTACGGCAAT CTCCCCTTTACATTTGGGGGGGGAACTAA AGTGGAGATTAAGCGCGCTGCAGCCATTG AAGTTATGTATCCGCCCCCGTATCTGGAT AACGAGAAATCTAATGGTACCATAATACA TGTGAAGGGGAAGCACCTCTGTCCATCAC CGCTGTTCCCCGGCCCTTCAAAACCTTTC TGGGTACTCGTTGTCGTGGGTGGAGTTCT GGCCTGCTATAGTCTGCTGGTGACCGTGG CGTTTATCATCTTCTGGGTAAGATCCAAA AGAAGCCGCCTGCTCCATAGCGATTACAT GAATATGACTCCACGCCGCCCTGGCCCCA CAAGGAAACACTACCAGCCTTACGCACCA CCTAGAGATTTCGCTGCCTATCGGAGCAG GGTGAAGTTTTCCAGATCTGCAGATGCAC CAGCGTATCAGCAGGGCCAGAACCAACTG TATAACGAGCTCAACCTGGGACGCAGGGA AGAGTATGACGTTTTGGACAAGCGCAGAG GACGGGACCCTGAGATGGGTGGCAAACCA AGACGAAAAAACCCCCAGGAGGGTCTCTA TAATGAGCTGCAGAAGGATAAGATGGCTG AAGCCTATTCTGAAATAGGCATGAAAGGA GAGCGGAGAAGGGGAAAAGGGCACGACGG TTTGTACCAGGGACTCAGCACTGCTACGA AGGATACTTATGACGCTCTCCACATGCAA GCCCTGCCACCTAGG | 195 | QVQLQESGPGLVKPSQ TLSLTCTVSGGSISSG GFYWSWIRQHPGKGLE WIGYIHHSGSTHYNPS LKSRVTISIDTSKNLF SLRLSSVTAADTAVYY CASLVYCGGDCYSGFD YWGQGTLVTVSSGGGG SGGGGSGGGGSDIQLT QSPSSLSASVGDRVSF TCQASQDINNFLNWYQ QKPGKAPKLLIYDASN LETGVPSRFSGSGSGT DFTFTISSLQPEDIAT YYCQQYGNLPFTFGGG TKVEIKRAAAIEVMYP PPYLDNEKSNGTIIHV KGKHLCPSPLFPGPSK PFWVLVVVGGVLACYS LLVTVAFIIFWVRSKR SRLLHSDYMNMTPRRP GPTRKHYQPYAPPRDF AAYRSRVKFSRSADAP AYQQGQNQLYNELNLG RREEYDVLDKRRGRDP EMGGKPRRKNPQEGLY NELQKDKMAEAYSEIG MKGERRRGKGHDGLYQ GLSTATKDTYDALHMQ ALPPR | 196 |
| (CAR2.3) Clone 24C8 CD8 CAR DNA HxL | ATGGCACTCCCCGTAACTGCTCTGCTGCT GCCGTTGGCATTGCTCCTGCACGCCGCAC GCCCGCAGGTGCAGTTGCAGGAAAGCGGG CCTGGCCTTGTGAAACCAAGCCAGACACT GAGCCTGACATGCACTGTGTCCGGCGGGT CCATATCTTCCGGGGGTTTTTATTGGTCC | 197 | MALPVTALLLPLALLL HAARPQVQLQESGPGL VKPSQTLSLTCTVSGG SISSGGFYWSWIRQHP GKGLEWIGYIHHSGST HYNPSLKSRVTISIDT | 198 |

TABLE 2-continued

Example CAR Sequences

| CAR Construct | Nucleotide Sequence | SEQ ID NO: | Amino Acid Sequence | SEQ ID NO: |
|---|---|---|---|---|
| | TGGATACGCCAGCATCCCGGGAAAGGACT<br>TGAATGGATTGGATATATCCACCATTCCG<br>GAAGCACCCACTACAATCCAAGCCTTAAA<br>TCCCGGGTGACAATCTCCATCGACACCTC<br>AAAGAATCTTTTTTCCCTGCGGTTGTCTT<br>CAGTAACTGCCGCCGATACCGCTGTGTAC<br>TACTGTGCCAGCCTCGTCTATTGCGGCGG<br>AGATTGTTATTCTGGGTTCGATTATTGGG<br>GTCAAGGCACACTGGTAACTGTCAGCAGC<br>GGAGGCGGCGGTTCCGGGGGCGGGGGCAG<br>TGGAGGGGGGGATCTGACATTCAGCTTA<br>CGCAGTCCCCATCTTCACTTAGCGCCAGC<br>GTTGGCGATCGGGTCAGCTTCACGTGTCA<br>AGCAAGTCAGGATATCAACAACTTTCTTA<br>ACTGGTACCAGCAGAAGCCAGGCAAGGCA<br>CCCAAGTTGCTGATTTACGATGCTTCTAA<br>CCTCGAGACGGGAGTGCCTAGCCGCTTCT<br>CCGGGAGCGGCAGCGGCACAGACTTTACC<br>TTTACGATTTCCAGTCTGCAGCCAGAGGA<br>TATAGCAACTTATTACTGTCAGCAGTATG<br>GCAACCTCCCTTTTACCTTCGGTGGTGGC<br>ACAAAGGTCGAGATTAAAAGAGCCGCAGC<br>GTTGTCCAACTCCATAATGTATTTTTCTC<br>ATTTTGTGCCCGTCTTTCTGCCTGCCAAA<br>CCTACCACCACCCCCGCCCCACGACCACC<br>TACTCCAGCCCCCACCATCGCCTCCCAGC<br>CCCTCAGCCTGAGGCCAGAGGCTTGTCGC<br>CCTGCTGCGGGGGCGCTGTCCATACCAG<br>AGGACTCGACTTCGCCTGCGATATTTATA<br>TATGGGCCCCCTCGCCGGCACCTGCGGA<br>GTCTTGCTCCTGAGCCTTGTGATCACGCT<br>TTATTGTAACCATCGGAATAGATCCAAAA<br>GAAGCCGCCTGCTCCATAGCGATTACATG<br>AATATGACTCCACGCCGCCCTGGCCCCAC<br>AAGGAAACACTACCAGCCTTACGCACCAC<br>CTAGAGATTTCGCTGCCTATCGGAGCAGG<br>GTGAAGTTTTCCAGATCTGCAGATGCACC<br>AGCGTATCAGCAGGGCCAGAACCAACTGT<br>ATAACGAGCTCAACCTGGGACGCAGGGAA<br>GAGTATGACGTTTTGGACAAGCGCAGAGG<br>ACGGGACCCTGAGATGGGTGGCAAACCAA<br>GACGAAAAAACCCCCAGGAGGGTCTCTAT<br>AATGAGCTGCAGAAGGATAAGATGGCTGA<br>AGCCTATTCTGAAATAGGCATGAAAGGAG<br>AGCGGAGAAGGGGAAAAGGGCACGACGGT<br>TTGTACCAGGGACTCAGCACTGCTACGAA<br>GGATACTTATGACGCTCTCCACATGCAAG<br>CCCTGCCACCTAGGTAA | | SKNLFSLRLSSVTAAD<br>TAVYYCASLVYCGGDC<br>YSGFDYWGQGTLVTVS<br>SGGGGSGGGGSGGGGS<br>DIQLTQSPSSLSASVG<br>DRVSFTCQASQDINNF<br>LNWYQQKPGKAPKLLI<br>YDASNLETGVPSRFSG<br>SGSGTDFTFTISSLQP<br>EDIATYYCQQYGNLPF<br>TFGGGTKVEIKRAAAL<br>SNSIMYFSHFVPVFLP<br>AKPTTTPAPRPPTPAP<br>TIASQPLSLRPEACRP<br>AAGGAVHTRGLDFACD<br>IYIWAPLAGTCGVLLL<br>SLVITLYCNHRNRSKR<br>SRLLHSDYMNMTPRRP<br>GPTRKHYQPYAPPRDF<br>AAYRSRVKFSRSADAP<br>AYQQGQNQLYNELNLG<br>RREEYDVLDKRRGRDP<br>EMGGKPRRKNPQEGLY<br>NELQKDKMAEAYSEIG<br>MKGERRRGKGHDGLYQ<br>GLSTATKDTYDALHMQ<br>ALPPR | |
| (CAR2.3)<br>Clone 24C8<br>CD8 CAR<br>DNA HxL | CAGGTGCAGTTGCAGGAAAGCGGGCCTGG<br>CCTTGTGAAACCAAGCCAGACACTGAGCC<br>TGACATGCACTGTGTCCGGCGGGTCCATA<br>TCTTCCGGGGTTTTTATTGGTCCTGGAT<br>ACGCCAGCATCCCGGGAAAGGACTTGAAT<br>GGATTGGATATATCCACCATTCCGGAAGC<br>ACCCACTACAATCCAAGCCTTAAATCCCG<br>GGTGACAATCTCCATCGACACCTCAAAGA<br>ATCTTTTTTCCCTGCGGTTGTCTTCAGTA<br>ACTGCCGCCGATACCGCTGTGTACTACTG<br>TGCCAGCCTCGTCTATTGCGGCGGAGATT<br>GTTATTCTGGGTTCGATTATTGGGGTCAA<br>GGCACACTGGTAACTGTCAGCAGCGGAGG<br>CGGCGGTTCCGGGGGCGGGGGCAGTGGAG<br>GGGGCGGATCTGACATTCAGCTTACGCAG<br>TCCCCATCTTCACTTAGCGCCAGCGTTGG<br>CGATCGGGTCAGCTTCACGTGTCAAGCAA<br>GTCAGGATATCAACAACTTTCTTAACTGG<br>TACCAGCAGAAGCCAGGCAAGGCACCCAA<br>GTTGCTGATTTACGATGCTTCTAACCTCG<br>AGACGGGAGTGCCTAGCCGCTTCTCCGGG<br>AGCGGCAGCGGCACAGACTTTACCTTTAC<br>GATTTCCAGTCTGCAGCCAGAGGATATAG<br>CAACTTATTACTGTCAGCAGTATGGCAAC<br>CTCCCTTTTACCTTCGGTGGTGGCACAAA | 199 | QVQLQESGPGLVKPSQ<br>TLSLTCTVSGGSISSG<br>GFYWSWIRQHPGKGLE<br>WIGYIHHSGSTHYNPS<br>LKSRVTISIDTSKNLF<br>SLRLSSVTAADTAVYY<br>CASLVYCGGDCYSGFD<br>YWGQGTLVTVSSGGGG<br>SGGGGSGGGGSDIQLT<br>QSPSSLSASVGDRVSF<br>TCQASQDINNFLNWYQ<br>QKPGKAPKLLIYDASN<br>LETGVPSRFSGSGSGT<br>DFTFTISSLQPEDIAT<br>YYCQQYGNLPFTFGGG<br>TKVEIKRAAALSNSIM<br>YFSHFVPVFLPAKPTT<br>TPAPRPPTPAPTIASQ<br>PLSLRPEACRPAAGGA<br>VHTRGLDFACDIYIWA<br>PLAGTCGVLLLSLVIT<br>LYCNHRNRSKRSRLLH<br>SDYMNMTPRRPGPTRK<br>HYQPYAPPRDFAAYRS<br>RVKFSRSADAPAYQQG | 200 |

TABLE 2-continued

Example CAR Sequences

| CAR Construct | Nucleotide Sequence | SEQ ID NO: | Amino Acid Sequence | SEQ ID NO: |
|---|---|---|---|---|
| | GGTCGAGATTAAAAGAGCCGCAGCGTTGT CCAACTCCATAATGTATTTTTCTCATTTT GTGCCCGTCTTTCTGCCTGCCAAACCTAC CACCACCCCCGCCCCACGACCACCTACTC CAGCCCCCACCATCGCCTCCCAGCCCCTC AGCCTGAGGCCAGAGGCTTGTCGCCCTGC TGCGGGGGCGCTGTCCATACCAGAGGAC TCGACTTCGCCTGCGATATTTATATATGG GCCCCCCTCGCCGGCACCTGCGGAGTCTT GCTCCTGAGCCTTGTGATCACGCTTTATT GTAACCATCGGAATAGATCCAAAAGAAGC CGCCTGCTCCATAGCGATTACATGAATAT GACTCCACGCCGCCCTGGCCCCACAAGGA AACACTACCAGCCTTACGCACCACCTAGA GATTTCGCTGCCTATCGGAGCAGGGTGAA GTTTTCCAGATCTGCAGATGCACCAGCGT ATCAGCAGGGCCAGAACCAACTGTATAAC GAGCTCAACCTGGGACGCAGGGAAGAGTA TGACGTTTTGGACAAGCGCAGAGGACGGG ACCCTGAGATGGGTGGCAAACCAAGACGA AAAAACCCCCAGGAGGGTCTCTATAATGA GCTGCAGAAGGATAAGATGGCTGAAGCCT ATTCTGAAATAGGCATGAAGGAGAGCGG AGAAGGGGAAAAGGGCACGACGTTTGTA CCAGGGACTCAGCACTGCTACGAAGGATA CTTATGACGCTCTCCACATGCAAGCCCTG CCACCTAGG | | QNQLYNELNLGRREEY DVLDKRRGRDPEMGGK PRRKNPQEGLYNELQK DKMAEAYSEIGMKGER RRGKGHDGLYQGLSTA TKDTYDALHMQALPPR | |
| (CAR3.1) Clone 20C5.1 THD CAR DNA HxL | ATGGCACTCCCCGTAACTGCTCTGCTGCT GCCGTTGGCATTGCTCCTGCACGCCGCAC GCCCGCAGGTCCAACTGGTGCAGTCCGGA GCCGAAGTCAAGAAACCAGGTGCCTCCGT TAAAGTGAGTTGCAAAGTCTCTGGATACA CTCTGACCGAGCTCTCTATGCACTGGGTC CGGCAGGCCCCCGGCAAGGGATTGGAATG GATGGGCGGGTTCGATCCTGAGGACGGAG AGACTATCTACGCTCAAAAATTCCAGGGA CGAGTGACTGTGACCGAAGACACTAGTAC CGACACTGCCTACATGGAACTTTCCTCTC TGCGATCAGAAGATACCGCAGTGTACTAC TGTGCTACTGAATCTAGGGGCATTGGATG GCCCTACTTCGATTACTGGGGTCAGGGAA CTCTGGTGACTGTCTCCAGCGGTGGAGGT GGCAGCGGTGGTGGCGGAAGCGGGGGGGG CGGCTCTGATATTCAGATGACTCAATCTC CTTCTTCTCTGTCCGCTTCCGTGGGCGAT AGAGTGACCATTACTTGTAGGGCGTCCCA GTCAATCTCCAGTTATTTGAATTGGTATC AGCAGAAGCCCGGAAAGCACCTAAGCTG TTGATCAGCGGGGCTTCTAGCCTGAAGAG TGGGGTACCTTCACGGTTCAGCGGAAGCG GAAGCGGAACCGATTTCACCCTGACTATC AGCAGCCTGCCACCTGAGGACTTTGCAAC TTACTACTGCCAACAGTCATACAGCACTC CGATCACTTTCGGCCAGGGCACCCGGCTC GAAATCAAGCGCGCTGCTGCTTTGGACAA TGAGAAGTCAAACGGCACCATCATACATG TTAAAGGTAAACATCTGTGTCCCTCCCCG CTGTTCCCGGCCCTTCCAAACCGTTCTG GGTTCTGGTGGTGGTCGGAGGCGTACTCG CTTGCTATAGTCTGCTGGTAACTGTCGCC TTCATCATCTTTTGGGTGAGATCCAAAAG AAGCCGCCTGCTCCATAGCGATTACATGA ATATGACTCCACGCCGCCCTGGCCCCACA AGGAAACACTACCAGCCTTACGCACCACC TAGAGATTTCGCTGCCTATCGGAGCAGGG TGAAGTTTTCCAGATCTGCAGATGCACCA GCGTATCAGCAGGGCCAGAACCAACTGTA TAACGAGCTCAACCTGGGACGCAGGGAAG AGTATGACGTTTTGGACAAGCGCAGAGGA CGGGACCCTGAGATGGGTGGCAAACCAAG ACGAAAAAACCCCCAGGAGGGTCTCTATA ATGAGCTGCAGAAGGATAAGATGGCTGAA GCCTATTCTGAAATAGGCATGAAAGGAGA | 201 | MALPVTALLLPLALLL HAARPQVQLVQSGAEV KKPGASVKVSCKVSGY TLTELSMHWVRQAPGK GLEWMGGFDPEDGETI YAQKFQGRVTVTEDTS TDTAYMELSSLRSEDT AVYYCATESRGIGWPY FDYWGQGTLVTVSSGG GGSGGGGSGGGGSDIQ MTQSPSSLSASVGDRV TITCRASQSISSYLNW YQQKPGKAPKLLISGA SSLKSGVPSRFSGSGS GTDFTLTISSLPPEDF ATYYCQQSYSTPITFG QGTRLEIKRAAALDNE KSNGTIIHVKGKHLCP SPLFPGPSKPFWVLVV VGGVLACYSLLVTVAF IIFWVRSKRSRLLHSD YMNMTPRRPGPTRKHY QPYAPPRDFAAYRSRV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | 202 |

TABLE 2-continued

Example CAR Sequences

| CAR Construct | Nucleotide Sequence | SEQ ID NO: | Amino Acid Sequence | SEQ ID NO: |
|---|---|---|---|---|
| | GCGGAGAAGGGGAAAAGGGCACGACGGTT TGTACCAGGGACTCAGCACTGCTACGAAG GATACTTATGACGCTCTCCACATGCAAGC CCTGCCACCTAGGTAA | | | |
| (CAR3.1) Clone 20C5.1 THD CAR DNA HxL | CAGGTCCAACTGGTGCAGTCCGGAGCCGA AGTCAAGAAACCAGGTGCCTCCGTTAAAG TGAGTTGCAAAGTCTCTGGATACACTCTG ACCGAGCTCTCTATGCACTGGGTCCGGCA GGCCCCCGGCAAGGGATTGGAATGGATGG GCGGGTTCGATCCTGAGGACGGAGAGACT ATCTACGCTCAAAAATTCCAGGGACGAGT GACTGTGACCGAAGACACTAGTACCGACA CTGCCTACATGGAACTTTCCTCTCTGCGA TCAGAAGATACCGCAGTGTACTACTGTGC TACTGAATCTAGGGGCATTGGATGGCCCT ACTTCGATTACTGGGGTCAGGGAACTCTG GTGACTGTCTCCAGCGGTGGAGGTGGCAG CGGTGGTGGCGGAAGCGGGGGGGGCGGCT CTGATATTCAGATGACTCAATCTCCTTCT TCTCTGTCCGCTTCCGTGGGCGATAGAGT GACCATTACTTGTAGGGCGTCCCAGTCAA TCTCCAGTTATTTGAATTGGTATCAGCAG AAGCCCGGGAAAGCACCTAAGCTGTTGAT CAGCGGGGCTTCTAGCCTGAAGAGTGGGG TACCTTCACGGTTCAGCGGAAGCGGAAGC GGAACCGATTTCACCCTGACTATCAGCAG CCTGCCACCTGAGGACTTTGCAACTTACT ACTGCCAACAGTCATACAGCACTCCGATC ACTTTCGGCCAGGGCACCCGGCTCGAAAT CAAGCGCGCTGCTGCTTTGGACAATGAGA AGTCAAACGGCACCATCATACATGTTAAA GGTAAACATCTGTGTCCCTCCCCGCTGTT CCCCGGCCCTTCCAAACCGTTCTGGGTTC TGGTGGTGGTCGGAGGCGTACTCGCTTGC TATAGTCTGCTGGTAACTGTCGCCTTCAT CATCTTTTGGGTGAGATCCAAAAGAAGCC GCCTGCTCCATAGCGATTACATGAATATG ACTCCACGCCGCCCTGGCCCCACAAGGAA ACACTACCAGCCTTACGCACCACCTAGAG ATTTCGCTGCCTATCGGAGCAGGGTGAAG TTTTCCAGATCTGCAGATGCACCAGCGTA TCAGCAGGGCCAGAACCAACTGTATAACG AGCTCAACCTGGGACGCAGGGAAGAGTAT GACGTTTTGGACAAGCGCAGAGGACGGGA CCCTGAGATGGGTGGCAAACCAAGACGAA AAAACCCCCAGGAGGGTCTCTATAATGAG CTGCAGAAGGATAAGATGGCTGAAGCCTA TTCTGAAATAGGCATGAAAGGAGAGCGGA GAAGGGGAAAAGGGCACGACGGTTTGTAC CAGGGACTCAGCACTGCTACGAAGGATAC TTATGACGCTCTCCACATGCAAGCCCTGC CACCTAGG | 203 | QVQLVQSGAEVKKPGA SVKVSCKVSGYTLTEL SMHWVRQAPGKGLEWM GGFDPEDGETIYAQKF QGRVTVTEDTSTDTAY MELSSLRSEDTAVYYC ATESRGIGWPYFDYWG QGTLVTVSSGGGGSGG GGSGGGGSDIQMTQSP SSLSASVGDRVTITCR ASQSISSYLNWYQQKP GKAPKLLISGASSLKS GVPSRFSGSGSGTDFT LTISSLPPEDFATYYC QQSYSTPITFGQGTRL EIKRAAALDNEKSNGT IIHVKGKHLCPSPLFP GPSKPFWVLVVVGGVL ACYSLLVTVAFIIFWV RSKRSRLLHSDYMNMT PRRPGPTRKHYQPYAP PRDFAAYRSRVKFSRS ADAPAYQQGQNQLYNE LNLGRREEYDVLDKRR GRDPEMGGKPRRKNPQ EGLYNELQKDKMAEAY SEIGMKGERRRGKGHD GLYQGLSTATKDTYDA LHMQALPPR | 204 |
| (CAR3.2) Clone 20C5.1 CHD CAR DNA HxL | ATGGCACTCCCCGTAACTGCTCTGCTGCT GCCGTTGGCATTGCTCCTGCACGCCGCAC GCCCGCAGGTGCAGCTTGTGCAGAGCGGA GCCGAGGTGAAGAAGCCCGGGGCCAGCGT CAAAGTGTCCTGTAAGGTCAGCGGTTACA CCCTCACCGAGCTGAGCATGCACTGGGTA CGGCAGGCTCCCGGCAAGGTCTTGAGTG GATGGGTGGATTTGATCCAGAAGATGGAG AGACTATCTACGCCCAGAAGTTCCAGGGC CGGGTCACCGTAACAGAAGACACCTCAAC TGACACGCTTACATGGAGCTGAGTTCAC TGCGGTCCGAGGACACGGCCGTGTATTAT TGTGCCACCGAGAGCCGCGGAATCGGATG GCCTTACTTCGACTACTGGGGACAGGGTA CACTTGTTACAGTATCATCCGGGGGTGGC GGCTCTGGTGGGGCGGCTCCGGAGGGGG TGGATCAGATATCCAAATGACTCAAAGTC CAAGTTCCCTGTCTGCCTCAGTCGGAGAT AGAGTCACCATAACCTGCAGGGCAAGTCA GTCCATCTCCTCCTATCTGAACTGGTACC | 205 | MALPVTALLLPLALLL HAARPQVQLVQSGAEV KKPGASVKVSCKVSGY TLTELSMHWVRQAPGK GLEWMGGFDPEDGETI YAQKFQGRVTVTEDTS TDTAYMELSSLRSEDT AVYYCATESRGIGWPY FDYWGQGTLVTVSSGG GGSGGGGSGGGGSDIQ MTQSPSSLSASVGDRV TITCRASQSISSYLNW YQQKPGKAPKLLISGA SSLKSGVPSRFSGSGS GTDFTLTISSLPPEDF ATYYCQQSYSTPITFG QGTRLEIKRAAAIEVM YPPPYLDNEKSNGTII HVKGKHLCPSPLFPGP SKPFWVLVVVGGVLAC | 206 |

TABLE 2-continued

Example CAR Sequences

| CAR Construct | Nucleotide Sequence | SEQ ID NO: | Amino Acid Sequence | SEQ ID NO: |
|---|---|---|---|---|
| | AACAGAAACCTGGAAAGGCGCCTAAGCTC CTGATCTCCGGAGCCTCATCTTTGAAATC CGGTGTCCCATCTCGCTTCAGTGGCTCTG GAAGCGGTACAGATTTTACTTTGACCATT AGCAGCCTCCCACCGGAAGACTTTGCTAC ATATTACTGCCAGCAGTCTTACTCAACCC CAATCACCTTCGGGCAAGGCACCAGACTC GAAATAAAAGAGCAGCTGCTATCGAGGT TATGTACCCACCGCCGTACTTGGATAACG AAAAAAAGCAATGGGACCATCATTCATGTG AAGGGTAAGCACCTTTGCCCTAGCCCACT GTTTCCTGGCCCGAGTAAACCCTTTTGGG TACTTGTGGTCGTCGGCGGCGTGCTGGCC TGCTACTCACTCCTGGTTACCGTCGCATT CATCATCTTTTGGGTGAGATCCAAAAGAA GCCGCCTGCTCCATAGCGATTACATGAAT ATGACTCCACGCCGCCCTGGCCCCACAAG GAAACACTACCAGCCTTACGCACCACCTA GAGATTTCGCTGCCTATCGGAGCAGGGTG AAGTTTTCCAGATCTGCAGATGCACCAGC GTATCAGCAGGGCCAGAACCAACTGTATA ACGAGCTCAACCTGGGACGCAGGGAAGAG TATGACGTTTTGGACAAGCGCAGAGGACG GGACCCTGAGATGGGTGGCAAACCAAGAC GAAAAAACCCCCAGGAGGGTCTCTATAAT GAGCTGCAGAAGGATAAGATGGCTGAAGC CTATTCTGAAATAGGCATGAAAGGAGAGC GGAGAAGGGGAAAAGGGCACGACGGTTTG TACCAGGGACTCAGCACTGCTACGAAGGA TACTTATGACGCTCTCCACATGCAAGCCC TGCCACCTAGGTAA | | YSLLVTVAFIIFWVRS KRSRLLHSDYMNMTPR RPGPTRKHYQPYAPPR DFAAYRSRVKFSRSAD APAYQQGQNQLYNELN LGRREEYDVLDKRRGR DPEMGGKPRRKNPQEG LYNELQKDKMAEAYSE IGMKGERRRGKGHDGL YQGLSTATKDTYDALH MQALPPR | |
| (CAR3.2) Clone 20C5.1 CHD CAR DNA HxL | CAGGTGCAGCTTGTGCAGAGCGGGGCCGA GGTGAAGAAGCCCGGGGCCAGCGTCAAAG TGTCCTGTAAGGTCAGCGGTTACACCCTC ACCGAGCTGAGCATGCACTGGGTACGGCA GGCTCCCGGCAAAGGTCTTGAGTGGATGG GTGGATTTGATCCAGAAGATGGAGAGACT ATCTACGCCCAGAAGTTCCAGGGCCGGGT CACCGTAACAGAAGACACCTCAACTGACA CCGCTTACATGGAGCTGAGTTCACTGCGG TCCGAGGACACGGCCGTGTATTATTGTGC CACCGAGAGCCGCGGAATCGGATGGCCTT ACTTCGACTACTGGGGACAGGGTACACTT GTTACAGTATCATCCGGGGGTGGCGGCTC TGGTGGGGGCGGCTCCGGAGGGGTGGAT CAGATATCCAAATGACTCAAAGTCCAAGT TCCCTGTCTGCCTCAGTCGGAGATAGAGT CACCATAACCTGCAGGGCAAGTCAGTCCA TCTCCTCCTATCTGAACTGGTACCAACAG AAACCTGGAAAGGCGCCTAAGCTCCTGAT CTCCGGAGCCTCATCTTTGAAATCCGGTG TCCCATCTCGCTTCAGTGGCTCTGGAAGC GGTACAGATTTTACTTTGACCATTAGCAG CCTCCCACCGGAAGACTTTGCTACATATT ACTGCCAGCAGTCTTACTCAACCCCAATC ACCTTCGGGCAAGGCACCAGACTCGAAAT AAAAGAGCAGCTGCTATCGAGGTTATGT ACCCACCGCCGTACTTGGATAACGAAAAA AGCAATGGGACCATCATTCATGTGAAGGG TAAGCACCTTTGCCCTAGCCCACTGTTTC CTGGCCCGAGTAAACCCTTTTGGGTACTT GTGGTCGTCGGCGGCGTGCTGGCCTGCTA CTCACTCCTGGTTACCGTCGCATTCATCA TCTTTTGGGTGAGATCCAAAAGAAGCCGC CTGCTCCATAGCGATTACATGAATATGAC TCCACGCCGCCCTGGCCCCACAAGGAAAC ACTACCAGCCTTACGCACCACCTAGAGAT TTCGCTGCCTATCGGAGCAGGGTGAAGTT TTCCAGATCTGCAGATGCACCAGCGTATC AGCAGGGCCAGAACCAACTGTATAACGAG CTCAACCTGGGACGCAGGGAAGAGTATGA CGTTTTGGACAAGCGCAGAGGACGGGACC CTGAGATGGGTGGCAAACCAAGACGAAAA | 207 | QVQLVQSGAEVKKPGA SVKVSCKVSGYTLTEL SMHWVRQAPGKGLEWM GGFDPEDGETIYAQKF QGRVTVTEDTSTDTAY MELSSLRSEDTAVYYC ATESRGIGWPYFDYWG QGTLVTVSSGGGGSGG GGSGGGGSDIQMTQSP SSLSASVGDRVTITCR ASQSIISYLNWYQQKP GKAPKLLISGASSLKS GVPSRFSGSGSGTDFT LTISSLPPEDFATYYC QQSYSTPITFGQGTRL EIKRAAAIEVMYPPPY LDNEKSNGTIIHVKGK HLCPSPLFPGPSKPFW VLVVVGGVLACYSLLV TVAFIIFWVRSKRSRL LHSDYMNMTPRRPGPT RKHYQPYAPPRDFAAY RSRVKFSRSADAPAYQ QGQNQLYNELNLGRRE EYDVLDKRRGRDPEMG GKPRRKNPQEGLYNEL QKDKMAEAYSEIGMKG ERRRGKGHDGLYQGLS TATKDTYDALHMQALP PR | 208 |

TABLE 2-continued

Example CAR Sequences

| CAR Construct | Nucleotide Sequence | SEQ ID NO: | Amino Acid Sequence | SEQ ID NO: |
|---|---|---|---|---|
| | AACCCCCAGGAGGGTCTCTATAATGAGCT GCAGAAGGATAAGATGGCTGAAGCCTATT CTGAAATAGGCATGAAAGGAGAGCGGAGA AGGGGAAAAGGGCACGACGGTTTGTACCA GGGACTCAGCACTGCTACGAAGGATACTT ATGACGCTCTCCACATGCAAGCCCTGCCA CCTAGG | | | |
| (CAR3.3) Clone 20C5.1 CD8 CAR DNA HxL | ATGGCACTCCCCGTAACTGCTCTGCTGCT GCCGTTGGCATTGCTCCTGCACGCCGCAC GCCCGCAGGTGCAGTTGGTGCAAAGCGGT GCAGAAGTTAAGAAACCTGGGGCGTCAGT TAAGGTGTCTTGCAAAGTATCTGGCTATA CCCTCACTGAGCTGTCCATGCATTGGGTA AGGCAGGCTCCTGGAAAGGGGCTCGAATG GATGGGAGGATTTGACCCTGAAGACGGAG AGACCATCTACGCCCAGAAATTCCAGGGT AGAGTAACAGTGACTGAGGACACTAGCAC TGACACAGCGTACATGGAGCTGAGTTCTC TGAGAAGTGAGGACACAGCCGTTTACTAC TGCGCTACCGAGTCCAGAGGTATTGGCTG GCCATACTTCGACTATTGGGGTCAGGGCA CCCTGGTTACAGTGAGTTCAGGAGGCGGG GGCTCTGGGGGGGCGGTTCCGGAGGGGG GGGCTCAGATATACAGATGACGCAGAGTC CATCAAGTCTCTCAGCCAGCGTGGGAGAT CGCGTGACTATTACTTGCCGCGCCAGCCA GAGTATTAGCTCCTATCTGAATTGGTACC AGCAAAAGCCCGGGAAGGCCCCTAAGCTT CTGATTTCTGGCGCCTCCTCTTTGAAGTC AGGTGTGCCAAGCAGATTTAGCGGGTCTG GAAGTGGCACTGACTTTACACTTACTATC TCCAGCCTGCCCCCAGAGGATTTTGCCAC ATATTACTGTCAGCAAAGCTACTCTACTC CAATCACTTTCGGCCAGGGCACAAGATTG GAGATTAAGAGGGCTGCCGCACTTTCAAA TTCCATCATGTATTTCAGCCATTTTGTGC CTGTTTTTCTTCCGGCCAAACCTACAACC ACTCCCGCCCCACGCCCACCTACTCCCGC CCCTACCATTGCCTCCCAGCCTCTGTCTC TTAGACCTGAGGCTTGTAGACCTGCTGCC GGCGGAGCCGTGCACACTCGCGGTCTGGA CTTCGCCTGCGACATCTATATCTGGGCCC CTCTGGCCGGCACCTGCGGCGTTCTCCTT CTCTCACTCGTAATCACACTCTATTGCAA TCACAGGAACAGATCCAAAAGAAGCCGCC TGCTCCATAGCGATTACATGAATATGACT CCACGCCGCCCTGGCCCCACAAGGAAACA CTACCAGCCTTACGCACCACCTAGAGATT TCGCTGCCTATCGGAGCAGGGTGAAGTTT TCCAGATCTGCAGATGCACCAGCGTATCA GCAGGGCCAGAACCAACTGTATAACGAGC TCAACCTGGGACGCAGGGAAGAGTATGAC GTTTTGGACAAGCGCAGAGGACGGGACCC TGAGATGGGTGGCAAACCAAGACGAAAAA ACCCCCAGGAGGGTCTCTATAATGAGCTG CAGAAGGATAAGATGGCTGAAGCCTATTC TGAAATAGGCATGAAAGGAGAGCGGAGAA GGGGAAAAGGGCACGACGGTTTGTACCAG GGACTCAGCACTGCTACGAAGGATACTTA TGACGCTCTCCACATGCAAGCCCTGCCAC CTAGGTAA | 209 | MALPVTALLLPLALLL HAARPQVQLVQSGAEV KKPGASVKVSCKVSGY TLTELSMHWVRQAPGK GLEWMGGFDPEDGETI YAQKFQGRVTVTEDTS TDTAYMELSSLRSEDT AVYYCATESRGIGWPY FDYWGQGTLVTVSSGG GGSGGGGSGGGGSDIQ MTQSPSSLSASVGDRV TITCRASQSISSYLNW YQQKPGKAPKLLISGA SSLKSGVPSRFSGSGS GTDFTLTISSLPPEDF ATYYCQQSYSTPITFG QGTRLEIKRAAALSNS IMYFSHFVPVFLPAKP TTTPAPRPPTPAPTIA SQPLSLRPEACRPAAG GAVHTRGLDFACDIYI WAPLAGTCGVLLLSLV ITLYCNHRNRSKRSRL LHSDYMNMTPRRPGPT RKHYQPYAPPRDFAAY RSRVKFSRSADAPAYQ QGQNQLYNELNLGRRE EYDVLDKRRGRDPEMG GKPRRKNPQEGLYNEL QKDKMAEAYSEIGMKG ERRRGKGHDGLYQGLS TATKDTYDALHMQALP PR | 210 |
| (CAR3.3) Clone 20C5.1 CD8 CAR DNA HxL | CAGGTGCAGTTGGTGCAAAGCGGCGCAGA AGTTAAGAAACCTGGGGCGTCAGTTAAGG TGTCTTGCAAAGTATCTGGCTATACCCTC ACTGAGCTGTCCATGCATTGGGTAAGGCA GGCTCCTGGAAAGGGGCTCGAATGGATGG GAGGATTTGACCCTGAAGACGGAGAGACC ATCTACGCCCAGAAATTCCAGGGTAGAGT AACAGTGACTGAGGACACTAGCACTGACA CAGCGTACATGGAGCTGAGTTCTCTGAGA AGTGAGGACACAGCCGTTTACTACTGCGC TACCGAGTCCAGAGGTATTGGCTGGCCAT | 211 | QVQLVQSGAEVKKPGA SVKVSCKVSGYTLTEL SMHWVRQAPGKGLEWM GGFDPEDGETIYAQKF QGRVTVTEDTSTDTAY MELSSLRSEDTAVYYC ATESRGIGWPYFDYWG QGTLVTVSSGGGGSGG GGSGGGGSDIQMTQSP SSLSASVGDRVTITCR ASQSISSYLNWYQQKP | 212 |

TABLE 2-continued

Example CAR Sequences

| CAR Construct | Nucleotide Sequence | SEQ ID NO: | Amino Acid Sequence | SEQ ID NO: |
|---|---|---|---|---|
| | ACTTCGACTATTGGGTCAGGGCACCCTG GTTACAGTGAGTTCAGGAGGCGGGGGCTC TGGGGGGGGCGGTTCCGGAGGGGGGGCT CAGATATACAGATGACGCAGAGTCCATCA AGTCTCTCAGCCAGCGTGGGAGATCGCGT GACTATTACTTGCCGCGCCAGCCAGAGTA TTAGCTCCTATCTGAATTGGTACCAGCAA AAGCCCGGGAAGGCCCCTAAGCTTCTGAT TTCTGGCGCCTCCTCTTTGAAGTCAGGTG TGCCAAGCAGATTTAGCGGGTCTGGAAGT GGCACTGACTTTACACTTACTATCTCCAG CCTGCCCCCAGAGGATTTTGCCACATATT ACTGTCAGAAAGCTACTCTACTCCAATC ACTTTCGGCCAGGGCACAAGATTGGAGAT TAAGAGGGCTGCCGCACTTTCAAATTCCA TCATGTATTTCAGCCATTTTGTGCCTGTT TTTCTTCCGGCCAAACCTACAACCACTCC CGCCCCACGCCCACCTACTCCCGCCCCTA CCATTGCCTCCCAGCCTCTGTCTCTTAGA CCTGAGGCTTGTAGACCTGCTGCCGGCGG AGCCGTGCACACTCGCGGTCTGGACTTCG CCTGCGACATCTATATCTGGGCCCCTCTG GCCGGCACCTGCGGCGTTCTCCTTCTCTC ACTCGTAATCACACTCTATTGCAATCACA GGAACAGATCCAAAAGAAGCCGCCTGCTC CATAGCGATTACATGAATATGACTCCACG CCGCCCTGGCCCCACAAGGAAACACTACC AGCCTTACGCACCACCTAGAGATTTCGCT GCCTATCGGAGCAGGGTGAAGTTTTCCAG ATCTGCAGATGCACCAGCGTATCAGCAGG GCCAGAACCAACTGTATAACGAGCTCAAC CTGGGACGCAGGGAAGAGTATGACGTTTT GGACAAGCGCAGAGGACGGGACCCTGAGA TGGGTGGCAAACCAAGACGAAAAAACCCC CAGGAGGGTCTCTATAATGAGCTGCAGAA GGATAAGATGGCTGAAGCCTATTCTGAAA TAGGCATGAAAGGAGAGCGGAGAAGGGGA AAAGGGCACGACGGTTTGTACCAGGGACT CAGCACTGCTACGAAGGATACTTATGACG CTCTCCACATGCAAGCCCTGCCACCTAGG | | GKAPKLLISGASSLKS GVPSRFSGSGSGTDFT LTISSLPPEDFATYYC QQSYSTPITFGQGTRL EIKRAAALSNSIMYFS HFVPVFLPAKPTTTPA PRPPTPAPTIASQPLS LRPEACRPAAGGAVHT RGLDFACDIYIWAPLA GTCGVLLLSLVITLYC NHRNRSKRSRLLHSDY MNMTPRRPGPTRKHYQ PYAPPRDFAAYRSRVK FSRSADAPAYQQGQNQ LYNELNLGRREEYDVL DKRRGRDPEMGGKPRR KNPQEGLYNELQKDKM AEAYSEIGMKGERRRG KGHDGLYQGLSTATKD TYDALHMQALPPR | |
| (CAR4.1) Clone 20C5.2 THD CAR DNA HxL | ATGGCACTCCCCGTAACTGCTCTGCTGCT GCCGTTGGCATTGCTCCTGCACGCCGCAC GCCCGCAGGTCCAGTTGGTCGAAAGTGGC GGTGGTGTAGTGCAGCCGGGCCGCAGTTT GAGGCTTTCCTGTGCGGCTTCAGGCTTTA CTTTTTCCAGCTATGGAATGCACTGGGTG CGGCAGGCCCCCGGCAAAGGACTTGAGTG GGTGGCCGTCATTTCTTATGACGGATCAG ATAAGTACTACGTGGACAGCGTCAAGGGC AGATTCACCATCTCTAGGGACAACAGTAA AAATAGACTCTACCTCCAGATGAATAGCC TCAGAGCTGAAGACACGGCCGTCTACTAT TGTGCTCGGGAGCGGTATAGTGGCAGAGA CTACTGGGGGCAGGGCACACTCGTTACAG TGAGTAGCGGCGGAGGGGGAGTGGGGGC GGTGGCTCCGGTGGAGGAGGTTCTGAGAT TGTTATGACCCAGAGTCCTGCGACCCTCT CAGTCAGCCCCGGGGAGCGCGCAACTTTG TCTTGCAGAGCTAGTCAGTCCGTGTCCTC TCTTCTGACATGGTACCAGCAAAAGCCCG GGCAGGCTCCGCGCCTTTTGATCTTTGGG GCTTCAACAAGAGCCACTGGGATTCCCGC ACGATTCTCTGGCTCCGGGAGCGGTACTG GTTTCACCCTGACGATTAGCAGTCTCCAG AGCGAGGACTTCGCCGTATACTACTGCCA GCAGTACGATACGTGGCCATTCACTTTTG GACCAGGGACTAAAGTGGATTTTAAGCGC GCCGCCGCTCTCGATAACGAAAAGTCAAA TGGCACCATAATCCACGTCAAAGGCAAGC ACCTGTGCCCTTCCCCGCTCTTCCCCGGA CCCAGTAAACCATTTTGGGTGCTGGTTGT TGTGGGGGGCGTGCTGGCCTGCTATAGCC TTTTGGTCACTGTAGCCTTCATTATTTTT | 213 | MALPVTALLLPLALLL HAARPQVQLVESGGGV VQPGRSLRLSCAASGF TFSSYGMHWVRQAPGK GLEWVAVISYDGSDKY YVDSVKGRFTISRDNS KNRLYLQMNSLRAEDT AVYYCARERYSGRDYW GQGTLVTVSSGGGGSG GGGSGGGGSEIVMTQS PATLSVSPGERATLSC RASQSVSSLLTWYQQK PGQAPRLLIFGASTRA TGIPARFSGSGSGTGF TLTISSLQSEDFAVYY CQQYDTWPFTFGPGTK VDFKRAAALDNEKSNG TIIHVKGKHLCPSPLF PGPSKPFWVLVVVGGV LACYSLLVTVAFIIFW VRSKRSRLLHSDYMNM TPRRPGPTRKHYQPYA PPRDFAAYRSRVKFSR SADAPAYQQGQNQLYN ELNLGRREEYDVLDKR RGRDPEMGGKPRRKNP QEGLYNELQKDKMAEA YSEIGMKGERRRGKGH DGLYQGLSTATKDTYD ALHMQALPPR | 214 |

TABLE 2-continued

Example CAR Sequences

| CAR Construct | Nucleotide Sequence | SEQ ID NO: | Amino Acid Sequence | SEQ ID NO: |
|---|---|---|---|---|
| | TGGGTCAGATCCAAAAGAAGCCGCCTGCT CCATAGCGATTACATGAATATGACTCCAC GCCGCCCTGGCCCCACAAGGAAACACTAC CAGCCTTACGCACCACCTAGAGATTTCGC TGCCTATCGGAGCAGGGTGAAGTTTTCCA GATCTGCAGATGCACCAGCGTATCAGCAG GGCCAGAACCAACTGTATAACGAGCTCAA CCTGGGACGCAGGGAAGAGTATGACGTTT TGGACAAGCGCAGAGGACGGGACCCTGAG ATGGGTGGCAAACCAAGACGAAAAAACCC CCAGGAGGGTCTCTATAATGAGCTGCAGA AGGATAAGATGGCTGAAGCCTATTCTGAA ATAGGCATGAAAGGAGAGCGGAGAAGGGG AAAAGGGCACGACGGTTTGTACCAGGGAC TCAGCACTGCTACGAAGGATACTTATGAC GCTCTCCACATGCAAGCCCTGCCACCTAG GTAA | | | |
| (CAR4.1) Clone 20C5.2 THD CAR DNA HxL | CAGGTCCAGTTGGTCGAAAGTGGCGGTGG TGTAGTGCAGCCGGGCCGCAGTTTGAGGC TTTCCTGTGCGGCTTCAGGCTTTACTTTT TCCAGCTATGGAATGCACTGGGTGCGGCA GGCCCCCGGCAAAGGACTTGAGTGGGTGG CCGTCATTTCTTATGACGGATCAGATAAG TACTACGTGGACAGCGTCAAGGGCAGATT CACCATCTCTAGGGACAACAGTAAAAATA GACTCTACCTCCAGATGAATAGCCTCAGA GCTGAAGACACGGCCGTCTACTATTGTGC TCGGGAGCGGTATAGTGGCAGAGACTACT GGGGGCAGGGCACACTCGTTACAGTGAGT AGCGGCGGAGGAGGGAGTGGGGGCGGTGG CTCCGGTGGAGGAGGTTCTGAGATTGTTA TGACCCAGAGTCCTGCGACCCTCTCAGTC AGCCCCGGGGAGCGCGCAACTTTGTCTTG CAGAGCTAGTCAGTCCGTGTCCTCTCTTC TGACATGGTACCAGCAAAAGCCCGGGCAG GCTCCGCGCCTTTTGATCTTTGGGGCTTC AACAAGAGCCACTGGGATTCCCGCACGAT TCTCTGGCTCCGGGAGCGGTACTGGTTTC ACCCTGACGATTAGCAGTCTCCAGAGCGA GGACTTCGCCGTATACTACTGCCAGCAGT ACGATACGTGGCCATTCACTTTTGGACCA GGGACTAAAGTGGATTTTAAGCGCGCCGC CGCTCTCGATAACGAAAAGTCAAATGGCA CCATAATCCACGTCAAAGGCAAGCACCTG TGCCCTTCCCCGCTCTTCCCCGGACCCAG TAAACCATTTTGGGTGCTGGTTGTTGTGG GGGGCGTGCTGGCCTGCTATAGCCTTTTG GTCACTGTAGCCTTCATTATTTTTTGGGT CAGATCCAAAAGAAGCCGCCTGCTCCATA GCGATTACATGAATATGACTCCACGCCGC CCTGGCCCCACAAGGAAACACTACCAGCC TTACGCACCACCTAGAGATTTCGCTGCCT ATCGGAGCAGGGTGAAGTTTTCCAGATCT GCAGATGCACCAGCGTATCAGCAGGGCCA GAACCAACTGTATAACGAGCTCAACCTGG GACGCAGGGAAGAGTATGACGTTTTGGAC AAGCGCAGAGGACGGGACCCTGAGATGGG TGGCAAACCAAGACGAAAAAACCCCCAGG AGGGTCTCTATAATGAGCTGCAGAAGGAT AAGATGGCTGAAGCCTATTCTGAAATAGG CATGAAAGGAGAGCGGAGAAGGGGAAAAG GGCACGACGGTTTGTACCAGGGACTCAGC ACTGCTACGAAGGATACTTATGACGCTCT CCACATGCAAGCCCTGCCACCTAGG | 215 | QVQLVESGGGVVQPGR SLRLSCAASGFTFSSY GMHWVRQAPGKGLEWV AVISYDGSDKYYVDSV KGRFTISRDNSKNRLY LQMNSLRAEDTAVYYC ARERYSGRDYWGQGTL VTVSSGGGGSGGGGSG GGGSEIVMTQSPATLS VSPGERATLSCRASQS VSSLLTWYQQKPGQAP RLLIFGASTRATGIPA RFSGSGSGTGFTLTIS SLQSEDFAVYYCQQYD TWPFTFGPGTKVDFKR AAALDNEKSNGTIIHV KGKHLCPSPLFPGPSK PFWVLVVVGGVLACYS LLVTVAFIIFWVRSKR SRLLHSDYMNMTPRRP GPTRKHYQPYAPPRDF AAYRSRVKFSRSADAP AYQQGQNQLYNELNLG RREEYDVLDKRRGRDP EMGGKPRRKNPQEGLY NELQKDKMAEAYSEIG MKGERRRGKGHDGLYQ GLSTATKDTYDALHMQ ALPPR | 216 |
| (CAR4.2) Clone 20C5.2 CHD CAR DNA HxL | ATGGCACTCCCCGTAACTGCTCTGCTGCT GCCGTTGGCATTGCTCCTGCACGCCGCAC GCCCGCAGGTGCAGCTCGTGGAGTCTGGC GGCGGCGTGGTCCAGCCCGGCCGGTCCCT GCGCCTGTCCTGCGCCGCCAGCGGGTTTA CTTTTTCCTCCTACGGCATGCACTGGGTG CGCCAGGCTCCCGGCAAGGGCCTCGAGTG GGTCGCCGTGATCTCATACGATGGGTCAG | 217 | MALPVTALLLPLALLL HAARPQVQLVESGGGV VQPGRSLRLSCAASGF TFSSYGMHWVRQAPGK GLEWVAVISYDGSDKY YVDSVKGRFTISRDNS KNRLYLQMNSLRAEDT AVYYCARERYSGRDYW | 218 |

TABLE 2-continued

Example CAR Sequences

| CAR Construct | Nucleotide Sequence | SEQ ID NO: | Amino Acid Sequence | SEQ ID NO: |
|---|---|---|---|---|
| | ACAAATACTATGTCGATTCTGTTAAAGGG CGGTTTACCATTTCAAGAGATAACTCTAA GAATAGGCTGTATTTGCAGATGAACAGCC TGAGGGCTGAAGATACCGCAGTGTACTAT TGCGCTAGGGAGCGGTATAGTGGCCGCGA TTACTGGGGACAGGGTACACTGGTGACCG TGAGCTCTGGGGGTGGCGGAAGCGGGGGT GGCGGAAGCGGCGGAGGGGGTAGTGAAAT TGTGATGACCCAGTCTCCGGCTACACTTT CAGTCTCCCCTGGGGAGAGAGCTACACTG TCATGCAGAGCGTCCCAGTCCGTCTCTTC TCTCCTTACCTGGTATCAGCAGAAGCCCG GCCAGGCTCCTCGACTGCTGATCTTCGGT GCCTCCACAAGGGCGACCGGGATTCCAGC CCGCTTCTCAGGTTCTGGGAGCGGAACTG GTTTCACTTTGACAATCAGTTCACTGCAG TCAGAGGATTCGCCGTGTACTACTGCCA GCAATACGACACATGGCCATTCACTTTCG GACCCGGTACCAAAGTCGATTTCAAGAGA GCCGCGGCCATCGAGGTTATGTACCCACC ACCATATCTGGACAATGAAAAAGCAATG GAACCATTATCCATGTGAAGGGTAAACAC CTCTGCCCTAGCCCACTTTTCCCTGGCCC ATCAAAGCCCTTCTGGGTCTTGGTGGTCG TGGGGGGTGTGCTGGCCTGTTACAGCCTT CTGGTGACGGTTGCTTTCATTATCTTCTG GGTTAGATCCAAAAGAAGCCGCCTGCTCC ATAGCGATTACATGAATATGACTCCACGC CGCCCTGGCCCCACAAGGAAACACTACCA GCCTTACGCACCACCTAGAGATTCGCTG CCTATCGGAGCAGGGTGAAGTTTTCCAGA TCTGCAGATGCACCAGCGTATCAGCAGGG CCAGAACCAACTGTATAACGAGCTCAACC TGGGACGCAGGGAAGAGTATGACGTTTTG GACAAGCGCAGAGGACGGGACCCTGAGAT GGGTGGCAAACCAAGACGAAAAAACCCCC AGGAGGGTCTCTATAATGAGCTGCAGAAG GATAAGATGGCTGAAGCCTATTCTGAAAT AGGCATGAAAGGAGAGCGGAGAAGGGGAA AAGGGCACGACGGTTTGTACCAGGGACTC AGCACTGCTACGAAGGATACTTATGACGC TCTCCACATGCAAGCCCTGCCACCTAGGT AA | | GQGTLVTVSSGGGGSG GGGSGGGGSEIVMTQS PATLSVSPGERATLSC RASQSVSSLLTWYQQK PGQAPRLLIFGASTRA TGIPARFSGSGSGTGF TLTISSLQSEDFAVYY CQQYDTWPFTFGPGTK VDFKRAAAIEVMYPPP YLDNEKSNGTIIHVKG KHLCPSPLFPGPSKPF WVLVVVGGVLACYSLL VTVAFIIFWVRSKRSR LLHSDYMNMTPRRPGP TRKHYQPYAPPRDFAA YRSRVKFSRSADAPAY QQGQNQLYNELNLGRR EEYDVLDKRRGRDPEM GGKPRRKNPQEGLYNE LQKDKMAEAYSEIGMK GERRRGKGHDGLYQGL STATKDTYDALHMQAL PPR | |
| (CAR4.2) Clone 20C5.2 CHD CAR DNA HxL | CAGGTGCAGCTCGTGGAGTCTGGCGGCGG CGTGGTCCAGCCCGGCCGGTCCCTGCGCC TGTCCTGCGCCGCCAGCGGGTTTACTTTT TCCTCCTACGGCATGCACTGGGTGCCA GGCTCCCGGCAAGGGCCTCGAGTGGGTCG CCGTGATCTCATACGATGGGTCAGACAAA TACTATGTCGATTCTGTTAAAGGGCGGTT TACCATTTCAAGAGATAACTCTAAGAATA GGCTGTATTTGCAGATGAACAGCCTGAGG GCTGAAGATACCGCAGTGTACTATTGCGC TAGGGAGCGGTATAGTGGCCGCGATTACT GGGGACAGGGTACACTGGTGACCGTGAGC TCTGGGGGTGGCGGAAGCGGGGGTGGCGG AAGCGGCGGAGGGGGTAGTGAAATTGTGA TGACCCAGTCTCCGGCTACACTTTCAGTC TCCCCTGGGGAGAGAGCTACACTGTCATG CAGAGCGTCCCAGTCCGTCTCTTCTCC TTACCTGGTATCAGCAGAAGCCCGGCCAG GCTCCTCGACTGCTGATCTTCGGTGCCTC CACAAGGGCGACCGGGATTCCAGCCCGCT TCTCAGGTTCTGGGAGCGGAACTGGTTTC ACTTTGACAATCAGTTCACTGCAGTCAGA GGATTTCGCCGTGTACTACTGCCAGCAAT ACGACACATGGCCATTCACTTTCGGACCC GGTACCAAAGTCGATTTCAAGAGAGCCGC GGCCATCGAGGTTATGTACCCACCACCAT ATCTGGACAATGAAAAAGCAATGGAACC ATTATCCATGTGAAGGGTAAACACCTCTG CCCTAGCCCACTTTTCCCTGGCCCATCAA AGCCCTTCTGGGTCTTGGTGGTCGTGGGG | 219 | QVQLVESGGGVVQPGR SLRLSCAASGFTFSSY GMHWVRQAPGKGLEWV AVISYDGSDKYYVDSV KGRFTISRDNSKNRLY LQMNSLRAEDTAVYYC ARERYSGRDYWGQGTL VTVSSGGGGSGGGGSG GGSEIVMTQSPATLS VSPGERATLSCRASQS VSSLLTWYQQKPGQAP RLLIFGASTRATGIPA RFSGSGSGTGFTLTIS SLQSEDFAVYYCQQYD TWPFTFGPGTKVDFKR AAAIEVMYPPPYLDNE KSNGTIIHVKGKHLCP SPLFPGPSKPFWVLVV VGGVLACYSLLVTVAF IIFWVRSKRSRLLHSD YMNMTPRRPGPTRKHY QPYAPPRDFAAYRSRV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | 220 |

TABLE 2-continued

Example CAR Sequences

| CAR Construct | Nucleotide Sequence | SEQ ID NO: | Amino Acid Sequence | SEQ ID NO: |
|---|---|---|---|---|
| | GGTGTGCTGGCCTGTTACAGCCTTCTGGT GACGGTTGCTTTCATTATCTTCTGGGTTA GATCCAAAAGAAGCCGCCTGCTCCATAGC GATTACATGAATATGACTCCACGCCGCCC TGGCCCCACAAGGAAACACTACCAGCCTT ACGCACCACCTAGAGATTTCGCTGCCTAT CGGAGCAGGGTGAAGTTTTCCAGATCTGC AGATGCACCAGCGTATCAGCAGGGCCAGA ACCAACTGTATAACGAGCTCAACCTGGGA CGCAGGGAAGAGTATGACGTTTTGGACAA GCGCAGAGGACGGGACCCTGAGATGGGTG GCAAACCAAGACGAAAAAACCCCCAGGAG GGTCTCTATAATGAGCTGCAGAAGGATAA GATGGCTGAAGCCTATTCTGAAATAGGCA TGAAAGGAGAGCGGAGAAGGGGAAAAGGG CACGACGGTTTGTACCAGGGACTCAGCAC TGCTACGAAGGATACTTATGACGCTCTCC ACATGCAAGCCCTGCCACCTAGG | | | |
| (CAR4.3) Clone 20C5.2 CD8 CAR DNA HxL | ATGGCACTCCCCGTAACTGCTCTGCTGCT GCCGTTGGCATTGCTCCTGCACGCCGCAC GCCCCGCAGGTGCAGTTGGTTGAATCAGGA GGGGGTGTGGTGCAACCCGGTCGGTCGT GCGCCTCAGTTGTGCTGCTTCCGGGTTA CTTTCAGCTCATATGGGATGCACTGGGTA CGGCAGGCTCCAGGTAAAGGCTTGGAATG GGTGGCGGTGATCAGCTATGACGGCTCTG ACAAATATTATGTGGACTCCGTGAAAGGC AGATTCACCATCAGTCGAGACAACTCAAA GAATAGACTCTACTTGCAGATGAATAGCC TCCGGGCCGAAGATACTGCAGTCTATTAT TGCGCCCGGGAGCGCTACAGTGGAAGAGA CTATTGGGGGCAAGGAACTCTTGTCACAG TCTCATCTGGCGGCGGCGGCAGCGGTGGG GGCGGATCTGGCGGGGCGGCAGCGAAAT CGTTATGACTCAGAGTCCTGCCACACTGA GCGTTAGCCCTGGTGAGAGAGCAACACTT AGCTGCAGAGCTAGTCAGAGTGTTTCCAG TCTTTTGACATGGTACCAACAGAAGCCCG GTCAAGCTCCACGACTGCTCATCTTCGGT GCATCCACCCGCGCAACCGGGATACCCGC CCGGTTTTCCGGTTCTGGAAGTGGCACAG GATTCACGCTCACCATTTCTTCTCTGCAG TCTGAAGACTTTGCCGTGTATTACTGCCA GCAGTACGATACCTGGCCCTTTACCTTTG GCCCAGGTACTAAAGTGGATTTTAAACGA GCTGCTGCACTTTCCAATAGTATTATGTA CTTTTCACATTTTGTGCCCGTGTTCCTGC CTGCGAAGCCTACGACAACCCCAGCCCCT AGGCCGCCCACACCGGCCCCAACTATTGC CTCCCAGCCATTGTCTCTGAGACCCGAAG CTTGCAGACCTGCTGCTGGAGGCGCCGTT CACACCCGAGGATTGGATTTCGCATGTGA CATTTACATCTGGGCCCCTTTGGCCGGAA CCTGCGGTGTGCTGCTGCTGTCACTCGTG ATTACACTTTACTGCAACCACCGAAACAG ATCCAAAAGAAGCCGCCTGCTCCATAGCG ATTACATGAATATGACTCCACGCCGCCCT GGCCCCACAAGGAAACACTACCAGCCTTA CGCACCACCTAGAGATTTCGCTGCCTATC GGAGCAGGGTGAAGTTTTCCAGATCTGCA GATGCACCAGCGTATCAGCAGGGCCAGAA CCAACTGTATAACGAGCTCAACCTGGGAC GCAGGGAAGAGTATGACGTTTTGGACAAG CGCAGAGGACGGGACCCTGAGATGGGTGG CAAACCAAGACGAAAAAACCCCCAGGAGG GTCTCTATAATGAGCTGCAGAAGGATAAG ATGGCTGAAGCCTATTCTGAAATAGGCAT GAAAGGAGAGCGGAGAAGGGGAAAGGGC ACGACGGTTTGTACCAGGGACTCAGCACT GCTACGAAGGATACTTATGACGCTCTCCA CATGCAAGCCCTGCCACCTAGGTAA | 221 | MALPVTALLLPLALLL HAARPQVQLVESGGGV VQPGRSLRLSCAASGF TFSSYGMHWVRQAPGK GLEWVAVISYDGSDKY YVDSVKGRFTISRDNS KNRLYLQMNSLRAEDT AVYYCARERYSGRDYW GQGTLVTVSSGGGGSG GGGSGGGGSEIVMTQS PATLSVSPGERATLSC RASQSVSSLLTWYQQK PGQAPRLLIFGASTRA TGIPARFSGSGSGTGF TLTISSLQSEDFAVYY CQQYDTWPFTFGPGTK VDFKRAAALSNSIMYF SHFVPVFLPAKPTTTP APRPPTPAPTIASQPL SLRPEACRPAAGGAVH TRGLDFACDIYIWAPL AGTCGVLLLSLVITLY CNHRNRSKRSRLLHSD YMNMTPRRPGPTRKHY QPYAPPRDFAAYRSRV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | 222 |

TABLE 2-continued

Example CAR Sequences

| CAR Construct | Nucleotide Sequence | SEQ ID NO: | Amino Acid Sequence | SEQ ID NO: |
|---|---|---|---|---|
| (CAR4.3) Clone 20C5.2 CD8 CAR DNA HxL | CAGGTGCAGTTGGTTGAATCAGGAGGGGG TGTGGTCAACCCGGTCGGTCACTGCGCC TCAGTTGTGCTGCTTCCGGGTTTACTTTC AGCTCATATGGGATGCACTGGGTACGGCA GGCTCCAGGTAAAGGCTTGGAATGGGTGG CGGTGATCAGCTATGACGGCTCTGACAAA TATTATGTGGACTCCGTGAAAGGCAGATT CACCATCAGTCGAGACAACTCAAAGAATA GACTCTACTTGCAGATGAATAGCCTCCGG GCCGAAGATACTGCAGTCTATTATTGCGC CCGGGAGCGCTACAGTGGAAGAGACTATT GGGGGCAAGGAACTCTTGTCACAGTCTCA TCTGGCGGCGGCGGCAGCGGTGGGGGCGG ATCTGGCGGGGGCGGCAGCGAAATCGTTA TGACTCAGAGTCCTGCCACACTGAGCGTT AGCCCTGGTGAGAGAGCAACACTTAGCTG CAGAGCTAGTCAGAGTGTTTCCAGTCTTT TGACATGGTACCAACAGAAGCCCGGTCAA GCTCCACGACTGCTCATCTTCGGTGCATC CACCCGCGCAACCGGGATACCCGCCCGGT TTTCCGGTTCTGGAAGTGGCACAGGATTC ACGCTCACCATTTCTTCTCTGCAGTCTGA AGACTTTGCCGTGTATTACTGCCAGCAGT ACGATACCTGGCCCTTTACCTTTGGCCCA GGTACTAAAGTGGATTTTAAACGAGCTGC TGCACTTTCCAATAGTATTATGTACTTTT CACATTTTGTGCCCGTGTTCCTGCCTGCG AAGCCTACGACAACCCCAGCCCCTAGGCC GCCCACACCGGCCCCAACTATTGCCTCCC AGCCATTGTCTCTGAGACCCGAAGCTTGC AGACCTGCTGCTGGAGGCGCCGTTCACAC CGAGGATTGGATTTCGCATGTGACATTT ACATCTGGGCCCCTTTGGCCGGAACCTGC GGTGTGCTGCTGCTGTCACTCGTGATTAC ACTTTACTGCAACCACCGAAACAGATCCA AAAGAAGCCGCCTGCTCCATAGCGATTAC ATGAATATGACTCCACGCCGCCCTGGCCC CACAAGGAAACACTACCAGCCTTACGCAC CACCTAGAGATTTCGCTGCCTATCGGAGC AGGGTGAAGTTTTCCAGATCTGCAGATGC ACCAGCGTATCAGCAGGGCCAGAACCAAC TGTATAACGAGCTCAACCTGGGACGCAGG GAAGAGTATGACGTTTTGGACAAGCGCAG AGGACGGGACCCTGAGATGGGTGGCAAAC CAAGACGAAAAAACCCCCAGGAGGGTCTC TATAATGAGCTGCAGAAGGATAAGATGGC TGAAGCCTATTCTGAAATAGGCATGAAAG GAGAGCGGAGAAGGGGAAAAGGGCACGAC GGTTTGTACCAGGGACTCAGCACTGCTAC GAAGGATACTTATGACGCTCTCCACATGC AAGCCCTGCCACCTAGG | 223 | QVQLVESGGGVVQPGR SLRLSCAASGFTFSSY GMHWVRQAPGKGLEWV AVISYDGSDKYYVDSV KGRFTISRDNSKNRLY LQMNSLRAEDTAVYYC ARERYSGRDYWGQGTL VTVSSGGGGSGGGGSG GGGSEIVMTQSPATLS VSPGERATLSCRASQS VSSLLTWYQQKPGQAP RLLIFGASTRATGIPA RFSGSGSGTGFTLTIS SLQSEDFAVYYCQQYD TWPFTFGPGTKVDFKR AAALSNSIMYFSHFVP VFLPAKPTTTPAPRPP TPAPTIASQPLSLRPE ACRPAAGGAVHTRGLD FACDIYIWAPLAGTCG VLLLSLVITLYCNHRN RSKRSRLLHSDYMNMT PRRPGPTRKHYQPYAP PRDFAAYRSRVKFSRS ADAPAYQQGQNQLYNE LNLGRREEYDVLDKRR GRDPEMGGKPRRKNPQ EGLYNELQKDKMAEAY SEIGMKGERRRGKGHD GLYQGLSTATKDTYDA LHMQALPPR | 224 |
| (CAR4.4) Clone 20C5.2 THD CAR DNA LxH | ATGGCACTCCCCGTAACTGCTCTGCTGCT GCCGTTGGCATTGCTCCTGCACGCCGCAC GCCCGGAGATTGTGATGACCCAGTCCCCT GCTACCCTGTCCGTCAGTCCGGGCAGAGC AGCCACCTTGTCATGCCGGGCCAGCCAGT CCGTCAGCAGTCTCCTGACTTGGTATCAG CAAAAACCAGGGCAGGCACCGCGGCTTTT GATTTTTGGTGCAAGCACACGCGCCACTG GCATTCCAGCTAGGTTTTCTGGAAGTGGA TCTGGGACAGGCTTCACTCTGACAATCAG TAGCCTGCAGAGTGAGGACTTTGCTGTTT ACTACTGTCAACAGTACGACACCTGGCCA TTCACATTCGGGCCCGGCACCAAGGTCGA CTTCAAGAGGGGCGGTGGAGGTTCAGGTG GTGGCGGGTCAGGCGGCGGTGGGTCTCAG GTTCAACTGGTGGAATCAGGTGGCGGCTC TGTCCAACCGGGGCGATCACTTCGACTTT CCTGTGCTGCCTCAGGCTTTACTTTTTCA TCCTATGGGATGCACTGGGTTCGGCAGGC TCCCGGAAAAGGACTCGAGTGGGTTGCAG TGATCTCTTACGATGGCTCAGACAAGTAT | 225 | MALPVTALLLPLALLL HAARPEIVMTQSPATL SVSPGERATLSCRASQ SVSSLLTWYQQKPGQA PRLLIFGASTRATGIP ARFSGSGSGTGFTLTI SSLQSEDFAVYYCQQY DTWPFTFGPGTKVDFK RGGGGSGGGGSGGGGS QVQLVESGGGVVQPGR SLRLSCAASGFTFSSY GMHWVRQAPGKGLEWV AVISYDGSDKYYVDSV KGRFTISRDNSKNRLY LQMNSLRAEDTAVYYC ARERYSGRDYWGQGTL VTVSSAAALDNEKSNG TIIHVKGKHLCPSPLF PGPSKPFWVLVVVGGV LACYSLLVTVAFIIFW VRSKRSRLLHSDYMNM | 226 |

TABLE 2-continued

Example CAR Sequences

| CAR Construct | Nucleotide Sequence | SEQ ID NO: | Amino Acid Sequence | SEQ ID NO: |
|---|---|---|---|---|
| | TATGTGGACTCAGTCAAGGGGAGATTCAC AATAAGCCGAGACAACTCCAAAAACCGGC TTTATCTCCAGATGAACAGCCTTAGAGCG GAAGATACCGCGGTATACTACTGTGCCCG CGAGAGGTATTCCGGCAGAGACTACTGGG GACAGGGCACACTGGTCACCGTGAGTTCT GCCGCAGCGCTCGATAACGAAAAGAGCAA CGGAACCATTATCCACGTTAAGGGCAAGC ACCTGTGCCCCAGTCCCCTCTTCCCAGGA CCATCTAAACCCTTCTGGGTTCTGGTAGT AGTTGGAGGGGTCCTTGCATGTTACTCCC TTTTGGTCACCGTCGCCTTCATTATTTTC TGGGTGAGATCCAAAAGAAGCCGCCTGCT CCATAGCGATTACATGAATATGACTCCAC GCCGCCCTGGCCCCACAAGGAAACACTAC CAGCCTTACGCACCACCTAGAGATTTCGC TGCCTATCGGAGCAGGGTGAAGTTTTCCA GATCTGCAGATGCACCAGCGTATCAGCAG GGCCAGAACCAACTGTATAACGAGCTCAA CCTGGGACGCAGGGAAGAGTATGACGTTT TGGACAAGCGCAGAGGACGGGACCCTGAG ATGGGTGGCAAACCAAGACGAAAAAACCC CCAGGAGGGTCTCTATAATGAGCTGCAGA AGGATAAGATGGCTGAAGCCTATTCTGAA ATAGGCATGAAAGGAGAGCGGAGAAGGGG AAAAGGGCACGACGGTTTGTACCAGGGAC TCAGCACTGCTACGAAGGATACTTATGAC GCTCTCCACATGCAAGCCCTGCCACCTAG GTAA | | TPRRPGPTRKHYQPYA PPRDFAAYRSRVKFSR SADAPAYQQGQNQLYN ELNLGRREEYDVLDKR RGRDPEMGGKPRRKNP QEGLYNELQKDKMAEA YSEIGMKGERRRGKGH DGLYQGLSTATKDTYD ALHMQALPPR | |
| (CAR4.4) Clone 20C5.2 THD CAR DNA LxH | GAGATTGTGATGACCCAGTCCCCTGCTAC CCTGTCCGTCAGTCCGGGCGAGAGAGCCA CCTTGTCATGCCGGGCCAGCCAGTCCGTC AGCAGTCTCCTGACTTGGTATCAGCAAAA ACCAGGGCAGGCACCGCGGCTTTTGATTT TTGGTGCAAGCACACGCGCCACTGGCATT CCAGCTAGGTTTTCTGGAAGTGGATCTGG GACAGGCTTCACTCTGACAATCAGTAGCC TGCAGAGTGAGGACTTTGCTGTTTACTAC TGTCAACAGTACGACACCTGGCCATTCAC ATTCGGGCCCGGCACCAAGGTCGACTTCA AGAGGGGCGGTGGAGGTTCAGGTGGTGGC GGGTCAGGCGGCGGTGGGTCTCAGGTTCA ACTGGTGGAATCAGGTGGCGGCGTTGTCC AACCGGGGCGATCACTTCGACTTTCCTGT GCTGCCTCAGGCTTTACTTTTTCATCCTA TGGGATGCACTGGGTTCGGCAGGCTCCCG GAAAAGGACTCGAGTGGGTTGCAGTGATC TCTTACGATGGCTCAGACAAGTATTATGT GGACTCAGTCAAGGGGAGATTCACAATAA GCCGAGACAACTCCAAAAACCGGCTTTAT CTCCAGATGAACAGCCTTAGAGCGGAAGA TACCGCGGTATACTACTGTGCCCGCGAGA GGTATTCCGGCAGAGACTACTGGGGACAG GGCACACTGGTCACCGTGAGTTCTGCCGC AGCGCTCGATAACGAAAAGAGCAACGGAA CCATTATCCACGTTAAGGGCAAGCACCTG TGCCCCAGTCCCCTCTTCCCAGGACCATC TAAACCCTTCTGGGTTCTGGTAGTAGTTG GAGGGGTCCTTGCATGTTACTCCCTTTTG GTCACCGTCGCCTTCATTATTTTCTGGGT GAGATCCAAAAGAAGCCGCCTGCTCCATA GCGATTACATGAATATGACTCCACGCCGC CCTGGCCCCACAAGGAAACACTACCAGCC TTACGCACCACCTAGAGATTTCGCTGCCT ATCGGAGCAGGGTGAAGTTTTCCAGATCT GCAGATGCACCAGCGTATCAGCAGGGCCA GAACCAACTGTATAACGAGCTCAACCTGG GACGCAGGGAAGAGTATGACGTTTGGAC AAGCGCAGAGGACGGGACCCTGAGATGGG TGGCAAACCAAGACGAAAAAACCCCCAGG AGGGTCTCTATAATGAGCTGCAGAAGGAT AAGATGGCTGAAGCCTATTCTGAAATAGG CATGAAAGGAGAGCGGAGAAGGGGAAAAG | 227 | EIVMTQSPATLSVSPG ERATLSCRASQSVSSL LTWYQQKPGQAPRLLI FGASTRATGIPARFSG SGSGTGFTLTISSLQS EDFAVYYCQQYDTWPF TFGPGTKVDFKRGGGG SGGGGSGGGGSQVQLV ESGGGVVQPGRSLRLS CAASGFTFSSYGMHWV RQAPGKGLEWVAVISY DGSDKYYVDSVKGRFT ISRDNSKNRLYLQMNS LRAEDTAVYYCARERY SGRDYWGQGTLVTVSS AAALDNEKSNGTIIHV KGKHLCPSPLFPGPSK PFWVLVVVGGVLACYS LLVTVAFIIFWVRSKR SRLLHSDYMNMTPRRP GPTRKHYQPYAPPRDF AAYRSRVKFSRSADAP AYQQGQNQLYNELNLG RREEYDVLDKRRGRDP EMGGKPRRKNPQEGLY NELQKDKMAEAYSEIG MKGERRRGKGHDGLYQ GLSTATKDTYDALHMQ ALPPR | 228 |

TABLE 2-continued

Example CAR Sequences

| CAR Construct | Nucleotide Sequence | SEQ ID NO: | Amino Acid Sequence | SEQ ID NO: |
|---|---|---|---|---|
| | GGCACGACGGTTTGTACCAGGGACTCAGC ACTGCTACGAAGGATACTTATGACGCTCT CCACATGCAAGCCCTGCCACCTAGG | | | |
| (CAR4.5) Clone 20C5.2 CHD CAR DNA LxH | ATGGCACTCCCCGTAACTGCTCTGCTGCT GCCGTTGGCATTGCTCCTGCACGCCGCAC GCCCGGAGATCGTCATGACACAGAGTCCA GCTACCCTGAGCGTGTCCCCTGGAGAGAG AGCCACCCTGTCCTGTAGGGCTAGTCAGA GTGTGTCCAGCCTCCTCACCTGGTATCAA CAGAAGCCTGGTCAAGCTCCCCGGCTGCT TATCTTCGGGGCCAGCACGCGAGCCACAG GCATCCCGGCCAGATTCTCTGGCTCTGGC AGTGGCACCGGGTTCACTCTCACGATCTC ATCCCTGCAGTCAGAGGATTTCGCTGTGT ATTACTGTCAGCAGTACGATACATGGCCC TTCACCTTCGGCCCGGGCACAAAAGTAGA TTTCAAGCGCGGCGGCGGGGGTAGTGGGG GCGGGGGATCAGGAGGAGGGGGCTCCCAA GTACAGCTGGTTGAGAGCGGCGGCGGGGT GGTTCAGCCCGGGCGCAGCCTCAGGCTGA GTTGCGCAGCATCAGGATTCACATTCAGT TCTTATGGAATGCATTGGGTCAGACAGGC TCCCGGGAAGGGCCTTGAATGGGTGGCAG TCATTAGCTACGACGGAAGCGATAAGTAC TATGTGGACTCAGTTAAAGGGAGATTTAC TATCAGCCGCGACAATTCCAAAAACAGAT TGTATTTGCAGATGAACTCCCTCAGGGCG GAGGACACTGCTGTATATTACTGCGCACG AGAGAGATACTCCGGCCGAGACTATTGGG GCCAAGGAACATTGGTAACTGTGAGCTCC GCCGCAGCTATTGAGGTCATGTACCCCCC ACCTTATCTCGATAATGAGAAGAGTAATG GGACTATAATTCACGTAAAGGGCAAACAC CTGTGCCCTTCCCCGCTGTTTCCAGGTCC AAGTAAGCCGTTCTGGGTCCTGGTTGTGG TGGGAGGGGTGCTGGCCTGCTATTCTCTG TTGGTTACCGTGGCCTTTATCATTTTCTG GGTGAGATCCAAAAGAAGCCGCCTGCTCC ATAGCGATTACATGAATATGACTCCACGC CGCCCTGGCCCCACAAGGAAACACTACCA GCCTTACGCACCACCTAGAGATTCGCTG CCTATCGGAGCAGGGTGAAGTTTTCCAGA TCTGCAGATGCACCAGCGTATCAGCAGGG CCAGAACCAACTGTATAACGAGCTCAACC TGGGACGCAGGGAAGAGTATGACGTTTTG GACAAGCGCAGAGGACGGGACCCTGAGAT GGGTGGCAAACCAAGACGAAAAAACCCCC AGGAGGGTCTCTATAATGAGCTGCAGAAG GATAAGATGGCTGAAGCCTATTCTGAAAT AGGCATGAAAGGAGAGCGGAGAAGGGGAA AAGGGCACGACGGTTTGTACCAGGGACTC AGCACTGCTACGAAGGATACTTATGACGC TCTCCACATGCAAGCCCTGCCACCTAGGT AA | 229 | MALPVTALLLPLALLL HAARPEIVMTQSPATL SVSPGERATLSCRASQ SVSSLLTWYQQKPGQA PRLLIFGASTRATGIP ARFSGSGSGTGFTLTI SSLQSEDFAVYYCQQY DTWPFTFGPGTKVDFK RGGGGSGGGGSGGGGS QVQLVESGGGVVQPGR SLRLSCAASGFTFSSY GMHWVRQAPGKGLEWV AVISYDGSDKYYVDSV KGRFTISRDNSKNRLY LQMNSLRAEDTAVYYC ARERYSGRDYWGQGTL VTVSSAAAIEVMYPPP YLDNEKSNGTIIHVKG KHLCPSPLFPGPSKPF WVLVVVGGVLACYSLL VTVAFIIFWVRSKRSR LLHSDYMNMTPRRPGP TRKHYQPYAPPRDFAA YRSRVKFSRSADAPAY QQGQNQLYNELNLGRR EEYDVLDKRRGRDPEM GGKPRRKNPQEGLYNE LQKDKMAEAYSEIGMK GERRRGKGHDGLYQGL STATKDTYDALHMQAL PPR | 230 |
| (CAR4.5) Clone 20C5.2 CHD CAR DNA LxH | GAGATCGTCATGACACAGAGTCCAGCTAC CCTGAGCGTGTCCCCTGGAGAGAGAGCCA CCCTGTCCTGTAGGGCTAGTCAGAGTGTG TCCAGCCTCCTCACCTGGTATCAACAGAA GCCTGGTCAAGCTCCCCGGCTGCTTATCT TCGGGGCCAGCACGCGAGCCACAGGCATC CCGGCCAGATTCTCTGGCTCTGGCAGTGG CACCGGGTTCACTCTCACGATCTCATCCC TGCAGTCAGAGGATTTCGCTGTGTATTAC TGTCAGCAGTACGATACATGGCCCTTCAC CTTCGGCCCGGGCACAAAAGTAGATTTCA AGCGCGGCGGCGGGGGTAGTGGGGGCGGG GGATCAGGAGGAGGGGGCTCCCAAGTACA GCTGGTTGAGAGCGGCGGCGGGGTGGTTC AGCCCGGGCGCAGCCTCAGGCTGAGTTGC GCAGCATCAGGATTCACATTCAGTTCTTA TGGAATGCATTGGGTCAGACAGGCTCCCG GGAAGGGCCTTGAATGGGTGGCAGTCATT | 231 | EIVMTQSPATLSVSPG ERATLSCRASQSVSSL LTWYQQKPGQAPRLLI FGASTRATGIPARFSG SGSGTGFTLTISSLQS EDFAVYYCQQYDTWPF TFGPGTKVDFKRGGGG SGGGGSGGGGSQVQLV ESGGGVVQPGRSLRLS CAASGFTFSSYGMHWV RQAPGKGLEWVAVISY DGSDKYYVDSVKGRFT ISRDNSKNRLYLQMNS LRAEDTAVYYCARERY SGRDYWGQGTLVTVSS AAAIEVMYPPPYLDNE KSNGTIIHVKGKHLCP SPLFPGPSKPFWVLVV | 232 |

TABLE 2-continued

Example CAR Sequences

| CAR Construct | Nucleotide Sequence | SEQ ID NO: | Amino Acid Sequence | SEQ ID NO: |
|---|---|---|---|---|
| | AGCTACGACGGAAGCGATAAGTACTATGT GGACTCAGTTAAAGGGAGATTTACTATCA GCCGCGACAATTCCAAAAACAGATTGTAT TTGCAGATGAACTCCCTCAGGGCGGAGGA CACTGCTGTATATTACTGCGCACGAGAGA GATACTCCGGCCGAGACTATTGGGGCCAA GGAACATTGGTAACTGTGAGCTCCGCCGC AGCTATTGAGGTCATGTACCCCCCACCTT ATCTCGATAATGAGAAGAGTAATGGGACT ATAATTCACGTAAAGGGCAAACACCTGTG CCCTTCCCGCTGTTTCCAGGTCCAAGTA AGCCGTTCTGGGTCCTGGTTGTGGTGGGA GGGGTGCTGGCCTGCTATTCTCTGTTGGT TACCGTGGCCTTTATCATTTTCTGGGTGA GATCCAAAAGAAGCCGCCTGCTCCATAGC GATTACATGAATATGACTCCACGCCGCCC TGGCCCCACAAGGAAACACTACCAGCCTT ACGCACCACCTAGAGATTTCGCTGCCTAT CGGAGCAGGGTGAAGTTTTCCAGATCTGC AGATGCACCAGCGTATCAGCAGGGCCAGA ACCAACTGTATAACGAGCTCAACCTGGGA CGCAGGGAAGAGTATGACGTTTTGGACAA GCGCAGAGGACGGGACCCTGAGATGGGTG GCAAACCAAGACGAAAAAACCCCCAGGAG GGTCTCTATAATGAGCTGCAGAAGGATAA GATGGCTGAAGCCTATTCTGAAATAGGCA TGAAAGGAGAGCGGAGAAGGGGAAAAGGG CACGCAGGTTTGTACCAGGGACTCAGCAC TGCTACGAAGGATACTTATGACGCTCTCC ACATGCAAGCCCTGCCACCTAGG | | VGGVLACYSLLVTVAF IIFWVRSKRSRLLHSD YMNMTPRRPGPTRKHY QPYAPPRDFAAYRSRV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | |
| (CAR4.6) Clone 20C5.2 CD8 CAR DNA LxH | ATGGCACTCCCCGTAACTGCTCTGCTGCT GCCGTTGGCATTGCTCCTGCACGCCGCAC GCCCGGAAATAGTGATGACTCAGTCCCCG GCCACCCTCAGCGTGTCCCCCGGGGAGCG AGCGACCCTGTCATGCAGGGCTTCCCAGA GTGTCAGCTCCCTGCTCACTTGGTATCAG CAAAAGCCGGGGCAGGCTCCCCGCCTCCT CATCTTCGGGGCATCAACTAGGGCCACCG GCATTCCTGCAAGATTTTCCGGGTCTGGC AGCGGCACCGGCTTCACCCTTACCATTAG CTCTCTGCAGTCTGAGGACTTCGCCGTTT ACTATTGTCAGCAGTATGATACTTGGCCC TTTACCTTCGGTCCCGGAACTAAGGTGGA CTTCAAGCGCGGGGGGGGTGGATCTGGAG GTGGTGGCTCCGGGGGCGGTGGAAGCCAG GTCCAGTTGGTTGAGAGCGGCGGCGGAGT GGTGCAGCCCGGGAGGTCCTTGCGGCTGA GCTGTGCAGCCTCCGGTTTTACTTTTTCT AGCTATGGAATGCATTGGGTAAGACAGGC TCCCGGAAAAGGCCTCGAGTGGGTGGCGG TCATTAGCTATGATGGATCTGATAAATAC TATGTGGACTCAGTTAAGGGGCGCTTCAC AATCTCAAGAGACAATAGCAAAAATAGAC TGTACCTGCAGATGAATAGTCTGCGCGCC GAGGACACTGCCGTGTACTACTGCGCCCG CGAGAGATACAGCGGACGGGATTACTGGG GCCAGGGTACCCTCGTAACGGTGTCCTCC GCTGCCGCCCTTAGCAACAGCATTATGTA CTTTTCTCATTTCGTGCCAGTCTTTCTCC CAGCAAAGCCCACCACTACCCCGGCCCC AGGCCGCCTACTCCTGCCCCCACTATCGC GTCTCAGCCTCTCTCCTTGCGGCCCGAGG CCTGCCGGCCAGCCGCAGGGGCGCCGTA CATACTCGGGGTTTGGATTTCGCTTGCGA CATATATATTTGGGCCCCCCTCGCCGGCA CATGTGGAGTGCTGCTCCTGAGTCTCGTT ATAACCCTCTATTGCAACCATAGAAACAG ATCCAAAAGAAGCCGCCTGCTCCATAGCG ATTACATGAATATGACTCCACGCCGCCCT GGCCCCACAAGGAAACACTACCAGCCTTA CGCACCACCTAGAGATTTCGCTGCCTATC GGAGCAGGGTGAAGTTTTCCAGATCTGCA GATGCACCAGCGTATCAGCAGGGCCAGAA | 233 | MALPVTALLLPLALLL HAARPEIVMTQSPATL SVSPGERATLSCRASQ SVSSLLTWYQQKPGQA PRLLIFGASTRATGIP ARFSGSGSGTGFTLTI SSLQSEDFAVYYCQQY DTWPFTFGPGTKVDFK RGGGGSGGGGSGGGGS QVQLVESGGGVVQPGR SLRLSCAASGFTFSSY GMHWVRQAPGKGLEWV AVISYDGSDKYYVDSV KGRFTISRDNSKNRLY LQMNSLRAEDTAVYYC ARERYSGRDYWGQGTL VTVSSAAALSNSIMYF SHFVPVFLPAKPTTTP APRPPTPAPTIASQPL SLRPEACRPAAGGAVH TRGLDFACDIYIWAPL AGTCGVLLLSLVITLY CNHRNRSKRSRLLHSD YMNMTPRRPGPTRKHY QPYAPPRDFAAYRSRV KFSRSADAPAYQQGQN QLYNELNLGRREEYDV LDKRRGRDPEMGGKPR RKNPQEGLYNELQKDK MAEAYSEIGMKGERRR GKGHDGLYQGLSTATK DTYDALHMQALPPR | 234 |

TABLE 2-continued

Example CAR Sequences

| CAR Construct | Nucleotide Sequence | SEQ ID NO: | Amino Acid Sequence | SEQ ID NO: |
|---|---|---|---|---|
| | CCAACTGTATAACGAGCTCAACCTGGGAC<br>GCAGGGAAGAGTATGACGTTTTGGACAAG<br>CGCAGAGGACGGGACCCTGAGATGGGTGG<br>CAAACCAAGACGAAAAAACCCCCAGGAGG<br>GTCTCTATAATGAGCTGCAGAAGGATAAG<br>ATGGCTGAAGCCTATTCTGAAATAGGCAT<br>GAAAGGAGAGCGGAGAAGGGGAAAAGGGC<br>ACGACGGTTTGTACCAGGGACTCAGCACT<br>GCTACGAAGGATACTTATGACGCTCTCCA<br>CATGCAAGCCCTGCCACCTAGGTAA | | | |
| (CAR4.6) Clone 20C5.2 CD8 CAR DNA LxH | GAAATAGTGATGACTCAGTCCCCGGCCAC<br>CCTCAGCGTGTCCCCGGGGAGCGAGCGA<br>CCCTGTCATGCAGGGCTTCCCAGAGTGTC<br>AGCTCCCTGCTCACTTGGTATCAGCAAAA<br>GCCGGGGCAGGCTCCCCGCCTCCTCATCT<br>TCGGGGCATCAACTAGGGCCACCGGCATT<br>CCTGCAAGATTTTCCGGGTCTGGCAGCGG<br>CACCGGCTTCACCCTTACCATTAGCTCTC<br>TGCAGTCTGAGGACTTCGCCGTTTACTAT<br>TGTCAGCAGTATGATACTTGGCCCTTTAC<br>CTTCGGTCCCGGAACTAAGGTGGACTTCA<br>AGCGCGGGGGGGTGGATCTGGAGGTGGT<br>GGCTCCGGGGCGGTGGAAGCCAGGTCCA<br>GTTGGTTGAGAGCGGCGGCGGAGTGGTGC<br>AGCCCGGGAGGTCCTTGCGGCTGAGCTGT<br>GCAGCCTCCGGTTTTACTTTTTCTAGCTA<br>TGGAATGCATTGGGTAAGACAGGCTCCCG<br>GAAAAGGCCTCGAGTGGGTGGCGGTCATT<br>AGCTATGATGGATCTGATAAATACTATGT<br>GGACTCAGTTAAGGGGCGCTTCACAATCT<br>CAAGAGACAATAGCAAAAATAGACTGTAC<br>CTGCAGATGAATAGTCTGCGCGCCGAGGA<br>CACTGCCGTGTACTACTGCGCCCGCGAGA<br>GATACAGCGGACGGGATTACTGGGGCCAG<br>GGTACCCTCGTAACGGTGTCCTCCGCTGC<br>CGCCCTTAGCAACAGCATTATGTACTTTT<br>CTCATTTCGTGCCAGTCTTTCTCCCAGCA<br>AAGCCCACCACTACCCGGCCCCCAGGCC<br>GCCTACTCCTGCCCCCACTATCGCGTCTC<br>AGCCTCTCTCCTTGCGGCCCGAGGCCTGC<br>CGGCCAGCCGCAGGGGCGCCGTACATAC<br>TCGGGGTTTGGATTTCGCTTGCGACATAT<br>ATATTTGGGCCCCCTCGCCGGCACATGT<br>GGAGTGCTGCTCCTGAGTCTCGTTATAAC<br>CCTCTATTGCAACCATAGAAACAGATCCA<br>AAAGAAGCCGCCTGCTCCATAGCGATTAC<br>ATGAATATGACTCCACGCCGCCCTGGCCC<br>CACAAGGAAACACTACCAGCCTTACGCAC<br>CACCTAGAGATTTCGCTGCCTATCGGAGC<br>AGGGTGAAGTTTTCCAGATCTGCAGATGC<br>ACCAGCGTATCAGCAGGGCCAGAACCAAC<br>TGTATAACGAGCTCAACCTGGGACGCAGG<br>GAAGAGTATGACGTTTTGGACAAGCGCAG<br>AGGACGGGACCCTGAGATGGGTGGCAAAC<br>CAAGACGAAAAAACCCCCAGGAGGGTCTC<br>TATAATGAGCTGCAGAAGGATAAGATGGC<br>TGAAGCCTATTCTGAAATAGGCATGAAAG<br>GAGAGCGGAGAAGGGGAAAAGGGCACGAC<br>GGTTTGTACCAGGGACTCAGCACTGCTAC<br>GAAGGATACTTATGACGCTCTCCACATGC<br>AAGCCCTGCCACCTAGG | 235 | EIVMTQSPATLSVSPG<br>ERATLSCRASQSVSSL<br>LTWYQQKPGQAPRLLI<br>FGASTRATGIPARFSG<br>SGSGTGFTLTISSLQS<br>EDFAVYYCQQYDTWPF<br>TFGPGTKVDFKRGGGG<br>SGGGGSGGGGSQVQLV<br>ESGGGVVQPGRSLRLS<br>CAASGFTFSSYGMHWV<br>RQAPGKGLEWVAVISY<br>DGSDKYYVDSVKGRFT<br>ISRDNSKNRLYLQMNS<br>LRAEDTAVYYCARERY<br>SGRDYWGQGTLVTVSS<br>AAALSNSIMYFSHFVP<br>VFLPAKPTTTPAPRPP<br>TPAPTIASQPLSLRPE<br>ACRPAAGGAVHTRGLD<br>FACDIYIWAPLAGTCG<br>VLLLSLVITLYCNHRN<br>RSKRSRLLHSDYMNMT<br>PRRPGPTRKHYQPYAP<br>PRDFAAYRSRVKFSRS<br>ADAPAYQQGQNQLYNE<br>LNLGRREEYDVLDKRR<br>GRDPEMGGKPRRKNPQ<br>EGLYNELQKDKMAEAY<br>SEIGMKGERRRGKGHD<br>GLYQGLSTATKDTYDA<br>LHMQALPPR | 236 |

In some embodiments, the polynucleotide of the present invention encodes a CAR, wherein the CAR comprises an amino acid sequence at least about 75%, at least about 85%, at least about 85%, at least about 90%, at least about 95%, at least about 96%, at least about 97%, at least about 98%, at least about 99%, or 100% identical to an amino acid sequence selected from the group consisting of SEQ ID NOs: 134, 136, 138, 140, 142, 144, 146, 148, 150, 152, 154, 156, 158, 160, 162, 164, 166, 168, 178, 180, 190, 192, 202, 204, 214, 216, 226, and 228. In certain embodiments, the CAR comprises an amino acid sequence selected from the group consisting of SEQ ID NOs: 134, 136, 138, 140, 142, 144, 146, 148, 150, 152, 154, 156, 158, 160, 162, 164, 166, 168, 178, 180, 190, 192, 202, 204, 214, 216, 226, and 228.

In some embodiments, the polynucleotide of the present invention comprises an nucleotide sequence at least about 50%, at least about 60%, at least about 65%, at least about 70%, at least about 75%, at least about 85%, at least about 85%, at least about 90%, at least about 95%, at least about 96%, at least about 97%, at least about 98%, at least about 99%, or 100% identical to an amino acid sequence selected from the group consisting of SEQ ID NOs: 133, 135, 137, 139, 141, 143, 145, 147, 149, 151, 153, 155, 157, 159, 161, 163, 165, 167, 177, 179, 189, 191, 201, 203, 213, 215, 225, and 227. In certain embodiments, the polynucleotide comprises a nucleotide sequence selected from the group consisting of SEQ ID NOs: 133, 135, 137, 139, 141, 143, 145, 147, 149, 151, 153, 155, 157, 159, 161, 163, 165, 167, 177, 179, 189, 191, 201, 203, 213, 215, 225, and 227.

II. Vectors, Cells, and Pharmaceutical Compositions

In certain aspects, provided herein are vectors comprising a polynucleotide of the present invention. In some embodiments, the present invention is directed to a vector or a set of vectors comprising a polynucleotide encoding a CAR or a TCR comprising the truncated hinge domain ("THD") domain, as described above.

Any vector known in the art can be suitable for the present invention. In some embodiments, the vector is a viral vector. In some embodiments, the vector is a retroviral vector, a DNA vector, a murine leukemia virus vector, an SFG vector, a plasmid, a RNA vector, an adenoviral vector, a baculoviral vector, an Epstein Barr viral vector, a papovaviral vector, a vaccinia viral vector, a herpes simplex viral vector, an adenovirus associated vector (AAV), a lentiviral vector, or any combination thereof.

In an embodiment, a vector that can be employed in the context of the present invention is pGAR and has the coding sequence:

(SEQ ID NO: 252)
CTGACGCGCCCTGTAGCGGCGCATTAAGCGCGGCGGGTGTGGTGGTTACG

CGCAGCGTGACCGCTACACTTGCCAGCGCCCTAGCGCCCGCTCCTTTCGC

TTTCTTCCCTTCCTTTCTCGCCACGTTCGCCGGCTTTCCCCGTCAAGCTC

TAAATCGGGGGCTCCCTTTAGGGTTCCGATTTAGTGCTTTACGGCACCTC

GACCCCAAAAAACTTGATTAGGGTGATGGTTCACGTAGTGGGCCATCGCC

CTGATAGACGGTTTTTCGCCCTTTGACGTTGGAGTCCACGTTCTTTAATA

GTGGACTCTTGTTCCAAACTGGAACAACACTCAACCCTATCTCGGTCTAT

TCTTTTGATTTATAAGGGATTTTGCCGATTTCGGCCTATTGGTTAAAAAA

TGAGCTGATTTAACAAAAATTTAACGCGAATTTTAACAAAATATTAACGC

TTACAATTTGCCATTCGCCATTCAGGCTGCGCAACTGTTGGGAAGGGCGA

TCGGTGCGGGCCTCTTCGCTATTACGCCAGCTGGCGAAAGGGGGATGTGC

TGCAAGGCGATTAAGTTGGGTAACGCCAGGGTTTTCCCAGTCACGACGTT

GTAAAACGACGGCCAGTGAATTGTAATACGACTCACTATAGGGCGACCCG

GGGATGGCGCGCCAGTAATCAATTACGGGGTCATTAGTTCATAGCCCATA

TATGGAGTTCCGCGTTACATAACTTACGGTAAATGGCCCGCCTGGCTGAC

CGCCCAACGACCCCCGCCCATTGACGTCAATAATGACGTATGTTCCCATA

GTAACGCCAATAGGGACTTTCCATTGACGTCAATGGGTGGAGTATTTACG

GTAAACTGCCCACTTGGCAGTACATCAAGTGTATCATATGCCAAGTACGC

CCCCTATTGACGTCAATGACGGTAAATGGCCCGCCTGGCATTATGCCCAG

TACATGACCTTATGGGACTTTCCTACTTGGCAGTACATCTACGTATTAGT

CATCGCTATTACCATGCTGATGCGGTTTTGGCAGTACATCAATGGGCGTG

GATAGCGGTTTGACTCACGGGGATTTCCAAGTCTCCACCCCATTGACGTC

AATGGGAGTTTGTTTTGGCACCAAAATCAACGGGACTTTCCAAAATGTCG

TAACAACTCCGCCCCATTGACGCAAATGGGCGGTAGGCGTGTACGGTGGG

AGGTCTATATAAGCAGAGCTGGTTTAGTGAACCGGGGTCTCTCTGGTTAG

ACCAGATCTGAGCCTGGGAGCTCTCTGGCTAACTAGGGAACCCACTGCTT

AAGCCTCAATAAAGCTTGCCTTGAGTGCTTCAAGTAGTGTGTGCCCGTCT

GTTGTGTGACTCTGGTAACTAGAGATCCCTCAGACCCTTTTAGTCAGTGT

GGAAAATCTCTAGCAGTGGCGCCCGAACAGGGACTTGAAAGCGAAAGGGA

AACCAGAGGAGCTCTCTCGACGCAGGACTCGGCTTGCTGAAGCGCGCACG

GCAAGAGGCGAGGGGCGGCGACTGGTGAGTACGCCAAAAATTTTGACTAG

CGGAGGCTAGAAGGAGAGAGATGGGTGCGAGAGCGTCAGTATTAAGCGGG

GGAGAATTAGATCGCGATGGGAAAAAATTCGGTTAAGGCCAGGGGGAAAG

AAAAAATATAAATTAAAACATATAGTATGGGCAAGCAGGGAGCTAGAACG

ATTCGCAGTTAATCCTGGCCTGTTAGAAACATCAGAAGGCTGTAGACAAA

TACTGGGACAGCTACAACCATCCCTTCAGACAGGATCAGAAGAACTTAGA

TCATTATATAATACAGTAGCAACCCTCTATTGTGTGCATCAAAGGATAGA

GATAAAAGACACCAAGGAAGCTTTAGACAAGATAGAGGAAGAGCAAACA

AAAGTAAGACCACCGCACAGCAAGCCGCCGCTGATCTTCAGACCTGGAGG

AGGAGATATGAGGGACAATTGGAGAAGTGAATTATATAAATATAAAGTAG

TAAAAATTGAACCATTAGGAGTAGCACCCACCAAGGCAAAGAGAAGAGTG

GTGCAGAGAGAAAAAAGAGCAGTGGGAATAGGAGCTTTGTTCCTTGGGTT

CTTGGGAGCAGCAGGAAGCACTATGGGCGCAGCGTCAATGACGCTGACGG

TACAGGCCAGACAATTATTGTCTGGTATAGTGCAGCAGCAGAACAATTTG

CTGAGGGCTATTGAGGCGCAACAGCATCTGTTGCAACTCACAGTCTGGGG

CATCAAGCAGCTCCAGGCAAGAATCCTGGCTGTGGAAAGATACCTAAAGG

ATCAACAGCTCCTGGGGATTTGGGGTTGCTCTGGAAAACTCATTTGCACC

ACTGCTGTGCCTTGGAATGCTAGTTGGAGTAATAAATCTCTGGAACAGAT

TTGGAATCACACGACCTGGATGGAGTGGGACAGAGAAATTAACAATTACA

CAAGCTTAATACACTCCTTAATTGAAGAATCGCAAAACCAGCAAGAAAAG

AATGAACAAGAATTATTGGAATTAGATAAATGGGCAAGTTTGTGGAATTG

GTTTAACATAACAAATTGGCTGTGGTATATAAAATTATTCATAATGATAG

TAGGAGGCTTGGTAGGTTTAAGAATAGTTTTTGCTGTACTTTCTATAGTG

AATAGAGTTAGGCAGGGATATTCACCATTATCGTTTCAGACCCACCTCCC

AACCCCGAGGGGACCCGACAGGCCCGAAGGAATAGAAGAAGAAGGTGGAG

AGAGAGACAGAGACAGATCCATTCGATTAGTGAACGGATCTCGACGGTAT

CGGTTAACTTTTAAAAGAAAAGGGGGGATTGGGGGGTACAGTGCAGGGGA

AAGAATAGTAGACATAATAGCAACAGACATACAAACTAAAGAATTACAAA

AACAAATTACAAAATTCAAAATTTTATCGCGATCGCGGAATGAAAGACCC

CACCTGTAGGTTTGGCAAGCTAGCTTAAGTAACGCCATTTTGCAAGGCAT

```
GGAAAATACATAACTGAGAATAGAGAAGTTCAGATCAAGGTTAGGAACAG
AGAGACAGCAGAATATGGGCCAAACAGGATATCTGTGGTAAGCAGTTCCT
GCCCCGGCTCAGGGCCAAGAACAGATGGTCCCCAGATGCGGTCCCGCCCT
CAGCAGTTTCTAGAGAACCATCAGATGTTTCCAGGGTGCCCCAAGGACCT
GAAAATGACCCTGTGCCTTATTTGAACTAACCAATCAGTTCGCTTCTCGC
TTCTGTTCGCGCGCTTCTGCTCCCCGAGCTCAATAAAAGAGCCCACAACC
CCTCACTCGGCGCGCCAGTCCTTCGAAGTAGATCTTTGTCGATCCTACCA
TCCACTCGACACACCCGCCAGCGGCCGCTGCCAAGCTTCCGAGCTCTCGA
ATTAATTCACGGTACCCACCATGGCCTAGGGAGACTAGTCGAATCGATAT
CAACCTCTGGATTACAAAATTTGTGAAAGATTGACTGGTATTCTTAACTA
TGTTGCTCCTTTTACGCTATGTGGATACGCTGCTTTAATGCCTTTGTATC
ATGCTATTGCTTCCCGTATGGCTTTCATTTTCTCCTCCTTGTATAAATCC
TGGTTGCTGTCTCTTTATGAGGAGTTGTGGCCCGTTGTCAGGCAACGTGG
CGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGC
TCGGCTGTTGGGCACTGACAATTCCGTGGTGTTGTCGGGGAAGCTGACGT
CCTTTTCATGGCTGCTCGCCTGTGTTGCCACCTGGATTCTGCGCGGGACG
TCCTTCTGCTACGTCCCTTCGGCCCTCAATCCAGCGGACCTTCCTTCCCG
CGGCCTGCTGCCGGCTCTGCGGCCTCTTCCGCGTCTTCGCCTTCGCCCTC
AGACGAGTCGGATCTCCCTTTGGGCCGCCTCCCCGCCTGGTTAATTAAAG
TACCTTTAAGACCAATGACTTACAAGGCAGCTGTAGATCTTAGCCACTTT
TTAAAAGAAAAGGGGGGACTGGAAGGGCGAATTCACTCCCAACGAAGACA
AGATCTGCTTTTTGCTTGTACTGGGTCTCTCTGGTTAGACCAGATCTGAG
CCTGGGAGCTCTCTGGCTAACTAGGGAACCCACTGCTTAAGCCTCAATAA
AGCTTGCCTTGAGTGCTTCAAGTAGTGTGTGCCCGTCTGTTGTGTGACTC
TGGTAACTAGAGATCCCTCAGACCCTTTTAGTCAGTGTGGAAAATCTCTA
GCAGGCATGCCAGACATGATAAGATACATTGATGAGTTTGGACAAACCAC
AACTAGAATGCAGTGAAAAAAATGCTTTATTTGTGAAATTTGTGATGCTA
TTGCTTTATTTGTAACCATTATAAGCTGCAATAAACAAGTTAACAACAAC
AATTGCATTCATTTTATGTTTCAGGTTCAGGGGGAGGTGTGGGAGGTTTT
TTGGCGCGCCATCGTCGAGGTTCCCTTTAGTGAGGGTTAATTGCGAGCTT
GGCGTAATCATGGTCATAGCTGTTTCCTGTGTGAAATTGTTATCCGCTCA
CAATTCCACACAACATACGAGCCGGAAGCATAAAGTGTAAAGCCTGGGGT
GCCTAATGAGTGAGCTAACTCACATTAATTGCGTTGCGCTCACTGCCCGC
TTTCCAGTCGGGAAACCTGTCGTGCCAGCTGCATTAATGAATCGGCCAAC
GCGCGGGGAGAGGCGGTTTGCGTATTGGGCGCTCTTCCGCTTCCTCGCTC
ACTGACTCGCTGCGCTCGGTCGTTCGGCTGCGGCGAGCGGTATCAGCTCA
CTCAAAGGCGGTAATACGGTTATCCACAGAATCAGGGGATAACGCAGGAA
AGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAA
AAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACC
CTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTC
GCTCCAAGCTGGGCTGTGTGCACGAACCCCCCGTTCAGCCCGACCGCTGC
GCCTTATCCGGTAACTATCGTCTTGAGTCCAACCCGGTAAGACACGACTT
ATCGCCACTGGCAGCAGCCACTGGTAACAGGATTAGCAGAGCGAGGTATG
TAGGCGGTGCTACAGAGTTCTTGAAGTGGTGGCCTAACTACGGCTACACT
AGAAGAACAGTATTTGGTATCTGCGCTCTGCTGAAGCCAGTTACCTTCGG
AAAAAGAGTTGGTAGCTCTTGATCCGGCAAACAAACCACCGCTGGTAGCG
GTGGTTTTTTGTTTGCAAGCAGCAGATTACGCGCAGAAAAAAAGGATCT
CAAGAAGATCCTTTGATCTTTTCTACGGGGTCTGACGCTCAGTGGAACGA
AAACTCACGTTAAGGGATTTTGGTCATGAGATTATCAAAAGGATCTTCA
CCTAGATCCTTTTAAATTAAAAATGAAGTTTTAAATCAATCTAAAGTATA
TATGAGTAAACTTGGTCTGACAGTTACCAATGCTTAATCAGTGAGGCACC
TATCTCAGCGATCTGTCTATTTCGTTCATCCATAGTTGCCTGACTCCCCG
TCGTGTAGATAACTACGATACGGGAGGGCTTACCATCTGGCCCCAGTGCT
GCAATGATACCGCGAGACCCACGCTCACCGGCTCCAGATTTATCAGCAAT
AAACCAGCCAGCCGGAAGGGCCGAGCGCAGAAGTGGTCCTGCAACTTTAT
CCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGT
GGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGC
TCCTTCGGTCCTCCGATCGTTGTCAGAAGTAAGTTGGCCGCAGTGTTATC
ACTCATGGTTATGGCAGCACTGCATAATTCTCTTACTGTCATGCCATCCG
TAAGATGCTTTTCTGTGACTGGTGAGTACTCAACCAAGTCATTCTGAGAA
TAGTGTATGCGGCGACCGAGTTGCTCTTGCCCGGCGTCAATACGGGATAA
TACCGCGCCACATAGCAGAACTTTAAAAGTGCTCATCATTGGAAAACGTT
CTTCGGGGCGAAAACTCTCAAGGATCTTACCGCTGTTGAGATCCAGTTCG
ATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGG
GAATAAGGGCGACACGGAAATGTTGAATACTCATACTCTTCCTTTTTCAA
TATTATTGAAGCATTTATCAGGGTTATTGTCTCATGAGCGGATACATATT
TGAATGTATTTAGAAAAATAAACAAATAGGGGTTCCGCGCACATTTCCCC
GAAAAGTGCCAC
```

Figure 20:
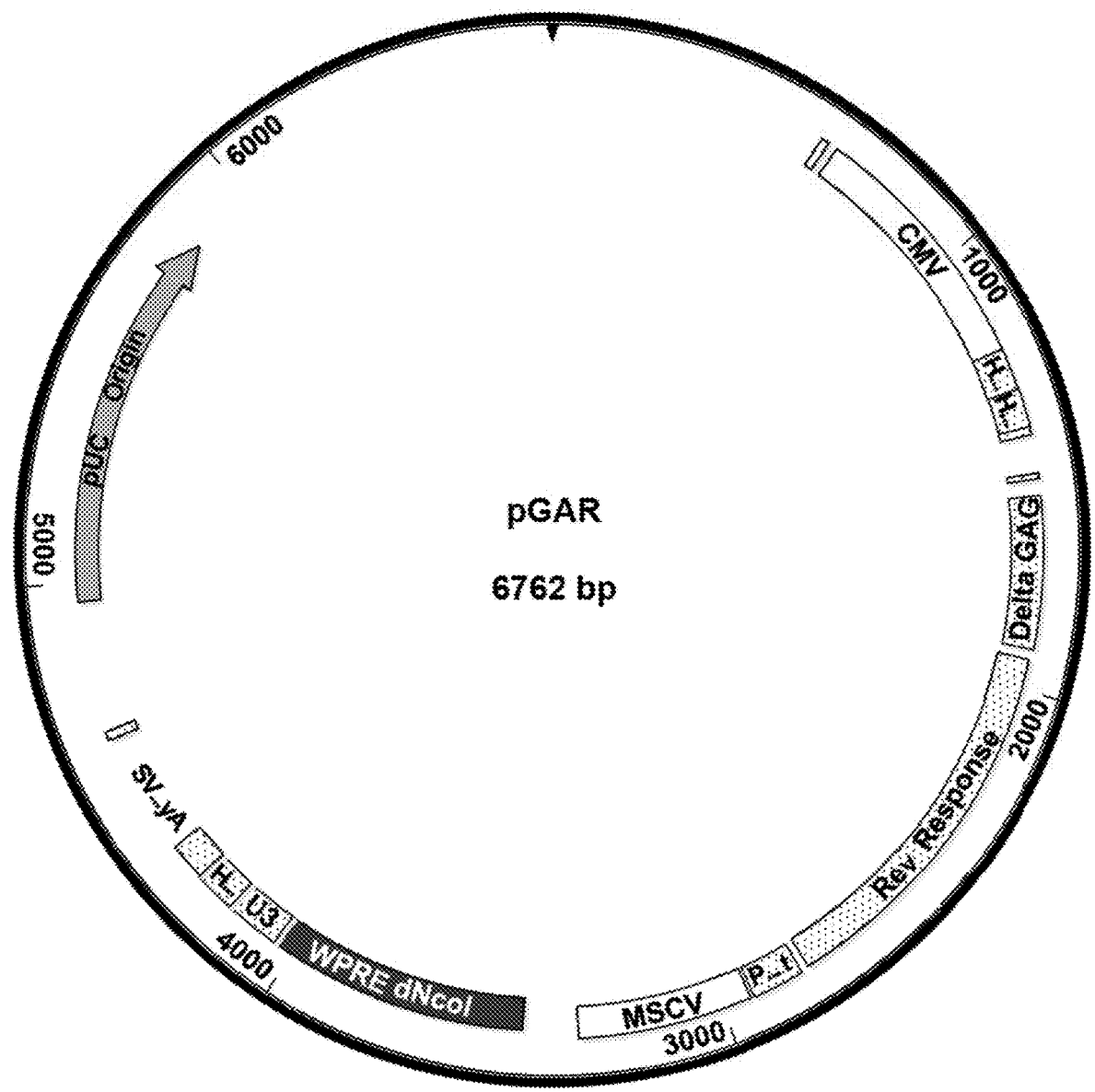
FIG. 20 is a schematic representation of the AGAR vector.

The pGAR vector map is set forth below: in FIG. 20.
Suitable additional exemplary vectors include e.g., pBABE-puro, pBABE-neo largeTcDNA, pBABE-hygro-hTERT, pMKO.1 GFP, MSCV-IRES-GFP, pMSCV PIG (Puro IRES GFP empty plasmid), pMSCV-loxp-dsRed-loxp-eGFP-Puro-WPRE, MSCV IRES Luciferase, pMIG, MDH1-PGK-GFP_2.0, TtRMPVIR, pMSCV-IRES-mCherry FP, pRetroX GFP T2A Cre, pRXTN, pLncEXP, and pLXIN-Luc.

In other aspects, provided herein are cells comprising a polynucleotide or a vector of the present invention. In some embodiments, the present invention is directed to cells, e.g., in vitro cells, comprising a polynucleotide encoding a CAR or a TCR comprising a TCD described herein. In other embodiments, the present invention is directed to cells, e.g., in vitro cells, comprising a polypeptide encoded by a CAR or a TCR comprising a TCD described herein.

Any cell may be used as a host cell for the polynucleotides, the vectors, or the polypeptides of the present invention. In some embodiments, the cell can be a prokaryotic cell, fungal cell, yeast cell, or higher eukaryotic cells such as a mammalian cell. Suitable prokaryotic cells include, without limitation, eubacteria, such as Gram-negative or Gram-positive organisms, for example, Enterobactehaceae such as *Escherichia*, e.g., *E. coli; Enterobacter; Erwinia; Klebsiella; Proteus; Salmonella*, e.g., *Salmonella typhimurium; Serratia*, e.g., *Serratia marcescans*, and *Shigella; Bacilli* such as *B. subtilis* and *B. licheniformis; Pseudomonas* such as *P. aeruginosa*; and *Streptomyces*. In some embodiments, the cell is a human cell. In some embodiments, the cell is an immune cell. In some embodiments, the immune cell is selected from the group consisting of a T cell, a B cell, a tumor infiltrating lymphocyte (TIL), a TCR expressing cell, a natural killer (NK) cell, a dendritic cell, a granulocyte, an innate lymphoid cell, a megakaryocyte, a monocyte, a macrophage, a platelet, a thymocyte, and a myeloid cell. In one embodiment, the immune cell is a T cell. In another embodiment, the immune cell is an NK cell. In certain embodiments, the T cell is a tumor-infiltrating lymphocyte (TIL), autologous T cell, engineered autologous T cell (eACT™), an allogeneic T cell, a heterologous T cell, or any combination thereof.

The cell of the present invention may be obtained through any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. In certain embodiments, the cells collected by apheresis are washed to remove the plasma fraction, and placed in an appropriate buffer or media for subsequent processing. In some embodiments, the cells are washed with PBS. As will be appreciated, a washing step can be used, such as by using a semiautomated flowthrough centrifuge, e.g., the Cobe™ 2991 cell processor, the Baxter CytoMate™, or the like. In some embodiments, the washed cells are resuspended in one or more biocompatible buffers, or other saline solution with or without buffer. In certain embodiments, the undesired components of the apheresis sample are removed. Additional methods of isolating T cells for a T cell therapy are disclosed in U.S. Patent Publication No. 2013/0287748, which is herein incorporated by references in its entirety.

In certain embodiments, T cells are isolated from PBMCs by lysing the red blood cells and depleting the monocytes, e.g., by using centrifugation through a PERCOLL™ gradient. In some embodiments, a specific subpopulation of T cells, such as $CD4^+$, $CD8^+$, $CD28^+$, $CD45RA^+$, and $CD45RO^+$ T cells is further isolated by positive or negative selection techniques known in the art. For example, enrichment of a T cell population by negative selection can be accomplished with a combination of antibodies directed to surface markers unique to the negatively selected cells. In some embodiments, cell sorting and/or selection via negative magnetic immunoadherence or flow cytometry that uses a cocktail of monoclonal antibodies directed to cell surface markers present on the cells negatively selected can be used. For example, to enrich for $CD4^+$ cells by negative selection, a monoclonal antibody cocktail typically includes antibodies to CD8, CD11b, CD14, CD16, CD20, and HLA-DR. In certain embodiments, flow cytometry and cell sorting are used to isolate cell populations of interest for use in the present invention.

In some embodiments, PBMCs are used directly for genetic modification with the immune cells (such as CARs or TCRs) using methods as described herein. In certain embodiments, after isolating the PBMCs, T lymphocytes are further isolated, and both cytotoxic and helper T lymphocytes are sorted into naive, memory, and effector T cell subpopulations either before or after genetic modification and/or expansion.

In some embodiments, $CD8^+$ cells are further sorted into naive, central memory, and effector cells by identifying cell surface antigens that are associated with each of these types of $CD8^+$ cells. In some embodiments, the expression of phenotypic markers of central memory T cells includes CCR7, CD3, CD28, CD45RO, CD62L, and CD127 and are negative for granzyme B. In some embodiments, central memory T cells are $CD8^+$, $CD45RO^+$, and $CD62L^+$ T cells. In some embodiments, effector T cells are negative for CCR7, CD28, CD62L, and CD127 and positive for granzyme B and perforin. In certain embodiments, $CD4^+$ T cells are further sorted into subpopulations. For example, $CD4^+$ T helper cells can be sorted into naive, central memory, and effector cells by identifying cell populations that have cell surface antigens.

In some embodiments, the immune cells, e.g., T cells, are genetically modified following isolation using known methods, or the immune cells are activated and expanded (or differentiated in the case of progenitors) in vitro prior to being genetically modified. In another embodiment, the immune cells, e.g., T cells, are genetically modified with the chimeric antigen receptors described herein (e.g., transduced with a viral vector comprising one or more nucleotide sequences encoding a CAR) and then are activated and/or expanded in vitro. Methods for activating and expanding T cells are known in the art and are described, e.g., in U.S. Pat. Nos. 6,905,874; 6,867,041; and 6,797,514; and PCT Publication No. WO 2012/079000, the contents of which are hereby incorporated by reference in their entirety. Generally, such methods include contacting PBMC or isolated T cells with a stimulatory agent and costimulatory agent, such as anti-CD3 and anti-CD28 antibodies, generally attached to a bead or other surface, in a culture medium with appropriate cytokines, such as IL-2. Anti-CD3 and anti-CD28 antibodies attached to the same bead serve as a "surrogate" antigen presenting cell (APC). One example is The Dynabeads® system, a CD3/CD28 activator/stimulator system for physiological activation of human T cells. In other embodiments, the T cells are activated and stimulated to proliferate with feeder cells and appropriate antibodies and cytokines using methods such as those described in U.S. Pat. Nos. 6,040,177 and 5,827,642 and PCT Publication No. WO 2012/129514, the contents of which are hereby incorporated by reference in their entirety.

In certain embodiments, the T cells are obtained from a donor subject. In some embodiments, the donor subject is human patient afflicted with a cancer or a tumor. In other embodiments, the donor subject is a human patient not afflicted with a cancer or a tumor.

Other aspects of the present invention are directed to compositions comprising a polynucleotide described herein, a vector described herein, a polypeptide described herein, or an in vitro cell described herein. In some embodiments, the composition comprises a pharmaceutically acceptable carrier, diluent, solubilizer, emulsifier, preservative and/or adjuvant. In some embodiments, the composition comprises an excipient. In one embodiment, the composition comprises a polynucleotide encoding a CAR or a TCR comprising a truncated hinge domain ("THD") described herein. In another embodiment, the composition comprises a CAR or a TCR comprising a TCD encoded by a polynucleotide of the present invention. In another embodiment, the composition comprises a T cell comprising a CAR or a TCR comprising a TCD described herein.

In other embodiments, the composition is selected for parenteral delivery, for inhalation, or for delivery through the digestive tract, such as orally. The preparation of such pharmaceutically acceptable compositions is within the ability of one skilled in the art. In certain embodiments, buffers are used to maintain the composition at physiological pH or at a slightly lower pH, typically within a pH range of from about 5 to about 8. In certain embodiments, when parenteral administration is contemplated, the composition is in the form of a pyrogen-free, parenterally acceptable aqueous solution comprising a composition described herein, with or without additional therapeutic agents, in a pharmaceutically acceptable vehicle. In certain embodiments, the vehicle for parenteral injection is sterile distilled water in which composition described herein, with or without at least one additional therapeutic agent, is formulated as a sterile, isotonic solution, properly preserved. In certain embodiments, the preparation involves the formulation of the desired molecule with polymeric compounds (such as polylactic acid or polyglycolic acid), beads or liposomes, that provide for the controlled or sustained release of the product, which are then be delivered via a depot injection. In certain embodiments, implantable drug delivery devices are used to introduce the desired molecule.

III. Methods of the Invention

Another aspect of the invention is directed to a method of making a cell expressing a CAR or a TCR comprising transducing a cell with a polynucleotide disclosed herein under suitable conditions. In some embodiments, the method comprises transducing a cell with a polynucleotide encoding a CAR or a TCR, as disclosed herein. In some embodiments, the method comprises transducing a cell with a vector comprising the polynucleotide encoding a CAR or a TCR.

Another aspect of the present invention is directed to a method of inducing an immunity against a tumor comprising administering to a subject an effective amount of a cell comprising a polynucleotide described herein, a vector described herein, or a CAR or a TCR described herein. In one embodiment, the method comprises administering to a subject an effective amount of a cell comprising a polynucleotide encoding a CAR or a TCR disclosed herein. In another embodiment, the method comprises administering to a subject an effective amount of a cell comprising a vector comprising a polynucleotide encoding a CAR or a TCR disclosed herein. In another embodiment, the method comprises administering to a subject an effective amount of a cell comprising a CAR or a TCR encoded by a polynucleotide disclosed herein.

Another aspect of the present invention is directed to a method of inducing an immune response in a subject comprising administering an effective amount of the engineered immune cells of the present application. In some embodiments, the immune response is a T cell-mediated immune response. In some embodiments, the T cell-mediated immune response is directed against one or more target cells. In some embodiments, the engineered immune cell comprises a CAR or a TCR, wherein the CAR or the TCR comprises a THD described in the present disclosure. In some embodiments, the target cell is a tumor cell.

Another aspect of the present invention is directed to a method for treating or preventing a malignancy, said method comprising administering to a subject in need thereof an effective amount of at least one immune cell, wherein the immune cell comprises at least one CAR or TCR, and wherein the CAR or the TCR comprises a THD described herein.

Another aspect of the present invention is directed to a method of treating a cancer in a subject in need thereof comprising administering to the subject a polynucleotide, a vector, a CAR or a TCR, a cell, or a composition disclosed herein. In one embodiment, the method comprises administering a polynucleotide encoding a CAR or a TCR. In another embodiment, the method comprises administering a vector comprising a polynucleotide encoding a CAR or a TCR. In another embodiment, the method comprises administering a CAR or a TCR encoded by a polynucleotide disclosed herein. In another embodiment, the method comprises administering a cell comprising the polynucleotide, or a vector comprising the polynucleotide, encoding a CAR or a TCR.

In some embodiments, the methods of treating a cancer in a subject in need thereof comprise a T cell therapy. In one embodiment, the T cell therapy of the present invention is engineered Autologous Cell Therapy (eACT™). According to this embodiment, the method can include collecting blood cells from the patient. The isolated blood cells (e.g., T cells) can then be engineered to express a CAR or a TCR of the present invention. In a particular embodiment, the CAR T cells or the TCR T cells are administered to the patient. In some embodiments, the CAR T cells or the TCR T cells treat a tumor or a cancer in the patient. In one embodiment the CAR T cells or the TCR T cells reduce the size of a tumor or a cancer.

In some embodiments, the donor T cells for use in the T cell therapy are obtained from the patient (e.g., for an autologous T cell therapy). In other embodiments, the donor T cells for use in the T cell therapy are obtained from a subject that is not the patient.

The T cells can be administered at a therapeutically effective amount. For example, a therapeutically effective amount of the T cells can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells is about $10^4$ cells, about $10^5$ cells, about $10^6$ cells, about $10^7$ cells, or about $10^8$ cells. In one particular embodiment, the therapeutically effective amount of the CAR T cells or the TCR T cells is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

IV. Cancer Treatment

The methods of the invention can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In some embodiments, the cancer is a hematologic cancer. In some embodiments, the cancer is of the white blood cells. In other embodiments, the cancer is of the plasma cells. In some embodiments, the cancer is leukemia, lymphoma, or myeloma. In certain embodiments, the cancer is acute lymphoblastic leukemia (ALL) (including non T cell ALL), acute lymphoid leukemia (ALL), and hemophagocytic lymphohistocytosis (HLH)), B cell prolymphocytic leukemia, B-cell acute lymphoid leukemia ("BALL"), blastic plasmacytoid dendritic cell neoplasm, Burkitt's lymphoma, chronic lymphocytic leukemia (CLL), chronic myelogenous leukemia (CML), chronic myeloid leukemia (CIVIL), chronic or acute granulomatous disease, chronic or acute leukemia, diffuse large B cell lymphoma, diffuse large B cell lymphoma (DLBCL), follicular lymphoma, follicular lymphoma (FL), hairy cell leukemia, hemophagocytic syndrome (Macrophage Activating Syndrome (MAS), Hodgkin's Disease, large cell granuloma, leukocyte adhesion deficiency, malignant lymphoproliferative conditions, MALT lymphoma, mantle cell lymphoma, Marginal zone lymphoma, monoclonal gammapathy of undetermined significance (MGUS), multiple myeloma, myelodysplasia and myelodysplastic syndrome (MDS), myeloid diseases including but not limited to acute myeloid leukemia (AML), non-Hodgkin's lymphoma (NHL), plasma cell proliferative disorders (e.g., asymptomatic myeloma (smoldering multiple myeloma or indolent myeloma), plasmablastic lymphoma, plasmacytoid dendritic cell neoplasm, plasmacytomas (e.g., plasma cell dyscrasia; solitary myeloma; solitary plasmacytoma; extramedullary plasmacytoma; and multiple plasmacytoma), POEMS syndrome (Crow-Fukase syndrome; Takatsuki disease; PEP syndrome), primary mediastinal large B cell lymphoma (PMBC), small cell- or a large cell-follicular lymphoma, splenic marginal zone lymphoma (SMZL), systemic amyloid light chain amyloidosis, T-cell acute lymphoid leukemia ("TALL"), T-cell lymphoma, transformed follicular lymphoma, Waldenstrom macroglobulinemia, or a combination thereof.

In one embodiment, the cancer is a myeloma. In one particular embodiment, the cancer is multiple myeloma. In another embodiment, the cancer is a leukemia. In one embodiment, the cancer is acute myeloid leukemia.

In some embodiments, the methods further comprise administering a chemotherapeutic. In certain embodiments, the chemotherapeutic selected is a lymphodepleting (preconditioning) chemotherapeutic. Beneficial preconditioning treatment regimens, along with correlative beneficial biomarkers are described in U.S. Provisional Patent Applications 62/262,143 and 62/167,750 which are hereby incorporated by reference in their entirety herein. These describe, e.g., methods of conditioning a patient in need of a T cell therapy comprising administering to the patient specified beneficial doses of cyclophosphamide (between 200 mg/m$^2$/day and 2000 mg/m$^2$/day) and specified doses of fludarabine (between 20 mg/m$^2$/day and 900 mg/m$^2$/day). One such dose regimen involves treating a patient comprising administering daily to the patient about 500 mg/m$^2$/day of cyclophosphamide and about 60 mg/m$^2$/day of fludarabine for three days prior to administration of a therapeutically effective amount of engineered T cells to the patient.

In other embodiments, the antigen binding molecule, transduced (or otherwise engineered) cells (such as CARs or TCRs), and the chemotherapeutic agent are administered each in an amount effective to treat the disease or condition in the subject.

In certain embodiments, compositions comprising CAR- and/or TCR-expressing immune effector cells disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; antiadrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL™, Bristol-Myers Squibb) and doxetaxel (TAXOTERE®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); ONTAK™ (denileukin diftitox); esperamicins; capecitabine; and pharmaceutically acceptable salts, acids or derivatives of any of the above. In some embodiments, compositions comprising CAR- and/or TCR-expressing immune effector cells disclosed herein may be administered in conjunction with an anti-hormonal agent that acts to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®), Doxorubicin (hydroxydoxorubicin), Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In some embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 inhibitors such as nivolumab (OPDIVO®), pembrolizumab (KEYTRUDA®), pembrolizumab, pidilizumab (CureTech), and atezolizumab (Roche).

Additional therapeutic agents suitable for use in combination with the invention include, but are not limited to, ibrutinib (IMBRUVICA®), ofatumumab (ARZERRA®), rituximab (RITUXAN®), bevacizumab (AVASTIN®), trastuzumab (HERCEPTIN®), trastuzumab emtansine (KADCYLA®), imatinib (GLEEVEC®), cetuximab (ERBITUX®), panitumumab (VECTIBIX®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising CAR- and/or TCR-containing immune are administered with an anti-inflammatory agent. Anti-inflammatory agents or drugs can include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular), and minocycline.

In certain embodiments, the compositions described herein are administered in conjunction with a cytokine. "Cytokine" as used herein is meant to refer to proteins released by one cell population that act on another cell as intercellular mediators. Examples of cytokines are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention. To the extent that any of the definitions or terms provided in the references incorporated by reference differ from the terms and discussion provided herein, the present terms and definitions control.

The present invention is further illustrated by the following examples which should not be construed as further limiting. The contents of all references cited throughout this application are expressly incorporated herein by reference.

EXAMPLES

Example 1

Figure 3:
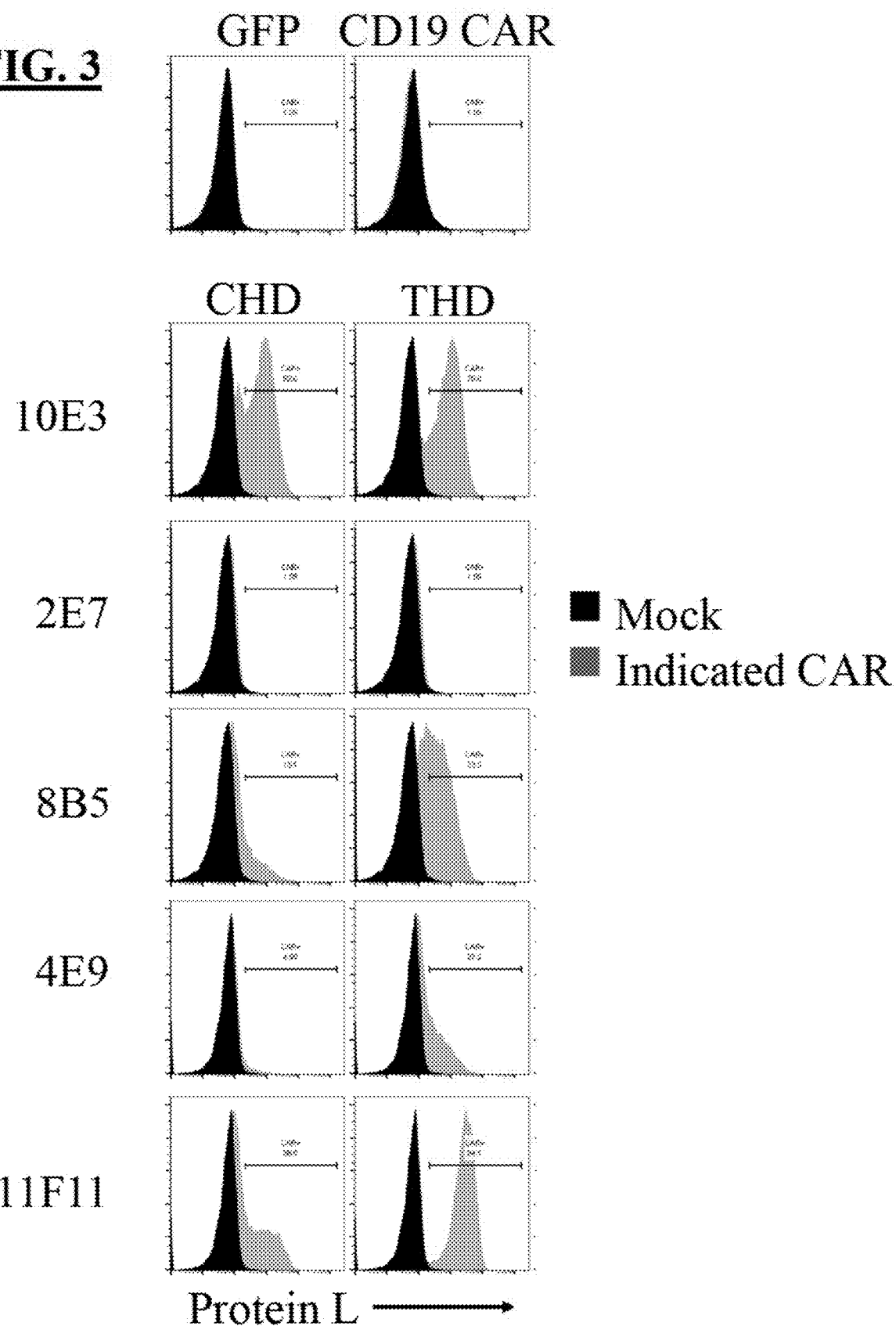
FIG. 3 depicts CAR expression in primary human T cells electroporated with mRNA encoding for various CARs. Data obtained from CAR having a complete hinge domain ("CHD") is shown and data obtained from CAR having a truncated hinge domain ("THD") is shown.
Figure 4A:
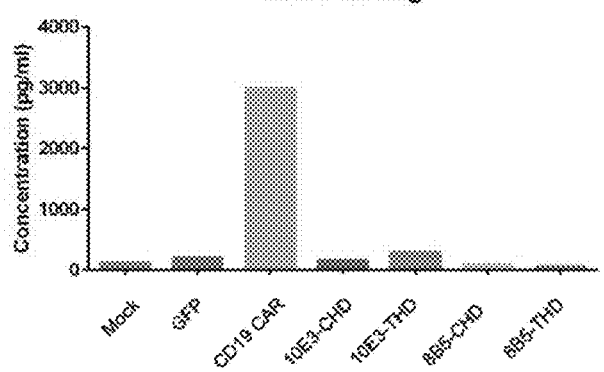
FIGS. 4A-4X show IFNγ, IL-2, and TNFα production by electroporated anti-FLT3 CART cells following 16 hours of co-culture with the indicated target cell lines.
Figure 4B:
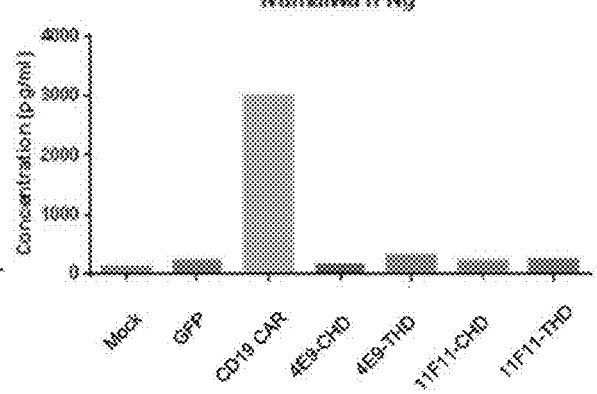
Figure 4C:
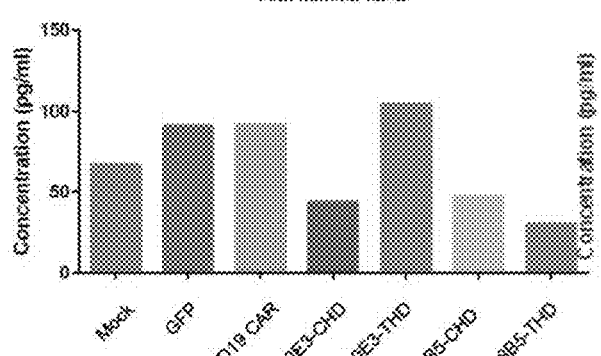
FIGS. 4C-4D, 4I-4J, 4O-4P, and 4U-4V show IL-2 production following co-culture with Namalwa, EoL-1, HL60, and MV4;11 target cells, respectively.
Figure 4D:
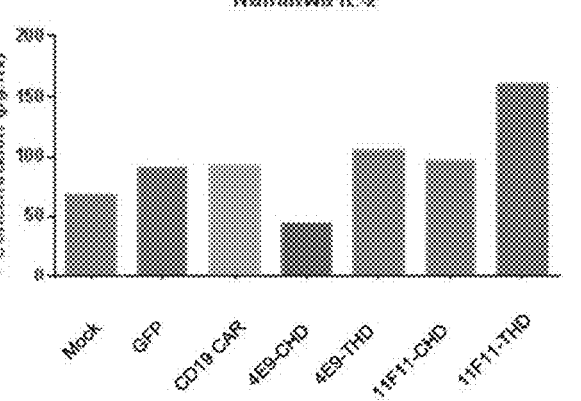
Figure 4E:
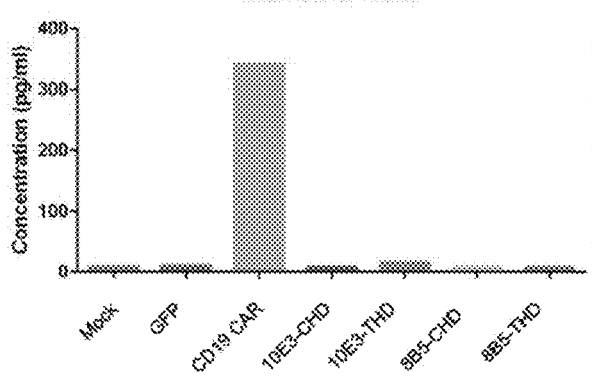
Figure 4F:
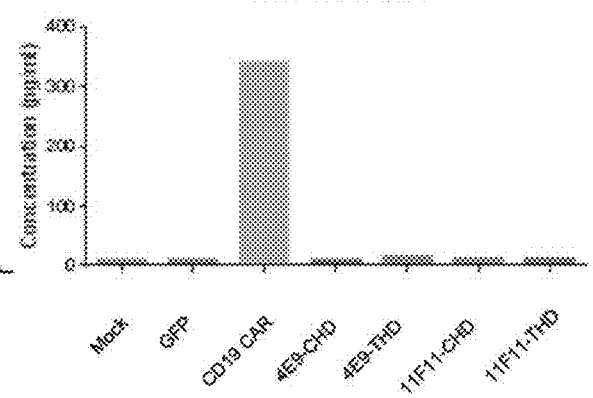
Figure 4G:
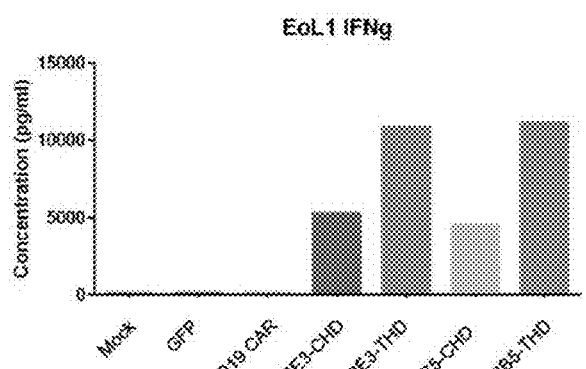
Figure 4H:
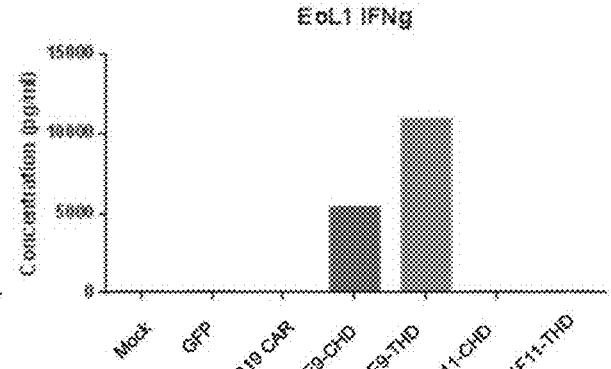
Figure 4I:
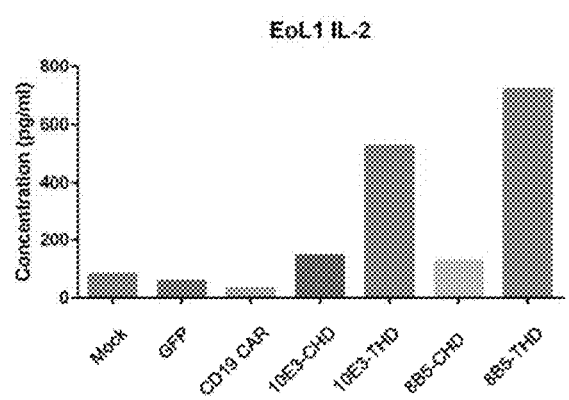
Figure 4J:
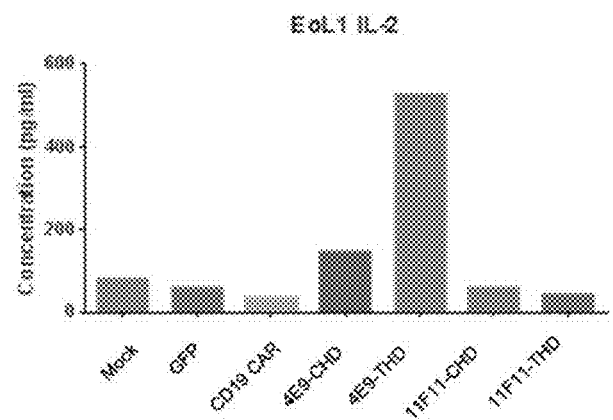
Figure 4K:
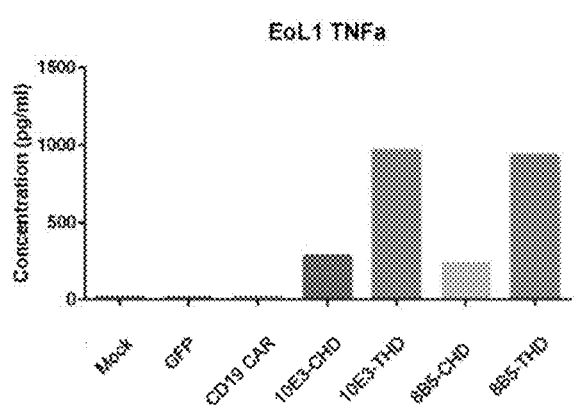
Figure 4L:
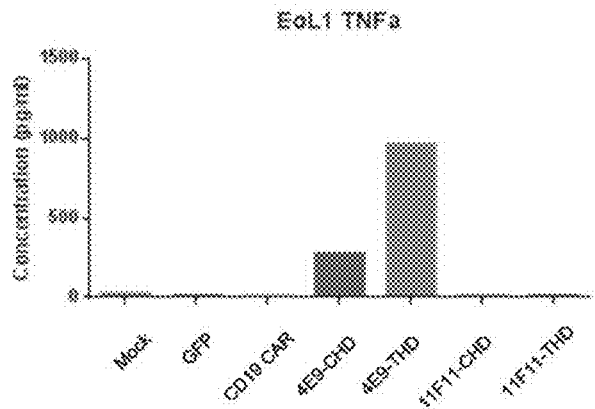
Figure 4M:
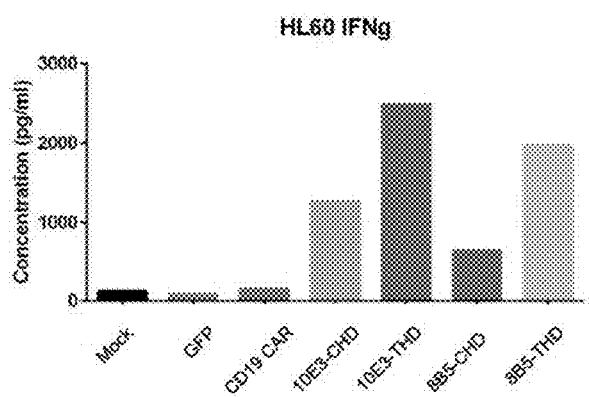
Figure 4N:
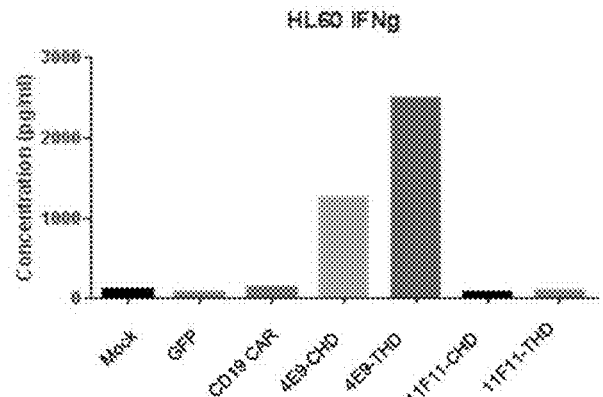
Figure 4O:
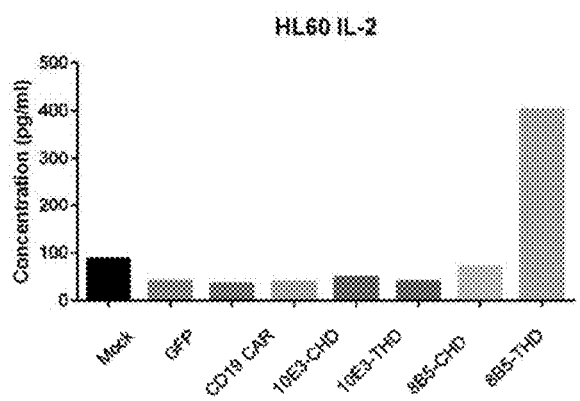
Figure 4P:
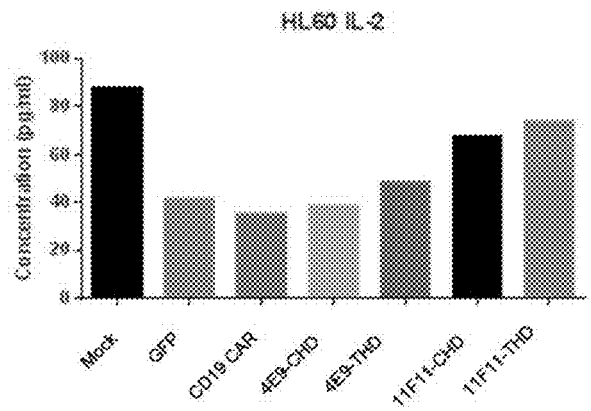
Figure 4Q:
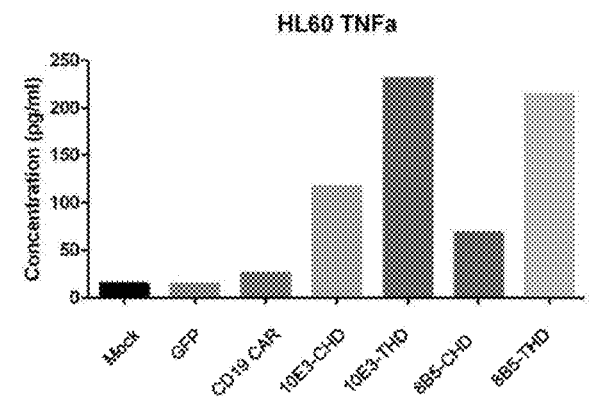
Figure 4R:
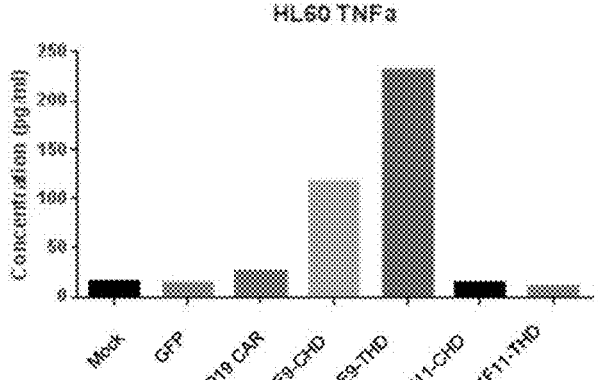
Figure 4S:
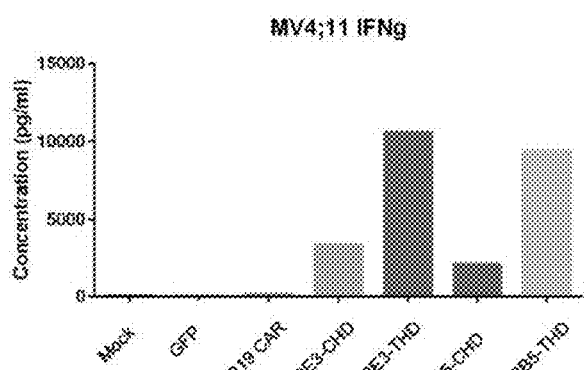
Figure 4T:
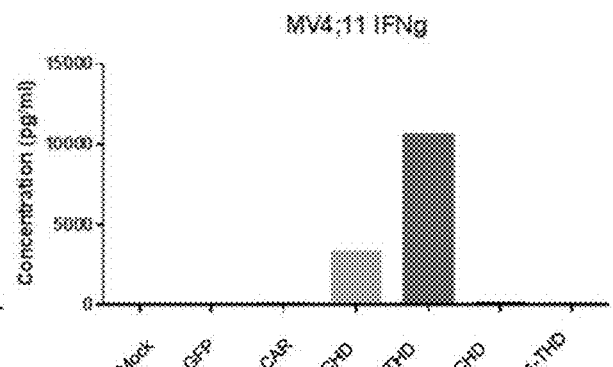
Figure 4U:
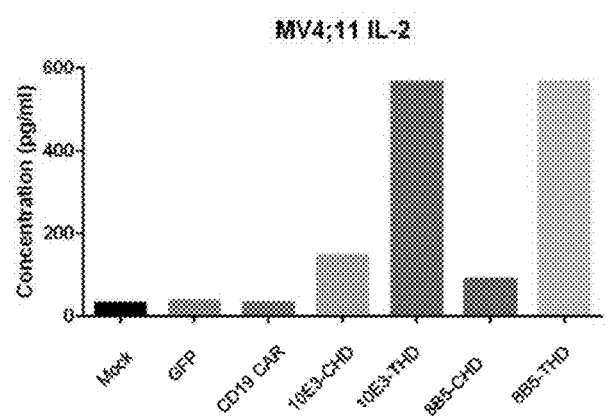
Figure 4V:
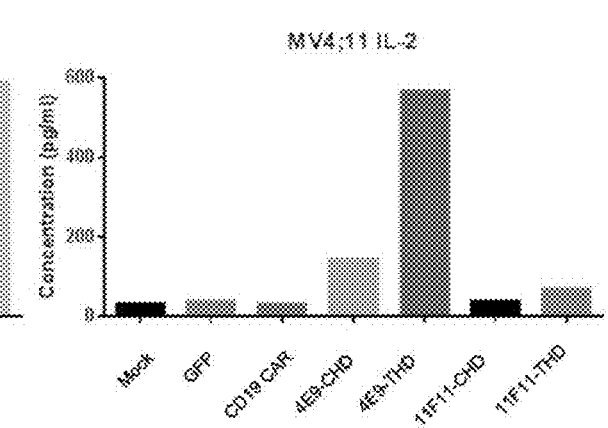
Figure 4W:
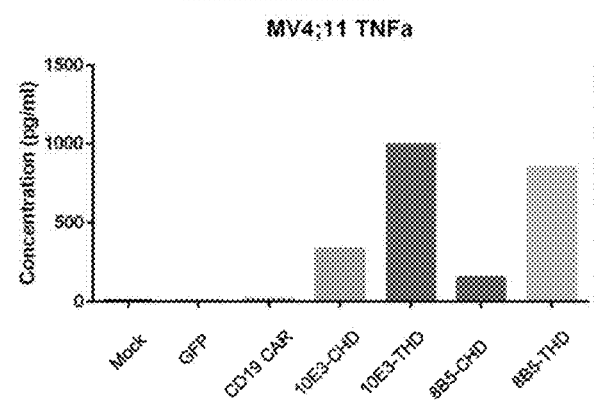
Figure 4X:
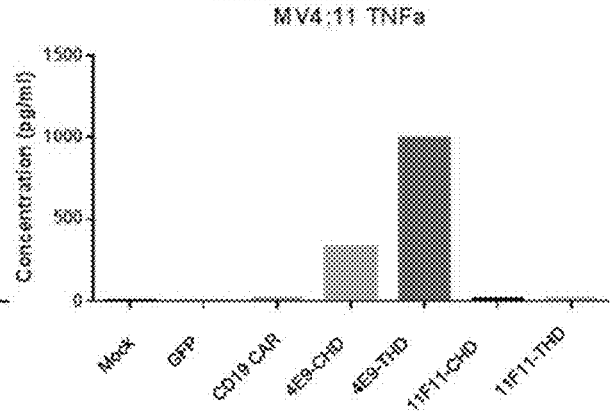

Plasmids encoding a T7 promoter, CAR construct and a beta globin stabilizing sequence were linearized by overnight digestion of 10 µg DNA with EcoRI and BamHI (NEB). DNA was then digested for 2 hours at 50° C. with proteinase K (Thermo Fisher, 600 U/ml) purified with phenol/chloroform and precipitated by adding sodium acetate and two volumes of ethanol. Pellets were then dried, resuspended in RNAse/DNAse-free water and quantified using NanoDrop. One µg of the linear DNA was then used for in vitro transcription using the mMESSAGE mMACHINE T7 Ultra (Thermo Fisher) following the manufacturer's instructions. RNA was further purified using the MEGAClear Kit (Thermo Fisher) following the manufacturer's instructions and quantified using NanoDrop. mRNA integrity was assessed using mobility on an agarose gel. PBMCs were isolated from healthy donor leukopaks (Hemacare) using ficoll-paque density centrifugation per manufacturer's instructions. PBMCs were stimulated using OKT3 (50 ng/ml, Miltenyi Biotec) in R10 medium+IL-2 (300 IU/ml, Proleukin®, Prometheus® Therapeutics and Diagnostics). Seven days post-stimulation, T cells were washed twice in Opti-MEM medium (Thermo Fisher Scientific) and resuspended at a final concentration of $2.5 \times 10^7$ cells/ml in Opti-MEM medium. Ten µg of mRNA was used per electroporation. Electroporation of cells was performed using a Gemini X2 system (Harvard Apparatus BTX) to deliver a single 400 V pulse for 0.5 ms in 2 mm cuvettes (Harvard Apparatus BTX). Cells were immediately transferred to R10+IL-2 medium and allowed to recover for 6 hours. To examine CAR expression, T cells were stained with FLT-=3-HIS (Sino Biological Inc.) or biotinylated Protein L (Thermo Scientific) in stain buffer (BD Pharmingen) for 30 minutes at 4° C. Cells were then washed and stained with anti-HIS-PE (Miltenyi Biotec) or PE Streptavidin (BD Pharmingen) in stain buffer for 30 minutes at 4° C. Cells were then washed and resuspended in stain buffer with propidium iodide (BD Pharmingen) prior to data acquisition. Expression of FLT3 CARs in electroporated T cells is shown in FIG. 3.

T cells were electroporated with plasmids encoding an anti-FLT3 CAR comprising a 10E3, 2E7, 8B5, 4E9, or 11F11 anti-FLT3 binding molecule and a hinge region selected from the full length hinge domain (a complete hinge domain or "CHD") or a truncated hinge domain ("THD"). The electroporated anti-FLT3 CAR T cells were then co-cultured with Namalwa (FLT3 negative), EoL1 (FLT3 positive), HL60 (FLT3 positive), or MV4;11 (FLT3 positive) target cells at a 1:1 E:T ratio in R10 medium. Sixteen hours post-co-culture, supernatants from Namalwa (FIGS. 4A-4F), EoL1 (FIGS. 4G-4L), HL60 (FIGS. 4M-4R, and MV4;11 (4S-4X) were analyzed by Luminex (EMD Millipore) for production of IFNγ (FIGS. 4A, 4B, 4G, 4H, 4M, 4N, 4S, and 4T), IL-2 (FIGS. 4C, 4D, 4I, 4J, 4O, 4P, 4U, and 4V), and TNFα (FIGS. 4E, 4F, 4K, 4L, 4Q, 4R, 4W, and 4X).

Figure 5E:
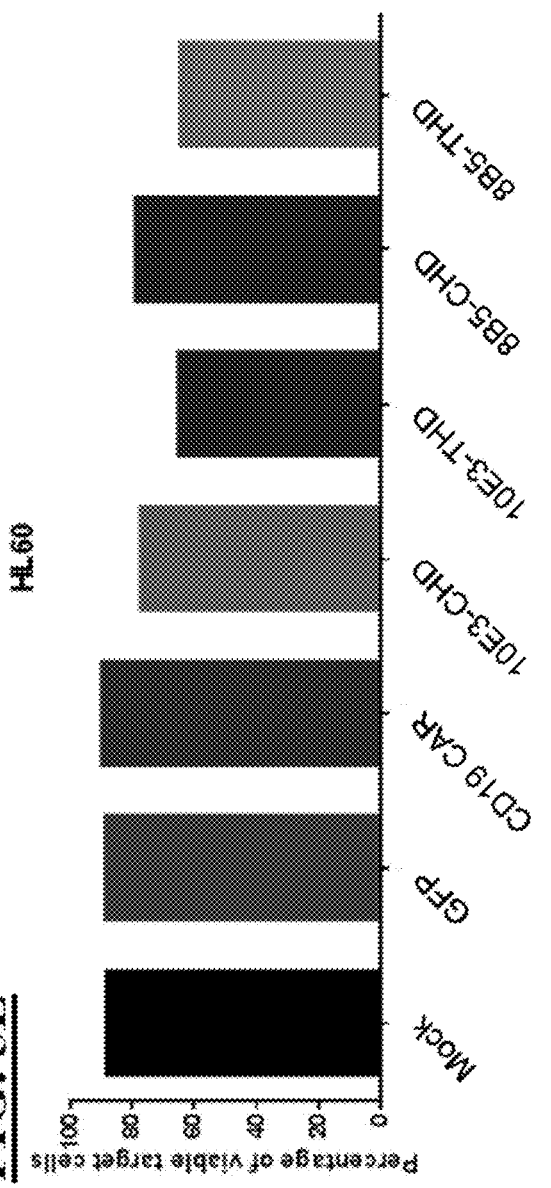
Figure 5F:
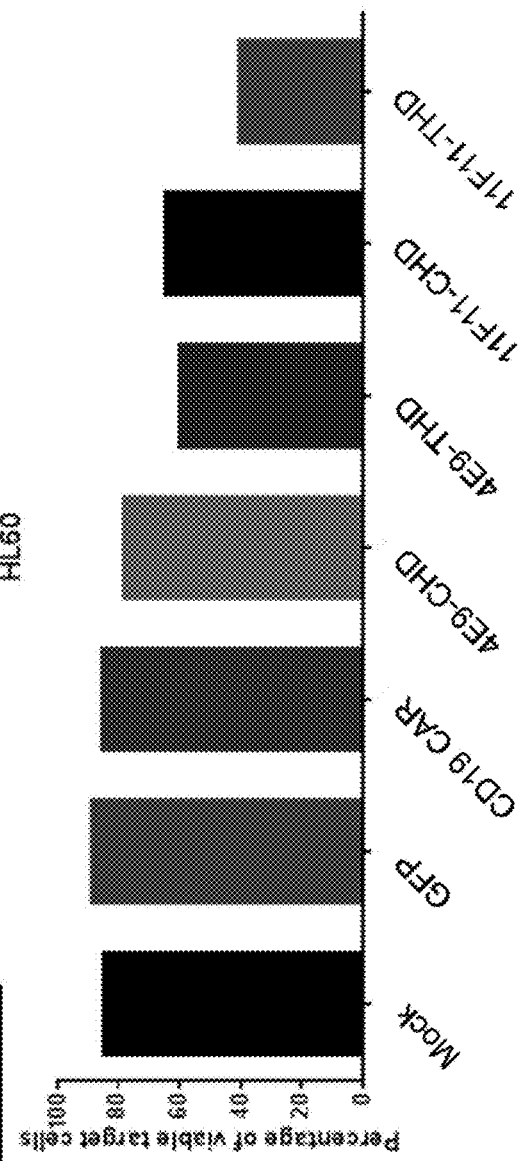
Figure 5G:
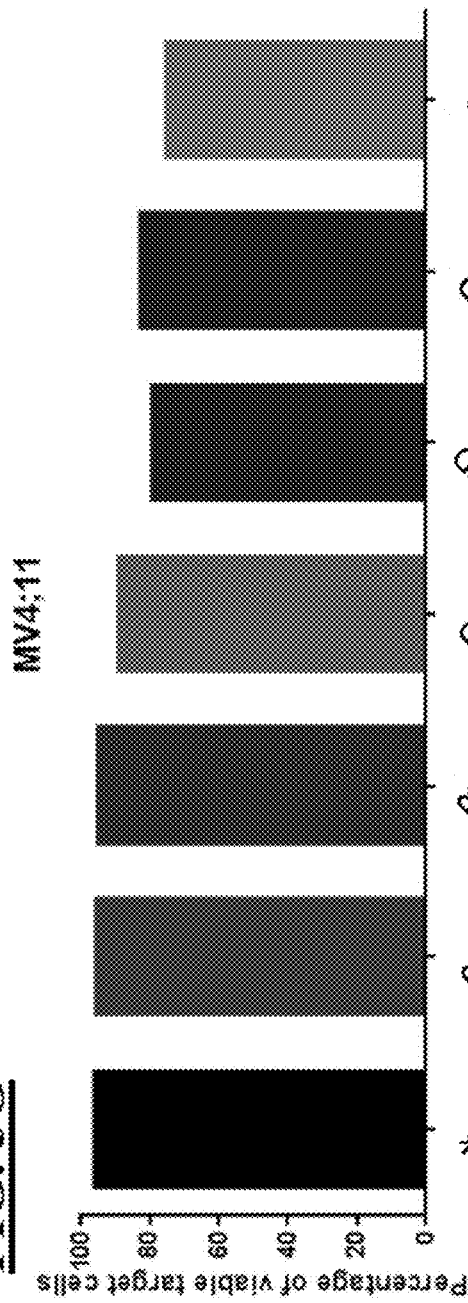
Figure 5H:
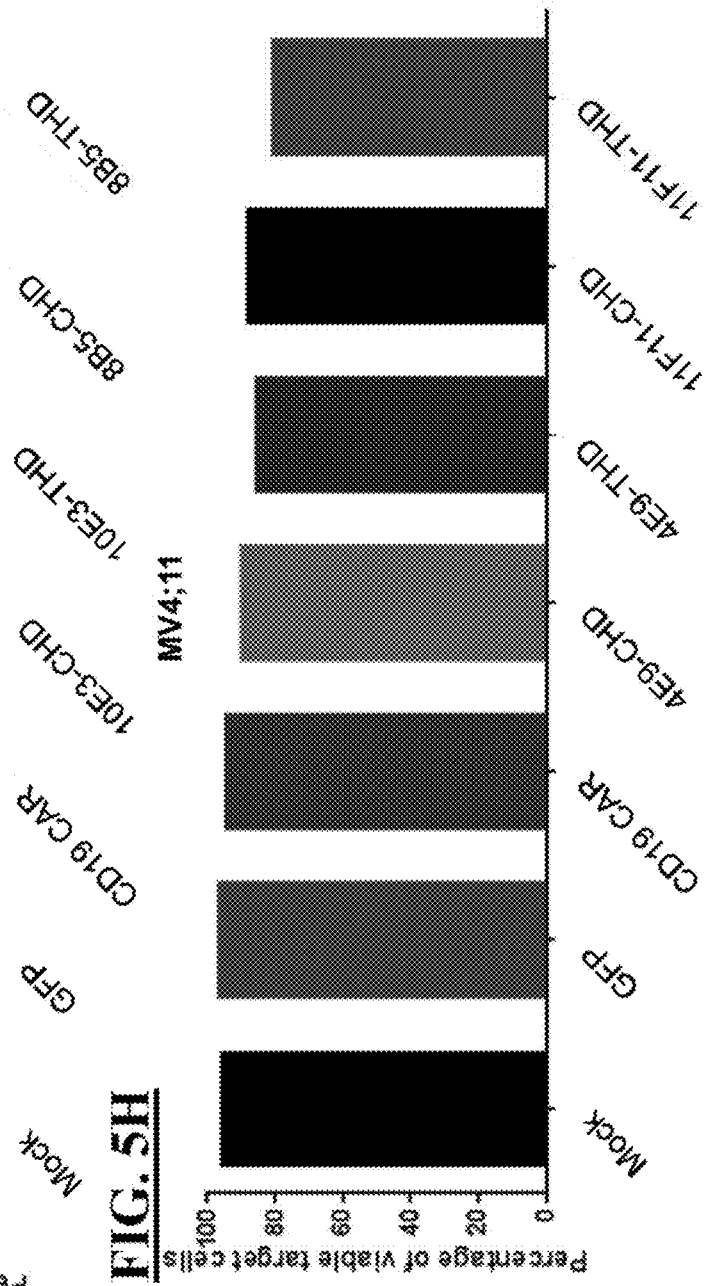

Target cell viability was assessed by flow cytometric analysis of propidium iodide (PI) uptake by CD3-negative cells. The electroporated anti-FLT3 CAR T cells were co-cultured with Namalwa (FIGS. 5A-5B), EoL1 (FIGS. 5C-5D), HL60 (FIGS. 5E-5F, and MV4;11 (5G-5H) target cells at 16 hours post-co-culture.

Example 2

Figure 6A:
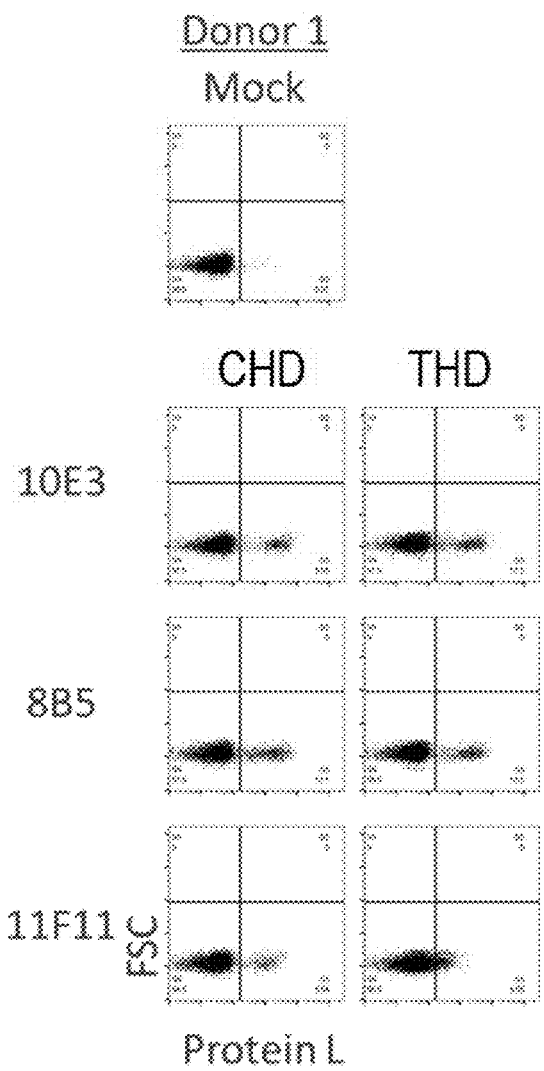
FIGS. 6A-6B depict CAR expression in lentivirus transduced primary human T cells from two healthy donors.
Figure 6B:
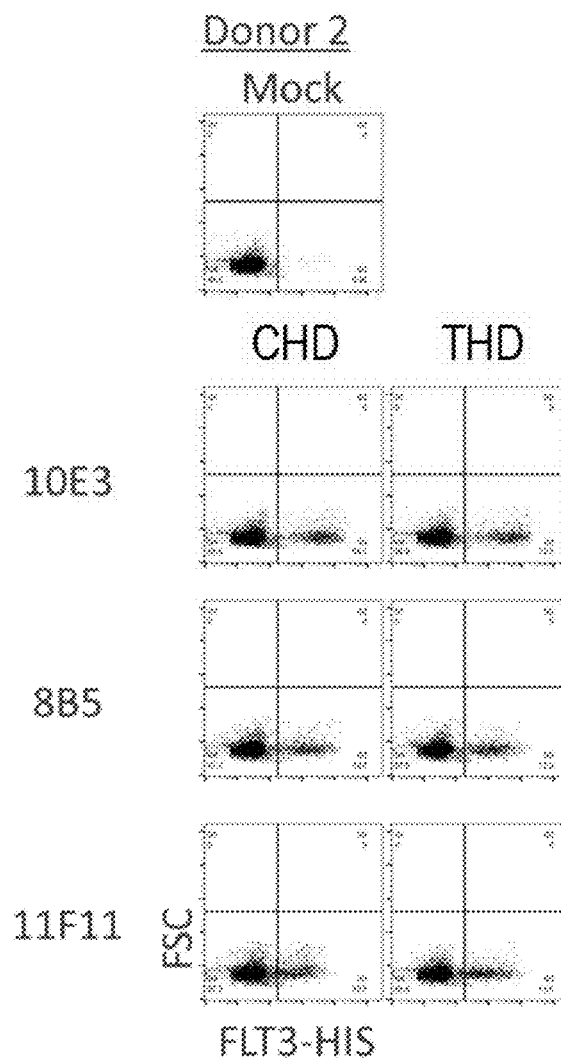

A third generation lentiviral transfer vector containing the different CAR constructs was used along with the ViraPower Lentiviral Packaging Mix (Life Technologies) to generate the lentiviral supernatants. Briefly, a transfection mix was generated by mixing 15 of DNA and 22.5 µl of polyethileneimine (Polysciences, 1 mg/ml) in 600 µl of OptiMEM medium. The mix was incubated for 5 minutes at room temperature. Simultaneously, 293T cells (ATCC) were trypsinized, counted and a total of $10 \times 10^6$ total cells were plated in a T75 flask along the transfection mix. Three days after the transfection, supernatants were collected and filtered through a 0.45 µm filter and stored at −80° C. until used. PBMCs were isolated from healthy donor leukopaks (Hemacare) using ficoll-paque density centrifugation per manufacturer's instructions. PBMCs were stimulated using OKT3 (50 ng/ml, Miltenyi Biotec) in R10 medium+IL-2 (300 IU/ml, PROLEUKIN®, PROMETHEUS® Therapeutics and Diagnostics). Forty eight hours post-stimulation, cells were transduced using lentivirus at an MOI=10. Cells were maintained at $0.5$-$2.0 \times 10^6$ cells/ml prior to use in activity assays. To examine CAR expression, T cells were stained with FLT-3-HIS (Sino Biological Inc.) or biotinylated Protein L (Thermo Scientific) in stain buffer (BD Pharmingen) for 30 minutes at 4° C. Cells were then washed and stained with anti-HIS-PE (Miltenyi Biotec) or PE Streptavidin (BD Pharmingen) in stain buffer for 30 minutes at 4° C. Cells were then washed and resuspended in stain buffer with propidium iodide (BD Pharmingen) prior to data acquisition. Expression of FLT3 CARs in T cells from two healthy donors is shown in FIG. 6A-6B.

Figure 7A:
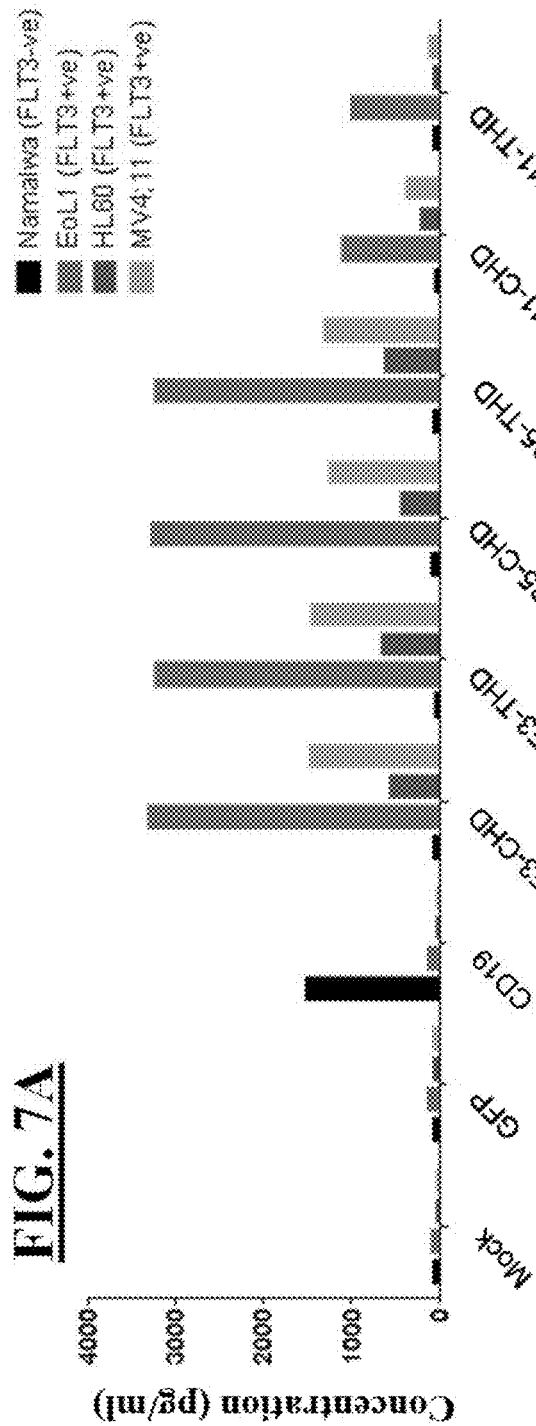
Figure 7B:
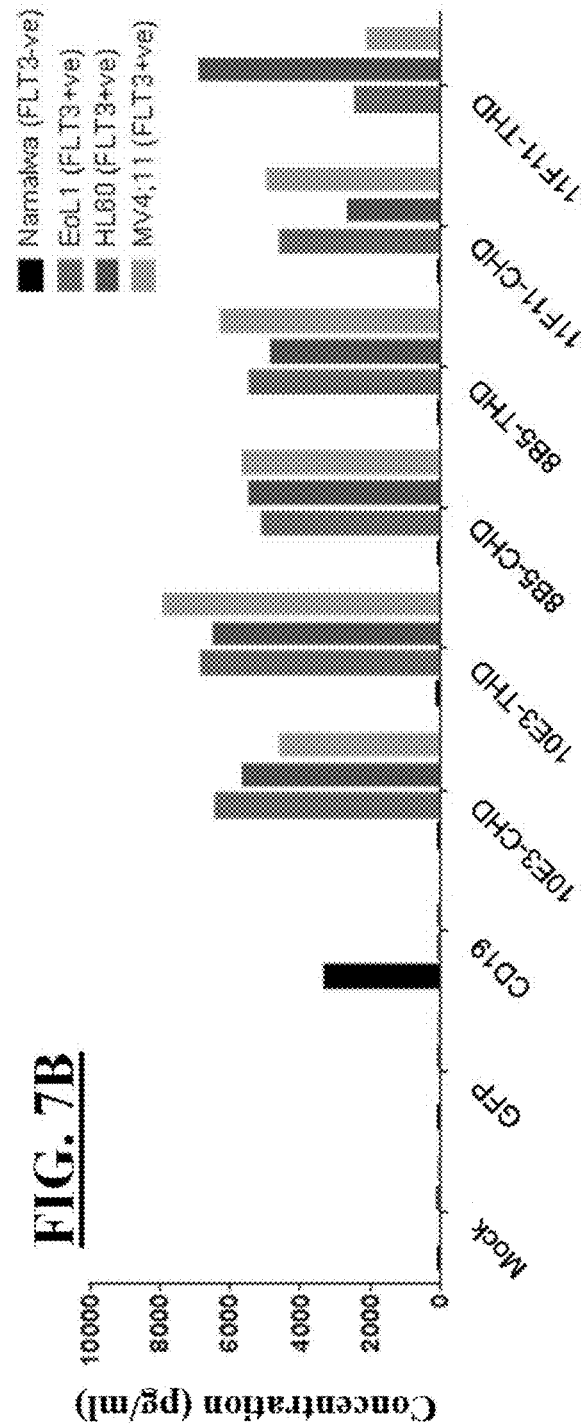
Figure 7E:
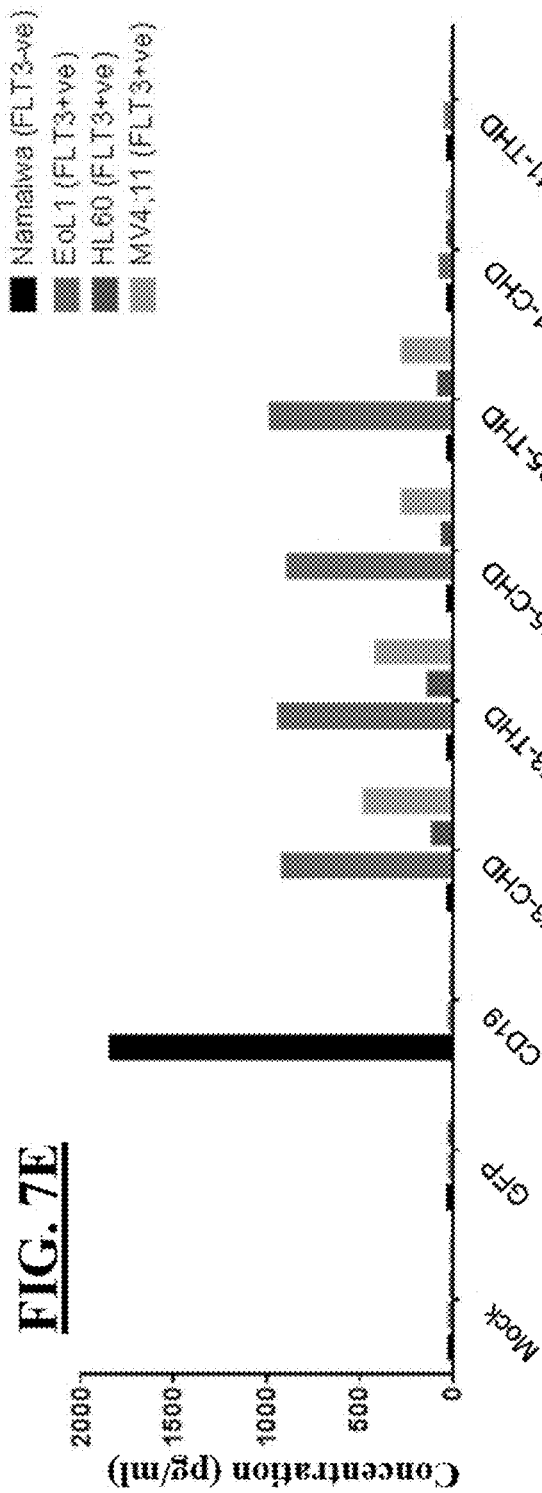
Figure 7F:
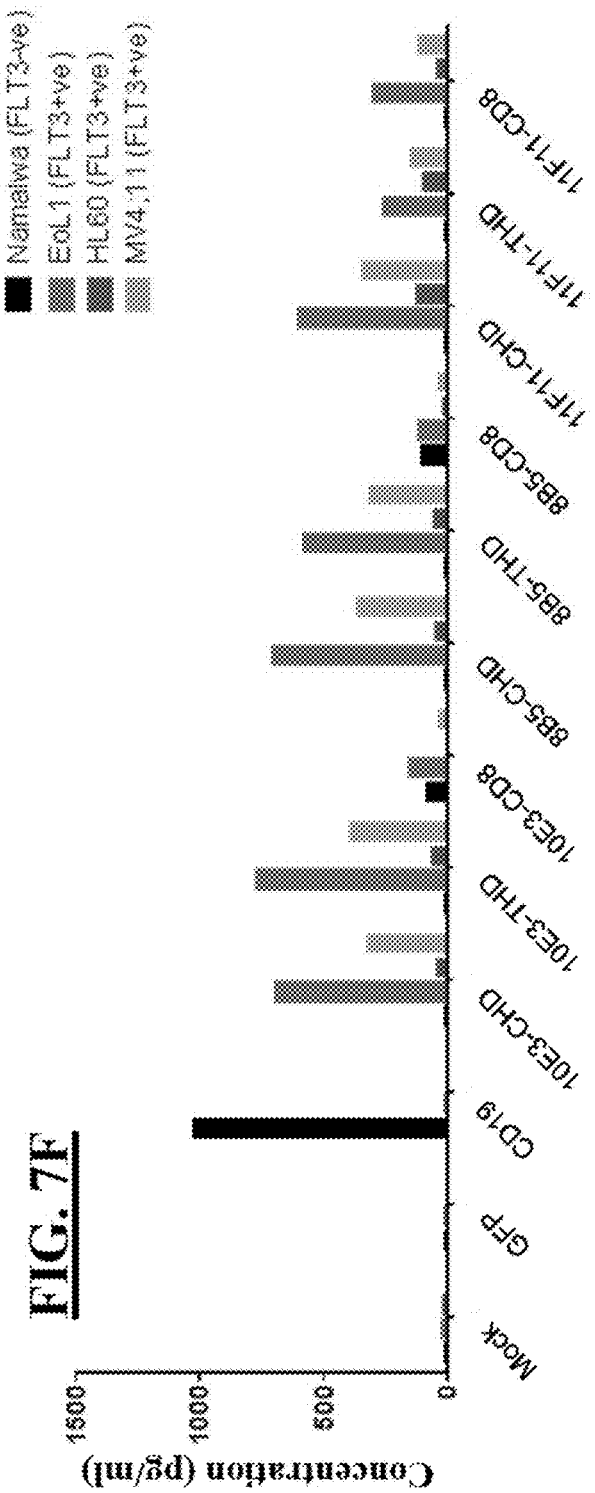

T cells from two healthy donors were transduced with lentiviral vectors encoding anti-FLT3 CAR T cells comprising a 10E3, 8B5, or 11F11 binding molecule and a hinge region selected from the complete hinge domain ("CHD"), a truncated hinge domain ("THD"), and the CD8 hinge region. Transduced T cells were co-cultured with target cells at a 1:1 E:T ratio in R10 medium. Sixteen hours post-co-culture, supernatants were analyzed by Luminex (EMD Millipore) for production of IFNγ (FIGS. 7A-7B), TNFα (FIGS. 7C-7D), and IL-2 (FIGS. 7E-7F).

Figure 8A:
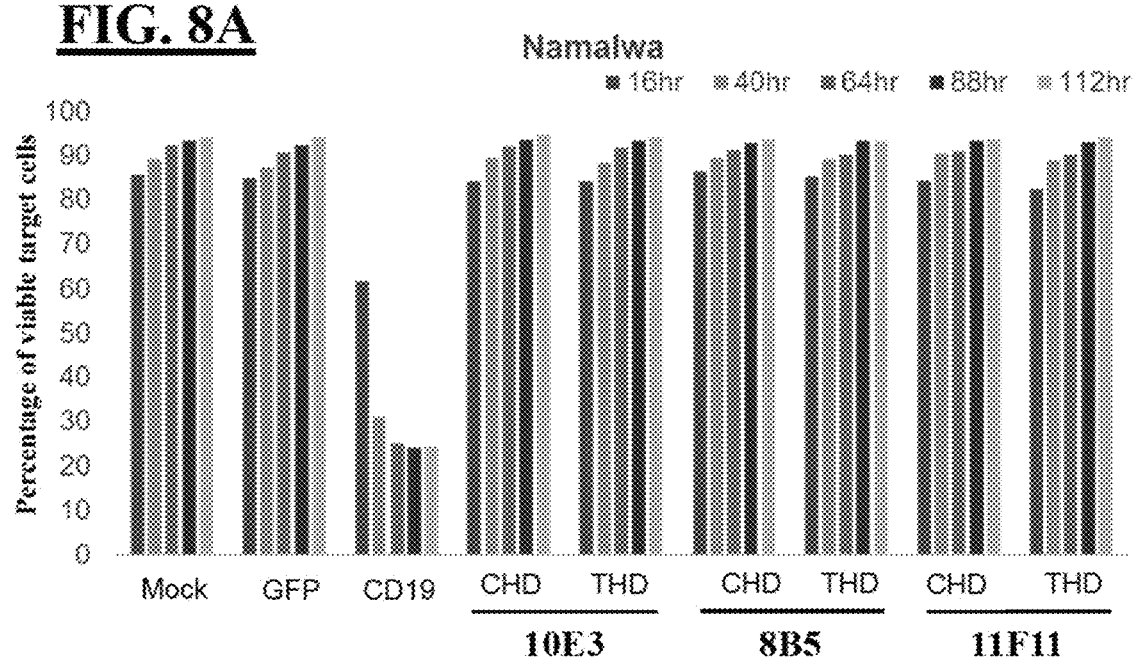
FIGS. 8A-8D show the average cytolytic activity over time from two healthy donors expressing the anti-FLT3 CAR constructs co-cultured with Namalwa (FIG. 8A), EoL1 (FIG. 8B), MV4;11 (FIG. 8C), and HL60 (FIG. 8D) target cell lines for 16, 40, 64, 88, or 112 hours.
Figure 8B:
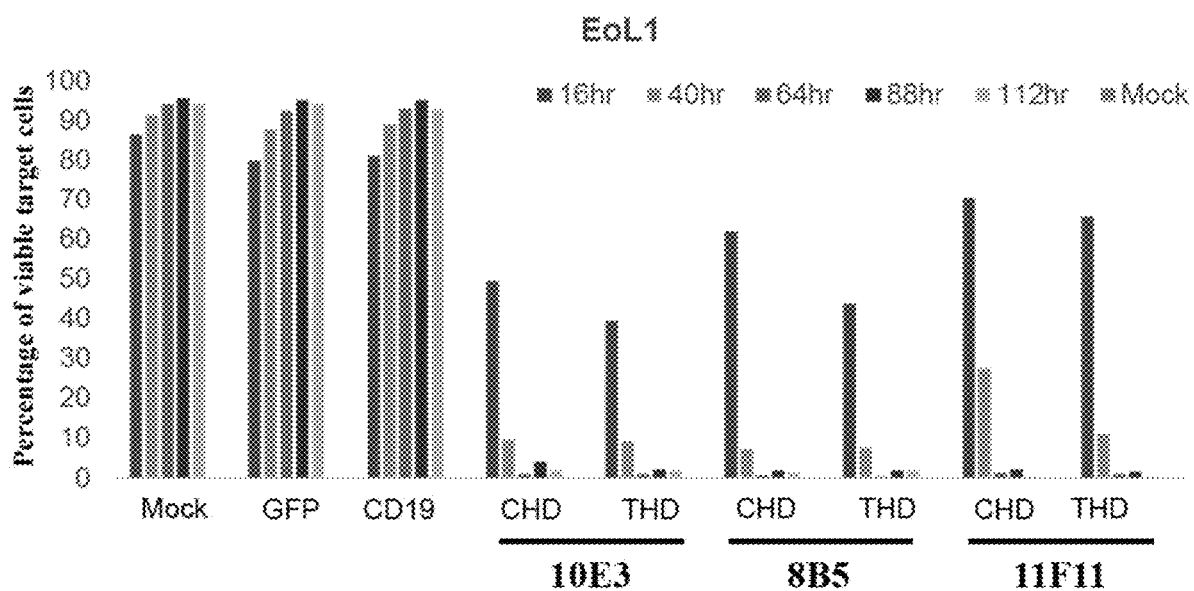
Figure 8C:
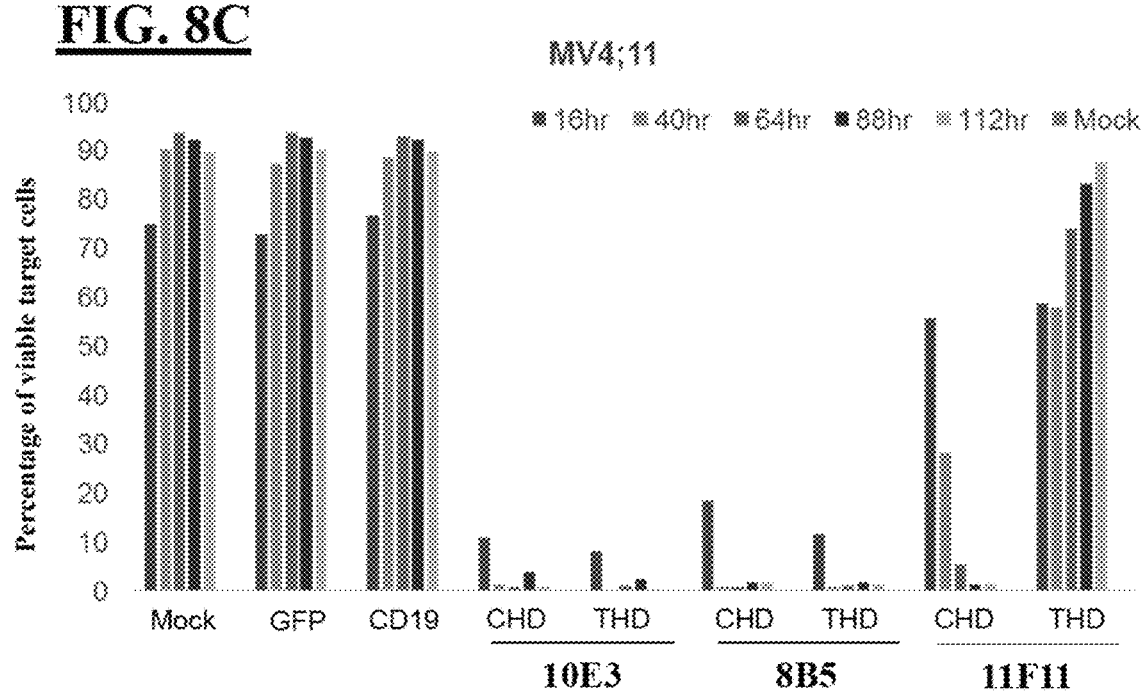
Figure 8D:
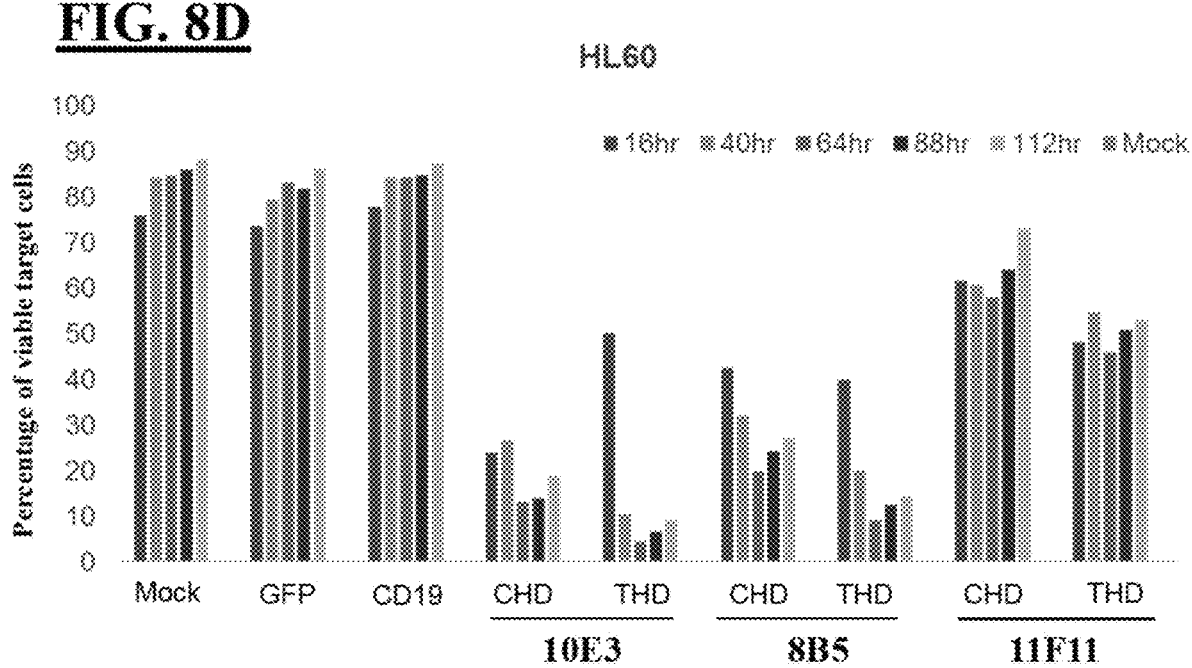

Target cell viability was assessed by flow cytometric analysis of propidium iodide (PI) uptake by CD3-negative cells. Average cytolytic activity of lentivirus-transduced CAR T cells (from two healthy donors) co-cultured with Namalwa (FIG. 8A), EoL1 (FIG. 8B), MV4;11 (FIG. 8C), and HL60 (FIG. 8D) target cells was measured.

Figure 9A:
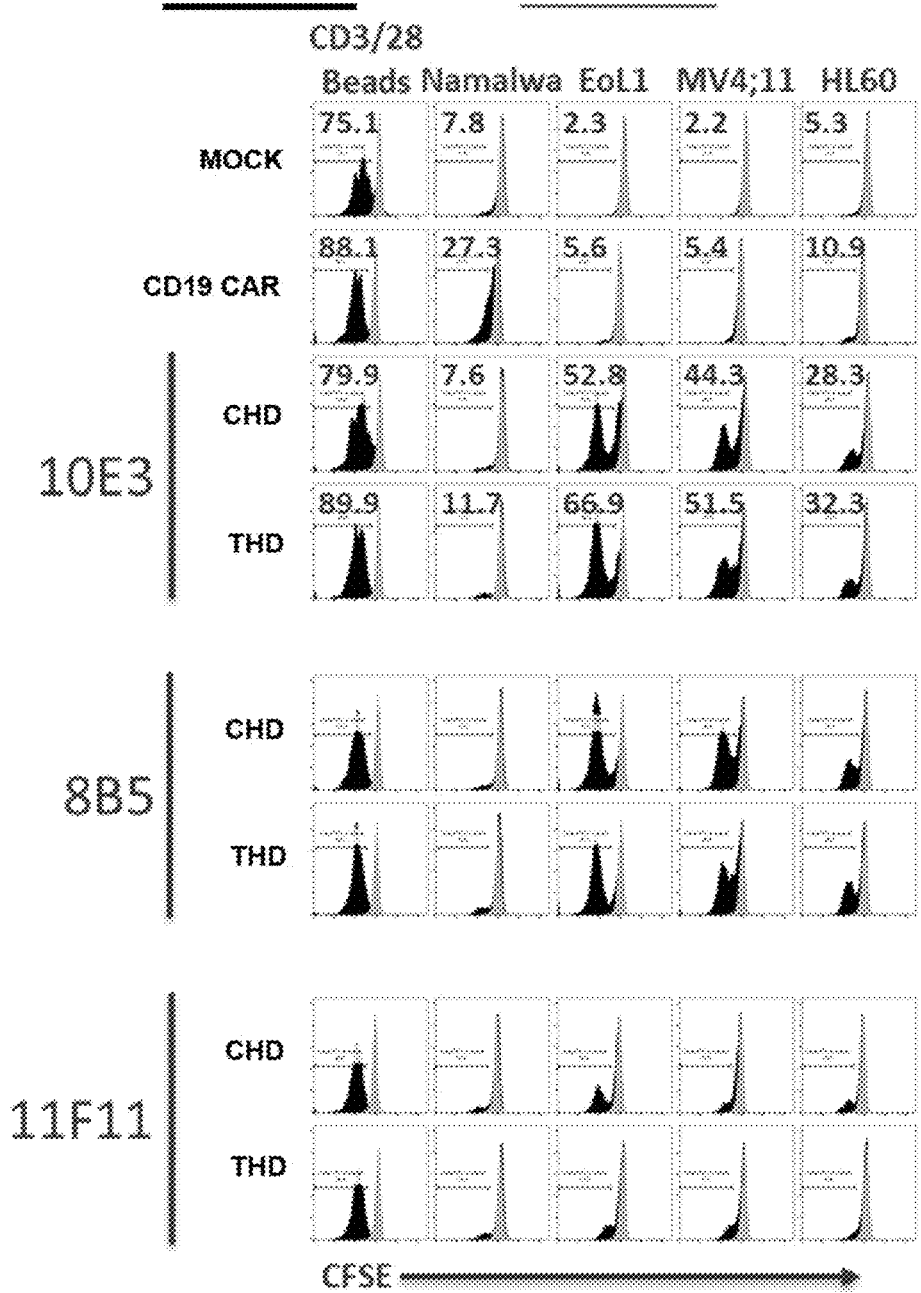

To assess CAR T cell proliferation in response to FLT3 expressing target cells, T cells were labeled with CFSE prior to co-culture with target cells at a 1:1 E:T ratio in R10 medium. Five days later, T cell proliferation was assessed by flow cytometric analysis of CFSE dilution. Proliferation of FLT3 CAR T cells is shown in FIGS. 9A-9B.

Example 3

Figure 10H:
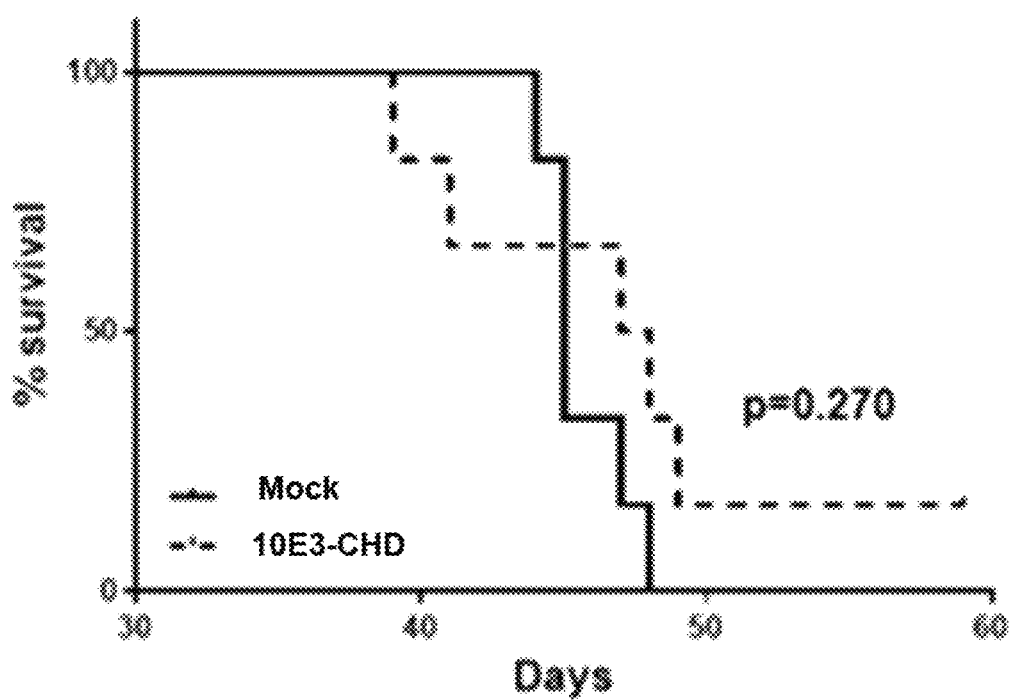
FIGS. 10H-10K show survival curves of mice injected with mock or 10E3-CHD (FIG. 10H), mock or 10E3-THD (FIG. 10I), mock or 8B5-THD (FIG. 10J), or 10E3-THD or 8B5-THD (FIG. 10K) CAR T cells.

To examine in vivo anti-leukemic activity, FLT3 CAR T cells were generated for use in a xenogeneic model of human AML. CAR expression of the various effector lines used in the xenogeneic model of human AML are shown in FIGS. 10A-10D. Luciferase-labeled MV4;11 cells ($2 \times 10^6$ cells/animal) were injected intravenously into 5 to 6 week-old female NSG mice. After 6 days, $6 \times 10^6$ T cells (~50% CAR+) in 200 µl PBS were injected intravenously, and the tumor burden of the animals was measured weekly using bioluminescence imaging (FIGS. 10E-10G). Survival analysis was performed by injection of controls (mock) or 10E3-

Figure 10I:
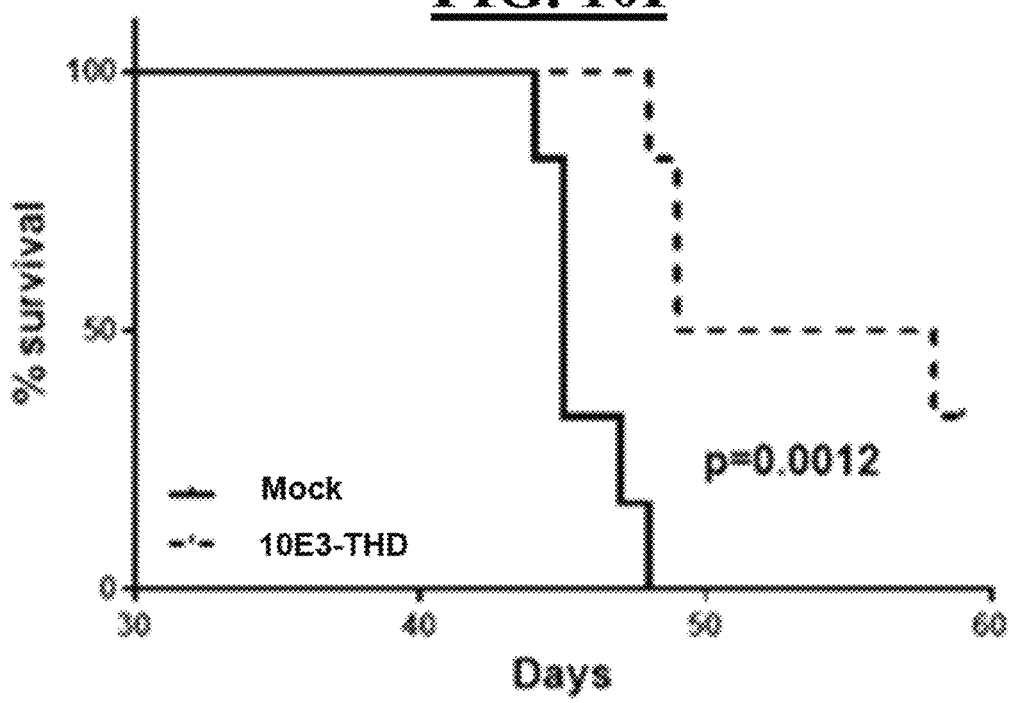
Figure 10J:
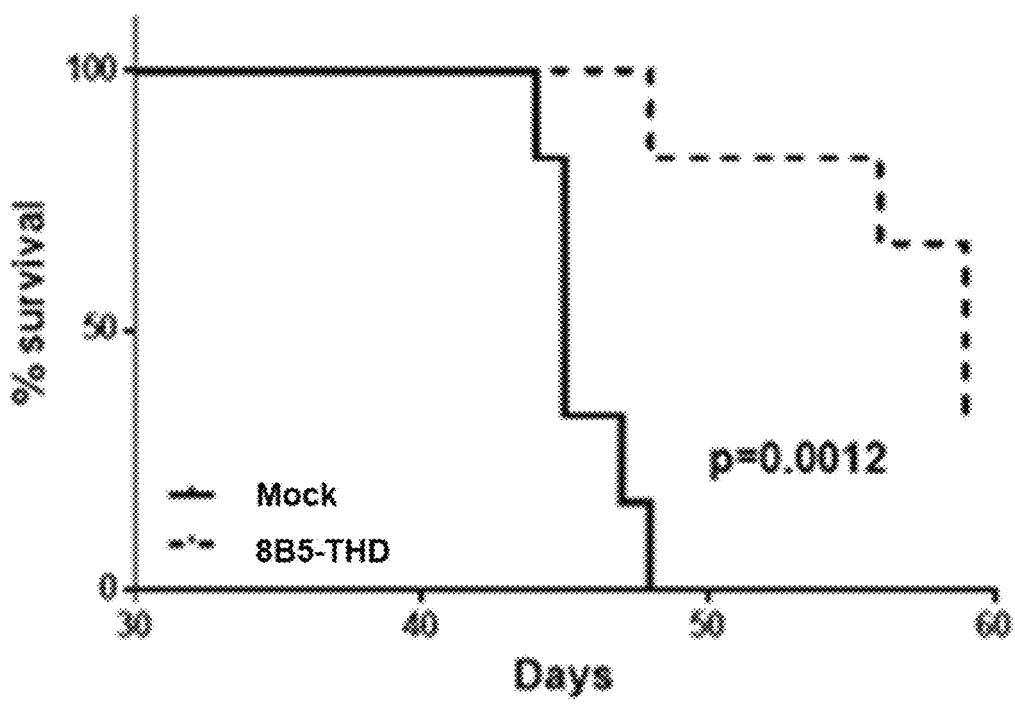
Figure 10K:
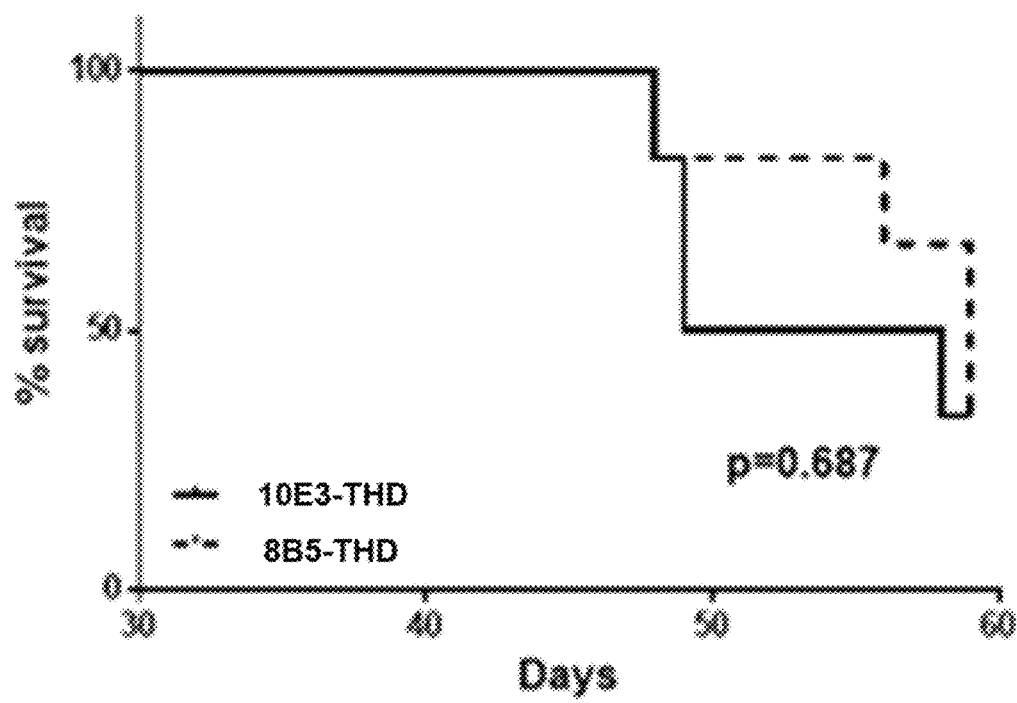
Figure 11B:
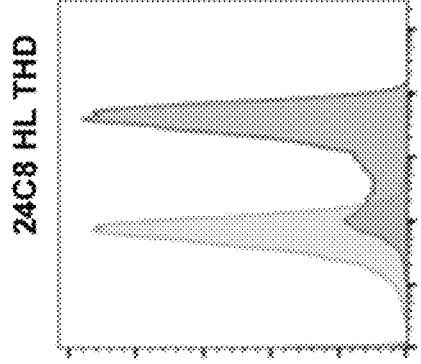
FIGS. 11A-11B shows CLL-1 CAR expression determined by protein L 6 hours post mRNA electroporation.
Figure 11A:
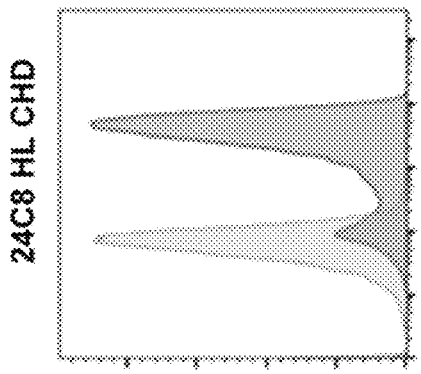

CHD (FIG. 10H), 10E3-THD (FIG. 10I), or 8B5-THD (FIG. 10J) expressing CAR T cells.

Example 4

Figure 12A:
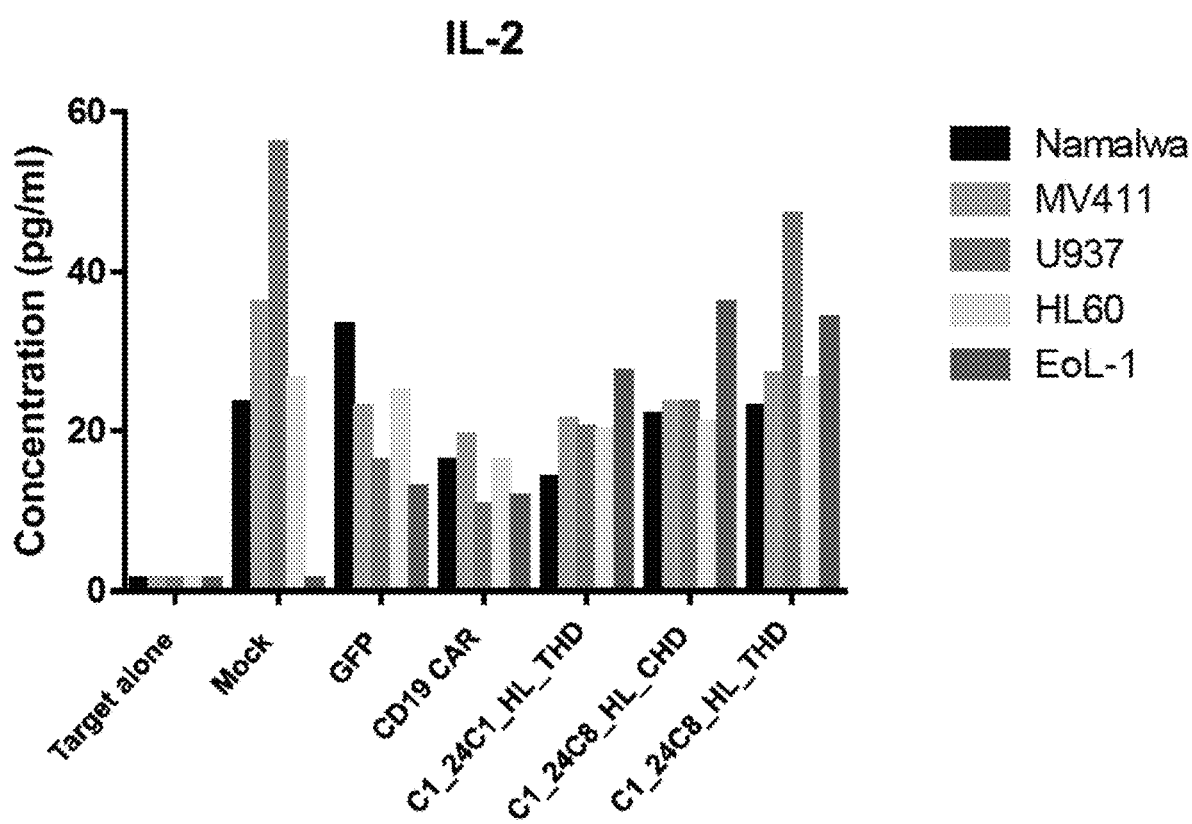
FIGS. 12A-12C show the results from a cytokine release assay from different CLL-1 CAR-T cell constructs 24 hours after mRNA electroporation. IL-2 (FIG. 12A), IFNγ(FIG. 12B), and TNFα (FIG. 12C) production levels are shown for controls (target alone, mock, GFP, and CD19 CAR T cells) and anti-CLL-1 CAR T cells (24C1_HL-THD, 24C1_HL_CHD, 24C8_HL-CHD, and 24C8_HL_THD) co-cultured with Namalwa, MV4;11, U937, HL60, and EoL-1 cells, as indicated.
Figure 12B:
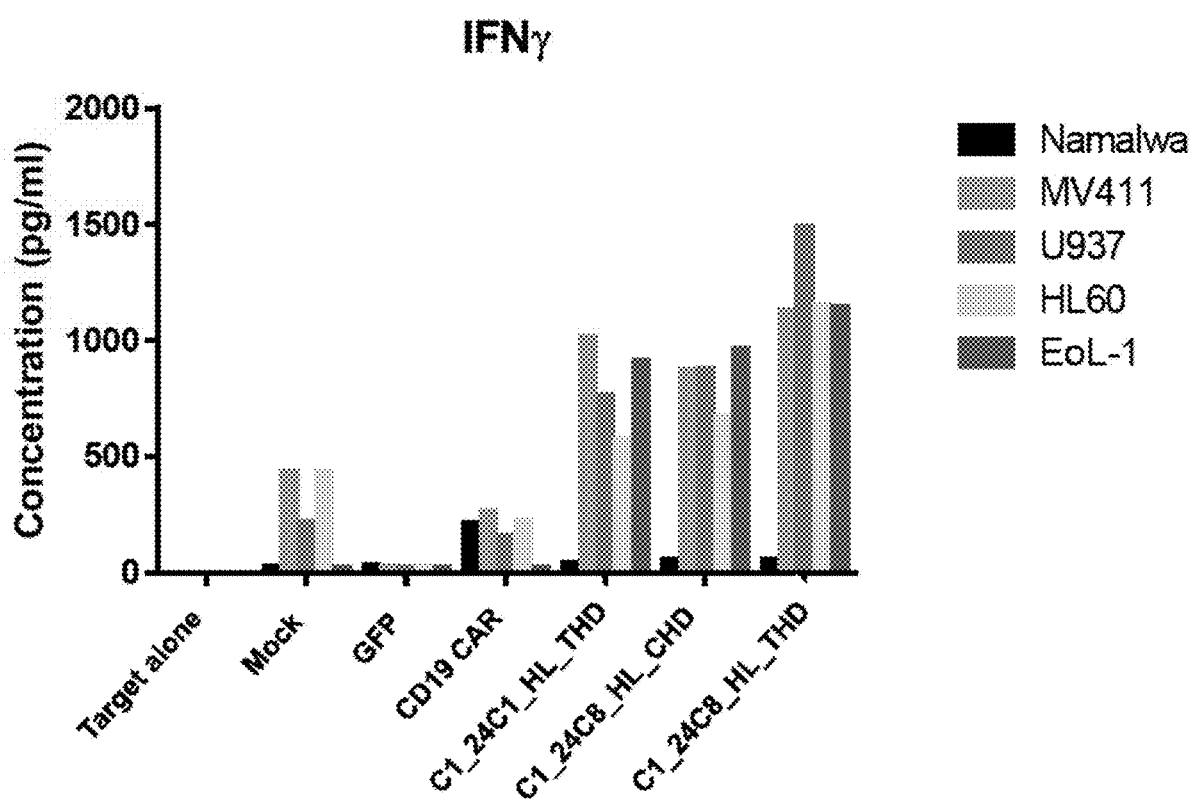
Figure 12C:
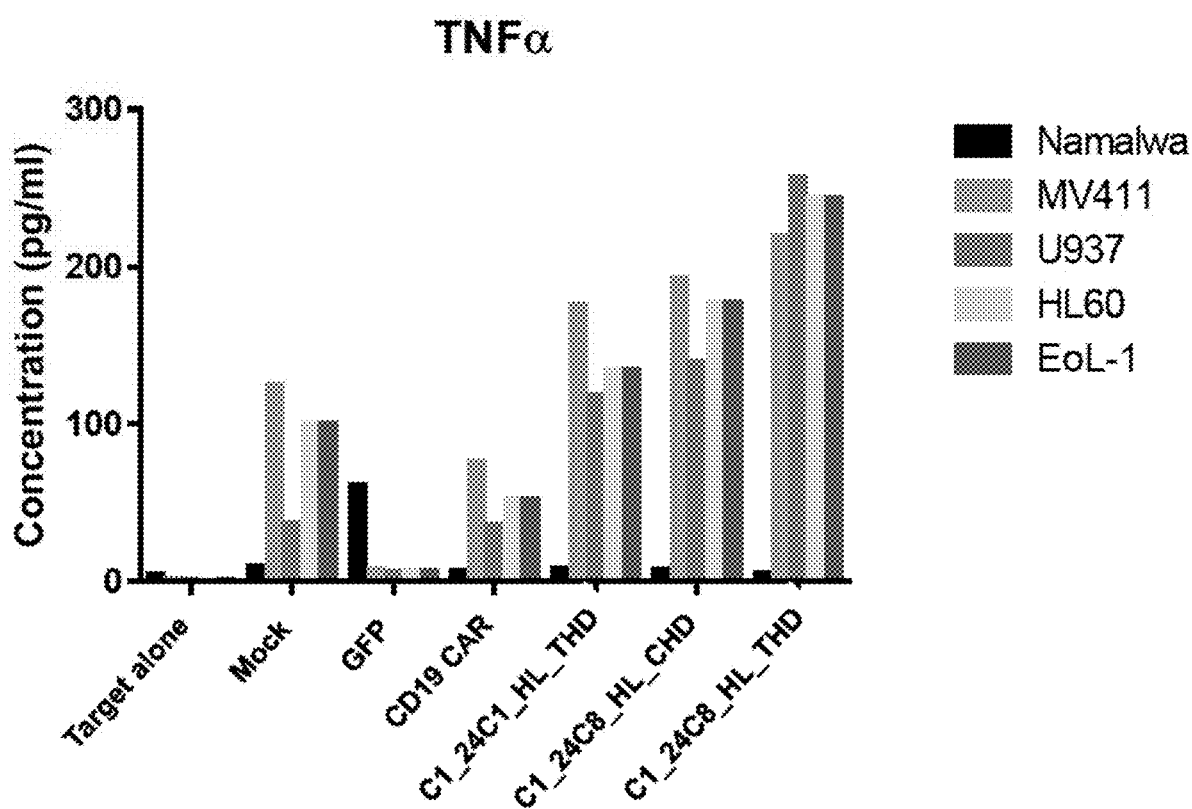

T cells were electroporated with plasmids encoding the anti-CLL-1 CAR constructs 24C8_HL-CHD CAR (comprising a complete hinge domain of the costimulatory protein) and 24C8_HL-THD CAR (comprising a truncated hinge domain of the costimulatory protein). Anti-CLL-1 expression by electroporated T cells is shown in FIGS. 11A-11D. The anti-CLL-1 CART cells were then cultured with the target Namalwa (ATCC; CLL-1 negative), U937 (ATCC; CLL-1 positive), HL-60 (ATCC; CLL-1 positive), EoL-1 (Sigma; CLL-1 positive), KG1a (ATCC; CLL-1 positive) and MV4;11 (ATCC; CLL-1 positive) cells at a 1:1 E:T ratio in R10 media 6 hours after mRNA electroporation. Sixteen hours post-co-culture, supernatants were analyzed by Luminex (EMD Millipore), according to the manufacturer's instructions, for production of IL-2 (FIG. 12A), IFNγ (FIG. 12B), and TNFα (FIG. 12C).

Figures 13A, 13B:
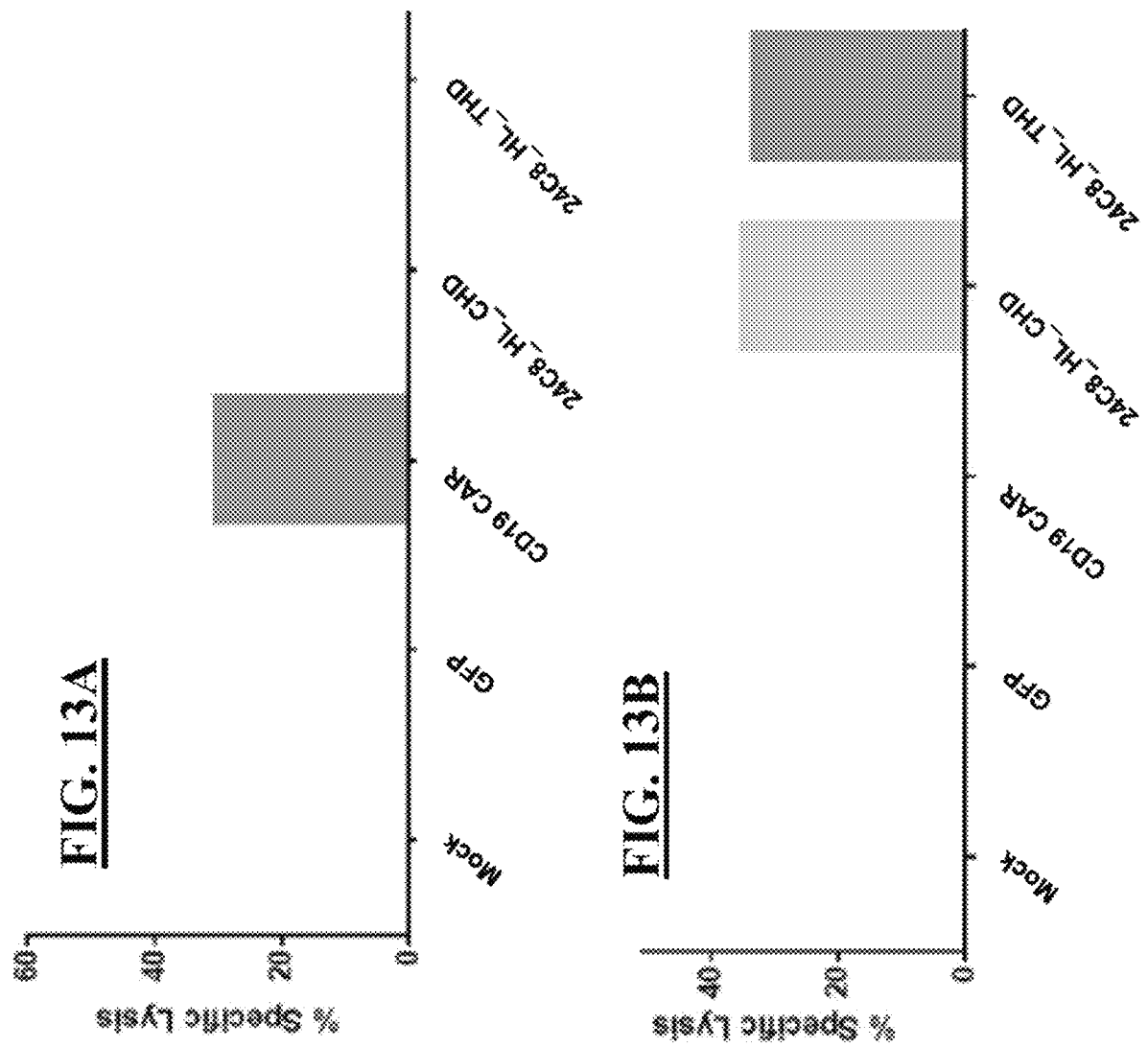

Target cell viability was assessed by flow cytometric analysis of propidium iodide (PI) uptake. The electroporated anti-CLL-1 CAR T cells were co-cultured with Namalwa (FIG. 13A), MV4;11 (FIG. 13B), EoL-1 (FIG. 13C), HL-60 (FIG. 13D), or U937 (FIG. 13E) target cells for 16 hours. As expected, Namalwa cells co-cultured with the anti-CLL-1 CART cells showed little change in target cell viability, relative to controls (FIG. 13A). However, increased cytolytic activity was observed in MV;411 cells co-cultured with 24C8_HL-CHD and 24C8_HL-THD T cells, relative to controls, with a greater target cell cytolytic activity observed in the 24C8_HL-THD T cell co-culture (FIG. 13B). In addition, increased cytolytic activity was observed in EoL-1 cells co-cultured with 24C8_HL-CHD and 24C8_HL-THD T cells, relative to controls (FIG. 13C). Increased cytolytic activity was observed in HL-60 cells co-cultured with 24C8_HL-CHD and 24C8_HL-THD T cells, relative to controls (FIG. 13D). Increased cytolytic activity was observed in U937 cells co-cultured with 24C8_HL-CHD and 24C8_HL-THD T cells, relative to controls, with a greater target cell cytolytic activity observed in the 24C8_HL-THD T cell co-culture (FIG. 13E).

Example 5

Figure 14A:
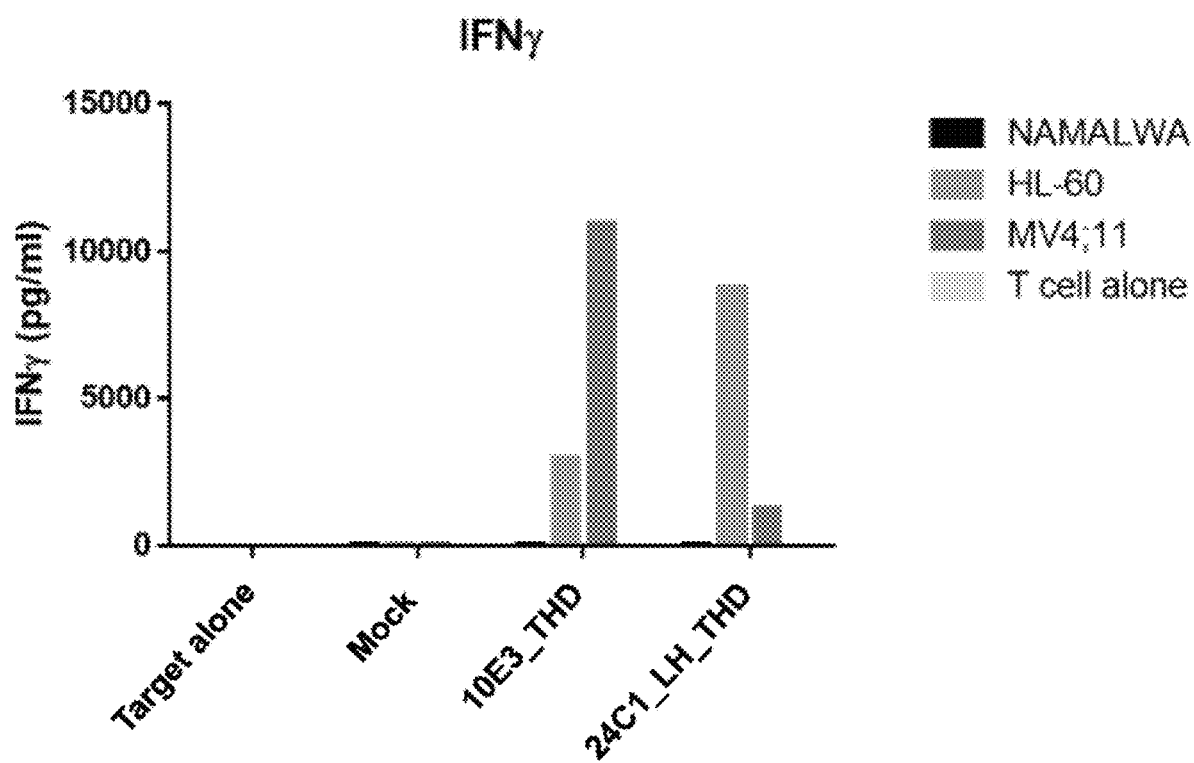
Figure 14B:
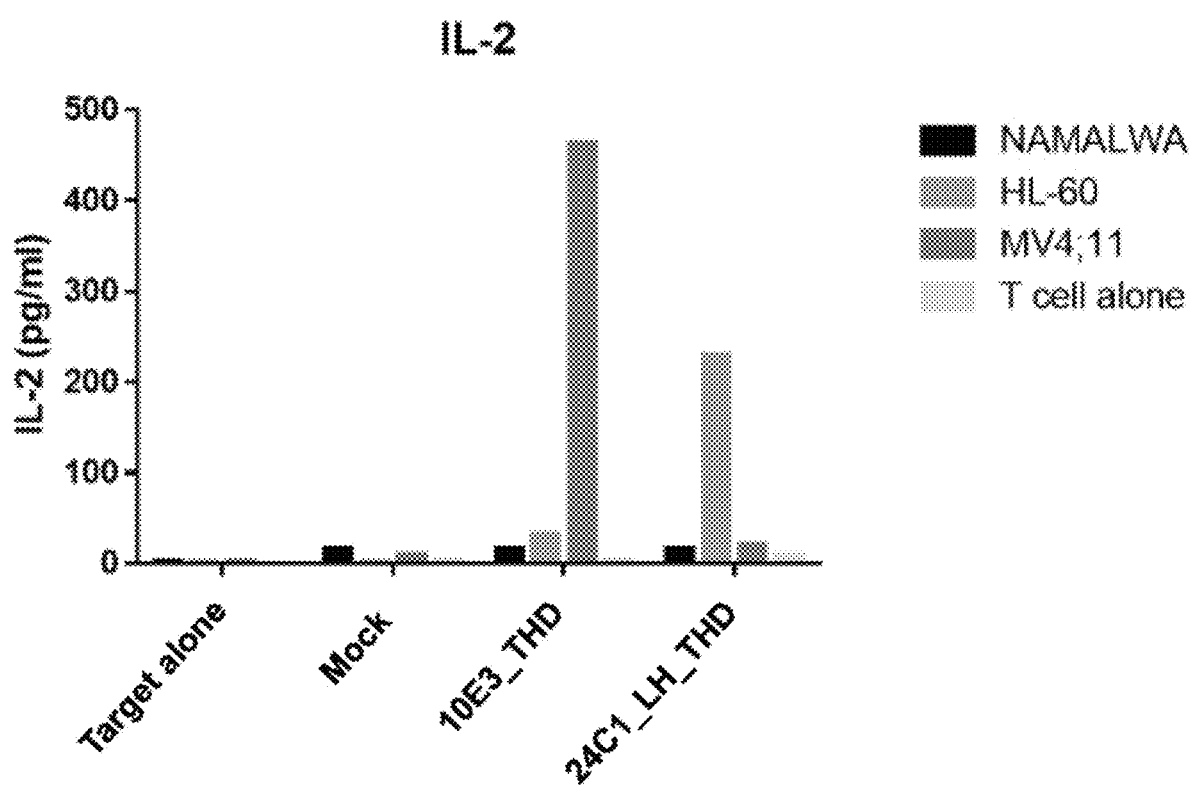

T cells transduced with lentiviral vectors comprising an anti-CLL-1 CAR construct with a truncated hinge domain ("THD") of the costimulatory protein, 10E3 THD or 24C1_LH_THD, were co-cultured with Namalwa, U937, HL-60, EoL-1, KG1a and MV4;11 target cells at a 1:1 E:T ratio in R10 media 12 days after T cell stimulation. Sixteen hours post-co-culture, supernatants were analyzed by Luminex (EMD Millipore), according to the manufacturer's instructions, for production of the cytokines IFNγ (FIG. 14A), IL-2 (FIG. 14B), and TNFα (FIG. 14C) in co-cultures of effector 10E3 THD CART cells and 24C1_LH_THD CAR T cells with target Namalwa, HL-60, or MVA;11 cells, as indicated.

Figure 15A:
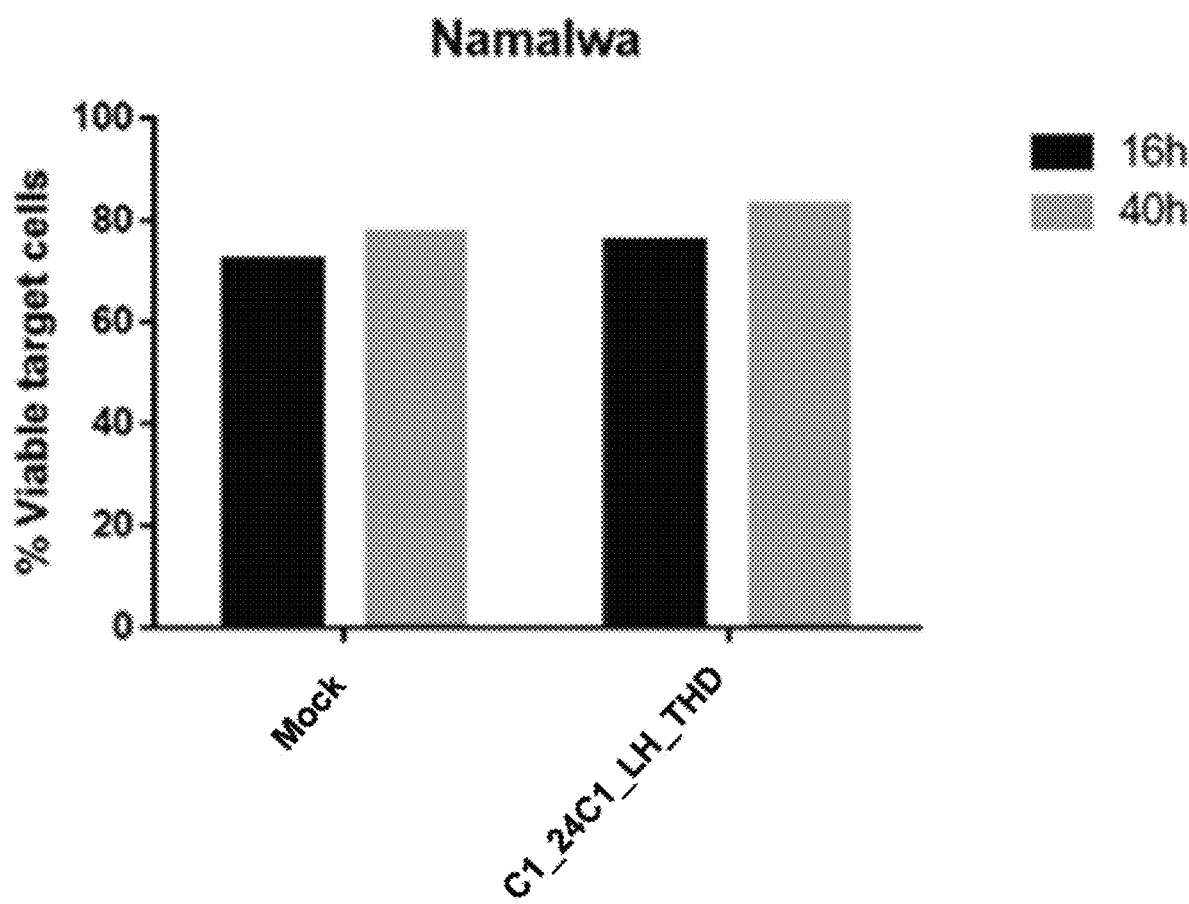
Figure 15B:
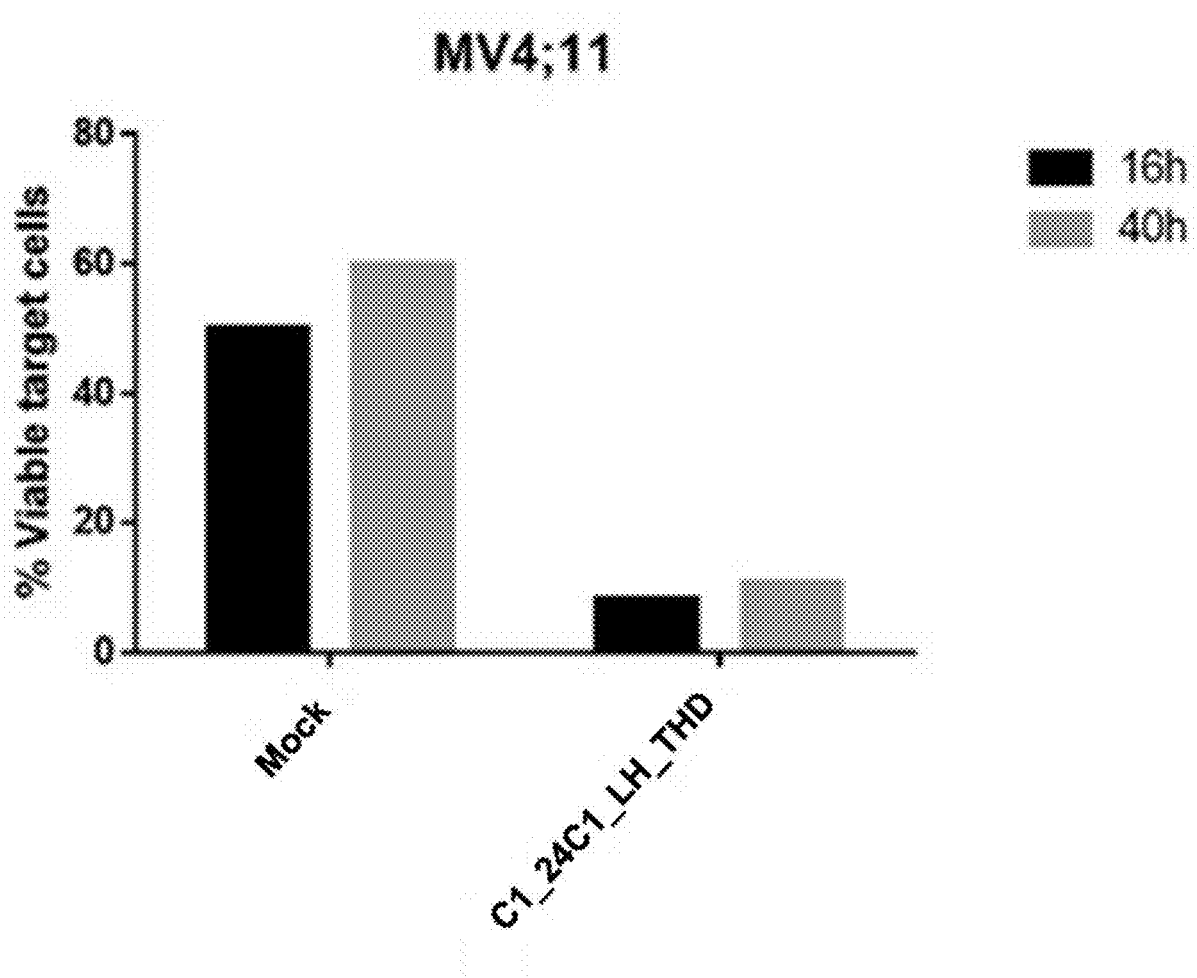

Target cell viability was assessed by flow cytometric analysis of propidium iodide (PI) uptake. Transduced effector 24C1_LH_THD CAR T cells were co-cultured with Namalwa, U937, HL-60, EoL-1, KG1a, or MV4;11 target cells for 16 hours or 40 hours. Co-culture of Namalwa target cells with transduced C1_24C1_LH_THD CART cells had no effect on the percent of viable Namalwa target cells at 16 hours and 40 hours, as compared to mock controls (FIG. 15A). However, C1_24C1_LH_THD CAR T cells co-cultured with either MV4;11 (FIG. 15B) or HL-60 (FIG. 15C) target cells resulted in a lower percent of viable target cells at both 16 hours and 40 hours, as compared to mock controls.

Example 6

Figure 16C:
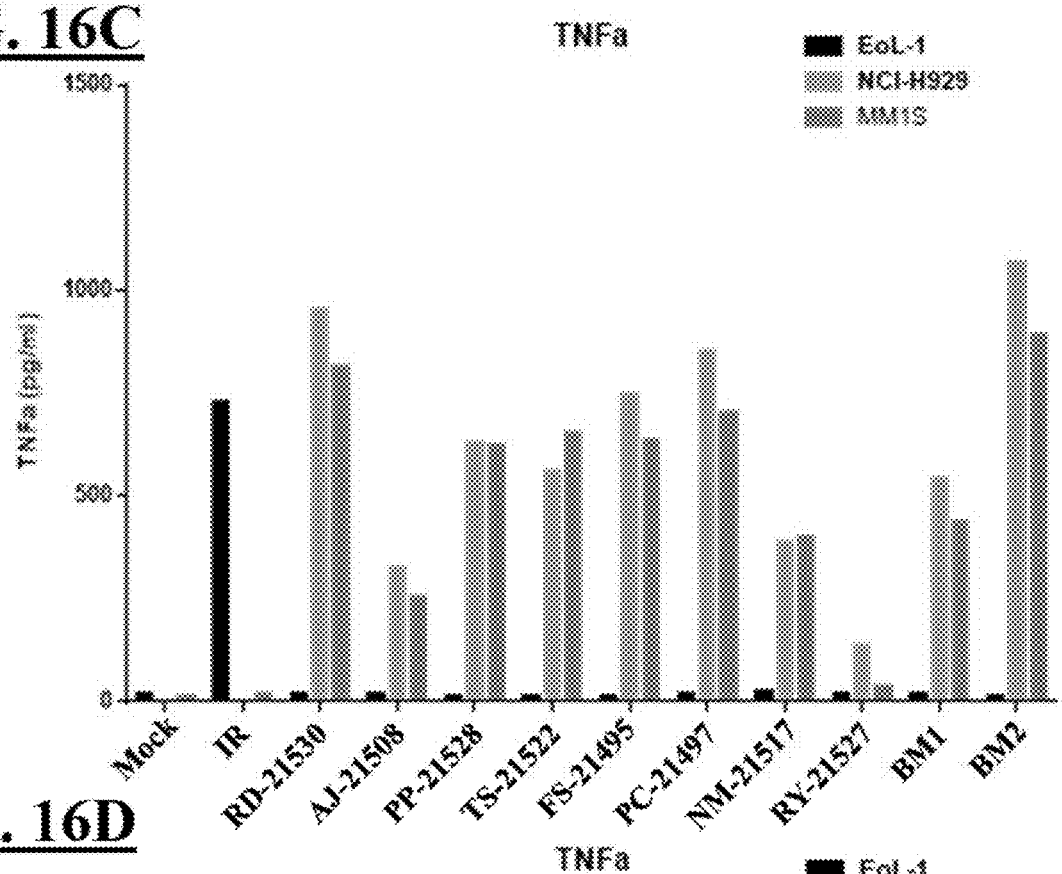
Figure 16D:
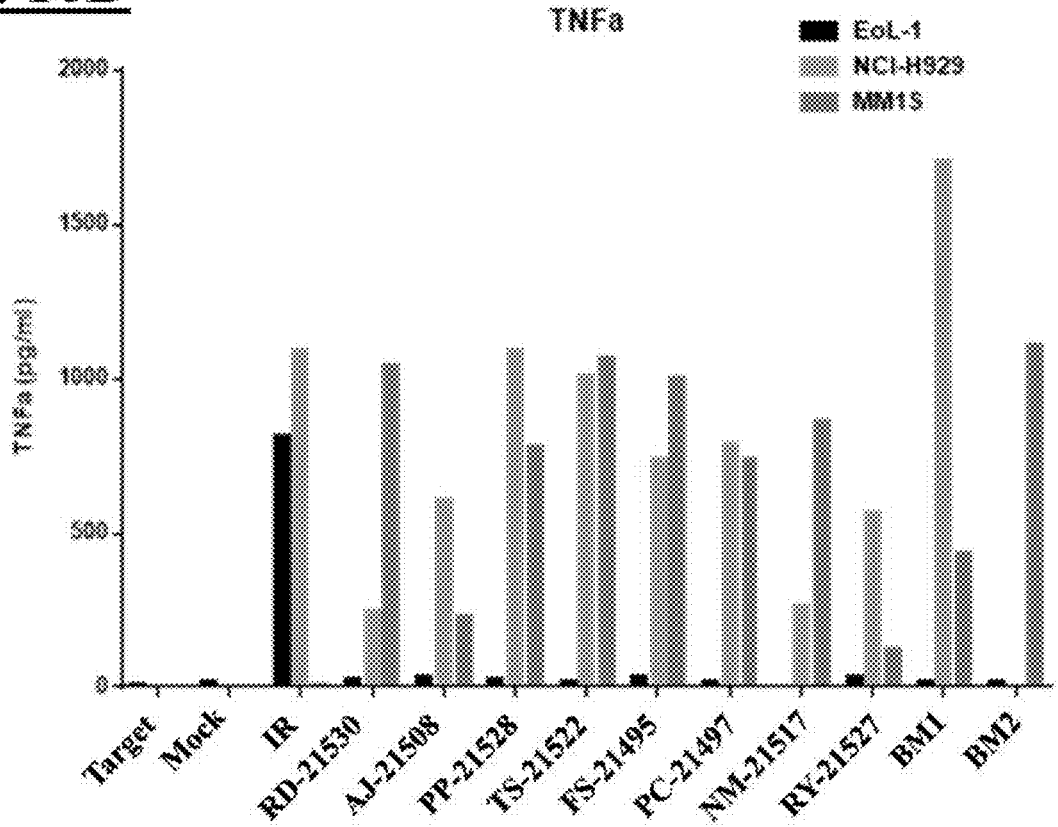
Figure 16E:
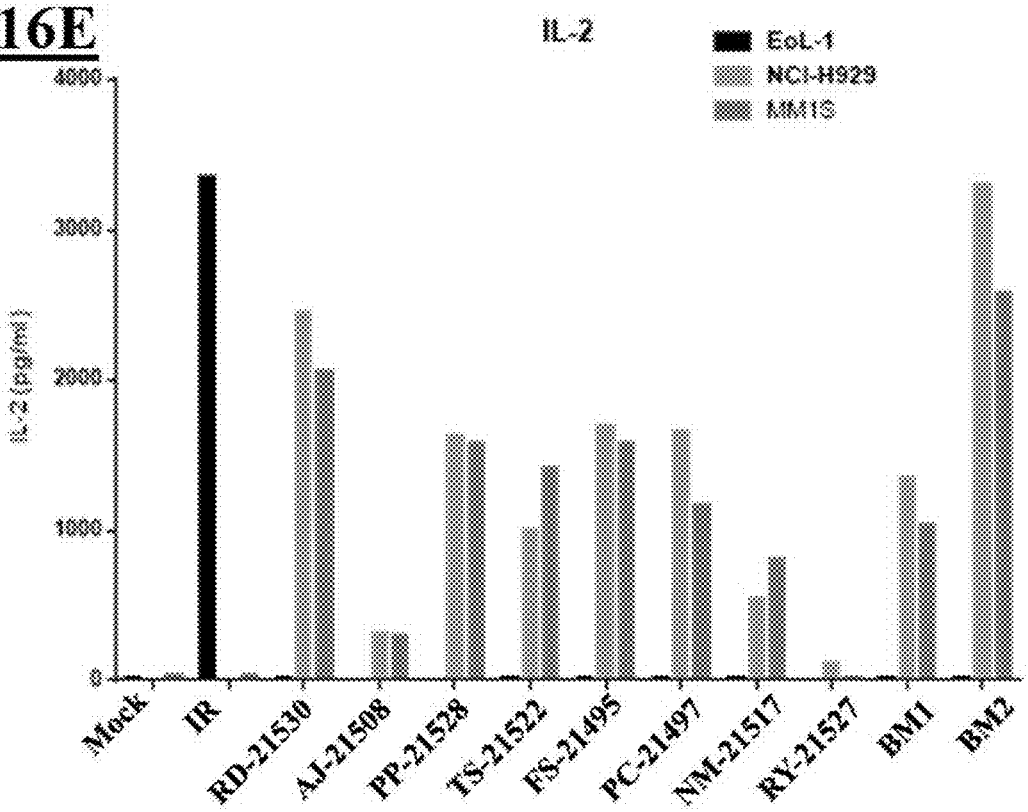
Figure 16F:
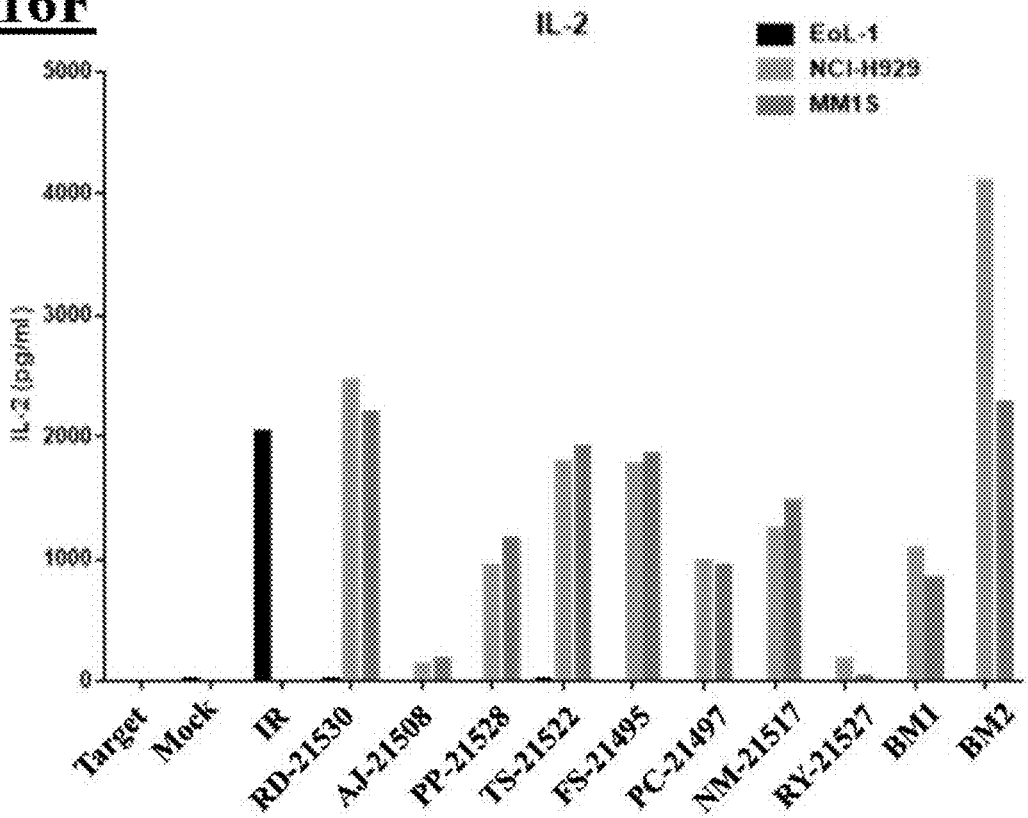

CAR T cells transduced with anti-BCMA CAR constructs comprising a truncated hinge domain ("THD") of the costimulatory protein were cultured with target cells at a 1:1 effector cell to target cell (E:T) ratio in R10 media 12 days after T cell stimulation. Cell lines tested included EoL-1 (Sigma; BCMA negative), NCI-H929 (Molecular Imaging; BCMA positive), and MM1S (Molecular Imaging; BCMA positive). Sixteen hours post-co-culture, supernatants were analyzed by Luminex (EMD Millipore), according to the manufacturer's instructions, for production of the cytokines IFNγ (FIGS. 16A-16B), TNFα (FIGS. 16C-16D), and IL-2 (FIGS. 16E-16F). IFNγ (FIGS. 16A-16B), TNFα (FIGS. 16C-16D), and IL-2 (FIGS. 16E-16F) were observed in the supernatant of NCI-H929 and MM1S target cell co-cultures for each anti-BCMA CAR T cell tested in both donors (FIGS. 16A-16B); however, IFNγ (FIGS. 16A-16B), TNFα (FIGS. 16C-16D), and IL-2 (FIGS. 16E-16F) were only observed in the supernatant of EoL-1 target cell co-cultures above background for the IR negative control T cells (FIG. 16A).

Figure 17A:
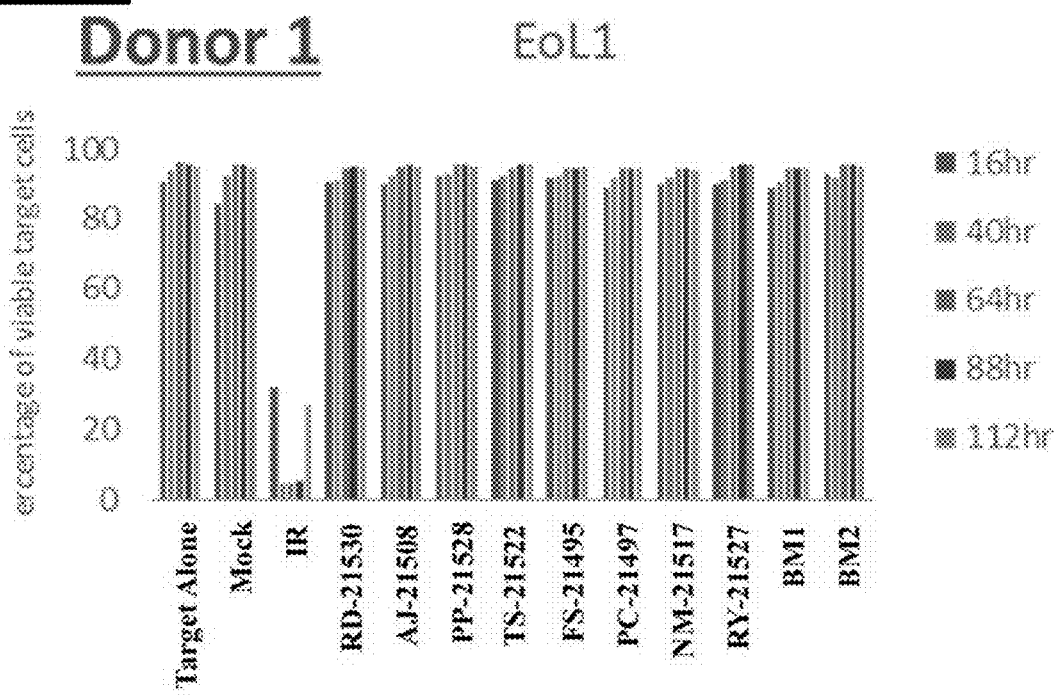
FIGS. 17A-17F show the average cytolytic activity (as a percentage of viable target cells remaining; y-axis) over time from two healthy donors expressing the indicated CARs co-cultured with EoL1 (FIGS. 17A and 17B), NCI-H929 (FIGS. 17C and 17D), or MM1S (FIGS. 17E and 17F) target cells for 16 hours, 40 hours, 64 hours, 88 hours, or 112 hours.
Figure 17B:
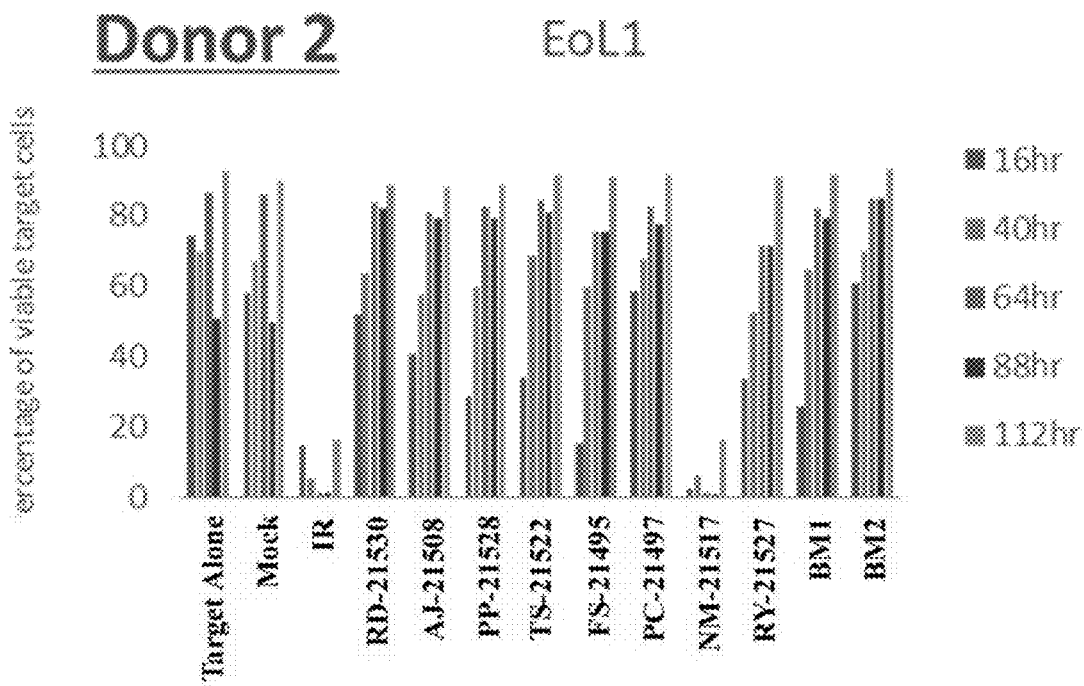
Figure 17C:
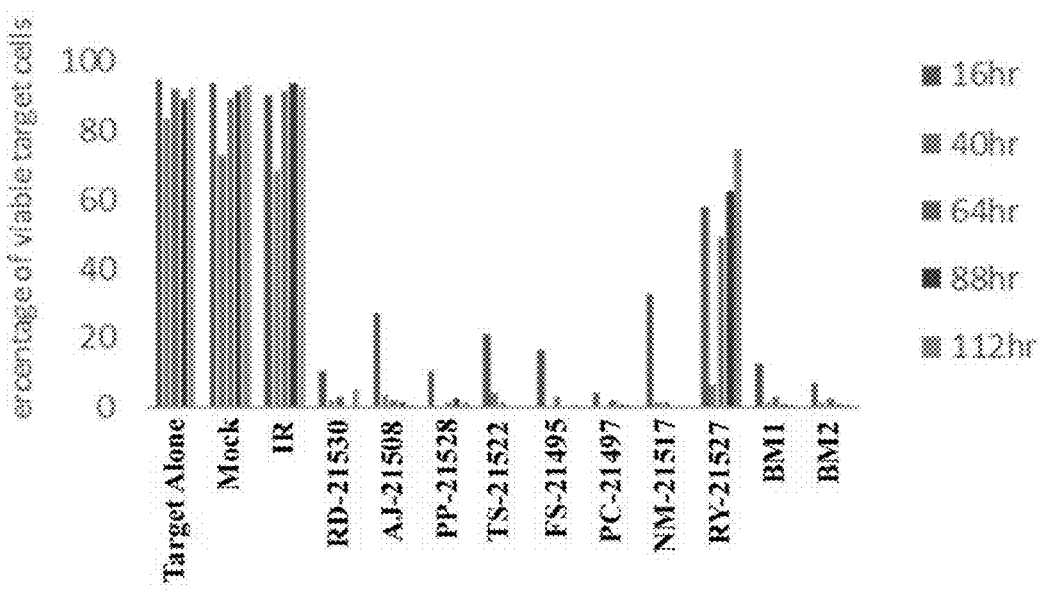
Figure 17D:
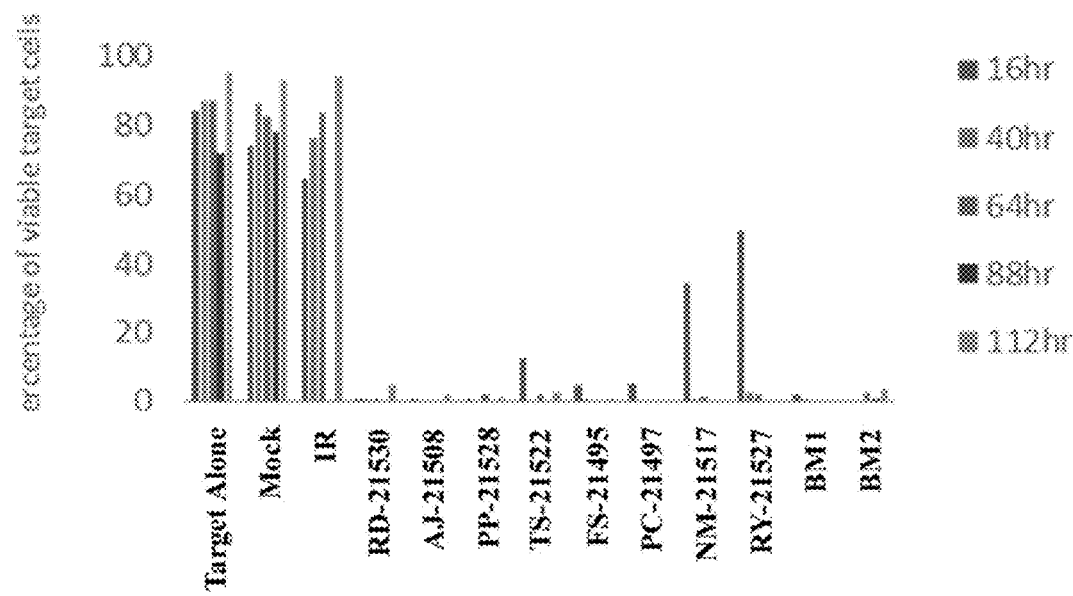
Figure 17E:
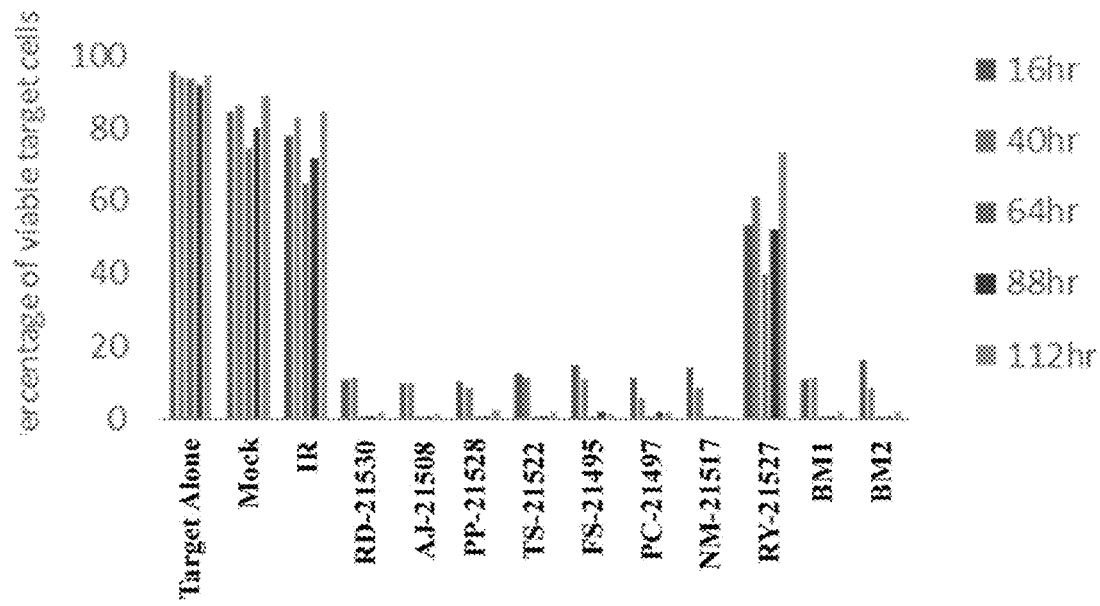
Figure 17F:
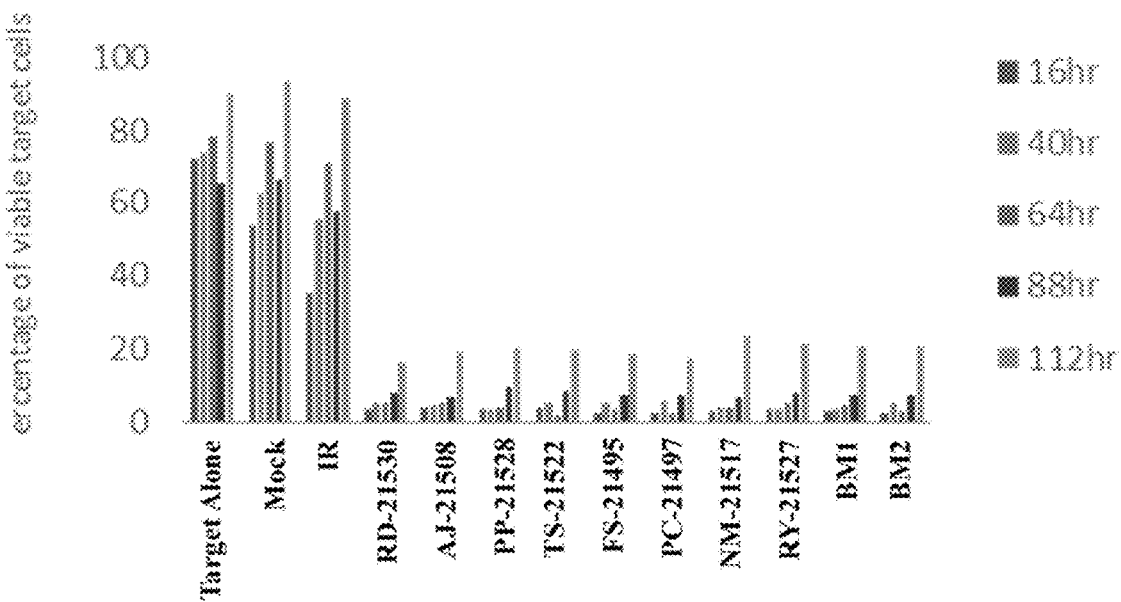

Target cell viability was assessed by flow cytometric analysis of propidium iodide (PI) uptake of CD3 negative cells. The anti-BCMA CAR T cells were co-cultured with EoL1 (FIGS. 17A-17B), NCI-H929 (FIGS. 17C-17D), or MM1S (FIGS. 17E-17F) target cells for 16 hours, 40 hours, 64 hours, 88 hours, or 112 hours. Little cytolytic activity was observed in the EoL-1 co-cultures at any time period for the anti-BCMA CAR T cells (FIG. 17A-17B). However, co-culture of the anti-BCMA CAR T cells and the NCI-H929 or MM1S target cells resulted in a decrease in the percentage of viable target cells at each time point measured for each of the anti-BCMA CAR T cells.

To examine proliferation, anti-BCMA CAR T cells were labeled with carboxyfluorescein succinimidyl ester (CFSE) prior to co-culture with EoL-1, NCI-H929, or MM1S target cells at a 1:1 E:T ratio in R10 media. Five days later, T cell proliferation was assessed by flow cytometric analysis of CFSE dilution (FIGS. 18A-18B).

Example 7

Enhanced stability is a desired property of proteins. This is often assessed by determining the melting temperature of a protein under various conditions. Proteins with a higher melting temperature are generally stable for longer times. When a CAR is more thermostable, it may be functionally active for longer periods of time on the surface of a cell.

Thermal stability of the CAR extracellular domain (ECD) with the longer hinge domain, i.e., the complete hinge domain ("CHD") and the thermal stability of the CAR ECD with a truncated hinge domain ("THD") was measured using a Bio-Rad C1000 thermal cycler, CFx96 Real-Time system. Unfolding of the proteins was monitored using the fluorescent dye SYPRO Orange (Invitrogen) which binds to hydrophobic amino acids that become solvent exposed as the protein unfolds. A temperature gradient was set up from 25° C. to 95° C. with 1° C./1 minute increments. Each sample contained 10 µM recombinant CAR ECD protein and 5×SYPRO Orange (Molecular Probes™ SYPRO™ Orange Protein Gel Stain (5,000× Concentrate in DMSO)). The assay was performed in PBS with or without 50 mM NaCl.

Figure 19A:
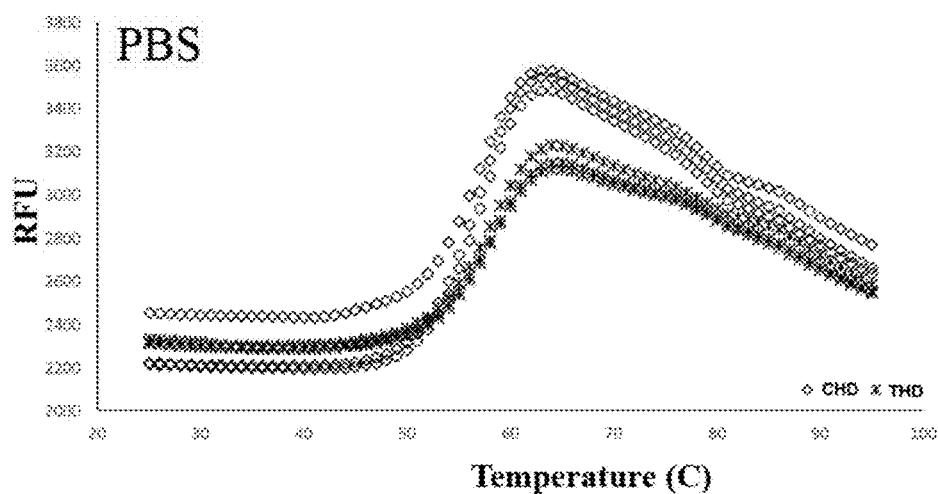
FIG. 19A and FIG. 19B are graphs showing thermostability of chimeric antigen receptors (CARs) of the present invention.
Figure 19B:
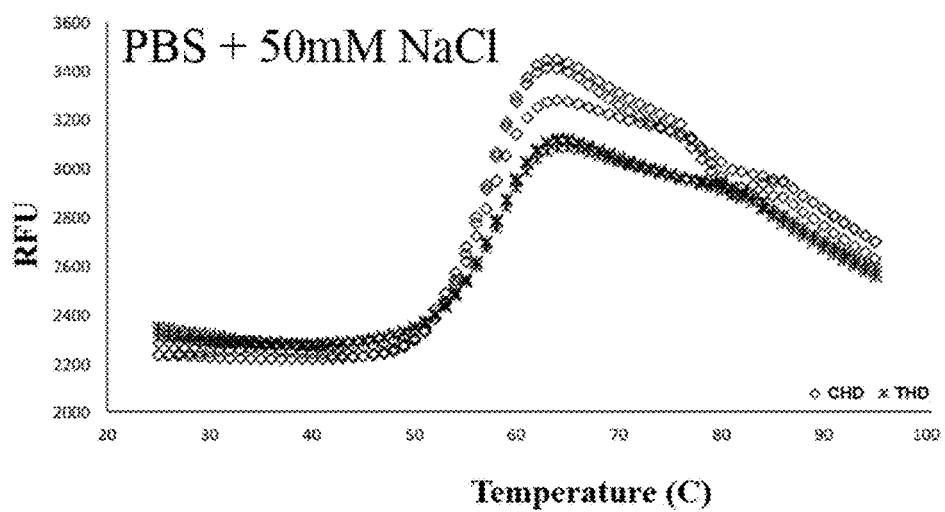

As shown in FIG. 19A and FIG. 19B, a CAR's ECD which has a THD shows enhanced thermostability compared to a CAR's ECD which has a CHD, e.g., including the IEVMYPPPY (SEQ ID NO: 250) motif. These methods described in this example is a useful method for testing stability of mRNA encoding a CAR and the CAR itself, because once a T cell has been transduced with the mRNA encoding a CAR, the transduced T cell will express the CAR and the stability of an individual mRNA or protein cannot be readily assessed.

What is claimed is:

1. An isolated polynucleotide encoding a chimeric antigen receptor (CAR) that comprises:
   (i) an antigen binding molecule;
   (ii) a costimulatory domain, consisting of SEQ ID NO: 241; and
   (iii) an intracellular activation domain from CD3 zeta;
   wherein the antigen binding molecule is linked to the costimulatory domain through 1 to 6 heterologous amino acids; and
   wherein the antigen is selected from ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD30, CD40, disialogangliosideGD2, ductal-epithelial mucine, gp36, TAG-72, glycosphingolipids, glioma-associated antigen, B-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, mutated p53, prostein, PSMA, survivin, telomerase, prostate-carcinoma tumor antigen-1(PCTA-1), MAGE, MAGE-A1, ELF2M, neutrophil elastase, ephrin B2, CD22, insulin growth factor (IGFI)-I, IGF-II, IGFI receptor, a major histocompatibility complex (MHC) molecule presenting a tumor-specific peptide epitope, 5T4, ROR1, Nkp30, NKG2D, tumor stromal antigen, the extra domain A (EDA) of fibronectin, the extra domain B (EDB) of fibronectin, the A1 domain of tenascin-C (TnC A1), fibroblast associated protein (fap), CD3, CD4, CD8, CD24, CD25, CD33, CD34, CD133, CD138, CTLA-4, B7-1 (CD80), B7-2 (CD86), endoglin, a major histocompatibility complex (MHC) molecule, an HIV-specific antigen, HIV gp120, an EBV-specific antigen, a CMV-specific antigen, an HPV-specific antigen, an HBV-specific antigen, an HCV-specific antigen, a Lassa Virus-specific antigen, an Influenza Virus-specific antigen, CD38, CA-125, MUC-1, CD44, surface adhesion molecule, vascular endothelial growth factor receptor-2 (VEGFR2), high molecular weight-melanoma associated antigen (HMW-MAA), epithelial tumor antigen, IL-13R-a2, GD2, GD3, prostate-specific antigen, melanoma-associated antigen, mutated ras, folate binding protein, HIV-l envelope glycoprotein gp41, CD123, CD23, CD56, c-Met, HERV-K, IL-11Ralpha, kappa chain, lambda chain, CSPG4, HER1-HER2 in combination, or HER2-HER3 in combination.

2. The polynucleotide of claim 1, wherein the antigen binding molecule comprises a heavy chain variable region (VH) and a light chain variable region (VL), wherein the VH comprises 3 complementarity determining regions (CDRs) and the VL comprises 3 CDRs.

3. The polynucleotide of claim 1, wherein the antigen binding molecule specifically binds an antigen selected from the group consisting of 5T4, alphafetoprotein, CA-125, carcinoembryonic antigen, CD19, CD20, CD22, CD23, CD30, CD33, CD56, CD123, CD138, c-Met, CSPG4, EGFRvIIi, epithelial tumor antigen, folate binding protein, GD2, GD3, HER1-HER2 in combination, HER2-HER3 in combination, ErbB2 (HER2/neu), HERV-K, HIV-1 envelope glycoprotein gp41, HIV-1 envelope glycoprotein gp120, IL-11Ralpha, kappa chain, lambda chain, melanoma associated antigen, mesothelin, MUC-1, mutated p53, mutated ras, prostate-specificantigen, ROR1, or VEGFR2.

4. The polynucleotide of claim 1, wherein the activation domain comprises SEQ ID NO: 9 or SEQ ID NO: 251.

5. The polynucleotide of claim 1, wherein the activation domain is encoded by a nucleotide sequence comprising SEQ ID NO: 8.

6. The polynucleotide of claim 1, wherein the CAR further comprises a leader peptide.

7. The polynucleotide of claim 6, wherein the leader peptide comprises an amino acid sequence comprising SEQ ID NO: 11.

8. The polynucleotide of claim 6, wherein the leader peptide is encoded by a nucleotide sequence comprising SEQ ID NO: 10.

9. A vector comprising the polynucleotide of claim 1.

10. The vector of claim 9, wherein the vector is an adenoviral vector, an adenovirus-associated vector, a DNA vector, a lentiviral vector, a plasmid, a retroviral vector, or an RNA vector, or any combination thereof.

11. A polypeptide encoded by the polynucleotide of claim 1.

12. A cell comprising the polynucleotide of claim 1.

13. The cell of claim 12, wherein the cell is a T cell.

14. The cell of claim 13, wherein the T cell is an allogeneic T cell, an autologous T cell, an engineered autologous T cell, or a tumor-infiltrating lymphocyte (TIL).

15. The cell of claim 13, wherein the T cell is a CD4+ T cell.

16. The cell of claim 13, wherein the T cell is a CD8+ T cell.

17. The cell of claim 13, wherein the T cell is an in vitro cell.

18. The cell of claim 13, wherein the T cell is an autologous T cell.

19. A composition comprising the polynucleotide of claim 1.

20. A method of making a cell expressing a CAR comprising transducing a cell with the polynucleotide of claim 1 under suitable conditions.

21. A polypeptide encoded by the vector of claim 9.

22. A cell comprising the vector of claim 9.

23. A composition comprising the vector of claim 9.

24. A cell comprising the polypeptide of claim 11.

25. A composition comprising the polypeptide of claim 11.

26. A composition comprising the cell of claim 12.

27. The isolated polynucleotide of claim 1, wherein the encoded CAR further comprises an intracellular domain comprising a signaling region of 4-1BB/CD137.

* * * * *

UNITED STATES PATENT AND TRADEMARK OFFICE
CERTIFICATE OF CORRECTION

| | | |
|---|---|---|
| PATENT NO. | : 10,603,380 B2 | Page 1 of 1 |
| APPLICATION NO. | : 15/475681 | |
| DATED | : March 31, 2020 | |
| INVENTOR(S) | : Jed Wiltzius | |

It is certified that error appears in the above-identified patent and that said Letters Patent is hereby corrected as shown below:

On the Title Page

In Column 2, item (74), Attorney, Agent, or Firm, Lines 1-2, delete "Arrigo LeeGuttman Mouta-Bellum" and insert -- Arrigo, Lee, Guttman & Mouta-Bellum LLP --.

In the Claims

In Column 465, Line 27, Claim 1, delete "disialogangliosideGD2," and insert -- disialoganglioside GD2, --.

In Column 465, Lines 33-34, Claim 1, delete "prostase" and insert -- prostate --.

In Column 465, Line 36, Claim 1, delete "1(PCTA-1)," and insert -- 1 (PCTA-1), --.

In Column 465, Line 59, Claim 1, delete "HIV-l" and insert -- HIV-1 --.

In Column 466, Line 18, Claim 3, delete "EGFRvIIi," and insert -- EGFRvIII, --.

In Column 466, Line 24, Claim 3, delete "prostate-specificantigen," and insert -- prostate-specific antigen, --.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*

```
                        SEQUENCE LISTING

<160> NUMBER OF SEQ ID NOS: 284

<210> SEQ ID NO 1
<211> LENGTH: 220
<212> TYPE: PRT
<213> ORGANISM: Homo sapiens

<400> SEQUENCE: 1

Met Leu Arg Leu Leu Ala Leu Asn Leu Phe Pro Ser Ile Gln Val
1               5                   10                  15

Thr Gly Asn Lys Ile Leu Val Lys Gln Ser Pro Met Leu Val Ala Tyr
                20                  25                  30

Asp Asn Ala Val Asn Leu Ser Cys Lys Tyr Ser Tyr Asn Leu Phe Ser
            35                  40                  45

Arg Glu Phe Arg Ala Ser Leu His Lys Gly Leu Asp Ser Ala Val Glu
        50                  55                  60

Val Cys Val Val Tyr Gly Asn Tyr Ser Gln Gln Leu Gln Val Tyr Ser
65                  70                  75                  80

Lys Thr Gly Phe Asn Cys Asp Gly Lys Leu Gly Asn Glu Ser Val Thr
                85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
        115                 120                 125

Asn Gly Thr Ile Ile His Val Lys Gly Lys His Leu Cys Pro Ser Pro
    130                 135                 140

Leu Phe Pro Gly Pro Ser Lys Pro Phe Trp Val Leu Val Val Val Gly
145                 150                 155                 160

Gly Val Leu Ala Cys Tyr Ser Leu Leu Val Thr Val Ala Phe Ile Ile
                165                 170                 175

Phe Trp Val Arg Ser Lys Arg Ser Arg Leu Leu His Ser Asp Tyr Met
            180                 185                 190

Asn Met Thr Pro Arg Arg Pro Gly Pro Thr Arg Lys His Tyr Gln Pro
        195                 200                 205

Tyr Ala Pro Pro Arg Asp Phe Ala Ala Tyr Arg Ser
        210                 215                 220

<210> SEQ ID NO 2
<211> LENGTH: 90
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Hinge Domain

<400> SEQUENCE: 2
cttgataatg aaaagtcaaa cggaacaatc attcacgtga agggcaagca cctctgtccg      60
tcacccttgt tccctggtcc atccaagcca                                       90

<210> SEQ ID NO 3
```

```
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Hinge Domain

<400> SEQUENCE: 3

Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro
            20                  25                  30

<210> SEQ ID NO 4
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TM Domain

<400> SEQUENCE: 4
ttctgggtgt tggtcgtagt gggtggagtc ctcgcttgtt actctctgct cgtcaccgtg    60
gcttttataa tcttctgggt t                                              81

<210> SEQ ID NO 5
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TM Domain

<400> SEQUENCE: 5

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 6
<211> LENGTH: 123
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Signaling/Costimunlatory Domain

<400> SEQUENCE: 6
agatccaaaa gaagccgcct gctccatagc gattacatga atatgactcc acgccgccct    60
ggccccacaa ggaaacacta ccagccttac gcaccaccta gagatttcgc tgcctatcgg   120
agc                                                                 123

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<223> OTHER INFORMATION: Signaling/Costimulatory Domain

<400> SEQUENCE: 7

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
            35                  40

<210> SEQ ID NO 8
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CD3z Activation Domain

<400> SEQUENCE: 8
agggtgaagt tttccagatc tgcagatgca ccagcgtatc agcagggcca gaaccaactg     60
tataacgagc tcaacctggg acgcagggaa gagtatgacg ttttggacaa gcgcagagga    120
cgggaccctg agatgggtgg caaaccaaga cgaaaaaacc cccaggaggg tctctataat    180
gagctgcaga aggataagat ggctgaagcc tattctgaaa taggcatgaa aggagagcgg    240
agaaggggaa aagggcacga cggtttgtac cagggactca gcactgctac gaaggatact    300
tatgacgctc tccacatgca agccctgcca cctagg                              336

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD3z Activation Domain

<400> SEQUENCE: 9

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 10
<211> LENGTH: 63
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide
<220> FEATURE:
<223> OTHER INFORMATION: Signal (leader) Peptide

<400> SEQUENCE: 10
atggcactcc cgtaactgc tctgctgctg ccgttggcat tgctcctgca cgccgcacgc    60
ccg                                                                 63

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Signal (leader) Peptide

<400> SEQUENCE: 11

Met Ala Leu Pro Val Thr Ala Leu Leu Leu Pro Leu Ala Leu Leu Leu
1               5                   10                  15

His Ala Ala Arg Pro
            20

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Linker

<400> SEQUENCE: 12

Gly Ser Thr Ser Gly Ser Gly Lys Pro Gly Ser Gly Glu Gly Ser Thr
1               5                   10                  15

Lys Gly

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 13

Gly Phe Thr Phe Ser Ser Tyr
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 14

Phe Thr Phe Ser Ser Tyr
```

```
<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 15

Gly Tyr Thr Phe Thr Ser Tyr
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 16

Gly Gly Ser Ile Ser Ser Ser Ser Tyr
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 17

Gly Phe Thr Phe Ser Ser Tyr
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 18

Gly Phe Thr Phe Ser Ser Tyr Gly Met His
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 19
```

Gly Gly Thr Phe Ser Ser Tyr
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 20

Gly Phe Thr Phe Ser Ser Tyr
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 21

Ser Gly Ser Gly Gly Ser
1               5

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 22

Ser Tyr Asp Gly Ser Asn Lys Tyr Tyr Ala Asp Ser Val Lys Gly
1               5                   10                  15

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 23

Asn Pro Gly Gly Gly Ser
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 24

Ser Tyr Ser Gly Ser
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 25

Ser Ser Ser Ser Ser Thr
1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 26

Ser Tyr Asp Gly Ser Asn
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 27

Ile Pro Ile Phe Gly Thr
1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 28

Ser Tyr Asp Gly Ser Asn
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

```
<400> SEQUENCE: 29

Ala Glu Met Gly Ala Val Phe Asp Ile
1               5

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 30

Asp Gly Thr Tyr Leu Gly Gly Leu Trp Tyr Phe Asp Leu
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 31

Glu Ser Trp Pro Met Asp Val
1               5

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 32

Gly Arg Gly Tyr Ala Thr Ser Leu Ala Phe Asp Ile
1               5                   10

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 33

Gly Ser Gln Glu His Leu Ile Phe Asp Tyr
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3
```

<400> SEQUENCE: 34

Thr Asp Phe Trp Ser Gly Ser Pro Pro Gly Leu Asp Tyr
1               5                   10

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 35

Thr Pro Glu Tyr Ser Ser Ser Ile Trp His Tyr Tyr Tyr Gly Met Asp
1               5                   10                  15
Val

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 36

Gly Pro Leu Gln Glu Pro Pro Tyr Asp Tyr Gly Met Asp Val
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 37

Arg Ala Ser Gln Ser Val Ser Arg Tyr Leu Ala
1               5                   10

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 38

Arg Ser Ser Gln Ser Leu Leu His Ser Asn Gly Tyr Asn Tyr Leu Asp
1               5                   10                  15

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<223> OTHER INFORMATION: VL CDR1

<400> SEQUENCE: 39

Arg Ala Ser Gln Ser Val Ser Ser Asn Leu Ala
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 40

Arg Ala Ser Gln Ser Val Ser Ser Tyr Leu Ala
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 41

Arg Ala Ser Gln Ser Val Ser Arg Tyr Leu Ala
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 42

Arg Ala Ser Gln Gly Ile Ser Ser Trp Leu Ala
1               5                   10

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 43

Lys Ser Ser Gln Ser Val Leu Tyr Ser Ser Asn Asn Lys Asn Tyr Leu
1               5                   10                  15

Ala

<210> SEQ ID NO 44
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 44

Arg Ala Ser Gln Ser Val Ser Ser Asn Leu Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 45

Asp Ala Ser Asn Arg Ala Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 46

Leu Gly Ser Asn Arg Ala Ser
1               5

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 47

Gly Ala Ser Thr Arg Ala Thr
1               5

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 48

Asp Ala Ser Asn Arg Ala Thr
1               5

<210> SEQ ID NO 49
<211> LENGTH: 7
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 49

Asp Ala Ser Asn Arg Ala Thr
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 50

Gly Ala Ser Ser Leu Gln Ser
1               5

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 51

Trp Ala Ser Thr Arg Glu Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 52

Ser Ala Ser Thr Arg Ala Thr
1               5

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 53

Gln Gln Arg Ile Ser Trp Pro Phe Thr
1               5

<210> SEQ ID NO 54
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 54

Met Gln Gly Leu Gly Leu Pro Leu Thr
1               5

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 55

Gln Gln Tyr Ala Ala Tyr Pro Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 56

Gln Gln Arg His Val Trp Pro Pro Thr
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 57

Gln Gln Arg Phe Tyr Tyr Pro Trp Thr
1               5

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 58

Gln Gln Ile Tyr Thr Phe Pro Phe Thr
1               5
```

```
<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 59

Gln Gln Phe Ala His Thr Pro Phe Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 60

Gln Gln His His Val Trp Pro Leu Thr
1               5

<210> SEQ ID NO 61
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 61
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcagct attagtggta gtggtggtag cacatactac      180
gcagactccg tgaagggccg gttcaccatc tccagagaca attccaagaa cacgctgtat    240
ctgcaaatga acagcctgag agccgaggac acggcggtgt actactgcgc aagagccgag    300
atgggagccg tattcgacat atggggtcag ggtacaatgg tcaccgtctc ctca           354

<210> SEQ ID NO 62
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 62
caggtgcagc tggtggagtc tgggggaggc gtggtccagc ctggggaggtc cctgagactc    60 tcctgtgcag cgtctggatt caccttcagt agctatggca tgcactgggt ccgccaggct    120
ccaggcaagg gctggagtg gtggcagtt atatcgtatg atggaagtaa taaatactat      180
gcagactccg tgaagggccg attcaccatc tccagagaca attccaagaa cacgctgtat    240
ctgcaaatga acagcctgag agccgaggac acggcggtgt actactgcgc cagagacggt    300
```

```
acttatctag gtggtctctg gtacttcgac ttatggggga gaggtaccct ggtcaccgtc    360
tcctca                                                                366

<210> SEQ ID NO 63
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 63
caggtgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg atgggaata atcaaccctg gtggtggtag cacaagctac    180
gcacagaagt tccagggcag agtcaccatg accagggaca cgtccacgag cacagtctac   240
atggagctga gcagcctgag atctgaggac acggcggtgt actactgcgc cagagagagt   300
tggccaatgg acgtatgggg ccagggaaca actgtcaccg tctcctca                348

<210> SEQ ID NO 64
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 64
cagctgcagc tgcaggagtc gggcccagga ctggtgaagc cttcggagac cctgtccctc    60
acctgcactg tctctggtgg ctccatcagc agtagtagtt actactgggg ctggatccgc   120
cagcccccag ggaaggggct ggagtggatt gggagtatct cctatagtgg gagcacctac   180
tacaacccgt ccctcaagag tcgagtcacc atatccgtag acacgtccaa gaaccagttc   240
tccctgaagc tgagttctgt gaccgccgca gacacggcgg tgtactactg cgccagaggc   300
aggggatatg caaccagctt agccttcgat atctggggtc agggtacaat ggtcaccgtc   360
tcctca                                                                366

<210> SEQ ID NO 65
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 65
gaggtgcagc tggtggagtc tgggggaggc ttggtacagc ctgggggtc cctgagactc    60 tcctgtgcag cctctggatt caccttcagt agctatagca tgaactgggt ccgccaggct   120
ccagggaagg gctggagtg gtttcaacc attagtagta gtagtagtac catatactac   180
gcagactctg tgaagggccg attcaccatc tccagagaca atgccaagaa ctcactgtat   240
ctgcaaatga acagcctgag agctgaggac acggcggtgt actactgcgc cagaggttct   300
```
caggagcacc tgattttcga ttattgggga cagggtacat tggtcaccgt ctcctca 357

<210> SEQ ID NO 66
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 66
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt atatcgtatg atggaagtaa taaatactat   180
gcagactccg tgaagggccg attcaccatc tccagagaca attccaagaa cacgctgtat   240
ctgcaaatga acagcctgag agccgaggac acggcggtgt actactgcgc cagaactgac   300
ttctggagcg atcccctcc aggcttagat tactggggac agggtacatt ggtcaccgtc   360
tcctca                                                              366

<210> SEQ ID NO 67
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 67
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag ggcttgagtg gatgggaggg atcatcccta tctttggtac agcaaactac   180
gcacagaagt tccagggcag agtcacgatt accgcggacg aatccacgag cacagcctac   240
atggagctga gcagcctgag atctgaggac acggcggtgt actactgcgc cagaactcct   300
gaatactcct ccagcatatg gcactattac tacggcatgg acgtatgggg ccagggaaca   360
actgtcaccg tctcctca                                                 378

<210> SEQ ID NO 68
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 68
caggtgcagc tggtggagtc tgggggaggc gtggtccagc ctggggaggtc cctgagactc    60 tcctgtgcag cgtctggatt caccttcagt agctatggca tgcactgggt ccgccaggct   120
ccaggcaagg ggctggagtg ggtggcagtt atatcgtatg atggaagtaa taaatactat   180
gcagactccg tgaagggccg attcaccatc tccagagaca attccaagaa cacgctgtat   240
ctgcaaatga acagcctgag agccgaggac acggcggtgt actactgcgt caaggggccg   300

```
ttgcaggagc cgccatacga ttatggaatg gacgtatggg gccagggaac aactgtcacc    360
gtctcctca                                                             369
```

<210> SEQ ID NO 69
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 69

```
gaaattgtgt tgacacagtc tccagccacc ctgtctttgt ctccagggga aagagccacc     60
ctctcctgca gggccagtca gagtgttagc aggtacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag agaatctcct ggcctttcac ttttggcgga    300
gggaccaagg ttgagatcaa a                                               321
```

<210> SEQ ID NO 70
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 70

```
gatattgtga tgactcagtc tccactctcc ctgcccgtca ccctggaga gccggcctcc      60 atctcctgca ggtctagtca gagcctcctg catagtaatg gatacaacta tttggattgg    120
tacctgcaga agccagggca gtctccacag ctcctgatct atttgggttc taatcgggcc    180
tccggggtcc ctgacaggtt cagtggcagt ggatcaggca cagattttac actgaaaatc    240
agcagagtgg aggctgagga tgttggggtt tattactgca tgcagggact cggcctccct    300
ctcacttttg gcggagggac caaggttgag atcaaa                               336
```

<210> SEQ ID NO 71
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 71

```
gaaatagtga tgacgcagtc tccagccacc ctgtctgtgt ctccagggga aagagccacc     60
ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag tacgccgcct accctacttt tggcggaggg    300
accaaggttg agatcaaa                                                   318
```

<210> SEQ ID NO 72
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 72
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag agacacgtct ggcctcctac ttttggcgga   300
gggaccaagg ttgagatcaa a                                              321

<210> SEQ ID NO 73
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 73
gaaattgtgt tgacacagtc tccagccacc ctgtctttgt ctccagggga aagagccacc    60
ctctcctgca gggccagtca gagtgttagc aggtacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag agattctact acccttggac ttttggcgga   300
gggaccaagg ttgagatcaa a                                              321

<210> SEQ ID NO 74
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 74
gacatccagt tgacccagtc tccatcttcc gtgtctgcat ctgtaggaga cagagtcacc    60
atcacttgtc gggcgagtca gggtattagc agctggttag cctggtatca gcagaaacca   120
gggaaagccc ctaagctcct gatctatggt gcatccagtt tgcaaagtgg ggtcccatca   180
aggttcagcg gcagtggatc tgggacagat ttcactctca ccatcagcag cctgcagcct   240
gaagattttg caacttatta ctgtcagcag atatacacct tccctttcac ttttggcgga   300
gggaccaagg ttgagatcaa a                                              321

<210> SEQ ID NO 75
<211> LENGTH: 339
<212> TYPE: DNA

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: VL DNA

<400> SEQUENCE: 75

```
gacatcgtga tgacccagtc tccagactcc ctggctgtgt ctctgggcga gagggccacc      60
atcaactgca gtccagcca gagtgtttta tacagctcca acaataagaa ctacttagct     120
tggtaccagc agaaaccagg acagcctcct aagctgctca tttactgggc atctacccgg     180
gaatccgggg tccctgaccg attcagtggc agcgggtctg ggacagattt cactctcacc     240
atcagcagcc tgcaggctga agatgtggca gtttattact gtcagcagtt cgcccacact     300
cctttcactt ttggcggagg gaccaaggtt gagatcaaa                            339
```

<210> SEQ ID NO 76
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: VL DNA

<400> SEQUENCE: 76

```
gaaatagtga tgacgcagtc tccagccacc ctgtctgtgt ctccagggga aagagccacc      60
ctctcctgca gggccagtca gagtgttagc agcaacttag cctggtacca gcagaaacct     120
ggccaggctc ccaggctcct catctatagc gcatccacca gggccactgg tatcccagcc     180
aggttcagtg gcagtgggtc tgggacagag ttcactctca ccatcagcag cctgcagtct     240
gaagattttg cagtttatta ctgtcagcag caccacgtct ggcctctcac ttttggcgga     300
gggaccaagg ttgagatcaa a                                               321
```

<210> SEQ ID NO 77
<211> LENGTH: 118
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: VH Protein

<400> SEQUENCE: 77

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Glu Met Gly Ala Val Phe Asp Ile Trp Gly Gln Gly Thr
            100                 105                 110
```

Met Val Thr Val Ser Ser
        115

<210> SEQ ID NO 78
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH Protein

<400> SEQUENCE: 78

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Thr Tyr Leu Gly Gly Leu Trp Tyr Phe Asp Leu Trp
            100                 105                 110

Gly Arg Gly Thr Leu Val Thr Val Ser Ser
        115                 120

<210> SEQ ID NO 79
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH Protein

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Gly Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Ser Trp Pro Met Asp Val Trp Gly Gln Gly Thr Thr Val
            100                 105                 110

Thr Val Ser Ser
        115

```
<210> SEQ ID NO 80
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH Protein

<400> SEQUENCE: 80

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Ser Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Arg Gly Tyr Ala Thr Ser Leu Ala Phe Asp Ile Trp
            100                 105                 110

Gly Gln Gly Thr Met Val Thr Val Ser Ser
        115                 120

<210> SEQ ID NO 81
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH Protein

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Thr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Gln Glu His Leu Ile Phe Asp Tyr Trp Gly Gln Gly
            100                 105                 110

Thr Leu Val Thr Val Ser Ser
        115

<210> SEQ ID NO 82
<211> LENGTH: 122
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<223> OTHER INFORMATION: VH Protein

<400> SEQUENCE: 82

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Asp Phe Trp Ser Gly Ser Pro Pro Gly Leu Asp Tyr Trp
            100                 105                 110

Gly Gln Gly Thr Leu Val Thr Val Ser Ser
        115                 120

<210> SEQ ID NO 83
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH Protein

<400> SEQUENCE: 83

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Pro Glu Tyr Ser Ser Ser Ile Trp His Tyr Tyr Tyr Gly
            100                 105                 110

Met Asp Val Trp Gly Gln Gly Thr Thr Val Thr Val Ser Ser
        115                 120                 125

<210> SEQ ID NO 84
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH Protein -continued

<400> SEQUENCE: 84

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Pro Leu Gln Glu Pro Pro Tyr Asp Tyr Gly Met Asp Val
            100                 105                 110

Trp Gly Gln Gly Thr Thr Val Thr Val Ser Ser
        115                 120
```

<210> SEQ ID NO 85
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL Protein

<400> SEQUENCE: 85

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Ser Trp Pro Phe
                85                  90                  95

Thr Phe Gly Gly Gly Thr Lys Val Glu Ile Lys
            100                 105
```

<210> SEQ ID NO 86
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL Protein

<400> SEQUENCE: 86

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30
```

```
Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Leu Gly Leu Pro Leu Thr Phe Gly Gly Gly Thr Lys Val Glu Ile Lys
            100                 105                 110

<210> SEQ ID NO 87
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL Protein

<400> SEQUENCE: 87

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Ala Ala Tyr Pro Thr
                 85                  90                  95

Phe Gly Gly Gly Thr Lys Val Glu Ile Lys
            100                 105

<210> SEQ ID NO 88
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL Protein

<400> SEQUENCE: 88

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
         35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg His Val Trp Pro Pro
                 85                  90                  95
```

Thr Phe Gly Gly Gly Thr Lys Val Glu Ile Lys
            100                 105

<210> SEQ ID NO 89
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL Protein

<400> SEQUENCE: 89

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Phe Tyr Tyr Pro Trp
                85                  90                  95

Thr Phe Gly Gly Gly Thr Lys Val Glu Ile Lys
            100                 105

<210> SEQ ID NO 90
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL Protein

<400> SEQUENCE: 90

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ile Tyr Thr Phe Pro Phe
                85                  90                  95

Thr Phe Gly Gly Gly Thr Lys Val Glu Ile Lys
            100                 105

<210> SEQ ID NO 91
<211> LENGTH: 113
<212> TYPE: PRT
<213> ORGANISM: Artificial Sequence
<220> FEATURE:
<223> OTHER INFORMATION: Description of Artificial Sequence: Synthetic

```
             polypeptide
<220> FEATURE:
<223> OTHER INFORMATION: VL Protein

<400> SEQUENCE: 91

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Phe Ala His Thr Pro Phe Thr Phe Gly Gly Gly Thr Lys Val Glu Ile
            100                 105                 110

Lys

<210> SEQ ID NO 92
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL Protein

<400> SEQUENCE: 92

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Ser Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln His His Val Trp Pro Leu
                85                  90                  95

Thr Phe Gly Gly Gly Thr Lys Val Glu Ile Lys
            100                 105

<210> SEQ ID NO 93
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 93

Gly Gly Ser Ile Ser Ser Tyr
1               5
```

```
<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 94

Gly Gly Ser Ile Ser Ser Gly Gly Phe
1               5

<210> SEQ ID NO 95
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 95

Gly Tyr Thr Leu Thr Glu Leu
1               5

<210> SEQ ID NO 96
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR1

<400> SEQUENCE: 96

Gly Phe Thr Phe Ser Ser Tyr
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 97

Tyr Tyr Ser Gly Ser
1               5

<210> SEQ ID NO 98
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 98

His His Ser Gly Ser
1               5
```

```
<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 99

Asp Pro Glu Asp Gly Glu
1               5

<210> SEQ ID NO 100
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR2

<400> SEQUENCE: 100

Ser Tyr Asp Gly Ser Asp
1               5

<210> SEQ ID NO 101
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 101

Leu Val Tyr Cys Gly Gly Asp Cys Tyr Ser Gly Phe Asp Tyr
1               5                   10

<210> SEQ ID NO 102
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 102

Leu Val Tyr Cys Gly Gly Asp Cys Tyr Ser Gly Phe Asp Tyr
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 103

Glu Ser Arg Gly Ile Gly Trp Pro Tyr Phe Asp Tyr
```

<210> SEQ ID NO 104
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VH CDR3

<400> SEQUENCE: 104

Glu Arg Tyr Ser Gly Arg Asp Tyr
1               5

<210> SEQ ID NO 105
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 105

Gln Ala Ser Gln Asp Ile Asn Asn Phe Leu Asn
1               5                   10

<210> SEQ ID NO 106
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 106

Gln Ala Ser Gln Asp Ile Asn Asn Phe Leu Asn
1               5                   10

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 107

Arg Ala Ser Gln Ser Ile Ser Ser Tyr Leu Asn
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR1

<400> SEQUENCE: 108

```
Arg Ala Ser Gln Ser Val Ser Ser Leu Leu Thr
1               5                   10
```

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 109

```
Asp Ala Ser Asn Leu Glu Thr
1               5
```

<210> SEQ ID NO 110
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 110

```
Asp Ala Ser Asn Leu Glu Thr
1               5
```

<210> SEQ ID NO 111
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 111

```
Gly Ala Ser Ser Leu Lys Ser
1               5
```

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR2

<400> SEQUENCE: 112

```
Gly Ala Ser Thr Arg Ala Thr
1               5
```

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 113

Gln Gln Tyr Gly Asn Leu Pro Phe Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 114

Gln Gln Tyr Gly Asn Leu Pro Phe Thr
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 115

Gln Gln Ser Tyr Ser Thr Pro Ile Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: VL CDR3

<400> SEQUENCE: 116

Gln Gln Tyr Asp Thr Trp Pro Phe Thr
1               5

<210> SEQ ID NO 117
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VH DNA

<400> SEQUENCE: 117
caggtgcagc tgcaggaatc cggaccgggg ctggtgaagc ccagcgagac tctgagtctc      60
acgtgtacag tttctggagg tagcattagc tcctactatt ggtcatggat aaggcagccc     120
cccgggaagg gattggaatg gatcggctat atttactaca gtgggagcac caattacaac     180
ccctcactga agtctagagt tacaatcagc gttgacacct caaagaatca gttcagtttg     240
aaattgtcta gcgtcacagc agctgataca gccgtctatt attgtgtttc tctggtctat     300
tgcggtgggg attgttacag tggctttgac tattgggggc agggtactct ggttacagtt     360
tcttcc                                                                366

<210> SEQ ID NO 118
<211> LENGTH: 372
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: VH DNA

<400> SEQUENCE: 118

```
caggtacagc tgcaggaatc tgggcccgga cttgtcaagc caagtcagac actttctctt    60
acatgtaccg tgagcggcgg aagtataagc agtggaggct tttactggtc ttggatacgg   120
cagcacccag gcaaaggctt ggagtggatt ggatacattc atcattcagg atctacacac   180
tataatccat cccttaagtc ccgggtcacc attagcattg atacgtctaa gaatctgttc   240
agtctcaggc tgtcctccgt cactgctgcc gacacagccg tgtactactg cgcctccttg   300
gtttactgcg gaggcgactg ttatagcggc tttgattatt ggggcagggg gaccctcgta   360
accgtgagct ct                                                        372
```

<210> SEQ ID NO 119
<211> LENGTH: 363
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: VH DNA

<400> SEQUENCE: 119

```
caggtccaac tggtgcagtc cggagccgaa gtcaagaaac caggtgcctc cgttaaagtg    60
agttgcaaag tctctggata cactctgacc gagctctcta tgcactgggt ccggcaggcc   120
cccggcaagg gattggaatg gatgggcggg ttcgatcctg aggacggaga gactatctac   180
gctcaaaaat tccagggacg agtgactgtg accgaagaca ctagtaccga cactgcctac   240
atggaacttt cctctctgcg atcagaagat accgcagtgt actactgtgc tactgaatct   300
aggggcattg gatggcccta cttcgattac tggggtcagg gaactctggt gactgtctcc   360
agc                                                                  363
```

<210> SEQ ID NO 120
<211> LENGTH: 351
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: VH DNA

<400> SEQUENCE: 120

```
caggtccagt tggtcgaaag tggcggtggt gtagtgcagc cgggccgcag tttgaggctt    60
tcctgtgcgg cttcaggctt tacttttcc agctatggaa tgcactgggt gcggcaggcc   120
cccggcaaag gacttgagtg gtggccgtc atttcttatg acggatcaga taagtactac   180
gtggacagcg tcaagggcag attcaccatc tctagggaca cagtaaaaa tagactctac   240
ctccagatga atagcctcag agctgaagac acggccgtct actattgtgc tcgggagcgg   300
tatagtggca gagactactg ggggcagggc acactcgtta cagtgagtag c             351
```

```
<210> SEQ ID NO 121
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 121
gacatccagt tgacacagag cccgagttcc ttgtccgcct ccgtcgggga tagagtgtca      60
tttacctgtc aggcctctca ggatattaat aactttctga attggtatca gcaaaagccc     120
ggaaaggcac ccaagctgtt gatttacgac gccagtaacc tggagacagg cgtgccctcc     180
cggtttagtg gtagcggaag cggtacggat tttacctttta ctatcagctc tctccaaccc    240
gaagacattg caacctacta ttgtcaacaa tatggaaacc tgcctttac atttggcggc      300 ggcaccaagg tggagattaa gcgg                                            324

<210> SEQ ID NO 122
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 122
gatatccagc tcactcaaag cccctctagt ctctctgcct cagtggggga tcgggtcagt      60
tttacttgtc aagcttcaca ggatatcaac aacttcctta attggtatca gcagaagcca     120
ggaaaagcac ccaagctgct catctatgat gcctcaaatt tggagacggg tgttcccagt     180
cgattctctg gtcagggtc cggaccgac tttacgttta cgatctcctc tctgcagccc       240
gaagacatcg ccacatacta ttgtcaacag tacggcaact tgcctttcac atttggggc      300 gggactaagg ttgaaatcaa gagg                                            324

<210> SEQ ID NO 123
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: VL DNA

<400> SEQUENCE: 123
gatattcaga tgactcaatc tccttcttct ctgtccgctt ccgtgggcga tagagtgacc      60
attacttgta gggcgtccca gtcaatctcc agttatttga attggtatca gcagaagccc     120
gggaaagcac ctaagctgtt gatcagcggg gcttctagcc tgaagagtgg ggtaccttca     180
cggttcagcg gaagcggaag cggaaccgat ttcaccctga ctatcagcag cctgccacct     240
gaggactttg caacttacta ctgccaacag tcatacagca ctccgatcac tttcggccag     300
ggcacccggc tcgaaatcaa gcgc                                            324

<210> SEQ ID NO 124
<211> LENGTH: 324
<212> TYPE: DNA
```

<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: VL DNA

<400> SEQUENCE: 124

```
gagattgtta tgacccagag tcctgcgacc ctctcagtca gccccgggga gcgcgcaact    60
ttgtcttgca gagctagtca gtccgtgtcc tctcttctga catggtacca gcaaaagccc   120
gggcaggctc cgcgcctttt gatctttggg gcttcaacaa gagccactgg gattcccgca   180
cgattctctg gctccgggag cggtactggt ttcaccctga cgattagcag tctccagagc   240
gaggacttcg ccgtatacta ctgccagcag tacgatacgt ggccattcac ttttggacca   300
gggactaaag tggattttaa gcgc                                          324
```

<210> SEQ ID NO 125
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: VH AA

<400> SEQUENCE: 125

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Ser Leu Val Tyr Cys Gly Gly Asp Cys Tyr Ser Gly Phe Asp Tyr Trp
            100                 105                 110

Gly Gln Gly Thr Leu Val Thr Val Ser Ser
        115                 120
```

<210> SEQ ID NO 126
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: VH AA

<400> SEQUENCE: 126

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45
```

Trp Ile Gly Tyr Ile His His Ser Gly Ser Thr His Tyr Asn Pro Ser
        50                  55                  60

Leu Lys Ser Arg Val Thr Ile Ser Ile Asp Thr Ser Lys Asn Leu Phe
 65                  70                  75                  80

Ser Leu Arg Leu Ser Ser Val Thr Ala Ala Asp Thr Ala Val Tyr Tyr
                 85                  90                  95

Cys Ala Ser Leu Val Tyr Cys Gly Gly Asp Cys Tyr Ser Gly Phe Asp
                100                 105                 110

Tyr Trp Gly Gln Gly Thr Leu Val Thr Val Ser Ser
            115                 120

<210> SEQ ID NO 127
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH AA

<400> SEQUENCE: 127

Gln Val Gln Leu Val Gln Ser Gly Ala Glu Val Lys Lys Pro Gly Ala
 1               5                  10                  15

Ser Val Lys Val Ser Cys Lys Val Ser Gly Tyr Thr Leu Thr Glu Leu
                 20                  25                  30

Ser Met His Trp Val Arg Gln Ala Pro Gly Lys Gly Leu Glu Trp Met
             35                  40                  45

Gly Gly Phe Asp Pro Glu Asp Gly Glu Thr Ile Tyr Ala Gln Lys Phe
        50                  55                  60

Gln Gly Arg Val Thr Val Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Glu Ser Arg Gly Ile Gly Trp Pro Tyr Phe Asp Tyr Trp Gly
                100                 105                 110

Gln Gly Thr Leu Val Thr Val Ser Ser
            115                 120

<210> SEQ ID NO 128
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH AA

<400> SEQUENCE: 128

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Ser Tyr Asp Gly Ser Asp Lys Tyr Tyr Val Asp Ser Val
        50                  55                  60

Lys Gly Arg Phe Thr Ile Ser Arg Asp Asn Ser Lys Asn Arg Leu Tyr

```
                65                  70                  75                  80
Leu Gln Met Asn Ser Leu Arg Ala Glu Asp Thr Ala Val Tyr Tyr Cys
                    85                  90                  95

Ala Arg Glu Arg Tyr Ser Gly Arg Asp Tyr Trp Gly Gln Gly Thr Leu
                100                 105                 110

Val Thr Val Ser Ser
        115

<210> SEQ ID NO 129
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL AA

<400> SEQUENCE: 129

Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg
                100                 105

<210> SEQ ID NO 130
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL AA

<400> SEQUENCE: 130

Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg
                100                 105
```

<210> SEQ ID NO 131
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: VL AA

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Ser Gly Ala Ser Ser Leu Lys Ser Gly Val Pro Ser Arg Phe Ser Gly
    50                  55                  60

Ser Gly Ser Gly Thr Asp Phe Thr Leu Thr Ile Ser Ser Leu Pro Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg
            100                 105

<210> SEQ ID NO 132
<211> LENGTH: 108
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: VL AA

<400> SEQUENCE: 132

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Leu
            20                  25                  30

Leu Thr Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Gly Phe Thr Leu Thr Ile Ser Ser Leu Gln Ser
65                  70                  75                  80

Glu Asp Phe Ala Val Tyr Tyr Cys Gln Gln Tyr Asp Thr Trp Pro Phe
                85                  90                  95

Thr Phe Gly Pro Gly Thr Lys Val Asp Phe Lys Arg
            100                 105

<210> SEQ ID NO 133
<211> LENGTH: 1437
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: FS-21495CARDNAHxL

<400> SEQUENCE: 133

```
atggcactcc ccgtaactgc tctgctgctg ccgttggcat tgctcctgca cgccgcacgc     60
ccggaggtgc agctgttgga gtctggggga ggcttggtac agcctggggg gtccctgaga    120
ctctcctgtg cagcctctgg attcaccttt agcagctatg ccatgagctg ggtccgccag    180
gctccaggga aggggctgga gtgggtctca gctattagtg gtagtggtgg tagcacatac    240
tacgcagact ccgtgaaggg ccggttcacc atctccagag acaattccaa gaacacgctg    300
tatctgcaaa tgaacagcct gagagccgag gacacggcgg tgtactactg cgcaagagcc    360
gagatgggag ccgtattcga catatggggt cagggtacaa tggtcaccgt ctcctcaggg    420
tctacatccg gctccgggaa gcccggaagt ggcgaaggta gtacaaaggg ggaaattgtg    480
ttgacacagt ctccagccac cctgtctttg tctccagggg aaagagccac cctctcctgc    540
agggccagtc agagtgttag caggtactta gcctggtacc aacagaaacc tggccaggct    600
cccaggctcc tcatctatga tgcatccaac agggccactg gcatcccagc caggttcagt    660
ggcagtgggt ctgggacaga cttcactctc accatcagca gcctagagcc tgaagatttt    720
gcagtttatt actgtcagca gagaatctcc tggccttttca cttttggcgg agggaccaag    780
gttgagatca aacgggccgc tgcccttgat aatgaaaagt caaacggaac aatcattcac    840
gtgaagggca agcacctctg tccgtcaccc ttgttccctg gtccatccaa gccattctgg    900
gtgttggtcg tagtgggtgg agtcctcgct tgttactctc tgctcgtcac cgtggctttt    960
ataatcttct gggttagatc caaaagaagc cgcctgctcc atagcgatta catgaatatg   1020
actccacgcc gccctggccc cacaaggaaa cactaccagc cttacgcacc acctagagat   1080
ttcgctgcct atcggagcag ggtgaagttt tccagatctg cagatgcacc agcgtatcag   1140
cagggccaga accaactgta taacgagctc aacctgggac gcagggaaga gtatgacgtt   1200
ttggacaagc gcagaggacg ggaccctgag atgggtggca aaccaagacg aaaaaacccc   1260
caggagggtc tctataatga gctgcagaag gataagatgg ctgaagccta ttctgaaata   1320
ggcatgaaag gagagcggag aaggggaaaa gggcacgacg gtttgtacca gggactcagc   1380
actgctacga aggatactta tgacgctctc cacatgcaag ccctgccacc taggtaa      1437
```

<210> SEQ ID NO 134
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: FS-21495CARHxL

<400> SEQUENCE: 134

```
Met Ala Leu Pro Val Thr Ala Leu Leu Leu Pro Leu Ala Leu Leu Leu
1               5                  10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ala Met Ser Trp Val Arg Gln Ala Pro Gly Lys
    50                  55                  60

Gly Leu Glu Trp Val Ser Ala Ile Ser Gly Ser Gly Gly Ser Thr Tyr
65                  70                  75                  80

Tyr Ala Asp Ser Val Lys Gly Arg Phe Thr Ile Ser Arg Asp Asn Ser
```

```
                    85                  90                  95
Lys Asn Thr Leu Tyr Leu Gln Met Asn Ser Leu Arg Ala Glu Asp Thr
                100                 105                 110

Ala Val Tyr Tyr Cys Ala Arg Ala Glu Met Gly Ala Val Phe Asp Ile
                115                 120                 125

Trp Gly Gln Gly Thr Met Val Thr Val Ser Ser Gly Ser Thr Ser Gly
            130                 135                 140

Ser Gly Lys Pro Gly Ser Gly Glu Gly Ser Thr Lys Gly Glu Ile Val
145                 150                 155                 160

Leu Thr Gln Ser Pro Ala Thr Leu Ser Leu Ser Pro Gly Glu Arg Ala
                165                 170                 175

Thr Leu Ser Cys Arg Ala Ser Gln Ser Val Ser Arg Tyr Leu Ala Trp
                180                 185                 190

Tyr Gln Gln Lys Pro Gly Gln Ala Pro Arg Leu Leu Ile Tyr Asp Ala
                195                 200                 205

Ser Asn Arg Ala Thr Gly Ile Pro Ala Arg Phe Ser Gly Ser Gly Ser
                210                 215                 220

Gly Thr Asp Phe Thr Leu Thr Ile Ser Ser Leu Glu Pro Glu Asp Phe
225                 230                 235                 240

Ala Val Tyr Tyr Cys Gln Gln Arg Ile Ser Trp Pro Phe Thr Phe Gly
                245                 250                 255

Gly Gly Thr Lys Val Glu Ile Lys Arg Ala Ala Ala Leu Asp Asn Glu
                260                 265                 270

Lys Ser Asn Gly Thr Ile Ile His Val Lys Gly Lys His Leu Cys Pro
                275                 280                 285

Ser Pro Leu Phe Pro Gly Pro Ser Lys Pro Phe Trp Val Leu Val Val
                290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
                340                 345                 350

Gln Pro Tyr Ala Pro Pro Arg Asp Phe Ala Ala Tyr Arg Ser Arg Val
                355                 360                 365

Lys Phe Ser Arg Ser Ala Asp Ala Pro Ala Tyr Gln Gln Gly Gln Asn
                370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
                420                 425                 430

Met Ala Glu Ala Tyr Ser Glu Ile Gly Met Lys Gly Glu Arg Arg Arg
                435                 440                 445

Gly Lys Gly His Asp Gly Leu Tyr Gln Gly Leu Ser Thr Ala Thr Lys
                450                 455                 460

Asp Thr Tyr Asp Ala Leu His Met Gln Ala Leu Pro Pro Arg
465                 470                 475

<210> SEQ ID NO 135
<211> LENGTH: 1437
<212> TYPE: DNA
<213> ORGANISM: Artificial Sequence
```

<220> FEATURE:
<223> OTHER INFORMATION: Description of Artificial Sequence: Synthetic
polynucleotide
<220> FEATURE:
<223> OTHER INFORMATION: FS-21495CARDNALxH

<400> SEQUENCE: 135

```
atggcactcc ccgtaactgc tctgctgctg ccgttggcat tgctcctgca cgccgcacgc      60
ccggaaattg tgttgacaca gtctccagcc accctgtctt tgtctccagg ggaaagagcc     120
accctctcct gcagggccag tcagagtgtt agcaggtact tagcctggta ccaacagaaa     180
cctggccagg ctcccaggct cctcatctat gatgcatcca acagggccac tggcatccca     240
gccaggttca gtggcagtgg gtctgggaca gacttcactc tcaccatcag cagcctagag     300
cctgaagatt ttgcagttta ttactgtcag cagagaatct cctggccttt cacttttggc     360
ggagggacca aggttgagat caaacggggg tctacatccg gctccgggaa gcccggaagt     420
ggcgaaggta gtacaaaggg ggaggtgcag ctgttggagt ctgggggagg cttggtacag     480
cctggggggt ccctgagact ctcctgtgca gcctctggat tcacctttag cagctatgcc     540
atgagctggg tccgccaggc tccagggaag gggctggagt gggtctcagc tattagtggt     600
agtggtggta gcacatacta cgcagactcc gtgaagggcc ggttcaccat ctccagagac     660
aattccaaga cacgctgta tctgcaaatg aacagcctga gagccgagga cacggcggtg     720
tactactgcg caagagccga gatgggagcc gtattcgaca tatggggtca gggtacaatg     780
gtcaccgtct cctcagccgc tgcccttgat aatgaaaagt caaacggaac aatcattcac     840
gtgaagggca gcaccctctg tccgtcaccc ttgttccctg gtccatccaa gccattctgg     900
gtgttggtcg tagtgggtgg agtcctcgct tgttactctc tgctcgtcac cgtggctttt     960
ataatcttct gggttagatc caaaagaagc cgcctgctcc atagcgatta catgaatatg    1020
actccacgcc gccctggccc cacaaggaaa cactaccagc cttacgcacc acctagagat    1080
ttcgctgcct atcggagcag ggtgaagttt tccagatctg cagatgcacc agcgtatcag    1140
cagggccaga accaactgta taacgagctc aacctgggac gcagggaaga gtatgacgtt    1200
ttggacaagc gcagaggacg ggaccctgag atgggtggca aaccaagacg aaaaaacccc    1260
caggagggtc tctataatga gctgcagaag gataagatgg ctgaagccta ttctgaaata    1320
ggcatgaaag agagcggag aaggggaaaa gggcacgacg gtttgtacca gggactcagc    1380
actgctacga aggatactta tgacgctctc cacatgcaag ccctgccacc taggtaa       1437
```

<210> SEQ ID NO 136
<211> LENGTH: 478
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: FS-21495CARLxH

<400> SEQUENCE: 136

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Arg Tyr Leu Ala Trp Tyr Gln Gln Lys Pro Gly Gln Ala
```

```
                50                  55                  60
Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Cys Gln Gln Arg
            100                 105                 110

Ile Ser Trp Pro Phe Thr Phe Gly Gly Gly Thr Lys Val Glu Ile Lys
            115                 120                 125

Arg Gly Ser Thr Ser Gly Ser Gly Lys Pro Gly Ser Gly Glu Gly Ser
130                 135                 140

Thr Lys Gly Glu Val Gln Leu Leu Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Tyr Ala Met Ser Trp Val Arg Gln Ala Pro Gly Lys Gly Leu
            180                 185                 190

Glu Trp Val Ser Ala Ile Ser Gly Ser Gly Gly Ser Thr Tyr Tyr Ala
            195                 200                 205

Asp Ser Val Lys Gly Arg Phe Thr Ile Ser Arg Asp Asn Ser Lys Asn
210                 215                 220

Thr Leu Tyr Leu Gln Met Asn Ser Leu Arg Ala Glu Asp Thr Ala Val
225                 230                 235                 240

Tyr Tyr Cys Ala Arg Ala Glu Met Gly Ala Val Phe Asp Ile Trp Gly
                245                 250                 255

Gln Gly Thr Met Val Thr Val Ser Ser Ala Ala Ala Leu Asp Asn Glu
            260                 265                 270

Lys Ser Asn Gly Thr Ile Ile His Val Lys Gly Lys His Leu Cys Pro
            275                 280                 285

Ser Pro Leu Phe Pro Gly Pro Ser Lys Pro Phe Trp Val Leu Val Val
            290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
            355                 360                 365

Lys Phe Ser Arg Ser Ala Asp Ala Pro Ala Tyr Gln Gln Gly Gln Asn
            370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
            435                 440                 445

Gly Lys Gly His Asp Gly Leu Tyr Gln Gly Leu Ser Thr Ala Thr Lys
            450                 455                 460

Asp Thr Tyr Asp Ala Leu His Met Gln Ala Leu Pro Pro Arg
465                 470                 475
```

<210> SEQ ID NO 137
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PC-21497CARDNAHxL

<400> SEQUENCE: 137

| | |
|---|---|
| atggcactcc ccgtaactgc tctgctgctg ccgttggcat tgctcctgca cgccgcacgc | 60 |
| ccgcaggtgc agctggtgga gtctggggga ggcgtggtcc agcctgggag gtccctgaga | 120 |
| ctctcctgtg cagcgtctgg attcaccttc agtagctatg gcatgcactg ggtccgccag | 180 |
| gctccaggca aggggctgga gtgggtggca gttatatcgt atgatggaag taataaatac | 240 |
| tatgcagact ccgtgaaggg ccgattcacc atctccagag acaattccaa gaacacgctg | 300 |
| tatctgcaaa tgaacagcct gagagccgag gacacggcgg tgtactactg cgccagagac | 360 |
| ggtacttatc taggtggtct ctggtacttc gacttatggg ggagaggtac cttggtcacc | 420 |
| gtctcctcag gtctacatc cggctccggg aagcccggaa gtggcgaagg tagtacaaag | 480 |
| ggggatattg tgatgactca gtctccactc tccctgcccg tcacccctgg agagccggcc | 540 |
| tccatctcct gcaggtctag tcagagcctc ctgcatagta tggatacaa ctatttggat | 600 |
| tggtacctgc agaagccagg gcagtctcca cagctcctga tctatttggg ttctaatcgg | 660 |
| gcctccgggg tccctgacag gttcagtggc agtggatcag gcacagattt tacactgaaa | 720 |
| atcagcagag tggaggctga ggatgttggg gtttattact gcatgcaggg actcggcctc | 780 |
| cctctcactt tggcggagg gaccaaggtt gagatcaaac gggccgctgc ccttgataat | 840 |
| gaaaagtcaa acggaacaat cattcacgtg aagggcaagc acctctgtcc gtcaccttg | 900 |
| ttccctggtc catccaagcc attctgggtg ttggtcgtag tgggtggagt cctcgcttgt | 960 |
| tactctctgc tcgtcaccgt ggcttttata atcttctggg ttagatccaa aagaagccgc | 1020 |
| ctgctccata gcgattacat gaatatgact ccacgccgcc ctggccccac aaggaaacac | 1080 |
| taccagcctt acgcaccacc tagagatttc gctgcctatc ggagcagggt gaagttttcc | 1140 |
| agatctgcag atgcaccagc gtatcagcag ggccagaacc aactgtataa cgagctcaac | 1200 |
| ctgggacgca gggaagagta tgacgttttg gacaagcgca gaggacggga ccctgagatg | 1260 |
| ggtggcaaac caagacgaaa aaaccccag gagggtctct ataatgagct gcagaaggat | 1320 |
| aagatggctg aagcctattc tgaaataggc atgaaggag agcggagaag gggaaaaggg | 1380 |
| cacgacggtt tgtaccaggg actcagcact gctacgaagg atacttatga cgctctccac | 1440 |
| atgcaagccc tgccacctag gtaa | 1464 |

<210> SEQ ID NO 138
<211> LENGTH: 487
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PC-21497CARHxL

<400> SEQUENCE: 138

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Gly Thr Tyr Leu Gly Gly Leu Trp
        115                 120                 125

Tyr Phe Asp Leu Trp Gly Arg Gly Thr Leu Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Asp Ile Val Met Thr Gln Ser Pro Leu Ser Leu Pro Val Thr Pro
                165                 170                 175

Gly Glu Pro Ala Ser Ile Ser Cys Arg Ser Ser Gln Ser Leu Leu His
            180                 185                 190

Ser Asn Gly Tyr Asn Tyr Leu Asp Trp Tyr Leu Gln Lys Pro Gly Gln
        195                 200                 205

Ser Pro Gln Leu Leu Ile Tyr Leu Gly Ser Asn Arg Ala Ser Gly Val
    210                 215                 220

Pro Asp Arg Phe Ser Gly Ser Gly Ser Gly Thr Asp Phe Thr Leu Lys
225                 230                 235                 240

Ile Ser Arg Val Glu Ala Glu Asp Val Gly Val Tyr Tyr Cys Met Gln
                245                 250                 255

Gly Leu Gly Leu Pro Leu Thr Phe Gly Gly Gly Thr Lys Val Glu Ile
            260                 265                 270

Lys Arg Ala Ala Ala Leu Asp Asn Glu Lys Ser Asn Gly Thr Ile Ile
        275                 280                 285

His Val Lys Gly Lys His Leu Cys Pro Ser Pro Leu Phe Pro Gly Pro
    290                 295                 300

Ser Lys Pro Phe Trp Val Leu Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 139
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PC-21497CARDNALxH

<400> SEQUENCE: 139

| | | | | | | |
|---|---|---|---|---|---|---|
| atggcactcc | ccgtaactgc | tctgctgctg | ccgttggcat | tgctcctgca | cgccgcacgc | 60 |
| ccggatattg | tgatgactca | gtctccactc | tccctgcccg | tcacccctgg | agagccggcc | 120 |
| tccatctcct | gcaggtctag | tcagagcctc | ctgcatagta | atggatacaa | ctatttggat | 180 |
| tggtacctgc | agaagccagg | gcagtctcca | cagctcctga | tctatttggg | ttctaatcgg | 240 |
| gcctccgggg | tccctgacag | gttcagtggc | agtggatcag | gcacagattt | tacactgaaa | 300 |
| atcagcagag | tggaggctga | ggatgttggg | gtttattact | gcatgcaggg | actcggcctc | 360 |
| cctctcactt | ttggcggagg | gaccaaggtt | gagatcaaac | gggggtctac | atccggctcc | 420 |
| ggaagcccg | aagtggcga | aggtagtaca | aagggcagg | tgcagctggt | ggagtctggg | 480 |
| ggaggcgtgg | tccagcctgg | gaggtccctg | agactctcct | gtgcagcgtc | tggattcacc | 540 |
| ttcagtagct | atggcatgca | ctgggtccgc | caggctccag | gcaaggggct | ggagtgggtg | 600 |
| gcagttatat | cgtatgatgg | aagtaataaa | tactatgcag | actccgtgaa | gggccgattc | 660 |
| accatctcca | gagacaattc | caagaacacg | ctgtatctgc | aaatgaacag | cctgagagcc | 720 |
| gaggacacgg | cggtgtacta | ctgcgccaga | gacggtactt | atctaggtgg | tctctggtac | 780 |
| ttcgacttat | gggggagagg | taccttggtc | accgtctcct | cagccgctgc | ccttgataat | 840 |
| gaaaagtcaa | acggaacaat | cattcacgtg | aagggcaagc | acctctgtcc | gtcacccttg | 900 |
| ttccctggtc | catccaagcc | attctgggtg | ttggtcgtag | tgggtggagt | cctcgcttgt | 960 |
| tactctctgc | tcgtcaccgt | ggcttttata | atcttctggg | ttagatccaa | aagaagccgc | 1020 |
| ctgctccata | gcgattacat | gaatatgact | ccacgccgcc | ctggccccac | aaggaaacac | 1080 |
| taccagcctt | acgcaccacc | tagagatttc | gctgcctatc | ggagcagggt | gaagttttcc | 1140 |
| agatctgcag | atgcaccagc | gtatcagcag | ggccagaacc | aactgtataa | cgagctcaac | 1200 |
| ctgggacgca | gggaagagta | tgacgttttg | gacaagcgca | gaggacggga | ccctgagatg | 1260 |
| ggtggcaaac | caagacgaaa | aaaccccag | gagggtctct | ataatgagct | gcagaaggat | 1320 |
| aagatggctg | aagcctattc | tgaaataggc | atgaaaggag | agcggagaag | gggaaagggg | 1380 |
| cacgacggtt | tgtaccaggg | actcagcact | gctacgaagg | atacttatga | cgctctccac | 1440 |
| atgcaagccc | tgccacctag | gtaa | | | | 1464 |

<210> SEQ ID NO 140
<211> LENGTH: 487
<212> TYPE: PRT

<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: PC-21497CARHxL

<400> SEQUENCE: 140

```
Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Leu His Ser Asn Gly Tyr Asn Tyr Leu Asp Trp Tyr Leu Gln
    50                  55                  60

Lys Pro Gly Gln Ser Pro Gln Leu Leu Ile Tyr Leu Gly Ser Asn Arg
65                  70                  75                  80

Ala Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Met Gln Gly Leu Gly Leu Pro Leu Thr Phe Gly Gly Gly Thr
        115                 120                 125

Lys Val Glu Ile Lys Arg Gly Ser Thr Ser Gly Ser Gly Lys Pro Gly
    130                 135                 140

Ser Gly Glu Gly Ser Thr Lys Gly Gln Val Gln Leu Val Glu Ser Gly
145                 150                 155                 160

Gly Gly Val Val Gln Pro Gly Arg Ser Leu Arg Leu Ser Cys Ala Ala
                165                 170                 175

Ser Gly Phe Thr Phe Ser Ser Tyr Gly Met His Trp Val Arg Gln Ala
            180                 185                 190

Pro Gly Lys Gly Leu Glu Trp Val Ala Val Ile Ser Tyr Asp Gly Ser
        195                 200                 205

Asn Lys Tyr Tyr Ala Asp Ser Val Lys Gly Arg Phe Thr Ile Ser Arg
210                 215                 220

Asp Asn Ser Lys Asn Thr Leu Tyr Leu Gln Met Asn Ser Leu Arg Ala
225                 230                 235                 240

Glu Asp Thr Ala Val Tyr Tyr Cys Ala Arg Asp Gly Thr Tyr Leu Gly
                245                 250                 255

Gly Leu Trp Tyr Phe Asp Leu Trp Gly Arg Gly Thr Leu Val Thr Val
            260                 265                 270

Ser Ser Ala Ala Ala Leu Asp Asn Glu Lys Ser Asn Gly Thr Ile Ile
        275                 280                 285

His Val Lys Gly Lys His Leu Cys Pro Ser Pro Leu Phe Pro Gly Pro
    290                 295                 300

Ser Lys Pro Phe Trp Val Leu Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
```

```
                 370                  375                  380
Ala Pro Ala Tyr Gln Gln Gly Gln Asn Gln Leu Tyr Asn Glu Leu Asn
385                 390                  395                  400

Leu Gly Arg Arg Glu Glu Tyr Asp Val Leu Asp Lys Arg Arg Gly Arg
                405                  410                  415

Asp Pro Glu Met Gly Gly Lys Pro Arg Arg Lys Asn Pro Gln Glu Gly
                420                  425                  430

Leu Tyr Asn Glu Leu Gln Lys Asp Lys Met Ala Glu Ala Tyr Ser Glu
                435                  440                  445

Ile Gly Met Lys Gly Glu Arg Arg Arg Gly Lys Gly His Asp Gly Leu
                450                  455                  460

Tyr Gln Gly Leu Ser Thr Ala Thr Lys Asp Thr Tyr Asp Ala Leu His
465                 470                  475                  480

Met Gln Ala Leu Pro Pro Arg
                485

<210> SEQ ID NO 141
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: AJ-21508CARDNAHxL

<400> SEQUENCE: 141
atggcactcc ccgtaactgc tctgctgctg ccgttggcat tgctcctgca cgccgcacgc      60
ccgcaggtgc agctggtgca gtctggggct gaggtgaaga agcctggggc ctcagtgaag     120
gtttcctgca aggcatctgg atacaccttc accagctact atatgcactg ggtgcgacag     180
gcccctggac aagggcttga gtggatggga ataatcaacc ctggtggtgg tagcacaagc     240
tacgcacaga agttccaggg cagagtcacc atgaccaggg acacgtccac gagcacagtc     300
tacatggagc tgagcagcct gagatctgag gacacggcgg tgtactactg cgccagagag     360
agttggccaa tggacgtatg gggccaggga caaactgtca ccgtctcctc agggtctaca     420
tccggctccg ggaagcccgg aagtggcgaa ggtagtacaa agggggaaat agtgatgacg     480
cagtctccag ccaccctgtc tgtgtctcca ggggaaagag ccaccctctc ctgcagggcc     540
agtcagagtg ttagcagcaa cttagcctgg taccagcaga aacctggcca ggctcccagg     600
ctcctcatct atggtgcatc caccagggcc actggtatcc cagccaggtt cagtggcagt     660
gggtctggga cagagttcac tctcaccatc agcagcctgc agtctgaaga ttttgcagtt     720
tattactgtc agcagtacgc cgcctaccct acttttggcg agggaccaa ggttgagatc     780 aaacgggccg ctgcccttga taatgaaaag tcaaacggaa caatcattca cgtgaagggc     840
aagcacctct gtccgtcacc cttgttccct ggtccatcca agccattctg ggtgttggtc     900
gtagtgggtg gagtcctcgc ttgttactct ctgctcgtca ccgtggcttt tataatcttc     960
tgggttagat ccaaaagaag ccgcctgctc catagcgatt acatgaatat gactccacgc    1020
cgccctggcc ccacaaggaa acactaccag ccttacgcac acctagaga tttcgctgcc    1080 tatcggagca gggtgaagtt ttccagatct gcagatgcac cagcgtatca gcagggccag    1140
aaccaactgt ataacgagct caacctggga cgcagggaag agtatgacgt tttggacaag    1200
cgcagaggac gggaccctga gatgggtggc aaaccaagac gaaaaaaccc ccaggagggt    1260
ctctataatg agctgcagaa ggataagatg gctgaagcct attctgaaat aggcatgaaa    1320
```

```
ggagagcgga gaaggggaaa agggcacgac ggtttgtacc agggactcag cactgctacg    1380
aaggatactt atgacgctct ccacatgcaa gccctgccac ctaggtaa                1428

<210> SEQ ID NO 142
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AJ-21508CARHxL

<400> SEQUENCE: 142

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Ala Ser Gly Tyr
            35                  40                  45

Thr Phe Thr Ser Tyr Tyr Met His Trp Val Arg Gln Ala Pro Gly Gln
        50                  55                  60

Gly Leu Glu Trp Met Gly Ile Ile Asn Pro Gly Gly Gly Ser Thr Ser
65                  70                  75                  80

Tyr Ala Gln Lys Phe Gln Gly Arg Val Thr Met Thr Arg Asp Thr Ser
                85                  90                  95

Thr Ser Thr Val Tyr Met Glu Leu Ser Ser Leu Arg Ser Glu Asp Thr
            100                 105                 110

Ala Val Tyr Tyr Cys Ala Arg Glu Ser Trp Pro Met Asp Val Trp Gly
        115                 120                 125

Gln Gly Thr Thr Val Thr Val Ser Ser Gly Ser Thr Ser Gly Ser Gly
130                 135                 140

Lys Pro Gly Ser Gly Glu Gly Ser Thr Lys Gly Glu Ile Val Met Thr
145                 150                 155                 160

Gln Ser Pro Ala Thr Leu Ser Val Ser Pro Gly Glu Arg Ala Thr Leu
                165                 170                 175

Ser Cys Arg Ala Ser Gln Ser Val Ser Ser Asn Leu Ala Trp Tyr Gln
            180                 185                 190

Gln Lys Pro Gly Gln Ala Pro Arg Leu Leu Ile Tyr Gly Ala Ser Thr
        195                 200                 205

Arg Ala Thr Gly Ile Pro Ala Arg Phe Ser Gly Ser Gly Ser Gly Thr
210                 215                 220

Glu Phe Thr Leu Thr Ile Ser Ser Leu Gln Ser Glu Asp Phe Ala Val
225                 230                 235                 240

Tyr Tyr Cys Gln Gln Tyr Ala Ala Tyr Pro Thr Phe Gly Gly Gly Thr
                245                 250                 255

Lys Val Glu Ile Lys Arg Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
```

```
                  325                 330                 335
Met Thr Pro Arg Arg Pro Gly Pro Thr Arg Lys His Tyr Gln Pro Tyr
              340                 345                 350
Ala Pro Pro Arg Asp Phe Ala Ala Tyr Arg Ser Arg Val Lys Phe Ser
              355                 360                 365
Arg Ser Ala Asp Ala Pro Ala Tyr Gln Gln Gly Gln Asn Gln Leu Tyr
370               375                 380
Asn Glu Leu Asn Leu Gly Arg Arg Glu Tyr Asp Val Leu Asp Lys
385               390                 395                 400
Arg Arg Gly Arg Asp Pro Glu Met Gly Gly Lys Pro Arg Arg Lys Asn
              405                 410                 415
Pro Gln Glu Gly Leu Tyr Asn Glu Leu Gln Lys Asp Lys Met Ala Glu
              420                 425                 430
Ala Tyr Ser Glu Ile Gly Met Lys Gly Glu Arg Arg Gly Lys Gly
              435                 440                 445
His Asp Gly Leu Tyr Gln Gly Leu Ser Thr Ala Thr Lys Asp Thr Tyr
              450                 455                 460
Asp Ala Leu His Met Gln Ala Leu Pro Pro Arg
465               470                 475

<210> SEQ ID NO 143
<211> LENGTH: 1428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: AJ-21508CARDNALxH

<400> SEQUENCE: 143
atggcactcc ccgtaactgc tctgctgctg ccgttggcat tgctcctgca cgccgcacgc      60
ccggaaatag tgatgacgca gtctccagcc accctgtctg tgtctccagg ggaaagagcc     120
accctctcct gcagggccag tcagagtgtt agcagcaact agcctggta ccagcagaaa      180 cctggccagg ctcccaggct cctcatctat ggtgcatcca ccagggccac tggtatccca     240
gccaggttca gtggcagtgg gtctgggaca gagttcactc tcaccatcag cagcctgcag     300
tctgaagatt ttgcagttta ttactgtcag cagtacgccg cctaccctac ttttggcgga     360
gggaccaagg ttgagatcaa acgggggtct acatccggct ccgggaagcc cggaagtggc     420
gaaggtagta caaggggca ggtgcagctg gtgcagtctg ggctgaggt gaagaagcct       480 ggggcctcag tgaaggtttc ctgcaaggca tctggataca ccttcaccag ctactatatg     540
cactgggtgc gacaggcccc tggacaaggg cttgagtgga tggaataat caaccctggt     600 ggtggtagca caagctacgc acagaagttc cagggcagag tcaccatgac cagggacacg     660
tccacgagca cagtctacat ggagctgagc agcctgagat ctgaggacac ggcggtgtac     720
tactgcgcca gagagagttg gccaatggac gtatggggcc agggaacaac tgtcaccgtc     780
tcctcagccg ctgcccttga taatgaaaag tcaaacgaa caatcattca cgtgaagggc     840 agcacctct gtccgtcacc cttgttccct ggtccatcca agccattctg ggtgttggtc      900
gtagtgggtg gagtcctcgc ttgttactct ctgctcgtca ccgtggcttt tataatcttc     960
tgggttagat ccaaaagaag ccgcctgctc catagcgatt acatgaatat gactccacgc    1020
cgccctggcc ccacaaggaa acactaccag cccttacgcac cacctagaga tttcgctgcc    1080
tatcggagca gggtgaagtt ttccagatct gcagatgcac cagcgtatca gcagggccag    1140
```

```
aaccaactgt ataacgagct caacctggga cgcagggaag agtatgacgt tttggacaag    1200
cgcagaggac gggaccctga gatgggtggc aaaccaagac gaaaaaaccc ccaggagggt    1260
ctctataatg agctgcagaa ggataagatg gctgaagcct attctgaaat aggcatgaaa    1320
ggagagcgga gaaggggaaa agggcacgac ggtttgtacc agggactcag cactgctacg    1380
aaggatactt atgacgctct ccacatgcaa gccctgccac ctaggtaa                1428
```

<210> SEQ ID NO 144
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: AJ-21508CARLxH

<400> SEQUENCE: 144

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln Tyr
            100                 105                 110

Ala Ala Tyr Pro Thr Phe Gly Gly Gly Thr Lys Val Glu Ile Lys Arg
        115                 120                 125

Gly Ser Thr Ser Gly Ser Gly Lys Pro Gly Ser Gly Glu Gly Ser Thr
    130                 135                 140

Lys Gly Gln Val Gln Leu Val Gln Ser Gly Ala Glu Val Lys Lys Pro
145                 150                 155                 160

Gly Ala Ser Val Lys Val Ser Cys Lys Ala Ser Gly Tyr Thr Phe Thr
                165                 170                 175

Ser Tyr Tyr Met His Trp Val Arg Gln Ala Pro Gly Gln Gly Leu Glu
            180                 185                 190

Trp Met Gly Ile Ile Asn Pro Gly Gly Gly Ser Thr Ser Tyr Ala Gln
        195                 200                 205

Lys Phe Gln Gly Arg Val Thr Met Thr Arg Asp Thr Ser Thr Ser Thr
    210                 215                 220

Val Tyr Met Glu Leu Ser Ser Leu Arg Ser Glu Asp Thr Ala Val Tyr
225                 230                 235                 240

Tyr Cys Ala Arg Glu Ser Trp Pro Met Asp Val Trp Gly Gln Gly Thr
                245                 250                 255

Thr Val Thr Val Ser Ser Ala Ala Ala Leu Asp Asn Glu Lys Ser Asn
            260                 265                 270

Gly Thr Ile Ile His Val Lys Gly Lys His Leu Cys Pro Ser Pro Leu
        275                 280                 285

Phe Pro Gly Pro Ser Lys Pro Phe Trp Val Leu Val Val Val Gly Gly
```

| | | | | | 290 | | | | 295 | | | | 300 | | |
|---|---|---|---|---|---|---|---|---|---|---|---|---|---|---|---|

Val Leu Ala Cys Tyr Ser Leu Leu Val Thr Val Ala Phe Ile Ile Phe
305 310 315 320

Trp Val Arg Ser Lys Arg Ser Arg Leu Leu His Ser Asp Tyr Met Asn
325 330 335

Met Thr Pro Arg Arg Pro Gly Pro Thr Arg Lys His Tyr Gln Pro Tyr
340 345 350

Ala Pro Pro Arg Asp Phe Ala Ala Tyr Arg Ser Arg Val Lys Phe Ser
355 360 365

Arg Ser Ala Asp Ala Pro Ala Tyr Gln Gln Gly Gln Asn Gln Leu Tyr
370 375 380

Asn Glu Leu Asn Leu Gly Arg Arg Glu Glu Tyr Asp Val Leu Asp Lys
385 390 395 400

Arg Arg Gly Arg Asp Pro Glu Met Gly Gly Lys Pro Arg Arg Lys Asn
405 410 415

Pro Gln Glu Gly Leu Tyr Asn Glu Leu Gln Lys Asp Lys Met Ala Glu
420 425 430

Ala Tyr Ser Glu Ile Gly Met Lys Gly Glu Arg Arg Arg Gly Lys Gly
435 440 445

His Asp Gly Leu Tyr Gln Gly Leu Ser Thr Ala Thr Lys Asp Thr Tyr
450 455 460

Asp Ala Leu His Met Gln Ala Leu Pro Pro Arg
465 470 475

<210> SEQ ID NO 145
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: NM-21517CARDNAHxL

<400> SEQUENCE: 145

| | | | | |
|---|---|---|---|---|
| atggcactcc ccgtaactgc tctgctgctg ccgttggcat tgctcctgca cgccgcacgc | 60 |
| ccgcagctgc agctgcagga gtcgggccca ggactggtga agccttcgga gaccctgtcc | 120 |
| ctcacctgca ctgtctctgg tggctccatc agcagtagta gttactactg gggctggatc | 180 |
| cgccagcccc cagggaaggg gctggagtgg attgggagta tctcctatag tgggagcacc | 240 |
| tactacaacc cgtccctcaa gagtcgagtc accatatccg tagacacgtc caagaaccag | 300 |
| ttctccctga agctgagttc tgtgaccgcc gcagacacgg cggtgtacta ctgcgccaga | 360 |
| ggcaggggat atgcaaccag cttagccttc gatatctggg gtcagggtac aatggtcacc | 420 |
| gtctcctcag gtctacatcc ggctccgggg aagcccggaa gtggcgaagg tagtacaaag | 480 |
| ggggaaattg tgttgacaca gtctccagcc accctgtctt tgtctccagg ggaaagagcc | 540 |
| accctctcct gcagggccag tcagagtgtt agcagctact tagcctggta ccaacagaaa | 600 |
| cctggccagg ctcccaggct cctcatctat gatgcatcca acagggccac tggcatccca | 660 |
| gccaggttca gtggcagtgg gtctgggaca gacttcactc tcaccatcag cagcctagag | 720 |
| cctgaagatt ttgcagttta ttactgtcag cagagacacg tctggcctcc tactttggc | 780 |
| ggagggacca aggttgagat caaacgggcc gctgccttg ataatgaaaa gtcaaacgga | 840 |
| acaatcattc acgtgaaggg caagcaccte tgtccgtcac ccttgttccc tggtccatcc | 900 |
| aagccattct gggtgttggt cgtagtgggt ggagtcctcg cttgttactc tctgctcgtc | 960 |

```
accgtggctt ttataatctt ctgggttaga tccaaaagaa gccgcctgct ccatagcgat   1020
tacatgaata tgactccacg ccgccctggc cccacaagga acactacca gccttacgca   1080 ccacctagag atttcgctgc ctatcggagc agggtgaagt tttccagatc tgcagatgca   1140
ccagcgtatc agcagggcca gaaccaactg tataacgagc tcaacctggg acgcaggaa    1200 gagtatgacg ttttggacaa gcgcagagga cgggaccctg agatgggtgg caaaccaaga   1260
cgaaaaaacc cccaggaggg tctctataat gagctgcaga aggataagat ggctgaagcc   1320
tattctgaaa taggcatgaa aggagagcgg agaagggaa aagggcacga cggtttgtac    1380
cagggactca gcactgctac gaaggatact tatgacgctc tccacatgca agccctgcca   1440
cctaggtaa                                                           1449
```

<210> SEQ ID NO 146
<211> LENGTH: 482
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: NM-21517CARHxL

<400> SEQUENCE: 146

```
Met Ala Leu Pro Val Thr Ala Leu Leu Leu Pro Leu Ala Leu Leu Leu
1               5                   10                  15

His Ala Ala Arg Pro Gln Leu Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Ser Ser Tyr Tyr Trp Gly Trp Ile Arg Gln Pro Pro
    50                  55                  60

Gly Lys Gly Leu Glu Trp Ile Gly Ser Ile Ser Tyr Ser Gly Ser Thr
65                  70                  75                  80

Tyr Tyr Asn Pro Ser Leu Lys Ser Arg Val Thr Ile Ser Val Asp Thr
                85                  90                  95

Ser Lys Asn Gln Phe Ser Leu Lys Leu Ser Ser Val Thr Ala Ala Asp
            100                 105                 110

Thr Ala Val Tyr Tyr Cys Ala Arg Gly Arg Gly Tyr Ala Thr Ser Leu
        115                 120                 125

Ala Phe Asp Ile Trp Gly Gln Gly Thr Met Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Glu Ile Val Leu Thr Gln Ser Pro Ala Thr Leu Ser Leu Ser Pro
                165                 170                 175

Gly Glu Arg Ala Thr Leu Ser Cys Arg Ala Ser Gln Ser Val Ser Ser
            180                 185                 190

Tyr Leu Ala Trp Tyr Gln Gln Lys Pro Gly Gln Ala Pro Arg Leu Leu
        195                 200                 205

Ile Tyr Asp Ala Ser Asn Arg Ala Thr Gly Ile Pro Ala Arg Phe Ser
    210                 215                 220

Gly Ser Gly Ser Gly Thr Asp Phe Thr Leu Thr Ile Ser Ser Leu Glu
225                 230                 235                 240

Pro Glu Asp Phe Ala Val Tyr Tyr Cys Gln Gln Arg His Val Trp Pro
                245                 250                 255
```

```
Pro Thr Phe Gly Gly Gly Thr Lys Val Glu Ile Lys Arg Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg
```

<210> SEQ ID NO 147
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: NM-21517CARDNALxH

<400> SEQUENCE: 147

```
atggcactcc ccgtaactgc tctgctgctg ccgttggcat tgctcctgca cgccgcacgc      60
ccggaaattg tgttgacaca gtctccagcc accctgtctt tgtctccagg ggaaagagcc     120
accctctcct gcagggccag tcagagtgtt agcagctact tagcctggta ccaacagaaa     180
cctggccagg ctcccaggct cctcatctat gatgcatcca acagggccac tggcatccca     240
gccaggttca gtggcagtgg gtctgggaca gacttcactc tcaccatcag cagcctagag     300
cctgaagatt ttgcagttta ttactgtcag cagagacacg tctggcctcc tacttttggc     360
ggagggacca aggttgagat caaacggggg tctacatccg gctccgggaa gcccggaagt     420
ggcgaaggta gtacaaaggg cagctgcagc tgcaggagtc gggcccagg actggtgaag     480 ccttcggaga ccctgtccct cacctgcact gtctctggtg gctccatcag cagtagtagt     540
tactactggg gctggatccg ccagcccca gggaaggggc tggagtggat tgggagtatc     600
tcctatagtg ggagcaccta ctacaacccg tccctcaaga gtcgagtcac catatccgta     660
```

```
gacacgtcca agaaccagtt ctccctgaag ctgagttctg tgaccgccgc agacacggcg      720
gtgtactact gcgccagagg caggggatat gcaaccagct tagccttcga tatctggggt      780
cagggtacaa tggtcaccgt ctcctcagcc gctgcccttg ataatgaaaa gtcaaacgga      840
acaatcattc acgtgaaggg caagcacctc tgtccgtcac ccttgttccc tggtccatcc      900
aagccattct gggtgttggt cgtagtgggt ggagtcctcg cttgttactc tctgctcgtc      960
accgtggctt ttataatctt ctgggttaga tccaaaagaa gccgcctgct ccatagcgat     1020
tacatgaata tgactccacg ccgccctggc ccacaagga aacactacca gccttacgca      1080
ccacctagag atttcgctgc ctatcggagc agggtgaagt tttccagatc tgcagatgca     1140
ccagcgtatc agcagggcca gaaccaactg tataacgagc tcaacctggg acgcagggaa     1200
gagtatgacg ttttggacaa gcgcagagga cgggaccctg agatgggtgg caaaccaaga     1260
cgaaaaaacc cccaggaggg tctctataat gagctgcaga aggataagat ggctgaagcc     1320
tattctgaaa taggcatgaa aggagagcgg agaaggggaa aagggcacga cggttttgtac     1380 cagggactca gcactgctac gaaggatact tatgacgctc tccacatgca agccctgcca     1440
cctaggtaa                                                              1449
```

<210> SEQ ID NO 148
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: NM-21517CARLxH

<400> SEQUENCE: 148

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Ser Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

His Val Trp Pro Pro Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Leu Gln Leu Gln Glu Ser Gly Pro Gly Leu Val Lys
145                 150                 155                 160

Pro Ser Glu Thr Leu Ser Leu Thr Cys Thr Val Ser Gly Gly Ser Ile
                165                 170                 175

Ser Ser Ser Ser Tyr Tyr Trp Gly Trp Ile Arg Gln Pro Pro Gly Lys
            180                 185                 190

Gly Leu Glu Trp Ile Gly Ser Ile Ser Tyr Ser Gly Ser Thr Tyr Tyr
```

```
            195                 200                 205
Asn Pro Ser Leu Lys Ser Arg Val Thr Ile Ser Val Asp Thr Ser Lys
    210                 215                 220

Asn Gln Phe Ser Leu Lys Leu Ser Ser Val Thr Ala Ala Asp Thr Ala
225                 230                 235                 240

Val Tyr Tyr Cys Ala Arg Gly Arg Gly Tyr Ala Thr Ser Leu Ala Phe
                245                 250                 255

Asp Ile Trp Gly Gln Gly Thr Met Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg
```

<210> SEQ ID NO 149
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TS-21522CARDNAHxL

<400> SEQUENCE: 149
atggcactcc ccgtaactgc tctgctgctg ccgttggcat tgctcctgca cgccgcacgc      60
ccggaggtgc agctggtgga gtctggggga ggcttggtac agcctggggg gtccctgaga     120
ctctcctgtg cagcctctgg attcaccttc agtagctata gcatgaactg ggtccgccag     180
gctccaggga aggggctgga gtgggtttca accattagta gtagtagtag taccatatac     240
tacgcagact ctgtgaaggg ccgattcacc atctccagag acaatgccaa gaactcactg     300
tatctgcaaa tgaacagcct gagagctgag gacacggcgg tgtactactg cgccagaggt     360

```
tctcaggagc acctgatttt cgattattgg ggacagggta cattggtcac cgtctcctca    420
gggtctacat ccggctccgg gaagcccgga agtggcgaag gtagtacaaa gggggaaatt    480
gtgttgacac agtctccagc caccctgtct ttgtctccag gggaagagc caccctctcc     540
tgcaggccca gtcagagtgt tagcaggtac ttagcctggt accaacagaa acctggccag    600
gctcccaggc tcctcatcta tgatgcatcc aacagggcca ctggcatccc agccaggttc    660
agtggcagtg gtctgggac agacttcact ctcaccatca gcagcctaga gcctgaagat     720
tttgcagttt attactgtca gcagagattc tactaccctt ggacttttgg cggagggacc    780
aaggttgaga tcaaacgggc cgctgccctt gataatgaaa agtcaaacgg aacaatcatt    840
cacgtgaagg gcaagcacct ctgtccgtca cccttgttcc ctggtccatc caagccattc    900
tgggtgttgg tcgtagtggg tggagtcctc gcttgttact ctctgctcgt caccgtggct    960
tttataatct tctgggttag atccaaaaga agccgcctgc tccatagcga ttacatgaat   1020
atgactccac gccgccctgg ccccacaagg aaacactacc agccttacgc accacctaga   1080
gatttcgctg cctatcggag cagggtgaag ttttccagat ctgcagatgc accagcgtat   1140
cagcagggcc agaaccaact gtataacgag ctcaacctgg gacgcaggga agagtatgac   1200
gttttggaca gcgcagagg acgggaccct gagatgggtg gcaaaccaag acgaaaaaac   1260
ccccaggagg gtctctataa tgagctgcag aaggataaga tggctgaagc ctattctgaa   1320
ataggcatga aggagagcg gagaagggga aaagggcacg acggtttgta ccagggactc   1380
agcactgcta cgaaggatac ttatgacgct ctccacatgc aagccctgcc acctaggtaa   1440
```

<210> SEQ ID NO 150
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TS-21522CARHxL

<400> SEQUENCE: 150

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Ser Tyr Ser Met Asn Trp Val Arg Gln Ala Pro Gly Lys
    50                  55                  60

Gly Leu Glu Trp Val Ser Thr Ile Ser Ser Ser Ser Thr Ile Tyr
65                  70                  75                  80

Tyr Ala Asp Ser Val Lys Gly Arg Phe Thr Ile Ser Arg Asp Asn Ala
                85                  90                  95

Lys Asn Ser Leu Tyr Leu Gln Met Asn Ser Leu Arg Ala Glu Asp Thr
            100                 105                 110

Ala Val Tyr Tyr Cys Ala Arg Gly Ser Gln Glu His Leu Ile Phe Asp
        115                 120                 125

Tyr Trp Gly Gln Gly Thr Leu Val Thr Val Ser Ser Gly Ser Thr Ser
    130                 135                 140

Gly Ser Gly Lys Pro Gly Ser Gly Glu Gly Ser Thr Lys Gly Glu Ile
145                 150                 155                 160
```

Val Leu Thr Gln Ser Pro Ala Thr Leu Ser Leu Ser Pro Gly Glu Arg
                165                 170                 175

Ala Thr Leu Ser Cys Arg Ala Ser Gln Ser Val Ser Arg Tyr Leu Ala
            180                 185                 190

Trp Tyr Gln Gln Lys Pro Gly Gln Ala Pro Arg Leu Leu Ile Tyr Asp
        195                 200                 205

Ala Ser Asn Arg Ala Thr Gly Ile Pro Ala Arg Phe Ser Gly Ser Gly
    210                 215                 220

Ser Gly Thr Asp Phe Thr Leu Thr Ile Ser Ser Leu Glu Pro Glu Asp
225                 230                 235                 240

Phe Ala Val Tyr Tyr Cys Gln Gln Arg Phe Tyr Tyr Pro Trp Thr Phe
                245                 250                 255

Gly Gly Gly Thr Lys Val Glu Ile Lys Arg Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475

<210> SEQ ID NO 151
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: TS-21522CARDNALxH

<400> SEQUENCE: 151
atggcactcc cgtaactgc tctgctgctg ccgttggcat tgctcctgca cgccgcacgc      60
ccggaaattg tgttgacaca gtctccagcc accctgtctt tgtctccagg ggaaagagcc    120
accctctcct gcagggccag tcagagtgtt agcaggtact tagcctggta ccaacagaaa    180

```
cctggccagg ctcccaggct cctcatctat gatgcatcca acagggccac tggcatccca    240
gccaggttca gtggcagtgg gtctgggaca gacttcactc tcaccatcag cagcctagag    300
cctgaagatt ttgcagttta ttactgtcag cagagattct actacccttg gacttttggc    360
ggagggacca aggttgagat caaacggggg tctacatccg gctccgggaa gcccggaagt    420
ggcgaaggta gtacaaaggg ggaggtgcag ctggtggagt ctgggggagg cttggtacag    480
cctggggggt ccctgagact ctcctgtgca gcctctggat tcaccttcag tagctatagc    540
atgaactggg tccgccaggc tccagggaag gggctggagt gggtttcaac cattagtagt    600
agtagtagta ccatatacta cgcagactct gtgaagggcc gattcaccat ctccagagac    660
aatgccaaga actcactgta tctgcaaatg aacagcctga gactgaggga cacggcggtg    720
tactactgcg ccagaggttc tcaggagcac ctgattttcg attattgggg acagggtaca    780
ttggtcaccg tctcctcagc cgctgccctt gataatgaaa agtcaaacgg aacaatcatt    840
cacgtgaagg gcaagcacct ctgtccgtca cccttgttcc ctggtccatc aagccattc    900 tgggtgttgg tcgtagtggg tggagtcctc gcttgttact ctctgctcgt caccgtggct    960
tttataatct tctgggttag atccaaaaga agccgcctgc tccatagcga ttacatgaat   1020
atgactccac gccgcctggc cccacaagg aaacactacc agccttacgc accacctaga   1080
gatttcgctg cctatcggag cagggtgaag ttttccagat ctgcagatgc accagcgtat   1140
cagcagggcc agaaccaact gtataacgag ctcaacctgg gacgcaggga gagtatgac   1200 gttttggaca gcgcagagg acgggaccct gagatgggtg gcaaaccaag acgaaaaaac   1260
ccccaggagg gtctctataa tgagctgcag aaggataaga tggctgaagc ctattctgaa   1320
ataggcatga aggagagcg gagaagggga aagggcacg acggtttgta ccagggactc   1380
agcactgcta cgaaggatac ttatgacgct ctccacatgc aagccctgcc acctaggtaa   1440
```

<210> SEQ ID NO 152
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: TS-21522CARLxH

<400> SEQUENCE: 152

```
Met Ala Leu Pro Val Thr Ala Leu Leu Leu Pro Leu Ala Leu Leu Leu
1               5                   10                  15

His Ala Ala Arg Pro Glu Ile Val Leu Thr Gln Ser Pro Ala Thr Leu
            20                  25                  30

Ser Leu Ser Pro Gly Glu Arg Ala Thr Leu Ser Cys Arg Ala Ser Gln
        35                  40                  45

Ser Val Ser Arg Tyr Leu Ala Trp Tyr Gln Gln Lys Pro Gly Gln Ala
    50                  55                  60

Pro Arg Leu Leu Ile Tyr Asp Ala Ser Asn Arg Ala Thr Gly Ile Pro
65                  70                  75                  80

Ala Arg Phe Ser Gly Ser Gly Ser Gly Thr Asp Phe Thr Leu Thr Ile
                85                  90                  95

Ser Ser Leu Glu Pro Glu Asp Phe Ala Val Tyr Tyr Cys Gln Gln Arg
            100                 105                 110

Phe Tyr Tyr Pro Trp Thr Phe Gly Gly Gly Thr Lys Val Glu Ile Lys
        115                 120                 125
```

Arg Gly Ser Thr Ser Gly Ser Gly Lys Pro Gly Ser Gly Glu Gly Ser
            130                 135                 140

Thr Lys Gly Glu Val Gln Leu Val Glu Ser Gly Gly Gly Leu Val Gln
145                 150                 155                 160

Pro Gly Gly Ser Leu Arg Leu Ser Cys Ala Ala Ser Gly Phe Thr Phe
                165                 170                 175

Ser Ser Tyr Ser Met Asn Trp Val Arg Gln Ala Pro Gly Lys Gly Leu
            180                 185                 190

Glu Trp Val Ser Thr Ile Ser Ser Ser Ser Thr Ile Tyr Tyr Ala
        195                 200                 205

Asp Ser Val Lys Gly Arg Phe Thr Ile Ser Arg Asp Asn Ala Lys Asn
    210                 215                 220

Ser Leu Tyr Leu Gln Met Asn Ser Leu Arg Ala Glu Asp Thr Ala Val
225                 230                 235                 240

Tyr Tyr Cys Ala Arg Gly Ser Gln Glu His Leu Ile Phe Asp Tyr Trp
                245                 250                 255

Gly Gln Gly Thr Leu Val Thr Val Ser Ser Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475

<210> SEQ ID NO 153
<211> LENGTH: 1449
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RY-21527CARDNAHxL

<400> SEQUENCE: 153

```
atggcactcc ccgtaactgc tctgctgctg ccgttggcat tgctcctgca cgccgcacgc    60
ccgcaggtgc agctggtgga gtctggggga ggcgtggtcc agcctgggag gtccctgaga   120
ctctcctgtg cagcgtctgg attcaccttc agtagctatg gcatgcactg ggtccgccag   180
gctccaggca aggggctgga gtgggtggca gttatatcgt atgatggaag taataaatac   240
tatgcagact ccgtgaaggg ccgattcacc atctccagag acaattccaa gaacacgctg   300
tatctgcaaa tgaacagcct gagagccgag gacacggcgg tgtactactg cgccagaact   360
gacttctgga gcggatcccc tccaggctta gattactggg gacagggtac attggtcacc   420
gtctcctcag gtctacatc  cggctccggg aagcccggaa gtggcgaagg tagtacaaag   480
ggggacatcc agttgaccca gtctccatct ccgtgtctg  catctgtagg agacagagtc   540
accatcactt gtcgggcgag tcagggtatt agcagctggt tagcctggta tcagcagaaa   600
ccagggaaag cccctaagct cctgatctat ggtgcatcca gtttgcaaag tggggtccca   660
tcaaggttca gcggcagtgg atctgggaca gatttcactc tcaccatcag cagcctgcag   720
cctgaagatt ttgcaactta ttactgtcag cagatataca ccttcccttt cacttttggc   780
ggagggacca aggttgagat caaacgggcc gctgcccttg ataatgaaaa gtcaaacgga   840
acaatcattc acgtgaaggg caagcacctc tgtccgtcac ccttgttccc tggtccatcc   900
aagccattct gggtgttggt cgtagtgggt ggagtcctcg cttgttactc tctgctcgtc   960
accgtggctt ttataatctt ctgggttaga tccaaaagaa gccgcctgct ccatagcgat  1020
tacatgaata tgactccacg ccgccctggc cccacaagga acactacca gccttacgca   1080 ccacctagag atttcgctgc ctatcggagc agggtgaagt tttccagatc tgcagatgca  1140
ccagcgtatc agcagggcca gaaccaactg tataacgagc tcaacctggg acgcagggaa  1200
gagtatgacg ttttggacaa gcgcagagga cgggaccctg atgggtgg  caaaccaaga   1260 cgaaaaaacc cccaggaggg tctctataat gagctgcaga aggataagat ggctgaagcc  1320
tattctgaaa taggcatgaa aggagagcgg agaagggaa aagggcacga cggtttgtac   1380
cagggactca gcactgctac gaaggatact tatgacgctc tccacatgca agccctgcca  1440
cctaggtaa                                                          1449
```

<210> SEQ ID NO 154
<211> LENGTH: 482
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: RY-21527CARHxL

<400> SEQUENCE: 154

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Ser Tyr Asp Gly Ser Asn Lys Tyr
65                  70                  75                  80
```

```
Tyr Ala Asp Ser Val Lys Gly Arg Phe Thr Ile Ser Arg Asp Asn Ser
                 85                  90                  95

Lys Asn Thr Leu Tyr Leu Gln Met Asn Ser Leu Arg Ala Glu Asp Thr
            100                 105                 110

Ala Val Tyr Tyr Cys Ala Arg Thr Asp Phe Trp Ser Gly Ser Pro Pro
        115                 120                 125

Gly Leu Asp Tyr Trp Gly Gln Gly Thr Leu Val Thr Val Ser Ser Gly
    130                 135                 140

Ser Thr Ser Gly Ser Gly Lys Pro Gly Ser Gly Glu Gly Ser Thr Lys
145                 150                 155                 160

Gly Asp Ile Gln Leu Thr Gln Ser Pro Ser Ser Val Ser Ala Ser Val
                165                 170                 175

Gly Asp Arg Val Thr Ile Thr Cys Arg Ala Ser Gln Gly Ile Ser Ser
            180                 185                 190

Trp Leu Ala Trp Tyr Gln Gln Lys Pro Gly Lys Ala Pro Lys Leu Leu
        195                 200                 205

Ile Tyr Gly Ala Ser Ser Leu Gln Ser Gly Val Pro Ser Arg Phe Ser
    210                 215                 220

Gly Ser Gly Ser Gly Thr Asp Phe Thr Leu Thr Ile Ser Ser Leu Gln
225                 230                 235                 240

Pro Glu Asp Phe Ala Thr Tyr Tyr Cys Gln Gln Ile Tyr Thr Phe Pro
                245                 250                 255

Phe Thr Phe Gly Gly Gly Thr Lys Val Glu Ile Lys Arg Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
    450                 455                 460

Thr Ala Thr Lys Asp Thr Tyr Asp Ala Leu His Met Gln Ala Leu Pro
465                 470                 475                 480

Pro Arg

<210> SEQ ID NO 155
```

<211> LENGTH: 1449
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: RY-21527CARDNALxH

<400> SEQUENCE: 155

```
atggcactcc ccgtaactgc tctgctgctg ccgttggcat tgctcctgca cgccgcacgc      60
ccggacatcc agttgaccca gtctccatct tccgtgtctg catctgtagg agacagagtc     120
accatcactt gtcgggcgag tcagggtatt agcagctggt tagcctggta tcagcagaaa     180
ccagggaaag cccctaagct cctgatctat ggtgcatcca gtttgcaaag tggggtccca     240
tcaaggttca gcggcagtgg atctgggaca gatttcactc tcaccatcag cagcctgcag     300
cctgaagatt ttgcaactta ttactgtcag cagatataca ccttcccttt cacttttggc     360
ggagggacca aggttgagat caaacgggg tctacatccg ctccgggaa gcccggaagt     420
ggcgaaggta gtacaaaggg gcaggtgcag ctggtggagt ctgggggagg cgtggtccag     480
cctggaggt ccctgagact ctcctgtgca gcgtctggat tcaccttcag tagctatggc     540
atgcactggg tccgccaggc tccaggcaag gggctggagt gggtggcagt tatatcgtat     600
gatggaagta ataaatacta tgcagactcc gtgaagggcc gattcaccat ctccagagac     660
aattccaaga cacgctgta tctgcaaatg aacagcctga gccgagga cacggcggtg     720
tactactgcg ccagaactga cttctggagc ggatccccctc aggcttaga ttactgggga     780
cagggtacat tggtcaccgt ctcctcagcc gctgcccttg ataatgaaaa gtcaaacgga     840
acaatcattc acgtgaaggg caagcacctc tgtccgtcac ccttgttccc tggtccatcc     900
aagccattct gggtgttggt cgtagtgggt ggagtcctcg cttgttactc tctgctcgtc     960
accgtggctt ttataatctt ctgggttaga tccaaaagaa gccgcctgct ccatagcgat    1020
tacatgaata tgactccacg ccgccctggc cccacaagga acactacca gccttacgca    1080
ccacctagag atttcgctgc ctatcggagc agggtgaagt tttccagatc tgcagatgca    1140
ccagcgtatc agcagggcca gaaccaactg tataacgagc tcaacctggg acgcaggaa    1200
gagtatgacg ttttggacaa gcgcagagga cgggaccctg agatgggtgg caaaccaaga    1260
cgaaaaacc cccaggaggg tctctataat gagctgcaga aggataagat ggctgaagcc    1320
tattctgaaa taggcatgaa aggagagcgg agaaggggaa aagggcacga cggtttgtac    1380
cagggactca gcactgctac gaaggatact tatgacgctc tccacatgca agccctgcca    1440
cctaggtaa                                                           1449
```

<210> SEQ ID NO 156
<211> LENGTH: 482
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: RY-21527CARLxH

<400> SEQUENCE: 156

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Val
            20                  25                  30
```

```
Ser Ala Ser Val Gly Asp Arg Val Thr Ile Thr Cys Arg Ala Ser Gln
            35                  40                  45

Gly Ile Ser Ser Trp Leu Ala Trp Tyr Gln Gln Lys Pro Gly Lys Ala
 50                  55                  60

Pro Lys Leu Leu Ile Tyr Gly Ala Ser Ser Leu Gln Ser Gly Val Pro
 65                  70                  75                  80

Ser Arg Phe Ser Gly Ser Gly Ser Gly Thr Asp Phe Thr Leu Thr Ile
                 85                  90                  95

Ser Ser Leu Gln Pro Glu Asp Phe Ala Thr Tyr Tyr Cys Gln Gln Ile
            100                 105                 110

Tyr Thr Phe Pro Phe Thr Phe Gly Gly Gly Thr Lys Val Glu Ile Lys
            115                 120                 125

Arg Gly Ser Thr Ser Gly Ser Gly Lys Pro Gly Ser Gly Glu Gly Ser
        130                 135                 140

Thr Lys Gly Gln Val Gln Leu Val Glu Ser Gly Gly Gly Val Val Gln
145                 150                 155                 160

Pro Gly Arg Ser Leu Arg Leu Ser Cys Ala Ala Ser Gly Phe Thr Phe
                165                 170                 175

Ser Ser Tyr Gly Met His Trp Val Arg Gln Ala Pro Gly Lys Gly Leu
            180                 185                 190

Glu Trp Val Ala Val Ile Ser Tyr Asp Gly Ser Asn Lys Tyr Tyr Ala
            195                 200                 205

Asp Ser Val Lys Gly Arg Phe Thr Ile Ser Arg Asp Asn Ser Lys Asn
        210                 215                 220

Thr Leu Tyr Leu Gln Met Asn Ser Leu Arg Ala Glu Asp Thr Ala Val
225                 230                 235                 240

Tyr Tyr Cys Ala Arg Thr Asp Phe Trp Ser Gly Ser Pro Pro Gly Leu
                245                 250                 255

Asp Tyr Trp Gly Gln Gly Thr Leu Val Thr Val Ser Ser Ala Ala Ala
            260                 265                 270

Leu Asp Asn Glu Lys Ser Asn Gly Thr Ile Ile His Val Lys Gly Lys
        275                 280                 285

His Leu Cys Pro Ser Pro Leu Phe Pro Gly Pro Ser Lys Pro Phe Trp
        290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Arg Val Lys Phe Ser Arg Ser Ala Asp Ala Pro Ala Tyr Gln
    370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Arg Lys Asn Pro Gln Glu Gly Leu Tyr Asn Glu Leu
            420                 425                 430

Gln Lys Asp Lys Met Ala Glu Ala Tyr Ser Glu Ile Gly Met Lys Gly
        435                 440                 445
```

Glu Arg Arg Arg Gly Lys Gly His Asp Gly Leu Tyr Gln Gly Leu Ser
        450                 455                 460

Thr Ala Thr Lys Asp Thr Tyr Asp Ala Leu His Met Gln Ala Leu Pro
465                 470                 475                 480

Pro Arg

<210> SEQ ID NO 157
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PP-21528CARDNAHxL

<400> SEQUENCE: 157

```
atggcactcc ccgtaactgc tctgctgctg ccgttggcat tgctcctgca cgccgcacgc      60
ccgcaggtgc agctggtgca gtctgggget gaggtgaaga agcctgggtc ctcggtgaag     120
gtctcctgca aggcttctgg aggcaccttc agcagctatg ctatcagctg ggtgcgacag     180
gcccctggac aagggcttga gtggatggga gggatcatcc ctatctttgg tacagcaaac     240
tacgcacaga gttccaggg cagagtcacg attaccgcgg acgaatccac gagcacagcc      300
tacatggagc tgagcagcct gagatctgag gacacggcgg tgtactactg cgccagaact     360
cctgaatact cctccagcat atggcactat tactacggca tggacgtatg gggccaggga     420
acaactgtca ccgtctcctc agggtctaca tccggctccg ggaagcccgg aagtggcgaa     480
ggtagtacaa agggggacat cgtgatgacc cagtctccag actccctggc tgtgtctctg     540
ggcgagaggg ccaccatcaa ctgcaagtcc agccagagtg ttttatacag ctccaacaat     600
aagaactact agcttggta ccagcagaaa ccaggacagc ctcctaagct gctcatttac     660
tgggcatcta cccgggaatc cggggtccct gaccgattca gtggcagcgg gtctgggaca     720
gatttcactc tcaccatcag cagcctgcag gctgaagatg tggcagttta ttactgtcag     780
cagttcgccc acactccttt cacttttggc ggagggacca aggttgagat caaacgggcc     840
gctgcccttg ataatgaaaa gtcaaacgga acaatcattc acgtgaaggg caagcacctc     900
tgtccgtcac ccttgttccc tggtccatcc aagccattct gggtgttggt cgtagtgggt     960
ggagtcctcg cttgttactc tctgctcgtc accgtggctt ttataatctt ctgggttaga    1020
tccaaaagaa gccgcctgct ccatagcgat tacatgaata tgactccacg ccgccctggc    1080
cccacaagga acactacca gccttacgca ccacctagag atttcgctgc ctatcggagc    1140
agggtgaagt tttccagatc tgcagatgca ccagcgtatc agcagggcca gaaccaactg    1200
tataacgagc tcaacctggg acgcaggaa gagtatgacg ttttggacaa gcgcagagga    1260
cgggaccctg agatgggtgg caaaccaaga cgaaaaaacc cccaggaggg tctctataat    1320
gagctgcaga aggataagat ggctgaagcc tattctgaaa taggcatgaa aggagagcgg    1380
agaaggggaa aagggcacga cggtttgtac cagggactca gcactgctac gaaggatact    1440
tatgacgctc tccacatgca agccctgcca cctaggtaa                          1479
```

<210> SEQ ID NO 158
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide <220> FEATURE:
<223> OTHER INFORMATION: PP-21528CARHxL

<400> SEQUENCE: 158

```
Met Ala Leu Pro Val Thr Ala Leu Leu Leu Pro Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Ser Tyr Ala Ile Ser Trp Val Arg Gln Ala Pro Gly Gln
    50                  55                  60

Gly Leu Glu Trp Met Gly Gly Ile Ile Pro Ile Phe Gly Thr Ala Asn
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Arg Thr Pro Glu Tyr Ser Ser Ser Ile Trp
        115                 120                 125

His Tyr Tyr Gly Met Asp Val Trp Gly Gln Gly Thr Thr Val Thr
    130                 135                 140

Val Ser Ser Gly Ser Thr Ser Gly Ser Gly Lys Pro Gly Ser Gly Glu
145                 150                 155                 160

Gly Ser Thr Lys Gly Asp Ile Val Met Thr Gln Ser Pro Asp Ser Leu
                165                 170                 175

Ala Val Ser Leu Gly Glu Arg Ala Thr Ile Asn Cys Lys Ser Ser Gln
            180                 185                 190

Ser Val Leu Tyr Ser Ser Asn Asn Lys Asn Tyr Leu Ala Trp Tyr Gln
        195                 200                 205

Gln Lys Pro Gly Gln Pro Pro Lys Leu Leu Ile Tyr Trp Ala Ser Thr
    210                 215                 220

Arg Glu Ser Gly Val Pro Asp Arg Phe Ser Gly Ser Gly Ser Gly Thr
225                 230                 235                 240

Asp Phe Thr Leu Thr Ile Ser Ser Leu Gln Ala Glu Asp Val Ala Val
                245                 250                 255

Tyr Tyr Cys Gln Gln Phe Ala His Thr Pro Phe Thr Phe Gly Gly Gly
            260                 265                 270

Thr Lys Val Glu Ile Lys Arg Ala Ala Ala Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

Phe Trp Val Arg Ser Lys Arg Ser Arg Leu Leu His Ser Asp Tyr Met
            340                 345                 350

Asn Met Thr Pro Arg Arg Pro Gly Pro Thr Arg Lys His Tyr Gln Pro
        355                 360                 365

Tyr Ala Pro Pro Arg Asp Phe Ala Ala Tyr Arg Ser Arg Val Lys Phe
    370                 375                 380

Ser Arg Ser Ala Asp Ala Pro Ala Tyr Gln Gln Gly Gln Asn Gln Leu
385                 390                 395                 400
```

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 159
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: PP-21528CARDNALxH

<400> SEQUENCE: 159
atggcactcc ccgtaactgc tctgctgctg ccgttggcat tgctcctgca cgccgcacgc     60
ccggacatcg tgatgaccca gtctccagac tccctggctg tgtctctggg cgagagggcc    120
accatcaact gcaagtccag ccagagtgtt ttatacagct ccaacaataa gaactactta    180
gcttggtacc agcagaaacc aggacagcct cctaagctgc tcatttactg ggcatctacc    240
cgggaatccg gggtccctga ccgattcagt ggcagcgggt ctgggacaga tttcactctc    300
accatcagca gcctgcaggc tgaagatgtg gcagtttatt actgtcagca gttcgcccac    360
actcctttca cttttggcgg agggaccaag gttgagatca acggggggtc tacatccggc    420
tccgggaagc ccggaagtgg cgaaggtagt acaaaggggc aggtgcagct ggtgcagtct    480
ggggctgagt tgaagaagcc tgggtcctcg gtgaaggtct cctgcaaggc ttctggaggc    540
accttcagca gctatgctat cagctgggtg cgacaggccc ctggacaagg gcttgagtgg    600
atgggaggga tcatccctat ctttggtaca gcaaactacg cacagaagtt ccagggcaga    660
gtcacgatta ccgcggacga atccacgagc acagcctaca tggagctgag cagcctgaga    720
tctgaggaca cggcggtgta ctactgcgcc agaactcctg aatactcctc agcatatgg     780 cactattact acggcatgga cgtatggggc caggaacaa ctgtcaccgt ctcctcagcc     840
gctgcccttg ataatgaaaa gtcaaacgga caatcattc acgtgaaggg caagcacctc     900
tgtccgtcac ccttgttccc tggtccatcc aagccattct gggtgttggt cgtagtgggt    960
ggagtcctcg cttgttactc tctgctcgtc accgtggctt ttataatctt ctgggttaga   1020
tccaaaagaa gccgcctgct ccatagcgat tacatgaata tgactccacg ccgcccggc    1080 cccacaagga aacactacca gccttacgca ccacctagag atttcgctgc ctatcggagc   1140
agggtgaagt tttccagatc tgcagatgca ccagcgtatc agcagggcca gaaccaactg   1200
tataacgagc tcaacctggg acgcagggaa gagtatgacg ttttggacaa gcgcagagga   1260
cgggaccctg agatgggtgg caaaccaaga cgaaaaaacc cccaggaggg tctctataat   1320
gagctgcaga aggataagat ggctgaagcc tattctgaaa taggcatgaa aggagagcgg   1380 agaagggga aagggcacga cggtttgtac cagggactca gcactgctac gaaggatact   1440
tatgacgctc tccacatgca agccctgcca cctaggtaa                               1479

<210> SEQ ID NO 160
<211> LENGTH: 492
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: PP-21528CARLxH

<400> SEQUENCE: 160

Met Ala Leu Pro Val Thr Ala Leu Leu Leu Pro Leu Ala Leu Leu Leu
1               5                   10                  15

His Ala Ala Arg Pro Asp Ile Val Met Thr Gln Ser Pro Asp Ser Leu
            20                  25                  30

Ala Val Ser Leu Gly Glu Arg Ala Thr Ile Asn Cys Lys Ser Ser Gln
        35                  40                  45

Ser Val Leu Tyr Ser Ser Asn Asn Lys Asn Tyr Leu Ala Trp Tyr Gln
    50                  55                  60

Gln Lys Pro Gly Gln Pro Pro Lys Leu Leu Ile Tyr Trp Ala Ser Thr
65                  70                  75                  80

Arg Glu Ser Gly Val Pro Asp Arg Phe Ser Gly Ser Gly Ser Gly Thr
                85                  90                  95

Asp Phe Thr Leu Thr Ile Ser Ser Leu Gln Ala Glu Asp Val Ala Val
            100                 105                 110

Tyr Tyr Cys Gln Gln Phe Ala His Thr Pro Phe Thr Phe Gly Gly Gly
        115                 120                 125

Thr Lys Val Glu Ile Lys Arg Gly Ser Thr Ser Gly Ser Gly Lys Pro
130                 135                 140

Gly Ser Gly Glu Gly Ser Thr Lys Gly Gln Val Gln Leu Val Gln Ser
145                 150                 155                 160

Gly Ala Glu Val Lys Lys Pro Gly Ser Ser Val Lys Val Ser Cys Lys
                165                 170                 175

Ala Ser Gly Gly Thr Phe Ser Ser Tyr Ala Ile Ser Trp Val Arg Gln
            180                 185                 190

Ala Pro Gly Gln Gly Leu Glu Trp Met Gly Gly Ile Ile Pro Ile Phe
        195                 200                 205

Gly Thr Ala Asn Tyr Ala Gln Lys Phe Gln Gly Arg Val Thr Ile Thr
    210                 215                 220

Ala Asp Glu Ser Thr Ser Thr Ala Tyr Met Glu Leu Ser Ser Leu Arg
225                 230                 235                 240

Ser Glu Asp Thr Ala Val Tyr Tyr Cys Ala Arg Thr Pro Glu Tyr Ser
                245                 250                 255

Ser Ser Ile Trp His Tyr Tyr Gly Met Asp Val Trp Gly Gln Gly
            260                 265                 270

Thr Thr Val Thr Val Ser Ser Ala Ala Ala Leu Asp Asn Glu Lys Ser
        275                 280                 285

Asn Gly Thr Ile Ile His Val Lys Gly Lys His Leu Cys Pro Ser Pro
    290                 295                 300

Leu Phe Pro Gly Pro Ser Lys Pro Phe Trp Val Leu Val Val Val Gly
305                 310                 315                 320

Gly Val Leu Ala Cys Tyr Ser Leu Leu Val Thr Val Ala Phe Ile Ile
                325                 330                 335

```
Phe Trp Val Arg Ser Lys Arg Ser Arg Leu Leu His Ser Asp Tyr Met
                340                 345                 350

Asn Met Thr Pro Arg Arg Pro Gly Pro Thr Arg Lys His Tyr Gln Pro
            355                 360                 365

Tyr Ala Pro Pro Arg Asp Phe Ala Ala Tyr Arg Ser Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 161
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RD-21530CARDNAHxL

<400> SEQUENCE: 161

```
atggcactcc  cgtaactgc   tctgctgctg  ccgttggcat  tgctcctgca  cgccgcacgc    60
ccgcaggtgc  agctggtgga  gtctggggga  ggcgtggtcc  agcctgggag  gtccctgaga   120
ctctcctgtg  cagcgtctgg  attcaccttc  agtagctatg  gcatgcactg  ggtccgccag   180
gctccaggca  aggggctgga  gtgggtggca  gttatatcgt  atgatggaag  taataaatac   240
tatgcagact  ccgtgaaggg  ccgattcacc  atctccagag  acaattccaa  gaacacgctg   300
tatctgcaaa  tgaacagcct  gagagccgag  gacacggcgg  tgtactactg  cgtcaagggg   360
ccgttgcagg  agccgccata  cgattatgga  atggacgtat  ggggccaggg  aacaactgtc   420
accgtctcct  cagggtctac  atccggctcc  gggaagcccg  aagtggcga   aggtagtaca   480
aagggggaaa  tagtgatgac  gcagtctcca  gccaccctgt  ctgtgtctcc  aggggaaaga   540
gccaccctct  cctgcaggc   cagtcagagt  gttagcagca  acttagcctg  gtaccagcag   600
aaacctggcc  aggctcccag  gctcctcatc  tatagcgcat  ccaccagggc  cactggtatc   660
ccagccaggt  tcagtggcag  tgggtctggg  acagagttca  ctctcaccat  cagcagcctg   720
cagtctgaag  attttgcagt  ttattactgt  cagcagcacc  acgtctggcc  tctcactttt   780
ggcggaggga  ccaaggttga  gatcaaacgg  gccgctgccc  ttgataatga  aaagtcaaac   840
ggaacaatca  ttcacgtgaa  gggcaagcac  ctctgtccgt  cacccttgtt  ccctggtcca   900
tccaagccat  tctgggtgtt  ggtcgtagtg  ggtggagtcc  tgcttgtta   ctctctgctc   960
gtcaccgtgg  cttttataat  cttctgggtt  agatccaaaa  gaagccgcct  gctccatagc  1020
gattacatga  atatgactcc  acgccgccct  ggccccacaa  ggaaacacta  ccagccttac  1080
```

```
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa accccagga gggtctctat aatgagctgc agaaggataa gatggctgaa   1320
gcctattctg aaataggcat gaaggagag cggagaaggg gaaaagggca cgacggtttg   1380
taccagggac tcagcactgc tacgaaggat acttatgacg ctctccacat gcaagccctg   1440
ccacctaggt aa                                                      1452
```

<210> SEQ ID NO 162
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: RD-21530CARHxL

<400> SEQUENCE: 162

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asn Lys Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Lys Gly Pro Leu Gln Glu Pro Pro Tyr Asp
        115                 120                 125

Tyr Gly Met Asp Val Trp Gly Gln Gly Thr Thr Val Thr Val Ser Ser
    130                 135                 140

Gly Ser Thr Ser Gly Ser Gly Lys Pro Gly Ser Gly Glu Gly Ser Thr
145                 150                 155                 160

Lys Gly Glu Ile Val Met Thr Gln Ser Pro Ala Thr Leu Ser Val Ser
                165                 170                 175

Pro Gly Glu Arg Ala Thr Leu Ser Cys Arg Ala Ser Gln Ser Val Ser
            180                 185                 190

Ser Asn Leu Ala Trp Tyr Gln Gln Lys Pro Gly Gln Ala Pro Arg Leu
        195                 200                 205

Leu Ile Tyr Ser Ala Ser Thr Arg Ala Thr Gly Ile Pro Ala Arg Phe
    210                 215                 220

Ser Gly Ser Gly Ser Gly Thr Glu Phe Thr Leu Thr Ile Ser Ser Leu
225                 230                 235                 240

Gln Ser Glu Asp Phe Ala Val Tyr Tyr Cys Gln Gln His Val Trp His
                245                 250                 255

Pro Leu Thr Phe Gly Gly Gly Thr Lys Val Glu Ile Lys Arg Ala Ala
            260                 265                 270

Ala Leu Asp Asn Glu Lys Ser Asn Gly Thr Ile Ile His Val Lys Gly
```

```
                275                 280                 285
Lys His Leu Cys Pro Ser Pro Leu Phe Pro Gly Pro Ser Lys Pro Phe
        290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
        340                 345                 350

Thr Arg Lys His Tyr Gln Pro Tyr Ala Pro Pro Arg Asp Phe Ala Ala
                355                 360                 365

Tyr Arg Ser Arg Val Lys Phe Ser Arg Ser Ala Asp Ala Pro Ala Tyr
370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
                420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
450                 455                 460

Ser Thr Ala Thr Lys Asp Thr Tyr Asp Ala Leu His Met Gln Ala Leu
465                 470                 475                 480

Pro Pro Arg

<210> SEQ ID NO 163
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: RD-21530CARDNALxH

<400> SEQUENCE: 163
atggcactcc ccgtaactgc tctgctgctg ccgttggcat tgctcctgca cgccgcacgc      60
ccggaaatag tgatgacgca gtctccagcc accctgtctg tgtctccagg ggaaagagcc     120
accctctcct gcagggccag tcagagtgtt agcagcaact tagcctggta ccagcagaaa     180
cctggccagg ctcccaggct cctcatctat agcgcatcca ccagggccac tggtatccca     240
gccaggttca gtggcagtgg gtctgggaca gagttcactc tcaccatcag cagcctgcag     300
tctgaagatt ttgcagtttta ttactgtcag cagcaccacg tctggcctct cacttttggc     360
ggagggacca aggttgagat caaacggggg tctacatccg gctccgggaa gcccggaagt     420
ggcgaaggta gtacaaaggg gcaggtgcag ctggtggagt ctgggggagg cgtggtccag     480 cctggaggt ccctgagact ctcctgtgca gcgtctggat tcaccttcag tagctatggc     540
atgcactggg tccgccaggc tccaggcaag gggctggagt gggtggcagt tatatcgtat     600
gatggaagta ataaatacta tgcagactcc gtgaagggcc gattcaccat ctccagagac     660
aattccaaga acacgctgta tctgcaaatg aacagcctga gaccgaggga cacggcggtg     720
tactactgcg tcaaggggcc cgttgcaggag ccgccatacg attatggaat ggacgtatgg     780
```

```
ggccagggaa caactgtcac cgtctcctca gccgctgccc ttgataatga aaagtcaaac    840
ggaacaatca ttcacgtgaa gggcaagcac ctctgtccgt caccctttgtt ccctggtcca    900 tccaagccat tctgggtgtt ggtcgtagtg ggtggagtcc tcgcttgtta ctctctgctc    960
gtcaccgtgg cttttataat cttctgggtt agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa accccccagga gggtctctat aatgagctgc agaaggataa gatggctgaa   1320
gcctattctg aaataggcat gaaaggagag cggagaaggg gaaaagggca cgacggtttg   1380
taccagggac tcagcactgc tacgaaggat acttatgacg ctctccacat gcaagccctg   1440
ccacctaggt aa                                                       1452
```

<210> SEQ ID NO 164
<211> LENGTH: 483
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: RD-21530CARLxH

<400> SEQUENCE: 164

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Asn Leu Ala Trp Tyr Gln Gln Lys Pro Gly Gln Ala
    50                  55                  60

Pro Arg Leu Leu Ile Tyr Ser Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Ser Ser Leu Gln Ser Glu Asp Phe Ala Val Tyr Tyr Cys Gln Gln His
            100                 105                 110

His Val Trp Pro Leu Thr Phe Gly Gly Gly Thr Lys Val Glu Ile Lys
        115                 120                 125

Arg Gly Ser Thr Ser Gly Ser Gly Lys Pro Gly Ser Gly Glu Gly Ser
    130                 135                 140

Thr Lys Gly Gln Val Gln Leu Val Glu Ser Gly Gly Gly Val Val Gln
145                 150                 155                 160

Pro Gly Arg Ser Leu Arg Leu Ser Cys Ala Ala Ser Gly Phe Thr Phe
                165                 170                 175

Ser Ser Tyr Gly Met His Trp Val Arg Gln Ala Pro Gly Lys Gly Leu
            180                 185                 190

Glu Trp Val Ala Val Ile Ser Tyr Asp Gly Ser Asn Lys Tyr Tyr Ala
        195                 200                 205

Asp Ser Val Lys Gly Arg Phe Thr Ile Ser Arg Asp Asn Ser Lys Asn
    210                 215                 220
```

Thr Leu Tyr Leu Gln Met Asn Ser Leu Arg Ala Glu Asp Thr Ala Val
225                 230                 235                 240

Tyr Tyr Cys Val Lys Gly Pro Leu Gln Glu Pro Pro Tyr Asp Tyr Gly
            245                 250                 255

Met Asp Val Trp Gly Gln Gly Thr Thr Val Thr Val Ser Ser Ala Ala
            260                 265                 270

Ala Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
            325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 165
<211> LENGTH: 1440
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: anti-CLL-1 CAR construct

<400> SEQUENCE: 165
atggcactcc ccgtaactgc tctgctgctg ccgttggcat tgctcctgca cgccgcacgc      60
ccgcaggtcc aactgcaaga aagcggaccc ggactggtga agccttctga cacttagt     120 ctgacgtgca cggtcagtgg cggctccatc tcctcctatt attggtcatg gatacgacaa     180 ccccaggta agggcctgga atggattggc tatatctact attcaggaag cacgaactac     240
aatcccagcc tgaagtcccg agtgacaatt tcagtagata ccagtaaaaa ccagttcagt     300
cttaaactgt caagcgtgac agctgccgac accgctgtgt attactgcgt ctcactggtg     360
tattgtggag gggattgtta tagcgggttc gattattggg gacagggaac cctggtgact     420
gtatcttccg gcggcggcgg ctcaggggt ggcggtagtg gcggtggggg ttccgatatt     480

```
caactgacac aatcccccag ctcactcagc gccagcgtgg gggacagggt tagctttacc    540
tgtcaagcct ctcaggatat aaataacttt ctgaactggt atcaacagaa gcctgggaag    600
gcgcccaaac tcctgatcta tgatgcgtcc aacctggaaa ctggcgtgcc ttcacgcttt    660
agcggctctg gcagtggtac agacttcact tttaccatct cttcacttca gccggaggac    720
atcgccacat attactgtca acagtacgga aacttgccct ttacttttgg aggcggcacc    780
aaagttgaaa tcaaagggc cgctgccctg gataacgaaa agagcaatgg gactataata    840
catgttaaag gaaacacct gtgtccatct ccctgttcc ctggaccgtc aaagccattt    900
tgggtgctcg tggttgtcgg tggcgttctc gcctgttata gcttgctggt gacagtagcc    960
ttcattatct tttgggtgag atccaaaaga agccgcctgc tccatagcga ttacatgaat   1020
atgactccac gccgccctgg ccccacaagg aaacactacc agccttacgc accacctaga   1080
gatttcgctg cctatcggag cagggtgaag ttttccagat ctgcagatgc accagcgtat   1140
cagcagggcc agaaccaact gtataacgag ctcaacctgg gacgcaggga agagtatgac   1200
gttttggaca gcgcagagg acgggaccct gagatgggtg gcaaaccaag acgaaaaaac   1260
ccccaggagg gtctctataa tgagctgcag aaggataaga tggctgaagc ctattctgaa   1320
ataggcatga aggagagcg gagaagggga aaagggcacg acggtttgta ccagggactc   1380
agcactgcta cgaaggatac ttatgacgct ctccacatgc aagccctgcc acctaggtaa   1440
```

<210> SEQ ID NO 166
<211> LENGTH: 479
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 166

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Tyr Tyr Trp Ser Trp Ile Arg Gln Pro Pro Gly Lys
    50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Val Ser Leu Val Tyr Cys Gly Gly Asp Cys Tyr Ser
        115                 120                 125

Gly Phe Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Leu Thr Gln Ser Pro Ser Ser Leu Ser Ala Ser Val Gly Asp Arg
                165                 170                 175

Val Ser Phe Thr Cys Gln Ala Ser Gln Asp Ile Asn Asn Phe Leu Asn

```
            180                 185                 190
Trp Tyr Gln Gln Lys Pro Gly Lys Ala Pro Lys Leu Leu Ile Tyr Asp
        195                 200                 205

Ala Ser Asn Leu Glu Thr Gly Val Pro Ser Arg Phe Ser Gly Ser Gly
    210                 215                 220

Ser Gly Thr Asp Phe Thr Phe Thr Ile Ser Ser Leu Gln Pro Glu Asp
225                 230                 235                 240

Ile Ala Thr Tyr Tyr Cys Gln Gln Tyr Gly Asn Leu Pro Phe Thr Phe
                245                 250                 255

Gly Gly Gly Thr Lys Val Glu Ile Lys Arg Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
305                 310                 315                 320

Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
        435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475

<210> SEQ ID NO 167
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 167
caggtccaac tgcaagaaag cggacccgga ctggtgaagc cttctgagac acttagtctg      60
acgtgcacgg tcagtggcgg ctccatctcc tcctattatt ggtcatggat acgacaaccc     120
ccaggtaagg gcctggaatg gattggctat atctactatt caggaagcac gaactacaat     180
cccagcctga gtcccgagt gacaatttca gtagatacca gtaaaaacca gttcagtctt     240
aaactgtcaa gcgtgacagc tgccgacacc gctgtgtatt actgcgtctc actggtgtat     300
```

```
tgtggagggg attgttatag cgggttcgat tattgggac agggaaccct ggtgactgta      360
tcttccggcg gcggcggctc aggggtggc ggtagtggcg gtgggggttc cgatattcaa       420
ctgacacaat cccccagctc actcagcgcc agcgtggggg acagggttag ctttacctgt      480
caagcctctc aggatataaa taactttctg aactggtatc aacagaagcc tgggaaggcg      540
cccaaactcc tgatctatga tgcgtccaac ctggaaactg gcgtgccttc acgctttagc     600
ggctctggca gtggtacaga cttcactttt accatctctt cacttcagcc ggaggacatc     660
gccacatatt actgtcaaca gtacggaaac ttgcccttta cttttggagg cggcaccaaa     720
gttgaaatca aaagggccgc tgccctggat aacgaaaaga gcaatgggac tataatacat     780
gttaaaggaa aacacctgtg tccatctccc ctgttccctg accgtcaaa gccattttgg      840 gtgctcgtgg ttgtcggtgg cgttctcgcc tgttatagct tgctggtgac agtagccttc     900
attatctttt gggtgagatc caaaagaagc cgcctgctcc atagcgatta catgaatatg     960
actccacgcc gccctggccc cacaaggaaa cactaccagc cttacgcacc acctagagat    1020
ttcgctgcct atcggagcag ggtgaagttt tccagatctg cagatgcacc agcgtatcag   1080
cagggccaga accaactgta taacgagctc aacctgggac gcaggaaga gtatgacgtt    1140 ttggacaagc gcagaggacg ggaccctgag atgggtggca aaccaagacg aaaaaacccc    1200
caggagggtc tctataatga gctgcagaag gataagatgg ctgaagccta ttctgaaata    1260
ggcatgaaag gagagcggag aaggggaaaa ggcacgacg gtttgtacca gggactcagc    1320
actgctacga aggatactta tgacgctctc cacatgcaag ccctgccacc tagg           1374
```

<210> SEQ ID NO 168
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 168

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Ser Leu Val Tyr Cys Gly Gly Asp Cys Tyr Ser Gly Phe Asp Tyr Trp
            100                 105                 110

Gly Gln Gly Thr Leu Val Thr Val Ser Ser Gly Gly Gly Gly Ser Gly
        115                 120                 125

Gly Gly Gly Ser Gly Gly Gly Gly Ser Asp Ile Gln Leu Thr Gln Ser
    130                 135                 140

Pro Ser Ser Leu Ser Ala Ser Val Gly Asp Arg Val Ser Phe Thr Cys
145                 150                 155                 160
```

```
Gln Ala Ser Gln Asp Ile Asn Asn Phe Leu Asn Trp Tyr Gln Gln Lys
            165                 170                 175
Pro Gly Lys Ala Pro Lys Leu Leu Ile Tyr Asp Ala Ser Asn Leu Glu
        180                 185                 190
Thr Gly Val Pro Ser Arg Phe Ser Gly Ser Gly Ser Gly Thr Asp Phe
    195                 200                 205
Thr Phe Thr Ile Ser Ser Leu Gln Pro Glu Asp Ile Ala Thr Tyr Tyr
210                 215                 220
Cys Gln Gln Tyr Gly Asn Leu Pro Phe Thr Phe Gly Gly Gly Thr Lys
225                 230                 235                 240
Val Glu Ile Lys Arg Ala Ala Ala Leu Asp Asn Glu Lys Ser Asn Gly
            245                 250                 255
Thr Ile Ile His Val Lys Gly Lys His Leu Cys Pro Ser Pro Leu Phe
        260                 265                 270
Pro Gly Pro Ser Lys Pro Phe Trp Val Leu Val Val Val Gly Gly Val
    275                 280                 285
Leu Ala Cys Tyr Ser Leu Leu Val Thr Val Ala Phe Ile Ile Phe Trp
290                 295                 300
Val Arg Ser Lys Arg Ser Arg Leu Leu His Ser Asp Tyr Met Asn Met
305                 310                 315                 320
Thr Pro Arg Arg Pro Gly Pro Thr Arg Lys His Tyr Gln Pro Tyr Ala
            325                 330                 335
Pro Pro Arg Asp Phe Ala Ala Tyr Arg Ser Arg Val Lys Phe Ser Arg
        340                 345                 350
Ser Ala Asp Ala Pro Ala Tyr Gln Gln Gly Gln Asn Gln Leu Tyr Asn
    355                 360                 365
Glu Leu Asn Leu Gly Arg Arg Glu Glu Tyr Asp Val Leu Asp Lys Arg
370                 375                 380
Arg Gly Arg Asp Pro Glu Met Gly Gly Lys Pro Arg Arg Lys Asn Pro
385                 390                 395                 400
Gln Glu Gly Leu Tyr Asn Glu Leu Gln Lys Asp Lys Met Ala Glu Ala
            405                 410                 415
Tyr Ser Glu Ile Gly Met Lys Gly Glu Arg Arg Arg Gly Lys Gly His
        420                 425                 430
Asp Gly Leu Tyr Gln Gly Leu Ser Thr Ala Thr Lys Asp Thr Tyr Asp
    435                 440                 445
Ala Leu His Met Gln Ala Leu Pro Pro Arg
450                 455
```

<210> SEQ ID NO 169
<211> LENGTH: 1467
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: anti-CLL-1 CAR construct

<400> SEQUENCE: 169

```
atggcactcc ccgtaactgc tctgctgctg ccgttggcat tgctcctgca cgccgcacgc      60
ccgcaggtgc agctgcagga atccggaccg gggctggtga agcccagcga gactctgagt     120
ctcacgtgta cagtttctgg aggtagcatt agctcctact attggtcatg gataaggcag     180
cccccgggga agggattgga atggatcggc tatatttact acagtgggag caccaattac     240 aaccccctcac tgaagtctag agttacaatc agcgttgaca cctcaaagaa tcagttcagt     300
```

```
ttgaaattgt ctagcgtcac agcagctgat acagccgtct attattgtgt ttctctggtc    360
tattgcggtg gggattgtta cagtggcttt gactattggg ggcagggtac tctggttaca    420
gtttcttccg ggggggagg ctctgggggc ggaggctcag gtggtggagg cagcgacatc    480
cagttgacac agagcccgag ttccttgtcc gcctccgtcg gggatagagt gtcatttacc    540
tgtcaggcct ctcaggatat taataacttt ctgaattggt atcagcaaaa gcccggaaag    600
gcacccaagc tgttgattta cgacgccagt aacctggaga caggcgtgcc ctcccggttt    660
agtggtagcg gaagcggtac ggattttacc tttactatca gctctctcca acccgaagac    720
attgcaacct actattgtca acaatatgga aacctgcctt ttacatttgg cggcggcacc    780
aaggtggaga ttaagcgggc ggcagctatt gaggtgatgt atccaccgcc ttacctggat    840
aacgaaaaga gtaacggtac catcattcac gtgaaaggta aacacctgtg tccttctccc    900
ctcttccccg ggccatcaaa gcccttctgg gttcttgtgg tcgtgggagg cgtgcttgct    960
tgttattctc tgctcgttac cgtggcgttt atcattttt gggttagatc caaaagaagc   1020
cgcctgctcc atagcgatta catgaatatg actccacgcc gccctggccc cacaaggaaa   1080
cactaccagc cttacgcacc acctagagat ttcgctgcct atcggagcag ggtgaagttt   1140
tccagatctg cagatgcacc agcgtatcag cagggccaga accaactgta taacgagctc   1200
aacctgggac gcagggaaga gtatgacgtt ttggacaagc gcagaggacg ggaccctgag   1260
atgggtggca aaccaagacg aaaaaacccc caggagggtc tctataatga gctgcagaag   1320
gataagatgg ctgaagccta ttctgaaata ggcatgaaag gagagcggag aaggggaaaa   1380
gggcacgacg gtttgtacca gggactcagc actgctacga aggatactta tgacgctctc   1440
cacatgcaag ccctgccacc taggtaa                                        1467
```

<210> SEQ ID NO 170
<211> LENGTH: 488
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: anti-CLL-1 CAR construct

<400> SEQUENCE: 170

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Glu Thr Leu Ser Leu Thr Cys Thr Val Ser Gly Gly
        35                  40                  45

Ser Ile Ser Ser Tyr Tyr Trp Ser Trp Ile Arg Gln Pro Pro Gly Lys
    50                  55                  60

Gly Leu Glu Trp Ile Gly Tyr Ile Tyr Tyr Ser Gly Ser Thr Asn Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Val Ser Leu Val Tyr Cys Gly Gly Asp Cys Tyr Ser
        115                 120                 125

Gly Phe Asp Tyr Trp Gly Gln Gly Thr Leu Val Thr Val Ser Ser Gly

```
            130                 135                 140
Gly Gly Gly Ser Gly Gly Gly Ser Gly Gly Gly Ser Asp Ile
145                 150                 155                 160

Gln Leu Thr Gln Ser Pro Ser Leu Ser Ala Ser Val Gly Asp Arg
                165                 170                 175

Val Ser Phe Thr Cys Gln Ala Ser Gln Asp Ile Asn Asn Phe Leu Asn
            180                 185                 190

Trp Tyr Gln Gln Lys Pro Gly Lys Ala Pro Lys Leu Leu Ile Tyr Asp
                195                 200                 205

Ala Ser Asn Leu Glu Thr Gly Val Pro Ser Arg Phe Ser Gly Ser Gly
            210                 215                 220

Ser Gly Thr Asp Phe Thr Phe Thr Ile Ser Ser Leu Gln Pro Glu Asp
225                 230                 235                 240

Ile Ala Thr Tyr Tyr Cys Gln Gln Tyr Gly Asn Leu Pro Phe Thr Phe
            245                 250                 255

Gly Gly Gly Thr Lys Val Glu Ile Lys Arg Ala Ala Ala Ile Glu Val
            260                 265                 270

Met Tyr Pro Pro Pro Tyr Leu Asp Asn Glu Lys Ser Asn Gly Thr Ile
            275                 280                 285

Ile His Val Lys Gly Lys His Leu Cys Pro Ser Pro Leu Phe Pro Gly
            290                 295                 300

Pro Ser Lys Pro Phe Trp Val Leu Val Val Val Gly Gly Val Leu Ala
305                 310                 315                 320

Cys Tyr Ser Leu Leu Val Thr Val Ala Phe Ile Ile Phe Trp Val Arg
            325                 330                 335

Ser Lys Arg Ser Arg Leu Leu His Ser Asp Tyr Met Asn Met Thr Pro
            340                 345                 350

Arg Arg Pro Gly Pro Thr Arg Lys His Tyr Gln Pro Tyr Ala Pro Pro
            355                 360                 365

Arg Asp Phe Ala Ala Tyr Arg Ser Arg Val Lys Phe Ser Arg Ser Ala
            370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 171
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct
```

<400> SEQUENCE: 171

```
caggtgcagc tgcaggaatc cggaccgggg ctggtgaagc ccagcgagac tctgagtctc    60
acgtgtacag tttctggagg tagcattagc tcctactatt ggtcatggat aaggcagccc   120
cccgggaagg gattggaatg gatcggctat atttactaca gtgggagcac caattacaac   180
ccctcactga agtctagagt tacaatcagc gttgacacct caaagaatca gttcagtttg   240
aaattgtcta gcgtcacagc agctgataca gccgtctatt attgtgtttc tctggtctat   300
tgcggtgggg attgttacag tggctttgac tattggggc agggtactct ggttacagtt   360
tcttccgggg gggaggctc tggggcgga ggctcaggtg gtggaggcag cgacatccag   420
ttgacacaga gcccgagttc cttgtccgcc tccgtcgggg atagagtgtc atttacctgt   480
caggcctctc aggatattaa taactttctg aattggtatc agcaaaagcc cggaaaggca   540
cccaagctgt tgatttacga cgccagtaac ctggagacag gcgtgccctc ccggtttagt   600
ggtagcggaa gcggtacgga ttttacctt actatcagct ctctccaacc cgaagacatt   660
gcaacctact attgtcaaca atatggaaac ctgccttta catttggcgg cggcaccaag   720
gtggagatta gcgggcggc agctattgag gtgatgtatc caccgcctta cctggataac   780
gaaaagagta acgtaccat cattcacgtg aaaggtaaac acctgtgtcc ttctcccctc   840
ttccccgggc catcaaagcc cttctgggtt cttgtggtcg tgggaggcgt gcttgcttgt   900
tattctctgc tcgttaccgt ggcgtttatc attttttggg ttagatccaa agaagccgc   960
ctgctccata gcgattacat gaatatgact ccacgccgcc ctggccccac aaggaaacac  1020
taccagcctt acgcaccacc tagagatttc gctgcctatc ggagcagggt gaagttttcc  1080
agatctgcag atgcaccagc gtatcagcag ggccagaacc aactgtataa cgagctcaac  1140
ctgggacgca gggaagagta tgacgttttg acaagcgca gaggacggga ccctgagatg  1200
ggtggcaaac caagacgaaa aaaccccag gagggtctct ataatgagct gcagaaggat  1260
aagatggctg aagcctattc tgaaataggc atgaaggag agcggagaag gggaaagggg  1320
cacgacggtt tgtaccaggg actcagcact gctacgaagg atacttatga cgctctccac  1380
atgcaagccc tgccacctag g                                             1401
```

<210> SEQ ID NO 172
<211> LENGTH: 467
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 172

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
```

```
                   85                 90                 95
      Ser Leu Val Tyr Cys Gly Gly Asp Cys Tyr Ser Gly Phe Asp Tyr Trp
                  100                105                110

Gly Gln Gly Thr Leu Val Thr Val Ser Ser Gly Gly Gly Ser Gly
                  115                120                125

Gly Gly Gly Ser Gly Gly Gly Ser Asp Ile Gln Leu Thr Gln Ser
      130                135                140

Pro Ser Ser Leu Ser Ala Ser Val Gly Asp Arg Val Ser Phe Thr Cys
      145                150                155                160

Gln Ala Ser Gln Asp Ile Asn Asn Phe Leu Asn Trp Tyr Gln Lys
                      165                170                175

Pro Gly Lys Ala Pro Lys Leu Leu Ile Tyr Asp Ala Ser Asn Leu Glu
                      180                185                190

Thr Gly Val Pro Ser Arg Phe Ser Gly Ser Gly Ser Gly Thr Asp Phe
                      195                200                205

Thr Phe Thr Ile Ser Ser Leu Gln Pro Glu Asp Ile Ala Thr Tyr Tyr
                      210                215                220

Cys Gln Gln Tyr Gly Asn Leu Pro Phe Thr Phe Gly Gly Gly Thr Lys
      225                230                235                240

Val Glu Ile Lys Arg Ala Ala Ile Glu Val Met Tyr Pro Pro Pro
                      245                250                255

Tyr Leu Asp Asn Glu Lys Ser Asn Gly Thr Ile Ile His Val Lys Gly
                      260                265                270

Lys His Leu Cys Pro Ser Pro Leu Phe Pro Gly Pro Ser Lys Pro Phe
                      275                280                285

Trp Val Leu Val Val Val Gly Gly Val Leu Ala Cys Tyr Ser Leu Leu
                      290                295                300

Val Thr Val Ala Phe Ile Ile Phe Trp Val Arg Ser Lys Arg Ser Arg
      305                310                315                320

Leu Leu His Ser Asp Tyr Met Asn Met Thr Pro Arg Arg Pro Gly Pro
                      325                330                335

Thr Arg Lys His Tyr Gln Pro Tyr Ala Pro Pro Arg Asp Phe Ala Ala
                      340                345                350

Tyr Arg Ser Arg Val Lys Phe Ser Arg Ser Ala Asp Ala Pro Ala Tyr
                      355                360                365

Gln Gln Gly Gln Asn Gln Leu Tyr Asn Glu Leu Asn Leu Gly Arg Arg
                      370                375                380

Glu Glu Tyr Asp Val Leu Asp Lys Arg Gly Arg Asp Pro Glu Met
      385                390                395                400

Gly Gly Lys Pro Arg Arg Lys Asn Pro Gln Glu Gly Leu Tyr Asn Glu
                      405                410                415

Leu Gln Lys Asp Lys Met Ala Glu Ala Tyr Ser Glu Ile Gly Met Lys
                      420                425                430

Gly Glu Arg Arg Arg Gly Lys Gly His Asp Gly Leu Tyr Gln Gly Leu
                      435                440                445

Ser Thr Ala Thr Lys Asp Thr Tyr Asp Ala Leu His Met Gln Ala Leu
                      450                455                460

Pro Pro Arg
      465

<210> SEQ ID NO 173
<211> LENGTH: 1548
<212> TYPE: DNA
<213> ORGANISM: Artificial Sequence
```

<220> FEATURE:
<223> OTHER INFORMATION: Description of Artificial Sequence: Synthetic
    polynucleotide
<220> FEATURE:
<223> OTHER INFORMATION: anti-CLL-1 CAR construct

<400> SEQUENCE: 173

```
atggcactcc ccgtaactgc tctgctgctg ccgttggcat tgctcctgca cgccgcacgc      60
ccgcaggtgc aattgcaaga gtccggcccc ggactcgtta aacccagtga cgcgcttagc     120
ctgacctgta ccgtctcagg gggcagcatc tcctcttatt actggagctg atcaggcag      180
cctccaggaa aaggccttga atggattggg tacatctact actctggctc aacaaattat     240
aatccatccc tgaagtcccg cgtgactatc tctgtggaca ccagcaagaa tcagttttca     300
ctgaagttgt ctagtgttac cgcggccgac accgccgtat actactgtgt gtctcttgtg     360
tactgtggcg gcgactgcta ttccgggttc gactactggg gccaagggac tctggtaacc     420
gtgtcctcag gcggcggcgg gtcaggagga ggcggcagtg gaggtggcgg ctccgacatc     480
cagctgacac aatcaccatc ttcccttcca gcttcagtcg gggacagagt gtccttcaca     540
tgccaggcca gccaggatat caataacttc ctgaactggt accaacagaa acccggaaag     600
gctccaaagc tcctgatcta tgatgcttcc aacctggaga ccggcgtgcc ctccaggttc     660
agtggttcag gatcaggcac tgactttacg ttcaccatat ccagtcttca gcccgaagac     720
attgcaacct attactgcca acaatacggg aaccttccct ttacattcgg aggcggcacc     780
aaggtggaaa tcaaaagggc tgcagcattg agcaactcaa taatgtattt tagtcacttt     840
gtaccagtgt tcttgccggc taagcctact accacacccg ctccacgccc acctacccca     900
gctcctacca tcgcttcaca gcctctgtcc ctgcgcccag aggcttgccg accggccgca     960
gggggcgctg ttcataccag aggactggat ttcgcctgcg atatctatat ctgggcaccc    1020
ctggccggaa cctgcggcgt actcctgctg tccctggtca tcacgctcta ttgtaatcac    1080
aggaacagat ccaaaagaag ccgcctgctc catagcgatt acatgaatat gactccacgc    1140
cgccctggcc ccacaaggaa acactaccag ccttacgcac acctagaga tttcgctgcc    1200
tatcggagca gggtgaagtt ttccagatct gcagatgcac cagcgtatca gcagggccag    1260
aaccaactgt ataacgagct caacctggga cgcaggaag agtatgacgt tttggacaag    1320
cgcagaggac gggaccctga tgggtggc aaaccaagac gaaaaaaccc ccaggaggg    1380
ctctataatg agctgcagaa ggataagatg gctgaagcct attctgaaat aggcatgaaa    1440
ggagagcgga aaggggaaa agggcacgac ggtttgtacc agggactcag cactgctacg    1500
aaggatactt atgacgctct ccacatgcaa gccctgccac ctaggtaa               1548
```

<210> SEQ ID NO 174
<211> LENGTH: 515
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: anti-CLL-1 CAR construct

<400> SEQUENCE: 174

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30
```

Val Lys Pro Ser Glu Thr Leu Ser Leu Thr Cys Thr Val Ser Gly Gly
          35                  40                  45

Ser Ile Ser Ser Tyr Tyr Trp Ser Trp Ile Arg Gln Pro Pro Gly Lys
 50                  55                  60

Gly Leu Glu Trp Ile Gly Tyr Ile Tyr Tyr Ser Gly Ser Thr Asn Tyr
65                   70                  75                  80

Asn Pro Ser Leu Lys Ser Arg Val Thr Ile Ser Val Asp Thr Ser Lys
              85                  90                  95

Asn Gln Phe Ser Leu Lys Leu Ser Ser Val Thr Ala Ala Asp Thr Ala
             100                 105                 110

Val Tyr Tyr Cys Val Ser Leu Val Tyr Cys Gly Gly Asp Cys Tyr Ser
         115                 120                 125

Gly Phe Asp Tyr Trp Gly Gln Gly Thr Leu Val Thr Val Ser Ser Gly
     130                 135                 140

Gly Gly Gly Ser Gly Gly Gly Gly Ser Gly Gly Gly Ser Asp Ile
145                 150                 155                 160

Gln Leu Thr Gln Ser Pro Ser Ser Leu Ser Ala Ser Val Gly Asp Arg
                 165                 170                 175

Val Ser Phe Thr Cys Gln Ala Ser Gln Asp Ile Asn Asn Phe Leu Asn
             180                 185                 190

Trp Tyr Gln Gln Lys Pro Gly Lys Ala Pro Lys Leu Leu Ile Tyr Asp
         195                 200                 205

Ala Ser Asn Leu Glu Thr Gly Val Pro Ser Arg Phe Ser Gly Ser Gly
     210                 215                 220

Ser Gly Thr Asp Phe Thr Phe Thr Ile Ser Ser Leu Gln Pro Glu Asp
225                 230                 235                 240

Ile Ala Thr Tyr Tyr Cys Gln Gln Tyr Gly Asn Leu Pro Phe Thr Phe
                 245                 250                 255

Gly Gly Gly Thr Lys Val Glu Ile Lys Arg Ala Ala Ala Leu Ser Asn
             260                 265                 270

Ser Ile Met Tyr Phe Ser His Phe Val Pro Val Phe Leu Pro Ala Lys
         275                 280                 285

Pro Thr Thr Thr Pro Ala Pro Arg Pro Pro Thr Pro Ala Pro Thr Ile
     290                 295                 300

Ala Ser Gln Pro Leu Ser Leu Arg Pro Glu Ala Cys Arg Pro Ala Ala
305                 310                 315                 320

Gly Gly Ala Val His Thr Arg Gly Leu Asp Phe Ala Cys Asp Ile Tyr
                 325                 330                 335

Ile Trp Ala Pro Leu Ala Gly Thr Cys Gly Val Leu Leu Leu Ser Leu
             340                 345                 350

Val Ile Thr Leu Tyr Cys Asn His Arg Asn Arg Ser Lys Arg Ser Arg
         355                 360                 365

Leu Leu His Ser Asp Tyr Met Asn Met Thr Pro Arg Arg Pro Gly Pro
     370                 375                 380

Thr Arg Lys His Tyr Gln Pro Tyr Ala Pro Pro Arg Asp Phe Ala Ala
385                 390                 395                 400

Tyr Arg Ser Arg Val Lys Phe Ser Arg Ser Ala Asp Ala Pro Ala Tyr
                 405                 410                 415

Gln Gln Gly Gln Asn Gln Leu Tyr Asn Glu Leu Asn Leu Gly Arg Arg
             420                 425                 430

Glu Glu Tyr Asp Val Leu Asp Lys Arg Gly Arg Asp Pro Glu Met
         435                 440                 445

Gly Gly Lys Pro Arg Arg Lys Asn Pro Gln Glu Gly Leu Tyr Asn Glu

```
                450             455             460
Leu Gln Lys Asp Lys Met Ala Glu Ala Tyr Ser Glu Ile Gly Met Lys
465                 470                 475                 480

Gly Glu Arg Arg Gly Lys Gly His Asp Gly Leu Tyr Gln Gly Leu
                485                 490                 495

Ser Thr Ala Thr Lys Asp Thr Tyr Asp Ala Leu His Met Gln Ala Leu
            500                 505                 510

Pro Pro Arg
      515

<210> SEQ ID NO 175
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 175
caggtgcaat tgcaagagtc cggccccgga ctcgttaaac ccagtgagac gcttagcctg      60
acctgtaccg tctcaggggg cagcatctcc tcttattact ggagctggat caggcagcct    120
ccaggaaaag gccttgaatg gattgggtac atctactact ctggctcaac aaattataat    180
ccatccctga agtcccgcgt gactatctct gtggacacca gcaagaatca gttttcactg    240
aagttgtcta gtgttaccgc ggccgacacc gccgtatact actgtgtgtc tcttgtgtac    300
tgtggcggcg actgctattc cgggttcgac tactggggcc aagggactct ggtaaccgtg    360
tcctcaggcg gcggcgggtc aggaggaggc ggcagtggag gtggcggctc cgacatccag    420
ctgacacaat caccatcttc cctttcagct tcagtcgggg acagagtgtc cttcacatgc    480
caggccagcc aggatatcaa taacttcctg aactggtacc aacagaaacc cggaaaggct    540
ccaaagctcc tgatctatga tgcttccaac ctggagaccg gcgtgccctc caggttcagt    600
ggttcaggat caggcactga ctttacgttc accatatcca gtcttcagcc cgaagacatt    660
gcaacctatt actgccaaca atacgggaac cttccctta cattcggagg cggcaccaag    720
gtggaaatca aaagggctgc agcattgagc aactcaataa tgtattttag tcactttgta    780
ccagtgttct tgccggctaa gcctactacc acacccgctc acggccacc taccccagct    840 cctaccatcg cttcacagcc tctgtccctg cgcccagagg cttgccgacc ggccgcaggg    900
ggcgctgttc ataccagagg actggatttc gcctgcgata tctatatctg gcacccctg    960 gccggaacct gcggcgtact cctgctgtcc ctggtcatca cgctctattg taatcacagg    1020
aacagatcca aaagaagccg cctgctccat agcgattaca tgaatatgac tccacgccgc    1080
cctggcccca caggaaaaca ctaccagcct tacgcaccac ctagagattt cgctgcctat    1140
cggagcaggg tgaagttttc cagatctgca gatgcaccag cgtatcagca gggccagaac    1200
caactgtata acgagctcaa cctgggacgc agggaagagt atgacgtttt ggacaagcgc    1260
agaggacggg accctgagat gggtggcaaa ccaagacgaa aaaccccca ggagggtctc    1320 tataatgagc tgcagaagga taagatggct gaagcctatt ctgaaatagg catgaaagga    1380
gagcggagaa ggggaaaagg gcacgacggt ttgtaccagg gactcagcac tgctacgaag    1440
gatacttatg acgctctcca catgcaagcc ctgccaccta gg                        1482

<210> SEQ ID NO 176
```

```
<211> LENGTH: 494
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 176
```

| | | | | | | | | | | | | | | |
|---|---|---|---|---|---|---|---|---|---|---|---|---|---|---|
| Gln | Val | Gln | Leu | Gln | Glu | Ser | Gly | Pro | Gly | Leu | Val | Lys | Pro | Ser | Glu |
| 1 | | | | 5 | | | | | 10 | | | | | 15 | |
| Thr | Leu | Ser | Leu | Thr | Cys | Thr | Val | Ser | Gly | Gly | Ser | Ile | Ser | Ser | Tyr |
| | | | 20 | | | | | 25 | | | | | 30 | | |
| Tyr | Trp | Ser | Trp | Ile | Arg | Gln | Pro | Pro | Gly | Lys | Gly | Leu | Glu | Trp | Ile |
| | | 35 | | | | | 40 | | | | | 45 | | | |
| Gly | Tyr | Ile | Tyr | Tyr | Ser | Gly | Ser | Thr | Asn | Tyr | Asn | Pro | Ser | Leu | Lys |
| | 50 | | | | | 55 | | | | | 60 | | | | |
| Ser | Arg | Val | Thr | Ile | Ser | Val | Asp | Thr | Ser | Lys | Asn | Gln | Phe | Ser | Leu |
| 65 | | | | | 70 | | | | | 75 | | | | | 80 |
| Lys | Leu | Ser | Ser | Val | Thr | Ala | Ala | Asp | Thr | Ala | Val | Tyr | Tyr | Cys | Val |
| | | | | 85 | | | | | 90 | | | | | 95 | |
| Ser | Leu | Val | Tyr | Cys | Gly | Gly | Asp | Cys | Tyr | Ser | Gly | Phe | Asp | Tyr | Trp |
| | | | 100 | | | | | 105 | | | | | 110 | | |
| Gly | Gln | Gly | Thr | Leu | Val | Thr | Val | Ser | Ser | Gly | Gly | Gly | Gly | Ser | Gly |
| | | 115 | | | | | 120 | | | | | 125 | | | |
| Gly | Gly | Gly | Ser | Gly | Gly | Gly | Ser | Asp | Ile | Gln | Leu | Thr | Gln | Ser |
| | 130 | | | | | 135 | | | | | 140 | | | | |
| Pro | Ser | Ser | Leu | Ser | Ala | Ser | Val | Gly | Asp | Arg | Val | Ser | Phe | Thr | Cys |
| 145 | | | | | 150 | | | | | 155 | | | | | 160 |
| Gln | Ala | Ser | Gln | Asp | Ile | Asn | Asn | Phe | Leu | Asn | Trp | Tyr | Gln | Gln | Lys |
| | | | | 165 | | | | | 170 | | | | | 175 | |
| Pro | Gly | Lys | Ala | Pro | Lys | Leu | Leu | Ile | Tyr | Asp | Ala | Ser | Asn | Leu | Glu |
| | | | 180 | | | | | 185 | | | | | 190 | | |
| Thr | Gly | Val | Pro | Ser | Arg | Phe | Ser | Gly | Ser | Gly | Ser | Gly | Thr | Asp | Phe |
| | | 195 | | | | | 200 | | | | | 205 | | | |
| Thr | Phe | Thr | Ile | Ser | Ser | Leu | Gln | Pro | Glu | Asp | Ile | Ala | Thr | Tyr | Tyr |
| | 210 | | | | | 215 | | | | | 220 | | | | |
| Cys | Gln | Gln | Tyr | Gly | Asn | Leu | Pro | Phe | Thr | Phe | Gly | Gly | Gly | Thr | Lys |
| 225 | | | | | 230 | | | | | 235 | | | | | 240 |
| Val | Glu | Ile | Lys | Arg | Ala | Ala | Ala | Leu | Ser | Asn | Ser | Ile | Met | Tyr | Phe |
| | | | | 245 | | | | | 250 | | | | | 255 | |
| Ser | His | Phe | Val | Pro | Val | Phe | Leu | Pro | Ala | Lys | Pro | Thr | Thr | Thr | Pro |
| | | | 260 | | | | | 265 | | | | | 270 | | |
| Ala | Pro | Arg | Pro | Pro | Thr | Pro | Ala | Pro | Thr | Ile | Ala | Ser | Gln | Pro | Leu |
| | | 275 | | | | | 280 | | | | | 285 | | | |
| Ser | Leu | Arg | Pro | Glu | Ala | Cys | Arg | Pro | Ala | Ala | Gly | Gly | Ala | Val | His |
| | 290 | | | | | 295 | | | | | 300 | | | | |
| Thr | Arg | Gly | Leu | Asp | Phe | Ala | Cys | Asp | Ile | Tyr | Ile | Trp | Ala | Pro | Leu |
| 305 | | | | | 310 | | | | | 315 | | | | | 320 |
| Ala | Gly | Thr | Cys | Gly | Val | Leu | Leu | Leu | Ser | Leu | Val | Ile | Thr | Leu | Tyr |
| | | | | 325 | | | | | 330 | | | | | 335 | |
| Cys | Asn | His | Arg | Asn | Arg | Ser | Lys | Arg | Ser | Arg | Leu | Leu | His | Ser | Asp |
| | | | 340 | | | | | 345 | | | | | 350 | | |
| Tyr | Met | Asn | Met | Thr | Pro | Arg | Arg | Pro | Gly | Pro | Thr | Arg | Lys | His | Tyr |
| | | 355 | | | | | 360 | | | | | 365 | | | |

```
Gln Pro Tyr Ala Pro Pro Arg Asp Phe Ala Ala Tyr Arg Ser Arg Val
        370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
        420                 425                 430

Arg Lys Asn Pro Gln Glu Gly Leu Tyr Asn Glu Leu Gln Lys Asp Lys
    435                 440                 445

Met Ala Glu Ala Tyr Ser Glu Ile Gly Met Lys Gly Glu Arg Arg Arg
        450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490

<210> SEQ ID NO 177
<211> LENGTH: 1440
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 177
atggcactcc ccgtaactgc tctgctgctg ccgttggcat tgctcctgca cgccgcacgc      60
ccggatatcc agctcacgca atccccctca agcttgagtg cctccgtggg cgaccgggtg     120
tccttcacat gtcaggcaag ccaagacata ataatttcc tgaattggta ccaacaaaaa     180
cccggcaagg ctcccaaact cctgatttat gatgcctcca atctggagac cggggtccct     240
tctagattca gcggaagtgg cagcggcaca gactttacat ttactatctc ttctctgcaa     300
ccagaggaca tcgccacata ctattgccag caatacggca atctgccctt caccttcgga     360
ggcggaacca aggtagaaat taaaggggc ggtggaggct ccggaggggg gggctctggc     420
ggagggggct cccaagtaca attgcaggag tcagggcctg gactcgtgaa gccttcagaa     480
actttgtcac tgacatgtac agtgtccggc ggaagcattt ccagttacta ttggtcctgg     540
attagacagc acccggcaa aggactggaa tggattggat atatctacta ctctggatct     600
acaaactata tcccagcct caaatccagg gtcactatta gtgtggatac atcaaagaat     660
cagttctcct tgaagctgag ctcagtcact gctgccgaca ccgcagtgta ctattgtgtg     720
agcctggtct actgcggcgg agattgctac agcggtttcg attactgggg ccagggcacc     780
ctggttaccg ttagtccgc ggctgctctt gataacgaga agtccaacgg tacgattatc     840
cacgttaagg gtaagcacct ttgccctagc ccgctgttcc caggcccag taagcccttt     900 tgggtcctcg ttgtggtagg tgggtactc gcctgctact ccctgctcgt cactgtcgca     960
ttcatcatct tctgggtcag atccaaaaga agccgcctgc tccatagcga ttacatgaat    1020
atgactccac gccgccctgg ccccacaagg aaacactacc agccttacgc accacctaga    1080
gatttcgctg cctatcggag cagggtgaag ttttccagat ctgcagatgc accagcgtat    1140
cagcagggcc agaaccaact gtataacgag ctcaacctgg gacgcaggga agagtatgac    1200
gttttggaca gcgcagagg acgggaccct gagatgggtg gcaaaccaag acgaaaaaac    1260
```

```
cccaggagg gtctctataa tgagctgcag aaggataaga tggctgaagc ctattctgaa    1320
ataggcatga aaggagagcg gagaaggggga aaagggcacg acggtttgta ccagggactc    1380
agcactgcta cgaaggatac ttatgacgct ctccacatgc aagccctgcc acctaggtaa    1440
```

<210> SEQ ID NO 178
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 178

```
Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Ser Phe Thr Cys Gln Ala Ser Gln
        35                  40                  45

Asp Ile Asn Asn Phe Leu Asn Trp Tyr Gln Gln Lys Pro Gly Lys Ala
    50                  55                  60

Pro Lys Leu Leu Ile Tyr Asp Ala Ser Asn Leu Glu Thr Gly Val Pro
65                  70                  75                  80

Ser Arg Phe Ser Gly Ser Gly Ser Gly Thr Asp Phe Thr Phe Thr Ile
                85                  90                  95

Ser Ser Leu Gln Pro Glu Asp Ile Ala Thr Tyr Tyr Cys Gln Gln Tyr
            100                 105                 110

Gly Asn Leu Pro Phe Thr Phe Gly Gly Gly Thr Lys Val Glu Ile Lys
        115                 120                 125

Arg Gly Gly Gly Gly Ser Gly Gly Gly Gly Ser Gly Gly Gly Gly Ser
    130                 135                 140

Gln Val Gln Leu Gln Glu Ser Gly Pro Gly Leu Val Lys Pro Ser Glu
145                 150                 155                 160

Thr Leu Ser Leu Thr Cys Thr Val Ser Gly Gly Ser Ile Ser Ser Tyr
                165                 170                 175

Tyr Trp Ser Trp Ile Arg Gln Pro Pro Gly Lys Gly Leu Glu Trp Ile
            180                 185                 190

Gly Tyr Ile Tyr Tyr Ser Gly Ser Thr Asn Tyr Asn Pro Ser Leu Lys
        195                 200                 205

Ser Arg Val Thr Ile Ser Val Asp Thr Ser Lys Asn Gln Phe Ser Leu
    210                 215                 220

Lys Leu Ser Ser Val Thr Ala Ala Asp Thr Ala Val Tyr Tyr Cys Val
225                 230                 235                 240

Ser Leu Val Tyr Cys Gly Gly Asp Cys Tyr Ser Gly Phe Asp Tyr Trp
                245                 250                 255

Gly Gln Gly Thr Leu Val Thr Val Ser Ser Ala Ala Ala Leu Asp Asn
            260                 265                 270

Glu Lys Ser Asn Gly Thr Ile Ile His Val Lys Gly Lys His Leu Cys
        275                 280                 285

Pro Ser Pro Leu Phe Pro Gly Pro Ser Lys Pro Phe Trp Val Leu Val
    290                 295                 300

Val Val Gly Gly Val Leu Ala Cys Tyr Ser Leu Leu Val Thr Val Ala
305                 310                 315                 320
```

```
Phe Ile Ile Phe Trp Val Arg Ser Lys Arg Ser Arg Leu Leu His Ser
                325                 330                 335

Asp Tyr Met Asn Met Thr Pro Arg Arg Pro Gly Pro Thr Arg Lys His
            340                 345                 350

Tyr Gln Pro Tyr Ala Pro Pro Arg Asp Phe Ala Ala Tyr Arg Ser Arg
        355                 360                 365

Val Lys Phe Ser Arg Ser Ala Asp Ala Pro Ala Tyr Gln Gln Gly Gln
    370                 375                 380

Asn Gln Leu Tyr Asn Glu Leu Asn Leu Gly Arg Arg Glu Glu Tyr Asp
385                 390                 395                 400

Val Leu Asp Lys Arg Arg Gly Arg Asp Pro Glu Met Gly Gly Lys Pro
                405                 410                 415

Arg Arg Lys Asn Pro Gln Glu Gly Leu Tyr Asn Glu Leu Gln Lys Asp
            420                 425                 430

Lys Met Ala Glu Ala Tyr Ser Glu Ile Gly Met Lys Gly Glu Arg Arg
435                 440                 445

Arg Gly Lys Gly His Asp Gly Leu Tyr Gln Gly Leu Ser Thr Ala Thr
    450                 455                 460

Lys Asp Thr Tyr Asp Ala Leu His Met Gln Ala Leu Pro Pro Arg
465                 470                 475
```

<210> SEQ ID NO 179
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 179

```
gatatccagc tcacgcaatc cccctcaagc ttgagtgcct ccgtgggcga ccgggtgtcc      60
ttcacatgtc aggcaagcca agacataaat aatttcctga attggtacca acaaaaaccc     120
ggcaaggctc ccaaactcct gatttatgat gcctccaatc tggagaccgg ggtcccttct     180
agattcagcg gaagtggcag cggcacagac tttacattta ctatctcttc tctgcaacca     240
gaggacatcg ccatatacta ttgccagcaa tacggcaatc tgcccttcac cttcggaggc     300
ggaaccaagg tagaaattaa aaggggcggt ggaggctccg gagggggggg ctctggcgga     360
gggggctccc aagtacaatt gcaggagtca gggcctggac tcgtgaagcc ttcagaaact     420
ttgtcactga catgtacagt gtccggcgga agcatttcca gttactattg gtcctggatt     480
agacagccac ccggcaaagg actggaatgg attggatata tctactactc tggatctaca     540
aactataatc ccagcctcaa atccagggtc actattagtg tggatacatc aaagaatcag     600
ttctccttga agctgagctc agtcactgct gccgacaccg cagtgtacta ttgtgtgagc     660
ctggtctact gcggcggaga ttgctacagc ggtttcgatt actggggcca gggcaccctg     720
gttaccgtta gttccgcggc tgctcttgat aacgagaagt ccaacggtac gattatccac     780
gttaagggta agcacctttg ccctagcccg ctgttcccag ccccagtaa gcccttttgg     840
gtcctcgttg tggtaggtgg ggtactcgcc tgctactccc tgctcgtcac tgtcgcattc     900
atcatcttct gggtcagatc caaaagaagc cgcctgctcc atagcgatta catgaatatg     960
actccacgcc gccctggccc cacaaggaaa cactaccagc ttacgcacc acctagagat     1020
ttcgctgcct atcggagcag ggtgaagttt ccagatctg cagatgcacc agcgtatcag    1080
```

```
caggggccaga accaactgta taacgagctc aacctgggac gcagggaaga gtatgacgtt    1140
ttggacaagc gcagaggacg ggaccctgag atgggtggca aaccaagacg aaaaaacccc    1200
caggagggtc tctataatga gctgcagaag gataagatgg ctgaagccta ttctgaaata    1260
ggcatgaaag gagagcggag aaggggaaaa gggcacgacg gtttgtacca gggactcagc    1320
actgctacga aggatactta tgacgctctc cacatgcaag ccctgccacc tagg          1374
```

<210> SEQ ID NO 180
<211> LENGTH: 458
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: anti-CLL-1 CAR construct

<400> SEQUENCE: 180

```
Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Gln Val Gln Leu Gln
        115                 120                 125

Glu Ser Gly Pro Gly Leu Val Lys Pro Ser Glu Thr Leu Ser Leu Thr
    130                 135                 140

Cys Thr Val Ser Gly Gly Ser Ile Ser Ser Tyr Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Val Ser Leu Val Tyr Cys
    210                 215                 220

Gly Gly Asp Cys Tyr Ser Gly Phe Asp Tyr Trp Gly Gln Gly Thr Leu
225                 230                 235                 240

Val Thr Val Ser Ser Ala Ala Ala Leu Asp Asn Glu Lys Ser Asn Gly
                245                 250                 255

Thr Ile Ile His Val Lys Gly Lys His Leu Cys Pro Ser Pro Leu Phe
            260                 265                 270

Pro Gly Pro Ser Lys Pro Phe Trp Val Leu Val Val Val Gly Gly Val
        275                 280                 285

Leu Ala Cys Tyr Ser Leu Leu Val Thr Val Ala Phe Ile Ile Phe Trp
```

Val Arg Ser Lys Arg Ser Arg Leu Leu His Ser Asp Tyr Met Asn Met
305                 310                 315                 320

Thr Pro Arg Arg Pro Gly Pro Thr Arg Lys His Tyr Gln Pro Tyr Ala
            325                 330                 335

Pro Pro Arg Asp Phe Ala Ala Tyr Arg Ser Arg Val Lys Phe Ser Arg
            340                 345                 350

Ser Ala Asp Ala Pro Ala Tyr Gln Gln Gly Gln Asn Gln Leu Tyr Asn
            355                 360                 365

Glu Leu Asn Leu Gly Arg Arg Glu Glu Tyr Asp Val Leu Asp Lys Arg
    370                 375                 380

Arg Gly Arg Asp Pro Glu Met Gly Gly Lys Pro Arg Arg Lys Asn Pro
385                 390                 395                 400

Gln Glu Gly Leu Tyr Asn Glu Leu Gln Lys Asp Lys Met Ala Glu Ala
                405                 410                 415

Tyr Ser Glu Ile Gly Met Lys Gly Glu Arg Arg Arg Gly Lys Gly His
                420                 425                 430

Asp Gly Leu Tyr Gln Gly Leu Ser Thr Ala Thr Lys Asp Thr Tyr Asp
        435                 440                 445

Ala Leu His Met Gln Ala Leu Pro Pro Arg
        450                 455

<210> SEQ ID NO 181
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 181
atggcactcc ccgtaactgc tctgctgctg ccgttggcat tgctcctgca cgccgcacgc     60
ccggatatcc agctgaccca gtctccatcc tctttgagtg cctccgtggg tgaccgcgtc    120
tctttcactt gccaagccag ccaagacatc aacaactttc tgaattggta ccagcagaaa    180
ccaggcaaag caccaaagct cctcatctac gacgcctcca acctggaaac cggggtgccc    240
agcaggttta gcgggagcgg ttctggcacg gattttacgt tcaccatctc ctctctgcag    300
cccgaggata tagctactta ttactgtcag cagtacggga atctgccatt tactttttggg    360 ggtggaacta aggtggaaat caaaaggggc ggcggggaa gcggggcgg gggctcaggt    420 ggcggaggga gccaggtgca actccaggaa gtgggccag gattggtgaa gcccagcgag    480
acccttcccc ttacttgtac tgttagcgga ggcagcataa gcagctacta ttggtcctgg    540
atcagacagc caccagggaa agggcttgaa tggattggct acatttacta ttccgggtcc    600
accaactaca acccatccct caagtcccgc gtgacaattt ccgtcgacac aagcaagaac    660
cagttctccc tgaaacttag tagcgtcact gctgcagata cagcagtgta ctattgtgtc    720
agccttgtct actgtggcgg cgactgctac agtggctttg attactgggg acagggcacg    780
ctcgtgacag tgtccagcgc tgcggctatc gaggtaatgt atccgccacc gtatctggac    840
aacgagaagt ctaatgggac aatcattcac gtgaagggga agcacctgtg tccatccccc    900
ctgtttccgg gtcccagtaa acccttctgg gtgcttgttg tcgttggcgg ggtgctggcc    960
tgctattccc tgctggtgac cgtcgcgttt attattttct gggttagatc caaaagaagc    1020

```
cgcctgctcc atagcgatta catgaatatg actccacgcc gccctggccc cacaaggaaa    1080
cactaccagc cttacgcacc acctagagat ttcgctgcct atcggagcag ggtgaagttt    1140
tccagatctg cagatgcacc agcgtatcag cagggccaga accaactgta taacgagctc    1200
aacctgggac gcagggaaga gtatgacgtt ttggacaagc gcagaggacg ggaccctgag    1260
atgggtggca aaccaagacg aaaaaacccc caggagggtc tctataatga gctgcagaag    1320
gataagatgg ctgaagccta ttctgaaata ggcatgaaag gagagcggag aaggggaaaa    1380
gggcacgacg gtttgtacca gggactcagc actgctacga aggatactta tgacgctctc    1440
cacatgcaag ccctgccacc taggtaa                                        1467
```

<210> SEQ ID NO 182
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 182

Met Ala Leu Pro Val Thr Ala Leu Leu Leu Pro Leu Ala Leu Leu Leu
1               5                   10                  15

His Ala Ala Arg Pro Asp Ile Gln Leu Thr Gln Ser Pro Ser Ser Leu
            20                  25                  30

Ser Ala Ser Val Gly Asp Arg Val Ser Phe Thr Cys Gln Ala Ser Gln
        35                  40                  45

Asp Ile Asn Asn Phe Leu Asn Trp Tyr Gln Gln Lys Pro Gly Lys Ala
    50                  55                  60

Pro Lys Leu Leu Ile Tyr Asp Ala Ser Asn Leu Glu Thr Gly Val Pro
65                  70                  75                  80

Ser Arg Phe Ser Gly Ser Gly Ser Gly Thr Asp Phe Thr Phe Thr Ile
                85                  90                  95

Ser Ser Leu Gln Pro Glu Asp Ile Ala Thr Tyr Tyr Cys Gln Gln Tyr
            100                 105                 110

Gly Asn Leu Pro Phe Thr Phe Gly Gly Gly Thr Lys Val Glu Ile Lys
        115                 120                 125

Arg Gly Gly Gly Gly Ser Gly Gly Gly Ser Gly Gly Gly Gly Ser
    130                 135                 140

Gln Val Gln Leu Gln Glu Ser Gly Pro Gly Leu Val Lys Pro Ser Glu
145                 150                 155                 160

Thr Leu Ser Leu Thr Cys Thr Val Ser Gly Gly Ser Ile Ser Ser Tyr
                165                 170                 175

Tyr Trp Ser Trp Ile Arg Gln Pro Pro Gly Lys Gly Leu Glu Trp Ile
            180                 185                 190

Gly Tyr Ile Tyr Tyr Ser Gly Ser Thr Asn Tyr Asn Pro Ser Leu Lys
        195                 200                 205

Ser Arg Val Thr Ile Ser Val Asp Thr Ser Lys Asn Gln Phe Ser Leu
    210                 215                 220

Lys Leu Ser Ser Val Thr Ala Ala Asp Thr Ala Val Tyr Tyr Cys Val
225                 230                 235                 240

Ser Leu Val Tyr Cys Gly Gly Asp Cys Tyr Ser Gly Phe Asp Tyr Trp
                245                 250                 255

Gly Gln Gly Thr Leu Val Thr Val Ser Ser Ala Ala Ala Ile Glu Val
            260                 265                 270

```
Met Tyr Pro Pro Tyr Leu Asp Asn Glu Lys Ser Asn Gly Thr Ile
            275                 280                 285

Ile His Val Lys Gly Lys His Leu Cys Pro Ser Pro Leu Phe Pro Gly
    290                 295                 300

Pro Ser Lys Pro Phe Trp Val Leu Val Val Val Gly Gly Val Leu Ala
305                 310                 315                 320

Cys Tyr Ser Leu Leu Val Thr Val Ala Phe Ile Ile Phe Trp Val Arg
                325                 330                 335

Ser Lys Arg Ser Arg Leu Leu His Ser Asp Tyr Met Asn Met Thr Pro
                340                 345                 350

Arg Arg Pro Gly Pro Thr Arg Lys His Tyr Gln Pro Tyr Ala Pro Pro
            355                 360                 365

Arg Asp Phe Ala Ala Tyr Arg Ser Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 183
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 183
gatatccagc tgacccagtc tccatcctct ttgagtgcct ccgtgggtga ccgcgtctct      60
ttcacttgcc aagccagcca agacatcaac aactttctga attggtacca gcagaaacca     120
ggcaaagcac caaagctcct catctacgac gcctccaacc tggaaaccgg ggtgcccagc     180
aggtttagcg ggagcggttc tggcacggat tttacgttca ccatctcctc tctgcagccc     240
gaggatatag ctacttatta ctgtcagcag tacgggaatc tgccatttac ttttgggggt     300
ggaactaagg tggaaatcaa aaggggcggc gggggaagcg ggggcggggg ctcaggtggc     360
ggagggagcc aggtgcaact ccaggaaagt ggcccaggat tggtgaagcc cagcgagacc     420
ctttccctta cttgtactgt tagcggaggc agcataagca gctactattg gtcctggatc     480
agacagccac cagggaaagg gcttgaatgg attggctaca tttactattc cgggtccacc     540
aactacaacc catccctcaa gtcccgcgtg acaattccg tcgacacaag caagaaccag     600
ttctcccctg aacttagtag cgtcactgct gcagatacag cagtgtacta ttgtgtcagc     660
cttgtctact gtggcggcga ctgctacagt ggctttgatt actggggaca gggcacgctc     720
```

```
gtgacagtgt ccagcgctgc ggctatcgag gtaatgtatc cgccaccgta tctggacaac    780
gagaagtcta atgggacaat cattcacgtg aaggggaagc acctgtgtcc atcccccctg    840
tttccgggtc ccagtaaacc cttctggtg cttgttgtcg ttggcggggt gctggcctgc    900
tattccctgc tggtgaccgt cgcgtttatt attttctggg ttagatccaa agaagccgc     960 ctgctccata gcgattacat gaatatgact ccacgccgcc ctggccccac aaggaaacac   1020
taccagcctt acgcaccacc tagagatttc gctgcctatc ggagcagggt gaagttttcc   1080
agatctgcag atgcaccagc gtatcagcag ggccagaacc aactgtataa cgagctcaac   1140
ctgggacgca gggaagagta tgacgttttg acaagcgca gaggacggga ccctgagatg     1200
ggtggcaaac caagacgaaa aaaccccccag gagggtctct ataatgagct gcagaaggat   1260
aagatggctg aagcctattc tgaaataggc atgaaaggag agcggagaag gggaaagggg   1320
cacgacggtt tgtaccaggg actcagcact gctacgaagg atacttatga cgctctccac   1380
atgcaagccc tgccacctag g                                              1401
```

<210> SEQ ID NO 184
<211> LENGTH: 467
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 184

```
Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Gln Val Gln Leu Gln
        115                 120                 125

Glu Ser Gly Pro Gly Leu Val Lys Pro Ser Glu Thr Leu Ser Leu Thr
    130                 135                 140

Cys Thr Val Ser Gly Gly Ser Ile Ser Ser Tyr Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
        195                 200                 205

Thr Ala Ala Asp Thr Ala Val Tyr Tyr Cys Val Ser Leu Val Tyr Cys
    210                 215                 220
```

Gly Gly Asp Cys Tyr Ser Gly Phe Asp Tyr Trp Gly Gln Gly Thr Leu
225                 230                 235                 240

Val Thr Val Ser Ser Ala Ala Ala Ile Glu Val Met Tyr Pro Pro Pro
            245                 250                 255

Tyr Leu Asp Asn Glu Lys Ser Asn Gly Thr Ile Ile His Val Lys Gly
        260                 265                 270

Lys His Leu Cys Pro Ser Pro Leu Phe Pro Gly Pro Ser Lys Pro Phe
    275                 280                 285

Trp Val Leu Val Val Val Gly Gly Val Leu Ala Cys Tyr Ser Leu Leu
290                 295                 300

Val Thr Val Ala Phe Ile Ile Phe Trp Val Arg Ser Lys Arg Ser Arg
305                 310                 315                 320

Leu Leu His Ser Asp Tyr Met Asn Met Thr Pro Arg Arg Pro Gly Pro
            325                 330                 335

Thr Arg Lys His Tyr Gln Pro Tyr Ala Pro Pro Arg Asp Phe Ala Ala
        340                 345                 350

Tyr Arg Ser Arg Val Lys Phe Ser Arg Ser Ala Asp Ala Pro Ala Tyr
    355                 360                 365

Gln Gln Gly Gln Asn Gln Leu Tyr Asn Glu Leu Asn Leu Gly Arg Arg
370                 375                 380

Glu Glu Tyr Asp Val Leu Asp Lys Arg Arg Gly Arg Asp Pro Glu Met
385                 390                 395                 400

Gly Gly Lys Pro Arg Arg Lys Asn Pro Gln Glu Gly Leu Tyr Asn Glu
            405                 410                 415

Leu Gln Lys Asp Lys Met Ala Glu Ala Tyr Ser Glu Ile Gly Met Lys
        420                 425                 430

Gly Glu Arg Arg Arg Gly Lys Gly His Asp Gly Leu Tyr Gln Gly Leu
    435                 440                 445

Ser Thr Ala Thr Lys Asp Thr Tyr Asp Ala Leu His Met Gln Ala Leu
450                 455                 460

Pro Pro Arg
465

<210> SEQ ID NO 185
<211> LENGTH: 1548
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 185
atggcactcc ccgtaactgc tctgctgctg ccgttggcat tgctcctgca cgccgcacgc     60
ccggacattc aattgaccca gtcccctagc agtctctcag caagtgtggg agatagggtg    120
tcattcacct gtcaggcttc acaggacatc aacaacttcc tcaattggta tcagcagaag    180
ccagggaagg caccaaagct gctcatatat gacgcttcaa accttgaaac cggagtacct    240
agccgcttca gcggaagcgg atcagggact gacttcactt ttaccatctc ttcactgcag    300
cccgaagaca tcgccacata ctactgccag cagtacggaa acttgccttt acatttggg     360 ggcggcacca agtggagat taagcgaggg ggaggcggct caggaggcgg tggctccgga    420
ggcgggggtt cccaggtcca gctccaggaa tccggcccag gtctggttaa gccagtgaa    480 actttgtccc tcacgtgtac tgtgagcggt ggttcaatct cctcatacta ttggtcttgg    540

```
atacggcaac ctcctggaaa gggcctcgag tggatcggct atatctacta tagtggctcc    600
actaattaca acccttccct caagtccaga gtcaccattt ccgtggacac atctaagaac    660
cagttcagtc tgaagttgtc cagcgttaca gccgcagaca cagccgttta ttactgtgtg    720
tctcttgttt actgcggggg agactgttat agcggcttcg attactgggg ccagggcacc    780
ttggtcacag tctcttccgc ggccgccctc tctaacagta ttatgtactt ttctcatttt    840
gtaccgtgt tccttcccgc taagccaact actaccccgg ccccacggcc gcctacccct    900
gcacccacaa tagccagtca gcctttgagc ctgagacctg aggcttgtcg gccggctgct    960
gggggtgcag tgcacacacg aggtcttgat tttgcttgcg acatatacat ctgggcccct   1020
ctggccggga cctgtggggt gctgcttctg agcttggtca tcacgctcta ttgcaaccat   1080
cgcaacagat ccaaaagaag ccgcctgctc catagcgatt acatgaatat gactccacgc   1140
cgccctggcc ccacaaggaa acactaccag ccttacgcac acctagaga tttcgctgcc   1200
tatcggagca gggtgaagtt ttccagatct gcagatgcac cagcgtatca gcagggccag   1260
aaccaactgt ataacgagct caacctggga cgcagggaag agtatgacgt tttggacaag   1320
cgcagaggac gggaccctga gatgggtggc aaaccaagac gaaaaaaccc ccaggagggt   1380
ctctataatg agctgcagaa ggataagatg gctgaagcct attctgaaat aggcatgaaa   1440
ggagagcgga aaggggaaa agggcacgac ggtttgtacc agggactcag cactgctacg   1500
aaggatactt atgacgctct ccacatgcaa gccctgccac ctaggtaa                1548
```

<210> SEQ ID NO 186
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 186

```
Met Ala Leu Pro Val Thr Ala Leu Leu Leu Pro Leu Ala Leu Leu Leu
1               5                  10                  15

His Ala Ala Arg Pro Asp Ile Gln Leu Thr Gln Ser Pro Ser Ser Leu
            20                  25                  30

Ser Ala Ser Val Gly Asp Arg Val Ser Phe Thr Cys Gln Ala Ser Gln
        35                  40                  45

Asp Ile Asn Asn Phe Leu Asn Trp Tyr Gln Gln Lys Pro Gly Lys Ala
    50                  55                  60

Pro Lys Leu Leu Ile Tyr Asp Ala Ser Asn Leu Glu Thr Gly Val Pro
65                  70                  75                  80

Ser Arg Phe Ser Gly Ser Gly Ser Gly Thr Asp Phe Thr Phe Thr Ile
                85                  90                  95

Ser Ser Leu Gln Pro Glu Asp Ile Ala Thr Tyr Tyr Cys Gln Gln Tyr
            100                 105                 110

Gly Asn Leu Pro Phe Thr Phe Gly Gly Gly Thr Lys Val Glu Ile Lys
        115                 120                 125

Arg Gly Gly Gly Gly Ser Gly Gly Gly Ser Gly Gly Gly Gly Ser
    130                 135                 140

Gln Val Gln Leu Gln Glu Ser Gly Pro Gly Leu Val Lys Pro Ser Glu
145                 150                 155                 160

Thr Leu Ser Leu Thr Cys Thr Val Ser Gly Gly Ser Ile Ser Ser Tyr
```

```
                165                 170                 175
Tyr Trp Ser Trp Ile Arg Gln Pro Pro Gly Lys Gly Leu Glu Trp Ile
            180                 185                 190
Gly Tyr Ile Tyr Tyr Ser Gly Ser Thr Asn Tyr Asn Pro Ser Leu Lys
            195                 200                 205
Ser Arg Val Thr Ile Ser Val Asp Thr Ser Lys Asn Gln Phe Ser Leu
            210                 215                 220
Lys Leu Ser Ser Val Thr Ala Ala Asp Thr Ala Val Tyr Tyr Cys Val
225                 230                 235                 240
Ser Leu Val Tyr Cys Gly Gly Asp Cys Tyr Ser Gly Phe Asp Tyr Trp
                245                 250                 255
Gly Gln Gly Thr Leu Val Thr Val Ser Ser Ala Ala Ala Leu Ser Asn
            260                 265                 270
Ser Ile Met Tyr Phe Ser His Phe Val Pro Val Phe Leu Pro Ala Lys
            275                 280                 285
Pro Thr Thr Thr Pro Ala Pro Arg Pro Pro Thr Pro Ala Pro Thr Ile
            290                 295                 300
Ala Ser Gln Pro Leu Ser Leu Arg Pro Glu Ala Cys Arg Pro Ala Ala
305                 310                 315                 320
Gly Gly Ala Val His Thr Arg Gly Leu Asp Phe Ala Cys Asp Ile Tyr
                325                 330                 335
Ile Trp Ala Pro Leu Ala Gly Thr Cys Gly Val Leu Leu Leu Ser Leu
            340                 345                 350
Val Ile Thr Leu Tyr Cys Asn His Arg Asn Arg Ser Lys Arg Ser Arg
            355                 360                 365
Leu Leu His Ser Asp Tyr Met Asn Met Thr Pro Arg Arg Pro Gly Pro
370                 375                 380
Thr Arg Lys His Tyr Gln Pro Tyr Ala Pro Pro Arg Asp Phe Ala Ala
385                 390                 395                 400
Tyr Arg Ser Arg Val Lys Phe Ser Arg Ser Ala Asp Ala Pro Ala Tyr
                405                 410                 415
Gln Gln Gly Gln Asn Gln Leu Tyr Asn Glu Leu Asn Leu Gly Arg Arg
            420                 425                 430
Glu Glu Tyr Asp Val Leu Asp Lys Arg Arg Gly Arg Asp Pro Glu Met
            435                 440                 445
Gly Gly Lys Pro Arg Arg Lys Asn Pro Gln Glu Gly Leu Tyr Asn Glu
            450                 455                 460
Leu Gln Lys Asp Lys Met Ala Glu Ala Tyr Ser Glu Ile Gly Met Lys
465                 470                 475                 480
Gly Glu Arg Arg Arg Gly Lys Gly His Asp Gly Leu Tyr Gln Gly Leu
                485                 490                 495
Ser Thr Ala Thr Lys Asp Thr Tyr Asp Ala Leu His Met Gln Ala Leu
            500                 505                 510
Pro Pro Arg
        515

<210> SEQ ID NO 187
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct
```

<400> SEQUENCE: 187

```
gacattcaat tgacccagtc ccctagcagt ctctcagcaa gtgtgggaga tagggtgtca      60
ttcacctgtc aggcttcaca ggacatcaac aacttcctca attggtatca gcagaagcca     120
gggaaggcac caaagctgct catatatgac gcttcaaacc ttgaaaccgg agtacctagc     180
cgcttcagcg gaagcggatc agggactgac ttcacttta ccatctcttc actgcagccc     240
gaagacatcg ccacatacta ctgccagcag tacggaaact tgccttttac atttggggc     300
ggcaccaaag tggagattaa gcgaggggga ggcggctcag gaggcggtgg ctccggaggc     360
gggggttccc aggtccagct ccaggaatcc ggcccaggtc tggttaagcc cagtgaaact     420
tgtccctca cgtgtactgt gagcggtggt tcaatctcct catactattg gtcttggata     480
cggcaacctc ctggaaaggg cctcgagtgg atcggctata tctactatag tggctccact     540
aattacaacc cttccctcaa gtccagagtc accatttccg tggacacatc taagaaccag     600
ttcagtctga agttgtccag cgttacagcc gcagacacag ccgtttatta ctgtgtgtct     660
cttgtttact gcgggggaga ctgttatagc ggcttcgatt actggggcca gggcaccttg     720
gtcacagtct cttccgcggc cgccctctct aacagtatta tgtacttttc tcattttgta     780
cccgtgttcc ttcccgctaa gccaactact accccggccc cacggccgcc tacccctgca     840
cccacaatag ccagtcagcc tttgagcctg agacctgagg cttgtcggcc ggctgctggg     900
ggtgcagtgc acacacgagg tcttgatttt gcttgcgaca tatacatctg gccccctctg     960
gccgggacct gtggggtgct gcttctgagc ttggtcatca cgctctattg caaccatcgc    1020
aacagatcca aaagaagccg cctgctccat agcgattaca tgaatatgac tccacgccgc    1080
cctggcccca caaggaaaca ctaccagcct tacgcaccac ctagagattt cgctgcctat    1140
cggagcaggg tgaagtttc cagatctgca gatgcaccag cgtatcagca gggccagaac    1200
caactgtata acgagctcaa cctgggacgc agggaagagt atgacgtttt ggacaagcgc    1260
agaggacggg accctgagat gggtggcaaa ccaagacgaa aaaccccca ggagggtctc    1320
tataatgagc tgcagaagga taagatggct gaagcctatt ctgaaatagg catgaaagga    1380
gagcggagaa gggaaaagg gcacgacggt ttgtaccagg gactcagcac tgctacgaag    1440
gatacttatg acgctctcca catgcaagcc ctgccaccta gg                      1482
```

<210> SEQ ID NO 188
<211> LENGTH: 494
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 188

```
Asp Ile Gln Leu Thr Gln Ser Pro Ser Ser Leu Ser Ala Ser Val Gly
1               5                   10                  15

Asp Arg Val Ser Phe Thr Cys Gln Ala Ser Gln Asp Ile Asn Asn Phe
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80
```

-continued

```
Glu Asp Ile Ala Thr Tyr Tyr Cys Gln Gln Tyr Gly Asn Leu Pro Phe
                85                  90                  95

Thr Phe Gly Gly Gly Thr Lys Val Glu Ile Lys Arg Gly Gly Gly Gly
            100                 105                 110

Ser Gly Gly Gly Gly Ser Gly Gly Gly Ser Gln Val Gln Leu Gln
        115                 120                 125

Glu Ser Gly Pro Gly Leu Val Lys Pro Ser Glu Thr Leu Ser Leu Thr
    130                 135                 140

Cys Thr Val Ser Gly Gly Ser Ile Ser Ser Tyr Tyr Trp Ser Trp Ile
145                 150                 155                 160

Arg Gln Pro Pro Gly Lys Gly Leu Glu Trp Ile Gly Tyr Ile Tyr Tyr
                165                 170                 175

Ser Gly Ser Thr Asn Tyr Asn Pro Ser Leu Lys Ser Arg Val Thr Ile
            180                 185                 190

Ser Val Asp Thr Ser Lys Asn Gln Phe Ser Leu Lys Leu Ser Ser Val
    195                 200                 205

Thr Ala Ala Asp Thr Ala Val Tyr Tyr Cys Val Ser Leu Val Tyr Cys
210                 215                 220

Gly Gly Asp Cys Tyr Ser Gly Phe Asp Tyr Trp Gly Gln Gly Thr Leu
225                 230                 235                 240

Val Thr Val Ser Ser Ala Ala Ala Leu Ser Asn Ser Ile Met Tyr Phe
            245                 250                 255

Ser His Phe Val Pro Val Phe Leu Pro Ala Lys Pro Thr Thr Thr Pro
        260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
            325                 330                 335

Cys Asn His Arg Asn Arg Ser Lys Arg Ser Arg Leu Leu His Ser Asp
        340                 345                 350

Tyr Met Asn Met Thr Pro Arg Arg Pro Gly Pro Thr Arg Lys His Tyr
    355                 360                 365

Gln Pro Tyr Ala Pro Pro Arg Asp Phe Ala Ala Tyr Arg Ser Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
            405                 410                 415

Leu Asp Lys Arg Arg Gly Arg Asp Pro Glu Met Gly Gly Lys Pro Arg
        420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
            485                 490
```

<210> SEQ ID NO 189
<211> LENGTH: 1446
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: anti-CLL-1 CAR construct

<400> SEQUENCE: 189

```
atggcactcc ccgtaactgc tctgctgctg ccgttggcat tgctcctgca cgccgcacgc        60
ccgcaggtac agctgcagga atctggggcc ggacttgtca agccaagtca gacactttct       120
cttacatgta ccgtgagcgg cggaagtata agcagtggag cttttactg gtcttggata        180
cggcagcacc caggcaaagg cttggagtgg attggataca ttcatcattc aggatctaca       240
cactataatc catcccttaa gtcccgggtc accattagca ttgatacgtc taagaatctg       300
ttcagtctca gctgtcctc cgtcactgct gccgacacag ccgtgtacta ctgcgcctcc        360
ttggtttact gcggaggcga ctgttatagc ggctttgatt attggggggca ggggaccctc      420
gtaaccgtga gctctggagg gggtgggagc ggggaggag gttcagggg gggcggctcc         480
gatatccagc tcactcaaag cccctctagt ctctctgcct cagtggggga tcgggtcagt      540
tttacttgtc aagcttcaca ggatatcaac aacttccta attggtatca gcagaagcca        600
ggaaaagcac ccaagctgct catctatgat gcctcaaatt tggagacggg tgttcccagt       660
cgattctctg gtcagggtc cggaccgac tttacgttta cgatctcctc tctgcagccc         720
gaagacatcg ccacatacta ttgtcaacag tacggcaact gccttttcac atttgggggc      780
gggactaagg ttgaaatcaa gagggccgct gcactggaca tgagaagtc caacggcacc       840
atcatccacg tgaagggcaa gcacctgtgc cctagtcctc tgttcccagg cccatccaaa       900
ccttttggg ttcttgttgt ggtcggggg gtgctggcct gctattctct gctggtcacg       960
gtggccttca taattttctg ggttagatcc aaaagaagcc gcctgctcca tagcgattac      1020
atgaatatga ctccacgccg ccctggcccc acaaggaaac actaccagcc ttacgcacca      1080
cctagagatt tcgctgccta tcggagcagg gtgaagtttt ccagatctgc agatgcacca      1140
gcgtatcagc agggccagaa ccaactgtat aacgagctca acctgggacg cagggaagag      1200
tatgacgttt tggacaagcg cagaggacgg gaccctgaga tgggtggcaa accaagacga      1260
aaaaacccc aggagggtct ctataatgag ctgcagaagg ataagatggc tgaagcctat      1320
tctgaaatag gcatgaaagg agagcggaga agggaaaag gcacgacgg tttgtaccag      1380
ggactcagca ctgctacgaa ggatacttat gacgctctcc acatgcaagc cctgccacct      1440
aggtaa                                                                1446
```

<210> SEQ ID NO 190
<211> LENGTH: 481
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 190

Met Ala Leu Pro Val Thr Ala Leu Leu Leu Pro Leu Ala Leu Leu Leu
1               5                   10                  15

-continued

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Gly
         35                  40                  45

Ser Ile Ser Ser Gly Gly Phe Tyr Trp Ser Trp Ile Arg Gln His Pro
     50                  55                  60

Gly Lys Gly Leu Glu Trp Ile Gly Tyr Ile His His Ser Gly Ser Thr
65                  70                  75                  80

His Tyr Asn Pro Ser Leu Lys Ser Arg Val Thr Ile Ser Ile Asp Thr
                 85                  90                  95

Ser Lys Asn Leu Phe Ser Leu Arg Leu Ser Ser Val Thr Ala Ala Asp
            100                 105                 110

Thr Ala Val Tyr Tyr Cys Ala Ser Leu Val Tyr Cys Gly Gly Asp Cys
        115                 120                 125

Tyr Ser Gly Phe Asp Tyr Trp Gly Gln Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Ser Phe Thr Cys Gln Ala Ser Gln Asp Ile Asn Asn Phe
            180                 185                 190

Leu Asn Trp Tyr Gln Gln Lys Pro Gly Lys Ala Pro Lys Leu Leu Ile
        195                 200                 205

Tyr Asp Ala Ser Asn Leu Glu Thr Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys Gln Gln Tyr Gly Asn Leu Pro Phe
                245                 250                 255

Thr Phe Gly Gly Gly Thr Lys Val Glu Ile Lys Arg Ala Ala Ala Leu
            260                 265                 270

Asp Asn Glu Lys Ser Asn Gly Thr Ile Ile His Val Lys Gly Lys His
        275                 280                 285

Leu Cys Pro Ser Pro Leu Phe Pro Gly Pro Ser Lys Pro Phe Trp Val
    290                 295                 300

Leu Val Val Val Gly Gly Val Leu Ala Cys Tyr Ser Leu Leu Val Thr
305                 310                 315                 320

Val Ala Phe Ile Ile Phe Trp Val Arg Ser Lys Arg Ser Arg Leu Leu
                325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
        355                 360                 365

Ser Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu 435                 440                 445
Arg Arg Arg Gly Lys Gly His Asp Gly Leu Tyr Gln Gly Leu Ser Thr
       450                 455                 460

Ala Thr Lys Asp Thr Tyr Asp Ala Leu His Met Gln Ala Leu Pro Pro
465                 470                 475                 480

Arg

<210> SEQ ID NO 191
<211> LENGTH: 1380
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 191
caggtacagc tgcaggaatc tgggcccgga cttgtcaagc caagtcagac actttctctt      60
acatgtaccg tgagcggcgg aagtataagc agtggaggct tttactggtc ttggatacgg     120
cagcacccag gcaaaggctt ggagtggatt ggatacattc atcattcagg atctacacac     180
tataatccat cccttaagtc ccgggtcacc attagcattg atacgtctaa gaatctgttc     240
agtctcaggc tgtcctccgt cactgctgcc gacacagccg tgtactactg cgcctccttg     300
gtttactgcg gaggcgactg ttatagcggc tttgattatt gggggcaggg gaccctcgta     360
accgtgagct ctggaggggg tgggagcggg ggaggaggtt caggggggggg cggctccgat     420 atccagctca ctcaaagccc ctctagtctc tctgcctcag tggggatcg ggtcagtttt      480 acttgtcaag cttcacagga tatcaacaac ttccttaatt ggtatcagca gaagccagga     540
aaagcaccca gctgctcat ctatgatgcc tcaaatttgg agacgggtgt tcccagtcga      600
ttctctgggt cagggtccgg gaccgacttt acgtttacga tctcctctct gcagcccgaa     660
gacatcgcca catactattg tcaacagtac ggcaacttgc ctttcacatt tggggcgggg     720
actaaggttg aaatcaagag ggccgctgca ctggacaatg agaagtccaa cggcaccatc     780
atccacgtga agggcaagca cctgtgccct agtcctctgt tcccaggccc atccaaacct     840
ttttgggttc ttgttgtggt cggggggggtg ctggcctgct attctctgct ggtcacggtg     900
gccttcataa tttctgggt tagatccaaa agaagccgcc tgctccatag cgattacatg     960
aatatgactc cacgccgccc tggccccaca aggaaacact accagcctta cgcaccacct    1020
agagatttcg ctgcctatcg gagcagggtg aagttttcca gatctgcaga tgcaccagcg    1080
tatcagcagg gccagaacca actgtataac gagctcaacc tgggacgcag ggaagagtat    1140
gacgttttgg acaagcgcag aggacgggac cctgagatgg gtggcaaacc aagacgaaaa    1200 aaccccagg agggtctcta taatgagctg cagaaggata agatggctga agcctattct    1260
gaaataggca tgaaaggaga gcggagaagg ggaaaagggc acgacggttt gtaccaggga    1320
ctcagcactg ctacgaagga tacttatgac gctctccaca tgcaagccct gccacctagg    1380

<210> SEQ ID NO 192
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 192

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45

Trp Ile Gly Tyr Ile His Ser Gly Ser Thr His Tyr Asn Pro Ser
50                  55                  60

Leu Lys Ser Arg Val Thr Ile Ser Ile Asp Thr Ser Lys Asn Leu Phe
65                  70                  75                  80

Ser Leu Arg Leu Ser Ser Val Thr Ala Ala Asp Thr Ala Val Tyr Tyr
                85                  90                  95

Cys Ala Ser Leu Val Tyr Cys Gly Asp Cys Tyr Ser Gly Phe Asp
            100                 105                 110

Tyr Trp Gly Gln Gly Thr Leu Val Thr Val Ser Ser Gly Gly Gly
        115                 120                 125

Ser Gly Gly Gly Gly Ser Gly Gly Gly Ser Asp Ile Gln Leu Thr
130                 135                 140

Gln Ser Pro Ser Ser Leu Ser Ala Ser Val Gly Asp Arg Val Ser Phe
145                 150                 155                 160

Thr Cys Gln Ala Ser Gln Asp Ile Asn Asn Phe Leu Asn Trp Tyr Gln
                165                 170                 175

Gln Lys Pro Gly Lys Ala Pro Lys Leu Leu Ile Tyr Asp Ala Ser Asn
            180                 185                 190

Leu Glu Thr Gly Val Pro Ser Arg Phe Ser Gly Ser Gly Ser Gly Thr
        195                 200                 205

Asp Phe Thr Phe Thr Ile Ser Ser Leu Gln Pro Glu Asp Ile Ala Thr
210                 215                 220

Tyr Tyr Cys Gln Gln Tyr Gly Asn Leu Pro Phe Thr Phe Gly Gly Gly
225                 230                 235                 240

Thr Lys Val Glu Ile Lys Arg Ala Ala Ala Leu Asp Asn Glu Lys Ser
                245                 250                 255

Asn Gly Thr Ile Ile His Val Lys Gly Lys His Leu Cys Pro Ser Pro
            260                 265                 270

Leu Phe Pro Gly Pro Ser Lys Pro Phe Trp Val Leu Val Val Val Gly
        275                 280                 285

Gly Val Leu Ala Cys Tyr Ser Leu Leu Val Thr Val Ala Phe Ile Ile
290                 295                 300

Phe Trp Val Arg Ser Lys Arg Ser Arg Leu Leu His Ser Asp Tyr Met
305                 310                 315                 320

Asn Met Thr Pro Arg Arg Pro Gly Pro Thr Arg Lys His Tyr Gln Pro
                325                 330                 335

Tyr Ala Pro Pro Arg Asp Phe Ala Ala Tyr Arg Ser Arg Val Lys Phe
            340                 345                 350

Ser Arg Ser Ala Asp Ala Pro Ala Tyr Gln Gln Gly Gln Asn Gln Leu
        355                 360                 365

Tyr Asn Glu Leu Asn Leu Gly Arg Arg Glu Glu Tyr Asp Val Leu Asp
370                 375                 380

Lys Arg Arg Gly Arg Asp Pro Glu Met Gly Gly Lys Pro Arg Arg Lys
385                 390                 395                 400

Asn Pro Gln Glu Gly Leu Tyr Asn Glu Leu Gln Lys Asp Lys Met Ala

```
                    405                 410                 415
Glu Ala Tyr Ser Glu Ile Gly Met Lys Gly Glu Arg Arg Gly Lys
            420                 425                 430

Gly His Asp Gly Leu Tyr Gln Gly Leu Ser Thr Ala Thr Lys Asp Thr
            435                 440                 445

Tyr Asp Ala Leu His Met Gln Ala Leu Pro Pro Arg
            450                 455                 460

<210> SEQ ID NO 193
<211> LENGTH: 1473
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 193
atggcactcc ccgtaactgc tctgctgctg ccgttggcat tgctcctgca cgccgcacgc      60
ccgcaggtgc agctgcagga aagcggtccg ggacttgtca agccgtccca aacgctgagt     120
ctgacgtgta ctgtctctgg tggctctatt tcttccgggg cttttattg gtcttggatc     180 agacaacacc ctggcaaagg gctggagtgg ataggtata ttcaccactc tgggtccact     240
cactacaacc catcattgaa atccagagtg actatctcaa tcgacacatc caagaacctt     300
ttcagcctga ggttgtcatc agttaccgcc gctgacaccg cggtgtatta ttgcgcctct     360
ctcgtgtact gcgtggcga ttgttatagt ggctttgact actggggca ggggacattg       420 gttaccgttt caagtggagg cggtgggtct ggcgggggcg gtagcggagg tgggggagc      480 gacatacagc ttacgcagag ccccccagc ctttcagcct ccgtgggga tagggtgtcc       540 tttacctgcc aggcttccca ggacataaac aacttcctca attggtatca gcaaaagccc     600
gggaaagcac caaagctgct catctacgat gccagcaacc tggaaaccgg agtgccgtct     660
cgcttctctg gaagtggcag tgggaccgat ttcactttta caatctcaag tttgcagcca     720
gaagacattg caacatacta ctgtcaacag tacggcaatc tcccctttac atttgggggg     780
ggaactaaag tggagattaa gcgcgctgca gccattgaag ttatgtatcc gccccgtat      840 ctggataacg agaaatctaa tggtaccata atacatgtga agggaaagca cctctgtcca     900
tcaccgctgt ccccggcccc ttcaaaacct ttctgggtac tcgttgtcgt gggtggagtt     960
ctggcctgct atagtctgct ggtgaccgtg gcgtttatca tcttctgggt aagatccaaa    1020
agaagccgcc tgctccatag cgattacatg aatatgactc cacgccgccc tggccccaca    1080
aggaaacact accagcctta cgcaccacct agagatttcg ctgcctatcg agcagggtg     1140 aagtttccca gatctgcaga tgcaccagcg tatcagcagg gccagaacca actgtataac    1200
gagctcaacc tgggacgcag ggaagagtat gacgtttgg acaagcgcag aggacgggac    1260
cctgagatgg gtggcaaacc aagacgaaaa aaccccagg agggtctcta taatgagctg    1320
cagaaggata gatggctga agcctattct gaaataggca tgaaggaga gcggagaagg    1380 ggaaaagggc acgacggttt gtaccaggga ctcagcactg ctacgaagga tacttatgac   1440
gctctccaca tgcaagccct gccacctagg taa                                1473

<210> SEQ ID NO 194
<211> LENGTH: 490
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 194

Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Gly
        35                  40                  45

Ser Ile Ser Ser Gly Gly Phe Tyr Trp Ser Trp Ile Arg Gln His Pro
    50                  55                  60

Gly Lys Gly Leu Glu Trp Ile Gly Tyr Ile His Ser Gly Ser Thr
65                  70                  75                  80

His Tyr Asn Pro Ser Leu Lys Ser Arg Val Thr Ile Ser Ile Asp Thr
                85                  90                  95

Ser Lys Asn Leu Phe Ser Leu Arg Leu Ser Ser Val Thr Ala Ala Asp
            100                 105                 110

Thr Ala Val Tyr Tyr Cys Ala Ser Leu Val Tyr Cys Gly Gly Asp Cys
        115                 120                 125

Tyr Ser Gly Phe Asp Tyr Trp Gly Gln Gly Thr Leu Val Thr Val Ser
    130                 135                 140

Ser Gly Gly Gly Gly Ser Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Ser Phe Thr Cys Gln Ala Ser Gln Asp Ile Asn Asn Phe
            180                 185                 190

Leu Asn Trp Tyr Gln Gln Lys Pro Gly Lys Ala Pro Lys Leu Leu Ile
        195                 200                 205

Tyr Asp Ala Ser Asn Leu Glu Thr Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys Gln Gln Tyr Gly Asn Leu Pro Phe
                245                 250                 255

Thr Phe Gly Gly Gly Thr Lys Val Glu Ile Lys Arg Ala Ala Ala Ile
            260                 265                 270

Glu Val Met Tyr Pro Pro Pro Tyr Leu Asp Asn Glu Lys Ser Asn Gly
        275                 280                 285

Thr Ile Ile His Val Lys Gly Lys His Leu Cys Pro Ser Pro Leu Phe
    290                 295                 300

Pro Gly Pro Ser Lys Pro Phe Trp Val Leu Val Val Val Gly Gly Val
305                 310                 315                 320

Leu Ala Cys Tyr Ser Leu Leu Val Thr Val Ala Phe Ile Ile Phe Trp
                325                 330                 335

Val Arg Ser Lys Arg Ser Arg Leu Leu His Ser Asp Tyr Met Asn Met
            340                 345                 350

Thr Pro Arg Arg Pro Gly Pro Thr Arg Lys His Tyr Gln Pro Tyr Ala
        355                 360                 365

Pro Pro Arg Asp Phe Ala Ala Tyr Arg Ser Arg Val Lys Phe Ser Arg
    370                 375                 380
```

```
Ser Ala Asp Ala Pro Ala Tyr Gln Gly Gln Asn Gln Leu Tyr Asn
385                 390                 395                 400

Glu Leu Asn Leu Gly Arg Arg Glu Glu Tyr Asp Val Leu Asp Lys Arg
            405                 410                 415

Arg Gly Arg Asp Pro Glu Met Gly Gly Lys Pro Arg Arg Lys Asn Pro
        420                 425                 430

Gln Glu Gly Leu Tyr Asn Glu Leu Gln Lys Asp Lys Met Ala Glu Ala
    435                 440                 445

Tyr Ser Glu Ile Gly Met Lys Gly Glu Arg Arg Arg Gly Lys Gly His
450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 195
<211> LENGTH: 1407
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 195
caggtgcagc tgcaggaaag cggtccggga cttgtcaagc cgtcccaaac gctgagtctg      60
acgtgtactg tctctggtgg ctctatttct tccgggggct tttattggtc ttggatcaga     120
caacaccctg gcaaagggct ggagtggata gggtatattc accactctgg gtccactcac     180
tacaacccat cattgaaatc cagagtgact atctcaatcg acacatccaa gaacctttc      240 agcctgaggt tgtcatcagt taccgccgct gacaccgcgg tgtattattg cgcctctctc     300
gtgtactgcg gtggcgattg ttatagtggc tttgactact gggggcaggg gacattggtt     360
accgtttcaa gtggaggcgg tgggtctggc ggggcggta gcggaggtgg gggagcgac       420 atacagctta cgcagagccc ctccagcctt tcagcctccg tggggatag gtgtcctt       480 acctgccagg cttcccagga cataaacaac ttcctcaatt ggtatcagca aaagcccggg     540
aaagcaccaa agctgctcat ctacgatgcc agcaacctgg aaaccggagt gccgtctcgc     600
ttctctggaa gtggcagtgg gaccgatttc acttttacaa tctcaagttt gcagccagaa     660
gacattgcaa catactactg tcaacagtac ggcaatctcc cctttacatt tgggggggga     720
actaaagtgg agattaagcg cgctgcagcc attgaagtta tgtatccgcc ccgtatctg      780 gataacgaga aatctaatgg taccataata catgtgaagg ggaagcacct ctgtccatca     840
ccgctgttcc ccggcccttc aaaaccttc tgggtactcg ttgtcgtggg tggagttctg     900
gcctgctata gtctgctggt gaccgtggcg tttatcatct ctgggtaag atccaaaaga     960 agccgcctgc tccatagcga ttacatgaat atgactccac gccgcctgg ccccacaagg    1020 aaacactacc agcttacgc accacctaga gatttcgctg cctatcggag cagggtgaag    1080
ttttccagat ctgcagatgc accagcgtat cagcagggcc agaaccaact gtataacgag    1140
ctcaacctgg gacgcaggga gagtatgac gttttggaca gcgcagagg acgggaccct    1200 gagatgggtg gcaaaccaag acgaaaaaac ccccaggagg gtctctataa tgagctgcag    1260
aaggataaga tggctgaagc ctattctgaa ataggcatga aggagagcg gagaagggga    1320
```

```
aaagggcacg acggtttgta ccagggactc agcactgcta cgaaggatac ttatgacgct    1380
ctccacatgc aagccctgcc acctagg                                         1407
```

<210> SEQ ID NO 196
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 196

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45

Trp Ile Gly Tyr Ile His His Ser Gly Ser Thr His Tyr Asn Pro Ser
    50                  55                  60

Leu Lys Ser Arg Val Thr Ile Ser Ile Asp Thr Ser Lys Asn Leu Phe
65                  70                  75                  80

Ser Leu Arg Leu Ser Ser Val Thr Ala Ala Asp Thr Ala Val Tyr Tyr
                85                  90                  95

Cys Ala Ser Leu Val Tyr Cys Gly Gly Asp Cys Tyr Ser Gly Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Ile Gln Leu Thr
    130                 135                 140

Gln Ser Pro Ser Ser Leu Ser Ala Ser Val Gly Asp Arg Val Ser Phe
145                 150                 155                 160

Thr Cys Gln Ala Ser Gln Asp Ile Asn Asn Phe Leu Asn Trp Tyr Gln
                165                 170                 175

Gln Lys Pro Gly Lys Ala Pro Lys Leu Leu Ile Tyr Asp Ala Ser Asn
            180                 185                 190

Leu Glu Thr Gly Val Pro Ser Arg Phe Ser Gly Ser Gly Ser Gly Thr
        195                 200                 205

Asp Phe Thr Phe Thr Ile Ser Ser Leu Gln Pro Glu Asp Ile Ala Thr
    210                 215                 220

Tyr Tyr Cys Gln Gln Tyr Gly Asn Leu Pro Phe Thr Phe Gly Gly Gly
225                 230                 235                 240

Thr Lys Val Glu Ile Lys Arg Ala Ala Ala Ile Glu Val Met Tyr Pro
                245                 250                 255

Pro Pro Tyr Leu Asp Asn Glu Lys Ser Asn Gly Thr Ile Ile His Val
            260                 265                 270

Lys Gly Lys His Leu Cys Pro Ser Pro Leu Phe Pro Gly Pro Ser Lys
        275                 280                 285

Pro Phe Trp Val Leu Val Val Val Gly Gly Val Leu Ala Cys Tyr Ser
    290                 295                 300

Leu Leu Val Thr Val Ala Phe Ile Ile Phe Trp Val Arg Ser Lys Arg
305                 310                 315                 320

Ser Arg Leu Leu His Ser Asp Tyr Met Asn Met Thr Pro Arg Arg Pro
                325                 330                 335
```

```
Gly Pro Thr Arg Lys His Tyr Gln Pro Tyr Ala Pro Pro Arg Asp Phe
                340                 345                 350

Ala Ala Tyr Arg Ser Arg Val Lys Phe Ser Arg Ser Ala Asp Ala Pro
            355                 360                 365

Ala Tyr Gln Gln Gly Gln Asn Gln Leu Tyr Asn Glu Leu Asn Leu Gly
370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415

Asn Glu Leu Gln Lys Asp Lys Met Ala Glu Ala Tyr Ser Glu Ile Gly
                420                 425                 430

Met Lys Gly Glu Arg Arg Arg Gly Lys Gly His Asp Gly Leu Tyr Gln
            435                 440                 445

Gly Leu Ser Thr Ala Thr Lys Asp Thr Tyr Asp Ala Leu His Met Gln
    450                 455                 460

Ala Leu Pro Pro Arg
465

<210> SEQ ID NO 197
<211> LENGTH: 1554
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 197
atggcactcc ccgtaactgc tctgctgctg ccgttggcat tgctcctgca cgccgcacgc      60
ccgcaggtgc agttgcagga aagcgggcct ggccttgtga aaccaagcca gacactgagc     120
ctgacatgca ctgtgtccgg cgggtccata tcttccgggg ttttttattg gtcctggata     180
cgccagcatc ccgggaaagg acttgaatgg attggatata tccaccattc cggaagcacc     240
cactacaatc caagccttaa atcccgggtg acaatctcca tcgacacctc aaagaatctt     300
ttttccctgc ggttgtcttc agtaactgcc gccgataccg ctgtgtacta ctgtgccagc     360
ctcgtctatt gcggcggaga ttgttattct gggttcgatt attggggtca aggcacactg     420
gtaactgtca gcagcggagg cggcggttcc gggggcgggg gcagtggagg gggcggatct     480
gacattcagc ttacgcagtc ccatcttca cttagcgcca gcgttggcga tcgggtcagc     540
ttcacgtgtc aagcaagtca ggatatcaac aactttctta actggtacca gcagaagcca     600
ggcaaggcac ccaagttgct gatttacgat gcttctaacc tcgagacggg agtgcctagc     660
cgcttctccg ggagcggcag cggcacagac tttacctta cgatttccag tctgcagcca     720
gaggatatag caacttatta ctgtcagcag tatggcaacc tcccttttac cttcggtggt     780
ggcacaaagg tcgagattaa aagagccgca gcgttgtcca actccataat gtatttttct     840
cattttgtgc ccgtctttct gcctgccaaa cctaccacca ccccgcccc acgaccacct     900 actccagccc ccaccatcgc ctcccagccc ctcagcctga ggccagaggc ttgtcgccct     960
gctgcggggg gcgctgtcca taccagagga ctcgacttcg cctgcgatat ttatatatgg    1020
gcccccctcg ccggcacctg cggagtcttg ctcctgagcc ttgtgatcac gctttattgt    1080
aaccatcgga atagatccaa aagaagccgc ctgctccata gcgattacat gaatatgact    1140
```

-continued

```
ccacgccgcc ctggccccac aaggaaacac taccagcctt acgcaccacc tagagatttc    1200
gctgcctatc ggagcagggt gaagttttcc agatctgcag atgcaccagc gtatcagcag    1260
ggccagaacc aactgtataa cgagctcaac ctgggacgca gggaagagta tgacgttttg    1320
gacaagcgca gaggacggga ccctgagatg ggtggcaaac caagacgaaa aaaccccag    1380 gagggtctct ataatgagct gcagaaggat aagatggctg aagcctattc tgaaataggc    1440
atgaaaggag agcggagaag gggaaaaggg cacgacggtt tgtaccaggg actcagcact    1500
gctacgaagg atacttatga cgctctccac atgcaagccc tgccacctag gtaa          1554
```

<210> SEQ ID NO 198
<211> LENGTH: 517
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: anti-CLL-1 CAR construct

<400> SEQUENCE: 198

```
Met Ala Leu Pro Val Thr Ala Leu Leu Leu Pro Leu Ala Leu Leu Leu
1               5                   10                  15

His Ala Ala Arg Pro Gln Val Gln Leu Gln Glu Ser Gly Pro Gly Leu
            20                  25                  30

Val Lys Pro Ser Gln Thr Leu Ser Leu Thr Cys Thr Val Ser Gly Gly
        35                  40                  45

Ser Ile Ser Ser Gly Gly Phe Tyr Trp Ser Trp Ile Arg Gln His Pro
    50                  55                  60

Gly Lys Gly Leu Glu Trp Ile Gly Tyr Ile His His Ser Gly Ser Thr
65                  70                  75                  80

His Tyr Asn Pro Ser Leu Lys Ser Arg Val Thr Ile Ser Ile Asp Thr
                85                  90                  95

Ser Lys Asn Leu Phe Ser Leu Arg Leu Ser Ser Val Thr Ala Ala Asp
            100                 105                 110

Thr Ala Val Tyr Tyr Cys Ala Ser Leu Val Tyr Cys Gly Gly Asp Cys
        115                 120                 125

Tyr Ser Gly Phe Asp Tyr Trp Gly Gln Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Ser Phe Thr Cys Gln Ala Ser Gln Asp Ile Asn Asn Phe
            180                 185                 190

Leu Asn Trp Tyr Gln Gln Lys Pro Gly Lys Ala Pro Lys Leu Leu Ile
        195                 200                 205

Tyr Asp Ala Ser Asn Leu Glu Thr Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys Gln Gln Tyr Gly Asn Leu Pro Phe
                245                 250                 255

Thr Phe Gly Gly Gly Thr Lys Val Glu Ile Lys Arg Ala Ala Ala Leu
            260                 265                 270

Ser Asn Ser Ile Met Tyr Phe Ser His Phe Val Pro Val Phe Leu Pro
```

```
                275                 280                 285
Ala Lys Pro Thr Thr Pro Ala Pro Arg Pro Pro Thr Pro Ala Pro
        290                 295                 300
Thr Ile Ala Ser Gln Pro Leu Ser Leu Arg Pro Glu Ala Cys Arg Pro
305                 310                 315                 320
Ala Ala Gly Gly Ala Val His Thr Arg Gly Leu Asp Phe Ala Cys Asp
                325                 330                 335
Ile Tyr Ile Trp Ala Pro Leu Ala Gly Thr Cys Gly Val Leu Leu Leu
            340                 345                 350
Ser Leu Val Ile Thr Leu Tyr Cys Asn His Arg Asn Arg Ser Lys Arg
                355                 360                 365
Ser Arg Leu Leu His Ser Asp Tyr Met Asn Met Thr Pro Arg Arg Pro
        370                 375                 380
Gly Pro Thr Arg Lys His Tyr Gln Pro Tyr Ala Pro Pro Arg Asp Phe
385                 390                 395                 400
Ala Ala Tyr Arg Ser Arg Val Lys Phe Ser Arg Ser Ala Asp Ala Pro
                405                 410                 415
Ala Tyr Gln Gln Gly Gln Asn Gln Leu Tyr Asn Glu Leu Asn Leu Gly
            420                 425                 430
Arg Arg Glu Glu Tyr Asp Val Leu Asp Lys Arg Arg Gly Arg Asp Pro
        435                 440                 445
Glu Met Gly Gly Lys Pro Arg Arg Lys Asn Pro Gln Glu Gly Leu Tyr
450                 455                 460
Asn Glu Leu Gln Lys Asp Lys Met Ala Glu Ala Tyr Ser Glu Ile Gly
465                 470                 475                 480
Met Lys Gly Glu Arg Arg Arg Gly Lys Gly His Asp Gly Leu Tyr Gln
                485                 490                 495
Gly Leu Ser Thr Ala Thr Lys Asp Thr Tyr Asp Ala Leu His Met Gln
            500                 505                 510
Ala Leu Pro Pro Arg
        515

<210> SEQ ID NO 199
<211> LENGTH: 1488
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 199
caggtgcagt tgcaggaaag cgggcctggc cttgtgaaac caagccagac actgagcctg      60
acatgcactg tgtccggcgg gtccatatct tccgggggtt tttattggtc ctggatacgc     120
cagcatcccg ggaaaggact tgaatggatt ggatatatcc accattccgg aagcacccac     180
tacaatccaa gccttaaatc ccgggtgaca atctccatcg acacctcaaa gaatcttttt     240
tccctgcggt tgtcttcagt aactgccgcc gataccgctg tgtactactg tgccagcctc     300
gtctattgcg gcggagattg ttattctggg ttcgattatt ggggtcaagg cacactggta     360
actgtcagca gcggaggcgg cggttccggg ggcggggca gtggagggg cggatctgac     420 attcagctta cgcagtcccc atcttcactt agcgccagcg ttggcgatcg ggtcagcttc     480
acgtgtcaag caagtcagga tatcaacaac tttcttaact ggtaccagca gaagccaggc     540
aaggcaccca agttgctgat ttacgatgct tctaacctcg agacgggagt gcctagccgc     600
```

```
ttctccggga gcggcagcgg cacagacttt acctttacga tttccagtct gcagccagag    660
gatatagcaa cttattactg tcagcagtat ggcaacctcc cttttacctt cggtggtggc    720
acaaaggtcg agattaaaag agccgcagcg ttgtccaact ccataatgta ttttctcat    780
tttgtgcccg tctttctgcc tgccaaacct accaccaccc ccgccccacg accacctact    840
ccagccccca ccatcgcctc ccagcccctc agcctgaggc cagaggcttg tcgccctgct    900
gcgggggggcg ctgtccatac cagaggactc gacttcgcct gcgatattta tatgggcc    960
cccctcgccg gcacctgcgg agtcttgctc ctgagccttg tgatcacgct ttattgtaac   1020
catcggaata gatccaaaag aagccgcctg ctccatagcg attacatgaa tatgactcca   1080
cgccgccctg gccccacaag gaaacactac cagccttacg caccacctag agatttcgct   1140
gcctatcgga gcagggtgaa gttttccaga tctgcagatg caccagcgta tcagcagggc   1200
cagaaccaac tgtataacga gctcaacctg ggacgcaggg aagagtatga cgttttggac   1260
aagcgcagag gacgggaccc tgagatgggt ggcaaaccaa gacgaaaaaa ccccaggag    1320
ggtctctata atgagctgca gaaggataag atggctgaag cctattctga aataggcatg   1380
aaaggagagc ggagaagggg aaaagggcac gacggtttgt accagggact cagcactgct   1440
acgaaggata cttatgacgc tctccacatg caagccctgc cacctagg              1488
```

<210> SEQ ID NO 200
<211> LENGTH: 496
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 200

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Tyr Trp Ser Trp Ile Arg Gln His Pro Gly Lys Gly Leu Glu
        35                  40                  45

Trp Ile Gly Tyr Ile His His Ser Gly Ser Thr His Tyr Asn Pro Ser
    50                  55                  60

Leu Lys Ser Arg Val Thr Ile Ser Ile Asp Thr Ser Lys Asn Leu Phe
65                  70                  75                  80

Ser Leu Arg Leu Ser Ser Val Thr Ala Ala Asp Thr Ala Val Tyr Tyr
                85                  90                  95

Cys Ala Ser Leu Val Tyr Cys Gly Gly Asp Cys Tyr Ser Gly Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Ser Asp Ile Gln Leu Thr
    130                 135                 140

Gln Ser Pro Ser Ser Leu Ser Ala Ser Val Gly Asp Arg Val Ser Phe
145                 150                 155                 160

Thr Cys Gln Ala Ser Gln Asp Ile Asn Asn Phe Leu Asn Trp Tyr Gln
                165                 170                 175

Gln Lys Pro Gly Lys Ala Pro Lys Leu Leu Ile Tyr Asp Ala Ser Asn
            180                 185                 190
```

```
Leu Glu Thr Gly Val Pro Ser Arg Phe Ser Gly Ser Gly Ser Gly Thr
        195                 200                 205

Asp Phe Thr Phe Thr Ile Ser Ser Leu Gln Pro Glu Asp Ile Ala Thr
    210                 215                 220

Tyr Tyr Cys Gln Gln Tyr Gly Asn Leu Pro Phe Thr Phe Gly Gly Gly
225                 230                 235                 240

Thr Lys Val Glu Ile Lys Arg Ala Ala Ala Leu Ser Asn Ser Ile Met
                245                 250                 255

Tyr Phe Ser His Phe Val Pro Val Phe Leu Pro Ala Lys Pro Thr Thr
                260                 265                 270

Thr Pro Ala Pro Arg Pro Pro Thr Pro Ala Pro Thr Ile Ala Ser Gln
            275                 280                 285

Pro Leu Ser Leu Arg Pro Glu Ala Cys Arg Pro Ala Ala Gly Gly Ala
        290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Asn His Arg Asn Arg Ser Lys Arg Ser Arg Leu Leu His
                340                 345                 350

Ser Asp Tyr Met Asn Met Thr Pro Arg Arg Pro Gly Pro Thr Arg Lys
            355                 360                 365

His Tyr Gln Pro Tyr Ala Pro Pro Arg Asp Phe Ala Ala Tyr Arg Ser
        370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495

<210> SEQ ID NO 201
<211> LENGTH: 1437
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 201
atggcactcc ccgtaactgc tctgctgctg ccgttggcat tgctcctgca cgccgcacgc      60
ccgcaggtcc aactggtgca gtccggagcc gaagtcaaga accaggtgc ctccgttaaa     120 gtgagttgca aagtctctgg atacactctg accgagctct ctatgcactg gtccggcag     180 gccccccggca agggattgga atggatgggc gggttcgatc ctgaggacgg agagactatc    240
```

```
tacgctcaaa aattccaggg acgagtgact gtgaccgaag acactagtac cgacactgcc      300
tacatggaac tttcctctct gcgatcagaa gataccgcag tgtactactg tgctactgaa      360 tctagggggca ttggatggcc ctacttcgat tactggggtc agggaactct ggtgactgtc     420
tccagcggtg gaggtggcag cggtggtggc ggaagcgggg ggggcggctc tgatattcag      480
atgactcaat ctccttcttc tctgtccgct tccgtgggcg atagagtgac cattacttgt     540
agggcgtccc agtcaatctc cagttatttg aattggtatc agcagaagcc cgggaaagca     600
cctaagctgt tgatcagcgg ggcttctagc ctgaagagtg gggtacctte acggttcagc     660 ggaagcggaa gcggaaccga tttcaccctg actatcagca gcctgccacc tgaggacttt     720
gcaacttact actgccaaca gtcatacagc actccgatca ctttcggcca gggcacccgg     780
ctcgaaatca gcgcgctgc tgctttggac aatgagaagt caaacggcac catcatacat      840
gttaaaggta aacatctgtg tccctccccg ctgttccccg gccttccaa accgttctgg       900 gttctggtgg tggtcggagg cgtactcgct tgctatagtc tgctggtaac tgtcgccttc     960
atcatctttt gggtgagatc caaaagaagc cgcctgctcc atagcgatta catgaatatg     1020
actccacgcc gccctggccc cacaaggaaa cactaccagc cttacgcacc acctagagat    1080
ttcgctgcct atcggagcag ggtgaagttt tccagatctg cagatgcacc agcgtatcag    1140
cagggccaga accaactgta taacgagctc aacctgggac gcagggaaga gtatgacgtt    1200
ttggacaagc gcagaggacg ggaccctgag atgggtggca aaccaagacg aaaaaacccc    1260
caggagggtc tctataatga gctgcagaag gataagatgg ctgaagccta ttctgaaata    1320
ggcatgaaag gagagcggag aaggggaaaa gggcacgacg gtttgtacca gggactcagc    1380
actgctacga aggatactta tgacgctctc cacatgcaag ccctgccacc taggtaa       1437
```

<210> SEQ ID NO 202
<211> LENGTH: 478
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 202

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Val Ser Gly Tyr
            35                  40                  45

Thr Leu Thr Glu Leu Ser Met His Trp Val Arg Gln Ala Pro Gly Lys
        50                  55                  60

Gly Leu Glu Trp Met Gly Gly Phe Asp Pro Glu Asp Gly Glu Thr Ile
65                  70                  75                  80

Tyr Ala Gln Lys Phe Gln Gly Arg Val Thr Val Thr Glu Asp Thr Ser
                85                  90                  95

Thr Asp Thr Ala Tyr Met Glu Leu Ser Ser Leu Arg Ser Glu Asp Thr
            100                 105                 110

Ala Val Tyr Tyr Cys Ala Thr Glu Ser Arg Gly Ile Gly Trp Pro Tyr
        115                 120                 125

Phe Asp Tyr Trp Gly Gln Gly Thr Leu Val Thr Val Ser Ser Gly Gly
    130                 135                 140

Gly Gly Ser Gly Gly Gly Ser Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Ser Ile Ser Ser Tyr Leu Asn Trp
            180                 185                 190

Tyr Gln Gln Lys Pro Gly Lys Ala Pro Lys Leu Leu Ile Ser Gly Ala
        195                 200                 205

Ser Ser Leu Lys Ser Gly Val Pro Ser Arg Phe Ser Gly Ser Gly Ser
    210                 215                 220

Gly Thr Asp Phe Thr Leu Thr Ile Ser Ser Leu Pro Pro Glu Asp Phe
225                 230                 235                 240

Ala Thr Tyr Tyr Cys Gln Gln Ser Tyr Ser Thr Pro Ile Thr Phe Gly
            245                 250                 255

Gln Gly Thr Arg Leu Glu Ile Lys Arg Ala Ala Ala Leu Asp Asn Glu
        260                 265                 270

Lys Ser Asn Gly Thr Ile Ile His Val Lys Gly Lys His Leu Cys Pro
    275                 280                 285

Ser Pro Leu Phe Pro Gly Pro Ser Lys Pro Phe Trp Val Leu Val Val
290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
            325                 330                 335

Tyr Met Asn Met Thr Pro Arg Arg Pro Gly Pro Thr Arg Lys His Tyr
        340                 345                 350

Gln Pro Tyr Ala Pro Pro Arg Asp Phe Ala Ala Tyr Arg Ser Arg Val
    355                 360                 365

Lys Phe Ser Arg Ser Ala Asp Ala Pro Ala Tyr Gln Gln Gly Gln Asn
370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
            405                 410                 415

Arg Lys Asn Pro Gln Glu Gly Leu Tyr Asn Glu Leu Gln Lys Asp Lys
        420                 425                 430

Met Ala Glu Ala Tyr Ser Glu Ile Gly Met Lys Gly Glu Arg Arg Arg
    435                 440                 445

Gly Lys Gly His Asp Gly Leu Tyr Gln Gly Leu Ser Thr Ala Thr Lys
450                 455                 460

Asp Thr Tyr Asp Ala Leu His Met Gln Ala Leu Pro Pro Arg
465                 470                 475

<210> SEQ ID NO 203
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 203
caggtccaac tggtgcagtc cggagccgaa gtcaagaaac caggtgcctc cgttaaagtg      60

```
agttgcaaag tctctggata cactctgacc gagctctcta tgcactgggt ccggcaggcc      120
cccggcaagg gattggaatg gatgggcggg ttcgatcctg aggacggaga gactatctac      180
gctcaaaaat tccagggacg agtgactgtg accgaagaca ctagtaccga cactgcctac      240
atggaacttt cctctctgcg atcagaagat accgcagtgt actactgtgc tactgaatct      300
aggggcattg gatggcccta cttcgattac tggggtcagg gaactctggt gactgtctcc      360
agcggtggag gtggcagcgg tggtggcgga agcggggggg gcggctctga tattcagatg      420
actcaatctc cttcttctct gtccgcttcc gtgggcgata gagtgaccat tacttgtagg      480
gcgtcccagt caatctccag ttatttgaat tggtatcagc agaagcccgg aaaagcaccc      540
aagctgttga tcagcggggc ttctagcctg aagagtgggg taccttcacg gttcagcgga      600
agcggaagcg gaaccgattt caccctgact atcagcagcc tgcaacctga ggactttgca      660
acttactact gccaacagtc atacagcact ccgatcactt tcggccaggg cacccggctc      720
gaaatcaagc gcgctgctgc tttggacaat gagaagtcaa acggaccat catacatgtt       780
aaaggtaaac atctgtgtcc ctccccgctg ttccccggcc cttccaaacc gttctgggtt      840
ctggtggtgg tcggaggcgt actcgcttgc tatagtctgc tggtaactgt cgccttcatc      900
atctttgggg tgagatccaa aagaagccgc ctgctccata gcgattacat gaatatgact      960
ccacgccgcc ctggccccac aaggaaacac taccagcctt acgcaccacc tagagatttc     1020
gctgcctatc ggagcagggt gaagttttcc agatctgcag atgcaccagc gtatcagcag     1080
ggccagaacc aactgtataa cgagctcaac ctgggacgca gggaagagta tgacgttttg     1140
gacaagcgca gaggacggga ccctgagatg ggtggcaaac caagacgaaa aaaccccag     1200
gagggtctct ataatgagct gcagaaggat aagatggctg aagcctattc tgaaataggc     1260
atgaaaggag agcggagaag gggaaaaggg cacgacggtt tgtaccaggg actcagcact     1320
gctacgaagg atacttatga cgctctccac atgcaagccc tgccacctag g              1371
```

<210> SEQ ID NO 204
<211> LENGTH: 457
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 204

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Val Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Ser Arg Gly Ile Gly Trp Pro Tyr Phe Asp Tyr Trp Gly
            100                 105                 110

Gln Gly Thr Leu Val Thr Val Ser Ser Gly Gly Gly Gly Ser Gly Gly
```

```
                    115                 120                 125
Gly Gly Ser Gly Gly Gly Ser Asp Ile Gln Met Thr Gln Ser Pro
        130                 135                 140
Ser Ser Leu Ser Ala Ser Val Gly Asp Arg Val Thr Ile Thr Cys Arg
145                 150                 155                 160
Ala Ser Gln Ser Ile Ser Ser Tyr Leu Asn Trp Tyr Gln Gln Lys Pro
                165                 170                 175
Gly Lys Ala Pro Lys Leu Leu Ile Ser Gly Ala Ser Ser Leu Lys Ser
            180                 185                 190
Gly Val Pro Ser Arg Phe Ser Gly Ser Gly Ser Gly Thr Asp Phe Thr
        195                 200                 205
Leu Thr Ile Ser Ser Leu Pro Pro Glu Asp Phe Ala Thr Tyr Tyr Cys
        210                 215                 220
Gln Gln Ser Tyr Ser Thr Pro Ile Thr Phe Gly Gln Gly Thr Arg Leu
225                 230                 235                 240
Glu Ile Lys Arg Ala Ala Ala Leu Asp Asn Glu Lys Ser Asn Gly Thr
                245                 250                 255
Ile Ile His Val Lys Gly Lys His Leu Cys Pro Ser Pro Leu Phe Pro
            260                 265                 270
Gly Pro Ser Lys Pro Phe Trp Val Leu Val Val Val Gly Gly Val Leu
        275                 280                 285
Ala Cys Tyr Ser Leu Leu Val Thr Val Ala Phe Ile Ile Phe Trp Val
        290                 295                 300
Arg Ser Lys Arg Ser Arg Leu Leu His Ser Asp Tyr Met Asn Met Thr
305                 310                 315                 320
Pro Arg Arg Pro Gly Pro Thr Arg Lys His Tyr Gln Pro Tyr Ala Pro
                325                 330                 335
Pro Arg Asp Phe Ala Ala Tyr Arg Ser Arg Val Lys Phe Ser Arg Ser
            340                 345                 350
Ala Asp Ala Pro Ala Tyr Gln Gln Gly Gln Asn Gln Leu Tyr Asn Glu
        355                 360                 365
Leu Asn Leu Gly Arg Arg Glu Glu Tyr Asp Val Leu Asp Lys Arg Arg
370                 375                 380
Gly Arg Asp Pro Glu Met Gly Gly Lys Pro Arg Arg Lys Asn Pro Gln
385                 390                 395                 400
Glu Gly Leu Tyr Asn Glu Leu Gln Lys Asp Lys Met Ala Glu Ala Tyr
                405                 410                 415
Ser Glu Ile Gly Met Lys Gly Glu Arg Arg Arg Gly Lys Gly His Asp
            420                 425                 430
Gly Leu Tyr Gln Gly Leu Ser Thr Ala Thr Lys Asp Thr Tyr Asp Ala
        435                 440                 445
Leu His Met Gln Ala Leu Pro Pro Arg
        450                 455

<210> SEQ ID NO 205
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 205
atggcactcc ccgtaactgc tctgctgctg ccgttggcat tgctcctgca cgccgcacgc     60
```

```
ccgcaggtgc agcttgtgca gagcggggcc gaggtgaaga agcccggggc cagcgtcaaa    120
gtgtcctgta aggtcagcgg ttacaccctc accgagctga gcatgcactg ggtacggcag    180
gctcccggca aggtcttga gtggatgggt ggatttgatc cagaagatgg agagactatc    240
tacgcccaga gttccaggg ccgggtcacc gtaacagaag acacctcaac tgacaccgct    300
tacatggagc tgagttcact gcggtccgag gacacggccg tgtattattg cgccaccgag    360
agccgcggaa tcggatggcc ttacttcgac tactggggac agggtacact tgttacagta    420
tcatccgggg gtggcggctc tggtggggc ggctccggag gggtggatc agatatccaa    480
atgactcaaa gtccaagttc cctgtctgcc tcagtcggag atagagtcac cataacctgc    540
agggcaagtc agtccatctc ctcctatctg aactggtacc aacagaaacc tggaaaggcg    600
cctaagctcc tgatctccgg agcctcatct ttgaaatccg gtgtcccatc tcgcttcagt    660
ggctctggaa gcggtacaga ttttactttg accattagca gcctcccacc ggaagacttt    720
gctacatatt actgccagca gtcttactca accccaatca ccttcgggca aggcaccaga    780
ctcgaaataa aaagagcagc tgctatcgag gttatgtacc caccgccgta cttggataac    840
gaaaaaagca atgggaccat cattcatgtg aagggtaagc acctttgccc tagcccactg    900
tttcctggcc cgagtaaacc cttttgggta cttgtggtcg tcggcggcgt gctggcctgc    960
tactcactcc tggttaccgt cgcattcatc atcttttggg tgagatccaa agaagccgc    1020
ctgctccata gcgattacat gaatatgact ccacgccgcc ctggccccac aaggaaacac    1080
taccagcctt acgcaccacc tagagatttc gctgcctatc ggagcagggt gaagttttcc    1140
agatctgcag atgcaccagc gtatcagcag ggccagaacc aactgtataa cgagctcaac    1200
ctgggacgca gggaagagta tgacgttttg gacaagcgca gaggacggga ccctgagatg    1260
ggtggcaaac caagacgaaa aaaccccag gagggtctct ataatgagct gcagaaggat    1320
aagatggctg aagcctattc tgaaataggc atgaaaggag agcggagaag gggaaaaggg    1380
cacgacggtt tgtaccaggg actcagcact gctacgaagg atacttatga cgctctccac    1440
atgcaagccc tgccacctag gtaa                                          1464
```

<210> SEQ ID NO 206
<211> LENGTH: 487
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 206

```
Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ala Ser Val Lys Val Ser Cys Lys Val Ser Gly Tyr
        35                  40                  45

Thr Leu Thr Glu Leu Ser Met His Trp Val Arg Gln Ala Pro Gly Lys
    50                  55                  60

Gly Leu Glu Trp Met Gly Gly Phe Asp Pro Glu Asp Gly Glu Thr Ile
65                  70                  75                  80

Tyr Ala Gln Lys Phe Gln Gly Arg Val Thr Val Thr Glu Asp Thr Ser
                85                  90                  95
```

```
Thr Asp Thr Ala Tyr Met Glu Leu Ser Ser Leu Arg Ser Glu Asp Thr
            100                 105                 110

Ala Val Tyr Tyr Cys Ala Thr Glu Ser Arg Gly Ile Gly Trp Pro Tyr
            115                 120                 125

Phe Asp Tyr Trp Gly Gln Gly Thr Leu Val Thr Val Ser Ser Gly Gly
            130                 135                 140

Gly Gly Ser Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Ser Ile Ser Ser Tyr Leu Asn Trp
            180                 185                 190

Tyr Gln Gln Lys Pro Gly Lys Ala Pro Lys Leu Leu Ile Ser Gly Ala
            195                 200                 205

Ser Ser Leu Lys Ser Gly Val Pro Ser Arg Phe Ser Gly Ser Gly Ser
210                 215                 220

Gly Thr Asp Phe Thr Leu Thr Ile Ser Ser Leu Pro Pro Glu Asp Phe
225                 230                 235                 240

Ala Thr Tyr Tyr Cys Gln Gln Ser Tyr Ser Thr Pro Ile Thr Phe Gly
            245                 250                 255

Gln Gly Thr Arg Leu Glu Ile Lys Arg Ala Ala Ile Glu Val Met
            260                 265                 270

Tyr Pro Pro Pro Tyr Leu Asp Asn Glu Lys Ser Asn Gly Thr Ile Ile
            275                 280                 285

His Val Lys Gly Lys His Leu Cys Pro Ser Pro Leu Phe Pro Gly Pro
            290                 295                 300

Ser Lys Pro Phe Trp Val Leu Val Val Gly Gly Val Leu Ala Cys
305                 310                 315                 320

Tyr Ser Leu Leu Val Thr Val Ala Phe Ile Ile Phe Trp Val Arg Ser
            325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
            355                 360                 365

Asp Phe Ala Ala Tyr Arg Ser Arg Val Lys Phe Ser Arg Ser Ala Asp
            370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Gly Arg
            405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
            485

<210> SEQ ID NO 207
<211> LENGTH: 1398
```

```
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 207
caggtgcagc ttgtgcagag cggggccgag gtgaagaagc ccggggccag cgtcaaagtg      60
tcctgtaagg tcagcggtta caccctcacc gagctgagca tgcactgggt acggcaggct     120
cccggcaaag gtcttgagtg gatgggtgga tttgatccag aagatggaga gactatctac     180
gcccagaagt tccagggccg ggtcaccgta acagaagaca cctcaactga caccgcttac     240
atggagctga gttcactgcg gtccgaggac acggccgtgt attattgtgc caccgagagc     300
cgcggaatcg gatggcctta cttcgactac tggggacagg gtacacttgt tacagtatca     360
tccgggggtg gcggctctgg tggggcggc tccggagggg gtggatcaga tatccaaatg      420
actcaaagtc caagttccct gtctgcctca gtcggagata gagtcaccat aacctgcagg     480
gcaagtcagt ccatctcctc ctatctgaac tggtaccaac agaaacctgg aaaggcgcct     540
aagctcctga tctccggagc ctcatctttg aaatccggtg tcccatctcg cttcagtggc     600
tctggaagcg gtacagattt tactttgacc attagcagcc tcccaccgga agactttgct     660
acatattact gccagcagtc ttactcaacc ccaatcacct cgggcaagg caccagactc      720
gaaataaaaa gagcagctgc tatcgaggtt atgtaccac cgccgtactt ggataacgaa      780
aaaagcaatg gaccatcat tcatgtgaag ggtaagcacc tttgccctag cccactgttt      840
cctggcccga gtaaacccct ttgggtactt gtggtcgtcg gcggcgtgct ggcctgctac     900
tcactcctgg ttaccgtcgc attcatcatc ttttgggtga gatccaaaag aagccgcctg     960
ctccatagcg attacatgaa tatgactcca cgccgccctg ccccacaag aaacactac     1020
cagcttacg caccacctag agatttcgct gcctatcgga gcagggtgaa gttttccaga    1080
tctgcagatg caccagcgta tcagcagggc cagaaccaac tgtataacga gctcaacctg    1140
ggacgcaggg aagagtatga cgttttggac aagcgcagag acgggacccc tgagatgggt    1200
ggcaaaccaa gacgaaaaaa cccccaggag ggtctctata atgagctgca gaaggataag    1260
atggctgaag cctattctga aataggcatg aaaggagagc ggagaagggg aaaagggcac    1320
gacggtttgt accagggact cagcactgct acgaaggata cttatgacgc tctccacatg    1380
caagccctgc cacctagg                                                 1398

<210> SEQ ID NO 208
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 208

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45
```

```
Gly Gly Phe Asp Pro Glu Asp Gly Glu Thr Ile Tyr Ala Gln Lys Phe
 50                  55                  60

Gln Gly Arg Val Thr Val Thr Glu Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Thr Glu Ser Arg Gly Ile Gly Trp Pro Tyr Phe Asp Tyr Trp Gly
            100                 105                 110

Gln Gly Thr Leu Val Thr Val Ser Ser Gly Gly Gly Ser Gly Gly
            115                 120                 125

Gly Gly Ser Gly Gly Gly Ser Asp Ile Gln Met Thr Gln Ser Pro
130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Ser Gly Ala Ser Ser Leu Lys Ser
            180                 185                 190

Gly Val Pro Ser Arg Phe Ser Gly Ser Gly Ser Gly Thr Asp Phe Thr
            195                 200                 205

Leu Thr Ile Ser Ser Leu Pro Pro Glu Asp Phe Ala Thr Tyr Tyr Cys
    210                 215                 220

Gln Gln Ser Tyr Ser Thr Pro Ile Thr Phe Gly Gln Gly Thr Arg Leu
225                 230                 235                 240

Glu Ile Lys Arg Ala Ala Ala Ile Glu Val Met Tyr Pro Pro Pro Tyr
                245                 250                 255

Leu Asp Asn Glu Lys Ser Asn Gly Thr Ile Ile His Val Lys Gly Lys
            260                 265                 270

His Leu Cys Pro Ser Pro Leu Phe Pro Gly Pro Ser Lys Pro Phe Trp
            275                 280                 285

Val Leu Val Val Val Gly Gly Val Leu Ala Cys Tyr Ser Leu Leu Val
            290                 295                 300

Thr Val Ala Phe Ile Ile Phe Trp Val Arg Ser Lys Arg Ser Arg Leu
305                 310                 315                 320

Leu His Ser Asp Tyr Met Asn Met Thr Pro Arg Arg Pro Gly Pro Thr
                325                 330                 335

Arg Lys His Tyr Gln Pro Tyr Ala Pro Pro Arg Asp Phe Ala Ala Tyr
            340                 345                 350

Arg Ser Arg Val Lys Phe Ser Arg Ser Ala Asp Ala Pro Ala Tyr Gln
            355                 360                 365

Gln Gly Gln Asn Gln Leu Tyr Asn Glu Leu Asn Leu Gly Arg Arg Glu
            370                 375                 380

Glu Tyr Asp Val Leu Asp Lys Arg Arg Gly Arg Asp Pro Glu Met Gly
385                 390                 395                 400

Gly Lys Pro Arg Arg Lys Asn Pro Gln Glu Gly Leu Tyr Asn Glu Leu
                405                 410                 415

Gln Lys Asp Lys Met Ala Glu Ala Tyr Ser Glu Ile Gly Met Lys Gly
            420                 425                 430

Glu Arg Arg Arg Gly Lys Gly His Asp Gly Leu Tyr Gln Gly Leu Ser
            435                 440                 445

Thr Ala Thr Lys Asp Thr Tyr Asp Ala Leu His Met Gln Ala Leu Pro
450                 455                 460
```

Pro Arg
465

<210> SEQ ID NO 209
<211> LENGTH: 1545
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 209

| | | | | | |
|---|---|---|---|---|---|
| atggcactcc | ccgtaactgc | tctgctgctg | ccgttggcat | tgctcctgca | cgccgcacgc | 60 |
| ccgcaggtgc | agttggtgca | aagcggcgca | gaagttaaga | acctggggc | gtcagttaag | 120 |
| gtgtcttgca | aagtatctgg | ctatacccctc | actgagctgt | ccatgcattg | ggtaaggcag | 180 |
| gctcctggaa | aggggctcga | atggatggga | ggatttgacc | ctgaagacgg | agagaccatc | 240 |
| tacgcccaga | aattccaggg | tagagtaaca | gtgactgagg | acactagcac | tgacacagcg | 300 |
| tacatggagc | tgagttctct | gagaagtgag | gacacagccg | tttactactg | cgctaccgag | 360 |
| tccagaggta | ttggctggcc | atacttcgac | tattggggtc | agggcaccct | ggttacagtg | 420 |
| agttcaggag | gcgggggctc | tgggggggc | ggttccggag | ggggggctc | agatatacag | 480 |
| atgacgcaga | gtccatcaag | tctctcagcc | agcgtgggga | tcgcgtgac | tattacttgc | 540 |
| cgcgccagcc | agagtattag | ctcctatctg | aattggtacc | agcaaaagcc | cgggaaggcc | 600 |
| cctaagcttc | tgatttctgg | cgcctcctct | ttgaagtcag | gtgtgccaag | cagatttagc | 660 |
| gggtctggaa | gtggcactga | ctttacactt | actatctcca | gcctgccccc | agaggatttt | 720 |
| gccacatatt | actgtcagca | aagctactct | actccaatca | ctttcggcca | gggcacaaga | 780 |
| ttggagatta | agagggctgc | cgcactttca | aattccatca | tgtatttcag | ccattttgtg | 840 |
| cctgttttc | ttccggccaa | acctacaacc | actcccgccc | cacgcccacc | tactcccgcc | 900 |
| cctaccattg | cctcccagcc | tctgtctctt | agacctgagg | cttgtagacc | tgctgccggc | 960 |
| ggagccgtgc | acactcgcgg | tctggacttc | gcctgcgaca | tctatatctg | gccccctctg | 1020 |
| gccggcacct | gcggcgttct | ccttctctca | ctcgtaatca | cactctattg | caatcacagg | 1080 |
| aacagatcca | aaagaagccg | cctgctccat | agcgattaca | tgaatatgac | tccacgccgc | 1140 |
| cctggcccca | aaggaaaaca | ctaccagcct | tacgcaccac | ctagagattt | cgctgcctat | 1200 |
| cggagcaggg | tgaagttttc | cagatctgca | gatgcaccag | cgtatcagca | gggccagaac | 1260 |
| caactgtata | acgagctcaa | cctgggacgc | agggaagagt | atgacgtttt | ggacaagcgc | 1320 |
| agaggacggg | accctgagat | gggtggcaaa | ccaagacgaa | aaaccccca | ggagggtctc | 1380 |
| tataatgagc | tgcagaagga | taagatggct | gaagcctatt | ctgaaatagg | catgaaagga | 1440 |
| gagcggagaa | ggggaaaagg | gcacgacggt | ttgtaccagg | gactcagcac | tgctacgaag | 1500 |
| gatacttatg | acgctctcca | catgcaagcc | ctgccaccta | ggtaa | | 1545 |

<210> SEQ ID NO 210
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

```
<400> SEQUENCE: 210

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ala Ser Val Lys Val Ser Cys Lys Val Ser Gly Tyr
            35                  40                  45

Thr Leu Thr Glu Leu Ser Met His Trp Val Arg Gln Ala Pro Gly Lys
        50                  55                  60

Gly Leu Glu Trp Met Gly Gly Phe Asp Pro Glu Asp Gly Glu Thr Ile
65                  70                  75                  80

Tyr Ala Gln Lys Phe Gln Gly Arg Val Thr Val Thr Glu Asp Thr Ser
                85                  90                  95

Thr Asp Thr Ala Tyr Met Glu Leu Ser Ser Leu Arg Ser Glu Asp Thr
            100                 105                 110

Ala Val Tyr Tyr Cys Ala Thr Glu Ser Arg Gly Ile Gly Trp Pro Tyr
        115                 120                 125

Phe Asp Tyr Trp Gly Gln Gly Thr Leu Val Thr Val Ser Ser Gly Gly
130                 135                 140

Gly Gly Ser Gly Gly Gly Gly Ser Gly Gly Gly Gly Ser Asp Ile Gln
145                 150                 155                 160

Met Thr Gln Ser Pro Ser Ser Leu Ser Ala Ser Val Gly Asp Arg Val
                165                 170                 175

Thr Ile Thr Cys Arg Ala Ser Gln Ser Ile Ser Ser Tyr Leu Asn Trp
            180                 185                 190

Tyr Gln Gln Lys Pro Gly Lys Ala Pro Lys Leu Leu Ile Ser Gly Ala
        195                 200                 205

Ser Ser Leu Lys Ser Gly Val Pro Ser Arg Phe Ser Gly Ser Gly Ser
210                 215                 220

Gly Thr Asp Phe Thr Leu Thr Ile Ser Ser Leu Pro Pro Glu Asp Phe
225                 230                 235                 240

Ala Thr Tyr Tyr Cys Gln Gln Ser Tyr Ser Thr Pro Ile Thr Phe Gly
                245                 250                 255

Gln Gly Thr Arg Leu Glu Ile Lys Arg Ala Ala Ala Leu Ser Asn Ser
            260                 265                 270

Ile Met Tyr Phe Ser His Phe Val Pro Val Phe Leu Pro Ala Lys Pro
        275                 280                 285

Thr Thr Thr Pro Ala Pro Arg Pro Pro Thr Pro Ala Pro Thr Ile Ala
290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Ile Tyr Ile
                325                 330                 335

Trp Ala Pro Leu Ala Gly Thr Cys Gly Val Leu Leu Leu Ser Leu Val
            340                 345                 350

Ile Thr Leu Tyr Cys Asn His Arg Asn Arg Ser Lys Arg Ser Arg Leu
        355                 360                 365

Leu His Ser Asp Tyr Met Asn Met Thr Pro Arg Arg Pro Gly Pro Thr
370                 375                 380

Arg Lys His Tyr Gln Pro Tyr Ala Pro Pro Arg Asp Phe Ala Ala Tyr
385                 390                 395                 400

Arg Ser Arg Val Lys Phe Ser Arg Ser Ala Asp Ala Pro Ala Tyr Gln
                405                 410                 415
```

```
Gln Gly Gln Asn Gln Leu Tyr Asn Glu Leu Asn Leu Gly Arg Arg Glu
            420                 425                 430

Glu Tyr Asp Val Leu Asp Lys Arg Arg Gly Arg Asp Pro Glu Met Gly
            435                 440                 445

Gly Lys Pro Arg Arg Lys Asn Pro Gln Glu Gly Leu Tyr Asn Glu Leu
450                 455                 460

Gln Lys Asp Lys Met Ala Glu Ala Tyr Ser Glu Ile Gly Met Lys Gly
465                 470                 475                 480

Glu Arg Arg Arg Gly Lys Gly His Asp Gly Leu Tyr Gln Gly Leu Ser
            485                 490                 495

Thr Ala Thr Lys Asp Thr Tyr Asp Ala Leu His Met Gln Ala Leu Pro
            500                 505                 510

Pro Arg

<210> SEQ ID NO 211
<211> LENGTH: 1479
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 211
caggtgcagt tggtgcaaag cggcgcagaa gttaagaaac ctggggcgtc agttaaggtg      60
tcttgcaaag tatctggcta taccctcact gagctgtcca tgcattgggt aaggcaggct     120
cctggaaagg ggctcgaatg gatgggagga tttgaccctg aagacggaga gaccatctac     180
gcccagaaat tccagggtag agtaacagtg actgaggaca ctagcactga cacagcgtac     240
atggagctga gttctctgag aagtgaggac acagccgttt actactgcgc taccgagtcc     300
agaggtattg gctggccata cttcgactat tggggtcagg gcaccctggt acagtgagt     360 tcaggaggcg ggggctctgg ggggggcggt tccggagggg ggggctcaga tatacagatg     420
acgcagagtc catcaagtct ctcagccagc gtggagatc gcgtgactat tacttgccgc     480
gccagccaga gtattagctc ctatctgaat tggtaccagc aaaagcccgg aaggcccct     540 aagcttctga tttctggcgc ctcctctttg aagtcaggtg tgccaagcag atttagcggg     600
tctggaagtg gcactgactt tacacttact atctccagcc tgcccccaga ggattttgcc     660
acatattact gtcagcaaag ctactctact ccaatcactt tcggccaggg cacaagattg     720
gagattaaga gggctgccgc actttcaaat tccatcatgt atttcagcca ttttgtgcct     780 gttttttcttc cggccaaacc tacaaccact cccgccccac gcccacctac tcccgccct     840 accattgcct cccagcctct gtctcttaga cctgaggctt gtagacctgc tgccggcgga     900
gccgtgcaca ctcgcggtct ggacttcgcc tgcgacatct atatctgggc ccctctggcc     960
ggcacctgcg gcgttctcct tctctcactc gtaatcacac tctattgcaa tcacaggaac    1020
agatccaaaa gaagccgcct gctccatagc gattacatga atatgactcc acgccgccct    1080
ggccccacaa ggaaacacta ccagcctac gcaccacta gagatttcgc tgcctatcgg    1140
agcagggtga agttttccag atctgcagat gcaccagcgt atcagcaggg ccagaaccaa    1200
ctgtataacg agctcaacct gggacgcagg gaagagtatg acgttttgga caagcgcaga    1260
ggacgggacc ctgagatggg tggcaaacca agacgaaaaa acccccagga gggtctctat    1320
aatgagctgc agaaggataa gatggctgaa gcctattctg aaataggcat gaaggagag     1380
```
cggagaaggg gaaaagggca cgacggtttg taccagggac tcagcactgc tacgaaggat    1440
acttatgacg ctctccacat gcaagccctg ccacctagg                            1479

<210> SEQ ID NO 212
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 212

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Val Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Ser Arg Gly Ile Gly Trp Pro Tyr Phe Asp Tyr Trp Gly
            100                 105                 110

Gln Gly Thr Leu Val Thr Val Ser Ser Gly Gly Gly Gly Ser Gly Gly
        115                 120                 125

Gly Gly Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ser Ser Tyr Leu Asn Trp Tyr Gln Gln Lys Pro
                165                 170                 175

Gly Lys Ala Pro Lys Leu Leu Ile Ser Gly Ala Ser Ser Leu Lys Ser
            180                 185                 190

Gly Val Pro Ser Arg Phe Ser Gly Ser Gly Ser Gly Thr Asp Phe Thr
        195                 200                 205

Leu Thr Ile Ser Ser Leu Pro Pro Glu Asp Phe Ala Thr Tyr Tyr Cys
    210                 215                 220

Gln Gln Ser Tyr Ser Thr Pro Ile Thr Phe Gly Gln Gly Thr Arg Leu
225                 230                 235                 240

Glu Ile Lys Arg Ala Ala Ala Leu Ser Asn Ser Ile Met Tyr Phe Ser
                245                 250                 255

His Phe Val Pro Val Phe Leu Pro Ala Lys Pro Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys

```
                    325                 330                 335
Asn His Arg Asn Arg Ser Lys Arg Ser Arg Leu Leu His Ser Asp Tyr
                340                 345                 350

Met Asn Met Thr Pro Arg Arg Pro Gly Pro Thr Arg Lys His Tyr Gln
            355                 360                 365

Pro Tyr Ala Pro Pro Arg Asp Phe Ala Ala Tyr Arg Ser Arg Val Lys
        370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 213
<211> LENGTH: 1425
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: anti-CLL-1 CAR construct

<400> SEQUENCE: 213

```
atggcactcc ccgtaactgc tctgctgctg ccgttggcat tgctcctgca cgccgcacgc    60
ccgcaggtcc agttggtcga aagtggcggt ggtgtagtgc agccgggccg cagtttgagg   120
ctttcctgtg cggcttcagg ctttactttt ccagctatg gaatgcactg ggtgcggcag   180
gcccccggca aggacttga gtgggtggcc gtcatttctt atgacggatc agataagtac   240
tacgtggaca gcgtcaaggg cagattcacc atctctaggg acaacagtaa aaatagactc   300
tacctccaga tgaatagcct cagagctgaa gacacggccg tctactattg tgctcgggag   360
cggtatagtg gcagagacta ctgggggcag ggcacactcg ttacagtgag tagcggcgga   420
ggagggagtg gggcggtgg ctccggtgga ggaggttctg agattgttat gacccagagt   480
cctgcgaccc tctcagtcag ccccggggag cgcgcaactt tgtcttgcag agctagtcag   540
tccgtgtcct ctcttctgac atggtaccag caaaagcccg gcaggctcc cgcccttttg   600
atctttgggg cttcaacaag agccactggg attcccgcac gattctctgg ctccggagc   660
ggtactggtt tcaccctgac gattagcagt ctccagagcg aggacttcgc cgtatactac   720
tgccagcagt acgatacgtg gccattcact tttggaccag ggactaaagt ggattttaag   780
cgcgccgccg ctctcgataa cgaaaagtca atggcacca taatccacgt caaaggcaag   840
cacctgtgcc cttccccgct cttccccgga cccagtaaac cattttgggt gctggttgtt   900
gtggggggcg tgctggcctg ctatagcctt ttggtcactg tagccttcat tattttttgg   960
gtcagatcca aaagaagccg cctgctccat agcgattaca tgaatatgac tccacgccgc  1020
```

```
cctggcccca caaggaaaca ctaccagcct tacgcaccac ctagagattt cgctgcctat   1080
cggagcaggg tgaagttttc cagatctgca gatgcaccag cgtatcagca gggccagaac   1140
caactgtata acgagctcaa cctgggacgc agggaagagt atgacgtttt ggacaagcgc   1200
agaggacggg accctgagat gggtggcaaa ccaagacgaa aaaccccca ggagggtctc     1260 tataatgagc tgcagaagga taagatggct gaagcctatt ctgaaatagg catgaaagga   1320
gagcggagaa ggggaaaagg gcacgacggt ttgtaccagg gactcagcac tgctacgaag   1380
gatacttatg acgctctcca catgcaagcc ctgccaccta ggtaa                   1425

<210> SEQ ID NO 214
<211> LENGTH: 474
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 214

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asp Lys Tyr
65                  70                  75                  80

Tyr Val Asp Ser Val Lys Gly Arg Phe Thr Ile Ser Arg Asp Asn Ser
                85                  90                  95

Lys Asn Arg Leu Tyr Leu Gln Met Asn Ser Leu Arg Ala Glu Asp Thr
            100                 105                 110

Ala Val Tyr Tyr Cys Ala Arg Glu Arg Tyr Ser Gly Arg Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Ile Val Met Thr Gln Ser
145                 150                 155                 160

Pro Ala Thr Leu Ser Val Ser Pro Gly Glu Arg Ala Thr Leu Ser Cys
                165                 170                 175

Arg Ala Ser Gln Ser Val Ser Ser Leu Leu Thr Trp Tyr Gln Gln Lys
            180                 185                 190

Pro Gly Gln Ala Pro Arg Leu Leu Ile Phe Gly Ala Ser Thr Arg Ala
        195                 200                 205

Thr Gly Ile Pro Ala Arg Phe Ser Gly Ser Gly Ser Gly Thr Gly Phe
    210                 215                 220

Thr Leu Thr Ile Ser Ser Leu Gln Ser Glu Asp Phe Ala Val Tyr Tyr
225                 230                 235                 240

Cys Gln Gln Tyr Asp Thr Trp Pro Phe Thr Phe Gly Pro Gly Thr Lys
                245                 250                 255

Val Asp Phe Lys Arg Ala Ala Ala Leu Asp Asn Glu Lys Ser Asn Gly
            260                 265                 270

Thr Ile Ile His Val Lys Gly Lys His Leu Cys Pro Ser Pro Leu Phe
```

```
                275                 280                 285
Pro Gly Pro Ser Lys Pro Phe Trp Val Leu Val Val Gly Gly Val
    290                 295                 300
Leu Ala Cys Tyr Ser Leu Leu Val Thr Val Ala Phe Ile Ile Phe Trp
305                 310                 315                 320
Val Arg Ser Lys Arg Ser Arg Leu Leu His Ser Asp Tyr Met Asn Met
                325                 330                 335
Thr Pro Arg Arg Pro Gly Pro Thr Arg Lys His Tyr Gln Pro Tyr Ala
            340                 345                 350
Pro Pro Arg Asp Phe Ala Ala Tyr Arg Ser Arg Val Lys Phe Ser Arg
            355                 360                 365
Ser Ala Asp Ala Pro Ala Tyr Gln Gln Gly Gln Asn Gln Leu Tyr Asn
        370                 375                 380
Glu Leu Asn Leu Gly Arg Arg Glu Glu Tyr Asp Val Leu Asp Lys Arg
385                 390                 395                 400
Arg Gly Arg Asp Pro Glu Met Gly Gly Lys Pro Arg Arg Lys Asn Pro
                405                 410                 415
Gln Glu Gly Leu Tyr Asn Glu Leu Gln Lys Asp Lys Met Ala Glu Ala
            420                 425                 430
Tyr Ser Glu Ile Gly Met Lys Gly Glu Arg Arg Arg Gly Lys Gly His
            435                 440                 445
Asp Gly Leu Tyr Gln Gly Leu Ser Thr Ala Thr Lys Asp Thr Tyr Asp
450                 455                 460
Ala Leu His Met Gln Ala Leu Pro Pro Arg
465                 470
```

<210> SEQ ID NO 215
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 215

```
caggtccagt tggtcgaaag tggcggtggt gtagtgcagc cgggccgcag tttgaggctt    60
tcctgtgcgg cttcaggctt tactttttcc agctatggaa tgcactgggt gcggcaggcc   120
cccggcaaag gacttgagtg ggtggccgtc atttcttatg acggatcaga taagtactac   180
gtggacagcg tcaagggcag attcaccatc tctaggggaca acagtaaaaa tagactctac   240
ctccagatga atagcctcag agctgaagac acggccgtct actattgtgc tcgggagcgg   300
tatagtggca gagactactg ggggcagggc acactcgtta cagtgagtag cggcggagga   360
gggagtgggg gcggtggctc cggtggagga ggttctgaga ttgttatgac ccagagtcct   420
gcgaccctct cagtcagccc cggggagcgc gcaactttgt cttgcagagc tagtcagtcc   480
gtgtcctctc ttctgacatg gtaccagcaa aagcccgggc aggctccgcg cctttttgatc   540
tttgggcttc aacaagagc cactgggatt cccgcacgat tctctggctc cgggagcggt   600
actggtttca ccctgacgat tagcagtctc cagagcgagg acttcgccgt atactactgc   660
cagcagtacg atacgtggcc attcactttt ggaccaggga ctaaagtgga ttttaagcgc   720
gccgccgctc tcgataacga aaagtcaaat ggcaccataa tccacgtcaa aggcaagcac   780
ctgtgccctt ccccgctctt ccccggaccc agtaaaccat ttgggtgcgc tggttgttgtg   840
```

```
gggggcgtgc tggcctgcta tagccttttg gtcactgtag ccttcattat tttttgggtc    900
agatccaaaa gaagccgcct gctccatagc gattacatga atatgactcc acgccgcct     960 ggccccacaa ggaaacacta ccagccttac gcaccaccta gagatttcgc tgcctatcgg   1020
agcagggtga agttttccag atctgcagat gcaccagcgt atcagcaggg ccagaaccaa   1080
ctgtataacg agctcaacct gggacgcagg gaagagtatg acgttttgga caagcgcaga   1140
ggacgggacc ctgagatggg tggcaaacca agacgaaaaa accccaggag ggtctctat    1200 aatgagctgc agaaggataa gatggctgaa gcctattctg aaataggcat gaaaggagag   1260
cggagaaggg gaaaagggca cgacggtttg taccagggac tcagcactgc tacgaaggat   1320
acttatgacg ctctccacat gcaagccctg ccacctagg                          1359
```

<210> SEQ ID NO 216
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 216

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Val Asp Ser Val
    50                  55                  60

Lys Gly Arg Phe Thr Ile Ser Arg Asp Asn Ser Lys Asn Arg Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Ser Gly Arg Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Met Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Ser Ser Leu Leu Thr Trp Tyr Gln Gln Lys Pro Gly Gln Ala Pro
                165                 170                 175

Arg Leu Leu Ile Phe Gly Ala Ser Thr Arg Ala Thr Gly Ile Pro Ala
            180                 185                 190

Arg Phe Ser Gly Ser Gly Ser Gly Thr Gly Phe Thr Leu Thr Ile Ser
        195                 200                 205

Ser Leu Gln Ser Glu Asp Phe Ala Val Tyr Tyr Cys Gln Gln Tyr Asp
    210                 215                 220

Thr Trp Pro Phe Thr Phe Gly Pro Gly Thr Lys Val Asp Phe Lys Arg
225                 230                 235                 240

Ala Ala Ala Leu Asp Asn Glu Lys Ser Asn Gly Thr Ile Ile His Val
                245                 250                 255

```
Lys Gly Lys His Leu Cys Pro Ser Pro Leu Phe Pro Gly Pro Ser Lys
            260                 265                 270

Pro Phe Trp Val Leu Val Val Val Gly Gly Val Leu Ala Cys Tyr Ser
        275                 280                 285

Leu Leu Val Thr Val Ala Phe Ile Ile Phe Trp Val Arg Ser Lys Arg
    290                 295                 300

Ser Arg Leu Leu His Ser Asp Tyr Met Asn Met Thr Pro Arg Arg Pro
305                 310                 315                 320

Gly Pro Thr Arg Lys His Tyr Gln Pro Tyr Ala Pro Pro Arg Asp Phe
                325                 330                 335

Ala Ala Tyr Arg Ser Arg Val Lys Phe Ser Arg Ser Ala Asp Ala Pro
            340                 345                 350

Ala Tyr Gln Gln Gly Gln Asn Gln Leu Tyr Asn Glu Leu Asn Leu Gly
        355                 360                 365

Arg Arg Glu Glu Tyr Asp Val Leu Asp Lys Arg Arg Gly Arg Asp Pro
    370                 375                 380

Glu Met Gly Gly Lys Pro Arg Arg Lys Asn Pro Gln Glu Gly Leu Tyr
385                 390                 395                 400

Asn Glu Leu Gln Lys Asp Lys Met Ala Glu Ala Tyr Ser Glu Ile Gly
                405                 410                 415

Met Lys Gly Glu Arg Arg Arg Gly Lys Gly His Asp Gly Leu Tyr Gln
            420                 425                 430

Gly Leu Ser Thr Ala Thr Lys Asp Thr Tyr Asp Ala Leu His Met Gln
        435                 440                 445

Ala Leu Pro Pro Arg
    450

<210> SEQ ID NO 217
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 217
atggcactcc ccgtaactgc tctgctgctg ccgttggcat tgctcctgca cgccgcacgc        60
ccgcaggtgc agctcgtgga gtctggcggc ggcgtggtcc agcccggccg gtccctgcgc       120
ctgtcctgcg ccgccagcgg gtttactttt cctcctacg gcatgcactg ggtgcgccag        180
gctcccggca agggcctcga gtgggtcgcc gtgatctcat acgatgggtc agacaaatac       240
tatgtcgatt ctgttaaagg gcggtttacc atttcaagag ataactctaa gaataggctg       300
tatttgcaga tgaacagcct gagggctgaa gataccgcag tgtactattg cgctagggag       360
cggtatagtg ccgcgattac tggggacag ggtacactgg tgaccgtgag ctctgggggt        420
ggcggaagcg ggggtggcgg aagcggcgga gggggtagtg aaattgtgat gacccagtct       480
ccggctacac tttcagtctc ccctggggag agagctacac tgtcatgcag agcgtcccag       540
tccgtctctt ctctccttac ctggtatcag cagaagcccg ccaggctcc tcgactgctg        600 atcttcggtg cctccacaag ggcgaccggg attccagccc gcttctcagg ttctggagc        660 ggaactggtt tcactttgac aatcagttca ctgcagtcag aggatttcgc cgtgtactac       720
tgccagcaat acgacacatg gccattcact ttcggacccg gtaccaaagt cgatttcaag       780
agagccgcgg ccatcgaggt tatgtaccca ccaccatatc tggacaatga aaaaagcaat       840
```

```
ggaaccatta tccatgtgaa gggtaaacac ctctgcccta gcccactttt ccctggccca    900
tcaaagccct tctgggtctt ggtggtcgtg gggggtgtgc tggcctgtta cagccttctg    960
gtgacggttg ctttcattat cttctgggtt agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tggcaaacca   1260
agacgaaaaa acccccagga gggtctctat aatgagctgc agaaggataa gatggctgaa   1320
gcctattctg aaataggcat gaaggagag cggagaaggg gaaaagggca cgacggtttg   1380
taccagggac tcagcactgc tacgaaggat acttatgacg ctctccacat gcaagccctg   1440
ccacctaggt aa                                                      1452
```

<210> SEQ ID NO 218
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 218

```
Met Ala Leu Pro Val Thr Ala Leu Leu Pro Leu Ala Leu Leu Leu
 1               5                  10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asp Lys Tyr
 65                  70                  75                  80

Tyr Val Asp Ser Val Lys Gly Arg Phe Thr Ile Ser Arg Asp Asn Ser
                    85                  90                  95

Lys Asn Arg Leu Tyr Leu Gln Met Asn Ser Leu Arg Ala Glu Asp Thr
                100                 105                 110

Ala Val Tyr Tyr Cys Ala Arg Glu Arg Tyr Ser Gly Arg Asp Tyr Trp
            115                 120                 125

Gly Gln Gly Thr Leu Val Thr Val Ser Ser Gly Gly Gly Gly Ser Gly
        130                 135                 140

Gly Gly Gly Ser Gly Gly Gly Gly Ser Glu Ile Val Met Thr Gln Ser
145                 150                 155                 160

Pro Ala Thr Leu Ser Val Ser Pro Gly Glu Arg Ala Thr Leu Ser Cys
                165                 170                 175

Arg Ala Ser Gln Ser Val Ser Ser Leu Leu Thr Trp Tyr Gln Gln Lys
            180                 185                 190

Pro Gly Gln Ala Pro Arg Leu Leu Ile Phe Gly Ala Ser Thr Arg Ala
        195                 200                 205

Thr Gly Ile Pro Ala Arg Phe Ser Gly Ser Gly Ser Gly Thr Gly Phe
    210                 215                 220

Thr Leu Thr Ile Ser Ser Leu Gln Ser Glu Asp Phe Ala Val Tyr Tyr
```

```
                225                 230                 235                 240
Cys Gln Gln Tyr Asp Thr Trp Pro Phe Thr Phe Gly Pro Gly Thr Lys
                    245                 250                 255
Val Asp Phe Lys Arg Ala Ala Ala Ile Glu Val Met Tyr Pro Pro Pro
                260                 265                 270
Tyr Leu Asp Asn Glu Lys Ser Asn Gly Thr Ile Ile His Val Lys Gly
                275                 280                 285
Lys His Leu Cys Pro Ser Pro Leu Phe Pro Gly Pro Ser Lys Pro Phe
            290                 295                 300
Trp Val Leu Val Val Val Gly Gly Val Leu Ala Cys Tyr Ser Leu Leu
305                 310                 315                 320
Val Thr Val Ala Phe Ile Ile Phe Trp Val Arg Ser Lys Arg Ser Arg
                    325                 330                 335
Leu Leu His Ser Asp Tyr Met Asn Met Thr Pro Arg Arg Pro Gly Pro
                340                 345                 350
Thr Arg Lys His Tyr Gln Pro Tyr Ala Pro Pro Arg Asp Phe Ala Ala
            355                 360                 365
Tyr Arg Ser Arg Val Lys Phe Ser Arg Ser Ala Asp Ala Pro Ala Tyr
        370                 375                 380
Gln Gln Gly Gln Asn Gln Leu Tyr Asn Glu Leu Asn Leu Gly Arg Arg
385                 390                 395                 400
Glu Glu Tyr Asp Val Leu Asp Lys Arg Arg Gly Arg Asp Pro Glu Met
                    405                 410                 415
Gly Gly Lys Pro Arg Arg Lys Asn Pro Gln Glu Gly Leu Tyr Asn Glu
                420                 425                 430
Leu Gln Lys Asp Lys Met Ala Glu Ala Tyr Ser Glu Ile Gly Met Lys
            435                 440                 445
Gly Glu Arg Arg Arg Gly Lys Gly His Asp Gly Leu Tyr Gln Gly Leu
        450                 455                 460
Ser Thr Ala Thr Lys Asp Thr Tyr Asp Ala Leu His Met Gln Ala Leu
465                 470                 475                 480
Pro Pro Arg

<210> SEQ ID NO 219
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 219
caggtgcagc tcgtggagtc tggcggcggc gtggtccagc ccggccggtc cctgcgcctg      60
tcctgcgccg ccagcgggtt tactttttcc tcctacggca tgcactgggt cgcccaggct     120
cccggcaagg gcctcgagtg gtcgccgtg atctcatacg atgggtcaga caaatactat     180
gtcgattctg ttaaagggcg gtttaccatt tcaagagata actctaagaa taggctgtat     240
ttgcagatga acagcctgag ggctgaagat accgcagtgt actattgcgc tagggagcgg     300
tatagtggcc gcgattactg gggacagggt acactggtga ccgtgagctc tggggggtggc     360 ggaagcgggg gtggcggaag cggcggaggg ggtagtgaaa ttgtgatgac ccagtctccg     420
gctacacttt cagtctcccc tgggagaga gctacactgt catgcagagc gtcccagtcc     480
gtctcttctc tccttacctg gtatcagcag aagcccggcc aggctcctcg actgctgatc     540
```

-continued

```
ttcggtgcct ccacaagggc gaccgggatt ccagcccgct tctcaggttc tgggagcgga    600
actggtttca ctttgacaat cagttcactg cagtcagagg atttcgccgt gtactactgc    660
cagcaatacg acacatggcc attcactttc ggacccggta ccaaagtcga tttcaagaga    720
gccgcggcca tcgaggttat gtacccacca ccatatctgg acaatgaaaa agcaatgga    780 accattatcc atgtgaaggg taaacacctc tgccctagcc cactttccc tggcccatca    840 aagcccttct gggtcttggt ggtcgtgggg ggtgtgctgg cctgttacag ccttctggtg    900
acggttgctt tcattatctt ctgggttaga tccaaaagaa gccgcctgct ccatagcgat    960
tacatgaata tgactccacg ccgccctggc cccacaagga acactacca gccttacgca    1020 ccacctagag atttcgctgc ctatcggagc agggtgaagt tttccagatc tgcagatgca    1080
ccagcgtatc agcagggcca gaaccaactg tataacgagc tcaacctggg acgcaggaa    1140 gagtatgacg tttggacaa gcgcagagga cgggaccctg agatgggtgg caaaccaaga    1200
cgaaaaaacc cccaggaggg tctctataat gagctgcaga aggataagat ggctgaagcc    1260
tattctgaaa taggcatgaa aggagagcgg agaagggaa aagggcacga cggtttgtac    1320
cagggactca gcactgctac gaaggatact tatgacgctc tccacatgca agccctgcca    1380
cctagg                                                                1386
```

<210> SEQ ID NO 220
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 220

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asp Lys Tyr Tyr Val Asp Ser Val
    50                  55                  60

Lys Gly Arg Phe Thr Ile Ser Arg Asp Asn Ser Lys Asn Arg Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Ser Gly Arg Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Glu Ile Val Met Thr Gln Ser Pro Ala Thr Leu Ser
    130                 135                 140

Val Ser Pro Gly Glu Arg Ala Thr Leu Ser Cys Arg Ala Ser Gln Ser
145                 150                 155                 160

Val Ser Ser Leu Leu Thr Trp Tyr Gln Gln Lys Pro Gly Gln Ala Pro
                165                 170                 175

Arg Leu Leu Ile Phe Gly Ala Ser Thr Arg Ala Thr Gly Ile Pro Ala
            180                 185                 190
```

Arg Phe Ser Gly Ser Gly Ser Gly Thr Gly Phe Thr Leu Thr Ile Ser
        195                 200                 205

Ser Leu Gln Ser Glu Asp Phe Ala Val Tyr Tyr Cys Gln Gln Tyr Asp
    210                 215                 220

Thr Trp Pro Phe Thr Phe Gly Pro Gly Thr Lys Val Asp Phe Lys Arg
225                 230                 235                 240

Ala Ala Ala Ile Glu Val Met Tyr Pro Pro Pro Tyr Leu Asp Asn Glu
                245                 250                 255

Lys Ser Asn Gly Thr Ile Ile His Val Lys Gly Lys His Leu Cys Pro
                260                 265                 270

Ser Pro Leu Phe Pro Gly Pro Ser Lys Pro Phe Trp Val Leu Val Val
            275                 280                 285

Val Gly Gly Val Leu Ala Cys Tyr Ser Leu Leu Val Thr Val Ala Phe
        290                 295                 300

Ile Ile Phe Trp Val Arg Ser Lys Arg Ser Arg Leu Leu His Ser Asp
305                 310                 315                 320

Tyr Met Asn Met Thr Pro Arg Arg Pro Gly Pro Thr Arg Lys His Tyr
                325                 330                 335

Gln Pro Tyr Ala Pro Pro Arg Asp Phe Ala Ala Tyr Arg Ser Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 221
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 221
atggcactcc ccgtaactgc tctgctgctg ccgttggcat tgctcctgca cgccgcacgc    60
ccgcaggtgc agttggttga atcaggaggg ggtgtggtgc aacccggtcg gtcactgcgc   120
ctcagttgtg ctgcttccgg gtttactttc agctcatatg ggatgcactg ggtacggcag   180
gctccaggta aaggcttgga atgggtggcg gtgatcagct atgacggctc tgacaaatat   240
tatgtggact ccgtgaaagg cagattcacc atcagtcgag acaactcaaa gaatagactc   300
tacttgcaga tgaatagcct ccgggccgaa gatactgcag tctattattg cgcccgggag   360
cgctacagtg gaagagacta ttgggggcaa ggaactcttg tcacagtctc atctggcggc   420

-continued

```
ggcggcagcg gtgggggcgg atctggcggg ggcggcagcg aaatcgttat gactcagagt    480
cctgccacac tgagcgttag ccctggtgag agagcaacac ttagctgcag agctagtcag    540
agtgttttcca gtcttttgac atggtaccaa cagaagcccg gtcaagctcc acgactgctc    600
atcttcggtg catccacccg cgcaaccggg atacccgccc ggttttccgg ttctggaagt    660
ggcacaggat tcacgctcac catttcttct ctgcagtctg aagactttgc cgtgtattac    720
tgccagcagt acgatacctg ccctttacc tttggcccag gtactaaagt ggattttaaa    780
cgagctgctg cactttccaa tagtattatg tacttttcac attttgtgcc cgtgttcctg    840
cctgcgaagc ctacgacaac cccagcccct aggccgccca ccggccccca aactattgcc    900
tcccagccat tgtctctgag acccgaagct tgcagacctg ctgctggagg cgccgttcac    960
acccgaggat tggatttcgc atgtgacatt tacatctggg cccctttggc cggaaccctgc   1020
ggtgtgctgc tgctgtcact cgtgattaca ctttactgca accaccgaaa cagatccaaa   1080
agaagccgcc tgctccatag cgattacatg aatatgactc cacgccgccc tggccccaca   1140
aggaaacact accagcctta cgcaccacct agagatttcg ctgcctatcg gagcagggtg   1200
aagtttttcca gatctgcaga tgcaccagcg tatcagcagg gccagaacca actgtataac   1260
gagctcaacc tgggacgcag ggaagagtat gacgttttgg acaagcgcag aggacgggac   1320
cctgagatgg gtggcaaacc aagacgaaaa aacccccagg agggtctcta taatgagctg   1380
cagaaggata agatggctga agcctattct gaaataggca tgaaggaga gcggagaagg   1440
ggaaaagggc acgacggttt gtaccaggga ctcagcactg ctacgaagga tacttatgac   1500
gctctccaca tgcaagccct gccacctagg taa                                 1533
```

<210> SEQ ID NO 222
<211> LENGTH: 510
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: anti-CLL-1 CAR construct

<400> SEQUENCE: 222

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
        50                  55                  60

Gly Leu Glu Trp Val Ala Val Ile Ser Tyr Asp Gly Ser Asp Lys Tyr
65                  70                  75                  80

Tyr Val Asp Ser Val Lys Gly Arg Phe Thr Ile Ser Arg Asp Asn Ser
                85                  90                  95

Lys Asn Arg Leu Tyr Leu Gln Met Asn Ser Leu Arg Ala Glu Asp Thr
            100                 105                 110

Ala Val Tyr Tyr Cys Ala Arg Glu Arg Tyr Ser Gly Arg Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Ile Val Met Thr Gln Ser

```
            145                 150                 155                 160
Pro Ala Thr Leu Ser Val Ser Pro Gly Glu Arg Ala Thr Leu Ser Cys
                165                 170                 175

Arg Ala Ser Gln Ser Val Ser Ser Leu Leu Thr Trp Tyr Gln Gln Lys
                180                 185                 190

Pro Gly Gln Ala Pro Arg Leu Leu Ile Phe Gly Ala Ser Thr Arg Ala
                195                 200                 205

Thr Gly Ile Pro Ala Arg Phe Ser Gly Ser Gly Thr Gly Phe
210                 215                 220

Thr Leu Thr Ile Ser Ser Leu Gln Ser Glu Asp Phe Ala Val Tyr Tyr
225                 230                 235                 240

Cys Gln Gln Tyr Asp Thr Trp Pro Phe Thr Phe Gly Pro Gly Thr Lys
                245                 250                 255

Val Asp Phe Lys Arg Ala Ala Ala Leu Ser Asn Ser Ile Met Tyr Phe
                260                 265                 270

Ser His Phe Val Pro Val Phe Leu Pro Ala Lys Pro Thr Thr Thr Pro
                275                 280                 285

Ala Pro Arg Pro Pro Thr Pro Ala Pro Thr Ile Ala Ser Gln Pro Leu
                290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
                340                 345                 350

Cys Asn His Arg Asn Arg Ser Lys Arg Ser Arg Leu Leu His Ser Asp
                355                 360                 365

Tyr Met Asn Met Thr Pro Arg Arg Pro Gly Pro Thr Arg Lys His Tyr
                370                 375                 380

Gln Pro Tyr Ala Pro Pro Arg Asp Phe Ala Ala Tyr Arg Ser Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
                435                 440                 445

Arg Lys Asn Pro Gln Glu Gly Leu Tyr Asn Glu Leu Gln Lys Asp Lys
                450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 223
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct
```

<400> SEQUENCE: 223

```
caggtgcagt tggttgaatc aggagggggt gtggtgcaac ccggtcggtc actgcgcctc      60
agttgtgctg cttccgggtt tactttcagc tcatatggga tgcactgggt acggcaggct     120
ccaggtaaag gcttggaatg ggtggcggtg atcagctatg acggctctga caaatattat     180
gtggactccg tgaaaggcag attcaccatc agtcgagaca actcaaagaa tagactctac     240
ttgcagatga atagcctccg ggccgaagat actgcagtct attattgcgc ccgggagcgc     300
tacagtggaa gagactattg ggggcaagga actcttgtca cagtctcatc tggcggcggc     360
ggcagcggtg ggggcggatc tggcgggggc ggcagcgaaa tcgttatgac tcagagtcct     420
gccacactga gcgttagccc tggtgagaga gcaacactta gctgcagagc tagtcagagt     480
gtttccagtc ttttgacatg gtaccaacag aagcccggtc aagctccacg actgctcatc     540
ttcggtgcat ccacccgcgc aaccgggata cccgccggt tttccggttc tggaagtggc     600
acaggattca cgctcaccat ttcttctctg cagtctgaag actttgccgt gtattactgc     660
cagcagtacg ataccctggcc ctttaccttt ggcccaggta ctaaagtgga ttttaaacga     720
gctgctgcac tttccaatag tattatgtac ttttcacatt ttgtgcccgt gttcctgcct     780
gcgaagccta cgacaacccc agcccctagg ccgcccacac cggccccaac tattgcctcc     840
cagccattgt ctctgagacc cgaagcttgc agacctgctg ctggaggcgc cgttcacacc     900
cgaggattgg atttcgcatg tgacatttac atctgggccc cttggccgg aacctgcggt     960
gtgctgctgc tgtcactcgt gattacactt tactgcaacc accgaaacag atccaaaaga    1020
agccgcctgc tccatagcga ttacatgaat atgactccac gccgcctgg ccccacaagg    1080
aaacactacc agccttacgc accacctaga gatttcgctg cctatcggag cagggtgaag    1140
ttttccagat ctgcagatgc accagcgtat cagcagggcc agaaccaact gtataacgag    1200
ctcaacctgg gacgcaggga gagtatgac gttttggaca gcgcagagg acgggaccct    1260
gagatgggtg gcaaaccaag acgaaaaaac ccccaggagg gtctctataa tgagctgcag    1320
aaggataaga tggctgaagc ctattctgaa ataggcatga aggagagcg gagaagggga    1380
aaagggcacg acggtttgta ccagggactc agcactgcta cgaaggatac ttatgacgct    1440
ctccacatgc aagccctgcc acctagg                                        1467
```

<210> SEQ ID NO 224
<211> LENGTH: 489
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 224

```
Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asp Lys Tyr Tyr Val Asp Ser Val
     50                  55                  60

Lys Gly Arg Phe Thr Ile Ser Arg Asp Asn Ser Lys Asn Arg Leu Tyr
 65                  70                  75                  80
```

```
Leu Gln Met Asn Ser Leu Arg Ala Glu Asp Thr Ala Val Tyr Tyr Cys
                85                  90                  95

Ala Arg Glu Arg Tyr Ser Gly Arg Asp Tyr Trp Gly Gln Gly Thr Leu
            100                 105                 110

Val Thr Val Ser Ser Gly Gly Gly Ser Gly Gly Gly Ser Gly
            115                 120                 125

Gly Gly Gly Ser Glu Ile Val Met Thr Gln Ser Pro Ala Thr Leu Ser
        130                 135                 140

Val Ser Pro Gly Glu Arg Ala Thr Leu Ser Cys Arg Ala Ser Gln Ser
145                 150                 155                 160

Val Ser Ser Leu Leu Thr Trp Tyr Gln Gln Lys Pro Gly Gln Ala Pro
                165                 170                 175

Arg Leu Leu Ile Phe Gly Ala Ser Thr Arg Ala Thr Gly Ile Pro Ala
            180                 185                 190

Arg Phe Ser Gly Ser Gly Ser Gly Thr Gly Phe Thr Leu Thr Ile Ser
        195                 200                 205

Ser Leu Gln Ser Glu Asp Phe Ala Val Tyr Tyr Cys Gln Gln Tyr Asp
    210                 215                 220

Thr Trp Pro Phe Thr Phe Gly Pro Gly Thr Lys Val Asp Phe Lys Arg
225                 230                 235                 240

Ala Ala Ala Leu Ser Asn Ser Ile Met Tyr Phe Ser His Phe Val Pro
                245                 250                 255

Val Phe Leu Pro Ala Lys Pro Thr Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Asn His Arg Asn
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 225
<211> LENGTH: 1425
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: anti-CLL-1 CAR construct

<400> SEQUENCE: 225

```
atggcactcc ccgtaactgc tctgctgctg ccgttggcat tgctcctgca cgccgcacgc      60
ccggagattg tgatgaccca gtcccctgct accctgtccg tcagtccggg cgagagagcc     120
accttgtcat gccgggccag ccagtccgtc agcagtctcc tgacttggta tcagcaaaaa     180
ccagggcagg caccgcggct tttgattttt ggtgcaagca cacgcgccac tggcattcca     240
gctaggtttt ctggaagtgg atctgggaca ggcttcactc tgacaatcag tagcctgcag     300
agtgaggact ttgctgttta ctactgtcaa cagtacgaca cctggccatt cacattcggg     360
cccggcacca aggtcgactt caagaggggc ggtggaggtt caggtggtgg cgggtcaggc     420
ggcggtgggt ctcaggttca actggtggaa tcaggtggcg gcgttgtcca accggggcga     480
tcacttcgac tttcctgtgc tgcctcaggc tttacttttt catcctatgg gatgcactgg     540
gttcggcagg ctcccggaaa aggactcgag tgggttgcag tgatctctta cgatggctca     600
gacaagtatt atgtggactc agtcaagggg agattcacaa taagccgaga caactccaaa     660
aaccggcttt atctccagat gaacagcctt agagcggaag ataccgcggt atactactgt     720
gcccgcgaga ggtattccgg cagagactac tggggacagg gcacactggt caccgtgagt     780
tctgccgcag cgctcgataa cgaaaagagc aacggaacca ttatccacgt taagggcaag     840
cacctgtgcc ccagtcccct cttcccagga ccatctaaac ccttctgggt tctggtagta     900
gttggagggg tccttgcatg ttactcccct ttggtcaccg tcgccttcat tatttctgg     960
gtgagatcca aaagaagccg cctgctccat agcgattaca tgaatatgac tccacgccgc    1020
cctggcccca aaggaaaaca ctaccagcct tacgcaccac ctagagattt cgctgcctat    1080
cggagcaggg tgaagttttc cagatctgca gatgcaccag cgtatcagca gggccagaac    1140
caactgtata acgagctcaa cctgggacgc agggaagagt atgacgtttt ggacaagcgc    1200
agaggacggg accctgagat gggtggcaaa ccaagacgaa aaaccccca ggagggtctc    1260
tataatgagc tgcagaagga taagatggct gaagcctatt ctgaaatagg catgaaagga    1320
gagcggagaa ggggaaaagg gcacgacggt ttgtaccagg gactcagcac tgctacgaag    1380
gatacttatg acgctctcca catgcaagcc ctgccaccta ggtaa                   1425
```

<210> SEQ ID NO 226
<211> LENGTH: 474
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 226

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

-continued

Ser Val Ser Pro Gly Glu Arg Ala Thr Leu Ser Cys Arg Ala Ser Gln
            35                  40                  45

Ser Val Ser Ser Leu Leu Thr Trp Tyr Gln Gln Lys Pro Gly Gln Ala
 50                  55                  60

Pro Arg Leu Leu Ile Phe Gly Ala Ser Thr Arg Ala Thr Gly Ile Pro
 65                  70                  75                  80

Ala Arg Phe Ser Gly Ser Gly Ser Gly Thr Gly Phe Thr Leu Thr Ile
                85                  90                  95

Ser Ser Leu Gln Ser Glu Asp Phe Ala Val Tyr Tyr Cys Gln Gln Tyr
                100                 105                 110

Asp Thr Trp Pro Phe Thr Phe Gly Pro Gly Thr Lys Val Asp Phe Lys
            115                 120                 125

Arg Gly Gly Gly Gly Ser Gly Gly Gly Gly Ser Gly Gly Gly Gly Ser
130                 135                 140

Gln Val Gln Leu Val Glu Ser Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Gly Met His Trp Val Arg Gln Ala Pro Gly Lys Gly Leu Glu Trp Val
            180                 185                 190

Ala Val Ile Ser Tyr Asp Gly Ser Asp Lys Tyr Tyr Val Asp Ser Val
            195                 200                 205

Lys Gly Arg Phe Thr Ile Ser Arg Asp Asn Ser Lys Asn Arg Leu Tyr
            210                 215                 220

Leu Gln Met Asn Ser Leu Arg Ala Glu Asp Thr Ala Val Tyr Tyr Cys
225                 230                 235                 240

Ala Arg Glu Arg Tyr Ser Gly Arg Asp Tyr Trp Gly Gln Gly Thr Leu
                245                 250                 255

Val Thr Val Ser Ser Ala Ala Ala Leu Asp Asn Glu Lys Ser Asn Gly
            260                 265                 270

Thr Ile Ile His Val Lys Gly Lys His Leu Cys Pro Ser Pro Leu Phe
            275                 280                 285

Pro Gly Pro Ser Lys Pro Phe Trp Val Leu Val Val Val Gly Gly Val
        290                 295                 300

Leu Ala Cys Tyr Ser Leu Leu Val Thr Val Ala Phe Ile Ile Phe Trp
305                 310                 315                 320

Val Arg Ser Lys Arg Ser Arg Leu Leu His Ser Asp Tyr Met Asn Met
                325                 330                 335

Thr Pro Arg Arg Pro Gly Pro Thr Arg Lys His Tyr Gln Pro Tyr Ala
            340                 345                 350

Pro Pro Arg Asp Phe Ala Ala Tyr Arg Ser Arg Val Lys Phe Ser Arg
            355                 360                 365

Ser Ala Asp Ala Pro Ala Tyr Gln Gln Gly Gln Asn Gln Leu Tyr Asn
        370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
            435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
465                 470

<210> SEQ ID NO 227
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 227
gagattgtga tgacccagtc ccctgctacc ctgtccgtca gtccgggcga gagagccacc      60
ttgtcatgcc gggccagcca gtccgtcagc agtctcctga cttggtatca gcaaaaacca     120
gggcaggcac cgcggctttt gattttggt gcaagcacac gcgccactgg cattccagct      180
aggttttctg gaagtggatc tgggacaggc ttcactctga caatcagtag cctgcagagt     240
gaggactttg ctgtttacta ctgtcaacag tacgacacct ggccattcac attcgggccc     300
ggcaccaagg tcgacttcaa gaggggcggt ggaggttcag gtggtggcgg tcaggcggc      360 ggtgggtctc aggttcaact ggtggaatca ggtggcggcg ttgtccaacc ggggcgatca     420
cttcgacttt cctgtgctgc ctcaggcttt acttttttcat cctatgggat gcactgggtt    480
cggcaggctc ccggaaaagg actcgagtgg gttgcagtga tctcttacga tggctcagac    540
aagtattatg tggactcagt caaggggaga ttcacaataa gccgagacaa ctccaaaaac    600
cggctttatc tccagatgaa cagccttaga gcggaagata ccgcggtata ctactgtgcc    660
cgcgagaggt attccggcag agactactgg ggacagggca cactggtcac cgtgagttct    720
gccgcagcgc tcgataacga aaagagcaac ggaaccatta ccacgttaa gggcaagcac     780 ctgtgcccca gtccctcttt cccaggacca tctaaaccct ctgggttct ggtagtagtt     840 ggagggtcc ttgcatgtta ctccccttttg gtcaccgtcg ccttcattat tttctgggtg    900
agatccaaaa gaagccgcct gctccatagc gattacatga atatgactcc acgccgccct    960
ggccccacaa ggaaacacta ccagccttac gcaccaccta gagatttcgc tgcctatcgg   1020
agcagggtga gttttccag atctgcagat gcaccagcgt atcagcaggg ccagaaccaa    1080
ctgtataacg agctcaacct gggacgcagg aagagtatg acgttttgga caagcgcaga    1140
ggacgggacc ctgagatggg tggcaaacca agacgaaaaa accccagga gggtctctat    1200 aatgagctgc agaaggataa gatggctgaa gcctattctg aaataggcat gaaaggagag   1260
cggagaaggg gaaaagggca cgacggttg taccagggac tcagcactgc tacgaaggat    1320
acttatgacg ctctccacat gcaagccctg ccacctagg                          1359

<210> SEQ ID NO 228
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 228

Glu Ile Val Met Thr Gln Ser Pro Ala Thr Leu Ser Val Ser Pro Gly

-continued

```
1               5                   10                  15
Glu Arg Ala Thr Leu Ser Cys Arg Ala Ser Gln Ser Val Ser Ser Leu
             20                  25                  30
Leu Thr Trp Tyr Gln Gln Lys Pro Gly Gln Ala Pro Arg Leu Leu Ile
             35                  40                  45
Phe Gly Ala Ser Thr Arg Ala Thr Gly Ile Pro Ala Arg Phe Ser Gly
             50                  55                  60
Ser Gly Ser Gly Thr Gly Phe Thr Leu Thr Ile Ser Ser Leu Gln Ser
65                  70                  75                  80
Glu Asp Phe Ala Val Tyr Tyr Cys Gln Gln Tyr Asp Thr Trp Pro Phe
                 85                  90                  95
Thr Phe Gly Pro Gly Thr Lys Val Asp Phe Lys Arg Gly Gly Gly Gly
                 100                 105                 110
Ser Gly Gly Gly Gly Ser Gly Gly Gly Ser Gln Val Gln Leu Val
             115                 120                 125
Glu Ser Gly Gly Gly Val Val Gln Pro Gly Arg Ser Leu Arg Leu Ser
             130                 135                 140
Cys Ala Ala Ser Gly Phe Thr Phe Ser Ser Tyr Gly Met His Trp Val
145                 150                 155                 160
Arg Gln Ala Pro Gly Lys Gly Leu Glu Trp Val Ala Val Ile Ser Tyr
                 165                 170                 175
Asp Gly Ser Asp Lys Tyr Tyr Val Asp Ser Val Lys Gly Arg Phe Thr
                 180                 185                 190
Ile Ser Arg Asp Asn Ser Lys Asn Arg Leu Tyr Leu Gln Met Asn Ser
             195                 200                 205
Leu Arg Ala Glu Asp Thr Ala Val Tyr Tyr Cys Ala Arg Glu Arg Tyr
             210                 215                 220
Ser Gly Arg Asp Tyr Trp Gly Gln Gly Thr Leu Val Thr Val Ser Ser
225                 230                 235                 240
Ala Ala Ala Leu Asp Asn Glu Lys Ser Asn Gly Thr Ile Ile His Val
                 245                 250                 255
Lys Gly Lys His Leu Cys Pro Ser Pro Leu Phe Pro Gly Pro Ser Lys
                 260                 265                 270
Pro Phe Trp Val Leu Val Val Val Gly Gly Val Leu Ala Cys Tyr Ser
                 275                 280                 285
Leu Leu Val Thr Val Ala Phe Ile Ile Phe Trp Val Arg Ser Lys Arg
             290                 295                 300
Ser Arg Leu Leu His Ser Asp Tyr Met Asn Met Thr Pro Arg Arg Pro
305                 310                 315                 320
Gly Pro Thr Arg Lys His Tyr Gln Pro Tyr Ala Pro Pro Arg Asp Phe
                 325                 330                 335
Ala Ala Tyr Arg Ser Arg Val Lys Phe Ser Arg Ser Ala Asp Ala Pro
                 340                 345                 350
Ala Tyr Gln Gln Gly Gln Asn Gln Leu Tyr Asn Glu Leu Asn Leu Gly
                 355                 360                 365
Arg Arg Glu Glu Tyr Asp Val Leu Asp Lys Arg Arg Gly Arg Asp Pro
             370                 375                 380
Glu Met Gly Gly Lys Pro Arg Arg Lys Asn Pro Gln Glu Gly Leu Tyr
385                 390                 395                 400
Asn Glu Leu Gln Lys Asp Lys Met Ala Glu Ala Tyr Ser Glu Ile Gly
                 405                 410                 415
Met Lys Gly Glu Arg Arg Arg Gly Lys Gly His Asp Gly Leu Tyr Gln
             420                 425                 430
```

Gly Leu Ser Thr Ala Thr Lys Asp Thr Tyr Asp Ala Leu His Met Gln
        435                 440                 445

Ala Leu Pro Pro Arg
    450

<210> SEQ ID NO 229
<211> LENGTH: 1452
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 229
atggcactcc ccgtaactgc tctgctgctg ccgttggcat tgctcctgca cgccgcacgc      60
ccggagatcg tcatgacaca gagtccagct accctgagcg tgtccctgg agagagagcc     120
accctgtcct gtagggctag tcagagtgtg tccagcctcc tcacctggta tcaacagaag    180
cctggtcaag ctccccggct gcttatcttc ggggccagca cgcgagccac aggcatcccg    240
gccagattct ctggctctgg cagtggcacc gggttcactc tcacgatctc atccctgcag    300
tcagaggatt tcgctgtgta ttactgtcag cagtacgata catggccctt caccttcggc    360
ccgggcacaa agtagattt caagcgcggc ggcgggggta gtggggggcgg gggatcagga    420
ggagggggct cccaagtaca gctggttgag agcggcggcg gggtggttca gcccgggcgc    480
agcctcaggc tgagttgcgc agcatcagga ttcacattca gttcttatgg aatgcattgg    540
gtcagacagg ctcccgggaa gggccttgaa tgggtggcag tcattagcta cgacggaagc    600
gataagtact atgtggactc agttaaaggg agatttacta tcagccgcga caattccaaa    660
aacagattgt attgcagat gaactccctc agggcggagg acactgctgt atattactgc    720
gcacgagaga gatactccgg ccgagactat tgggccaag gaacattggt aactgtgagc    780
tccgccgcag ctattgaggt catgtacccc ccaccttatc tcgataatga aagagtaat    840
gggactataa ttcacgtaaa gggcaaacac ctgtgcccct ccccgctgtt ccaggtcca    900
agtaagccgt tctgggtcct ggttgtggtg ggaggggtgc tggcctgcta ttctctgttg    960
gttaccgtgg cctttatcat tttctgggtg agatccaaaa gaagccgcct gctccatagc   1020
gattacatga atatgactcc acgccgccct ggccccacaa ggaaacacta ccagccttac   1080
gcaccaccta gagatttcgc tgcctatcgg agcagggtga agttttccag atctgcagat   1140
gcaccagcgt atcagcaggg ccagaaccaa ctgtataacg agctcaacct gggacgcagg   1200
gaagagtatg acgttttgga caagcgcaga ggacgggacc ctgagatggg tgcaaaacca   1260
agacgaaaaa accccagga gggtctctat aatgagctgc agaaggataa gatggctgaa   1320
gcctattctg aaataggcat gaaaggagag cggagaaggg gaaaagggca cgacggtttg   1380
taccagggac tcagcactgc tacgaaggat acttatgacg ctctccacat gcaagccctg   1440
ccacctaggt aa                                                       1452

<210> SEQ ID NO 230
<211> LENGTH: 483
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: anti-CLL-1 CAR construct

<400> SEQUENCE: 230

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Leu Leu Thr Trp Tyr Gln Gln Lys Pro Gly Gln Ala
    50                  55                  60

Pro Arg Leu Leu Ile Phe Gly Ala Ser Thr Arg Ala Thr Gly Ile Pro
65                  70                  75                  80

Ala Arg Phe Ser Gly Ser Gly Ser Gly Thr Gly Phe Thr Leu Thr Ile
                85                  90                  95

Ser Ser Leu Gln Ser Glu Asp Phe Ala Val Tyr Tyr Cys Gln Gln Tyr
            100                 105                 110

Asp Thr Trp Pro Phe Thr Phe Gly Pro Gly Thr Lys Val Asp Phe Lys
        115                 120                 125

Arg Gly Gly Gly Gly Ser Gly Gly Gly Ser Gly Gly Gly Gly Ser
    130                 135                 140

Gln Val Gln Leu Val Glu Ser Gly Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Gly Met His Trp Val Arg Gln Ala Pro Gly Lys Gly Leu Glu Trp Val
            180                 185                 190

Ala Val Ile Ser Tyr Asp Gly Ser Asp Lys Tyr Tyr Val Asp Ser Val
        195                 200                 205

Lys Gly Arg Phe Thr Ile Ser Arg Asp Asn Ser Lys Asn Arg Leu Tyr
    210                 215                 220

Leu Gln Met Asn Ser Leu Arg Ala Glu Asp Thr Ala Val Tyr Tyr Cys
225                 230                 235                 240

Ala Arg Glu Arg Tyr Ser Gly Arg Asp Tyr Trp Gly Gln Gly Thr Leu
                245                 250                 255

Val Thr Val Ser Ser Ala Ala Ile Glu Val Met Tyr Pro Pro Pro
            260                 265                 270

Tyr Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365

Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400
```

```
Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
        420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 231
<211> LENGTH: 1386
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 231
gagatcgtca tgacacagag tccagctacc ctgagcgtgt ccctggaga gagagccacc        60 ctgtcctgta gggctagtca gagtgtgtcc agcctcctca cctggtatca acagaagcct      120
ggtcaagctc cccggctgct tatcttcggg gccagcacgc gagccacagg catcccggcc      180
agattctctg gctctggcag tggcaccggg ttcactctca cgatctcatc cctgcagtca      240
gaggatttcg ctgtgtatta ctgtcagcag tacgatacat ggcccttcac cttcggcccg      300
ggcacaaaag tagatttcaa gcgcggcggc ggggtagtg gggcggggg atcaggagga       360 ggggctccc aagtacagct ggttgagagc ggcggcgggg tggttcagcc cgggcgcagc      420
ctcaggctga gttgcgcagc atcaggattc acattcagtt cttatggaat gcattgggtc      480
agacaggctc ccgggaaggg ccttgaatgg gtggcagtca ttagctacga cggaagcgat      540
aagtactatg tggactcagt taaagggaga tttactatca ccgcgacaa ttccaaaaac      600 agattgtatt tgcagatgaa ctccctcagg gcggaggaca ctgctgtata ttactgcgca      660
cgagagagat actccggccg agactattgg ggccaaggaa cattggtaac tgtgagctcc      720
gccgcagcta ttgaggtcat gtacccccca cccttatctcg ataatgagaa gagtaatggg      780
actataattc acgtaaaggg caaacacctg tgcccttcc cgctgtttcc aggtccaagt      840
aagccgttct gggtcctggt tgtggtggga gggtgctgg cctgctattc tctgttggtt      900
accgtggcct ttatcatttt ctgggtgaga tccaaaagaa gccgcctgct ccatagcgat      960
tacatgaata tgactccacg ccgccctggc cccacaagga aacactacca gccttacgca     1020
ccacctagag atttcgctgc ctatcggagc agggtgaagt tttccagatc tgcagatgca     1080
ccagcgtatc agcagggcca gaaccaactg tataacgagc tcaacctggg acgcagggaa     1140
gagtatgacg tttggacaa cgcagagga cgggaccctg agatgggtgg caaaccaaga     1200
cgaaaaaacc cccaggaggg tctctataat gagctgcaga aggataagat ggctgaagcc     1260
tattctgaaa taggcatgaa aggagagcgg agaagggaa aagggcacga cggtttgtac     1320
cagggactca gcactgctac gaaggatact tatgacgctc tccacatgca agccctgcca     1380
cctagg                                                              1386
```

```
<210> SEQ ID NO 232
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: anti-CLL-1 CAR construct

<400> SEQUENCE: 232
```

| | | | | | | | | | | | | | | | |
|---|---|---|---|---|---|---|---|---|---|---|---|---|---|---|---|
| Glu | Ile | Val | Met | Thr | Gln | Ser | Pro | Ala | Thr | Leu | Ser | Val | Ser | Pro | Gly |
| 1 | | | | 5 | | | | | 10 | | | | | 15 | |
| Glu | Arg | Ala | Thr | Leu | Ser | Cys | Arg | Ala | Ser | Gln | Ser | Val | Ser | Ser | Leu |
| | | | 20 | | | | | 25 | | | | | 30 | | |
| Leu | Thr | Trp | Tyr | Gln | Gln | Lys | Pro | Gly | Gln | Ala | Pro | Arg | Leu | Leu | Ile |
| | | | 35 | | | | | 40 | | | | | 45 | | |
| Phe | Gly | Ala | Ser | Thr | Arg | Ala | Thr | Gly | Ile | Pro | Ala | Arg | Phe | Ser | Gly |
| | | 50 | | | | | 55 | | | | | 60 | | | |
| Ser | Gly | Ser | Gly | Thr | Gly | Phe | Thr | Leu | Thr | Ile | Ser | Ser | Leu | Gln | Ser |
| 65 | | | | | 70 | | | | | 75 | | | | | 80 |
| Glu | Asp | Phe | Ala | Val | Tyr | Tyr | Cys | Gln | Gln | Tyr | Asp | Thr | Trp | Pro | Phe |
| | | | | 85 | | | | | 90 | | | | | 95 | |
| Thr | Phe | Gly | Pro | Gly | Thr | Lys | Val | Asp | Phe | Lys | Arg | Gly | Gly | Gly | Gly |
| | | | | 100 | | | | | 105 | | | | | 110 | |
| Ser | Gly | Gly | Gly | Gly | Ser | Gly | Gly | Gly | Ser | Gln | Val | Gln | Leu | Val |
| | | | 115 | | | | | 120 | | | | | 125 | | |
| Glu | Ser | Gly | Gly | Gly | Val | Val | Gln | Pro | Gly | Arg | Ser | Leu | Arg | Leu | Ser |
| | | 130 | | | | | 135 | | | | | 140 | | | |
| Cys | Ala | Ala | Ser | Gly | Phe | Thr | Phe | Ser | Ser | Tyr | Gly | Met | His | Trp | Val |
| 145 | | | | | 150 | | | | | 155 | | | | | 160 |
| Arg | Gln | Ala | Pro | Gly | Lys | Gly | Leu | Glu | Trp | Val | Ala | Val | Ile | Ser | Tyr |
| | | | | 165 | | | | | 170 | | | | | 175 | |
| Asp | Gly | Ser | Asp | Lys | Tyr | Tyr | Val | Asp | Ser | Val | Lys | Gly | Arg | Phe | Thr |
| | | | 180 | | | | | 185 | | | | | 190 | | |
| Ile | Ser | Arg | Asp | Asn | Ser | Lys | Asn | Arg | Leu | Tyr | Leu | Gln | Met | Asn | Ser |
| | | 195 | | | | | 200 | | | | | 205 | | | |
| Leu | Arg | Ala | Glu | Asp | Thr | Ala | Val | Tyr | Tyr | Cys | Ala | Arg | Glu | Arg | Tyr |
| | 210 | | | | | 215 | | | | | 220 | | | | |
| Ser | Gly | Arg | Asp | Tyr | Trp | Gly | Gln | Gly | Thr | Leu | Val | Thr | Val | Ser | Ser |
| 225 | | | | | 230 | | | | | 235 | | | | | 240 |
| Ala | Ala | Ala | Ile | Glu | Val | Met | Tyr | Pro | Pro | Pro | Tyr | Leu | Asp | Asn | Glu |
| | | | | 245 | | | | | 250 | | | | | 255 | |
| Lys | Ser | Asn | Gly | Thr | Ile | Ile | His | Val | Lys | Gly | Lys | His | Leu | Cys | Pro |
| | | | 260 | | | | | 265 | | | | | 270 | | |
| Ser | Pro | Leu | Phe | Pro | Gly | Pro | Ser | Lys | Pro | Phe | Trp | Val | Leu | Val | Val |
| | | 275 | | | | | 280 | | | | | 285 | | | |
| Val | Gly | Gly | Val | Leu | Ala | Cys | Tyr | Ser | Leu | Leu | Val | Thr | Val | Ala | Phe |
| | 290 | | | | | 295 | | | | | 300 | | | | |
| Ile | Ile | Phe | Trp | Val | Arg | Ser | Lys | Arg | Ser | Arg | Leu | Leu | His | Ser | Asp |
| 305 | | | | | 310 | | | | | 315 | | | | | 320 |
| Tyr | Met | Asn | Met | Thr | Pro | Arg | Arg | Pro | Gly | Pro | Thr | Arg | Lys | His | Tyr |
| | | | | 325 | | | | | 330 | | | | | 335 | |
| Gln | Pro | Tyr | Ala | Pro | Pro | Arg | Asp | Phe | Ala | Ala | Tyr | Arg | Ser | Arg | Val |
| | | | 340 | | | | | 345 | | | | | 350 | | |
| Lys | Phe | Ser | Arg | Ser | Ala | Asp | Ala | Pro | Ala | Tyr | Gln | Gln | Gly | Gln | Asn |

```
              355                 360                 365
Gln Leu Tyr Asn Glu Leu Asn Leu Gly Arg Arg Glu Glu Tyr Asp Val
        370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg
    450                 455                 460

<210> SEQ ID NO 233
<211> LENGTH: 1533
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 233
atggcactcc ccgtaactgc tctgctgctg ccgttggcat tgctcctgca cgccgcacgc      60
ccggaaatag tgatgactca gtccccggcc accctcagcg tgtccccggg ggagcgagcg     120
accctgtcat gcagggcttc ccagagtgtc agctccctgc tcacttggta tcagcaaaag     180
ccggggcagg ctcccgcct cctcatcttc ggggcatcaa ctagggccac ggcattcct      240 gcaagatttt ccgggtctgg cagcggcacc ggcttcaccc ttaccattag ctctctgcag     300
tctgaggact cgccgtttta ctattgtcag cagtatgata cttggccctt taccttcggt     360
cccggaacta aggtggactt caagcgcggg gggggtggat ctggaggtgg tggctccggg     420
ggcggtggaa gccaggtcca gttggttgag agcggcggcg gagtggtgca gcccgggagg     480
tccttgcggc tgagctgtgc agcctccggt tttacttttt ctagctatgg aatgcattgg     540
gtaagacagg ctcccggaaa aggcctcgag tgggtggcgg tcattagcta tgatggatct     600
gataaatact atgtggactc agttaagggg cgcttcacaa tctcaagaga caatagcaaa     660
aatagactgt acctgcagat gaatagtctg cgcgccgagg acactgccgt gtactactgc     720
gcccgcgaga gatacagcgg acgggattac tggggccagg gtaccctcgt aacggtgtcc     780
tccgctgccg cccttagcaa cagcattatg tactttctc atttcgtgcc agtctttctc     840
ccagcaaagc ccaccactac cccggccccc aggccgccta ctcctgcccc cactatcgcg     900
tctcagcctc tctccttgcg gcccgaggcc tgccggccag ccgcagggg cgccgtacat     960 actcggggtt tggatttcgc ttgcgacata tatatttggg cccccctcgc cggcacatgt    1020
ggagtgctgc tcctgagtct cgttataacc ctctattgca accatagaaa cagatccaaa    1080
agaagccgcc tgctccatag cgattacatg aatatgactc cacgccgccc tggccccaca    1140
aggaaacact accagcctta cgcaccacct agagatttcg ctgcctatcg agcagggtg    1200 aagttttcca gatctgcaga tgcaccagcg tatcagcagg ccagaaccca actgtataac    1260
gagctcaacc tggacgcag ggaagagtat gacgttttgg acaagcgcag aggacgggac     1320
cctgagatgg gtggcaaacc aagacgaaaa aaccccagg agggtctcta taatgagctg     1380
```

```
cagaaggata agatggctga agcctattct gaaataggca tgaaaggaga gcggagaagg    1440
ggaaaagggc acgacggttt gtaccaggga ctcagcactg ctacgaagga tacttatgac    1500
gctctccaca tgcaagccct gccacctagg taa                                 1533
```

<210> SEQ ID NO 234
<211> LENGTH: 510
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: anti-CLL-1 CAR construct

<400> SEQUENCE: 234

```
Met Ala Leu Pro Val Thr Ala Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Ser Leu Leu Thr Trp Tyr Gln Gln Lys Pro Gly Gln Ala
    50                  55                  60

Pro Arg Leu Leu Ile Phe Gly Ala Ser Thr Arg Ala Thr Gly Ile Pro
65                  70                  75                  80

Ala Arg Phe Ser Gly Ser Gly Ser Gly Thr Gly Phe Thr Leu Thr Ile
                85                  90                  95

Ser Ser Leu Gln Ser Glu Asp Phe Ala Val Tyr Tyr Cys Gln Gln Tyr
            100                 105                 110

Asp Thr Trp Pro Phe Thr Phe Gly Pro Gly Thr Lys Val Asp Phe Lys
        115                 120                 125

Arg Gly Gly Gly Gly Ser Gly Gly Gly Gly Ser Gly Gly Gly Gly Ser
    130                 135                 140

Gln Val Gln Leu Val Glu Ser Gly Gly Gly Val Val Gln Pro Gly Arg
145                 150                 155                 160

Ser Leu Arg Leu Ser Cys Ala Ala Ser Gly Phe Thr Phe Ser Ser Tyr
                165                 170                 175

Gly Met His Trp Val Arg Gln Ala Pro Gly Lys Gly Leu Glu Trp Val
            180                 185                 190

Ala Val Ile Ser Tyr Asp Gly Ser Asp Lys Tyr Tyr Val Asp Ser Val
        195                 200                 205

Lys Gly Arg Phe Thr Ile Ser Arg Asp Asn Ser Lys Asn Arg Leu Tyr
    210                 215                 220

Leu Gln Met Asn Ser Leu Arg Ala Glu Asp Thr Ala Val Tyr Tyr Cys
225                 230                 235                 240

Ala Arg Glu Arg Tyr Ser Gly Arg Asp Tyr Trp Gly Gln Gly Thr Leu
                245                 250                 255

Val Thr Val Ser Ser Ala Ala Ala Leu Ser Asn Ser Ile Met Tyr Phe
            260                 265                 270

Ser His Phe Val Pro Val Phe Leu Pro Ala Lys Pro Thr Thr Thr Pro
        275                 280                 285

Ala Pro Arg Pro Pro Thr Pro Ala Pro Thr Ile Ala Ser Gln Pro Leu
    290                 295                 300

Ser Leu Arg Pro Glu Ala Cys Arg Pro Ala Ala Gly Gly Ala Val His
305                 310                 315                 320
```

```
Thr Arg Gly Leu Asp Phe Ala Cys Asp Ile Tyr Ile Trp Ala Pro Leu
                325                 330                 335
Ala Gly Thr Cys Gly Val Leu Leu Leu Ser Leu Val Ile Thr Leu Tyr
            340                 345                 350
Cys Asn His Arg Asn Arg Ser Lys Arg Ser Arg Leu Leu His Ser Asp
        355                 360                 365
Tyr Met Asn Met Thr Pro Arg Arg Pro Gly Pro Thr Arg Lys His Tyr
    370                 375                 380
Gln Pro Tyr Ala Pro Pro Arg Asp Phe Ala Ala Tyr Arg Ser Arg Val
385                 390                 395                 400
Lys Phe Ser Arg Ser Ala Asp Ala Pro Ala Tyr Gln Gln Gly Gln Asn
                405                 410                 415
Gln Leu Tyr Asn Glu Leu Asn Leu Gly Arg Arg Glu Glu Tyr Asp Val
            420                 425                 430
Leu Asp Lys Arg Arg Gly Arg Asp Pro Glu Met Gly Gly Lys Pro Arg
        435                 440                 445
Arg Lys Asn Pro Gln Glu Gly Leu Tyr Asn Glu Leu Gln Lys Asp Lys
    450                 455                 460
Met Ala Glu Ala Tyr Ser Glu Ile Gly Met Lys Gly Glu Arg Arg Arg
465                 470                 475                 480
Gly Lys Gly His Asp Gly Leu Tyr Gln Gly Leu Ser Thr Ala Thr Lys
                485                 490                 495
Asp Thr Tyr Asp Ala Leu His Met Gln Ala Leu Pro Pro Arg
            500                 505                 510

<210> SEQ ID NO 235
<211> LENGTH: 1467
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: anti-CLL-1 CAR construct

<400> SEQUENCE: 235
gaaatagtga tgactcagtc cccggccacc ctcagcgtgt cccccgggga gcgagcgacc      60
ctgtcatgca gggcttccca gagtgtcagc tccctgctca cttggtatca gcaaagccg     120 gggcaggctc ccgcctcct catcttcggg gcatcaacta gggccaccgg cattcctgca     180
agattttccg gtctggcag cggcaccggc ttcacccta ccattagctc tctgcagtct     240
gaggacttcg ccgtttacta ttgtcagcag tatgatactt ggccctttac cttcggtccc     300
ggaactaagg tggacttcaa gcgcgggggg ggtggatctg gaggtggtgg ctccggggggc     360 ggtggaagcc aggtccagtt ggttgagagc ggcggcggag tggtgcagcc cgggaggtcc     420
ttgcggctga gctgtgcagc ctccggtttt acttttttcta gctatggaat gcattgggta     480
agacaggctc ccggaaaagg cctcgagtgg gtggcggtca ttagctatga tggatctgat     540
aaatactatg tggactcagt taaggggcgc ttcacaatct caagagacaa tagcaaaaat     600
agactgtacc tgcagatgaa tagtctgcgc gccgaggaca ctgccgtgta ctactgcgcc     660
cgcgagagat acagcggacg ggattactgg ggccaggta ccctcgtaac ggtgtcctcc     720
gctgccgccc ttagcaacag cattatgtac ttttctcatt tcgtgccagt ctttctccca     780
gcaaagccca ccactacccc ggcccccagg ccgcctactc ctgcccccac tatcgcgtct     840
cagcctctct ccttgcggcc cgaggcctgc cggccagccg caggggggcgc cgtacatact     900
```

```
cggggtttgg atttcgcttg cgacatatat atttgggccc ccctcgccgg cacatgtgga    960
gtgctgctcc tgagtctcgt tataaccctc tattgcaacc atagaaacag atccaaaaga   1020
agccgcctgc tccatagcga ttacatgaat atgactccac gccgcctggg ccccacaagg   1080
aaacactacc agcctacgc accacctaga gatttcgctg cctatcggag cagggtgaag    1140
ttttccagat ctgcagatgc accagcgtat cagcagggcc agaaccaact gtataacgag   1200
ctcaacctgg gacgcaggga agagtatgac gtttttggaca gcgcagagg acgggaccct   1260 gagatgggtg gcaaaccaag acgaaaaaac ccccaggagg gtctctataa tgagctgcag   1320
aaggataaga tggctgaagc ctattctgaa ataggcatga aggagagcg gagaagggga   1380 aaagggcacg acggtttgta ccagggactc agcactgcta cgaaggatac ttatgacgct   1440
ctccacatgc aagccctgcc acctagg                                       1467
```

<210> SEQ ID NO 236
<211> LENGTH: 489
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: anti-CLL-1 CAR construct

<400> SEQUENCE: 236

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Leu
            20                  25                  30

Leu Thr Trp Tyr Gln Gln Lys Pro Gly Gln Ala Pro Arg Leu Leu Ile
        35                  40                  45

Phe Gly Ala Ser Thr Arg Ala Thr Gly Ile Pro Ala Arg Phe Ser Gly
    50                  55                  60

Ser Gly Ser Gly Thr Gly Phe Thr Leu Thr Ile Ser Ser Leu Gln Ser
65                  70                  75                  80

Glu Asp Phe Ala Val Tyr Tyr Cys Gln Gln Tyr Asp Thr Trp Pro Phe
                85                  90                  95

Thr Phe Gly Pro Gly Thr Lys Val Asp Phe Lys Arg Gly Gly Gly Gly
            100                 105                 110

Ser Gly Gly Gly Gly Ser Gly Gly Gly Ser Gln Val Gln Leu Val
        115                 120                 125

Glu Ser Gly Gly Gly Val Val Gln Pro Gly Arg Ser Leu Arg Leu Ser
    130                 135                 140

Cys Ala Ala Ser Gly Phe Thr Phe Ser Ser Tyr Gly Met His Trp Val
145                 150                 155                 160

Arg Gln Ala Pro Gly Lys Gly Leu Glu Trp Val Ala Val Ile Ser Tyr
                165                 170                 175

Asp Gly Ser Asp Lys Tyr Tyr Val Asp Ser Val Lys Gly Arg Phe Thr
            180                 185                 190

Ile Ser Arg Asp Asn Ser Lys Asn Arg Leu Tyr Leu Gln Met Asn Ser
        195                 200                 205

Leu Arg Ala Glu Asp Thr Ala Val Tyr Tyr Cys Ala Arg Glu Arg Tyr
    210                 215                 220

Ser Gly Arg Asp Tyr Trp Gly Gln Gly Thr Leu Val Thr Val Ser Ser
225                 230                 235                 240

Ala Ala Ala Leu Ser Asn Ser Ile Met Tyr Phe Ser His Phe Val Pro
```

```
                    245                 250                 255

Val Phe Leu Pro Ala Lys Pro Thr Thr Thr Pro Ala Pro Arg Pro Pro
                260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
        290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Asn His Arg Asn
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
        355                 360                 365

Pro Arg Asp Phe Ala Ala Tyr Arg Ser Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: scFv G4s linker

<400> SEQUENCE: 237

Gly Gly Gly Gly Ser Gly Gly Gly Gly Ser Gly Gly Gly Gly Ser
1               5                   10                  15

<210> SEQ ID NO 238
<211> LENGTH: 288
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: CD8 extracellular

<400> SEQUENCE: 238
```

```
gctgcagcat tgagcaactc aataatgtat tttagtcact ttgtaccagt gttcttgccg      60
gctaagccta ctaccacacc cgctccacgg ccacctaccc cagctcctac catcgcttca     120
cagcctctgt ccctgcgccc agaggcttgc cgaccggccg caggggggcgc tgttcatacc    180 agaggactgg atttcgcctg cgatatctat atctgggcac ccctggccgg aacctgcggc    240
gtactcctgc tgtccctggt catcacgctc tattgtaatc acaggaac                288
```

<210> SEQ ID NO 239
<211> LENGTH: 96
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: Description of Combined DNA/RNA Molecule:
    Synthetic polypeptide
<220> FEATURE:
<223> OTHER INFORMATION: CD8 extracellular

<400> SEQUENCE: 239

```
Ala Ala Ala Leu Ser Asn Ser Ile Met Tyr Phe Ser His Phe Val Pro
1               5                   10                  15

Val Phe Leu Pro Ala Lys Pro Thr Thr Thr Pro Ala Pro Arg Pro Pro
                20                  25                  30

Thr Pro Ala Pro Thr Ile Ala Ser Gln Pro Leu Ser Leu Arg Pro Glu
            35                  40                  45

Ala Cys Arg Pro Ala Ala Gly Gly Ala Val His Thr Arg Gly Leu Asp
        50                  55                  60

Phe Ala Cys Asp Ile Tyr Ile Trp Ala Pro Leu Ala Gly Thr Cys Gly
65                  70                  75                  80

Val Leu Leu Leu Ser Leu Val Ile Thr Leu Tyr Cys Asn His Arg Asn
                85                  90                  95
```

<210> SEQ ID NO 240
<211> LENGTH: 294
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<223> OTHER INFORMATION: extracellular and intracellular domains

<400> SEQUENCE: 240

```
cttgataatg aaaagtcaaa cggaacaatc attcacgtga agggcaagca cctctgtccg     60
tcacccttgt tccctggtcc atccaagcca ttctgggtgt tggtcgtagt gggtggagtc    120
ctcgcttgtt actctctgct cgtcaccgtg gcttttataa tcttctgggt tagatccaaa    180
agaagccgcc tgctccatag cgattacatg aatatgactc cacgccgccc tggccccaca    240
aggaaacact accagcctta cgcaccacct agagatttcg ctgcctatcg agc           294
```

<210> SEQ ID NO 241
<211> LENGTH: 98
<212> TYPE: PRT
<213> ORGANISM: Artificial Sequence
<220> FEATURE:
<223> OTHER INFORMATION: Description of Artificial Sequence: Synthetic
    polypeptide
<220> FEATURE:
<223> OTHER INFORMATION: extracellular and intracellular domains

<400> SEQUENCE: 241

```
Leu Asp Asn Glu Lys Ser Asn Gly Thr Ile Ile His Val Lys Gly Lys
1               5                   10                  15

His Leu Cys Pro Ser Pro Leu Phe Pro Gly Pro Ser Lys Pro Phe Trp
            20                  25                  30

Val Leu Val Val Val Gly Gly Val Leu Ala Cys Tyr Ser Leu Leu Val
        35                  40                  45

Thr Val Ala Phe Ile Ile Phe Trp Val Arg Ser Lys Arg Ser Arg Leu
    50                  55                  60

Leu His Ser Asp Tyr Met Asn Met Thr Pro Arg Arg Pro Gly Pro Thr
65                  70                  75                  80

Arg Lys His Tyr Gln Pro Tyr Ala Pro Pro Arg Asp Phe Ala Ala Tyr
                85                  90                  95

Arg Ser
```

<210> SEQ ID NO 242
<211> LENGTH: 1482
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 10E3_CHD_DNA

<400> SEQUENCE: 242

```
atggcactcc ccgtaactgc tctgctgctg ccgttggcat tgctcctgca cgccgcacgc      60
ccgcaggtga ccctcaaaga gtctggaccc gtgctcgtaa aacctacgga gaccctgaca     120
ctcacctgca cagtctccgg cttcagcctc atcaatgcca ggatgggagt tcctggatc     180
aggcaaccgc ccgaaaggc cctggaatgg ctcgcacata ttttcagtaa cgctgaaaaa     240
agctatcgga cttctctgaa aagtcggctc acgattagta aggacacatc caagagccaa     300
gtggtgctta cgatgactaa catggaccct gtggatactg caacctatta ctgtgctcga     360
atccctggtt atggcggaaa tggggactac cactactacg gtatggatgt ctggggccaa     420
gggaccacgg ttactgtttc aagcggaggg ggagggagtg ggggtggcgg atctggcgga     480
ggaggcagcg atatccagat gacgcagtcc cctagttcac tttccgcatc cctgggggat     540
cgggttacca ttcatgccg cgcgtcacag ggtatccgga tgatctggg atggtaccag     600
cagaagccgg gaaaggctcc taagcgcctc atctacgcca gctccaccct gcagagtgga     660
gtgccctccc ggttttcagg cagtggctcc ggtacggagt ttactcttac aattagcagc     720
ctgcagccag aagattttgc aacttactac tgtttgcagc ataataattt ccctggacc     780
tttggtcagg gcaccaaggt ggagatcaaa agagcagccg ccatcgaagt aatgtatccc     840
cccccgtacc ttgacaatga aagtcaaat ggaaccatta tccatgttaa gggcaaacac     900
ctctgccctt ctccactgtt ccctggccct agtaagccgt tttgggtgct ggtggtagtc     960
ggtggggtgc tggcttgtta ctctcttctc gtgaccgtcg cctttataat ctttgggtc    1020
agatccaaaa gaagccgcct gctccatagc gattacatga atatgactcc acgccgccct    1080
ggccccacaa ggaaacacta ccagccttac gcaccaccta gagatttcgc tgcctatcgg    1140
agccgagtga atttttctag atcagctgat gctcccgcct atcagcaggg acagaatcaa    1200
ctttacaatg agctgaacct gggtcgcaga gaagagtacg acgttttgga caaacgccgg    1260
ggccgagatc tgagatgggg ggaagccg agaaggaaga atcctcaaga aggcctgtac    1320
aacgagcttc aaaaagacaa aatggctgag gcgtactctg agatcggcat gaagggcgag    1380
```

```
cggagacgag gcaagggtca cgatggcttg tatcagggcc tgagtacagc cacaaaggac    1440
acctatgacg ccctccacat gcaggcactg cccccacgct ag                      1482

<210> SEQ ID NO 243
<211> LENGTH: 493
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10E3_CHD_AA

<400> SEQUENCE: 243

Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
                20                  25                  30

Val Lys Pro Thr Glu Thr Leu Thr Leu Thr Cys Thr Val Ser Gly Phe
            35                  40                  45

Ser Leu Ile Asn Ala Arg Met Gly Val Ser Trp Ile Arg Gln Pro Pro
50                  55                  60

Gly Lys Ala Leu Glu Trp Leu Ala His Ile Phe Ser Asn Ala Glu Lys
65                  70                  75                  80

Ser Tyr Arg Thr Ser Leu Lys Ser Arg Leu Thr Ile Ser Lys Asp Thr
                85                  90                  95

Ser Lys Ser Gln Val Val Leu Thr Met Thr Asn Met Asp Pro Val Asp
            100                 105                 110

Thr Ala Thr Tyr Tyr Cys Ala Arg Ile Pro Gly Tyr Gly Gly Asn Gly
        115                 120                 125

Asp Tyr His Tyr Tyr Gly Met Asp Val Trp Gly Gln Gly Thr Thr Val
    130                 135                 140

Thr Val Ser Ser Gly Gly Gly Gly Ser Gly Gly Gly Gly Ser Gly Gly
145                 150                 155                 160

Gly Gly Ser Asp Ile Gln Met Thr Gln Ser Pro Ser Ser Leu Ser Ala
                165                 170                 175

Ser Leu Gly Asp Arg Val Thr Ile Thr Cys Arg Ala Ser Gln Gly Ile
            180                 185                 190

Arg Asn Asp Leu Gly Trp Tyr Gln Gln Lys Pro Gly Lys Ala Pro Lys
        195                 200                 205

Arg Leu Ile Tyr Ala Ser Ser Thr Leu Gln Ser Gly Val Pro Ser Arg
    210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Tyr Cys Leu Gln His Asn Asn
                245                 250                 255

Phe Pro Trp Thr Phe Gly Gln Gly Thr Lys Val Glu Ile Lys Arg Ala
            260                 265                 270

Ala Ala Ile Glu Val Met Tyr Pro Pro Pro Tyr Leu Asp Asn Glu Lys
        275                 280                 285

Ser Asn Gly Thr Ile Ile His Val Lys Gly Lys His Leu Cys Pro Ser
    290                 295                 300

Pro Leu Phe Pro Gly Pro Ser Lys Pro Phe Trp Val Leu Val Val Val
305                 310                 315                 320

Gly Gly Val Leu Ala Cys Tyr Ser Leu Leu Val Thr Val Ala Phe Ile
```

```
                    325                 330                 335
Ile Phe Trp Val Arg Ser Lys Arg Ser Arg Leu Leu His Ser Asp Tyr
            340                 345                 350
Met Asn Met Thr Pro Arg Arg Pro Gly Pro Thr Arg Lys His Tyr Gln
        355                 360                 365
Pro Tyr Ala Pro Pro Arg Asp Phe Ala Ala Tyr Arg Ser Arg Val Lys
    370                 375                 380
Phe Ser Arg Ser Ala Asp Ala Pro Ala Tyr Gln Gln Gly Gln Asn Gln
385                 390                 395                 400
Leu Tyr Asn Glu Leu Asn Leu Gly Arg Arg Glu Glu Tyr Asp Val Leu
                405                 410                 415
Asp Lys Arg Arg Gly Arg Asp Pro Glu Met Gly Gly Lys Pro Arg Arg
            420                 425                 430
Lys Asn Pro Gln Glu Gly Leu Tyr Asn Glu Leu Gln Lys Asp Lys Met
        435                 440                 445
Ala Glu Ala Tyr Ser Glu Ile Gly Met Lys Gly Glu Arg Arg Arg Gly
    450                 455                 460
Lys Gly His Asp Gly Leu Tyr Gln Gly Leu Ser Thr Ala Thr Lys Asp
465                 470                 475                 480
Thr Tyr Asp Ala Leu His Met Gln Ala Leu Pro Pro Arg
                485                 490
```

<210> SEQ ID NO 244
<211> LENGTH: 1455
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 10E3_THD_DNA

<400> SEQUENCE: 244

```
atggcactcc ccgtaactgc tctgctgctg ccgttggcat tgctcctgca cgccgcacgc      60
ccgcaagtta cttttgaagga gtctggacct gtactggtga agccaaccga gacactgaca    120
ctcacgtgta cagtgagtgg ttttttcctctg atcaacgcaa ggatgggcgt cagctggatc    180
aggcaacccc ctggcaaggc tctggaatgg ctcgctcaca tattcagcaa tgccgaaaaa    240
agctaccgga caagcctgaa atcccgcctg actatttcca aggacacttc taagtctcag    300
gtggtgctga ccatgaccaa catggacccg gtggacaccg ccacctatta ctgcgcaaga    360
atccctgggt atggtgggaa tggtgactac cattattatg ggatggatgt gtggggcaa    420
ggcacaaccg taacggtctc aagcggtggg ggaggctcag ggggcggagg ctccggaggt    480
ggcggctccg acattcagat gacccaaagc ccgtccagcc tgtccgccag cctgggagat    540
agagtgacaa tcacgtgtag agcttcccaa gggataagaa atgatctcgg tggtatcag    600
cagaagcccg gcaaagcccc caaaaggctt atatatgcta gtagtacact gcagtctgga    660
gttccttccc gattttcagg tagcggctcc ggtacagagt tcaccctcac gataagctca    720
ctccagcctg aggatttcgc aacgtactac tgcctccagc acaacaattt tccctggact    780
ttcggccagg gcaccaaggt ggagatcaag agggccgctg cccttgataa tgaaaagtca    840
aacggaacaa tcattcacgt gaagggcaag cacctctgtc cgtcacccct gttccctggt    900
ccatccaagc cattctgggt gttggtcgta gtgggtggag tcctcgcttg ttactctctg    960
ctcgtcaccg tggcttttat aatcttctgg gttagatcca aaagaagccg cctgctccat   1020
```

```
agcgattaca tgaatatgac tccacgccgc cctggcccca caaggaaaca ctaccagcct    1080
tacgcaccac ctagagattt cgctgcctat cggagccgag tgaaattttc tagatcagct    1140
gatgctcccg cctatcagca gggacagaat caactttaca atgagctgaa cctgggtcgc    1200
agagaagagt acgacgtttt ggacaaacgc cggggccgag atcctgagat ggggggggaag    1260 ccgagaagga agaatcctca agaaggcctg tacaacgagc ttcaaaaaga caaaatggct    1320
gaggcgtact ctgagatcgg catgaagggc gagcggagac gaggcaaggg tcacgatggc    1380
ttgtatcagg gcctgagtac agccacaaag gacacctatg acgccctcca catgcaggca    1440
ctgcccccac gctag                                                    1455

<210> SEQ ID NO 245
<211> LENGTH: 484
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 10E3_THD_AA

<400> SEQUENCE: 245

Met Ala Leu Pro Val Thr Ala Leu Leu Leu Pro Leu Ala Leu Leu Leu
1               5                   10                  15

His Ala Ala Arg Pro Gln Val Thr Leu Lys Glu Ser Gly Pro Val Leu
            20                  25                  30

Val Lys Pro Thr Glu Thr Leu Thr Leu Thr Cys Thr Val Ser Gly Phe
        35                  40                  45

Ser Leu Ile Asn Ala Arg Met Gly Val Ser Trp Ile Arg Gln Pro Pro
    50                  55                  60

Gly Lys Ala Leu Glu Trp Leu Ala His Ile Phe Ser Asn Ala Glu Lys
65                  70                  75                  80

Ser Tyr Arg Thr Ser Leu Lys Ser Arg Leu Thr Ile Ser Lys Asp Thr
                85                  90                  95

Ser Lys Ser Gln Val Val Leu Thr Met Thr Asn Met Asp Pro Val Asp
            100                 105                 110

Thr Ala Thr Tyr Tyr Cys Ala Arg Ile Pro Gly Tyr Gly Gly Asn Gly
        115                 120                 125

Asp Tyr His Tyr Tyr Gly Met Asp Val Trp Gly Gln Gly Thr Thr Val
    130                 135                 140

Thr Val Ser Ser Gly Gly Gly Ser Gly Gly Gly Gly Ser Gly Gly Gly
145                 150                 155                 160

Gly Gly Ser Asp Ile Gln Met Thr Gln Ser Pro Ser Ser Leu Ser Ala
                165                 170                 175

Ser Leu Gly Asp Arg Val Thr Ile Thr Cys Arg Ala Ser Gln Gly Ile
            180                 185                 190

Arg Asn Asp Leu Gly Trp Tyr Gln Gln Lys Pro Gly Lys Ala Pro Lys
        195                 200                 205

Arg Leu Ile Tyr Ala Ser Ser Thr Leu Gln Ser Gly Val Pro Ser Arg
    210                 215                 220

Phe Ser Gly Ser Gly Ser Gly Thr Glu Phe Thr Leu Thr Ile Ser Ser
225                 230                 235                 240

Leu Gln Pro Glu Asp Phe Ala Thr Tyr Tyr Cys Leu Gln His Asn Asn
                245                 250                 255

Phe Pro Trp Thr Phe Gly Gln Gly Thr Lys Val Glu Ile Lys Arg Ala
            260                 265                 270
```

```
Ala Ala Leu Asp Asn Glu Lys Ser Asn Gly Thr Ile Ile His Val Lys
            275                 280                 285

Gly Lys His Leu Cys Pro Ser Pro Leu Phe Pro Gly Pro Ser Lys Pro
    290                 295                 300

Phe Trp Val Leu Val Val Gly Gly Val Leu Ala Cys Tyr Ser Leu
305                 310                 315                 320

Leu Val Thr Val Ala Phe Ile Ile Phe Trp Val Arg Ser Lys Arg Ser
                325                 330                 335

Arg Leu Leu His Ser Asp Tyr Met Asn Met Thr Pro Arg Arg Pro Gly
            340                 345                 350

Pro Thr Arg Lys His Tyr Gln Pro Tyr Ala Pro Pro Arg Asp Phe Ala
        355                 360                 365

Ala Tyr Arg Ser Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 246
<211> LENGTH: 1464
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 8B5_CHD_DNA

<400> SEQUENCE: 246
atggcactcc ccgtaactgc tctgctgctg ccgttggcat tgctcctgca cgccgcacgc      60
ccgcagatcc agttggtgga atcagggggc ggtgtggtgc agccgggtag gagcctgaga     120
ctgtcatgcg tggcgtctgg cttcacattc aagaactacg gcatgcactg ggtgcgacag     180
gccccccgaa agggtttgga gtgggtcgcc gtgatctggt acgacggatc taatgagtat     240
tacggagatc ctgtgaaggg aaggttcacc atctcccgcg acaatagcaa aaatatgctc     300
tacctgcaaa tgaactcact cagggcggat gatacggcgg tctactattg cgctcgctca     360
gggattgctg tggccggcgc attcgattac tggggacagg gtaccctggt gacagtatca     420
agcggaggcg gcggctctgg cggcggcgga tctggcgggg gggaagtga gattgtgttg     480 acacagtctc ccgataccct gtcactgtca cccggcgaga aggcaacgct gagttgcaga     540
gcaagccagt cagtctcctc ttcttttctg gcctggtatc agcaaaaacc aggtcaggca     600
ccatctctcc tgatttacgt tgccagcaga cgggcggctg gcattcccga caggttctct     660
ggaagcggat ctgggaccga ttttaccctg acaattagcc gcttggagcc cgaagacttt     720
```

-continued

```
ggtatgttttt actgccagca ctacggaagg acacctttca catttggccc gggcacgaaa    780
gtcgatataa aacgcgcagc cgccattgaa gtaatgtacc caccaccttta tttggacaat    840 gaaaagtcca atggtaccat tattcacgtc aagggaaagc atctctgtcc aagccctctg    900
ttccccggcc cctccaaacc attctgggtg ctggtggtcg tcggcggagt tctggcctgc    960
tattctctgc tcgtgactgt tgcattcatc attttctggg tgagatccaa agaagccgc    1020 ctgctccata gcgattacat gaatatgact ccacgccgcc ctggcccac aaggaaacac    1080 taccagcctt acgcaccacc tagagatttc gctgcctatc ggagccgagt gaaattttct    1140
agatcagctg atgctcccgc ctatcagcag ggacagaatc aactttacaa tgagctgaac    1200
ctgggtcgca gagaagagta cgacgttttg gacaaacgcc ggggccgaga tcctgagatg    1260 gggggggaagc cgagaaggaa gaatcctcaa gaaggcctgt acaacgagct tcaaaaagac    1320
aaaatggctg aggcgtactc tgagatcggc atgaagggcg agcggagacg aggcaagggt    1380
cacgatggct tgtatcaggg cctgagtaca gccacaaagg acacctatga cgccctccac    1440
atgcaggcac tgccccacg ctag                                              1464
```

<210> SEQ ID NO 247
<211> LENGTH: 487
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 8B5_CHD_AA

<400> SEQUENCE: 247

```
Met Ala Leu Pro Val Thr Ala Leu Leu Leu Pro Leu Ala Leu Leu Leu
1               5                   10                  15

His Ala Ala Arg Pro Gln Ile Gln Leu Val Glu Ser Gly Gly Gly Val
            20                  25                  30

Val Gln Pro Gly Arg Ser Leu Arg Leu Ser Cys Val Ala Ser Gly Phe
        35                  40                  45

Thr Phe Lys Asn Tyr Gly Met His Trp Val Arg Gln Ala Pro Gly Lys
    50                  55                  60

Gly Leu Glu Trp Val Ala Val Ile Trp Tyr Asp Gly Ser Asn Glu Tyr
65                  70                  75                  80

Tyr Gly Asp Pro Val Lys Gly Arg Phe Thr Ile Ser Arg Asp Asn Ser
                85                  90                  95

Lys Asn Met Leu Tyr Leu Gln Met Asn Ser Leu Arg Ala Asp Asp Thr
            100                 105                 110

Ala Val Tyr Tyr Cys Ala Arg Ser Gly Ile Ala Val Ala Gly Ala Phe
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Glu Ile Val Leu
145                 150                 155                 160

Thr Gln Ser Pro Asp Thr Leu Ser Leu Ser Pro Gly Glu Lys Ala Thr
                165                 170                 175

Leu Ser Cys Arg Ala Ser Gln Ser Val Ser Ser Ser Phe Leu Ala Trp
            180                 185                 190

Tyr Gln Gln Lys Pro Gly Gln Ala Pro Ser Leu Leu Ile Tyr Val Ala
        195                 200                 205

Ser Arg Arg Ala Ala Gly Ile Pro Asp Arg Phe Ser Gly Ser Gly Ser
```

```
        210                 215                 220
Gly Thr Asp Phe Thr Leu Thr Ile Ser Arg Leu Glu Pro Glu Asp Phe
225                 230                 235                 240

Gly Met Phe Tyr Cys Gln His Tyr Gly Arg Thr Pro Phe Thr Phe Gly
            245                 250                 255

Pro Gly Thr Lys Val Asp Ile Lys Arg Ala Ala Ala Ile Glu Val Met
                260                 265                 270

Tyr Pro Pro Pro Tyr Leu Asp Asn Glu Lys Ser Asn Gly Thr Ile Ile
            275                 280                 285

His Val Lys Gly Lys His Leu Cys Pro Ser Pro Leu Phe Pro Gly Pro
        290                 295                 300

Ser Lys Pro Phe Trp Val Leu Val Val Gly Gly Val Leu Ala Cys
305                 310                 315                 320

Tyr Ser Leu Leu Val Thr Val Ala Phe Ile Ile Phe Trp Val Arg Ser
                325                 330                 335

Lys Arg Ser Arg Leu Leu His Ser Asp Tyr Met Asn Met Thr Pro Arg
            340                 345                 350

Arg Pro Gly Pro Thr Arg Lys His Tyr Gln Pro Tyr Ala Pro Pro Arg
        355                 360                 365

Asp Phe Ala Ala Tyr Arg Ser Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
            485
```

<210> SEQ ID NO 248
<211> LENGTH: 1437
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 8B5_THD_DNA
<400> SEQUENCE: 248

```
atggcactcc cgtaactgc tctgctgctg ccgttggcat tgctcctgca cgccgcacgc      60
ccgcagattc agctcgtgga gtcaggtggt ggcgtggttc agcccggacg gtccctgcga     120
ctctcttgtg tggcaagcgg atttaccttt aagaactatg catgcactgg ggtgaggcag     180
gcccctggaa aaggactgga gtgggttgct gtgatctggt acgacgggtc caacgaatat     240
tatggcgatc ctgtgaaggg acggtttaca atctcacgcg ataactcaaa gaacatgctg     300
tacctgcaaa tgaactctct cgcgcgctga tgacactgccg tgtattattg cgctcggagt   360
ggtatcgccg tcgcaggagc atttgattat tgggggcaag ggaccctcgt gacagtgagt     420
```

```
tccggagggg gaggttctgg tggaggcggc tctggtgggg gaggcagcga gatcgttctg      480
acccagtctc ctgacacact gtcactgtcc cctggtgaaa aggccacact gtcttgtaga      540
gcgtcccaga gcgtttccag ttccttcctt gcatggtatc aacaaaaacc cgggcaggct      600
ccaagcttgc tgatctacgt ggccagccgc cgggccgcag gcatccctga taggtttagc      660
ggttctggga gcgggacgga cttcaccttg acaatatcac ggctggaacc cgaagacttc      720
ggaatgtttt attgccagca ctacggaaga actccattca cctttggccc gggaacgaag      780
gtagacatca agagagcagc agccctcgac aacgagaaat ccaatggaac cattatccat      840
gtgaagggga acatctctg cccttcacca ttgttccctg acccagcaa gccttttgg        900 gttctggtcg tggtggggg cgtcctggct tgttactccc tcctcgttac agtcgccttc       960
ataatctttt gggttagatc caaaagaagc cgcctgctcc atagcgatta catgaatatg     1020
actccacgcc gccctggccc cacaaggaaa cactaccagc cttacgcacc acctagagat     1080
ttcgctgcct atcggagccg agtgaaattt tctagatcag ctgatgctcc cgcctatcag     1140
cagggacaga atcaacttta caatgagctg aacctgggtc gcagagaaga gtacgacgtt     1200
ttggacaaac gccggggccg agatcctgag atggggggga agccgagaag gaagaatcct     1260
caagaaggcc tgtacaacga gcttcaaaaa gacaaaatgg ctgaggcgta ctctgagatc     1320
ggcatgaagg gcgagcggag acgaggcaag ggtcacgatg gcttgtatca gggcctgagt     1380
acagccacaa aggacaccta tgacgccctc cacatgcagg cactgccccc acgctag        1437
```

<210> SEQ ID NO 249
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 8B5_THD_AA

<400> SEQUENCE: 249

Met Ala Leu Pro Val Thr Ala Leu Leu Leu Pro Leu Ala Leu Leu Leu
1               5                   10                  15

His Ala Ala Arg Pro Gln Ile Gln Leu Val Glu Ser Gly Gly Gly Val
                20                  25                  30

Val Gln Pro Gly Arg Ser Leu Arg Leu Ser Cys Val Ala Ser Gly Phe
            35                  40                  45

Thr Phe Lys Asn Tyr Gly Met His Trp Val Arg Gln Ala Pro Gly Lys
        50                  55                  60

Gly Leu Glu Trp Val Ala Val Ile Trp Tyr Asp Gly Ser Asn Glu Tyr
65                  70                  75                  80

Tyr Gly Asp Pro Val Lys Gly Arg Phe Thr Ile Ser Arg Asp Asn Ser
                85                  90                  95

Lys Asn Met Leu Tyr Leu Gln Met Asn Ser Leu Arg Ala Asp Asp Thr
            100                 105                 110

Ala Val Tyr Tyr Cys Ala Arg Ser Gly Ile Ala Val Ala Gly Ala Phe
        115                 120                 125

Asp Tyr Trp Gly Gln Gly Thr Leu Val Thr Val Ser Gly Gly Gly
    130                 135                 140

Gly Ser Gly Gly Gly Gly Ser Gly Gly Gly Ser Glu Ile Val Leu
145                 150                 155                 160

Thr Gln Ser Pro Asp Thr Leu Ser Leu Ser Pro Gly Glu Lys Ala Thr

```
            165             170                 175

Leu Ser Cys Arg Ala Ser Gln Ser Val Ser Ser Phe Leu Ala Trp
            180                 185                 190

Tyr Gln Gln Lys Pro Gly Gln Ala Pro Ser Leu Leu Ile Tyr Val Ala
            195                 200                 205

Ser Arg Arg Ala Ala Gly Ile Pro Asp Arg Phe Ser Gly Ser Gly Ser
    210                 215                 220

Gly Thr Asp Phe Thr Leu Thr Ile Ser Arg Leu Glu Pro Glu Asp Phe
225                 230                 235                 240

Gly Met Phe Tyr Cys Gln His Tyr Gly Arg Thr Pro Phe Thr Phe Gly
                245                 250                 255

Pro Gly Thr Lys Val Asp Ile Lys Arg Ala Ala Leu Asp Asn Glu
            260                 265                 270

Lys Ser Asn Gly Thr Ile Ile His Val Lys Gly Lys His Leu Cys Pro
            275                 280                 285

Ser Pro Leu Phe Pro Gly Pro Ser Lys Pro Phe Trp Val Leu Val Val
    290                 295                 300

Val Gly Gly Val Leu Ala Cys Tyr Ser Leu Leu Val Thr Val Ala Phe
305                 310                 315                 320

Ile Ile Phe Trp Val Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
            355                 360                 365

Lys Phe Ser Arg Ser Ala Asp Ala Pro Ala Tyr Gln Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
            435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg
465                 470                 475

<210> SEQ ID NO 250
<211> LENGTH: 9
<212> TYPE: PRT
<213> ORGANISM: Homo sapiens

<400> SEQUENCE: 250

Ile Glu Val Met Tyr Pro Pro Pro Tyr
1               5

<210> SEQ ID NO 251
<211> LENGTH: 112
<212> TYPE: PRT
<213> ORGANISM: Homo sapiens

<400> SEQUENCE: 251

Arg Val Lys Phe Ser Arg Ser Ala Asp Ala Pro Ala Tyr Lys Gln Gly
```

| | 1 | | | | 5 | | | | | 10 | | | | | 15 | |
|---|---|---|---|---|---|---|---|---|---|---|---|---|---|---|---|---|

Gln Asn Gln Leu Tyr Asn Glu Leu Asn Leu Gly Arg Arg Glu Glu Tyr
              20                   25                 30

Asp Val Leu Asp Lys Arg Arg Gly Arg Asp Pro Glu Met Gly Gly Lys
        35                   40                   45

Pro Arg Arg Lys Asn Pro Gln Glu Gly Leu Tyr Asn Glu Leu Gln Lys
 50                    55                   60

Asp Lys Met Ala Glu Ala Tyr Ser Glu Ile Gly Met Lys Gly Glu Arg
65             70                   75                   80

Arg Arg Gly Lys Gly His Asp Gly Leu Tyr Gln Gly Leu Ser Thr Ala
              85                   90                   95

Thr Lys Asp Thr Tyr Asp Ala Leu His Met Gln Ala Leu Pro Pro Arg
        100                   105                 110

```
<210> SEQ ID NO 252
<211> LENGTH: 6762
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 252
ctgacgcgcc ctgtagcggc gcattaagcg cggcgggtgt ggtggttacg cgcagcgtga    60
ccgctacact tgccagcgcc ctagcgcccg ctcctttcgc tttcttccct tcctttctcg   120
ccacgttcgc cggctttccc cgtcaagctc taaatcgggg gctcccttta gggttccgat   180
ttagtgcttt acggcacctc gaccccaaaa aacttgatta gggtgatggt tcacgtagtg   240
ggccatcgcc ctgatagacg gttttttcgcc ctttgacgtt ggagtccacg ttctttaata   300
gtggactctt gttccaaact ggaacaacac tcaaccctat ctcggtctat tcttttgatt   360
tataagggat tttgccgatt tcggcctatt ggttaaaaaa tgagctgatt taacaaaaat   420
ttaacgcgaa ttttaacaaa atattaacgc ttacaatttg ccattcgcca ttcaggctgc   480
gcaactgttg ggaagggcga tcggtgcggg cctcttcgct attacgccag ctggcgaaag   540
ggggatgtgc tgcaaggcga ttaagttggg taacgccagg gttttcccag tcacgacgtt   600
gtaaaacgac ggccagtgaa ttgtaatacg actcactata gggcgacccg ggatggcgc   660 gccagtaatc aattacgggg tcattagttc atagcccata tatggagttc cgcgttacat   720
aacttacggt aaatggcccg cctggctgac cgcccaacga cccccgccca ttgacgtcaa   780
taatgacgta tgttcccata gtaacgccaa tagggacttt ccattgacgt caatgggtgg   840
agtatttacg gtaaactgcc cacttggcag tacatcaagt gtatcatatg ccaagtacgc   900
cccctattga cgtcaatgac ggtaaatggc ccgcctggca ttatgcccag tacatgacct   960
tatgggactt tcctacttgg cagtacatct acgtattagt catcgctatt accatgctga  1020
tgcggttttg gcagtacatc aatgggcgtg gatagcggtt tgactcacgg ggatttccaa  1080
gtctccaccc cattgacgtc aatgggagtt tgttttggca ccaaaatcaa cgggactttc  1140
caaaatgtcg taacaactcc gccccattga cgcaaatggg cggtaggcgt gtacggtggg  1200
aggtctatat aagcagagct ggtttagtga accgggtct ctctggttag accagatctg  1260
agcctgggag ctctctggct aactagggaa cccactgctt aagcctcaat aaagcttgcc  1320
ttgagtgctt caagtagtgt gtgcccgtct gttgtgtgac tctggtaact agagatccct  1380
cagacccttt tagtcagtgt ggaaaatctc tagcagtggc gcccgaacag ggacttgaaa  1440
```

```
gcgaaaggga aaccagagga gctctctcga cgcaggactc ggcttgctga agcgcgcacg    1500
gcaagaggcg aggggcggcg actggtgagt acgccaaaaa ttttgactag cggaggctag    1560
aaggagagag atgggtgcga gagcgtcagt attaagcggg ggagaattag atcgcgatgg    1620
gaaaaaattc ggttaaggcc agggggaaag aaaaaatata aattaaaaca tatagtatgg    1680
gcaagcaggg agctagaacg attcgcagtt aatcctggcc tgttagaaac atcagaaggc    1740
tgtagacaaa tactgggaca gctacaacca tcccttcaga caggatcaga agaacttaga    1800
tcattatata atacagtagc aaccctctat tgtgtgcatc aaaggataga gataaaagac    1860
accaaggaag ctttagacaa gatagaggaa gagcaaaaca aaagtaagac caccgcacag    1920
caagccgccg ctgatcttca gacctggagg aggagatatg agggacaatt ggagaagtga    1980
attatataaa tataaagtag taaaaattga accattagga gtagcaccca ccaaggcaaa    2040
gagaagagtg gtgcagagag aaaaaagagc agtgggaata ggagctttgt tccttgggtt    2100
cttgggagca gcaggaagca ctatgggcgc agcgtcaatg acgctgacgg tacaggccag    2160
acaattattg tctggtatag tgcagcagca gaacaatttg ctgagggcta ttgaggcgca    2220
acagcatctg ttgcaactca cagtctgggg catcaagcag ctccaggcaa gaatcctggc    2280
tgtggaaaga tacctaaagg atcaacagct cctggggatt tggggttgct ctggaaaact    2340
catttgcacc actgctgtgc cttggaatgc tagttggagt aataaatctc tggaacagat    2400
ttggaatcac acgacctgga tggagtggga cagagaaatt aacaattaca caagcttaat    2460
acactcctta attgaagaat cgcaaaacca gcaagaaaag aatgaacaag aattattgga    2520
attagataaa tgggcaagtt tgtggaattg gtttaacata acaaattggc tgtggtatat    2580
aaaattattc ataatgatag taggaggctt ggtaggttta agaatagttt ttgctgtact    2640
ttctatagtg aatagagtta ggcagggata ttcaccatta tcgtttcaga cccacctccc    2700
aaccccgagg ggacccgaca ggcccgaagg aatagaagaa gaaggtggag agagagacag    2760
agacagatcc attcgattag tgaacggatc tcgacggtat cggttaactt ttaaaagaaa    2820 agggggatt gggggtaca gtgcagggga agaatagta gacataatag caacagacat    2880
acaaactaaa gaattacaaa aacaaattac aaaattcaaa attttatcgc gatcgcggaa    2940
tgaaagaccc cacctgtagg tttggcaagc tagcttaagt aacgccattt tgcaaggcat    3000
ggaaaataca taactgagaa tagagaagtt cagatcaagg ttaggaacag agagacagca    3060
gaatatgggc caaacaggat atctgtggta agcagttcct gccccggctc agggccaaga    3120
acagatggtc cccagatgcg gtcccgcccct cagcagtttc tagagaacca tcagatgttt    3180
ccagggtgcc ccaaggacct gaaaatgacc ctgtgcctta tttgaactaa ccaatcagtt    3240
cgcttctcgc ttctgttcgc gcgcttctgc tccccgagct caataaaaga gcccacaacc    3300
cctcactcgg cgcgccagtc cttcgaagta gatctttgtc gatcctacca tccactcgac    3360 acaccccgcca gcggccgctg ccaagcttcc gagctctcga attaattcac ggtacccacc    3420
atggcctagg gagactagtc gaatcgatat caacctctgg attacaaaat ttgtgaaaga    3480
ttgactggta ttcttaacta tgttgctcct tttacgctat gtggatacgc tgctttaatg    3540
cctttgtatc atgctattgc ttcccgtatg gctttcattt tctcctcctt gtataaatcc    3600
tggttgctgt ctctttatga ggagttgtgg cccgttgtca ggcaacgtgg cgtggtgtgc    3660
actgtgtttg ctgacgcaac ccccactggt tggggcattg ccaccacctg tcagctcctt    3720
tccgggactt tcgctttccc cctccctatt gccacgcgg aactcatcgc cgcctgcctt    3780
gcccgctgct ggacaggggc tcggctgttg ggcactgaca attccgtggt gttgtcgggg    3840
```

```
aagctgacgt cctttcatg gctgctcgcc tgtgttgcca cctggattct gcgcgggacg    3900
tccttctgct acgtccctc ggccctcaat ccagcggacc ttccttcccg cggcctgctg    3960
ccggctctgc ggcctcttcc gcgtcttcgc cttcgccctc agacgagtcg gatctccctt    4020
tgggccgcct ccccgcctgg ttaattaaag tacctttaag accaatgact acaaggcag    4080 ctgtagatct tagccacttt ttaaaagaaa agggggact ggaagggcga attcactccc    4140
aacgaagaca agatctgctt tttgcttgta ctgggtctct ctggttagac cagatctgag    4200
cctgggagct ctctggctaa ctagggaacc cactgcttaa gcctcaataa agcttgcctt    4260
gagtgcttca agtagtgtgt gcccgtctgt tgtgtgactc tggtaactag agatccctca    4320 gacccttta gtcagtgtgg aaaatctcta gcaggcatgc cagacatgat aagatacatt    4380
gatgagtttg gacaaaccac aactagaatg cagtgaaaaa aatgctttat ttgtgaaatt    4440
tgtgatgcta ttgctttatt tgtaaccatt ataagctgca ataaacaagt taacaacaac    4500
aattgcattc atttatgtt tcaggttcag ggggaggtgt gggaggtttt ttggcgcgcc    4560
atcgtcgagg ttccctttag tgagggttaa ttgcgagctt ggcgtaatca tggtcatagc    4620
tgtttcctgt gtgaaattgt tatccgctca caattccaca acatacga gccgaagca    4680 taaagtgtaa agcctggggt gcctaatgag tgagctaact cacattaatt gcgttgcgct    4740
cactgcccgc tttccagtcg ggaaacctgt cgtgccagct gcattaatga atcggccaac    4800
gcgcggggag aggcggtttg cgtattgggc gctcttccgc ttcctcgctc actgactcgc    4860
tgcgctcggt cgttcggctg cggcgagcgg tatcagctca ctcaaaggcg gtaatacggt    4920
tatccacaga atcaggggat aacgcaggaa agaacatgtg agcaaaaggc cagcaaaagg    4980
ccaggaaccg taaaaaggcc gcgttgctgg cgttttccca taggctccgc cccctgacg    5040 agcatcacaa aaatcgacgc tcaagtcaga ggtggcgaaa cccgacagga ctataaagat    5100
accaggcgtt tccccctgga agctccctcg tgcgctctcc tgttccgacc ctgccgctta    5160
ccggatacct gtccgccttt ctccttcgg gaagcgtggc gctttctcat agctcacgct    5220
gtaggtatct cagttcggtg taggtcgttc gctccaagct gggctgtgtg cacgaacccc    5280
ccgttcagcc cgaccgctgc gccttatccg gtaactatcg tcttgagtcc aacccggtaa    5340
gacacgactt atcgccactg gcagcagcca ctggtaacag gattagcaga gcgaggtatg    5400
taggcggtgc tacagagttc ttgaagtggt ggcctaacta cggctacact agaagaacag    5460
tatttggtat ctgcgctctg ctgaagccag ttaccttcgg aaaaagagtt ggtagctctt    5520
gatccggcaa acaaaccacc gctggtagcg gtggtttttt tgtttgcaag cagcagatta    5580
cgcgcagaaa aaaaggatct caagaagatc ctttgatctt ttctacgggg tctgacgctc    5640
agtggaacga aaactcacgt taagggattt tggtcatgag attatcaaaa aggatcttca    5700
cctagatcct tttaaattaa aaatgaagtt ttaaatcaat ctaaagtata tatgagtaaa    5760
cttggtctga cagttaccaa tgcttaatca gtgaggcacc tatctcagcg atctgtctat    5820
ttcgttcatc catagttgcc tgactccccg tcgtgtagat aactacgata cgggagggct    5880
taccatctgg ccccagtgct gcaatgatac cgcgagaccc acgctcaccg gctccagatt    5940
tatcagcaat aaaccagcca gccggaaggg ccgagcgcag aagtggtcct gcaactttat    6000
ccgcctccat ccagtctatt aattgttgcc gggaagctag agtaagtagt tcgccagtta    6060
atagtttgcg caacgttgtt gccattgcta caggcatcgt ggtgtcacgc tcgtcgtttg    6120
gtatggcttc attcagctcc ggttcccaac gatcaaggcg agttacatga tcccccatgt    6180
```

```
tgtgcaaaaa agcggttagc tccttcggtc ctccgatcgt tgtcagaagt aagttggccg   6240
cagtgttatc actcatggtt atggcagcac tgcataattc tcttactgtc atgccatccg   6300
taagatgctt ttctgtgact ggtgagtact caaccaagtc attctgagaa tagtgtatgc   6360
ggcgaccgag ttgctcttgc ccggcgtcaa tacgggataa taccgcgcca catagcagaa   6420
ctttaaaagt gctcatcatt ggaaaacgtt cttcggggcg aaaactctca aggatcttac   6480
cgctgttgag atccagttcg atgtaaccca ctcgtgcacc caactgatct tcagcatctt   6540
ttactttcac cagcgtttct gggtgagcaa aaacaggaag gcaaatgcc gcaaaaaagg    6600 gaataagggc gacacggaaa tgttgaatac tcatactctt cctttttcaa tattattgaa   6660
gcatttatca gggttattgt ctcatgagcg gatacatatt tgaatgtatt tagaaaaata   6720
aacaaatagg ggttccgcgc acatttcccc gaaaagtgcc ac                      6762
```

<210> SEQ ID NO 253
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1

<400> SEQUENCE: 253

Gly Phe Thr Phe Ser Ser Tyr
1               5

<210> SEQ ID NO 254
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1

<400> SEQUENCE: 254

Gly Phe Thr Phe Ser Ser Tyr
1               5

<210> SEQ ID NO 255
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1

<400> SEQUENCE: 255

Gly Tyr Thr Phe Thr Ser Tyr
1               5

<210> SEQ ID NO 256
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR1

<400> SEQUENCE: 256

Gly Gly Ser Ile Ser Ser Ser Ser Tyr
1               5

<210> SEQ ID NO 257
<211> LENGTH: 7

-continued

```
<212> TYPE: PRT
<213> ORGANISM: Artificial Sequence
<220> FEATURE:
<223> OTHER INFORMATION: Description of Artificial Sequence: Synthetic
      VH CDR1

<400> SEQUENCE: 257

Gly Phe Thr Phe Ser Ser Tyr
1               5

<210> SEQ ID NO 258
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1

<400> SEQUENCE: 258

Gly Phe Thr Phe Ser Ser Tyr
1               5

<210> SEQ ID NO 259
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1

<400> SEQUENCE: 259

Gly Gly Thr Phe Ser Ser Tyr
1               5

<210> SEQ ID NO 260
<211> LENGTH: 7
<212> TYPE: PRT
<213> ORGANISM: Artificial Sequence
<220> FEATURE:
<223> OTHER INFORMATION: Description of Artificial Sequence: Synthetic
      VH CDR1

<400> SEQUENCE: 260

Gly Phe Thr Phe Ser Ser Tyr
1               5

<210> SEQ ID NO 261
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2

<400> SEQUENCE: 261

Ala Ile Ser Gly Ser Gly Gly Ser Thr Tyr Tyr Ala Asp Ser Val Lys
1               5                   10                  15

Gly

<210> SEQ ID NO 262
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2

<400> SEQUENCE: 262
```

```
Val Ile Ser Tyr Asp Gly Ser Asn Lys Tyr Tyr Ala Asp Ser Val Lys
1               5                   10                  15

Gly

<210> SEQ ID NO 263
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2

<400> SEQUENCE: 263

Ile Ile Asn Pro Gly Gly Gly Ser Thr Ser Tyr Ala Gln Lys Phe Gln
1               5                   10                  15

Gly

<210> SEQ ID NO 264
<211> LENGTH: 16
<212> TYPE: PRT
<213> ORGANISM: Artificial Sequence
<220> FEATURE:
<223> OTHER INFORMATION: Description of Artificial Sequence: Synthetic
      VH CDR2

<400> SEQUENCE: 264

Ser Ile Ser Tyr Ser Gly Ser Thr Tyr Tyr Asn Pro Ser Leu Lys Ser
1               5                   10                  15

<210> SEQ ID NO 265
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2

<400> SEQUENCE: 265

Thr Ile Ser Ser Ser Ser Ser Thr Ile Tyr Tyr Ala Asp Ser Val Lys
1               5                   10                  15

Gly

<210> SEQ ID NO 266
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2

<400> SEQUENCE: 266

Val Ile Ser Tyr Asp Gly Ser Asn Lys Tyr Tyr Ala Asp Ser Val Lys
1               5                   10                  15

Gly

<210> SEQ ID NO 267
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2

<400> SEQUENCE: 267
```

```
Gly Ile Ile Pro Ile Phe Gly Thr Ala Asn Tyr Ala Gln Lys Phe Gln
1               5                   10                  15
Gly

<210> SEQ ID NO 268
<211> LENGTH: 17
<212> TYPE: PRT
<213> ORGANISM: Artificial Sequence
<220> FEATURE:
<223> OTHER INFORMATION: Description of Artificial Sequence: Synthetic
      VH CDR2

<400> SEQUENCE: 268

Val Ile Ser Tyr Asp Gly Ser Asn Lys Tyr Tyr Ala Asp Ser Val Lys
1               5                   10                  15
Gly

<210> SEQ ID NO 269
<211> LENGTH: 11
<212> TYPE: PRT
<213> ORGANISM: Artificial Sequence
<220> FEATURE:
<223> OTHER INFORMATION: Description of Artificial Sequence: Synthetic
      VH CDR3

<400> SEQUENCE: 269

Ala Arg Ala Glu Met Gly Ala Val Phe Asp Ile
1               5                   10

<210> SEQ ID NO 270
<211> LENGTH: 15
<212> TYPE: PRT
<213> ORGANISM: Artificial Sequence
<220> FEATURE:
<223> OTHER INFORMATION: Description of Artificial Sequence: Synthetic
      VH CDR3

<400> SEQUENCE: 270

Ala Arg Asp Gly Thr Tyr Leu Gly Gly Leu Trp Tyr Phe Asp Leu
1               5                   10                  15

<210> SEQ ID NO 271
<211> LENGTH: 9
<212> TYPE: PRT
<213> ORGANISM: Artificial Sequence
<220> FEATURE:
<223> OTHER INFORMATION: Description of Artificial Sequence: Synthetic
      VH CDR3

<400> SEQUENCE: 271

Ala Arg Glu Ser Trp Pro Met Asp Val
1               5

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence: Synthetic
      VH CDR3

<400> SEQUENCE: 272

Ala Arg Gly Arg Gly Tyr Ala Thr Ser Leu Ala Phe Asp Ile
1               5                   10

<210> SEQ ID NO 273
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      VH CDR3

<400> SEQUENCE: 273

Ala Arg Gly Ser Gln Glu His Leu Ile Phe Asp Tyr
1               5                   10

<210> SEQ ID NO 274
<211> LENGTH: 15
<212> TYPE: PRT
<213> ORGANISM: Artificial Sequence
<220> FEATURE:
<223> OTHER INFORMATION: Description of Artificial Sequence: Synthetic
      VH CDR3

<400> SEQUENCE: 274

Ala Arg Thr Asp Phe Trp Ser Gly Ser Pro Pro Gly Leu Asp Tyr
1               5                   10                  15

<210> SEQ ID NO 275
<211> LENGTH: 19
<212> TYPE: PRT
<213> ORGANISM: Artificial Sequence
<220> FEATURE:
<223> OTHER INFORMATION: Description of Artificial Sequence: Synthetic
      VH CDR3

<400> SEQUENCE: 275

Ala Arg Thr Pro Glu Tyr Ser Ser Ser Ile Trp His Tyr Tyr Tyr Gly
1               5                   10                  15

Met Asp Val

<210> SEQ ID NO 276
<211> LENGTH: 16
<212> TYPE: PRT
<213> ORGANISM: Artificial Sequence
<220> FEATURE:
<223> OTHER INFORMATION: Description of Artificial Sequence: Synthetic
      VH CDR3

<400> SEQUENCE: 276

Val Lys Gly Pro Leu Gln Glu Pro Pro Tyr Asp Tyr Gly Met Asp Val
1               5                   10                  15

<210> SEQ ID NO 277
<211> LENGTH: 10
<212> TYPE: PRT
<213> ORGANISM: Artificial Sequence
<220> FEATURE:
<223> OTHER INFORMATION: Description of Artificial Sequence: Synthetic
      VL CDR3

<400> SEQUENCE: 277

Gln Gln Arg Ile Ser Trp Pro Phe Thr Phe
1               5                   10

<210> SEQ ID NO 278
<211> LENGTH: 10
<212> TYPE: PRT
<213> ORGANISM: Artificial Sequence
<220> FEATURE:
<223> OTHER INFORMATION: Description of Artificial Sequence: Synthetic
      VL CDR3
```

```
<400> SEQUENCE: 278

Met Gln Gly Leu Gly Leu Pro Leu Thr Phe
1               5                   10

<210> SEQ ID NO 279
<211> LENGTH: 9
<212> TYPE: PRT
<213> ORGANISM: Artificial Sequence
<220> FEATURE:
<223> OTHER INFORMATION: Description of Artificial Sequence: Synthetic
      VL CDR3

<400> SEQUENCE: 279

Gln Gln Tyr Ala Ala Tyr Pro Thr Phe
1               5

<210> SEQ ID NO 280
<211> LENGTH: 10
<212> TYPE: PRT
<213> ORGANISM: Artificial Sequence
<220> FEATURE:
<223> OTHER INFORMATION: Description of Artificial Sequence: Synthetic
      VL CDR3

<400> SEQUENCE: 280

Gln Gln Arg His Val Trp Pro Pro Thr Phe
1               5                   10

<210> SEQ ID NO 281
<211> LENGTH: 10
<212> TYPE: PRT
<213> ORGANISM: Artificial Sequence
<220> FEATURE:
<223> OTHER INFORMATION: Description of Artificial Sequence: Synthetic
      VL CDR3

<400> SEQUENCE: 281

Gln Gln Arg Phe Tyr Tyr Pro Trp Thr Phe
1               5                   10

<210> SEQ ID NO 282
<211> LENGTH: 10
<212> TYPE: PRT
<213> ORGANISM: Artificial Sequence
<220> FEATURE:
<223> OTHER INFORMATION: Description of Artificial Sequence: Synthetic
      VL CDR3

<400> SEQUENCE: 282

Gln Gln Ile Tyr Thr Phe Pro Phe Thr Phe
1               5                   10

<210> SEQ ID NO 283
<211> LENGTH: 10
<212> TYPE: PRT
<213> ORGANISM: Artificial Sequence
<220> FEATURE:
<223> OTHER INFORMATION: Description of Artificial Sequence: Synthetic
      VL CDR3

<400> SEQUENCE: 283

Gln Gln Phe Ala His Thr Pro Phe Thr Phe
1               5                   10

<210> SEQ ID NO 284
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      VL CDR3

<400> SEQUENCE: 284

Gln Gln His His Val Trp Pro Leu Thr Phe
1               5                   10
```